US007303752B2

(12) United States Patent
Hotez et al.

(10) Patent No.: US 7,303,752 B2
(45) Date of Patent: Dec. 4, 2007

(54) HOOKWORM VACCINE

(75) Inventors: Peter Hotez, Rockville, MD (US); James Ashcom, Gaithersburg, MD (US); Mahnaz Bdamchian, Reston, VA (US); Bin Zhan, North Potomac, MD (US); Yan Wang, Rockville, MD (US); John Hawdon, Bowie, MD (US); Alexander Loukas, The Gap QLD (AU); Angela Williamson, Toowong QLD (AU); Brian Jones, Shelton, CT (US); Jeffrey Bethony, Washington, DC (US); Gaddam Goud, Gaithersburg, MD (US); Maria Elena Bottazzi, Washington, DC (US); Susana Mendez, Washington, DC (US)

(73) Assignee: The George Washington University, Washington, DC (US)

( * ) Notice: Subject to any disclaimer, the term of this patent is extended or adjusted under 35 U.S.C. 154(b) by 164 days.

(21) Appl. No.: 10/825,692

(22) Filed: Apr. 16, 2004

(65) Prior Publication Data

US 2005/0042232 A1 Feb. 24, 2005

Related U.S. Application Data

(63) Continuation-in-part of application No. PCT/US02/33106, filed on Oct. 17, 2002.

(60) Provisional application No. 60/505,848, filed on Sep. 26, 2003, provisional application No. 60/375,404, filed on Apr. 26, 2002, provisional application No. 60/332,007, filed on Nov. 23, 2001, provisional application No. 60/329,533, filed on Oct. 17, 2001.

(51) Int. Cl.
*A61K 39/00* (2006.01)
*A61K 39/002* (2006.01)

(52) U.S. Cl. ............................... 424/191.1; 424/184.1; 424/185.1; 530/350

(58) Field of Classification Search ............. 424/184.1, 424/185.1, 191.1; 530/350
See application file for complete search history.

(56) References Cited

FOREIGN PATENT DOCUMENTS

WO WO 01/62802 8/2001

OTHER PUBLICATIONS

Bowie et al (Science, 1990, 247: 1306-1310).*
Greenspan et al. (Nature Biotechnology 7: 936-937, 1999).*
Bin et al. (Molecular and Biochemical Parasitology, 1999, vol. 98, pp. 143-149).*

* cited by examiner

*Primary Examiner*—Robert A. Zeman
(74) *Attorney, Agent, or Firm*—Whitham Curtis Christofferson & Cook, P.C.

(57) ABSTRACT

Preparations which elicit an immune response to hookworm antigens and which may be utilized as hookworm vaccines are provided. In addition, a method of increasing the effectiveness of vaccinations against infectious diseases in patients infected with hookworm is provided. The method involves chemically treating the hookworm infestation prior to administering the vaccine.

4 Claims, 86 Drawing Sheets

```
ATGTTTTCTC CTGTAGTCGT CAGTGTGGTA TTCACAATCG CCTTCTGCAA
TGCGTCTCCA GCAAGAGACA GCTTCGGCTG CTCTAACAGT GGGATAACTG
ACAGCGACCG GCAAGCGTTC CTCGACTTCC ACAACAATGC TCGTCGACGG
GTTGCGAAAG GCCTTGAGGA TAGCAACTCC GGCAAACTGA ATCCAGCGAA
GAACATGTAC AAGCTGTCAT GGGACTGTGC AATGGAACAG CAGCTTCAGG
ATGCCATCCA GTCATGCCCA AGCGGCTTTG CTGGGATTCA AGGTGTTGCG
CAGAATACAA TGAGCTGGTC AAGCTCTGGT GGATACCCCG ATCCATCGGT
AAAGATAGAA CCAACGCTCT CCGGCTGGTG GAGTGGTGCG AAAAAGAACG
GCGTAGGCCC GGACAACAAA TACACCGGTG GTGGTCTCTT CGCCTTCTCT
AACATGGTAT ACTCCGAAAC GACGAAACTT GGCTGCGCTT ACAAGGTTTG
CGGCACTAAA CTGGCGGTTT CATGCATCTA TAATGGAGTC GGGTACATCA
CAAATCAACC TATGTGGGAG ACAGGTCAGG CTTGCCAGAC AGGAGCAGAC
TGCTCCACTT ACAAGAACTC AGGCTGCGAG GACGGCCTTT GCACGAAGGG
ACCAGATGTA CCAGAAACAA ACCAGCAGTG CCCCTCAAAC ACCGGAATGA
CTGATTCAGT CAGAGATACT TTCCTATCGG TGCACAATGA GTTCAGATCG
AGTGTTGCCC GAGGTCTGGA ACCCGACGCT CTGGGCGGAA ATGCACCAAA
AGCAGCTAAA ATGCTCAAGA TGGTGTATGA CTGTGAAGTG GAAGCATCGG
CCATCAGACA TGGAAATAAA TGCGTCTATC AACATTCTCA TGGTGAAGAC
AGACCTGGAC TAGGAGAAAA CATCTACAAA ACTAGTGTAC TCAAATTCGA
CAAGAACAAA GCAGCCAAGC AGGCTTCACA ACTCTGGTGG AATGAGTTAA
AAGAGTACGG CGTCGGCCCA TCCAACGTCC TTACCACTGC GTTATGGAAT
AGAcCCAACA TGCAGATTGG TCaCTACACC CAGATGGCAT GGGACACCAC
CTACAAACTT GGATGTGCAG TTGTTTTCTG CAATGATTTC ACATTCGGCG
TTTGTCAGTA TGGGCCAGGA GGCAATTACA TGGGTCATGT CATCTACACT
ATGGGCCAGC CGTGCTCTCA GTGTTCGCCT GGTGCTACTT GCAGCGTGAC
CGAAGGCTTG TGCAGCGCTC CTTAATCAG  TCAACAATAA ATATCTTA
CAGTGATGTT GTTGCTTACA AATTGCTTCT TTTCCAATAG AAATACCAAT
GTCAACATCA CGAGTTTCTT TAAATTCATC ACTTCCACTA CTAGGGGTGA
TTTGAATAAA ATTTCATTTC ATAAAGCAAT TACATCCGCA AAAAAAAAAA
AAAA
```

*Figure 1A*

```
MFSPVVVSVVFTIAFCNASPARDSFGCSNSGITDSDRQAFLDFHNNARRRVA
KGLEDSNSGKLNPAKNMYKLSWDCAMEQQLQDAIQSCPSGFAGIQGVAQNTM
SWSSSGGYPDPSVKIEPTLSGWWSGAKKNGVGPDNKYTGGGLFAFSNMVYSE
TTKLGCAYKVCGTKLAVSCIYNGVGYITNQPMWETGQACQTGADCSTYKNSG
CEDGLCTKGPDVPETNQQCPSNTGMTDSVRDTFLSVHNEFRSSVARGLEPDA
LGGNAPKAAKMLKMVYDCEVEASAIRHGNKCVYQHSHGEDRPGLGENIYKTS
VLKFDKNKAAKQASQLWWNELKEYGVGPSNVLTTALWNRPNMQIGHYTQMAW
DTTYKLGCAVVFCNDFTFGVCQYGPGGNYMGHVIYTMGQPCSQCSPGATCSV
```

*Figure 1B*

GGTACTGCAGGGTTTAATTACCCAAGTTTGAGACCCAACGCCATGATTTGGCGAACGTGG
CAAGTTCTCGTGGTTCTGTATGCGGCGCTGTCCATTACAGTTGTGAACGCCTATAAACAC
ATTAGCTCCGATCACGTTGTAAATACAACACTGGGTCAGATTCGAGGAGTACCACAGAAT
TTCGAAGGCAAAAAAGTTACCGCTTTTCTTGGTGTGCCATATGGTCAACCACCGACTGGG
GAACTACGATTCAGCAATCCGAAAATGGTGCAGCGTTGGGAAGGTATAAAGAATGCTACA
ACACCGGCTCAGCCATGCTTCCACTTCCCTGACAGTAAATTTAAGGGATTTCGTGGGTCA
GAGATGTGGAATCCGAAAGGAAATATGACCGAGGATTGCTTGAATATGAATATCTGGGTC
CCACACGATGCTGATGGTTCCGTGATTGTATGGATTTTCGGAGGCGGCTTCTTCACCGGT
TCACCATCTTTAGATGTTTACAACGGTACTGCTCTAGCAGCCAAGAAACGTACCATTGTT
GTGAACATAAACTATCGATTGGGTCCCTTCGGTTTCCTTTATCTCGGTGATGATTCTCGT
GCACAAGGGAATATGGGACTGCAAGATCAACAAGTTGCATTGCGATGGGTGCATAAACAT
ATAAGCTCCTTTGGTGGAGATCCGAGAAAAGTCACTCTTTTCGGCGAAGCATCAGGCGCT
GCTTCAGCAACCGCTCATCTAGCAGCACCGGGAAGCTATGAGTTTTTCGATAAGATAATT
GGCAACGGTGGCACAATCATGAATAGTTGGGCCAGTCGAACAAATACATCGATGCTTGAG
CTGTCAATGAAACTTGCTGAACGGTTGAACTGTACCAAGAAAAGAAAAGACCCGAATACT
GTACATCGCTGTTTGGTTAAACATCCAGCACATGTGGTTCTAAAAGAGGCCGCTGTTGTG
TCGTATCAAATTGGTCTCGTGCTGACGTTTGCCTTCATACCCATTACCTCTGATAAGAAC
TTCTTCCAGGGAAATGTCTTTGATCGTCTACGAGATAAAGACATTAAGAAGAATGTATCC
ATTGTGCTTGGTACTGTAAAAGACGAAGCAACCTTCTTTTTACCCTACTACTTTGGTCAC
AACGGTTTCTCTTTCAATAACTCATTCTTAGCAGATGGGGAAGAAAACAGAGCACTCATA
AATATATCACAGTATAATTATGCGATGAATGCAACTGCGCCATCACTTGAAAGCTCACTG
GAACCACTTTTAGAAGCTTATAAGAACGTTTCGACGCGAAAAGAAGAAGGTGAAAGATTA
CGCGATGGTGTTGGTCGATTCATGGGCGACTACTTcTAtACCTGCAGCGTCATTGATTTC
GCTAATATCGTCTCAGACATTATTAATGGATCTTTGTATATGTATTACTTTACTAAgAGG
TCAGTGGCAAATCCTTGGCCAGAGTGGATGGGTGTAATGCATGGTTATGAAATAGAATAC
GAATTTGGACAGCCTTTCCTAAATTCATCaCTGTACAAGGAAAAGCTTGAAAACGAAAAG
ATcTTCTCGAAAAATATCATGAGCTTTTGGAAAGATTTCATCAAGACTGGtGTCCCTGTC
GATTTTTGGCCGAAATACGATCGAAAGGAGCGGAAAGCGCTCGTACTTGGCGAGGAAAGC
GTGAACAATTCTTACCCTAATATGACTAATGTTCATGGaCCGTACTGTGAACTGATCGAA
GAAGCAAAGGcGTCTACAAATAATGGACTCaCCTTGAAGAAATACATTGAAGGGGAGATA
AAAAATAACGAAACGAACGTATTTTGATAGAATGATTTTGCaCAGAATGAAGAATTGAAT
ATCAAAAAAAAAAAAAAAAAAAAAAAAAAAAA

*Figure 2A*

MIWRTWQVLVVLYAALSITVVNAYKHISSDHVVNTTLGQIRGVPQNFEGKKVTAFLGVPY
GQPPTGELRFSNPKMVQRWEGIKNATTPAQPCFHFPDSKFKGFRGSEMWNPKGNMTEDCL
NMNIWVPHDADGSVIVWIFGGGFFTGSPSLDVYNGTALAAKKRTIVVNINYRLGPFGFLY
LGDDSRAQGNMGLQDQQVALRWVHKHISSFGGDPRKVTLFGEASGAASATAHLAAPGSYE
FFDKIIGNGGTIMNSWASRTNTSMLELSMKLAERLNCTKKRKDPNTVHRCLVKHPAHVVL
KEAAVVSYQIGLVLTFAFIPITSDKNFFQGNVFDRLRDKDIKKNVSIVLGTVKDEATFFL
PYYFGHNGFSFNNSFLADGEENRALINISQYNYAMNATAPSLESSLEPLLEAYKNVSTRK
EEGERLRDGVGRFMGDYFYTCSVIDFANIVSDIINGSLYMYYFTKRSVANPWPEWMGVMH
GYEIEYEFGQPFLNSSLYKEKLENEKIFSKNIMSFWKDFIKTGVPVDFWPKYDRKERKAL
VLGEESVNNSYPNMTNVHGPYCELIEEAKASTNNGLTLKKYIEGEIKNNETNVF

*Figure 2B*

CTCGTGCCGAATTCGGCACGAGCTCCATTCATCATGCAGCGATCATTCCTACTTCTACTTGTTGTGTTAGC
AGGTGCCTGGGCCGTAAACACAACAATCCCTCTGAAGCTGATGGGAGGTTTTACACCTATGAAATATCAA
TGTGTTGGTAGAGTTTCGGACATTTGGGCGGATGTGCTATTTCTGATCGAATCATCCGATATGATTACAA
AATCAGGATTCCGTCAAGTCATCGCATTCATTACGGCGACGACAAAGAAGATGACAATCGGTCAGGATGA
AAAGCAGACACGAGTTGGGTTCATCACATACGGGGAAGAAGCAAAACTAATCTACGATCTAGATCACTGG
AGGTCAACCGAGAAGCTCAGCGATTTAGTGCAAAAAATCCCATACGTAAAATCCTCTGGAACAAATATTG
CAGCAGCAATTGCGCTGGCTAACAAGGTATTCAACTCACCAACACATCGACCGAACGTCCCGAAAGTGAT
GGTTATTGTCGCTAATGGATTGAAGAAAGGTAGTCAGAATCCGATTCCCGTTGCGACCGCATTCAAGGAC
TTTGGAGGTATTATAATAACAATAGAATACACTCAATACGATAACATTCAAGTGCCAATTTTGAAGAAAAT
TGCTAGCGAAGGATACAATATTAGAAGCAATGACGAAGATTTCAGTGTCAGAACGTTAACGAACATGTTG
TTGCAGGCAAATTGTTTCTGTCCAGACCATTACGTTCCATTTCGTGTAAATAACCCTGAATTTGGTTGTTT
CGTAACTGCAAAAATTCCATCAATGTGGAGGGATGCAGCTGAAATGTGCCGCGCCGTTGAGGAAGGGAA
ATTAGTGAAAGTAGAGAATGAGGAAAAAGCTGCATTCATCATGAAATTGGTGGGACCG
AAAAAGGAAGCATGGATTGGATTGAGGTACTATGGGAACAAATTCCAGTGGACAGATGGCACTAAGCTCA
ATGCAGACGACTTCAACCTGTGGCCCGAAGATATAAAAGAATTGAATGGACCTCATTGTGTATCTATGTA
CCAAGATCAGAAGGACAAAAAGTATTATTGGAGAGCCGGTAAATGCCTTGAAGATATGAGATATGTATGC
GAAGTACAGCCATGCAGTGCATCCAACTACTGCTCGGAACCAGTGTTCATGTATCGTCAGAAGCATCGCG
CTCTCCTACCAGCACCACCACCACCACCAAACTAAGATCTAAAAAAATCTGTCCAAAAGAGATACCATTGA
CATGTACTTTGATTATGTTGAATAGTGTAATTAATCAGAATGGGGTGTAGTGAATAAACGTACAACTATTT
AAAAAAAAAAAAAAAAAAAAAA

*Figure 3A*

MQRSFLLLLVVLAGAWAVNTTIPLKLMGGFTPMKYQCVGRVSDIWADVLFLIESSDMITKSG
FRQVIAFITATTKKMTIGQDEKQTRVGFITYGEEAKLIYDLDHWRSTEKLSDLVQKIPYVKS
SGTNIAAAIALANKVFNSPTHRPNVPKVMVIVANGLKKGSQNPIPVATAFKDFGGIIITIEY
TQYDNIQVPILKKIASEGYNIRSNDEDFSVRTLTNMLLQANCFCPDHYVPFRVNNPEFGCFV
TAKIPSMWRDAAEMCRAVEEGKLVKVENEEKAAFIMKLVGPKKEAWIGLRYYGNKFQWTDGT
KLNADDFNLWPEDIKELNGPHCVSMYQDQKDKKYYWRAGKCLEDMRYVCEVQPCSASNYCSE
PVFMYRQKHRALLPAPPPPPN*

*Figure 3B* ggcacgaggg gagatggctc gacttgtatt cctactcgta ctatgtactc tggctgcagc
aagcgttcat cgacgactct ttcatcaagc tcgtcgtcat gtgacatcgg tatcgctttc
gcgtcagcca acacttcgtg aacgactgat cgcaagtggc agttgggagg attaccagaa
acaacgctac cattatcgaa agaaaattct agcaaaatat gctgctaaca aagcgtcaaa
gttacaatct gcaaacgaga tcgatgaatt gctccggaac tatatggatg cacaatacta
tggtgtcatc caaattggga ctccagctca gaatttcact gtgatcttcg acacgggttc
ctcaaatcta tgggtaccgt caagaaagtg tccattctat gacattgcat gtatgcttca
tcatcgttat gactccggag cctcgtcaac ctacaaggaa gatgggcgca agatggctat
tcagtatgga actggatcta tgaaaggatt catttctaag gatattgttt gtattgctgg
aatttgcgct gaagaacaac ctttcgcgga ggctacaagt gaacctggtc ttacatttat
cgctgctaag tttgatggaa tccttggaat ggcattcccg gaaattgctg ttctcggtgt
aactcctgtc ttccatacgt tcattgaaca gaagaaagtt cctagccctg tgtttgcttt
ctggctgaat aggaatccag agtcggaaat tggaggagag attacctttg gtggtgtgga
tacccgacgt tatgttgaac caattacatg gacaccagtg acacgtcgtg gatattggca
attcaaaatg gatatggtac aaggtggttc atcgtccatt gcgtgtccga atggatgcca
agctatcgct gatactggca cttctcttat tgctggaccg aaggcacagg ttgaggcaat
ccagaaatat atcggagcag agccgcttat gaaaggagaa tacatgattc cttgcgacaa
agtaccatcc cttcctgatg tttcgttcat catcgatggc aagacgttta cactcaaagg
ggaagattac gttctaaccg tgaaagccgc tggtaaatca atctgtttgt ctggcttcat
gggaatggac ttcccagaga agatcggcga attgtggatc cttggagatg ttttcattgg
aaaatactac accgtcttcg atgttggtca ggcacgtgtt ggatttgctc aagcaaagtc
agaagatgga ttccctgttg gcacccccgt tcgaacattc agacagcttc aggaagacag
cgatagcgac gaggacgatg tatttacttt ttaagtagtg ttaacatctc caacgtgctc
tgttacttct acgtgtacca tgtttcacgt gtttgctcat ttgataaatt attatcttcc
ct

*Figure 4A*

MARLVFLLVLCTLAAASVHRRLFHQARRHVTSVSLSRQPTLRER
LIASGSWEDYQKQRYHYRKKILAKYAANKASKLQSANEIDELLRNYMDAQYYGVIQIG
TPAQNFTVIFDTGSSNLWVPSRKCPFYDIACMLHHRYDSGASSTYKEDGRKMAIQYGT
GSMKGFISKDIVCIAGICAEEQPFAEATSEPGLTFIAAKFDGILGMAFPEIAVLGVTP
VFHTFIEQKKVPSPVFAFWLNRNPESEIGGEITFGGVDTRRYVEPITWTPVTRRGYWQ
FKMDMVQGGSSSIACPNGCQAIADTGTSLIAGPKAQVEAIQKYIGAEPLMKGEYMIPC
DKVPSLPDVSFIIDGKTFTLKGEDYVLTVKAAGKSICLSGFMGMDFPEKIGELWILGD
VFIGKYYTVFDVGQARVGFAQAKSEDGFPVGTPVRTFRQLQEDSDSDEDDVFTF

*Figure 4B*

```
ggcacgagag aatgcgttcg atactcgtgt tggtggctct gatcggatgc attgctgcgg
gtgtatataa aatccccattg aaaagaatca ctccgccgat gataaaaatg ttgagagctg
gtacttggga aacgtacgta gaaggaatga ggaagagaca attacagtta ctgaaggagc
acaaggttca tatccaagat gtactcggct atgctaacat ggagtacctc ggcgaaatta
ctattggaac tcctcaacag aagtttctgg tggttttgga cactggctcc tcgaatctgt
gggtccctga tgattcatgc tacaaggaga agagacctga tagatgtcta gtatcaaact
gtgatgctgg actggtttgt caagtcttct gtccagatcc taaatgctgt gaacatacga
gagaattcaa gcaagtaaac gcatgcaaag ataagcatcg atttgatcaa aagaattcca
acacttatgt taaaacaaac aaaacatggg caatagcgta tggaactgga gatgcgaggg
gatttttgg aagagataca gtccgtttgg gtgctgaagg aaaggatcag ctcgttatta
atgatacgtg gttcggacaa gcagagcata tagctgaatt tttcagtaat actttccttg
atggcattct cggactcgct tttcaagaac tgtcagaagg aggcgtcgct cctccaataa
ttcgtgccat tgaccttgga cttctcgatc aaccaatatt tactgtctat ttcgaaaatg
tcggagacaa agaaggtgtt tatggaggtg ttttcacctg gggtggtctc gatcccgatc
attgcgaaga tgaggtcaca tatgaacagc taaccgaagc aacttactgg cagtttagac
ttaaaggagt gtcgtctaag aacttctcgt cgacggctgg ttgggaagca atatccgaca
ctggtacctc gttaaatgga gcccctaggg ggatactaag aagtattgca agacagtata
atggacagta cgtcgcatct caaggtctct acgtcgtcga ctgcagtaaa aatgtgaccg
ttgacgtgac cattggcgac agaaactaca ctatgactgc gaaaaatctc gtacttgaaa
tacaggctga tatatgtatt atggcatttt tcgaaatgga catgttcatt ggaccagcat
ggattcttgg cgatccattt attcgagaat attgcaatat tcatgacatt gaaaagaagc
ggattggttt tgcagctgta aaacattgat cgattataaa tgtaatgggc tatttgtcat
aaattgctca ataaagtttt ttgactaaaa aaaaaaaaaa aaaaaa
```

*Figure 5A*

```
MRSILVLVALIGCIAAGVYKIPLKRITPPMIKMLRAGTWETYVE
GMRKRQLQLLKEHKVHIQDVLGYANMEYLGEITIGTPQQKFLVVLDTGSSNLWVPDDS
CYKEKRPDRCLVSNCDAGLVCQVFCPDPKCCEHTREFKQVNACKDKHRFDQKNSNTYV
KTNKTWAIAYGTGDARGFFGRDTVRLGAEGKDQLVINDTWFGQAEHIAEFFSNTFLDG
ILGLAFQELSEGGVAPPIIRAIDLGLLDQPIFTVYFENVGDKEGVYGGVFTWGGLDPD
HCEDEVTYEQLTEATYWQFRLKGVSSKNFSSTAGWEAISDTGTSLNGAPRGILRSIAR
QYNGQYVASQGLYVVDCSKNVTVDVTIGDRNYTMTAKNLVLEIQADICIMAFFEMDMF
IGPAWILGDPFIREYCNIHDIEKKRIGFAAVKH
```

*Figure 5B*

Figures 6A, 6B:
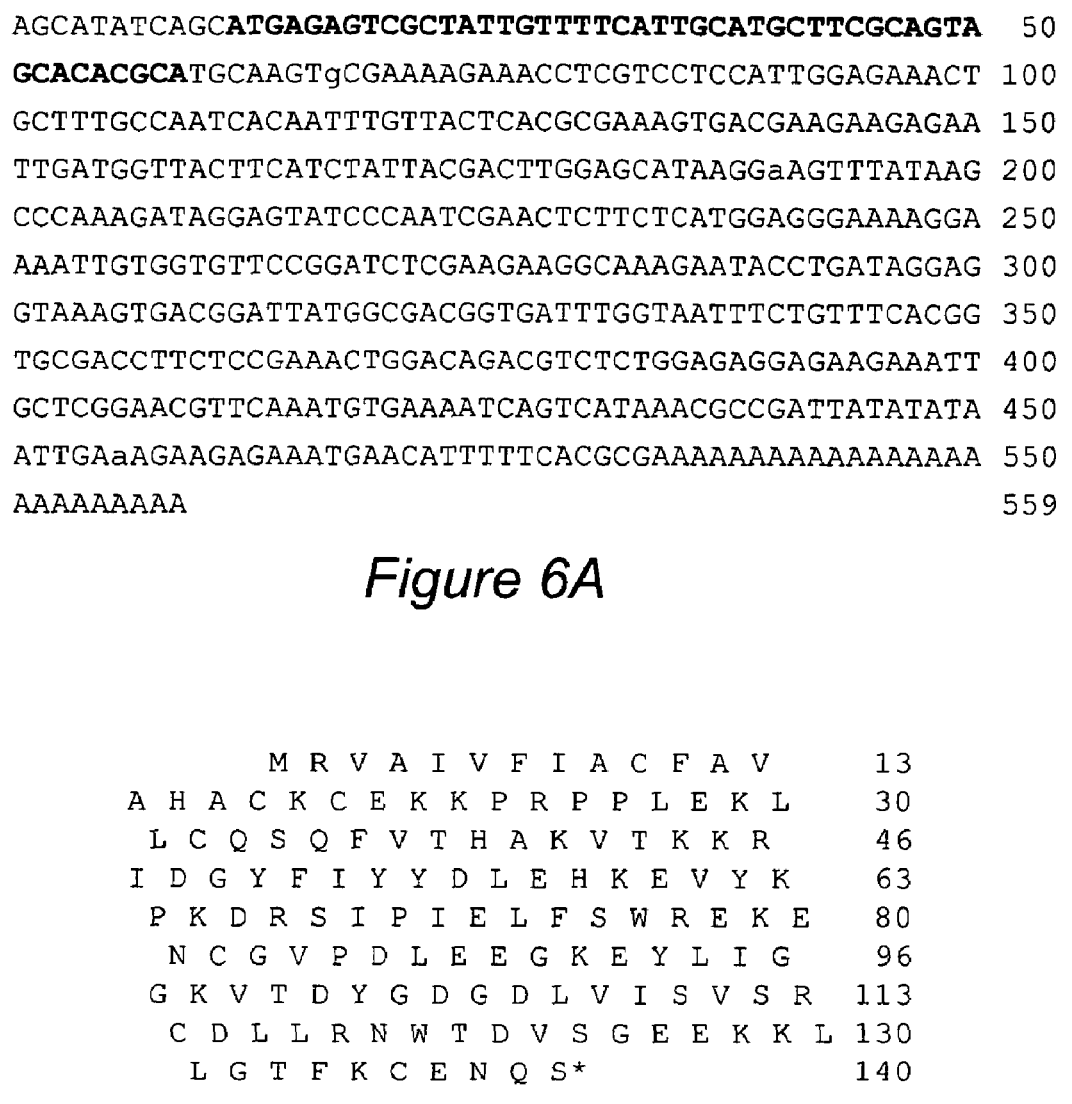

AGCATATCAGCATGAGAGTCGCTATTGTTTTCATTGCATGCTTCGCAGTA 50
GCACACGCATGCAAGTgCGAAAAGAAACCTCGTCCTCCATTGGAGAAACT 100
GCTTTGCCAATCACAATTTGTTACTCACGCGAAAGTGACGAAGAAGAGAA 150
TTGATGGTTACTTCATCTATTACGACTTGGAGCATAAGGaAGTTTATAAG 200
CCCAAAGATAGGAGTATCCCAATCGAACTCTTCTCATGGAGGGAAAAGGA 250
AAATTGTGGTGTTCCGGATCTCGAAGAAGGCAAAGAATACCTGATAGGAG 300
GTAAAGTGACGGATTATGGCGACGGTGATTTGGTAATTTCTGTTTCACGG 350
TGCGACCTTCTCCGAAACTGGACAGACGTCTCTGGAGAGGAGAAGAAATT 400
GCTCGGAACGTTCAAATGTGAAAATCAGTCATAAACGCCGATTATATATA 450
ATTGAaAGAAGAGAAATGAACATTTTTCACGCGAAAAAAAAAAAAAAAAA 550
AAAAAAAAA 559

GTGGTTTTCAACGTCCTCACATGGCTTAAATTAA
ACGAGAACAAAGATGACTCATCACCGGCTCCGAAGATATGGAATGTGGGAGAGCAAGATAATACACCCGTGCTGACAAAT
TTGTTAGTTTTGGAAAAAGAGGAGTTAGCAGCAAAGTTGAAGAAAACACCATATGAGGAGGTGGATGAGCAAACAGTTAG
ACAATCGTCGGTTATGAAACTCAGGAATATCAAAAATGCCCTGTTCACTCCAATAGAACCAGTAGCCTCAGCGTTGCCTC
CATTGCGTGTGAATGACCCGAAATATTGTCCGAGTTACGGTGAACCGGATAAGAAATATGCCTATCAGGAAGCAGCATCT
TATCTTCTCAGTGGTCTGGATCAGACTGTAGATCCATGCGAGGATCTCTATGCATTCACCTGTAATACGTACCTCAGAAA
TCACAACGCCACCGACATTGGCGTGAACCGAATCGGAACGTACAAAGACGCTCAAGATGACGTGAACGCTGAAATCGTGG
AAGCACTCGAAGAAGTTAACGTGAGCGACACAAAGTGGTCGGAGACGGAGAGGCTTGTGAAAGCGACTCTCTTCACATGT
GTACACCACACTCGAGCGAGGAAACCCATAGACAATTCGAAGAACGTTCTTATAGAGATGAGAGACTTGTTTGGCGGAAT
TCCATTCCTCAATCATACTCTGAAGAAGGACATTGATTTCTTTGATATAATGGGAAAGTTCGAGCAGAATCATGCGATGG
GAACCCTTCTCGGAGCAATGGTCTCGGTCGATTTCAAGAATGTGAACAAACACTCCTTATTCTTATCGCAGCCCTATCTT
CCAATGGCTCGAGATTTCTATGTTTTCCCACAACACACAAAGATGGTTGAGAATCGCGTAAGTCTCATCAACTCTGTGCT
GAGGTCGTTCGCAGAGGCTGTTCTGGATGATCCCTCGCCGTATCTCGATCTGATGTCAAGATCGGCAAGAGATGTAGTGA
AGCTGGAGATGCAGATTGCGATGGCATCGTGGCCAGAGAGTGAACTGAGGAACTACGCACAACAGCACAATCCACGCACT
TTGAATCAGTTGAAAGCAGCGTATCCAGCGATTAAATGGGACAGTTATTTCAATGCTCTGCTCTCCTCTGTGCAGGGAGT
CGATATGAATAGGCAGAACATCATACTTACCCAACCATCGTACTTCGGCTGGTTAAATGCTCTCTTCAACGGTGGCGCAG
ATGACAAAACCATTGCGAATTATCTTCTTGTTCACCTGATTCTCGAGGAGGCTGATTTCCTTGGTGGAGCACTTAAAACG
ATGGTTCAAAAATCTGATTATGTTCCATATGCCTTAGGAAGAGGAAAGGGAGTCACAAGAGTTGGCCAGCAACTTACTCG
ATCACATGACGATACTGTTGAGGATGCAAACATACAGTGCTTGAACAGCATGATGACGTATATGCCATTTGGACCAGGTT
ACGTGTACGTGAAATCAAGGAAGAACAGAGATGACGTTGTCAAGGACATAGAGCACCAGACCGAGCTGGTCTTCAAGAAC
TTTGTGAACATGATTGGTAACTTAAATTGGATGACAGACGCATCTCTGGAGCTCGCCATGGAGAAAGCTGATACGATGGT
GAAAAACTATGGATGGCCCAAGGATTTGTTTGGAAATTTCAGGGATAGTAGCAAGATTGATGCTTATCACAAGAAGGATT
ATGGTAACATCATTAACCTGTACAAGGAGAACATTACTCATAACTACTACCACATCCGCAGAACTATGATCAAAGGCTAT
TCCAACCATGAATCGCTGCGATTGCTGACTGAAGCGCCGAAAAGGGACCACTTCCTGTTGTCACCCGCTCTGGTGAATGC
GTGGTACATACCGGAGAGAAACTCCATCGCATTCCCTTACGCCTTCTGGAATCCACCCTATTACAATTACGAATATCCTC
AAGCATGCAACTACGCTGGTCAAGGTGGAACTGCTGGCCACGAATTAGTGCATGGATTCGATGACCAGGGAGTACAGTTC
GCTGCCGACGGAAGCCTTAGCGACTGCACGTGGATCGAGTGTGGATGGTTGGAAGAGAAGTCCAAGAAAGGATTCAGTGA
TATGGCACAATGTGTTGTCACACAGTATAGCACCCAATGCTGCCCTCAGACAGGTGGGGTCACCCACTGCGCTAATGGAG
CGACCACCCAAGGAGAAAACATCGCCGATCTTGGAGGTCAACTGGCAGCATATCGAGCCTACCGTGAATACATCACCAAG
GAAAGAGGAGAGGAGGAGAAGAGACTGCCGGGATTGGAGCAGTACACACCAAATCAGATCTTCTGGATAACATACGGATA
TTCGTGGTGCATGAGCCAAACAGATAGCAGTCTTATTAGACAACTCTTGACCGATGTTCACTCACCTGGCTCATGCCGTG
TTAACCAAGTCATGCAAGATATTCCGGAATTTGCACTCGATTTCGGATGTACAATGGGCCAGAAGATGTATCCAGAGCCT
GAGCAACGATGTCCGGTTTGGGTAGCAGAATAAATGTTCGAAAATGGACCGTCAGATCTCATGTTTTCACGTGAATATGA
CGCTCTTAACTGAGGTTTTTC

Figure 7A

MAKLLEVTTGLVVLLGVLGVISVVFNVLTWLKLNENKDDSSPAPKIWNVG
EQDNTPVLTNLLVLEKEELAAKLKKTPYEEVDEQTVRQSSVMKLRNIKNA
LFTPIEPVASALPPLRVNDPKYCPSYGEPDKKYAYQEAASYLLSGLDQTV
DPCEDLYAFTCNTYLRNHNATDIGVNRIGTYKDAQDDVNAEIVEALEEVN
VSDTKWSETERLVKATLFTCVHHTRARKPIDNSKNVLIEMRDLFGGIPFL
NHTLKKDIDFFDIMGKFEQNHAMGTLLGAMVSVDFKNVNKHSLFLSQPYL
PMARDFYVFPQHTKMVENRVSLINSVLRSFAEAVLDDPSPYLDLMSRSAR
DVVKLEMQIAMASWPESELRNYAQQHNPRTLNQLKAAYPAIKWDSYFNAL
LSSVQGVDMNRQNIILTQPSYFGWLNALFNGGADDKTIANYLLVHLILEE
ADFLGGALKTMVQKSDYVPYALGRGKGVTRVGQQLTRSHDDTVEDANIQC
LNSMMTYMPFGPGYVYVKSRKNRDDVVKDIEHQTELVFKNFVNMIGNLNW
MTDASLELAMEKADTMVKNYGWPKDLFGNFRDSSKIDAYHKKDYGNIINL
YKENITHNYYHIRRTMIKGYSNHESLRLLTEAPKRDHFLLSPALVNAWYI
PERNSIAFPYAFWNPPYYNYEYPQACNYAGQGGTAGHELVHGFDDQGVQF
AADGSLSDCTWIECGWLEEKSKKGFSDMAQCVVTQYSTQCCPQTGGVTHC
ANGATTQGENIADLGGQLAAYRAYREYITKERGEEEKRLPGLEQYTPNQI
FWITYGYSWCMSQTDSSLIRQLLTDVHSPGSCRVNQVMQDIPEFALDFGC
TMGQKMYPEPEQRCPVWVAE*

Figure 7B

GGGTTTAATTACCCAAGTTTGAGGATGAGGGTACTCCTGTTACTGCTACTTTTATCCATT
TGCGCGAGCGCTGGCTTTCTAGACACTAAATTCGGCCAGAAGATAAAGAAAACTCTTGAC
AAGATTAAAGCTGTGCTTAACGGCACTGCACTCATCGCGATTCGTGAAAAATTCATTCGA
CTAAGGGAAAAAATAAAAGCAAAGCTGACGCTCTCTCCAGCACGAAAGGCTATATTGGAC
GAAGTTATGAAGCaTATCAAAATGATCAAAAAGGATAAGATTCAAGAGAAGGGCGACTCA
ATCGATGAAATCAATGAAAAGAGTGCAATCGGACAGTTGCTGTACCAGGGTGACATCGTT
CTGACAGAAAAGCAAGCCCAGCAAATTACCGAAGACATTGAAAATGACAAAGGCGACCGC
GAAAAACGACAGGCGTTCCGTGATCGCAATTATCCGCGAACATTATGGTCGAAGGGAGTG
TACTTTCACTTTCATAGGAACGCAACTCCTGAAGTTAGAAGCGTTTTTGTGAAAGGCGCA
AAACTTTGGATGAAGGATACTTGCATCGACTTCTTCGAAAGCAACTCAGCGCCTGATAGG
ATTCGTGTGTTCAAAGAGAACGGATGTTGGTCGTACGTTGGTAGGCTGGGCGGTGAACAA
GATCTGTCACTGGGAGAaGGTTGTCAATCGGTTGGCACAGCTGCGCACGAAATTGGCCAC
GCTATTGGCTTCTACCACACTCACGCAAGACATGATCGCGATAACTTTaTTACATTCaAC
GCACAAAATGTCAAGCCCGATTGGTTGGACCAATTCACTCTTCAGACTCCGGCAACGAAT
GAGAACTATGGAATAACTTACGACTATGGAAGTATCATGCATTATGGTGCAAATAGCGCC
TCGCAGAACGGACGTCCTACAATGGTTCCGCATGATCCCAAATACGTAGAAACTCTTGGa
TCACCCATAATTtCCTTCTATGAGCTTCTCATGATCAACAAACACTACGACTGCACTAAG
AACTGTGACCCGGCTACTTCTGCGCAGTGTAAGATGGGTGGCTTCCCACATCCTCGGGAT
TGTACAAGATGCATTTGCCCTAGTGGATATGGAGGCAAACTGTGCGACCAGAAGCCAGCC
GGATGCGGATCTATATACcAGgCCACCAATCAGTACCAGACCTTGCACGACGAAATTGGA
GACAAGAGAGCGGGACAGAGACCTAGAGAAGACATGGACTTCTGCTATTATTGGATCACG
GCCCCAAAAGGTTCAAAAATCGAAATCAAAATTGCTGGATTATCACAAGGAGCCGCTGTT
GAAGGATGCCAGTACTGGGGAGTAGAAATCAAGACTCATGCCGATCAACGTCTTACCGGC
TACAGGTTCTGCGCACCAGAAGATGTTGGAGTTAGATTAGTGTCGAACTTCAACATCGTA
CCAATAATCACATACAACATATTCTACGCGACCTATGTCGATATTCAGTACCGTATCGTT
GGTGATAATGTTGGCGGTCCTATGCCTCAGCCACAACCAAATAGCAATTGTGTCGACAAT
GAACAGTGTGCGACACTCGTGAGAACAAAGAACTTCTGTCAGAGCAGATTTTTCACAGAG
TCCGTCaAAAGAGGTCTATGTCCAAAGTCCAGCGGTTTCTGTCGCTAACTTTTCAGCAAA
CAATGGAATAAATGTTGCACCATAAAAAAAAAAAAATAAAAAA

Figure 8A

MRVLLLLLLLSICASAGFLDTKFGQKIKKTLDKIKAVLNGTALIAIREKFIRLREKIKAK
LTLSPARKAILDEVMKHIKMIKKDKIQEKGDSIDEINEKSAIGQLLYQGDIVLTEKQAQQ
ITEDIENDKGDREKRQAFRDRNYPRTLWSKGVYFHFHRNATPEVRSVFVKGAKLWMKDTC
IDFFESNSAPDRIRVFKENGCWSYVGRLGGEQDLSLGEGCQSVGTAAHEIGHAIGFYHTH
ARHDRDNFITFNAQNVKPDWLDQFTLQTPATNENYGITYDYGSIMHYGANSASQNGRPTM
VPHDPKYVETLGSPIISFYELLMINKHYDCTKNCDPATSAQCKMGGFPHPRDCTRCICPS
GYGGKLCDQKPAGCGSIYQATNQYQTLHDEIGDKRAGQRPREDMDFCYYWITAPKGSKIE
IKIAGLSQGAAVEGCQYWGVEIKTHADQRLTGYRFCAPEDVGVRLVSNFNIVPIITYNIF
YATYVDIQYRIVGDNVGGPMPQPQPNSNCVDNEQCATLVRTKNFCQSRFFTESVKRGLCP
KSSGFCR*

Figure 8B

ATGTTTTCAC CTGTAATcGT CAGTGTGATT TTCACAATCG CCTTCTGCGA
tgcgtctcca gcaagagacG GCTTCGGCTG TTCAAACAGT GGGATAACTG
ACAAGGACCG GCAAGCATTC CTCGACTTCC ACAACAATGC TCGTCGACGG
GTTGCGAAAG GCGTTGAGGA TAGCAACTCC GGCAAACTGA ATCCAGCGAA
GAACATGTAC AAGCTgtCAT GGGACTGTGC AATGGAACAG CAGCTTCAGG
ATGCCATTCA GTCATGCCCA AGCGcgTTCG CTGGAATTCA AGGTGTTGCG
CAGAATGTAA TGAGCTGGTC AAGCTCTGGT GGATTCCCCG ATCCATCGGT
AAAGATAGAA CAAACGCTCT CCGGCTGGTG GAGTGGTGCT AAAAAGAACG
GCGTCGGCCC GGACAACAAA TACAACGGTG GCGGTCTCTT CGCCTTCTCT
AACATGGTAT ACTCCGAAAC GACGAAACTT GGCTGCGCcT ACAAGGTTTG
CGGCACTAAA CTGGCGGTTT CGTGCATCTA TAATGGAGTC GGGTACATCA
CAAATCAACC TATGTGGGAG ACAGGTCAGG CTTGCAAGAC AGGAGCAGAC
TGCTCCACTT ACAAGAACTC AGGCTGCGAG GATGGCCTTT GCACGAAAGG
ACCAGACGTA CCAGAAACAA ACCAGCAGTG CCCCTCAAAC ActGGAATga
ctgattcagt cagagatact ttcctatcgg tgcacaatga GTTCAGGTCG
AGTGTTGCCC GAGGTCTGGA ACCCGACGCT CTGGGCGGAA ATGCACCAAA
AGCAGCTAAA ATgCTCAAGA TGGTGTATGA CTGTGAAGTA GAAGCATCGG
CCATCAGACA TGGAAATAAA TGCGTCTATC AACATTCCCA TGGCGAAGAC
AGACCTGGAC TAGGAGAAAA CATCTACAAG ACTAGTGTAC TCAAATTCGA
TAAGAACAAA GCAGCCAAGC AGGCTTCACA ACTCTGGTGG AATGAGTTAA
AAGAGTTCGG CGTCGGCCCA TCCAACGTCC TTACCACTGC TTTATGGAAT
AGACCCGGCA TGCAGATTGG TCACTACACC CAGATGGCAT GGGACACCAC
CTACAAACTT GGATGTGCAG TTGTTTTCTG CAATGATTTC ACATTCGGTG
TTTGTCAGTA TGGGCCAGGA GGCAATTACA TGGGTCATGT CATCTACACT
ATGGGCCAGC CGTGTTCTCA GTGTTCGCCT GGTGCTACTT GCAGCGTGAC
CGAAGGCTTG TGCAGTGCTC CTTAATCAGT TCTTAACAAT GAATATCTTA
CAGTTGAAAA AAAAAAAAAA AAAAAAAA

Figure 9A

MFSPVIVSVIFTIAFCDASPARDGFGCSNSGITDKDRQAFLDFHNNARRRVAKGVEDSNS
GKLNPAKNMYKLSWDCAMEQQLQDAIQSCPSAFAGIQGVAQNVMSWSSSGGFPDPSVKIE
QTLSGWWSGAKKNGVGPDNKYNGGGLFAFSNMVYSETTKLGCAYKVCGTKLAVSCIYNGV
GYITNQPMWETGQACKTGADCSTYKNSGCEDGLCTKGPDVPETNQQCPSNTGMTDSVRDT
FLSVHNEFRSSVARGLEPDALGGNAPKAAKMLKMVYDCEVEASAIRHGNKCVYQHSHGED
RPGLGENIYKTSVLKFDKNKAAKQASQLWWNELKEFGVGPSNVLTTALWNRPGMQIGHYT
QMAWDTTYKLGCAVVFCNDFTFGVCQYGPGGNYMGHVIYTMGQPCSQCSPGATCSVTEGL
CSAP*

Figure 9B cGACACAACCAACGATGTTAGTTCTTGTACCACTTTTGGCTCTCTTGGCTGTTTCTGTTCATGGAAATTCTATGA
GATGCGGAAATAATGGAATGACCGACGAAGCCCGGCAGAAATTCCTCGACGTGCACAACAGTTACAGATCTATGG
TTGCCAAAGGACAGGCAAAGGATGCAATTTCGGGAAATGCTCCGAAGGCTGCCAAAATGAAGAAAATGATCTACG
ACTGCAACGTCGAATCAACTGCAATGCAAAATGCGAAAAAATGTGTTTTCGCCCATTCGCACAGGAAGGGAGTTG
GCGAAAATATTTGGATGTCGACTGCGCGTCAGATGGACAAAGCACAAGCTGCTCAACAGGCTAGTGACGGTTGGT
TCAGTGAGCTTGCGAAGTATGGTGTAGGCCAGGAAAACAAGCTAACAACGCAGTTGTGGAACAGGGGAGTTATGA
TAGGACATTACACTCAGATGGTCTGGCAGGAGTCCTACAAACTCGGATGTTATGTGGAATGGTGTTCATCGATGA
CCTATGGTGTCTGCCAGTACAGTCCTCAGGGTAATATGATGAACTCACTCATCTACGAGAAAGGAAACCCGTGCA
CAAAAGACTCTGACTGTGGCTCGAACGCCAGTTGCAGCGCTGGGGAGgCgCTTTGCgTCgTGCGTGGCTAgCTGG
ACATTCCCaACGTACAACAGCGTTATAgTTAATGCaACTTTTCtTTCATCtTAtTGAgTAAAGGCatTGAAAACa
aaaAAAAAAAAAAAAA

Figure 10A

MLVLVPLLALLAVSVHGNSMRCGNNGMTDEARQKFLDVHNSYRSMVAKGQAKDAISGNAPKAAKMKKMIY
DCNVESTAMQNAKKCVFAHSHRKGVGENIWMSTARQMDKAQAAQQASDGWFSELAKYGVGQENKLTTQLW
NRGVMIGHYTQMVWQESYKLGCYVEWCSSMTYGVCQYSPQGNMMNSLIYEKGNPCTKDSDCGSNASCSAG
EALCVVRG*

Figure 10B

ATAAGACAGCAATGAAGTCCTATCTTGTGATATCAGCTGCGATCCTCGGCATTGCTTA
TGCCGATGCTGATTATTCCAAGTGCCCGCAAAATGAAATAATGAACAACGATATGAGG
GAAAAAGTTACGGACATGCACAACGCCTACAGATCCAAATTCGCACGGGATCATCAAG
CTTCGAAAATGAGAAAATTGGTTTACGACTGTGCCATCGAAAAAGGAATCTACGAGTC
GGATACCAAGTGCGAGATGAAACCATCGATGGAGGAGGAGAACGTAGAAGTTATCGAC
GGCAACAGCGATGATCTCACTGTTATTTCAGAGGCCGGTAATTCGTGGTGGAGCGAGA
TTTTGGACCTGAAAGGAAAGGATGTGTACAACTCCGTGGACAATACATCGGAAATTGC
CAATATGGCTTGGGAAAGTCATGCGAAACTTGGTTGCGCAGTTGTTGAGTGCTCCAAG
AAAACCCATGTAGTCTGCCGATACGGACCGGAAGGAAAAGGTGAAGGAAAGAAAATTT
ACGAAAAGGGCGAAACATGCTCACAATGCAGTGATTACGGACAAGGTGTCACCTGTGA
CAATGACGAGTGGGAGGGATTACTCTGCTCATAATATTGGAAAAACATATGTGGATGA
TGATGTTCGCAAATAAATAAATCAATTACAAAAAAAAAAAAAAAAAAAA

*Figure 11A*

MKSYLVISAAILGIAYADADYSKCPQNEIMNNDMREKVTDMHNAYRSKFARDHQAS
KMRKLVYDCAIEKGIYESDTKCEMKPSMEEENVEVIDGNSDDLTVISEAGNSWWSE
ILDLKGKDVYNSVDNTSEIANMAWESHAKLGCAVVECSKKTHVVCRYGPEGKGEGK
KIYEKGETCSQCSDYGQGVTCDNDEWEGLLCS*

*Figure 11B*

AGAACATGATCAACATCCATTTCATAGCGCTTGCCATAACCTCTCTTTTGCCTGCCCTAT
CCGAAGGGAAACCGGTCGTATTTGTTGAACCACAGTGTAAGCCGAATGGTTACCTACACA
AGAATACAATCGACAACAATGTTCTTAAGCCGATAAATACTCGTCGAGAGGCTCTGGCCA
AGGGCACGCAACAGAATGGCTTTGACCCACCAAACCCACAAACATTCTTGCCACCAGCGA
CGGACATGACTAAACTGAGTTGGAGTTGTGATCTTGAGCAGAAGGCTATAAAAACTATCA
ACGGTAACTGTGTGAATCCGGCAAACCCAACCAAACCGAATAACGGCGAAGGATTGGCAG
ATGTCCTCTACTACGGCAACGACTATGATAACACGGTCGAAGGAGTGATCCAAGGCAATC
TCGAAGCTTGGCTGGTAAAAGCCGATTTCAATGTATTCCCTGTTACCACAAAAGGTACCG
TCATTAGCTATCCCACTTACAATGGCAACACAGATCTCTTGGCATACTCTAACTTAGTCC
GGCCTACCAATACTGAGATAGGATGTGTACTGGAAAGATGTCCAGCTACAGCCAATGTTC
CAAAGCTAGTCACGTTCTACTGTATTTTGAATGGAAAAAATATCACCAACGGAGAGGCTC
TCTATAAGGGCACAACTGTGAATACCGGAGGATGCAAAGAGGTCACATGCTCAGCGGGAT
ATGCCTGTAACAACGCCACCTTGCTATGTGAACGTAGTGCGACAACAAGCTCATCTACAT
CGGCAAGCACATCTTCATCAACAGCTTCCTCAACAAGTTCATCTATGGCAATAAGCACAT
CTTCGTCAACAAGCGCATCTGGGGCAACAACAACAAAAGCTCCTTCTCCGCAAGCGCAAT
TCCCCACAGGGACTAGCACTATGTGCAATACCAGGCATGCCTATGCTAACAGGATGACCG
ACAATCTCAGGAATGAATACGTAAGGCTGCACAACTTCCGAAGAGGCTTACTCGCAAAGG
GAGAAATTCCTCAGAAGGGTAACATATACCTACCAAAGGCGGCTGACATGTGGAAAATTA
GTTACGACTGCGGCCTGGAACAAGGAGCCATAGAACACGCAAGCCAGTGTCTCACAGGAG
GGTCCGGACAAAGCTCGAGACCAGGTGTGGGAGAGAACTTTAAAGTGATCCCAGCGGCAA
GATTTCCGACTTTCGAAGATGCAGCAAAAAAGACCGTTACTGAATGGTGGAAGCCGATTC
GTAACGTGGACTACTTCGGAAACAACGTCAACTTCCTCCCCATCTATGACCAAGACCCGA
TATCCTCCTTTACCCGGATGGCATGGGCCACAACTAACAAGGTGGGGTGCTCTATCGTAA
AGTGCACAACGGACAACGTATACGTAGGCGTGTGCCGATATAGTCCAATGGGTAACATTG
TGAACAGCAACATCTACCAAATTGGGAATCCCTGCAGTGTGAGACCTACTCAAGCGACCG
GGTGTGACCCAGTCGAGGGATTGTGGTACTAGGCGCACTTTTCCGCACTGAATGGCGATT
CTGTTTTGAATTTTTGAATATTACATTAATGGATGTTAACAATGGGTCCTTTAGTTTTCT
GTTGTTAACAAGGGTGGTTAGATTGGATTGGGAATAAATGATGCAATCGCCAAAAAAAAA
AAAAAAAAA

Figure 12A

MINIHFIALAITSLLPALSEGKPVVFVEPQCKPNGYLHKNTIDNNVLKPI
NTRREALAKGTQQNGFDPPNPQTFLPPATDMTKLSWSCDLEQKAIKTING
NCVNPANPTKPNNGEGLADVLYYGNDYDNTVEGVIQGNLEAWLVKADFNV
FPVTTKGTVISYPTYNGNTDLLAYSNLVRPTNTEIGCVLERCPATANVPK
LVTFYCILNGKNITNGEALYKGTTVNTGGCKEVTCSAGYACNNATLLCER
SATTSSSTSASTSSSTASSTSSSMAISTSSSTSASGATTTKAPSPQAQFP
TGTSTMCNTRHAYANRMTDNLRNEYVRLHNFRRGLLAKGEIPQKGNIYLP
KAADMWKISYDCGLEQGAIEHASQCLTGGSGQSSRPGVGENFKVIPAARF
PTFEDAAKKTVTEWWKPIRNVDYFGNNVNFLPIYDQDPISSFTRMAWATT
NKVGCSIVKCTTDNVYVGVCRYSPMGNIVNSNIYQIGNPCSVRPTQATGC
DPVEGLWY*

Figure 12B

ATACTACTGCAGTGTGCGTTTAGGAGAACTCTCACTGCATCGAAAATGCCGAATCTACTC
CTGCTGCTGTTTCTCTCGCTACCAGGAGCGATTCTTTCAACCACTTGTCCAGGAAATGAT
CTAACAGATGCTGAACGCACACTGCTAACTAGGGTGCACAATTCCATTCGACGGGAAATA
GCGCAAGGAGTTGCAAACAACTACCATGGTGGTAAACTGCCTGCTGGAAAGAACATATAC
AGGATGAGATACAGCTGTGAGCTGGAACAGGCTGCTATTGATGCTAGTCAAACCTTCTGT
TCCGCATCATTGGAGGAACCACAGAAATATGGACAAAACATCCAAGCATACGTCACACCA
TCTATAATCGCTCGCCCGAAAAACGACCTTCTTGAAGATGCAGTGAAACAATGGTATCTG
CCTGTTATCTACTACGGCCAGCGCGACGCGGCCAACAAGTTTACGGATCCGCGCTTGTAC
ACATTTGCAAACCTCGCCTACGACAAGAACACTGCACTTGGCTGTCACTATGCGAAATGT
CAAGGCCCTGACAGAATCGTCATTAGTTGCATGTACAACAACGTCGTTCCTGACAACGCA
GTGATCTACGAGCCTGGAACTGCTTGCGTAAAAGATGCGGACTGCACTACTTATCCTCAG
TCCACATGCAAGGACAGCCTTTGCATTATTCCTACGCCACATCCACCAAATCCACCAAAT
CCACCACCAGCAATGAGTCCAAACGCTGAAATGACTGATGCAGCACGAAAGAAGGTCCTC
GGCATGCACAACTGGCGCAGATCGCAGGTCGCTCTGGGAAACGTTCAAAACGGGAAAAAT
GCTTACAACTGCCCCACTGCAACAGACATGTACAAGATAGAATATGATTGCGACCTCGAG
AACAGCGCTCTAGCGTATGCAAAGCAATGTAGTCTCGTTGGTTCAGCAGAAGGAACTCGT
CCAGGAGAAGGCGAGAATGTCCACAAAGGCGCTCTCGTAACCGATCCGGAGGCTGCAGTT
CAGACCGCAGTTCAAGCATGGTGGAGTCAAATCTCACAAAATGGACTCAATGCACAGATG
AAATTCACTGCTTTCTTGAAGGACAAGCCTGACGCTCCGACAGCGTTTACACAGATGGCG
TGGGCCAAATCCGTAAAGCTTGGATGTGCTGTCTCTAATTGTCAGGCAGATACCTTCACC
GTCTGTAGATACAAAGCTGCCGGAAACATCGTGGGCGAATTCATCTATACCAAGGGAAAT
GTATGCGACGCCTGTAAAGCCACATGCATTACCGCGGAAGGTCTTTGCCCAACGCCTTGA
TTTTCACTGGACTGTTTCACGAACAGATCAGATAAATCGTTTCATCAAAAAAAAAAAAAA
AAAA

*Figure 13A*

MPNLLLLLFLSLPGAILSTTCPGNDLTDAERTLLTRVHNSIRREIAQGVANNYHGGKLPA
GKNIYRMRYSCELEQAAIDASQTFCSASLEEPQKYGQNIQAYVTPSIIARPKNDLLEDAV
KQWYLPVIYYGQRDAANKFTDPRLYTFANLAYDKNTALGCHYAKCQGPDRIVISCMYNNV
VPDNAVIYEPGTACVKDADCTTYPQSTCKDSLCIIPTPHPPNPPNPPPAMSPNAEMTDAA
RKKVLGMHNWRRSQVALGNVQNGKNAYNCPTATDMYKIEYDCDLENSALAYAKQCSLVGS
AEGTRPGEGENVHKGALVTDPEAAVQTAVQAWWSQISQNGLNAQMKFTAFLKDKPDAPTA
FTQMAWAKSVKLGCAVSNCQADTFTVCRYKAAGNIVGEFIYTKGNVCDACKATCITAEGL
CPTP*

*Figure 13B*

CAGCAATAGTCCAATGAAGCTCTTCATTCTGGTTTTGGTCGCTATCCTTGGCATTGCTCA
CGCCACTGATTTTCAATGCTGGAACTTCAAATCGACGGATACACTGCGGGAACATTACCT
CAAATCCATTAACAACCTAAGGAAGAAAATCGCCGATGGATCAGCGGAAAACAAATCAGG
AAAGTGCCCGCAGGGCAAGAATATCTACAAGCTAAGCTGGGATTGTGAATTGGAACTGAA
AGCACAGCAAGCTGTAGACCAGTGCAAACCGAATGTACCCGAACCCGCAGGATATTCGCA
AATACTAAAGAAGGTTAAAAGCACCTGCGACCCAACGAAGGTCCTGAAGAAACAGATAGA
AGCATGGTGGACTAAGTCCGTGAAAGATGCTGGAGTTGATAATCCTCCAAACAACAAACA
AGGTTTGGAAGATTTCGCAAAGTTAGCAAATGGAAAGGCTACGAAGATTGGTTGTGCGCA
GAAAAACTGCAACGAACAGTTGTACGTGGCATGTGTTATTAACGAACCGGCTCCTGCAGT
GGGTATGCCAATCTATGAGGTTGGAGCTGGATGTAATTCCAAAGACGATTGTACAACGTA
TCTGCAGTCGAAGTGCAGTAACAAAGTATGCGTCGCCGGGCACCCAGGTGATGCCACCAC
TACAACATCAACACCAGCPACAACAGCACCAACAACACCCACGATTCCTGCTGGACCAAC
AACTGCGCCAGCTCCACCACCAACAACTGCAGCTCCTACAACGACGAGTACGATTGGTTC
GATTGACAATACGATTTGTCCGCAAAACCAAGTGATCACCGACTCAGTCAGGCTCACATT
CTTGAATACGCACAACGGACTCAGATCTCAACTCGCGCAAGGTCAAATCTTTATGGGAAA
TGGCGCTAGGGCGCGTCCGGCATCGAAAATGAGGAGGATGGTATATAACTGTGATGCGGA
ATCAAGCGCTCGCAATTCGGCCGCTCAGTGCCTTAGCAGCCCCGGTTCACCTAGCGGCTA
CACTGAGAACTTGCATGTTATCAACAACAACTTTGTGGACCATAACAGTGCGGCTACTCA
GGCTTTTAACGCATGGTGGTCAGAAATTAACACAGGATATATGCGTCAGGCAGAGACGGA
AAGGAATATGTACTCTCTGAGCGTTGGAATACCAAACTTCGCTAAAATGGCTTGGGAAAC
CAATGCACATCTTGGTTGTGCTATAGTCAGATGCGGTTTGAACACGAACGTCGTCTGCCC
CTACTCCCCAAAATCGGATGGAGGCCAAATTTACAAGATGGGCCCCTTTTGCAGACGTTG
CCCCGACTACCCTGGGACTTTTTGCAACCAAGGACTCTGCTCATTTTAAGACCCGCCCCG
ATATATCTTTGGGGAGATAATTTTACGAGCAATAAACCAAGCGTGAAGAAAAAAAAAAAA
AAAAAAAAAAAAAAAAAAAAAAAAAA

*Figure 14A*

MKLFILVLVAILGIAHATDFQCWNFKSTDTLREHYLKSINNLRKKIADGSAENKSGKCPQGKNIYK
LSWDCELELKAQQAVDQCKPNVPEPAGYSQILKKVKSTCDPTKVLKKQIEAWWTKSVKDAGVDNP
PNNKQGLEDFAKLANGKATKIGCAQKNCNEQLYVACVINEPAPAVGMPIYEVGAGCNSKDDCTTY
LQSKCSNKVCVAGHPGDATTTTSTPATTAPTTPTIPAGPTTAPAPPPTTAAPTTTSTIGSIDNTI
CPQNQVITDSVRLTFLNTHNGLRSQLAQGQIFMGNGARARPASKMRRMVYNCDAESSARNSAAQC
LSSPGSPSGYTENLHVINNNFVDHNSAATQAFNAWWSEINTGYMRQAETERNMYSLSVGIPNFAK
MAWETNAHLGCAIVRCGLNTNVVCPYSPKSDGGQIYKMGPFCRRCPDYPGTFCNQGLCSF*

*Figure 14B*

```
1    GGGTTTAATT ACCCAAGTTT GAGAATGATT CAATTGTTTT TGTTAGCGCT
51   CGTACCTATG TGCATCTCAG TGAGGGAACA GTCGATAGCT GTTAAAGGAC
101  GACTTTTGTG TGGCGATCAA CCAGCTGCGA ACGTCAGAGT AAAGTTATGG
151  GAGGAAGACA CAGGACCAGA TCCAGATGAC CTACTGGATG CAGGATACAC
201  GAACTCCAAC GGTGAATTCC AACTCCAAGG CGGAACAATA GAGACGACTC
251  CTATTGACCC CGTCTTGAAA ATTTATCATG ATTGCAATGA CGTGACTGGT
301  TTCCTAAGCG TACCTAAACC TGGCAGCAGA AAGGTGAGGT TCTCCTTACC
351  AGACAAGTAC ATCAGCGATG GAATGGTTCC TAAGAAAGTT ATGGACATCG
401  GTGTTATCAA TCTTGAAGTG GAATTTGAAA AGGAAGGACG TGAATTTATC
451  GTTGACTAAG TGATCAATAA ACTCATCGCT TTCTCTTTCT ATGTAAACAT
501  TTTTGTTGTG AACAAATCAT ATGGTTGTAC ATAATCCGAA CTGTTGGTTT
551  TTCGAATACT GCACAAATAA AGCATTTCTT CTAAAAAAAA AAAAAAAAAA
601  AA
```

*Figure 15A*

```
1    MIQLFLLALV PMCISVREQS IAVKGRLLCG DQPAANVRVK LWEEDTGPDP
51   DDLLDAGYTN SNGEFQLQGG TIETTPIDPV LKIYHDCNDV TGFLSVPKPG
101  SRKVRFSLPD KYISDGMVPK KVMDIGVINL EVEFEKEGRE FIVD
```

*Figure 15B*

CACTTCCAGCGATGTTCTGTCGTGTTACTGTCGCCGTTTTGTTGTTGGCCGTATCGGCCTATGCCGGA
TTTTTCGATGACGTCAGTGGCATGGCCTCAGATGTTGGGAATTTCTTCACAAACCAATTCAACAATGT
GAAGGATTTGTTTGCTGGAAATCAATCGGAACTCGAGAAGAACATCAATCGAGTAAAGGATCTTCTGA
CGGCCGTCAAAGAAAAGGCTAAGATGCTTGAACCAATGGCCAATGATGCTCAGAAGAAGACGTTATCA
CAGGTGGACAACTACCTCAACGaAGTGCAACAGTTCGGTGAACAGGTAAGCAAAGAAGGCTCGGCGAA
GTTCGAGGAGAACAAGGGCAAGTGGCAGCAAATGCTGAACGACATCTTCGAGAAGGGCGGTCTGGACG
GCGTGCTGAAGCTGCTCAATCTGAAATCTGCCGGCCACTGCACACTCGTAGCGGCCATCGTCGCTCCA
GTAGTGCTGGCGTTCACCCGCTAAGCGCCACCCACTAATCGATAATTGTAGCCTGTCACCTGCCGTCG
ATCGATAATTGTTGTCGCGTGTGCGTATGCTTGCATCTATGTATGATGATGTGTATCTATATGTGATT
TGTATTCTACTTCGCCGCATTCAGCTCTGGTATTCTGAGACGGATTATCGCTTCTCGCACACACTCAC
ACACACAAATAACCCCCGATTATCTCCCGATTATCACCCGGTTAGTAGATGAGACATAATTTCCATCC
GTCCACATACTCTACTTCTATCTATGGTCAATGTGGTTCTTTATGTAAATAAACTTTTCCATCGAAAA
AAAAAAAAAAAAAAAAAAAAAA

*Figure 16A*

MFCRVTVAVLLLAVSAYAGFFDDVSGMASDVGNFFTNQFNNVKDLFAGNQSELEKNINRVK
DLLTAVKEKAKMLEPMANDAQKKTLSQVDNYLNEVQQFGEQVSKEGSAKFEENKGKWQQML
NDIFEKGGLDGVLKLLNLKSAGHCTLVAAIVAPVVLAFTR*

*Figure 16B*

TCACCGCTTCCGACCGATGCTTCAGGAAACTACGTCACCGACGAAGGAACTGTCATTGAGAAAGACGAT
GAGGGAAGACCATTGGGACCGGATGGACAAGTGTTGCCCACCGACGAATCTGGAAACTACATCTATCCT
GTCGTTGGACCCGATGGAAGCCCATTGCCAACTGACGAGCACAAGCGACCAATTCACCCAGTCCTTGGA
CCTGATGGCAGCCCACTGCCGACAGACGAATCAGGCCATCCACTAGGAGAAGACGGACAGCCACTTCCA
ACAGATGCTTCTGGCGTTCCTGTGGATAAGGACGGTCAGCCGTTGCCGACAGACAGCAGTGGACACTAC
GTCACAGTTCCACGTGAAGAAGCTGTCACGAAGGAGCTACCAACGGACGAGAGCGGAAATGTCATCTAC
CCAGTGACGAAACCTGATGGATCACCGCTTCCGACCGATGCTTCAGGAAACTACGTCACCGACGAAGGA
ACTGTCATTGAGAAAGACGATGAGGGAAGACCATTGGGACCGGACGGACAAGTGTTGCCCACCGACGAA
TCCGGAAACTACATCTATCCTGTCGTTGGACCCGATGGAAGCCCCCTGCCAACTGACGAGTACAAGCGA
CCAATTCACCCAGTCCTTGGACCTGATGGCAGCCCACTGCCGACAGACGAATCAGGCCATCCACTAGGA
GAGGACGGACAGCCACTTCCAACAGATGCTTCTGGCGTTCCTGTGGATAAGGACGGTCAGCCGCTGCCG
ACAGACAGCAGTGGACACTACGTCACAGTTCCACGTGAAGAAGCTGTCACGAAAGAGCTACCAACGGAC
GAGAGCGGAAATGTCATCTACCCAGTGACGAAACCTGATGGGTCACCGCTTCCAACCGATGCTTCCGGG
AACTTTATTACTGAAGAAGGACTGATCATTGGTCCCGATGGTGTTGCTCTTCCCTACCCGCGTAACAGG
ACCTGCTCCTTAAAGCAACTGAAGATGGATATCCTTTTCGCGGTAAGCACGACAAAAGTCTCGAAATCC
ACCTTTGATAGTATCCTGCGAGCAATATCAAAGTTTGCCGATGAAGTCGACTTATCTCCTGACGTTACC
CGCATTGGATTAGTATACGGCAGCAAGGACGTAGTCGTTCCACTTCCGCTTGGGGGGTACCAAGAAAAA
GATCATATGAGGGATGAAATTCGACGCATCGAATTTTCTGATGATGGATCGCAAGACTACATTTCTCTG
TATGGTCCCGCCAAGCAACAATTCGTCATGTTTCCTCGAGCGGACAGTGCGAAGATCGCTATCTTCCTC
ATTCAAGATGAAATAAGTTACTGCTTATCCACGAGAACGTTGAGATGTGGTTGCGCTACTGCTGTGGAT
AGCGATTGTCGTCGAATAAACAATGTCCTAGCGGATGACATCAAAGTGTGCAAGGTCCCTGAAACTGCT
GTAGTCCCTACTCCAGTTGTTCATCCACAAGGGTCAAGGGCCGTCTCGGTCGTTGTGCCTCGATTCTTT
AGTGCTCCGCCATTTGACACCCACAGTCCGTCAAGGCTGACACTGCTGGCAGATTTTGCTACGGAGAAA
GAACCTCTATGCGGGGAACATTCATTTTTATCCCCCCAGAAATGGGGCAAGAATCACTGTACGTTACGC
ATTCCTCTTTCGATGCCAGGAATAGATCACAAATCCGaTGaTCaCTACTaCTaTGaTGaCCAGACCCCA
TTAGAATCCGAATATTCATTGGATTTGTTTGGGAAAGCAGAATTGGTACGATTTTTCGTACAGGtCAAT
gTGGAACGaGAAcTGGaCCTTGCCCCCGAAACAGTACGATTCTCGtCGCTTCTTCGATCTAATGCaGCT
TATTACAAGTCtCCTGGATCTCGCCCAAACAACTCCAATTCGGCGACCAAACGAAGGAACAGCcCAGCC
GtCCcctGATCGGtGAACCCCAGGCTTTTAATGTTGACAACGTTTACTtTCTCGAACtCCTGCTACATT
TTTCAAAACaCAAATAAAACTTTTCAAAAAAAAAAAAAAAA

Figure 17A

SPLPTDASGNYVTDEGTVIEKDDEGRPLGPDGQVLPTDESGNYIYPVVGPDGSPLPTDEHK
RPIHPVLGPDGSPLPTDESGHPLGEDGQPLPTDASGVPVDKDGQPLPTDSSGHYVTVPREE
AVTKELPTDESGNVIYPVTKPDGSPLPTDASGNYVTDEGTVIEKDDEGRPLGPDGQVLPTD
ESGNYIYPVVGPDGSPLPTDEYKRPIHPVLGPDGSPLPTDESGHPLGEDGQPLPTDASGVP
VDKDGQPLPTDSSGHYVTVPREEAVTKELPTDESGNVIYPVTKPDGSPLPTDASGNFITEE
GLIIGPDGVALPYPRNRTCSLKQLKMDILFAVSTTKVSKSTFDSILRAISKFADEVDLSPD
VTRIGLVYGSKDVVVPLPLGGYQEKDHMRDEIRRIEFSDDGSQDYISLYGPAKQQFVMFPR
ADSAKIAIFLIQDEISYCLSTRTLRCGCATAVDSDCRRINNVLADDIKVCKVPETAVVPTP
VVHPQGSRAVSVVVPRFFSAPPFDTHSPSRLTLLADFATEKEPLCGEHSFLSPQKWGKNHC
TLRIPLSMPGIDHKSDDHYYYDDQTPLESEYSLDLFGKAELVRFFVQVNVERELDLAPETV
RFSSLLRSNAAYYKSPGSRPNNSNSATKRRNSPAVP*

Figure 17B

TTTTATTACCCAAGTTTGAGAGAGGCTCGTGAAGTTGGTAGAAGGCTTAC
AAGGATGAGGCTCATTTTACCACTTGTCGCCTTGATAGGTATTGGTCTCT
CAGCACATTATGAAAGGGACTGTCCATGTACGCCCGAAAAATTGTGGCTC
GACGTAGTGGTAGGTATCGACACCTCTATTGGTATGACAGAGGAAGGAGT
GACACAGGTCCTCGCCGATTTGTCTACGGTATTCGGAGACACAAAAATCG
CTCAAGGGGAAGGGCACCATTCCCGCATTGGAGTCGTTACATATGGGCTG
AATGCCGAAACTAGGTACAACTTGACTGATTTCAAATCAACAGACGATAT
GCTGGAGGCGATCTGGGATATTAAGTGCAGCGACGACAAGTACTCCAATC
TCTTTGCTGGACTGACGAGGACACAAGAAATTATGAAGAATGGCCGCCAA
GGAAGACTGAGAGCAAATGTCAGATCAGCCATTATTATCTACGCGAGCGA
TTTCAGGGAAGGCGACGTGAATGACGCAGTTCAGCTGGCACATCAGATCA
AGATCGGAGGAACGGATATCATCGTAGTTGCTTTTGACCAAAAAGGAAAA
GTCAATGCGCTTGAGGGGCTCCAGAAGATTGCTTCGCCTGGTCGCCTCTT
CAAGAGCACTACGAAAAACCTAGTCGGTCTAATCCAGGATGCTTTGTGCC
AGACAAACTGCTTTTGCAAAAAGCTCTGGACGCAATACGGGGACGGATCT
GTGAAATATGGAGAATGTCTAAGGATCGGTGGAATCGACGCCAACTGGTT
AGCAGCTAAAAAAGCATGTCAGAGACTCATCCCTGGAGGTCATCTCGCCA
CTGAGCTCGACAGCTACAAGCATGACTTTATTGCACGAATGTTCAAGGAT
GACTATAGACACGAGCCTCCATACATGTATCACATCGGACTTTCCTTCGA
CAAACAGAAGAATGATTACTTCTGGGAGCAACCCAAAGATAGGATGCCTC
TGCCGCTGAAGGACTCACCTTTCCGATATTGGAGTCGCGGTTTCCCTAAC
CCTCGGGAAAAGGATACTTGCGTACTTGCAGCTCAAACAACCATACTTTC
GCCCGAGATTGGCTGGCAGAACGAGCATTGCACCAAAGTTGCAAAGAGAT
ACATCTGTCAAGTGGAATCATGTGATACAGACAACTACTGTGCCAATCTA
TAAAAGTACGACAATAAACTGCTCACCTAACAAGAATAAAATATGACATC
AAAAAAAAAAAA

*Figure 18A*

MRLILPLVALIGIGLSAHYERDCPCTPEKLWLDVVVGIDTSIGMTEEGVTQVLADLSTVF
GDTKIAQGEGHHSRIGVVTYGLNAETRYNLTDFKSTDDMLEAIWDIKCSDDKYSNLFAGL
TRTQEIMKNGRQGRLRANVRSAIIIYASDFREGDVNDAVQLAHQIKIGGTDIIVVAFDQK
GKVNALEGLQKIASPGRLFKSTTKNLVGLIQDALCQTNCFCKKLWTQYGDGSVKYGECLR
IGGIDANWLAAKKACQRLIPGGHLATELDSYKHDFIARMFKDDYRHEPPYMYHIGLSFDK
QKNDYFWEQPKDRMPLPLKDSPFRYWSRGFPNPREKDTCVLAAQTTILSPEIGWQNEHCT
KVAKRYICQVESCDTDNYCANL*

*Figure 18B*

```
  1  GGTTTAATTA CCCAAGTTTG AGATGAAGCT ACTCGCTCTT TCCGCTCTCT
 51  TCGCGCTGGC CTTCGCTGCT CCTCGAGACA AGCGGCTAGC AGTGAGCACT
101  ATCACTGTCA CCGGAGGACT AGGTCTGTCC ACGGGATGCG TCGTCACTGG
151  CAACGTTCTA TATGCAAACG GTTTCCGAGT ACGTGAGATT ACACCATCGG
201  AGCAGCAAGA GTTGGTCAAA TACCAAAACG ACGTAGCTGA GTACAAGACG
251  GCTCTGAAAC AAGCAATCAA GGAGCGTGAG GAGAAAATCC GAGCCCGTCT
301  CGCCGGTAAG AAGGTGAAGG CCGTGGAGTC AACCAACCAA GAGGACCTAC
351  CGAAACCGCC ACAGAAGCCG TCATTCTGCA CACCAGAAGA CACTACCCAA
401  TTCTTCTTCG AAGGATGCAT GATCCAGAAC AACAAGATCT ACGTCGGAAA
451  CACTTTCGCT CGAGACCTGA CTCAGCCTGA AATCAGCGAA TTGAAAGAAT
501  TCGAGAAGAA ATTCAAGGTC TACCAGGACT ACGTACAGAA GCAGGCCGAA
551  CAGCAAGTGA ACAGCCTCTT CGGCGGCTCT GACTTCTTCT CGGCGTTGTT
601  CAGCGGCGGT GAGACGAGCA AGCCATCCAC GACCACCGTG GCACCAGAAC
651  TTCCGGAAGA CGCTCCCGAG CAGCCGCCCA CGCCGAACTT CTGCACCAGA
701  ATAATCTAAG CCTCTAAATT GTTCGTTTCG CTATTGGATT GGTTGGTTTG
751  GTGAATAGCG ATTCCGCTTC CCCTCTCGTA CTTACGGTGT CGACTAGCAC
801  ATTAGTCATG CGTTGCAATA TTTGAACATT GTATTGAGGT ATATTGTACA
851  TTTATATAAT AAAATTATTA TCTTAAAAAA AAAAAAAAAA AA
```

*Figure 19A*

```
  1  MKLLALSALF ALAFAAPRDK RLAVSTITVT GGLGLSTGCV VTGNVLYANG
 51  FRVREITPSE QQELVKYQND VAEYKTALKQ AIKEREEKIR ARLAGKKVKA
101  VESTNQEDLP KPPQKPSFCT PEDTTQFFFE GCMIQNNKIY VGNTFARDLT
151  QPEISELKEF EKKFKVYQDY VQKQAEQQVN SLFGGSDFFS ALFSGGETSK
201  PSTTTVAPEL PEDAPEQPPT PNFCTRII
```

*Figure 19B*

1 *gggtttaattacccaagtttgagg*ATGAGGGTACTCCTGTTACTGCTACTTTTATCCATTTGCGCGAGCGCTGGCTTTCT 80
81 AGACACTAAATTCGGCCAGAAGATAAAGAAAACTCTTGACAAGATTAAAGCTGTGCTTAACGGCACTGCACTCATCGCGA 160
161 TTCGTGAAAAATTCATTCGACTAAGGGAAAAAATAAAAGCAAAGCTGACGCTCTCTCCAGCACGAAAGGCTATATTGGAC 240
241 GAAGTTATGAAGCATATCAAAATGATCAAAAAGGATAAGATTCAAGAGAAGGGCGACTCAATCGATGAAATCAATGAAAA 320
321 GAGTGCAATCGGACAGTTGCTGTACCAGGGTGACATCGTTCTGACAGAAAAGCAAGCCCAGCAAATTACCGAAGACATTG 400
401 AAAATGACAAAGGCGACCGCGAAAAACGACAGGCGTTCCGTGATCGCAATTATCCGCGAACATTATGGTCGAAGGGAGTG 480
481 TACTTTCACTTTCATAGGAACGCAACTCCTGAAGTTAGAAGCGTTTTTGTGAAAGGCGCAAAACTTTGGATGAAGGATAC 560
561 TTGCATCGACTTCTTCGAAAGCAACTCAGCGCCTGATAGGATTCGTGTGTTCAAAGAGAACGGATGTTGGTCGTACGTTG 640
641 GTAGGCTGGGCGGTGAACAAGATCTGTCACTGGGAGAAGGTTGTCAATCGGTTGGCACAGCTGCGCACGAAATTGGCCAC 720
721 GCTATTGGCTTCTACCACACTCACGCAAGACATGATCGCGATAACTTTATTACATTCAACGCACAAAATGTCAAGCCCGA 800
801 TTGGTTGGACCAATTCACTCTTCAGACTCCGGCAACGAATGAGAACTATGGAATAACTTACGACTATGGAAGTATCATGC 880
881 ATTATGGTGCAAATAGCGCCTCGCAGAACGGACGTCCTACAATGGTTCCGCATGATCCCAAATACGTAGAAACTCTTGGA 960
Mtp 5-1 →
961 TCACCCATAATTTCCTTCTATGAGCTTCTCATGATCAACAAACACTACGACTGCACTAAGAACTGTGACCCGGCTACTTC 1040
1041 TGCGCAGTGTAAGATGGGTGGCTTCCCACATCCTCGGGATTGTACAAGATGCATTTGCCCTAGTGGATATGGAGGCAAAC 1120
1121 TGTGCGACCAGAAGCCAGCCGGATGCGGATCTATATACCAGGCCACCAATCAGTACCAGACCTTGCACGACGAAATTGGA 1200
1201 GACAAGAGAGCGGGACAGAGACCTAGAGAAGACATGGACTTCTGCTATTATTGGATCACGGCCCCAAAAGGTTCAAAAAT 1280
1281 CGAAATCAAAATTGCTGGATTATCACAAGGAGCCGCTGTTGAAGGATGCCAGTACTGGGGAGTAGAAATCAAGACTCATG 1360
← Mtp 3-1
1361 CCGATCAACGTCTTACCGGCTACAGGTTCTGCGCACCAGAAGATGTTGGAGTTAGATTAGTGTCGAACTTCAACATCGTA 1440
1441 CCAATAATCACATACAACATATTCTACGCGACCTATGTCGATATTCAGTACCGTATCGTTGGTGATAATGTTGGCGGTCC 1520
1521 TATGCCTCAGCCACAACCAAATAGCAATTGTGTCGACAATGAACAGTGTGCGACACTCGTGAGAACAAAGAACTTCTGTC 1600
1601 AGAGCAGATTTTTCACAGAGTCCGTCAAAAGAGGTCTATGTCCAAAGTCCAGCGGTTTCTGTCGCTAActtttcagcaaa 1680
1681 caatggaataaatgttgcaccataaaaaaaaaaaaaaaaaa 1722

*Figure 20A*

MRVLLLLLLLSICASAGFL
DTKFGQKIKKTLDKIKAVLNGTALIA
IREKFIRLREKIKAKLTLSPARKAILD
EVMKHIKMIKKDKIQEKGDSIDEINEK
SAIGQLLYQGDIVLTEKQAQQITEDI
ENDKG<u>DREK</u>RQAFRDRNYPRTLWSKGV
YFHFHRNATPEVRSVFVKGAKLWMKDT
[C]IDFFESNSAPDRIRVFKENG(C)WSYV
GRLGGEQDLSLGEG(C)QSVGTAAH<u>EIGH</u>
<u>AIGFYHTHARHDRD</u>NFITFNAQNVKPD
WLDQFTLQTPATNENYGITYDYG<u>SIM</u>
<u>HY</u>GANSASQNGRPTMVPHDPKYVETLG
         Mtp 5-1 →
SPIISFYELLMINKHYD[C]TKNCDPATS
AQCKMGGFPHPRDCTRCICPSGYGGK
LCDQKPAGCGSIYQATNQYQTLHDEIG
DKRAGQRPREDMDFCYYWITAPKGSKI
EIKIAGLSQGAAVEGCQYWGVEIKTH
       ← Mtp 3-1
ADQRLTGYRFCAPEDVGVRLVSNFNIV
PIITYNIFYATYVDIQYRIVGDNVGGP
MPQPQPNSNCVDNEQCATLVRTKNFC
QSRFFTESVKRGLCPKSSGFCR*

*Figure 20B*

TTTAATTACCCAAGTTTGAGCAATGAAATACTTTGTTCTCTGCTTCTGCGCCTTCTTCGTGGTCAATGCTGATGA
GGAAGACGATCTACCCCGCAATCCTTTGTGGGACGCTTACAAGGATGACAATGGCAAATATGTGATTCCGTACGT
CATTAACGGAAGTTATGGAGAGGAGAAAAAAGTTTTATTTGAAATGATGGACGAAATCGATAAGAATACCTGCGT
CCGCTTCATACCCAGATCGACAGAGCAGGATTATATCGAAATCGTAAACAGACTAGGAGAAGGAACCGGCGCTGT
TGTAGGTAAACCTGGAGGGAAAAGCATCGTGTTGTTGGAATCGAGCAAAATTCTAAATGATCCAACTCCTGCGCC
TGTAATGCAGACTTTGATGAAAATCATTGGCTTACCACCTGAACACATTCGACCAGAGAGGAAAGATCATATCAA
GATACACTGGGAGAACATCGAGAAAGGTTACGAAGCTTTCTTCGCCCTCTCCTCTGTTAAGCCCGATCCGTACGG
AATACCATATGATTACTACTCCATCATGCACTACAAGAAGGACGCCTTTGCCAAGCCGGGCACGATCACAATGGA
AACTTTGGATAAGCGCTACCAGGATATCATTGGGAATCAAGAGAAGCCGTCGAAGTTGGATTACAAGAAGATCTG
CACCAAGTATAAATGCGATATCTGCATGGGTGAGAAGATGAAGTATTAAAGAAAGGAATGACGTTAACATAAGGA
ATGGTTGCCGATTTCAACAAAACGAACGTCTAATACATCTGGTGTTGTTCCTCATGTTAGAAATCCAATAAAGCA
TTTCACCGAAAAAAAAAAAAAAAAA

Figure 21A

MKYFVLCFCAFFVVNADEEDDLPRNPLWDAYKDDNGKYVIPYVINGSYGEEKKVLFEMMDEIDKNTCVRF
IPRSTEQDYIEIVNRLGEGTGAVVGKPGGKSIVLLESSKILNDPTPAPVMQTLMKIIGLPPEHIRPERKD
HIKIHWENIEKGYEAFFALSSVKPDPYGIPYDYYSIMHYKKDAFAKPGTITMETLDKRYQDIIGNQEKPS
KLDYKKICTKYKCDICMGEKMKY*

Figure 21B

TTAATTACCCAAGTTTGAGAATGGCAACTATGCTCGCGGTATGTCGTTTGGTCGTCTTCCTCACCGCCG
TTCACACGGTGTCAGCAAGGGGAAGACCCATCAACATTTTCGAGCAAAAGGAAGGAGGAGACATCACAC
AGCTGAGAGAAAAAGGGAGCGCAATGTTCAACGCCCTTCACAGAACGTCGAGTCTGAAGTGGAACAAGA
GGGATTCAGACGGGAATTTTGTCATACCGTACATAATTACAGGACGCTATGACCGAACGGAGCGGGGAA
TATCAAGGAAGCAATGAGGCGCATCGAGGCAAATACGTGTATTCGTTTCAAGCAAAGAGACTATGAGAG
AGACTATATCGAGATCCAGAACAAAGCTGGACATGGATGTTACACCAATGTCGGTCGTGTCGGTGGCAG
AAGTATACTGATGCTCGAGTCCAGCTTCGAGGAAACATGCATGGAGACAGAAATCGTGCTGCACGAGTT
GATGCACGTTGTCGGTCTGTGGCACGAACACATGCGCCACGATCGTGACAAATACATCAAAGTGCACTA
CGAGAACATCGAAAGGAGTTACTGGAACCAATTCGAGAAAGTCTCACCGATGGAAGCTACCACGTATAA
CGTACCGTATGACTACAAATCCGTCATGCACTACGAGAAGTCGGCATTCGCCAGACCTGGACGAATCAG
CATGGAAACGCTTGATCCCAAATATCAGAACGTCATCGGACACCAGAAGGACGCCTCTCCCAGTGACTA
CCGTAAGATCTGCGAGATATACCAGTGTAAGAAGTGCATGAACGGCAAGATCGAGATCGGAGGCGACTC
GGACTCCAACCCGAAACCGCCAACCGAGGCCCCAGTCACCATCAGACCGGCGCCAGAAATCAACGGAGA
ATGCCGCGATATGATCCCGTCTTTCTGCCGAGCGTTGGCCCGCTCGCACATGATCGACTGCAGCTTCTT
CCATAAACAACAATGCTGTGCAACCTGCGCCGAGTTAGGGCACAGGGATCAGGACCAGGGAGGATGGTT
AGAACAAACAGGATGGCCATTCGACGGGCTCTTCCGAATATTCGGACAAGGAGGGTGGCCTTTCACCTT
CTTCAATCGCTGGTAACTAATACAGGTCAAATAAATATTTGCAAAATAAAAAAAAAAAAAAAA

Figure 22A

MATMLAVCRLVVFLTAVHTVSARGRPINIFEQKEGGDITQLREKGSAMFNALHRTSSLKWNKR
DSDGNFVIPYIITGRYDRTERGTIKEAMRRIEANTCIRFKQRDYERDYIEIQNKAGHGCYTNV
GRVGGRSILMLESSFEETCMETEIVLHELMHVVGLWHEHMRHDRDKYIKVHYENIERSYWNQF
EKVSPMEATTYNVPYDYKSVMHYEKSAFARPGRISMETLDPKYQNVIGHQKDASPSDYRKICE
IYQCKKCMNGKIEIGGDSDSNPKPPTEAPVTIRPAPEINGECRDMIPSFCRALARSHMIDCSF
FHKQQCCATCAELGHRDQDQGGWLEQTGWPFDGLFRIFGQGGWPFTFFNRW*

Figure 22B

```
CAAGTTTGAGCATGCTTCGACTAGCTCTCTTCGCGGTCCTCTTCGCTTGCGCATTTTCAG
CACCCAACGTTGAAGTGAACAAATTCGAGGATATTCCTGAGCAGTACAGAGAACTGATCC
CCAAGGAGGTAGCCGACCACATCAAGGCTATCACTGAGGAGGAGAAGACCATCTTGAAGG
AGGTGCTGAAGGACTACGCCAAATACAAGGACGAGAATGAGTATTTGGCAGCGCTGAAGG
AAAAGTCACCCAGCCTGCACGAGAAGGCAAAGAAGTTCCACGACTTCATTAAGGCTAAGG
TCGACGCACTTGGGGATGAAGCAAAGGCGTTCGTGAAGAAAGTGATTGCTGCTGCTCGCA
AACTGCACGCAGAGCTCCTTGCCGGGAACAAACCTTCTCTTGAGGAACTGAAGAACACTG
TCAAGAAATACGTGGCCGAATTCGACGCGCTGACCGCAGCCGCAAAAGAAGATCTCAAGA
AGCACTTCCCCATCCTCACTTCCATTTTCACCAACGAGAAGGCAAAGGCGTTGATGGACA
AGCACTTGCCGAACTAGGTGAAGCAGCAGTTGTTTTAGTCGAATAAATGTTTCAACTTT
TTAAAAAAAAAAAAAAAAAAA
```

Figure 23A

```
MLRLALFAVLFACAFSAPNVEVNKFEDIPEQYRELIPKEVADHIKAITEEEKTILKEVL
KDYAKYKDENEYLAALKEKSPSLHEKAKKFHDFIKAKVDALGDEAKAFVKKVIAAARKL
HAELLAGNKPSLEELKNTVKKYVAEFDALTAAAKEDLKKHFPILTSIFTNEKAKALMDK
HLPN*
```

Figure 23B

```
   1 GGCACTTCGA CATGAAGGTC CTTGCCTTAG TGTTACTTTG GGCTGCAACA
  51 GCCACTGCTC TGCTAGACAT ATGTAAGGAG GAAATCAAGA CTGGAAATTG
 101 TAGGGGGGCC TTCCGCAAGT TTGGCTACGA TCGATGCACG AATAAATGTA
 151 TTCCGTACAC GTATGGAGGC TGTGGAGGGT CGAGCAACAT GTTCGACACT
 201 TTGGAAGAAT GCCAAGAAAA ATGTGGCAAG CCCGAGGACC GCTGCTCAAA
 251 ACCACTGGAA AGAGGAATAT GTCTGGCATC AATGAAAAGA TATGGCTACG
 301 ATACAAGCAG TAAGAAGTGT AAGGCCTTCA TCTATGGCGG ATGTGGCGGT
 351 AACGAGAACA ATTTCGAGAC AATGGCTGAG TGCCGAGAAA CTTGCAAGGA
 401 CACCTCTTCT GAAGAAGAAT CAGTACCTGA TGCATGCCTA TTGCCATCAG
 451 AAGTGGGGCC ATGTAAAGGA AAAGAACGTC GCTTCTACTT TGATCAAAAA
 501 CGTGGCAACT GCAAGTCGTT CTTCTTCGGC GGTTGTGGTG GAAATGGAAA
 551 TAATTTCATG ACCAAAGCCA AATGCATGGA AACCTGCTCG AAACACATCA
 601 AACCTGAAAC AGAGCAAGAC GTCTGCTCAC AGCCAATTAA AGCTGGACCT
 651 TGCATGGCAA TGTTGAAAAG ATATGCGTAC GACAACAAGA AAAAGAGGTG
 701 CGTGCAGTTT ATCTATGGAG GATGTAAGGG AAACAAGAAC AACTTCGAGA
 751 GCATGGAAGA GTGCACCCGG ACATGTAAGA AAGCAGTACC AGAGCCTGAG
 801 CAGGACACCT GCTCACAGCC CATTGAAGTT GGACCTTGCA AGGCAATGTT
 851 GAAAAGATAT GCGTACGACA ACAAGAAAAA TAAGTGCGTA CGGTTTATCT
 901 ATGGAGGATG TAAGGGAAAC AAGAACAACT TCGAAAGCAT GGAAGAGTGC
 951 ACCCGGACAT GTAAGAAAGC AGTACCAGAG CCTGAGCAAG ACACCTGCTC
1001 ACAGCCCATT GAAGTTGGAC CTTGCAAGGC AATGTTGAAA AGATATGCGT
1051 ACGACAACAA GAAAAATAAG TGCGTGCGGT TTATCTATGG AGGATGTAAG
1101 GGAAATAAGA ACAACTTCGA AAGCATGGAA GAGTGCACCC GGACATGCAA
1151 GAAAGCAGTA CCAGAGCCTG AACCTGAGAA AGAGACCTGC TCACAGCCCA
1201 TTGAAGTTGG ACCTTGCAAG GCAATGTTGA AAAGATATGC GTACGACAAC
1251 AAGAAAAATA AGTGCGTACG GTTTATCTAT GGAGGATGTA AGGGAAACAA
1301 GAACAACTTC GAAAGCATGG AAGAGTGCAC CCGGACATGT AAGAAAGCAG
1351 TACCAGAGCC TGAGCAAGAC ACCTGCTCAC AGCCCATTGA AGTTGGACCT
1401 TGCAAGGCAA TGTTGAAAAG ATATGCGTAC GACAACAAGA AAAATAAGTG
1451 CGTGCGGTTT ATCTATGGAG GATGTAAGGG AAATAAGAAC AACTTCGAAA
```

Figure 24A

```
1501 GCATGGAAGA GTGCACCCGG ACATGCAAGA AAGCAGTACC AGAGCCTGAA
1551 CCTGAGAAAG AGACCTGCTC TCAGCCCATT GAAGCTGGTC CTTGCAAGGC
1601 AATGGTGAGA CGATTTGCTT ACGACAACGC AAAGGAAAAG TGCGTAGAGT
1651 TCTTTTACGG CGGATGCAAA GGAAACAAGA ACAACTTCGA AACCATGGAA
1701 GATTGTACTT TTACGTGTGA GCAACGGCTG GCAAAGCCCG AGCTTGAGAA
1751 GGATGTGTGT TCACAACCTA TCACGGCTGG TCCTTGCAGA GCATCAATAC
1801 CGCGATACGG CTATGATTCT AAAAAACGAA AGTGTGTGAA GTTCACCTAC
1851 GGAGGATGCA AAGGAAATGG TAATAGGTTC CCGACGAAGA ATGAATGTGA
1901 GAAGACATGC AAGAGAGGAG CAACTGGAAC TACGAATCCA GGAGGTGAAA
1951 ATGATAAATG CTTGCTGCCA ATTGTTACCG GCCCATGCAA AGGAAAAAAT
2001 CGTCGCTATG CTTACAACAA CAAGACAGGA AAATGCGTGA GATTCACCTA
2051 TGGTGGTTGC GGGGGAAACG AGAACAACTT CAAGACTAAG AAAGACTGCC
2101 AGGATGCGTG CGAAAACATA AATGCAGCTA GTCCATGCAC CCTTCCTATC
2151 GACAAAGGAG AAGGCGACTT GAATCTGACC AGATATGGCT TCAAAAATGG
2201 CAAGTGTGTC GCGTTCAAAT ACGGCGGACG ACGGGGAAAT CTCAACAATT
2251 TTGGAAGCAA AGCCGATTGC AAAGAAGCCT GCCTCAAGTA ACTACGAAGC
2301 TCCGCTGCAA ATCCCAGAAG ATCATTCGGT TGTCTCTGCC GTCTATGAAA
2351 CAATAAAGTA TTAATTTTGT TAAAAAAAAA AAAA
```

*Figure 24B*

```
  1 MKVLALVLLW AATATALLDI CKEEIKTGNC RGAFRKFGYD RCTNKCIPYT
 51 YGGCGGSSNM FDTLEECQEK CGKPEDRCSK PLERGICLAS MKRYGYDTSS
101 KKCKAFIYGG CGGNENNFET MAECRETCKD TSSEEESVPD ACLLPSEVGP
151 CKGKERRFYF DQKRGNCKSF FFGGCGGNGN NFMTKAKCME TCSKHIKPET
201 EQDVCSQPIK AGPCMAMLKR YAYDNKKKRC VQFIYGGCKG NKNNFESMEE
251 CTRTCKKAVP EPEQDTCSQP IEVGPCKAML KRYAYDNKKN KCVRFIYGGC
301 KGNKNNFESM EECTRTCKKA VPEPEQDTCS QPIEVGPCKA MLKRYAYDNK
351 KNKCVRFIYG GCKGNKNNFE SMEECTRTCK KAVPEPEPEK ETCSQPIEVG
401 PCKAMLKRYA YDNKKNKCVR FIYGGCKGNK NNFESMEECT RTCKKAVPEP
451 EQDTCSQPIE VGPCKAMLKR YAYDNKKNKC VRFIYGGCKG NKNNFESMEE
501 CTRTCKKAVP EPEPEKETCS QPIEAGPCKA MVRRFAYDNA KEKCVEFFYG
551 GCKGNKNNFE TMEDCTFTCE QRLAKPELEK DVCSQPITAG PCRASIPRYG
601 YDSKKRKCVK FTYGGCKGNG NRFPTKNECE KTCKRGATGT TNPGGENDKC
651 LLPIVTGPCK GKNRRYAYNN KTGKCVRFTY GGCGGNENNF KTKKDCQDAC
701 ENINAASPCT LPIDKGEGDL NLTRYGFKNG KCVAFKYGGR RGNLNNFGSK
751 ADCKEACLK*
```

*Figure 24C* ctcgcactat ttaccctagc tgtagctagc gtacacagaa ggacattcca ccacccgcgc
cgctatgtga agtcggtgtc gctttcgcgt caaccaacac ttcgtgaacg attgctcgga
actggcagtt gggaagacta tcagaaacag cgttaccact accagaagaa acttctggca
aagtatgcgg cgatcaaagc gacaaaactg cagtctacca atgaaattga cgagcttctt
cgcaactaca tggatgcgca atacttcggc accatccaaa tcggaactcc agcgcagaat
ttcacagtga ttttcgacac cggttcttcc aatctgtggg tgccgtccga gaaaatgcca
ttccacgaca tcgcgtgcat gcttcgtcac cgttatgact ccggagcatc gtcgacgtac
aaggaggatg gacgaaagat ggccatccag tatggcactg gctcaatgaa gggcttcatt
tcaaaggata atgtctgcat cgctggaatt tgcgctgaag agcaaccgtt tgctgaggca
acgagcgagc caggcctcac cttcatcgca gcgaagtttg atggaatcct tggcataacc
ttccctgaaa tctctgtgct cggagtaccg ccagtattcc acacgttcat tgaacagaag
aaagtgccga gcccggtgtt cgctctctgg ctcaacagaa atcctgactc ggaactcgga
ggtgagatca ccctcggtgg aatggacacc cgacgatacg ttgagccgat cacatggact
ccagtgacaa ggcgagggta ctggcagttc aagatggaca aggttcaagg aggatcaaca
tccattgctt gccccaatga atttctgga tgccaggcta ttgctgacac tggcacttcc
ctcattgctg gacctaaagc acagtcgagg gcatccagaa attcattggt gcttgagcca
acttatgaag gagagtacat gattccttgc gacaaggtgc ctttccctcc ccgattatcc
ttcgttatcg aagcccgcac tttcaccctc aagggtgagg attacgtctt gaccgtgaaa
gctggtggta aatcgatttg cctgtccggt ttcatgggaa tggacttccc agagaggatc
ggagagttgt ggattcttgg ggacgttttt attggaaagt actacaccgt cttcgatgtt
ggccaggccc gtcttggatt cgctcaagct aagtcagaag atggctatcc ggttggccct
gctgttcgaa ggtacaacaa gttctcggag gacagcggca gtgatgagga tgatgtattc
actctataag taacatgtat ccacaacttg ctctaatcct gatacgtgta ccgtgtctaa
cgtgcttcca cctttgataa actgattaat ctc

*Figure 25A*

LALFTLAVASVHRRTFHHPRRYVKSVSLSRQPTLRERLLGTGSW
EDYQKQRYHYQKKLLAKYAAIKATKLQSTNEIDELLRNYMDAQYFGTIQIGTPAQNFT
VIFDTGSSNLWVPSEKMPFHDIACMLRHRYDSGASSTYKEDGRKMAIQYGTGSMKGFI
SKDNVCIAGICAEEQPFAEATSEPGLTFIAAKFDGILGITFPEISVLGVPPVFHTFIE
QKKVPSPVFALWLNRNPDSELGGEITLGGMDTRRYVEPITWTPVTRRGYWQFKMDKVQ
GGSTSIACPNEFSGCQAIADTGTSLIAGPKAQSRASRNSLVLEPTYEGEYMIPCDKVP
FPPRLSFVIEARTFTLKGEDYVLTVKAGGKSICLSGFMGMDFPERIGELWILGDVFIG
KYYTVFDVGQARLGFAQAKSEDGYPVGPAVRRYNKFSEDSGSDEDDVFTL

*Figure 25B*

```
TTGACACAGGTTCATCAAATCTCTGGNGCTCCTGCATATTATGTGGAGGAAATCGTTCGAACCTGACCG
CAACGTACAACAAGGAACATGACCTCTACTACATCGACTGCAGAGCCAATGCGTCTATCACGCTCACAATT
GGCCAGCGCCAGTACAAAATTGAATCAAAGAACCTCATCATTCATGTCGAAGCAGATACATGCATCTTGG
CACTACATGGATACCACTTTCTCGGAGCAACATGGATCTTTGGTGCACCGTTCATAAGGCAGTTCTGTAA
TATTTATGATATGGGTAACAAAAGGATAGGATTCGCTCATTCGCTGCAGAATTAGCCTGCATTTACTAGT
TNTTATTCGACATTNTTAAACAACTCCCTCAATAAAGTATTGNGTTTCAAAAAAAAAAAAAANAAAAAAAA
```

Figure 26A

```
LTQVHQISGAPAYYVEEIASNLTATYNKEHDLYYIDCRANASITLTIGQRQYKIE
SKNLIIHVEADTCILALHGYHFLGATWIFGAPFIRQFCNIYDMGNKRIGFAHSLQN*
```

Figure 26B

```
  1 aaggcgtatc cggaatgcgg ggagaatgag tggctcgacg actgtggaac tcagaagcca
 61 tgcgaggcca agtgcaatga ggaacccccct gaggaggaag atccgatatg ccgctcacgt
121 ggttgtttat tacctcctgc ttgcgtatgc aaagacggat tctacagaga cacggtgatc
181 ggcgactgtg ttagggaaga agaatgcgac caacatgaga ttatacatgt ctgaacgaga
241 aagcaacaat aaccaaaggt tccaactctc gctctgcaaa atcgctagtt ggatgtctct
301 tttgcgtccg aatagtttta gttgatatta agtaagaact cctgctggaa agaataaagc
361 tttccaactc c
```

Figure 27A

```
KAYPECGENEWLDDCGTQKPCEAKCNEEPPEEEDPICRSRGCLL
PPACVCKDGFYRDTVIGDCVREEECDQHEIIHV
```

Figure 27B

GTTTTCTCCTGTAGTCGTCATCAGTGTGGTACTCACAGTCGCCTTTTGCGATGCAAGC
CCAGTGAAAGCCAGCTTTGGCTGCTCTAACAGTGGGATAACTGATAGCGATCGGCA
AGCGTTCCTCGACTTCCACAACAATGCTCGGAGACGAGTTGCGCAAGGAGTTGAGG
ATAACAAATCCGGCAAACTGAATCCAGCGAAGAACATGTATAAGCTGGACTGGGAC
TGTGAGATGGAACAGAAGCTCCAGGATGCTATCCAATCCTGCCCAGGCGGCTTTGCT
GGAATTCAAGGTGTTGCGCAGAATATAATAAGCTGGTCAGGCTCCGGTGGATTCCCG
AATCCATCAGAAAAGATAAACTCAACACTTGCCAGCTGGTGGGGTGGTGCAAAAAA
CAACGGCGTCGCCTCAGACAACAAATACACTGGTGGAGGTCTTTACGCCTTTTCCAA
TATGGTCTTCTCTGAGACGACAAAACTCGGTTGCGCCTACAAGGTTTGCGGCACTAA
ACTGACGCTATCGTGCATTTATAACGGAATTGGGTATATGACAGGCGCGCCAATGTG
GGAGACAGGTCAGGCTTGCAAGGCCGGAGCAGACTGCACCACATTCAAGAACTCAG
GTTGCGAAGACGGCCTCTGCACGAAAGGAGCAGATGTCCCTGAGACGAACCAGCAG
TGTCCGTCAAACACCGGAATGACTGATTCAGTCAGAGATACTTTCCTTTCATTGCAC
AACGAATTCAGGTCGAGTGTTGCCCGAGGTTTGGAACCCGATGCTCTTGGCGGAAAT
GCACCAAAAGCATCCAAAATGCTCAAGATGGTGTACGACTGTGAAGTAGAAGCATC
AGCCATCAGACATGGGAATAAATGCGTCTACCAACATTCTCACGGCGATGAAAGAC
CCGGCCTAGGAGAAAACATTTACAAAACCAGCATTGTCAAATTTGAGAAGAACAAA
GCAGCCAAGCAGGCTTCACAACTTTGGTGGAACGAGTTGAAAGAGTTCGGTGTCGG
CCCATCCAACATGCTCACTGATGCTCTCTGGAACAGGCCCAACATGCAGATTGGTCA
TTACACCCAGATGGCCTGGGAGAGCACCTACAAACTTGGATGCGCTGTTATATTCTG
CAATGATTTCACATTTGGTGTTTGTCAGTATGGACCAGGAGGCAATTACATGAATCA
CCTGATCTACACTATTGGTCAACCATGTTCCGAGTGTGAAGCTACCGCCACTTGCAG
CGTGACCGAAGGATTGTGCAGTGCTCCTTAATTAGTCTACAATAAAGATGCTACTTT
CCAAAAAAAAAAAAAAAA

Figure 28A

FSPVVVISVVLTVAFCDASPVKASFGCSNSGITDSDRQAFLDFHNNARRRVAQGVEDNK
SGKLNPAKNMYKLDWDCEMEQKLQDAIQSCPGGFAGIQGVAQNIISWSGSGGFPNPSEK
INSTLASWWGGAKNNGVASDNKYTGGGLYAFSNMVFSETTKLGCAYKVCGTKLTLSC
YNGIGYMTGAPMWETGQACKAGADCTTFKNSGCEDGLCTKGADVPETNQQCPSNTGM
TDSVRDTFLSLHNEFRSSVARGLEPDALGGNAPKASKMLKMVYDCEVEASAIRHGNKC
VYQHSHGDERPGLGENIYKTSIVKFEKNKAAKQASQLWWNELKEFGVGPSNMLTDAW
NRPNMQIGHYTQMAWESTYKLGCAVIFCNDFTFGVCQYGPGGNYMNHLIYTIGQPCSE
CEATATCSVTEGLCSAP*

Figure 28B

GTTCTCGTACCACTTCTGGTTCTACTGGCTGTTTCTGTTGATGCAAATTCCGTGAGAT
GCGGAAATAATGGAATGACCGACGAGGCCCGACAGAAATTCCTCGACATGCACAAC
GGTTACAGATCGCAGGTTGCCAAAGGACAGGCCAAGGATGCACTCTCAGGAAATGC
ACCAAAAGCTGCCAAAATGAAGAAAATGGTATATGACTGTGGtGTCgAATCAACTGC
AATGCAgAATGCTAAAAAATGtGTCTTCACTCATTCGCATATGAAGGGACTTGGCGA
AAACATATGGATGACgACTGCACgCgAGATGGATAAAGTGAAATCAGCTGAACAGGC
TAGTCAGGGTTGGTTCAGTGAACTCGCGGAATACGGTGTAGGGCCTGAAAATAAGC
TAACAATGCAGCTGTGGAACAGGCCAAATACTCAGATTGGACATTACACGCAGATG
GTCTGGCAGGACACCTACAAACTCGGATGTTATGTGGAATGGTGCTCATCTATGACC
TACGGCGTGTGTCAGTATAGCCCTCAAGGTAACATGATGAACTCAATCATCTACGAA
AAAGGAAACCCCTGCACTCAGGATTCGGACTGTGGCTCAAATGCCAGATGCACcGCT
GACAAGGCGCTTTGCATCGTGCATGGATAgCTGGGCTATCCCACGGTCAACAGCGCT
TCTACTAATTAGCTTTGCTTCCTCTATAAATAAATGCATTGAAACAAAAAAAAAAAA
AA

*Figure 29A*

VLVPLLVLLAVSVDANSVRCGNNGMTDEARQKFLDMHNGYRSQVAKGQAKDALSGN
APKAAKMKKMVYDCGVESTAMQNAKKCVFTHSHMKGLGENIWMTTAREMDKVKSA
EQASQGWFSELAEYGVGPENKLTMQLWNRPNTQIGHYTQMVWQDTYKLGCYVEWCS
SMTYGVCQYSPQGNMMNSIIYEKGNPCTQDSDCGSNARCTADKALCIVHG*

*Figure 29B*

GTTTGAGGATGAGGGTATTCCTTTTAGTCCTCTTGTTGGCTATTTGTGCGAGCGCTGG
TTTCTTTGACACCAAGCTTGGTGAGAAAATAAAGAAAACGCTTGGCAAAATCAAAG
CTGCGCTCAACGGCACCTTACTCATGAAAATTCGTGAAAAATTCATTGCACTGAGAG
AAAAAAATAAAGGCTAAGCTGAAGCTCTCCCCGGCACGAAAAGCCCTACTAGGCGAA
ATTATGAAGCACATTATTAAAATCAAAAAGGATAAAATTCAAGAGAAAGGTGACTC
AATCGAAGAAATCAACTCGAAAAGTGCTATCGGAGAGTTGCTGTACCAAGGTGACA
TCGTTCTGACAAATAAGCAAGCCCAGGAGATTGTTGATGACATTGAGGGTGATGAA
AATGACCGCGGAAAACGACAGGCGTTCCGTGATCGCAACTATCCACGGACATTATG
GTCGAAGGGAGTGTATTATTACTTCCATGGAAACGCAACTCCTGAGGTGAGAAGCGT
TTTCACGAAAGGCGCAAGACTTTGGATGAAAGATACTTGCATTGACTTCTTTGAGAG
CAACTCAGCACCCGATAGGATTCGAGTTTTCAAAGAACAAGGATGTTGGTCGTACGT
TGGTAGGATCGGGGGTCAGCAAGATCTGTCGCTGGGAAAAGGCTGTGAATCGGTTG
GAACAGCTGCACACGAAATCGGTCATGCTATTGGCTTCTACCACACTCACTCAAGAC
ACGATCGCGATAACTTCATCACATTTAACGCACAAAATGTCAAGCCTGATTGGTTGG
ACCAATTCACCAAGCAGACCCCGGCTACTAATGAGAACTACGGAATTACATACGAC
TACGGAAGTATTATGCACTATGGCGCAAATAGCGCCTCTGCGAATGGACAGCCTTCA
ATGGTTCCGTTTGACCCGAAATACGTAGAAACTCTCGGATCACCCATAATTTCCTTTT
ATGAACTTCTCATGATCAACAAACCCTACGAGTGCACCAAGAATTGCGATCCGAATA
CTTCTGCGCAGTGTAAGATGGGTGGCTTCCCACATCCTCGGGATTGTGGAAGATGCA
TTTGTCCCAGTGGATATGGAGGCCAACTATGCGACCAGAAGCCATCCGGATGCGGA
TCGATCCTCCAAGCGACCGCTCAGTACCAGAACTTGCACGACAAACGTGGAAACGA
AGCAGCAGGGCAGAGACCTAGAGAAGACATGGACTTCTGCTACTACTGGATTACGG
CTCCACAGGGTTCAAGAATCGAAATCAAAATCGCTGATCTATCTCGAGGAGCCGCTG
TTGATGGGTGTCAGTATTGGGGAGTAGAAATTAAGACTCACGCTGACCAGCGCCTCA
CTGGCTACAGGTTCTGTGCTCCAGAAGATGTCGGACGTACATTGGTGTCGAACTCTA
ACATCGTACCAATAATCACATACAATAGATTTTATGCAACCACTGTTGATATCCAGT
ACCGAATCGTTGGTGGTAATGTTGGCGGACCAAGGCCTCAGCCACAACCAAACAGC
AATTGCGTCGACAATGAACAGTGCGCGACCCTCATCAGAACAAAGAATTTCTGTCA
GAGCAGATCGTTCACAGAGTCCGTCAAAAGAGGTCTATGTCCAAAGGCATGCGGTT
TTTGCCGCTAACTTTTCACGAGACAATGAAATAAATATTCGCAGCATCAAAAAAAAA
AAAAAAA

*Figure 30A*

MRVFLLVLLLAICASAGFFDTKLGEKIKKTLGKIKAALNGTLLMKIREKFIALREKIKAKL
KLSPARKALLGEIMKHIIKIKKDKIQEKGDSIEEINSKSAIGELLYQGDIVLTNKQAQEIVDI
EGDENDRGKRQAFRDRNYPRTLWSKGVYYYFHGNATPEVRSVFTKGARLWMKDTCID
FFESNSAPDRIRVFKEQGCWSYVGRIGGQQDLSLGKGCESVGTAAHEIGHAIGFYHTHSR
HDRDNFITFNAQNVKPDWLDQFTKQTPATNENYGITYDYGSIMHYGANSASANGQPSM
VPFDPKYVETLGSPIISFYELLMINKPYECTKNCDPNTSAQCKMGGFPHPRDCGRCICPSG
YGGQLCDQKPSGCGSILQATAQYQNLHDKRGNEAAGQRPREDMDFCYYWITAPQGSRI
EIKIADLSRGAAVDGCQYWGVEIKTHADQRLTGYRFCAPEDVGRTLVSNSNIVPIITYNF
YATTVDIQYRIVGGNVGGPRPQPQPNSNCVDNEQCATLIRTKNFCQSRSFTESVKRGLCP
KACGFCR*

*Figure 30B*

```
  1 GGTTTAATTA CCCAAGTTTG AGATGAAGCT ACTCGCTCTT TCCGCTCTCT
 51 GCGCGCTGGC CTTCGCTGCT CCGCGAGACA AGCGGCTAGC TGTGAGCACT
101 ATCACTGTCA CTGGAGGACT AGGTCTCTCC ACGGGATGTG TCGTCACTGG
151 CAACGTTTTG TATGCAAATG GTTTCCGAGT ACGCGAAATT AATCCATCGG
201 AGCAGCAAGA GTTGGTCAAG TATCAGAACG ACGTAGCCGA ATATAAGACG
251 GCCCTGAAAC AAGCGATCAA GGAGCGAGAA GAGAAGATCC GAGCCCGTCT
301 CGCCGGCAAG AAGGTGAAGG CCGTTGAGTC GACCAAAGAA GAGGACCTGC
351 CGAAGCCGCC ACAGAAGCCG TCATTCTGCA CACCAGAAGA CACTACCCAG
401 TTCTTCTTTG AAGGATGCAT GATCCAGAAC AACAAGATCT ACGTCGGAAA
451 CACTTTCGCT CGTGACCTGA CCCAATCTGA AATCGGCGAA CTGAAGGAAT
501 TCGAGAAGAA ATTCAAGGTC TACCAGGACT ACGTTCAGAA GCAGGCCGAA
551 CAGCAAGTGA ACAGCCTCTT CGGCGGCTCT GACTTCTTCT CGGCACTGTT
601 CAGCGGCGGT GAGACCAAGC CATCCACGAC CACTGTGGCA CCAGAACTTC
651 CTGAAGACGC TCCCGAGCAG CCGCCCACGC CCAACTTCTG CACCAGAATA
701 ATCTAAACGT GCTCTGAATT GTCCACTTAG TTGTTGGATT GGTTGGTTTG
751 GTGAATAGCG ACTTCGCTTC CCCTCTCGTA CTTACGGTGT CGACTAGCAC
801 ATTAGTCATG CGTTGCAATA TTTGATCATT GTATTAAGGT ATATTGTACA
851 TTTATATAAT AAAATTATAT TTCAACTCAA AAAAAAAAAA AAA
```

*Figure 31A*

```
  1 MKLLALSALC ALAFAAPRDK RLAVSTITVT GGLGLSTGCV VTGNVLYANG
 51 FRVREINPSE QQELVKYQND VAEYKTALKQ AIKEREEKIR ARLAGKKVKA
101 VESTKEEDLP KPPQKPSFCT PEDTTQFFFE GCMIQNNKIY VGNTFARDLT
151 QSEIGELKEF EKKFKVYQDY VQKQAEQQVN SLFGGSDFFS ALFSGGETKP
201 STTTVAPELP EDAPEQPPTP NFCTRII
```

*Figure 31B*

```
  1 GGTTAATTAC CCAAGTTTGA GAATGATTCA ACTGTTGTTG TTAGCGCTAC
 51 TCCCTGTTTG CATCTCAGTG AGGGAACAGT CGATAGCAGT TAAAGGACGC
101 CTTCTGTGCG GTGAtCAACC AGCAGCGAAC GTCAGAGTGA AGTTGTGGGA
151 AGAAGACACA GGACCAGATC CAGATGACCT ACTGGATGCA GGATACACGA
201 ACTCTAATGG TGAATTCCAA CTCCAAGGCG GAACAATAGA GACGACTCCC
251 ATTGATCCCG TCTTGAAAAT TTACCATGAT TGCAATGACG TGACTGGTTT
301 TCTGAGCGTA CCTAAACCTG GCAGCAGAAA AGTGAGGTTC TCCTTACCGG
351 ACAAATACAT CAGCGATGGA ATGGTTCCTA AGAAAGTCAT GGACATCGGT
401 GTTATCA
```

Figure 32A

```
  1 MIQLLLLALL PVCISVREQS IAVKGRLLCG DQPAANVRVK LWEEDTGPDP
 51 DDLLDAGYTN SNGEFQLQGG TIETTPIDPV LKIYHDCNDV TGFLSVPKPG
101 SRKVRFSLPD KYISDGMVPK KVMDIGVI
```

Figure 32B

```
Ay-ASP1    1  -FSPVVVISVVLTVAFCDASPVKASFGCSNSGITDSDRQAFLDFHNNARRRVAQGVEDNK
Ad-ASP1    1  MFSSVVVISVISTIAFCDASPARASFGCSNNGITDSDRQAFLDFHNNARRRVAQGVEDNK
Na-ASP1    1  MFS-PVVVSVVFTIAFCNASPARDSFGCSNSGITDSDRQAFLDFHNNARRRVAKGLEDSN
Ac-ASP1    1  MFS-PVIMSVIFTIAFCDASPARDGFGCSNSGITDKDRQAFLDFHNNARRRVAKGVEDSN
               **  *  **  * *** ***    ***** **** ***************** * **

Ay-ASP1   60  SGKLNPAKNMYKLDWDCEMEQKLQDAIQSCPGGFAGIQGVAQNIISWSGSGGFPNPSEKI
Ad-ASP1   61  SGKLNPAKNMYKLEWDCKMEQQLQDAIQSCPGCSAGIQGFSQNVMSWSNSGGFPNSSEKI
Na-ASP1   60  SGKLNPAKNMYKLSWDCAMEQQLQDAIQSCPSGFAGIQGVAQNIMSWSSSGGYPDPSVKI
Ac-ASP1   60  SGKLNPAKNMYKLSWDCAMEQQLQDAIQSCPSAFAGIQGVAQNVMSWSSSGGFPDPSVKI
              ************* *** *** *********   *****  **  *** *** *  * **

Ay-ASP1  120  NSTLASWWGGAKNNGVASDNKYTGGGLYAFSNMVFSETTKLGCAYKVCGTKLILSCIYNG
Ad-ASP1  121  ESTLSGWWSGAKNNGVGSDNKYTGGGLYAFSNMVFSETTKTGCAYKVCGTKMATSCIYNG
Na-ASP1  120  EPTLSGWWSGAKKNGVGPDNKYTGGGLFAFSNMVYSETTKLGCAYKVCGTKLAVSCIYNG
Ac-ASP1  120  EQTLSGWWSGAKKNGVGPDNKYNGGGLFAFSNMVYSETTKLGCAYKVCGTKLAVSCIYNG
                **  ** *** ***  **** **** ****** ***** **********   ******

Ay-ASP1  180  IGYMIGAPMWETGQACKAGADCTTPKNSGCEDGLCTKGADVPETNQQCPSNTGNTDSVRD
Ad-ASP1  181  IGYITNAPMWETGQACKTGADCSTYKNSGCEDSLCTKGADVPETNQQCPSNTGNTDSVRD
Na-ASP1  180  VGYITNQPMWETGQACQTGADCSTYKNSGCEDGLCTKGPDVPETNQQCPSNTGNTDSVRD
Ac-ASP1  180  VGYITNQPMWETGQACKTGADCSTYKNSGCEDGLCTKGPDVPETNQQCPSNTGNTDSVRD
               ** *  *********  **** * ******* ***** *********************

Ay-ASP1  240  TFLSLHNEFRSSVARGLEPDALGGNAPKASKMLKMVYDCEVEASAIRHGNKCVYQHSHGD
Ad-ASP1  241  TFLSLHNGFRSSVARGLEPDALGGNAPKAAKMLKMVYDCEVEASAIRHGNKCVYQHSSGN
Na-ASP1  240  TFLSVHNEFRSSVARGLEPDALGGNAPKAAKMLKMVYDCEVEASAIRHGNKCVYQHSHGE
Ac-ASP1  240  TFLSVHNEFRSSVARGLEPDALGGNAPKAAKMLKMVYDCEVEASAIRHGNKCVYQHSHGE
              **** ** ********************* *************************** *

Ay-ASP1  300  ERPGLGENIYKTSIVKFEKNKAAKQASQLWWNELKEFGVGPSKMLTDALWNRPNMQIGHY
Ad-ASP1  301  DRPGLGENIYKTSVQKFEKNKAAKQASELWWNELREFGVGPSKNLTNALWNRPGMQIGHY
Na-ASP1  300  DRPGLGENIYKTSVLKFQKNKAAKQASQLWWNELKEYGVGPSNVLTTALWNRPNMQIGHY
Ac-ASP1  300  DRPGLGENIYKTSVLKFQKNKAAKQASQLWWNELKEFGVGPSNVLTTALWNRPGMQIGHY
               ************  ** ********* ****** * ****** ** ****** ******

Ay-ASP1  360  TQMAWESTYKLGCAVIFCNDFTFGVCQYGPGGNYMNHLIYTIGQPCSECEATATCSVTEG
Ad-ASP1  361  TQMAWDTTYKLGCAVVFCNDFTFGVCQYGPGGNYMNHLIYTMGQPCSQCAATATCSVTEG
Na-ASP1  360  TQMAWDTTYKLGCAVVFCNDFTFGVCQYGPGGNYMGHVIYTMGQPCSQCSPGATCSVTEG
Ac-ASP1  360  TQMAWDTTYKLGCAVVFCNDFTFGVCQYGPGGNYMGHVIYTMGQPCSQCSPGATCSVTEG
              ***** ********* ******************* * *** ***** *   ********

Ay-ASP1  420  LCSAP
Ad-ASP1  421  LCSAP        86%
Na-ASP1  420  LCSAP        85%
Ac-ASP1  420  LCSAP        85%
              *****
```

Figure 42

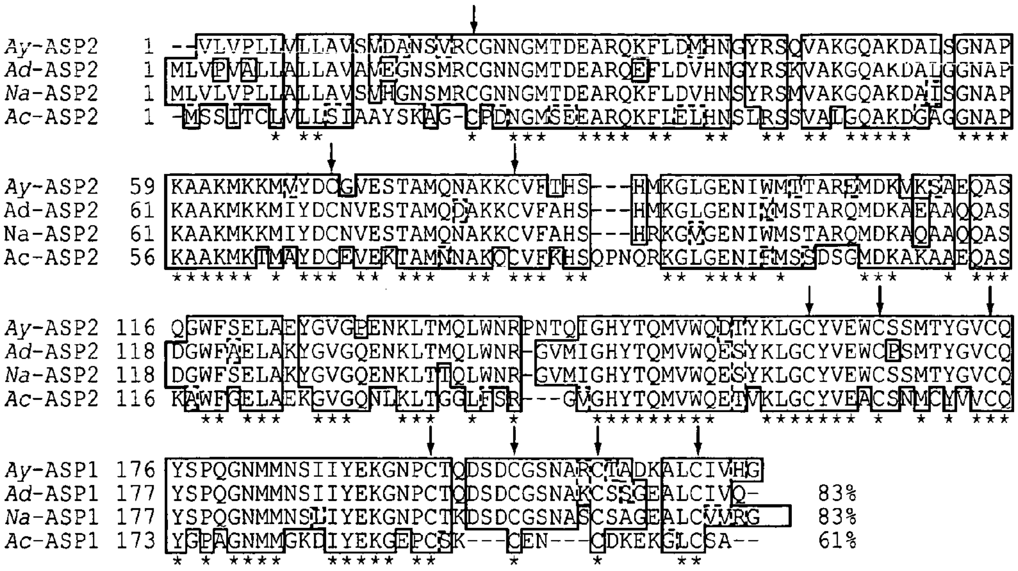

*Figure 43A*

```
  1 gaaaatcaca atgatgtctt ctatcacatg tttggttctt ctctcgattg cagcgtactc
 61 caaagccggt tgtcctgaca atggaatgtc agaggaagca cggcaaaaat tccttgaatt
121 gcacaattcg ttgagaagtt cggttgcatt gggacaggcc aaggatggag ctggtggaaa
181 tgccccgaaa gctgctaaga tgaagacgat ggcatacgat tgcgaagttg aaaagactgc
241 aatgaataac gcgaaacaat gtgtattcaa gcactcgcaa cctaaccaaa ggaaaggatt
301 gggagagaat atatttatgt cttcggatag cggtatggac aaagcaaagg ctgctgagca
361 ggctagcaaa gcttggttcg gcgaacttgc agaaaaagga gttggacaga atcttaagct
421 tacaggaggc ttgttcagca gaggagtcgg gcactataca cagatggtat ggcaagaaac
481 cgttaagctt ggatgctatg tggaagcgtg ctcaaatatg tgttatgtgg tgtgccagta
541 cggtcctgct ggaaatatga tgggcaagga tatctacgag aaaggagaac cgtgttcgaa
601 atgtgagaat tgcgacaagg agcagggtac ctgcagtgct tgattagttg tgttcagtga
661 agctcattac gctcacatac tttaacaaat cgtagtgatc tgtagttgct ttaatattca
721 aataaacatg atgccagcaa aaaaaaaaaa aaa
```

*Figure 43B*

GAAAGGTTTAATTACCCAAGTTTGAGGTGTAAAAATGGTCCACTACAAGCTGACCTACTT
CAACGGACGTGGCCTCGGCGAATGCGCGCGTCAGTTGTTCGCTCTTGCTGACCAACAATA
TGAGGATATTCGTGTTACACATGAGGATTTCCCCGAGATAAAACCAAATTTGCCATTTGG
ACAACTGCCGCTGCTTAACGAGGATGGTAAAGAACTCGCTCAGTCAAACGCCATCAATCG
TTACCTGGCTAGGAAATTCGGATTCGCTGGCAAAACGCCATTTGAGGAGGCTCTAGTGGA
CTCGCTGGCAGATCAGATGACGGACTACCGTGTAGAAATAAAACCATTCGTCTACACAGC
GTATGGACATCAGAAATTCGGTGACCTGGAGACGCTAAAAAAGGATGTGATGCTTCCTGC
ACGAGACAAGTTCCTCGGTTTCATCACCAAATTCTTAAAGAACAACCCATCAGGATTCTT
GGTTGGTGACTCGGTGACTTGGATAGATCTATTGCTCGCTGAACATGCTTCCGACATACA
GTCAAAGGTCCCCGAATACCTCGAAGGGTTTCCTGAGGTGAAGGCTCATATGGAAAAGGT
GCGATCTATTCCGAAACTGAAAAAATGGATCGAGACCAGACCGGAGACTCACTTCTGATC
GATACGCGGGATTTTTTC

*Figure 57A*

MVHYKLTYFNGRGLGECARQLFALADQQYEDIRVTHEDFPEIKPNLPFGQLPLLNEDGKE
LAQSNAINRYLARKFGFAGKTPFEEALVDSLADQMTDYRVEIKPFVYTAYGHQKFGDLET
LKKDVMLPARDKFLGFITKFLKNNPSGFLVGDSVTWIDLLLAEHASDIQSKVPEYLEGFP
EVKAHMEKVRSIPKLKKWIETRPETHF*

*Figure 57B*

```
GAAAGGTTTAATTACCCAAGTTTGAGGTGTAAAAATGGTCCACTACAAGCTGACCTACTT  60
                                   M  V  H  Y  K  L  T  Y  F   9
CAACGGACGTGGCCTCGGCGAATGCGCGCGTCAGTTGTTCGCTCTTGCTGACCAACAATA 120
 N  G  R  G  L  G  E  C  A  R  Q  L  F  A  L  A  D  Q  Q  Y   29
TGAGGATATTCGTGTTACACATGAGGATTTCCCCGAGATAAAACCAAATTTGCCATTTGG 180
 E  D  I  R  V  T  H  E  D  F  P  E  I  K  P  N  L  P  F  G   49
ACAACTGCCGCTGCTTAACGAGGATGGTAAAGAACTCGCTCAGTCAAACGCCATCAATCG 240
 Q  L  P  L  L  N  E  D  G  K  E  L  A  Q  S  N  A  I  N  R   69
TTACCTGGCTAGGAAATTCGGATTCGCTGGCAAAACGCCATTTGAGGAGGCTCTAGTGGA 300
 Y  L  A  R  K  F  G  F  A  G  K  T  P  F  E  E  A  L  V  D   89
CTCGCTGGCAGATCAGATGACGGACTACCGTGTAGAAATAAAACCATTCGTCTACACAGC 360
 S  L  A  D  Q  M  T  D  Y  R  V  E  I  K  P  F  V  Y  T  A  109
GTATGGACATCAGAAATTCGGTGACCTGGAGACGCTAAAAAAGGATGTGATGCTTCCTGC 420
 Y  G  H  Q  K  F  G  D  L  E  T  L  K  K  D  V  M  L  P  A  129
ACGAGACAAGTTCCTCGGTTTCATCACCAAATTCTTAAAGAACAACCCATCAGGATTCTT 480
 R  D  K  F  L  G  F  I  T  K  F  L  K  N  N  P  S  G  F  L  149
GGTTGGTGACTCGGTGACTTGGATAGATCTATTGCTCGCTGAACATGCTTCCGACATACA 540
 V  G  D  S  V  T  W  I  D  L  L  L  A  E  H  A  S  D  I  Q  169
GTCAAAGGTCCCCGAATACCTCGAAGGGTTTCCTGAGGTGAAGGCTCATATGGAAAAGGT 600
 S  K  V  P  E  Y  L  E  G  F  P  E  V  K  A  H  M  E  K  V  189
GCGATCTATTCCGAAACTGAAAAAATGGATCGAGACCAGACCGGAGACTCACTTCTGATC 660
 R  S  I  P  K  L  K  K  W  I  E  T  R  P  E  T  H  F  *     207
GATACGCGGGATTTTTTC
                                                             678
```

*Figure 57C*

GTTAAAGCCGTGTAAGCAACAGGGTTCTTTGTGATGTTAACTCTCGCTGCACTTCTGAT
TTCTGTTTCGCTGGTTGAGCCGACAGGCATAGGTGAGTTTCTTGCTCAACCAGCACCTG
CATATGCTAGAAGACTCACAGGGCAGGCCCTTGTTGACTACGTCAATTCGCACCACTCA
TTGTACAAGGCCAAATATTCACCAGATGCTCAAGAACGCATGAAATCTAGAATTATGGA
TTTGAGTTTCATGGTTGATGCGGAAGTCATGATGGAAGAAATGGACCAGCAGGAGGATA
TAGATCTCGCTGTTTCTTTACCTGAAAGTTTCGACGCTCGTGAAAAATGGCCAGAATGT
CCTTCAATAGGATTAATCCGTGATCAGTCCGCCGGTGGAGGATGTTGGGCAGTATCCTC
AGCAGAGGTGATGACCGACAGGATCTGTATACAATCAAATGGAACAAAGCAGGTGTATG
TTTCCGAAACGGATATCTTATCATGCTGTGGACAACGTTGCGGTAGCGGGTGTACCTCA
GGTGTGCCACGTCAAGCTTTCAACTATGCAATTCGTAAAGGTGTTTGCAGTGGAGGACC
ATATGGAACGAAGGGTGTTTGCAAACCCTATCCTTTCTATCCATGCGGCTATCATGCTC
ATCTGCCATATTATGGACCATGTCCAGATGGTATGTGGCCTACGCCAACATGCGAAAAG
GCATGTCAATCCGACTATACTGTTCCGTACAACGATGACAGGATCTTCGGCAGCAAAAC
TATTGTCTTGACGGGAGAGGAAAAAATTAAGCGAGAGATTTTCAATAACGGACCATTGG
TAGCCACGTATACAGTTTACGAAGATTTCGCTTATTACAAGAATGGAATTTACATGACT
GGTCTCGGTAGAGCGACAGGCGCACATGCAGTCAAAATTATTGGCTGGGGTGAAGAAAA
TGGAGTCAAGTATTGGTTGATTGCAAACTCGTGGAACACTGATTGGGGAGAGAATGGCT
TCTTCCGCATGCTTCGTGGAACAAACCTTTGCGATATTGAACTAAGCGCGACTGGAGGA
ACGTTCAAGGTGTGAACGTGATCGAAAAGAACGATTTTGAACAAAAATCTTCCCGTATT
GTCATCAAAAAAA

*Figure 61A*

MLTLAALLISVSLVEPTGIGEFLAQPAPAYARRLTGQALVDYVNSHHSLYKAKYSPDAQ
ERMKSRIMDLSFMVDAEVMMEEMDQQEDIDLAVSLPESFDAREKWPECPSIGLIRDQSA
GGGCWAVSSAEVMTDRICIQSNGTKQVYVSETDILSCCGQRCGSGCTSGVPRQAFNYAI
RKGVCSGGPYGTKGVCKPYPFYPCGYHAHLPYYGPCPDGMWPTPTCEKACQSDYTVPYN
DDRIFGSKTIVLTGEEKIKREIFNNGPLVATYTVYEDFAYYKNGIYMTGLGRATGAHAV
KIIGWGEENGVKYWLIANSWNTDWGENGFFRMLRGTNLCDIELSATGGTFKV*

*Figure 61B*

TTAATTCTTATTGCTCTGGTGGTGACGGCGTTGGCTCAACAGCCGCTTTCACTAAAGGA
GTATCTGGAACAGCCGATACCAGAGGAGGCAGAGAATCTTTCCGGAGAAGCGTTTGCGG
AGTTTCTGAACAAACGACAATCGTTTTTCACGGCTAAGTACACGCCAAATGCTTTAAAC
ATTCTTAAAATGCGTGTGATGGAATCGAGATTCCTGGACAATGAAGAAGGTGAAATGCT
AAAAGAGGAGGACATGGATTTCAGTGAAGAAATTCCTGTTAGTTTTGATGCTCGAGACA
AATGGCCCAAATGCACCTCCATAGGATTTATCCGTGATCAATCACACTGTGGTTCATGC
TGGGCAGTATCGTCAGCAGAAACGATGTCAGATCGACTCTGCGTGCAATCAAACGGTAC
AATTAAGGTACTTCTATCCGATACGGACATCCTTGCCTGTTGCCCGAATTGTGGTGCTG
GATGTGGAGGAGGCCACACAATTCGAGCGTGGGAATATTTTAAGAACACAGGCGTTTGC
ACTGGCGGACTATATGGAACAAAGGATTCCTGCAAACCATACGCTTTCTATCCATGTAA
AGACGAAAGTTACGGAAAGTGCCCCAAGGATTCTTTTCCAACACCAAAATGTCGAAAAA
TTTGTCAGTATAAATACAGTAAGAAGTACGCCGACGACAAATACTACGCGAATTCCGCA
TATCGAATTCCACAGAATGAGACGTGGATCAAATTGGAGATCATGAGAAACGGGCCTGT
GACAGCATCATTCAGGATTTATCCGGATTTTGGGTTTTACGAAAAAGGAGTTTATGTGA
CTTCAGGCGGAAGGGAACTAGGTGGGCACGCGATTAAAATCATTGGATGGGGAACGGA
AAAAGTAAACGGAACTGACCTACCTTACTGGTTGATTGCTAACTCTTGGGGTACTGACT
GGGGAGAGAATAACGGCTATTTCCGCATACTTCGCGGACAAAATCACTGCCAAATAGAA
CAGAAAGTTATCGCCGGTATGATAAAAGTACCACAACCGAAATCCGCCGGTCCACCACT
TCAACCCAATCCTTCAAGCTGAACCAAGTTGTAGTATTGTCCCCATCAATCCAAGCATT
TCTTGGGGTGATACTTTTACGAATAAAAACTACATTATAAAAAAAAAAAAAAAAAAA

*Figure 62A*

LILIALVVTALAQQPLSLKEYLEQPIPEEAENLSGEAFAEFLNKRQSFFTAKYTPNALN
ILKMRVMESRFLDNEEGEMLKEEDMDFSEEIPVSFDARDKWPKCTSIGFIRDQSHCGSC
WAVSSAETMSDRLCVQSNGTIKVLLSDTDILACCPNCGAGCGGGHTlRAWEYFKNTGVC
TGGLYGTKDSCKPYAFYPCKDESYGKCPKDSFPTPKCRKICQYKYSKKYADDKYYANSA
YRIPQNETWIKLEIMRNGPVTASFRIYPDFGFYEKGVYVTSGGRELGGHAIKIIGWGTE
KVNGTDLPYWLIANSWGTDWGENNGYFRILRGQNHCQIEQKVIAGMIKVPQPKSAGPPL
QPNPSS*

*Figure 62B*

TCGTTGAGGCGTTATTTCAAGCTTCTCTCGCCTCGATTTCAGATTCTCCAATTGTTTCA
GTGAATCGTGGAACAGTCAATCTCACTTTTGTGAGATCCAATGAAAGCTAATTTTGCGT
TGGTCGTCGTCCTTCTGGCAATAAACCAGTTATATGCAGATGAGCTGCTTCACAAACAA
GAGTCCGAACACGGACTTAGTGGCCAAGCGCTCGTTGACTACGTTAATTCGCACCAATC
ACTTTTCAAAACAGAATATTCGCCAACCAATGAACAATTCGTTAAAGCCCGTATAATGG
ACATAAAGTATATGACTGAGGCTAGCCACAAATATCCAAGAAAGGGCATTAATCTGAAC
GTTGAACTCCCTGAAAGGTTTGACGCACGTGAAAAATGGCCACATTGCGCCTCCATCGG
TCTCATTCGCGATCACTCTGCTTGCGGATCGTGTTGGGCTGTATCGGCAGCGTCGGTTA
TGTCAGATCGACTCTGTATCCAGACGAACGGCACAAACCAGAAGATCCTTTCGTCGGCG
GACATCCTTGCGTGTTGTGGAGAAGACTGTGGCTCAGGATGCGAAGGCGGTTATCCGAT
TCAGGCGTACTTCTACCTGGAAAATACTGGAGTATGTAGTGGAGGAGAGTATCGAGAAA
AGAATGTATGCAAACCATATCCCTTTTATCCGTGTGACGGAAACTATGGACCATGCCCC
AAGGAGGGTGCGTTCGACACTCCAAAGTGTCGGAAAATATGTCAGTTCCGATATCCTGT
TCCATACGAAGAAGATAAAGTGTTTGGAAAAAATTCACACATCCTTCTGCAAGACAACG
AGGCAAGAATCAGACAGGAAATTTTCATAAACGGACCAGTGGGAGCTAATTTTTACGTT
TTCGAAGACTTTATACACTACAAGGAAGGGATTTATAAGCAGACATATGGGAAATGGAT
AGGAGTACATGCAATCAAACTTATTGGTTGGGGCACAGAAAATGGAACAGATTATTGGT
TGGTTGCTAACTCGTACAACTACGACTGGGGAGAGAATGGCACCTTCCGCATTCTTCGT
GGAACTAATCACTGTTTGATAGAATCACAAGTGATCGCAACGGAGATGATTGTATGAAT
GTCTAATGAACGATTGGTCGCATGCCGATCTCTGAAGTAAAATGTGTTAATCAAAAAAA
A

*Figure 63A*

MKANFALVVVLLAINQLYADELLHKQESEHGLSGQALVDYVNSHQSLFKTEYSPTNEQF
VKARIMDIKYMTEASHKYPRKGINLNVELPERFDAREKWPHCASIGLIRDHSACGSCWA
VSAASVMSDRLCIQTNGTNQKILSSADILACCGEDCGSGCEGGYPIQAYFYLENTGVCS
GGEYREKNVCKPYPFYPCDGNYGPCPKEGAFDTPKCRKICQFRYPVPYEEDKVFGKNSH
ILLQDNEARIRQEIFINGPVGANFYVFEDFIHYKEGIYKQTYGKWIGVHAIKLIGWGTE
NGTDYWLVANSYNYDWGENGTFRILRGTNHCLIESQVIATEMIV*

*Figure 63B*

TAGATAATAATCTTTTTGCACGTCAGAGAATTTCTTTGATAAAACCACAATTAAACAAT
CTCAGCGCTGTAAACACGTGCAAAACTACTCGTTCATTTCTCTTCACTTTCCCTCCAAA
ACCAAACATTCAAGAGAAGCATGATAACCATCATTACCCTATTGCTTATCGCTTCTACA
GTGAAGTCACTAACAGTGGAGGAGTACTTGGCCCGACCAGTGCCGGAATATGCCACAAA
ACTGACAGGACAAGCCTACGTTGACTATGTTAATCAGCATCAATCATTCTACAAGGCTG
AATATTCCCCGCTGGTTGAACAGTATGCCAAAGCTGTGATGAGATCTGAGTTTATGACG
AAGCCGAACCAAAATTATGTGGTGAAGGACGTAGATCTAAACATCAATCTTCCAGAAAC
CTTCGACGCAAGGGAAAAATGGCCAAACTGCACATCAATAAGGACAATTCGCGATCAGT
CCAATTGTGGATCATGTTGGGCAGTATCAGCGGCGTCGGTAATGTCAGATCGTTTATGC
ATACAGTCGAACGGCACAATACAGTCATGGGCTTCTGATACGGATATTCTATCATGTTG
CTGGAATTGCGGAATGGGATGCGATGGAGGTAGACCGTTTGCGGCGTTCTTTTTCGCGA
TAGACAATGGTGTATGCACTGGAGGACCTTTCAGAGAGCCAAACGTGTGCAAACCATAC
GCTTTCTATCCATGCGGTCGCCACCAAAACCAGAAATACTTCGGACCTTGTCCAAAAGA
GCTCTGGCCCACTCCAAAATGTCGGAAAATGTGTCAACTAAAATATAATGTGGCCTACA
AAGACGATAAAATTTACGGGAATGATGCATACAGTCTCCCTAACAATGAGACACGAATC
ATGCAAGAAATTTTCACAAATGGACCTGTAGTGGGATCATTCAGCGTGTTTGCTGACTT
TGCAATTTATAAGAAAGGAGTATATGTGAGTAATGGAATTCAGCAGAATGGGGCTCATG
CAGTCAAAATTATTGGTTGGGGTGTGCAGGATGGACTAAAATATTGGTTGATTGCTAAT
TCCTGGAACAATGACTGGGGAGACGAAGGCTATGTCCGGTTCCTTCGTGGAGATAACCA
CTGTGGAATTGAATCAAGGGTGGTGACAGGAACTATGAAAGTGTAAAACAATAATTAGT
CTTTTCCTGACGATTTCAAATAAAATCTTTGCCACTAAAAAAAAAAAAAAAAAAA

*Figure 64A*

MITIITLLLIASTVKSLTVEEYLARPVPEYATKLTGQAYVDYVNQHQSFYKAEYSPLVE
QYAKAVMRSEFMTKPNQNYVVKDVDLNINLPETFDAREKWPNCTSIRTIRDQSNCGSCW
AVSAASVMSDRLCIQSNGTIQSWASDTDILSCCWNCGMGCDGGRPFAAFFFAIDNGVCT
GGPFREPNVCKPYAFYPCGRHQNQKYFGPCPKELWPTPKCRKMCQLKYNVAYKDDKIYG
NDAYSLPNNETRIMQEIFTNGPVVGSFSVFADFAIYKKGVYVSNGIQQNGAHAVKIIGW
GVQDGLKYWLIANSWNNDWGDEGYVRFLRGDNHCGIESRVVTGTMKV*

*Figure 64B*

ATTTTCAATGACCAAGCTCCTCGTAAGCACCGCCGGGTTGACTGGCGTCGTCGCGGCCC
TCTTCATCACTTCTCTGGTTTTCAGCATCCTTACATGGACACGTGTAAAAAATGACAAC
GATAACCCACCAAGACCTAAGGAGCCACTCAGTCGTCCAGTAGTGCAATTGTCTTCATC
TATTCAGACTACCGTAACCGAAAATGTAGTGACAGAACCCATAGTGACTGTGCCGACAG
TGTCACGCACCAGAGTTTCGGCAAAAACAATATCACCGAGAAGTTCCGCGACAACGTCA
ACTCGAACGCTTCGAACTCTCACCACACCGAAATTCGTCGCAACGGAGGCCGCACCGCG
ACGTAATCGTACGATAATGTGTCCGAACTATGGAGTTTCAGACAACTCATACGCATACC
AGGAAGCAGCATCGTTCATTCTTAGTGGCCTCGACGAACGTGTCAATCCGTGCGAAGAT
TTCTACGCTTTCACTTGTAACAAGTTTCTAAAAGATCATAAGGCTGAAGAACATGGGGT
CAGTCGTTACGGAGCTATAAAAGAACTTCAAGATGCAGTGAACACAGAAATAGTTGACG
CCCTCTTCGATGTGGATGTGAACGATAAGAAGCGGTCAGAAACAGAGAGAATAACGAAA
GCGCTTCTCCACGACTGCGTTTACCACATCTCGCCTAATGTTCCGACCGAAACAATCAT
TAATTTCCTTGAAGAAATTGCAAGAATGTTTGGAGGTATACCGTTCCTCAACCACACTC
TAAAAGAAGATTTTGACGTTTTCGCTGCAATGGGAGAAGTCGAACAAAATCACGCGATG
GGTACGCTTTTCAGCGCAATGGTTTCGGTCGACTACAAGAAGATCAAACAGAATTCACT
GTTCTTATCACAGCCTCGGCTTCCGATGCCAAGAGAATTCTACGTGCTTCCACAGTTTA
CGATGAAGCTTAAAAAACGTGGACTTCAAATTGCTGACGTTTTAAAGAAATTTGCCGAG
AAGATCTTAGAAGAACCCGATAAGTATAGGGATATGATAGAAAAGGCTGCGCAAGATGT
TGTGGAACTAGAGAGGAGGATCGCTCTGGCGTCTTGGGCAGATGCCGAAATGAGAAACT
ACGCACAACAGTACAATCCCTACGATCTGCCCACTTTGAAAAAGGCGTATCCATCTGTC
AAATGGGAGAGCTATCTACGTAGCCTTTTGTCAACCGTCGGTCCAGTCGATTTTTCTGG
TCCACATAAACGGCTCATAATCTCGCAACCGTCGTATTTTGGGTGGTTGAATGCTCTCT
TCAATGGTAACGTTGTTGACGAAAATACGATAGTAAACTATATAATCACGCACTTAATC
TTCGAAGATGCGGAATTCCTTGGTGGTATATTTAAAGAATCTGCAGAGGATTTAAATTA
CGTCCGGTATGCGCAGAGAAGTGGCAGAGGAGTTGCCCGAGTTGGAAGGCAACTTATGC
ATCAAAGAGATACCAGGGGCGACCCGAATATCCCGTGCATGAATTTCATCATGACGTAC
ATGCCGTATGGACCTGGTTATGTCTATGTAAGAAGCAAACAGCAGAGAAACGATGTTCA
AGCAGACATTAGGAAACAAACAGAACTCGTCATCGAGAGCTTTCTGAATATGACTTCGG
GCCTGAAGTGGATGTCTTCGGATTCGAAAGAAAAAGCTAGACAGAAGGCTAAGGGTATG
GTGAGGAACTACGGATGGCCTCAAAAACTCTTCGGAGACTTTAAAAGCAGCGAAGAGAT
TGATGAATATCACAAGAAGGATTATGCTGAAATCCTTGAGCTTACCAAGACGGAGAGGA
GCAGCCTTCGATATTACCGTATGCGCCGGGTGCTGATTAAAGGATATTCAAATCGCGAG
TCACTGCGTTTACTTTTGCAGGATGCAGACAGGTCCAATTTCCTCCTATCACCAGCGTT
AGTGAGCGCCTGGTACCAGCCGGAAAGGAACTCTATCACTTTCCCTTACGCGAGCTTCA
ATCCACCGTACTATAGCTATGAATATCCTCAAGCTTACAACTATGGTGGTCAGGGTGGA
ACTGCCGGTCATGAGCTAGTCCATGGATTTGACGACCAAGGAGTGCAGTTCGGTCCCGA
TGGAAGTCTAAGTAGGTGTACGTGGTATGATTGTGGATGGATGGATAAAAGATCAAAAG
ATGGTTTCAACGACATGGCCCAATGTGTTGTAACACATTATAGCACTTTCTGCTGCCCA
GAACAGGAAGGTAATATACACTGCGCAAATGGTGCAACCACACAAGGGGAAAATATTGC
TGATATTGGAGGTGAACATGCTGCATACATAGCATATCGAGAGTACATCAAATCACTAG
GACATGAAGAGAAAAGATTGCCAGGATTAGAACGATACACACCAAACCAGATCTTTTGG
ATTACATATGGATACTCATGGTGCAGGAGCGTAACAGAGGAATACCTTATTAGTCAACT
TCTCACCGACCCCCACGCACCAAGTGCTTGCCGCACTAACCAAGTAGTCCAAAGTATCC
CTGCGTTTGGACGGGATTTCGGGTGCTCATTAGGAGACAGAATGTATCCTGCACCAGAG
CAGCGATGTTCAGTTTGGGTTCAAGAGTAAATGGTCGGACGAAACTGTCGGATTTTATG
TTTCAGTCGGATTATAACACTATCAACTAAACATTTCGTTCAAAAAAAAAAAAA

*Figure 65A*

MTKLLVSTAGLTGVVAALFITSLVFSILTWTRVKNDNDNPPRPKEPLSRPVVQLSSSIQ
TTVTENVVTEPIVTVPTVSRTRVSAKTISPRSSATTSTRTLRTLTTPKFVATEAAPRRN
RTIMCPNYGVSDNSYAYQEAASFILSGLDERVNPCEDFYAFTCNKFLKDHKAEEHGVSR
YGAIKELQDAVNTEIVDALFDVDVNDKKRSETERITKALLHDCVYHISPNVPTETIINF
LEEIARMFGGIPFLNHTLKEDFDVFAAMGEVEQNHAMGTLFSAMVSVDYKKIKQNSLFL
SQPRLPMPREFYVLPQFTMKLKKRGLQIADVLKKFAEKILEEPDKYRDMIEKAAQDVVE
LERRIALASWADAEMRNYAQQYNPYDLPTLKKAYPSVKWESYLRSLLSTVGPVDFSGPH
KRLIISQPSYFGWLNALFNGNVVDENTIVNYIITHLIFEDAEFLGGIFKESAEDLNYVR
YAQRSGRGVARVGRQLMHQRDTRGDPNIPCMNFIMTYMPYGPGYVYVRSKQQRNDVQAD
IRKQTELVIESFLNMTSGLKWMSSDSKEKARQKAKGMVRNYGWPQKLFGDFKSSEEIDE
YHKKDYAEILELTKTERSSLRYYRMRRVLIKGYSNRESLRLLLQDADRSNFLLSPALVS
AWYQPERNSITFPYASFNPPYYSYEYPQAYNYGGQGGTAGHELVHGFDDQGVQFGPDGS
LSRCTWYDCGWMDKRSKDGFNDMAQCVVTHYSTFCCPEQEGNIHCANGATTQGENIADI
GGEHAAYIAYREYIKSLGHEEKRLPGLERYTPNQIFWITYGYSWCRSVTEEYLISQLLT
DPHAPSACRTNQVVQSIPAFGRDFGCSLGDRMYPAPEQRCSVWVQE*

Figure 65B

GAAAAGCCTACGCAGTCATGCTCAAACTCGTCGCCCTAGCCTGCTTAGCTGCGATCTGC
CTCGCTCAGGGTGGACCCGAAGGACCCCCTCCTTTCCTGAAGAGTGCTCCCCCCGAGAA
GGTGAAGGAATTCGACGCTCTTTTCGCCGATGCTGGAGGTCTGACTGATGCCCAGATCG
ACGCTAAGGTCAAGGGATGGATCGGAAAGCAGAGTCAGGATATCCAGAACGCATTCAAT
GCCTTCGAGAGTGAGGTGAAAGCCGCCCAGCAACAGGGTGAGCAAGCTCACCAGGCTGC
TGTCGCCAAATTCAGCGCTGAAGCCAAGGCTGCCGACGCCAAGCTCACCGCTATCGCCA
ATGACGCCTCCAAGACGAATGCACAGAAGGGAGCCGAGATCGACGCCGTTCTCAAGGGT
CTTCCACAAAAAGTCCGTGATGAAATCGAGAATGCAATGAAGGGATAAGAGGGCGTTGT
TTTGTATATATGAACCGATAAATATGCAAAATAAATATCTCCCCTTCAAAAAAAAAAAA
AAAAAAAAAAAAAAAAAAAA

Figure 66A

MLKLVALACLAAICLAQGGPEGPPPFLKSAPPEKVKEFDALFADAGGLTDAQIDAKVKG
WIGKQSQDIQNAFNAFESEVKAAQQQGEQAHQAAVAKFSAEAKAADAKLTAIANDASKT
NAQKGAEIDAVLKGLPQKVRDEIENAMKG*

Figure 66B

CAGTCATGCTCAAACTCGTCGCCCTAGCCTGCTTAGCTGCTATCTGCCTCGCTCAGGGT
GGACCCGAGGGACCCCCTCCTTTCCTGAAGAGTGCTCCCCCCGAGAAAGTGAAGGAATT
CGACGCTCTTTTCGCCGATGCTGGAGGTCTGACTGATGCCCAGATCGACGCTAAGGTCA
AGGGATGGATCGGAAAGCAGAGCCAGGACATCCAGAATGCATTCAATGCCTTCGAGAGT
GAGGTGAAAGCCGCCCAGCAACAGGGTGAGCAAGCTCACCAGGCTGCTGTCGCCAAATT
CAGCGCTGAGGCCAAGGCTGCCGACGCCAAGCTCACCGCTATCGCCAATGACGCCTCCA
AGACGAATGCGCAGAAGGGAGCCGAGATCGACGCCGTTCTCAAGGGTCTTCCACAAAAA
GTCCGTGATGAAATCGAGAATGCAATGAAGGGATAAGAGGGCGTTGTTTTGTATATATG
AACCGATAAA

*Figure 67A*

MLKLVALACLAAICLAQGGPEGPPPFLKSAPPEKVKEFDALFADAGGLTDAQIDAKVKG
WIGKQSQDIQNAFNAFESEVKAAQQQGEQAHQAAVAKFSAEAKAADAKLTAIANDASKT
NAQKGAEIDAVLKGLPQKVRDEIENAMKG*

*Figure 67B*

```
   1 tttgagatgt ggattctcgc tgcattagtg gtaacggcac ttgccgcaaa accgactacg
  61 gttgaggagt tccacgctca acctatagag gagcacgtta aagacctcag tggacaagct
 121 tttgttgact acatcaacga gcatcaatct ttctataggg cggaatattc accagaggcg
 181 gaagcgttcg tgaaagctcg gataatggac tcgaagtatt tagtggaacc taagaaagaa
 241 gaagtgctgg aggacgtata tggcaatgat ccgcctgcga gcttcgacgc tcgcacccac
 301 tggcctgaat gcagatccat tggcaccatt cgtgaccagt catcatgcgg ttcatgttgg
 361 gcagtatcct cagcggaagc catgtcggat gaaatatgtg ttcagtcgaa cagtacgata
 421 agggtgatga tttccgactc agatatactc tcgtgctgtg gaatttcctg tggatatgga
 481 tgccaaggtg gttggccgat cgaagcatac aaatggatgc aacgtgacgg tgttgttaca
 541 ggtggaaaat acagacagaa gaaagtgtgc aagccgtacg ccttctatcc gtgtgggcac
 601 caccaaaatg acccctacta tggaccttgc ccaggggggtt tatggcccac tccaaaatgt
 661 cgaaagacgt gtcagcgaaa atacaacaag tcctaccaag aagacaagca ctttgcaacg
 721 agggcctact acctcccgaa taatgaaagg aacatcaggc aagagattta caagaacgga
 781 cctgtggtcg cagctttcag agtctaccag gacttcagtt attacaaaaa aggaatctat
 841 gtgcacaagt ggggtggtca aacaggagca catgctgtca aagtcgttgg ttggggcaga
 901 gaaaatgcaa cagattactg gctgattgcg aactcgtgga acactgactg gggagaaagc
 961 ggctatttcc gtattgttcg tsgaactaac gagtgcggta tcgaagcaca aatggtcggt
1021 ggagcgatga gagtgtgaaa tactcgacta tgacgccgtt ctttaatcgg ctatcgtaat
1081 gaatcattct gag
```

*Figure 68A*

```
MWILAALVVTALAAKPTTVEEFHAQPIEEHVKDLSGQAFVDYINEHQSFYRAEYSPE
AEAFVKARIMDSKYLVEPKKEEVLEDVYGNDPPASFDARTHWPECRSIGTIRDQSSC
GSCWAVSSAEAMSDEICVQSNSTIRVMISDSDILSCCGISCGYGCQGGWPIEAYKWM
QRDGVVTGGKYRQKKVCKPYAFYPCGHHQNDPYYGPCPGGLWPTPKCRKTCQRKYNK
SYQEDKHFATRAYYLPNNERNIRQEIYKNGPVVAAFRVYQDFSYYKKGIYVHKWGGQ
TGAHAVKVVGWGRENATDYWLIANSWNTDWGESGYFRIVRGTNECGIEAQMVGGAMR
V*
```

*Figure 68B*

TTTAATTACCCAAGTTTGAGCAGCATGCCATACCTCGCATTCATTGTCGCACTACTAGC
CTGTACTGTTATGTCGGGTCACGGTCAAATGACGGGAGGATTAACGAAGCAGGATCCCA
ATGATCCTGAACACATGGCTAGAGCATGGAAGGCCGCAAAAGGCATCAATGAGGACGCT
TCTAACGCTGGACCGTACCACATGATTCCTATTAAGATCGTAAAGGCCGAATCTCAAGT
TGTCGCTGGAGTTAGGTACATATTTGAAGTGCTGTTCGGCGAATCCACGTGTAAGAAAG
GACATATGGCTGCAACCGAACTTTCTGCCTCCAACTGTGAGCTGAAAGAAGGAGGAAAC
CGAGCTCTATACAAAGTTGAGCTTTGGGAGAAGCCATGGGAAAACTTCGAGCAGTTCAA
CGTGGAGAAGATCCGAAATGTTGCCGCCGGCGAGCAAATCTAGCCGCTTCTTTAAGACA
CCTCACTGCGCCGGCGTCTATAT

*Figure 69A*

MPYLAFIVALLACTVMSGHGQMTGGLTKQDPNDPEHMARAWKAAKGINEDASNAGPYHM
IPIKIVKAESQVVAGVRYIFEVLFGESTCKKGHMAATELSASNCELKEGGNRALYKVEL
WEKPWENFEQFNVEKIRNVAAGEQI*

*Figure 69B*

TTAGTTTTGCAAGGGTTTGGTGCAGGAAACTGGGATCAACTTCGAGTTTGCTAACGAGA
CTCTTAACCGATCCTCATTCACCAGCACCTTATCGCGTTCTTGGAACGCTGCAGAACTT
CCCCGCATTTAAAGAAGCCTTCAATTGTCCGAAATCACCTTACGCACCAGATAAACACT
GTAACGTCTGGGTATCGGAGCTAGATACATCACATGGTGAGCCCAAGGTAAAAACAGAG
CTGAATATAGCGGCGCCTCCACAGATCACTCCGAACGACAAGGAAAAGTATGATGCCGC
CAAGGTGGCCATCAGTTTCTTTCAGGAATCCGTCAATACCTCTGTTGATCCATGTGAAG
ATTTCTACAAGTATGCTTGCGGAAAGTACCAAAAAGCGGTCTCCTTCCACTATGCCGAC
GCTAAAAACCTCGTAGCAATGGCTAACCAATTGACAAATAAGGACTACCAGAAAGTTAT
CAAGAGCTCAACAGCATTAACCAAGGAGAAGGCGTTCTTCGATGCGTGCGTAGCTGCAA
CGAAAGACTCTGGTCACAATAATCAGATCCTCATTTCCAATAATTATCTCATGAAACGA
GTAAGGAAGTTGGCTGACTACCTTGGAGCTGAGTTTACCTATGCACTTGGCGGCAGAGT
GGAGCGACTGCCCAATAAGGTTCAGCTGGCAAACGCTTTGGGTTACCTCTCCTTTGACC
AGAACATTCAAACGCTGGTGACACCTCTTGTCGACACATATTGGCCAGACCCGAATAAA
GGATACACGATGTTCCTCGATCAGAATACTGCATATATGAGCAAGACTTTCTACCACCC
GGATGCTTTCAAAACCATTAAGGAAAACTATATTAATTCTGCGACTAAGGTCATAGAAA
CGTTCGTAAAAACTCAGAATAAACCGATTGATCCTAAACTCAAGGATAAGGTGAGAGGC
CTGGTGGAATTTGAACAAATGATCGCGAACAAGTACAGCACCGATGATGACACACGCCG
AATCTACTTGCGATCATGGAATCTCAGAAGCATTAGGGAGCTACAGAACCAATTTGGTT
TCGTTGATTGGCAAACATATATGAAGATGGTTCCCATGGTTGCGCAAAACAAGGTGCAA
TCTGCGGATTTCAGAGTTTCCGTCATGGAGCCGGGTCAGTACGCCAACATGAGTCGTGA
TTATGCTGGATTTGACAAAGAAAAACTAGTGAACTACTTGTTTATGCGCCTGCTGCTAT
CTAATGCTCAGTATTTGCCAACCTATGCCAGCAGTTTCAAAGAGATGCCGGAAGAACCA
CTAGTTCTTGGACGGAAGCGACGCAACATCCATTTCTCAAAATCCGACACCCTTACTGA
TACGCAAGCGAATTGTGCAAAGGTGGCGAATGAGCTGATGATGTTTGCGAATGGACGAG
TTTTCGTCGACTATGTGTATCCCGACGAGAAATACAAGGACCTAATAAGGAGCAGTGCT
GGTGGTGTGATGCACAATGTTATCCATGCTTTCCAAAGCATGGTTGATCAACTTGACTG
GATGAGCGAAGCGACAAAGAGAAAAGCAATAGAAAAGAGCATGAATATCATAACAAACA
TAGCTTTCCCGGATTGGATTATGGACAACGCAAAGTTGGACCTGTATTACAAAAGCATC
ACCTTCGACCCAACCAAGGAAAACTACTACGATATTTGGACAAAGCTTACCATATTCAA
TATAGAAGCTCAGTACAAGCACTTAACAATGGCCACAGCTGATTACGAAGAATTCCTTA
TGCCGCCAGGTATTGTTAATGCATGGTATCAGCCGGAATTGAATACGATCACATTCCCC
GCTGGAATACTTCGTCCTCCTTATTTCCATCCTGATTGGCCAGCATCAATCAAATACGG
TGGAATTGGTCTAATAGCAGGACATGAACTGATTCACGGCTTTGACGATCAAGGTGTTC
AGTGGGGTCCAAAGGGACACATCTCTTACCCAGAGAAGAACTGTATTGGATGGATGGAT
GAGCAATCAACGAAAGGTTTCAATCGCTTGGCTCAATGTGTCATCGATGAGTATAGCAC
GTTCTGCCCTCTTGACAACAGGACATACACACCAAATTGTGTGAATGGAGCGCAGACCC
AAGGAGAGAACATCGCCGATAATGGAGGGGTACACGCGGCGTTCCGCGCTTACCGTACA
CACATCTCTCTCAATGGACCAGATCCACAGCTTCCTGACAGACTGTTCGGGCAGTTCAC
ACATGATCAGCTGTTCTTCTTGAACTTCGCACAGGTGTGGTGCGAGAAACGACGAGTCG
ATGACAGACTTTACCAGCAGCTCATGGTTGACCCCCACTCTCCAGCGATGTACCGAGTG
TTCGGTACTCTTCAGAACTATCCGGCCTTCAGAGCCGCATTCAACTGTCCGCTTAATTC
GCGATACGCTCCTAAGGATCATTGCAATGTTTGGGTGCCGAATTATATGCCATAAGAGG
AAGTTCTTCCTTGAAAACTACCTACTCAACATAAATAAAGTCTGTGATTTTAAAAAAAA
Aaa

*Figure 70A*

SFARVWCRKLGSTSSLLTRLLTDPHSPAPYRVLGTLQNFPAFKEAFNCPKSPYAPDKHC
NVWVSELDTSHGEPKVKTELNIAAPPQITPNDKEKYDAAKVAISFFQESVNTSVDPCED
FYKYACGKYQKAVSFHYADAKNLVAMANQLTNKDYQKVIKSSTALTKEKAFFDACVAAT
KDSGHNNQILISNNYLMKRVRKLADYLGAEFTYALGGRVERLPNKVQLANALGYLSFDQ
NIQTLVTPLVDTYWPDPNKGYTMFLDQNTAYMSKTFYHPDAFKTIKENYINSATKVIET
FVKTQNKPIDPKLKDKVRGLVEFEQMIANKYSTDDDTRRIYLRSWNLRSIRELQNQFGF
VDWQTYMKMVPMVAQNKVQSADFRVSVMEPGQYANMSRDYAGFDKEKLVNYLFMRLLLS
NAQYLPTYASSFKEMPEEPLVLGRKRRNIHFSKSDTLTDTQANCAKVANELMMFANGRV
FVDYVYPDEKYKDLIRSSAGGVMHNVIHAFQSMVDQLDWMSEATKRKAIEKSMNIITNI
AFPDWIMDNAKLDLYYKSITFDPTKENYYDIWTKLTIFNIEAQYKHLTMATADYEEFLM
PPGIVNAWYQPELNTITFPAGILRPPYFHPDWPASIKYGGIGLIAGHELIHGFDDQGVQ
WGPKGHISYPEKNCIGWMDEQSTKGFNRLAQCVIDEYSTFCPLDNRTYTPNCVNGAQTQ
GENIADNGGVHAAFRAYRTHISLNGPDPQLPDRLFGQFTHDQLFFLNFAQVWCEKRRVD
DRLYQQLMVDPHSPAMYRVFGTLQNYPAFRAAFNCPLNSRYAPKDHCNVWVPNYMP*

Figure 70B

ACAGATGAGATCTCTTTGCCTGCTGCTCGCTGTGGTGCTTGTCGCCGTCCACGCAAAAA
TGCAGAACGTCACCGTCAAGGGGACCACCATCTGCAACAAGAAGCGAATGGCCGATGTG
ACGGTGGAACTGTGGGAGAGAGACACCCTCGACCCCAACGACCTCCTCGACTCCAAGAA
GACCTCTAGGGAAGGCGAGTTCCTCGGGAAAGGTGGTCAGAACGAAGTCGGCTCGATTG
AGCCATTCCTCAAAATTACACACACCTGCAATGTCAAGAAACCGGGCTGCAAGAGAATC
ACTGAGTTCGACATCCCGAAGTCGAAGATCGACACGGTCTACGACATGACCTACGTGAC
GCTGGATATCATTTCCGCAGTCGATAAGGAGAAGTGCTACATGAACGCGTTGTTTTCCA
CGGCAATATTTTGTATAGACAGATGAACATTCCTTCCGAAAAAAAAAAAAAAAAAAAAA

Figure 71A

MRSLCLLLAVVLVAVHAKMQNVTVKGTTICNKKRMADVTVELWERDTLDPNDLLDSKKT
SREGEFLGKGGQNEVGSIEPFLKITHTCNVKKPGCKRITEFDIPKSKIDTVYDMTYVTL
DIISAVDKEKCYMNALFSTAIFCIDR*

Figure 71B

AGTGCCATTGCCGAGGGATGGCTCGCCTTGTACTGTTACTCGCACTATTTACCCTGGCT
GTGGCCAGCGTCCACAGGAGGACATTCCACCAGCCGCGTCGTTACGTGAAGTCGGTGTC
GCTTTCGCGTCAACCAACACTTCGTGAACGATTGCTGGGAACTGGCAGTTGGGAGGACT
ACCAGAAGCAACGCTATCACTACCAGAAGAAACTTCTGGCAAAATATGCGGCAAACAAG
GCGTCGAAACTACAGTCCACCAATGAGATTGACGAGCTCCTTCGTAACTATATGGATGC
ACAATATTTCGGCACCATCCAAATCGGAACTCCAGCGCAGAATTTCACAGTGATTTTCG
ACACCGGTTCATCCAACCTCTGGGTGCCGTCCAGGAAATGCCCATTCTACGACATCGCG
TGCATGCTTCACCACCGCTACGATTCTGGAGCATCGTCAACGTACAAGGAGGATGGACG
TAAGATGGCTATTCAATATGGAACTGGCTCAATGAAGGGCTTCATTTCTAAGGATAATG
TCTGCATCGCCGGAATTTGTGCTGTCGAGCAACCGTTTGCCGAGGCAACGAGCGAGCCA
GGCCTCACGTTCATCGCTGCGAAGTTCGACGGAATCCTTGGCATGGCCTTCCCTGAAAT
CTCCGTTCTCGGTGTACCACCAGTATTCCACACGTTCATTGAACAGAAGAAAGTGCCGA
GCCCGGTGTTCGCTTTCTGGCTCAACAGAAATCCCGACTCGGAACTCGGAGGGGAGATC
ACCCTCGGTGGAATGGACCCCCGCCGATATGTTGAGCCGATCACATGGACCCCAGTAAC
TCGACGAGGATATTGGCAGTTCAAGATGGACAAGGTTCAAGGAGGATCAACGTCCATTG
CCTGCCCCAACGGATGCCAGGCTATCGCTGACACTGGTACTTCACTGATTGCCGGACCT
AAGGCTCAAGTTGAGGCTATCCAGAAATTCATTGGTGCTGAGCCACTTATGAAGGGAGA
GTACATGATTCCCTGCGACAAGGTGCCTTCCCTCCCGGAGCTGTCCTTCGTTATCGAGG
GCCGGACTTTCATCCTCAAGGGTGAAGATTACGTATTGACCGTGAAAGCTGGTGGTAAA
TCGATCTGCCTGTCCGGTTTCATGGGAATGGACTTCCCGGAGAGGATCGGAGAGCTGTG
GATTCTTGGAGACGTCTTCATTGGAAAGTACTACACTGTCTTCGATATTGGCCAAGCTC
GTCTTGGATTTGCTCAGGCTAAGTCAGAAGATGGCTATCCGGTTGGTCCTGCTGTTCGA
AGGTACAACAAGTTCTCGGAGGACAGCGACAGTGACGAGGATGATGTATTCACTCTCTA
AATAACATGTATCCACAATTTGCTCTAATCTCGATACGTGTACCGTGTCTCACGTGTTT
CCACTTTTGATAAACTGATTATTCTG

*Figure 72A*

MARLVLLLALFTLAVASVHRRTFHQPRRYVKSVSLSRQPTLRERLLGTGSWEDYQKQRY
HYQKKLLAKYAANKASKLQSTNEIDELLRNYMDAQYFGTIQIGTPAQNFTVIFDTGSSN
LWVPSRKCPFYDIACMLHHRYDSGASSTYKEDGRKMAIQYGTGSMKGFISKDNVCIAGI
CAVEQPFAEATSEPGLTFIAAKFDGILGMAFPEISVLGVPPVFHTFIEQKKVPSPVFAF
WLNRNPDSELGGEITLGGMDPRRYVEPITWTPVTRRGYWQFKMDKVQGGSTSIACPNGC
QAIADTGTSLIAGPKAQVEAIQKFIGAEPLMKGEYMIPCDKVPSLPELSFVIEGRTFIL
KGEDYVLTVKAGGKSICLSGFMGMDFPERIGELWILGDVFIGKYYTVFDIGQARLGFAQ
AKSEDGYPVGPAVRRYNKFSEDSDSDEDDVFTL*

*Figure 72B*

GGTACTGCAGGGTTTAATTACCCAAGTTTGAGGAGCATGCCATACCTCGCATT
CATTGTCGCACTACTAGCCTGCACTGTTATGTCTGGTCACGGTCAAATGACGG
GTGGATTAACGAAGCAGGACCCCAATGATCCTGAGCACATGGCGAGAGCATG
GAAGGCGGCGAAAGGTATCAATGAGGATGCATCCAACGCTGGACCGTACCA
CATGATTCCCATTAAGATTGTCAAGGCTGAATCTCAAGTCGTGGCTGGGGTTA
GATACATATTTGAAGTATTGTTCGGCGAATCAACATGTAAGAAAGGACATAT
GGCTGCAACAGAGCTTTCTGCCTCCAACTGTGAACTAAAAGAAGGAGGAAAC
CGAGCTCTGTATAAAGTGGAGCTCTGGGAGAAGCCATGGGAGAACTTTGAGC
AGTTCAATGTTGAGAAGATCCGAAATGTTGCTGCTGGCGAGCAAATCTAACC
TGCTTCTTTAAGACACCTCACTGAATATTGAATATTTTGTATGTCATGTATAAT
ACGACGCGATTTTTTTATCTCACGTACTTTTTTCACTGTGACAATTGCCTTCT
CTGC

*Figure 73A*

MPYLAFIVALLACTVMSGHGQMTGGLTKQDPNDPEHMARAWKAAKGINEDAS
NAGPYHMIPIKIVKAESQVVAGVRYIFEVLFGESTCKKGHMAATELSASNCELKE
GGNRALYKVELWEKPWENFEQFNVEKIRNVAAGEQI*

*Figure 73B*

GAAAAGCCTCCATAGTCATGCTCAAGCTCGTTGCACTCGTTTGCCTGGTTGCA
ATCTGCTTCGCTCAGGGACCACAAGGACCCCCTCCGTTCCTGCAAAGTGCTCC
AGCGGCTGTTCAACAAGACTTCGACAAGCTCTTCGTCAATGCTGGCTCCAAG
ACTGATGCAGAAATCGACAAAATGGTCCAAGATTGGGTTGGCAAACAAGATG
CATCCATCAAGACCGCATTCGATGCGTTCGTGAAGGAAGTGAAAGCCGCTCA
AGCGCAAGGTGAAGCTGCCCATCAGGCTGCTATCGCCAAGTTCAGCGCAGAG
GCCAAAGCGGCTGATGCCAAGCTGAGCGCAATTGCGAACGACAGGTCGAAG
ACAAACGCGCAAAAGGGAGCTGAGATCGACTCGGTACTCAAGGGACTTCCTC
CAAATGTCCGCACAGAGATCGAAAACGCCATGAAAGGATAAGAAGTCTCTAT
TTTGTATATATGAACCGATAAATATGCACAATAAAAAAAAAAAAAAAAAA
AAAAAAAA

*Figure 74A*

MLKLVALVCLVAICFAQGPQGPPPFLQSAPAAVQQDFDKLFVNAGSKTDAEIDK
MVQDWVGKQDASIKTAFDAFVKEVKAAQAQGEAAHQAAIAKFSAEAKAADAK
LSAIANDRSKTNAQKGAEIDSVLKGLPPNVRTEIENAMKG*

*Figure 74B*

GAAAGGTTTAATTACCCAAGTTTGAGGATGAAGATTGCCCTGGTTGTTCTGCTGTTAGT
CGCCTACGCAAATTCTGCGGACATCTTCAGAACTGAATTTGGAGCTAAAATAAAAGCAG
AGGCGGATAAAAGTAAGACGAAACTAAATATCTCCTCTCTTCTTCAAGTCCGTGGGAAA
TTCCTCAAGTTAAGACAACAGATCAAGGAGAGCTTAGCTCTGACCCCGGAACGAAAAGA
GTTGTTGCATAAGTTGATGCAGAAATTAGTACACATCAAAAAGGATCATGTTCATAAGG
GTGGTGACTCAATCGATGAAATCAATAAGAAGGTTGGAATGTCAGATCTGCTCTACGAT
GGTGATATGGTTCTAACGAAAGAGCAAGCCGAGGAAATGGTTAGCGATATCGACGGAAG
TGGAAGCAACCGTGCAAAGCGTCAAGCGTATCGTAACAAACTTTATCCGAAAACACTTT
GGACCGATGGAGTTATCTATTATTTCCATCCTAGTGCAACGAATAGCATGCGAAGTGTG
TTCCTGAAAGCAGCAAAAGAATGGAGCTCTCAAACGTGTATCGATTTCCATGAGGATGT
GGTTGGAATGGGCCCAAACAGGATCAAGGTTTTCAAAGAGAAAGGTTGTTGGTCGATGG
TTGGACGACTCCCTCGTCCACAGGAGCTTTCGTTGGGAAGAGGATGTGATACGATTGCC
ACAGCACAACACGAGATCGGCCATGCGCTGGGATTCTTCCACCAGCAGGCTAGACACGA
TCGCGATGACTACATTGTATTTAATTCAGAGAATGTAGTGCCGCGATATCTGGATCAAT
TCAAGAAACAGAGCAAAGAAACAAACGATAATTACGGATTAACTTATGATTACGGAAGC
ACCATGCAGTACGGATCGACCAGCGGATCCCAAAATGGAAAACCTACAATGGTGCCAAA
AGATCCTAAATATATAGAAACCCTGGGATCACCTTTCATTGCATTCTACGATTTACTGG
CAATAAATACGCACTACAAATGTCTTGAGAAATGCGATAATAATGGGGCACAATGCAAA
ATGGGTGGATTCCCTAATCCAAGAGATTGCTCAAAATGCATTTGTCCCAGTGGATACGG
TGGCGCTACATGTGACCAGAAACCTGAAGGATGTGGTGAAGTACTTGAAGCAACGAAGG
AGGCTAAAACCCTCAAAAGTGAAATTGGAGATAAAAGTGCAGGAGATGAGGACAGAGAG
GACATGACCAAGTGTTACTATTGGATCAAGGCACCGGAAGGATCGAAAGTTGAGGTTAA
GATCGTAAACCTAGCTAAAGGTCTTGCCATTGATGGATGCAGATATTGGGGTGTGGAAA
TTAAAACTCAGGAGGATCAACGTGCTTCCGGATACAGATTCTGCGCTCCCGAAGATGCT
GGCGTCACTTTGGAGTCGCACTCGAATATTGTCCCTATAATAGCGTTCAATAGACACGG
CTCTACTGAATTTGAATTACAGTACCGAATCGTATAATTCTGCGTGACCAACGCTTCTC
CTAAGAGACGAGAAAGTTCTGCAACAATACTTTATTCATGTATAACAATATAGGAGAGT
TTTTCTTAGTAGAAGTACTTTCTTTGTTGGTTCTCCAGAAATAAACGATTTCCATGCAA
AAAAAAAAAAAAAAAAAAAA

Figure 75A

MKIALVVLLLVAYANSADIFRTEFGAKIKAEADKSKTKLNISSLLQVRGKFLKLRQQIK
ESLALTPERKELLHKLMQKLVHIKKDHVHKGGDSIDEINKKVGMSDLLYDGDMVLTKEQ
AEEMVSDIDGSGSNRAKRQAYRNKLYPKTLWTDGVIYYFHPSATNSMRSVFLKAAKEWS
SQTCIDFHEDVVGMGPNRIKVFKEKGCWSMVGRLPRPQELSLGRGCDTIATAQHEIGHA
LGFFHQQARHDRDDYIVFNSENVVPRYLDQFKKQSKETNDNYGLTYDYGSTMQYGSTSG
SQNGKPTMVPKDPKYIETLGSPFIAFYDLLAINTHYKCLEKCDNNGAQCKMGGFPNPRD
CSKCICPSGYGGATCDQKPEGCGEVLEATKEAKTLKSEIGDKSAGDEDREDMTKCYYWI
KAPEGSKVEVKIVNLAKGLAIDGCRYWGVEIKTQEDQRASGYRFCAPEDAGVTLESHSN
IVPIIAFNRHGSTEFELQYRIV*

Figure 75B

ACTTCAAGCGATGTTCCGTCCTGCTACTGCCGTCCTTCTATTGTTGGCCGCGTCCAGCA
CATTTGCTGGATTTTTCGATGATGTTGGAGGCTTACCCAGTGGTGTGGGAGATTTTTTC
ACAAAGCAGTTCAACAATGTGAAGGATCTTTTTGCTAAAGATCAAGATACTCTTGAGAA
GAATATCAATCTGGTAAAGGATCTATTGATTGCCATTAAGGAGAAGGCTAAGATGCTGG
AACCGATGGCCAACGAGGCTCAGAAGAAGACATTAGGGCAGGTGGACAACTATCTCAAT
GAAGTTCAACAGTTCGGCGATCAGGTAGCCAAGGAGGGTTCTACGAAATTTGAGGAGAA
CAAAGGGAAATGGCAGCAAATGTTGAACGATATCTTCGAGAAAGGTGGACTGGACAGCG
TGATGAAGTTGCTCAATCTGAAGTCCGGCGGTCGCTGCACGTTAGCCGCTGCACTCGTC
GCTCCCGTTGTGCTCGCGCTCATCCGCTAATTCACTTCTACCGCCGCCGACTACTGTAG
TTTACCCTGTGCCTGTGTGTGATATGTGGATTTGTGCATGATGTGTATCTATGATTTGT
GATTTATTTTTCTCTTGTACTTCCATGAATTCAGCTCTGGTATTCTGAGACGGACCAAC
ATCTCCGCAGTACTTTTTTGTATTGTTATCATCACCGTAATCCTGTGACTGGCGTAAAA
TGTTTAGTTTTCCGATAAAATACATTTCGAAAAAAAAAAAAAAAAAAAAaa

*Figure 76A*

MFRPATAVLLLLAASSTFAGFFDDVGGLPSGVGDFFTKQFNNVKDLFAKDQDTLEKNIN
LVKDLLIAIKEKAKMLEPMANEAQKKTLGQVDNYLNEVQQFGDQVAKEGSTKFEENKGK
WQQMLNDIFEKGGLDSVMKLLNLKSGGRCTLAAALVAPVVLALIR*

*Figure 76B*

SEQUENCE LISTING

```
<160> NUMBER OF SEQ ID NOS: 114

<210> SEQ ID NO 1
<211> LENGTH: 1451
<212> TYPE: DNA
<213> ORGANISM: Necator americanus

<400> SEQUENCE: 1

atgttttctc ctgtagtcgt cagtgtggta ttcacaatcg ccttctgcaa tgcgtctcca      60

gcaagagaca gcttcggctg ctctaacagt gggataactg acagcgaccg gcaagcgttc     120

ctcgacttcc acaacaatgc tcgtcgacgg gttgcgaaag gccttgagga tagcaactcc     180

ggcaaactga atccagcgaa gaacatgtac aagctgtcat gggactgtgc aatggaacag     240

cagcttcagg atgccatcca gtcatgccca agcggctttg ctgggattca aggtgttgcg     300
```

-continued

```
cagaatacaa tgagctggtc aagctctggt ggataccccg atccatcggt aaagatagaa    360
ccaacgctct ccggctggtg gagtggtgcg aaaaagaacg gcgtaggccc ggacaacaaa    420
tacaccggtg gtggtctctt cgccttctct aacatggtat actccgaaac gacgaaactt    480
ggctgcgctt acaaggtttg cggcactaaa ctggcggttt catgcatcta taatggagtc    540
gggtacatca caaatcaacc tatgtgggag acaggtcagg cttgccagac aggagcagac    600
tgctccactt acaagaactc aggctgcgag gacggccttt gcacgaaggg accagatgta    660
ccagaaacaa accagcagtg cccctcaaac accggaatga ctgattcagt cagagatact    720
ttcctatcgg tgcacaatga gttcagatcg agtgttgccc gaggtctgga acccgacgct    780
ctgggcggaa atgcaccaaa agcagctaaa atgctcaaga tggtgtatga ctgtgaagtg    840
gaagcatcgg ccatcagaca tggaaataaa tgcgtctatc aacattctca tggtgaagac    900
agacctggac taggagaaaa catctacaaa actagtgtac tcaaattcga caagaacaaa    960
gcagccaagc aggcttcaca actctggtgg aatgagttaa aagagtacgg cgtcggccca   1020
tccaacgtcc ttaccactgc gttatggaat agacccaaca tgcagattgg tcactacacc   1080
cagatggcat gggacaccac ctacaaactt ggatgtgcag ttgttttctg caatgatttc   1140
acattcggcg tttgtcagta tgggccagga ggcaattaca tgggtcatgt catctacact   1200
atgggccagc cgtgctctca gtgttcgcct ggtgctactt gcagcgtgac cgaaggcttg   1260
tgcagcgctc cttaatcagt caacaataaa tatcttacag tgatgttgtt gcttacaaat   1320
tgcttctttt ccaatagaaa taccaatgtc aacatcacga gtttctttaa attcatcact   1380
tccactacta ggggtgattt gaataaaatt tcatttcata aagcaattac atccgcaaaa   1440
aaaaaaaaaa a                                                        1451
```

<210> SEQ ID NO 2
<211> LENGTH: 424
<212> TYPE: PRT
<213> ORGANISM: Necator americanus

<400> SEQUENCE: 2

```
Met Phe Ser Pro Val Val Val Ser Val Val Phe Thr Ile Ala Phe Cys
1               5                   10                  15

Asn Ala Ser Pro Ala Arg Asp Ser Phe Gly Cys Ser Asn Ser Gly Ile
            20                  25                  30

Thr Asp Ser Asp Arg Gln Ala Phe Leu Asp Phe His Asn Asn Ala Arg
        35                  40                  45

Arg Arg Val Ala Lys Gly Leu Glu Asp Ser Asn Ser Gly Lys Leu Asn
    50                  55                  60

Pro Ala Lys Asn Met Tyr Lys Leu Ser Trp Asp Cys Ala Met Glu Gln
65                  70                  75                  80

Gln Leu Gln Asp Ala Ile Gln Ser Cys Pro Ser Gly Phe Ala Gly Ile
                85                  90                  95

Gln Gly Val Ala Gln Asn Thr Met Ser Trp Ser Ser Ser Gly Gly Tyr
            100                 105                 110

Pro Asp Pro Ser Val Lys Ile Glu Pro Thr Leu Ser Gly Trp Trp Ser
        115                 120                 125

Gly Ala Lys Lys Asn Gly Val Gly Pro Asp Asn Lys Tyr Thr Gly Gly
    130                 135                 140

Gly Leu Phe Ala Phe Ser Asn Met Val Tyr Ser Glu Thr Thr Lys Leu
145                 150                 155                 160
```

-continued

```
Gly Cys Ala Tyr Lys Val Cys Gly Thr Lys Leu Ala Val Ser Cys Ile
                165                 170                 175

Tyr Asn Gly Val Gly Tyr Ile Thr Asn Gln Pro Met Trp Glu Thr Gly
            180                 185                 190

Gln Ala Cys Gln Thr Gly Ala Asp Cys Ser Thr Tyr Lys Asn Ser Gly
        195                 200                 205

Cys Glu Asp Gly Leu Cys Thr Lys Gly Pro Asp Val Pro Glu Thr Asn
    210                 215                 220

Gln Gln Cys Pro Ser Asn Thr Gly Met Thr Asp Ser Val Arg Asp Thr
225                 230                 235                 240

Phe Leu Ser Val His Asn Glu Phe Arg Ser Ser Val Ala Arg Gly Leu
                245                 250                 255

Glu Pro Asp Ala Leu Gly Gly Asn Ala Pro Lys Ala Ala Lys Met Leu
            260                 265                 270

Lys Met Val Tyr Asp Cys Glu Val Glu Ala Ser Ala Ile Arg His Gly
        275                 280                 285

Asn Lys Cys Val Tyr Gln His Ser His Gly Glu Asp Arg Pro Gly Leu
    290                 295                 300

Gly Glu Asn Ile Tyr Lys Thr Ser Val Leu Lys Phe Asp Lys Asn Lys
305                 310                 315                 320

Ala Ala Lys Gln Ala Ser Gln Leu Trp Trp Asn Glu Leu Lys Glu Tyr
                325                 330                 335

Gly Val Gly Pro Ser Asn Val Leu Thr Thr Ala Leu Trp Asn Arg Pro
            340                 345                 350

Asn Met Gln Ile Gly His Tyr Thr Gln Met Ala Trp Asp Thr Thr Tyr
        355                 360                 365

Lys Leu Gly Cys Ala Val Val Phe Cys Asn Asp Phe Thr Phe Gly Val
    370                 375                 380

Cys Gln Tyr Gly Pro Gly Gly Asn Tyr Met Gly His Val Ile Tyr Thr
385                 390                 395                 400

Met Gly Gln Pro Cys Ser Gln Cys Ser Pro Gly Ala Thr Cys Ser Val
                405                 410                 415

Thr Glu Gly Leu Cys Ser Ala Pro
            420

<210> SEQ ID NO 3
<211> LENGTH: 1893
<212> TYPE: DNA
<213> ORGANISM: Necator americanus

<400> SEQUENCE: 3

ggtactgcag ggtttaatta cccaagtttg agacccaacg ccatgatttg gcgaacgtgg      60

caagttctcg tggttctgta tgcggcgctg tccattacag ttgtgaacgc ctataaacac     120

attagctccg atcacgttgt aaatacaaca ctgggtcaga ttcgaggagt accacagaat     180

ttcgaaggca aaaaagttac cgcttttctt ggtgtgccat atggtcaacc accgactggg     240

gaactacgat tcagcaatcc gaaaatggtg cagcgttggg aaggtataaa gaatgctaca     300

acaccggctc agccatgctt ccacttccct gacagtaaat ttaagggatt tcgtgggtca     360

gagatgtgga atccgaaagg aaatatgacc gaggattgct tgaatatgaa tatctgggtc     420

ccacacgatg ctgatggttc cgtgattgta tggattttcg gaggcggctt cttcaccggt     480

tcaccatctt tagatgttta caacggtact gctctagcag ccaagaaacg taccattgtt     540

gtgaacataa actatcgatt gggtcccttc ggtttccttt atctcggtga tgattctcgt     600
```

-continued

```
gcacaaggga atatgggact gcaagatcaa caagttgcat tgcgatgggt gcataaacat    660

ataagctcct ttggtggaga tccgagaaaa gtcactcttt tcggcgaagc atcaggcgct    720

gcttcagcaa ccgctcatct agcagcaccg ggaagctatg agtttttcga taagataatt    780

ggcaacggtg gcacaatcat gaatagttgg gccagtcgaa caaatacatc gatgcttgag    840

ctgtcaatga aacttgctga acggttgaac tgtaccaaga aaagaaaaga cccgaatact    900

gtacatcgct gtttggttaa acatccagca catgtggttc taaaagaggc cgctgttgtg    960

tcgtatcaaa ttggtctcgt gctgacgttt gccttcatac ccattacctc tgataagaac   1020

ttcttccagg gaaatgtctt tgatcgtcta cgagataaag acattaagaa gaatgtatcc   1080

attgtgcttg gtactgtaaa agacgaagca accttctttt taccctacta ctttggtcac   1140

aacggtttct ctttcaataa ctcattctta gcagatgggg aagaaaacag agcactcata   1200

aatatatcac agtataatta tgcgatgaat gcaactgcgc catcacttga aagctcactg   1260

gaaccacttt tagaagctta taagaacgtt tcgacgcgaa aagaagaagg tgaaagatta   1320

cgcgatggtg ttggtcgatt catgggcgac tacttctata cctgcagcgt cattgatttc   1380

gctaatatcg tctcagacat tattaatgga tctttgtata tgtattactt tactaagagg   1440

tcagtggcaa atccttggcc agagtggatg ggtgtaatgc atggttatga aatagaatac   1500

gaatttggac agcctttcct aaattcatca ctgtacaagg aaaagcttga aaacgaaaag   1560

atcttctcga aaaatatcat gagcttttgg aaagatttca tcaagactgg tgtccctgtc   1620

gatttttggc cgaaatacga tcgaaaggag cggaaagcgc tcgtacttgg cgaggaaagc   1680

gtgaacaatt cttaccctaa tatgactaat gttcatggac cgtactgtga actgatcgaa   1740

gaagcaaagg cgtctacaaa taatggactc accttgaaga aatacattga aggggagata   1800

aaaaataacg aaacgaacgt attttgatag aatgattttg cacagaatga agaattgaat   1860

atcaaaaaaa aaaaaaaaaa aaaaaaaaaa aaa                               1893
```

```
<210> SEQ ID NO 4
<211> LENGTH: 594
<212> TYPE: PRT
<213> ORGANISM: Necator americanus

<400> SEQUENCE: 4

Met Ile Trp Arg Thr Trp Gln Val Leu Val Val Leu Tyr Ala Ala Leu
1               5                   10                  15

Ser Ile Thr Val Val Asn Ala Tyr Lys His Ile Ser Ser Asp His Val
            20                  25                  30

Val Asn Thr Thr Leu Gly Gln Ile Arg Gly Val Pro Gln Asn Phe Glu
        35                  40                  45

Gly Lys Lys Val Thr Ala Phe Leu Gly Val Pro Tyr Gly Gln Pro Pro
    50                  55                  60

Thr Gly Glu Leu Arg Phe Ser Asn Pro Lys Met Val Gln Arg Trp Glu
65                  70                  75                  80

Gly Ile Lys Asn Ala Thr Thr Pro Ala Gln Pro Cys Phe His Phe Pro
                85                  90                  95

Asp Ser Lys Phe Lys Gly Phe Arg Gly Ser Glu Met Trp Asn Pro Lys
            100                 105                 110

Gly Asn Met Thr Glu Asp Cys Leu Asn Met Asn Ile Trp Val Pro His
        115                 120                 125

Asp Ala Asp Gly Ser Val Ile Val Trp Ile Phe Gly Gly Gly Phe Phe
    130                 135                 140
```

-continued

```
Thr Gly Ser Pro Ser Leu Asp Val Tyr Asn Gly Thr Ala Leu Ala Ala
145                 150                 155                 160

Lys Lys Arg Thr Ile Val Val Asn Ile Asn Tyr Arg Leu Gly Pro Phe
                165                 170                 175

Gly Phe Leu Tyr Leu Gly Asp Asp Ser Arg Ala Gln Gly Asn Met Gly
            180                 185                 190

Leu Gln Asp Gln Gln Val Ala Leu Arg Trp Val His Lys His Ile Ser
        195                 200                 205

Ser Phe Gly Gly Asp Pro Arg Lys Val Thr Leu Phe Gly Glu Ala Ser
    210                 215                 220

Gly Ala Ala Ser Ala Thr Ala His Leu Ala Ala Pro Gly Ser Tyr Glu
225                 230                 235                 240

Phe Phe Asp Lys Ile Ile Gly Asn Gly Gly Thr Ile Met Asn Ser Trp
                245                 250                 255

Ala Ser Arg Thr Asn Thr Ser Met Leu Glu Leu Ser Met Lys Leu Ala
            260                 265                 270

Glu Arg Leu Asn Cys Thr Lys Lys Arg Lys Asp Pro Asn Thr Val His
        275                 280                 285

Arg Cys Leu Val Lys His Pro Ala His Val Val Leu Lys Glu Ala Ala
    290                 295                 300

Val Val Ser Tyr Gln Ile Gly Leu Val Leu Thr Phe Ala Phe Ile Pro
305                 310                 315                 320

Ile Thr Ser Asp Lys Asn Phe Phe Gln Gly Asn Val Phe Asp Arg Leu
                325                 330                 335

Arg Asp Lys Asp Ile Lys Lys Asn Val Ser Ile Val Leu Gly Thr Val
            340                 345                 350

Lys Asp Glu Ala Thr Phe Phe Leu Pro Tyr Tyr Phe Gly His Asn Gly
        355                 360                 365

Phe Ser Phe Asn Asn Ser Phe Leu Ala Asp Gly Glu Glu Asn Arg Ala
    370                 375                 380

Leu Ile Asn Ile Ser Gln Tyr Asn Tyr Ala Met Asn Ala Thr Ala Pro
385                 390                 395                 400

Ser Leu Glu Ser Ser Leu Glu Pro Leu Leu Glu Ala Tyr Lys Asn Val
                405                 410                 415

Ser Thr Arg Lys Glu Glu Gly Glu Arg Leu Arg Asp Gly Val Gly Arg
            420                 425                 430

Phe Met Gly Asp Tyr Phe Tyr Thr Cys Ser Val Ile Asp Phe Ala Asn
        435                 440                 445

Ile Val Ser Asp Ile Ile Asn Gly Ser Leu Tyr Met Tyr Tyr Phe Thr
    450                 455                 460

Lys Arg Ser Val Ala Asn Pro Trp Pro Glu Trp Met Gly Val Met His
465                 470                 475                 480

Gly Tyr Glu Ile Glu Tyr Glu Phe Gly Gln Pro Phe Leu Asn Ser Ser
                485                 490                 495

Leu Tyr Lys Glu Lys Leu Glu Asn Glu Lys Ile Phe Ser Lys Asn Ile
            500                 505                 510

Met Ser Phe Trp Lys Asp Phe Ile Lys Thr Gly Val Pro Val Asp Phe
        515                 520                 525

Trp Pro Lys Tyr Asp Arg Lys Glu Arg Lys Ala Leu Val Leu Gly Glu
    530                 535                 540

Glu Ser Val Asn Asn Ser Tyr Pro Asn Met Thr Asn Val His Gly Pro
545                 550                 555                 560

Tyr Cys Glu Leu Ile Glu Glu Ala Lys Ala Ser Thr Asn Asn Gly Leu
```

-continued

```
                565                 570                 575

Thr Leu Lys Lys Tyr Ile Glu Gly Glu Ile Lys Asn Asn Glu Thr Asn
            580                 585                 590

Val Phe
```

<210> SEQ ID NO 5
<211> LENGTH: 1344
<212> TYPE: DNA
<213> ORGANISM: Necator americanus

<400> SEQUENCE: 5

```
ctcgtgccga attcggcacg agctccattc atcatgcagc gatcattcct acttctactt      60
gttgtgttag caggtgcctg ggccgtaaac acaacaatcc ctctgaagct gatgggaggt     120
tttacaccta tgaaatatca atgtgttggt agagtttcgg acatttgggc ggatgtgcta     180
tttctgatcg aatcatccga tatgattaca aaatcaggat tccgtcaagt catcgcattc     240
attacggcga cgacaaagaa gatgacaatc ggtcaggatg aaaagcagac acgagttggg     300
ttcatcacat acggggaaga agcaaaacta atctacgatc tagatcactg gaggtcaacc     360
gagaagctca gcgatttagt gcaaaaaatc ccatacgtaa aatcctctgg aacaaatatt     420
gcagcagcaa ttgcgctggc taacaaggta ttcaactcac caacacatcg accgaacgtc     480
ccgaaagtga tggttattgt cgctaatgga ttgaagaaag gtagtcagaa tccgattccc     540
gttgcgaccg cattcaagga ctttggaggt attataataa caatagaata cactcaatac     600
gataacattc aagtgccaat tttgaagaaa attgctagcg aaggatacaa tattagaagc     660
aatgacgaag atttcagtgt cagaacgtta acgaacatgt tgttgcaggc aaattgtttc     720
tgtccagacc attacgttcc atttcgtgta aataaccctg aatttggttg tttcgtaact     780
gcaaaaattc catcaatgtg gagggatgca gctgaaatgt gccgcgccgt tgaggaaggg     840
aaattagtga aagtagagaa tgaggaaaaa gctgcattca tcatgaaatt ggtgggaccg     900
aaaaaggaag catggattgg attgaggtac tatgggaaca aattccagtg gacagatggc     960
actaagctca atgcagacga cttcaacctg tggcccgaag atataaaaga attgaatgga    1020
cctcattgtg tatctatgta ccaagatcag aaggacaaaa agtattattg gagagccggt    1080
aaatgccttg aagatatgag atatgtatgc gaagtacagc catgcagtgc atccaactac    1140
tgctcggaac cagtgttcat gtatcgtcag aagcatcgcg ctctcctacc agcaccacca    1200
ccaccaccaa actaagatct aaaaaaatct gtccaaaaga gataccattg acatgtactt    1260
tgattatgtt gaatagtgta attaatcaga atggggtgta gtgaataaac gtacaactat    1320
ttaaaaaaaa aaaaaaaaaa aaaa                                           1344
```

<210> SEQ ID NO 6
<211> LENGTH: 393
<212> TYPE: PRT
<213> ORGANISM: Necator americanus

<400> SEQUENCE: 6

```
Met Gln Arg Ser Phe Leu Leu Leu Leu Val Val Leu Ala Gly Ala Trp
1               5                   10                  15

Ala Val Asn Thr Thr Ile Pro Leu Lys Leu Met Gly Gly Phe Thr Pro
            20                  25                  30

Met Lys Tyr Gln Cys Val Gly Arg Val Ser Asp Ile Trp Ala Asp Val
        35                  40                  45

Leu Phe Leu Ile Glu Ser Ser Asp Met Ile Thr Lys Ser Gly Phe Arg
```

-continued

```
    50                  55                  60

Gln Val Ile Ala Phe Ile Thr Ala Thr Thr Lys Lys Met Thr Ile Gly
65                  70                  75                  80

Gln Asp Glu Lys Gln Thr Arg Val Gly Phe Ile Thr Tyr Gly Glu Glu
                85                  90                  95

Ala Lys Leu Ile Tyr Asp Leu Asp His Trp Arg Ser Thr Glu Lys Leu
            100                 105                 110

Ser Asp Leu Val Gln Lys Ile Pro Tyr Val Lys Ser Ser Gly Thr Asn
        115                 120                 125

Ile Ala Ala Ala Ile Ala Leu Ala Asn Lys Val Phe Asn Ser Pro Thr
    130                 135                 140

His Arg Pro Asn Val Pro Lys Val Met Val Ile Val Ala Asn Gly Leu
145                 150                 155                 160

Lys Lys Gly Ser Gln Asn Pro Ile Pro Val Ala Thr Ala Phe Lys Asp
                165                 170                 175

Phe Gly Gly Ile Ile Ile Thr Ile Glu Tyr Thr Gln Tyr Asp Asn Ile
            180                 185                 190

Gln Val Pro Ile Leu Lys Lys Ile Ala Ser Glu Gly Tyr Asn Ile Arg
        195                 200                 205

Ser Asn Asp Glu Asp Phe Ser Val Arg Thr Leu Thr Asn Met Leu Leu
    210                 215                 220

Gln Ala Asn Cys Phe Cys Pro Asp His Tyr Val Pro Phe Arg Val Asn
225                 230                 235                 240

Asn Pro Glu Phe Gly Cys Phe Val Thr Ala Lys Ile Pro Ser Met Trp
                245                 250                 255

Arg Asp Ala Ala Glu Met Cys Arg Ala Val Glu Glu Gly Lys Leu Val
            260                 265                 270

Lys Val Glu Asn Glu Glu Lys Ala Ala Phe Ile Met Lys Leu Val Gly
        275                 280                 285

Pro Lys Lys Glu Ala Trp Ile Gly Leu Arg Tyr Tyr Gly Asn Lys Phe
    290                 295                 300

Gln Trp Thr Asp Gly Thr Lys Leu Asn Ala Asp Asp Phe Asn Leu Trp
305                 310                 315                 320

Pro Glu Asp Ile Lys Glu Leu Asn Gly Pro His Cys Val Ser Met Tyr
                325                 330                 335

Gln Asp Gln Lys Asp Lys Lys Tyr Tyr Trp Arg Ala Gly Lys Cys Leu
            340                 345                 350

Glu Asp Met Arg Tyr Val Cys Glu Val Gln Pro Cys Ser Ala Ser Asn
        355                 360                 365

Tyr Cys Ser Glu Pro Val Phe Met Tyr Arg Gln Lys His Arg Ala Leu
    370                 375                 380

Leu Pro Ala Pro Pro Pro Pro Pro Asn
385                 390
```

<210> SEQ ID NO 7
<211> LENGTH: 1442
<212> TYPE: DNA
<213> ORGANISM: Necator americanus

<400> SEQUENCE: 7

```
ggcacgaggg gagatggctc gacttgtatt cctactcgta ctatgtactc tggctgcagc     60

aagcgttcat cgacgactct ttcatcaagc tcgtcgtcat gtgacatcgg tatcgctttc    120

gcgtcagcca acacttcgtg aacgactgat cgcaagtggc agttgggagg attaccagaa    180
```

-continued

```
acaacgctac cattatcgaa agaaaattct agcaaaatat gctgctaaca aagcgtcaaa    240

gttacaatct gcaaacgaga tcgatgaatt gctccggaac tatatggatg cacaatacta    300

tggtgtcatc caaattggga ctccagctca gaatttcact gtgatcttcg acacgggttc    360

ctcaaatcta tgggtaccgt caagaaagtg tccattctat gacattgcat gtatgcttca    420

tcatcgttat gactccggag cctcgtcaac ctacaaggaa gatgggcgca agatggctat    480

tcagtatgga actggatcta tgaaaggatt catttctaag gatattgttt gtattgctgg    540

aatttgcgct gaagaacaac ctttcgcgga ggctacaagt gaacctggtc ttacatttat    600

cgctgctaag tttgatggaa tccttggaat ggcattcccg gaaattgctg ttctcggtgt    660

aactcctgtc ttccatacgt tcattgaaca gaagaaagtt cctagccctg tgtttgcttt    720

ctggctgaat aggaatccag agtcggaaat tggaggagag attacctttg gtggtgtgga    780

tacccgacgt tatgttgaac caattacatg gacaccagtg acacgtcgtg gatattggca    840

attcaaaatg gatatggtac aaggtggttc atcgtccatt gcgtgtccga atggatgcca    900

agctatcgct gatactggca cttctcttat tgctggaccg aaggcacagg ttgaggcaat    960

ccagaaatat atcggagcag agccgcttat gaaaggagaa tacatgattc cttgcgacaa   1020

agtaccatcc cttcctgatg tttcgttcat catcgatggc aagacgttta cactcaaagg   1080

ggaagattac gttctaaccg tgaaagccgc tggtaaatca atctgtttgt ctggcttcat   1140

gggaatggac ttcccagaga agatcggcga attgtggatc cttggagatg ttttcattgg   1200

aaaatactac accgtcttcg atgttggtca ggcacgtgtt ggatttgctc aagcaaagtc   1260

agaagatgga ttccctgttg gcacccccgt tcgaacattc agacagcttc aggaagacag   1320

cgatagcgac gaggacgatg tatttacttt ttaagtagtg ttaacatctc caacgtgctc   1380

tgttacttct acgtgtacca tgtttcacgt gtttgctcat ttgataaatt attatcttcc   1440

ct                                                                  1442
```

```
<210> SEQ ID NO 8
<211> LENGTH: 446
<212> TYPE: PRT
<213> ORGANISM: Necator americanus

<400> SEQUENCE: 8

Met Ala Arg Leu Val Phe Leu Leu Val Leu Cys Thr Leu Ala Ala Ala
1               5                   10                  15

Ser Val His Arg Arg Leu Phe His Gln Ala Arg Arg His Val Thr Ser
            20                  25                  30

Val Ser Leu Ser Arg Gln Pro Thr Leu Arg Glu Arg Leu Ile Ala Ser
        35                  40                  45

Gly Ser Trp Glu Asp Tyr Gln Lys Gln Arg Tyr His Tyr Arg Lys Lys
    50                  55                  60

Ile Leu Ala Lys Tyr Ala Ala Asn Lys Ala Ser Lys Leu Gln Ser Ala
65                  70                  75                  80

Asn Glu Ile Asp Glu Leu Leu Arg Asn Tyr Met Asp Ala Gln Tyr Tyr
                85                  90                  95

Gly Val Ile Gln Ile Gly Thr Pro Ala Gln Asn Phe Thr Val Ile Phe
            100                 105                 110

Asp Thr Gly Ser Ser Asn Leu Trp Val Pro Ser Arg Lys Cys Pro Phe
        115                 120                 125

Tyr Asp Ile Ala Cys Met Leu His His Arg Tyr Asp Ser Gly Ala Ser
    130                 135                 140
```

-continued

```
Ser Thr Tyr Lys Glu Asp Gly Arg Lys Met Ala Ile Gln Tyr Gly Thr
145                 150                 155                 160

Gly Ser Met Lys Gly Phe Ile Ser Lys Asp Ile Val Cys Ile Ala Gly
                165                 170                 175

Ile Cys Ala Glu Glu Gln Pro Phe Ala Glu Ala Thr Ser Glu Pro Gly
            180                 185                 190

Leu Thr Phe Ile Ala Ala Lys Phe Asp Gly Ile Leu Gly Met Ala Phe
        195                 200                 205

Pro Glu Ile Ala Val Leu Gly Val Thr Pro Val Phe His Thr Phe Ile
    210                 215                 220

Glu Gln Lys Lys Val Pro Ser Pro Val Phe Ala Phe Trp Leu Asn Arg
225                 230                 235                 240

Asn Pro Glu Ser Glu Ile Gly Gly Glu Ile Thr Phe Gly Gly Val Asp
                245                 250                 255

Thr Arg Arg Tyr Val Glu Pro Ile Thr Trp Thr Pro Val Thr Arg Arg
            260                 265                 270

Gly Tyr Trp Gln Phe Lys Met Asp Met Val Gln Gly Gly Ser Ser Ser
        275                 280                 285

Ile Ala Cys Pro Asn Gly Cys Gln Ala Ile Ala Asp Thr Gly Thr Ser
    290                 295                 300

Leu Ile Ala Gly Pro Lys Ala Gln Val Glu Ala Ile Gln Lys Tyr Ile
305                 310                 315                 320

Gly Ala Glu Pro Leu Met Lys Gly Glu Tyr Met Ile Pro Cys Asp Lys
                325                 330                 335

Val Pro Ser Leu Pro Asp Val Ser Phe Ile Ile Asp Gly Lys Thr Phe
            340                 345                 350

Thr Leu Lys Gly Glu Asp Tyr Val Leu Thr Val Lys Ala Ala Gly Lys
        355                 360                 365

Ser Ile Cys Leu Ser Gly Phe Met Gly Met Asp Phe Pro Glu Lys Ile
    370                 375                 380

Gly Glu Leu Trp Ile Leu Gly Asp Val Phe Ile Gly Lys Tyr Tyr Thr
385                 390                 395                 400

Val Phe Asp Val Gly Gln Ala Arg Val Gly Phe Ala Gln Ala Lys Ser
                405                 410                 415

Glu Asp Gly Phe Pro Val Gly Thr Pro Val Arg Thr Phe Arg Gln Leu
            420                 425                 430

Gln Glu Asp Ser Asp Ser Asp Glu Asp Asp Val Phe Thr Phe
        435                 440                 445


<210> SEQ ID NO 9
<211> LENGTH: 1366
<212> TYPE: DNA
<213> ORGANISM: Necator americanus

<400> SEQUENCE: 9

ggcacgagag aatgcgttcg atactcgtgt tggtggctct gatcggatgc attgctgcgg     60

gtgtatataa aatcccattg aaaagaatca ctccgccgat gataaaaatg ttgagagctg    120

gtacttggga aacgtacgta gaaggaatga ggaagagaca attacagtta ctgaaggagc    180

acaaggttca tatccaagat gtactcggct atgctaacat ggagtacctc ggcgaaatta    240

ctattggaac tcctcaacag aagtttctgg tggttttgga cactggctcc tcgaatctgt    300

gggtccctga tgattcatgc tacaaggaga agagacctga tagatgtcta gtatcaaact    360

gtgatgctgg actggtttgt caagtcttct gtccagatcc taaatgctgt gaacatacga    420
```

-continued

```
gagaattcaa gcaagtaaac gcatgcaaag ataagcatcg atttgatcaa aagaattcca    480

acacttatgt taaaacaaac aaaacatggg caatagcgta tggaactgga gatgcgaggg    540

gattttttgg aagagataca gtccgtttgg gtgctgaagg aaaggatcag ctcgttatta    600

atgatacgtg gttcggacaa gcagagcata tagctgaatt tttcagtaat actttccttg    660

atggcattct cggactcgct tttcaagaac tgtcagaagg aggcgtcgct cctccaataa    720

ttcgtgccat tgaccttgga cttctcgatc aaccaatatt tactgtctat ttcgaaaatg    780

tcggagacaa agaaggtgtt tatggaggtg ttttcacctg ggtggtctc gatcccgatc    840

attgcgaaga tgaggtcaca tatgaacagc taaccgaagc aacttactgg cagtttagac    900

ttaaaggagt gtcgtctaag aacttctcgt cgacggctgg ttgggaagca atatccgaca    960

ctggtacctc gttaaatgga gcccctaggg ggatactaag aagtattgca agacagtata   1020

atggacagta cgtcgcatct caaggtctct acgtcgtcga ctgcagtaaa aatgtgaccg   1080

ttgacgtgac cattggcgac agaaactaca ctatgactgc gaaaaatctc gtacttgaaa   1140

tacaggctga tatatgtatt atggcatttt tcgaaatgga catgttcatt ggaccagcat   1200

ggattcttgg cgatccattt attcgagaat attgcaatat tcatgacatt gaaaagaagc   1260

ggattggttt tgcagctgta aaacattgat cgattataaa tgtaatgggc tatttgtcat   1320

aaattgctca ataaagtttt ttgactaaaa aaaaaaaaaa aaaaaa                  1366


<210> SEQ ID NO 10
<211> LENGTH: 425
<212> TYPE: PRT
<213> ORGANISM: Necator americanus

<400> SEQUENCE: 10

Met Arg Ser Ile Leu Val Leu Val Ala Leu Ile Gly Cys Ile Ala Ala
1               5                   10                  15

Gly Val Tyr Lys Ile Pro Leu Lys Arg Ile Thr Pro Pro Met Ile Lys
            20                  25                  30

Met Leu Arg Ala Gly Thr Trp Glu Thr Tyr Val Glu Gly Met Arg Lys
        35                  40                  45

Arg Gln Leu Gln Leu Leu Lys Glu His Lys Val His Ile Gln Asp Val
    50                  55                  60

Leu Gly Tyr Ala Asn Met Glu Tyr Leu Gly Glu Ile Thr Ile Gly Thr
65                  70                  75                  80

Pro Gln Gln Lys Phe Leu Val Val Leu Asp Thr Gly Ser Ser Asn Leu
                85                  90                  95

Trp Val Pro Asp Asp Ser Cys Tyr Lys Glu Lys Arg Pro Asp Arg Cys
            100                 105                 110

Leu Val Ser Asn Cys Asp Ala Gly Leu Val Cys Gln Val Phe Cys Pro
        115                 120                 125

Asp Pro Lys Cys Cys Glu His Thr Arg Glu Phe Lys Gln Val Asn Ala
    130                 135                 140

Cys Lys Asp Lys His Arg Phe Asp Gln Lys Asn Ser Asn Thr Tyr Val
145                 150                 155                 160

Lys Thr Asn Lys Thr Trp Ala Ile Ala Tyr Gly Thr Gly Asp Ala Arg
                165                 170                 175

Gly Phe Phe Gly Arg Asp Thr Val Arg Leu Gly Ala Glu Gly Lys Asp
            180                 185                 190

Gln Leu Val Ile Asn Asp Thr Trp Phe Gly Gln Ala Glu His Ile Ala
        195                 200                 205
```

-continued

```
Glu Phe Phe Ser Asn Thr Phe Leu Asp Gly Ile Leu Gly Leu Ala Phe
    210                 215                 220

Gln Glu Leu Ser Glu Gly Gly Val Ala Pro Pro Ile Ile Arg Ala Ile
225                 230                 235                 240

Asp Leu Gly Leu Leu Asp Gln Pro Ile Phe Thr Val Tyr Phe Glu Asn
                245                 250                 255

Val Gly Asp Lys Glu Gly Val Tyr Gly Gly Val Phe Thr Trp Gly Gly
            260                 265                 270

Leu Asp Pro Asp His Cys Glu Asp Glu Val Thr Tyr Glu Gln Leu Thr
        275                 280                 285

Glu Ala Thr Tyr Trp Gln Phe Arg Leu Lys Gly Val Ser Ser Lys Asn
    290                 295                 300

Phe Ser Ser Thr Ala Gly Trp Glu Ala Ile Ser Asp Thr Gly Thr Ser
305                 310                 315                 320

Leu Asn Gly Ala Pro Arg Gly Ile Leu Arg Ser Ile Ala Arg Gln Tyr
                325                 330                 335

Asn Gly Gln Tyr Val Ala Ser Gln Gly Leu Tyr Val Val Asp Cys Ser
            340                 345                 350

Lys Asn Val Thr Val Asp Val Thr Ile Gly Asp Arg Asn Tyr Thr Met
        355                 360                 365

Thr Ala Lys Asn Leu Val Leu Glu Ile Gln Ala Asp Ile Cys Ile Met
    370                 375                 380

Ala Phe Phe Glu Met Asp Met Phe Ile Gly Pro Ala Trp Ile Leu Gly
385                 390                 395                 400

Asp Pro Phe Ile Arg Glu Tyr Cys Asn Ile His Asp Ile Glu Lys Lys
                405                 410                 415

Arg Ile Gly Phe Ala Ala Val Lys His
            420                 425


<210> SEQ ID NO 11
<211> LENGTH: 509
<212> TYPE: DNA
<213> ORGANISM: Ancylostoma caninum

<400> SEQUENCE: 11

agcatatcag catgagagtc gctattgttt tcattgcatg cttcgcagta gcacacgcat     60

gcaagtgcga aaagaaacct cgtcctccat tggagaaact gctttgccaa tcacaatttg    120

ttactcacgc gaaagtgacg aagaagagaa ttgatggtta cttcatctat tacgacttgg    180

agcataatta agtttataag cccaaagata ggagtatccc aatcgaactc ttctcatgga    240

gggaaaagga aaattgtggt gttccggatc tcgaagaagg caaagaatac ctgataggag    300

gtaaagtgac ggattatggc gacggtgatt tggtaatttc tgtttcacgg tgcgaccttc    360

tccgaaactg gacagacgtc tctggagagg agaagaaatt gctcggaacg ttcaaatgtg    420

aaaatcagtc ataaacgccg attatatata attgaaagaa gagaaatgaa catttttcac    480

gcgaaaaaaa aaaaaaaaaa aaaaaaaaa                                      509


<210> SEQ ID NO 12
<211> LENGTH: 140
<212> TYPE: PRT
<213> ORGANISM: Ancylostoma caninum

<400> SEQUENCE: 12

Met Arg Val Ala Ile Val Phe Ile Ala Cys Phe Ala Val Ala His Ala
1               5                   10                  15
```

-continued

```
Cys Lys Cys Glu Lys Lys Pro Arg Pro Pro Leu Glu Lys Leu Leu Cys
            20                  25                  30

Gln Ser Gln Phe Val Thr His Ala Lys Val Thr Lys Lys Arg Ile Asp
        35                  40                  45

Gly Tyr Phe Ile Tyr Tyr Asp Leu Glu His Lys Glu Val Tyr Lys Pro
    50                  55                  60

Lys Asp Arg Ser Ile Pro Ile Glu Leu Phe Ser Trp Arg Glu Lys Glu
65                  70                  75                  80

Asn Cys Gly Met Pro Asp Leu Glu Glu Gly Lys Glu Tyr Leu Ile Gly
                85                  90                  95

Gly Lys Val Thr Asp Tyr Gly Asp Gly Asp Leu Val Ile Ser Val Ser
            100                 105                 110

Arg Cys Asp Leu Leu Arg Asn Trp Thr Asp Val Ser Gly Glu Glu Lys
        115                 120                 125

Lys Leu Leu Gly Thr Phe Lys Cys Glu Asn Gln Ser
    130                 135                 140
```

<210> SEQ ID NO 13
<211> LENGTH: 2615
<212> TYPE: DNA
<213> ORGANISM: Ancylostoma caninum

<400> SEQUENCE: 13

```
gtggttttca acgtcctcac atggcttaaa ttaaacgaga acaaagatga ctcatcaccg     60

gctccgaaga tatggaatgt gggagagcaa gataatacac ccgtgctgac aaatttgtta    120

gttttggaaa aagaggagtt agcagcaaag ttgaagaaaa caccatatga ggaggtggat    180

gagcaaacag ttagacaatc gtcggttatg aaactcagga atatcaaaaa tgccctgttc    240

actccaatag aaccagtagc ctcagcgttg cctccattgc gtgtgaatga cccgaaatat    300

tgtccgagtt acggtgaacc ggataagaaa tatgcctatc aggaagcagc atcttatctt    360

ctcagtggtc tggatcagac tgtagatcca tgcgaggatc tctatgcatt cacctgtaat    420

acgtacctca gaaatcacaa cgccaccgac attggcgtga accgaatcgg aacgtacaaa    480

gacgctcaag atgacgtgaa cgctgaaatc gtggaagcac tcgaagaagt taacgtgagc    540

gacacaaagt ggtcggagac ggagaggctt gtgaaagcga ctctcttcac atgtgtacac    600

cacactcgag cgaggaaacc catagacaat tcgaagaacg ttcttataga gatgagagac    660

ttgtttggcg gaattccatt cctcaatcat actctgaaga aggacattga tttctttgat    720

ataatgggaa agttcgagca gaatcatgcg atgggaaccc ttctcggagc aatggtctcg    780

gtcgatttca agaatgtgaa caaacactcc ttattcttat cgcagcccta tcttccaatg    840

gctcgagatt tctatgtttt cccacaacac acaaagatgg ttgagaatcg cgtaagtctc    900

atcaactctg tgctgaggtc gttcgcagag gctgttctgg atgatccctc gccgtatctc    960

gatctgatgt caagatcggc aagagatgta gtgaagctgg agatgcagat tgcgatggca   1020

tcgtggccag agagtgaact gaggaactac gcacaacagc acaatccacg cactttgaat   1080

cagttgaaag cagcgtatcc agcgattaaa tgggacagtt atttcaatgc tctgctctcc   1140

tctgtgcagg gagtcgatat gaataggcag aacatcatac ttacccaacc atcgtacttc   1200

ggctggttaa atgctctctt caacggtggc gcagatgaca aaaccattgc gaattatctt   1260

cttgttcacc tgattctcga ggaggctgat ttccttggtg gagcacttaa aacgatggtt   1320

caaaaatctg attatgttcc atatgcctta ggaagaggaa agggagtcac aagagttggc   1380

cagcaactta ctcgatcaca tgacgatact gttgaggatg caaacataca gtgcttgaac   1440
```

-continued

```
agcatgatga cgtatatgcc atttggacca ggttacgtgt acgtgaaatc aaggaagaac   1500

agagatgacg ttgtcaagga catagagcac cagaccgagc tggtcttcaa gaactttgtg   1560

aacatgattg gtaacttaaa ttggatgaca gacgcatctc tggagctcgc catggagaaa   1620

gctgatacga tggtgaaaaa ctatggatgg cccaaggatt tgtttggaaa tttcagggat   1680

agtagcaaga ttgatgctta tcacaagaag gattatggta acatcattaa cctgtacaag   1740

gagaacatta ctcataacta ctaccacatc cgcagaacta tgatcaaagg ctattccaac   1800

catgaatcgc tgcgattgct gactgaagcg ccgaaaaggg accacttcct gttgtcaccc   1860

gctctggtga atgcgtggta cataccggag agaaactcca tcgcattccc ttacgccttc   1920

tggaatccac cctattacaa ttacgaatat cctcaagcat gcaactacgc tggtcaaggt   1980

ggaactgctg gccacgaatt agtgcatgga ttcgatgacc agggagtaca gttcgctgcc   2040

gacggaagcc ttagcgactg cacgtggatc gagtgtggat ggttggaaga gaagtccaag   2100

aaaggattca gtgatatggc acaatgtgtt gtcacacagt atagcaccca atgctgccct   2160

cagacaggtg gcgtcaccca ctgcgctaat ggagcgacca cccaaggaga aaacatcgcc   2220

gatcttggag gtcaactggc agcatatcga gcctaccgtg aatacatcac caaggaaaga   2280

ggagaggagg agaagagact gccgggattg gagcagtaca caccaaatca gatcttctgg   2340

ataacatacg gatattcgtg gtgcatgagc caaacagata gcagtcttat tagacaactc   2400

ttgaccgatg ttcactcacc tggctcatgc cgtgttaacc aagtcatgca agatattccg   2460

gaatttgcac tcgatttcgg atgtacaatg ggccagaaga tgtatccaga gcctgagcaa   2520

cgatgtccgg tttgggtagc agaataaatg ttcgaaaatg gaccgtcaga tctcatgttt   2580

tcacgtgaat atgacgctct taactgaggt ttttc                               2615
```

<210> SEQ ID NO 14
<211> LENGTH: 869
<212> TYPE: PRT
<213> ORGANISM: Ancylostoma caninum

<400> SEQUENCE: 14

```
Met Ala Lys Leu Leu Glu Val Thr Thr Gly Leu Val Val Leu Leu Gly
1               5                   10                  15

Val Leu Gly Val Ile Ser Val Val Phe Asn Val Leu Thr Trp Leu Lys
            20                  25                  30

Leu Asn Glu Asn Lys Asp Asp Ser Ser Pro Ala Pro Lys Ile Trp Asn
        35                  40                  45

Val Gly Glu Gln Asp Asn Thr Pro Val Leu Thr Asn Leu Leu Val Leu
    50                  55                  60

Glu Lys Glu Glu Leu Ala Ala Lys Leu Lys Lys Thr Pro Tyr Glu Glu
65                  70                  75                  80

Val Asp Glu Gln Thr Val Arg Gln Ser Ser Val Met Lys Leu Arg Asn
                85                  90                  95

Ile Lys Asn Ala Leu Phe Thr Ile Glu Pro Val Ala Ser Ala Leu Pro
            100                 105                 110

Pro Leu Arg Val Asn Asp Pro Lys Tyr Cys Pro Ser Tyr Gly Glu Pro
        115                 120                 125

Asp Lys Lys Tyr Ala Tyr Gln Glu Ala Ala Ser Tyr Leu Leu Ser Gly
    130                 135                 140

Leu Asp Gln Thr Val Asp Pro Cys Glu Asp Leu Tyr Ala Phe Thr Cys
145                 150                 155                 160
```

-continued

```
Asn Thr Tyr Leu Arg Asn His Asn Ala Thr Asp Ile Gly Val Asn Arg
                165                 170                 175

Ile Gly Thr Tyr Lys Asp Ala Gln Asp Asp Val Asn Ala Glu Ile Val
            180                 185                 190

Glu Ala Leu Glu Glu Val Asn Val Ser Asp Thr Lys Trp Ser Glu Thr
        195                 200                 205

Glu Arg Leu Val Lys Ala Thr Leu Phe Thr Cys Val His His Thr Arg
    210                 215                 220

Ala Arg Lys Pro Ile Asp Asn Ser Lys Asn Val Leu Ile Glu Met Arg
225                 230                 235                 240

Asp Leu Phe Gly Gly Ile Pro Phe Leu Asn His Thr Leu Lys Lys Asp
                245                 250                 255

Ile Asp Phe Phe Asp Ile Met Gly Lys Phe Glu Gln Asn His Ala Met
            260                 265                 270

Gly Thr Leu Leu Gly Ala Met Val Ser Val Asp Phe Lys Asn Val Asn
        275                 280                 285

Lys His Ser Leu Phe Leu Ser Gln Pro Tyr Leu Pro Met Ala Arg Asp
    290                 295                 300

Phe Tyr Val Phe Pro Gln His Thr Lys Met Val Glu Asn Arg Val Ser
305                 310                 315                 320

Leu Ile Asn Ser Val Leu Arg Ser Phe Ala Glu Ala Val Leu Asp Asp
                325                 330                 335

Pro Ser Pro Tyr Leu Asp Leu Met Ser Arg Ser Ala Arg Asp Val Val
            340                 345                 350

Lys Leu Glu Met Gln Ile Ala Met Ala Ser Trp Pro Glu Ser Glu Leu
        355                 360                 365

Arg Asn Tyr Ala Gln Gln His Asn Pro Arg Thr Leu Asn Gln Leu Lys
    370                 375                 380

Ala Ala Tyr Pro Ala Ile Lys Trp Asp Ser Tyr Phe Asn Ala Leu Leu
385                 390                 395                 400

Ser Ser Val Gln Gly Val Asp Met Asn Arg Gln Asn Ile Ile Leu Thr
                405                 410                 415

Gln Pro Ser Tyr Phe Gly Trp Leu Asn Ala Leu Phe Asn Gly Gly Ala
            420                 425                 430

Asp Asp Lys Thr Ile Ala Asn Tyr Leu Leu Val His Leu Ile Leu Glu
        435                 440                 445

Glu Ala Asp Phe Leu Gly Gly Ala Leu Lys Thr Met Val Gln Lys Ser
    450                 455                 460

Asp Tyr Val Pro Tyr Ala Leu Gly Arg Gly Lys Gly Val Thr Arg Val
465                 470                 475                 480

Gly Gln Gln Leu Thr Arg Ser His Asp Asp Thr Val Glu Asp Ala Asn
                485                 490                 495

Ile Gln Cys Leu Asn Ser Met Met Thr Tyr Met Pro Phe Gly Pro Gly
            500                 505                 510

Tyr Val Tyr Val Lys Ser Arg Lys Asn Arg Asp Asp Val Val Lys Asp
        515                 520                 525

Ile Glu His Gln Thr Glu Leu Val Phe Lys Asn Phe Val Asn Met Ile
    530                 535                 540

Gly Asn Leu Asn Trp Met Thr Asp Ala Ser Leu Glu Leu Ala Met Glu
545                 550                 555                 560

Lys Ala Asp Thr Met Val Lys Asn Tyr Gly Trp Pro Lys Asp Leu Phe
                565                 570                 575

Gly Asn Phe Arg Asp Ser Ser Lys Ile Asp Ala Tyr His Lys Lys Asp
```

-continued

```
            580                 585                 590

Tyr Gly Asn Ile Ile Asn Leu Tyr Lys Glu Asn Ile Thr His Asn Tyr
        595                 600                 605

Tyr His Ile Arg Arg Thr Met Ile Lys Gly Tyr Ser Asn His Glu Ser
    610                 615                 620

Leu Arg Leu Leu Thr Glu Ala Pro Lys Arg Asp His Phe Leu Leu Ser
625                 630                 635                 640

Pro Ala Leu Val Asn Ala Trp Tyr Ile Pro Glu Arg Asn Ser Ile Ala
                645                 650                 655

Phe Pro Tyr Ala Phe Trp Asn Pro Pro Tyr Tyr Asn Tyr Glu Tyr Pro
            660                 665                 670

Gln Ala Cys Asn Tyr Ala Gly Gln Gly Gly Thr Ala Gly His Glu Leu
        675                 680                 685

Val His Gly Phe Asp Asp Gln Gly Val Gln Phe Ala Ala Asp Gly Ser
    690                 695                 700

Leu Ser Asp Cys Thr Trp Ile Glu Cys Gly Trp Leu Glu Glu Lys Ser
705                 710                 715                 720

Lys Lys Gly Phe Ser Asp Met Ala Gln Cys Val Val Thr Gln Tyr Ser
                725                 730                 735

Thr Gln Cys Cys Pro Gln Thr Gly Gly Val Thr His Cys Ala Asn Gly
            740                 745                 750

Ala Thr Thr Gln Gly Glu Asn Ile Ala Asp Leu Gly Gly Gln Leu Ala
        755                 760                 765

Ala Tyr Arg Ala Tyr Arg Glu Tyr Ile Thr Lys Glu Arg Gly Glu Glu
    770                 775                 780

Glu Lys Arg Leu Pro Gly Leu Glu Gln Tyr Thr Pro Asn Gln Ile Phe
785                 790                 795                 800

Trp Ile Thr Tyr Gly Tyr Ser Trp Cys Met Ser Gln Thr Asp Ser Ser
                805                 810                 815

Leu Ile Arg Gln Leu Leu Thr Asp Val His Ser Pro Gly Ser Cys Arg
            820                 825                 830

Val Asn Gln Val Met Gln Asp Ile Pro Glu Phe Ala Leu Asp Phe Gly
        835                 840                 845

Cys Thr Met Gly Gln Lys Met Tyr Pro Glu Pro Glu Gln Arg Cys Pro
    850                 855                 860

Val Trp Val Ala Glu
865
```

<210> SEQ ID NO 15
<211> LENGTH: 1722
<212> TYPE: DNA
<213> ORGANISM: Ancylostoma caninum

<400> SEQUENCE: 15

```
gggtttaatt acccaagttt gaggatgagg gtactcctgt tactgctact tttatccatt      60

tgcgcgagcg ctggctttct agacactaaa ttcggccaga agataaagaa aactcttgac     120

aagattaaag ctgtgcttaa cggcactgca ctcatcgcga ttcgtgaaaa attcattcga     180

ctaagggaaa aaataaaagc aaagctgacg ctctctccag cacgaaaggc tatattggac     240

gaagttatga agcatatcaa aatgatcaaa aaggataaga ttcaagagaa gggcgactca     300

atcgatgaaa tcaatgaaaa gagtgcaatc ggacagttgc tgtaccaggg tgacatcgtt     360

ctgacagaaa agcaagccca gcaaattacc gaagacattg aaaatgacaa aggcgaccgc     420

gaaaaacgac aggcgttccg tgatcgcaat tatccgcgaa cattatggtc gaagggagtg     480
```

-continued

```
tactttcact ttcataggaa cgcaactcct gaagttagaa gcgtttttgt gaaaggcgca    540
aaactttgga tgaaggatac ttgcatcgac ttcttcgaaa gcaactcagc gcctgatagg    600
attcgtgtgt tcaaagagaa cggatgttgg tcgtacgttg gtaggctggg cggtgaacaa    660
gatctgtcac tgggagaagg ttgtcaatcg gttggcacag ctgcgcacga aattggccac    720
gctattggct tctaccacac tcacgcaaga catgatcgcg ataactttat tacattcaac    780
gcacaaaatg tcaagcccga ttggttggac caattcactc ttcagactcc ggcaacgaat    840
gagaactatg gaataactta cgactatgga agtatcatgc attatggtgc aaatagcgcc    900
tcgcagaacg gacgtcctac aatggttccg catgatccca aatacgtaga aactcttgga    960
tcacccataa tttccttcta tgagcttctc atgatcaaca aacactacga ctgcactaag   1020
aactgtgacc cggctacttc tgcgcagtgt aagatgggtg gcttcccaca tcctcgggat   1080
tgtacaagat gcatttgccc tagtggatat ggaggcaaac tgtgcgacca gaagccagcc   1140
ggatgcggat ctatatacca ggccaccaat cagtaccaga ccttgcacga cgaaattgga   1200
gacaagagag cgggacagag acctagagaa gacatggact tctgctatta ttggatcacg   1260
gccccaaaag gttcaaaaat cgaaatcaaa attgctggat tatcacaagg agccgctgtt   1320
gaaggatgcc agtactgggg agtagaaatc aagactcatg ccgatcaacg tcttaccggc   1380
tacaggttct gcgcaccaga agatgttgga gttagattag tgtcgaactt caacatcgta   1440
ccaataatca catacaacat attctacgcg acctatgtcg atattcagta ccgtatcgtt   1500
ggtgataatg ttggcggtcc tatgcctcag ccacaaccaa atagcaattg tgtcgacaat   1560
gaacagtgtg cgacactcgt gagaacaaag aacttctgtc agagcagatt tttcacagag   1620
tccgtcaaaa gaggtctatg tccaaagtcc agcggtttct gtcgctaact tttcagcaaa   1680
caatggaata aatgttgcac cataaaaaaa aaaaataaaa aa                      1722
```

<210> SEQ ID NO 16
<211> LENGTH: 536
<212> TYPE: PRT
<213> ORGANISM: Ancylostoma caninum

<400> SEQUENCE: 16

```
Met Arg Val Leu Leu Leu Leu Leu Leu Leu Ser Ile Cys Ala Ser Ala
1               5                   10                  15

Gly Phe Leu Asp Thr Lys Phe Gly Gln Lys Ile Lys Lys Thr Leu Asp
            20                  25                  30

Lys Ile Lys Ala Val Leu Asn Gly Thr Ala Leu Ile Ala Ile Arg Glu
        35                  40                  45

Lys Phe Ile Arg Leu Arg Glu Lys Ile Lys Ala Lys Leu Thr Leu Ser
    50                  55                  60

Pro Ala Arg Lys Ala Ile Leu Asp Glu Val Met Lys His Ile Lys Met
65                  70                  75                  80

Ile Lys Lys Asp Lys Ile Gln Glu Lys Gly Asp Ser Ile Asp Glu Ile
                85                  90                  95

Asn Glu Lys Ser Ala Ile Gly Gln Leu Leu Tyr Gln Gly Asp Ile Val
            100                 105                 110

Leu Thr Glu Lys Gln Ala Gln Gln Ile Thr Glu Asp Ile Glu Asn Asp
        115                 120                 125

Lys Gly Asp Arg Glu Lys Arg Gln Ala Phe Arg Asp Arg Asn Tyr Pro
    130                 135                 140

Arg Thr Leu Trp Ser Lys Gly Val Tyr Phe His Phe His Arg Asn Ala
```

-continued

```
145                 150                 155                 160

Thr Pro Glu Val Arg Ser Val Phe Val Lys Gly Ala Lys Leu Trp Met
                165                 170                 175

Lys Asp Thr Cys Ile Asp Phe Phe Glu Ser Asn Ser Ala Pro Asp Arg
            180                 185                 190

Ile Arg Val Phe Lys Glu Asn Gly Cys Trp Ser Tyr Val Gly Arg Leu
        195                 200                 205

Gly Gly Glu Gln Asp Leu Ser Leu Gly Glu Gly Cys Gln Ser Val Gly
    210                 215                 220

Thr Ala Ala His Glu Ile Gly His Ala Ile Gly Phe Tyr His Thr His
225                 230                 235                 240

Ala Arg His Asp Arg Asp Asn Phe Ile Thr Phe Asn Ala Gln Asn Val
                245                 250                 255

Lys Pro Asp Trp Leu Asp Gln Phe Thr Leu Gln Thr Pro Ala Thr Asn
            260                 265                 270

Glu Asn Tyr Gly Ile Thr Tyr Asp Tyr Gly Ser Ile Met His Tyr Gly
        275                 280                 285

Ala Asn Ser Ala Ser Gln Asn Gly Arg Pro Thr Met Val Pro His Asp
    290                 295                 300

Pro Lys Tyr Val Glu Thr Leu Gly Ile Asn Lys His Tyr Asp Cys Thr
305                 310                 315                 320

Lys Asn Cys Asp Pro Ala Thr Ser Ala Gln Cys Lys Met Gly Gly Phe
                325                 330                 335

Pro His Pro Arg Asp Cys Thr Arg Cys Ile Cys Pro Ser Gly Tyr Gly
            340                 345                 350

Gly Lys Leu Cys Asp Gln Lys Pro Ala Gly Cys Gly Ser Ile Tyr Gln
        355                 360                 365

Ala Thr Asn Gln Tyr Gln Thr Leu His Asp Glu Ile Gly Asp Lys Arg
    370                 375                 380

Ala Gly Gln Arg Pro Arg Glu Asp Met Asp Phe Cys Tyr Tyr Trp Ile
385                 390                 395                 400

Thr Ala Pro Lys Gly Ser Lys Ile Glu Ile Lys Ile Ala Gly Leu Ser
                405                 410                 415

Gln Gly Ala Ala Val Glu Gly Cys Gln Tyr Trp Gly Val Glu Ile Lys
            420                 425                 430

Thr His Ala Asp Gln Arg Leu Thr Gly Tyr Arg Phe Cys Ala Pro Glu
        435                 440                 445

Asp Val Gly Val Arg Leu Val Ser Asn Phe Asn Ile Val Pro Ile Ile
    450                 455                 460

Thr Tyr Asn Ile Phe Tyr Ala Thr Tyr Val Asp Ile Gln Tyr Arg Ile
465                 470                 475                 480

Val Gly Asp Asn Val Gly Gly Pro Met Pro Gln Pro Gln Pro Asn Ser
                485                 490                 495

Asn Cys Val Asp Asn Glu Gln Cys Ala Thr Leu Val Arg Thr Lys Asn
            500                 505                 510

Phe Cys Gln Ser Arg Phe Phe Thr Ser Ser Val Lys Arg Gly Leu Cys
        515                 520                 525

Pro Lys Ser Ser Gly Phe Cys Arg
    530                 535
```

<210> SEQ ID NO 17
<211> LENGTH: 1328
<212> TYPE: DNA
<213> ORGANISM: Ancylostoma caninum

<400> SEQUENCE: 17
atgttttcac ctgtaatcgt cagtgtgatt ttcacaatcg ccttctgcga tgcgtctcca 60
gcaagagacg gcttcggctg ttcaaacagt gggataactg acaaggaccg gcaagcattc 120
ctcgacttcc acaacaatgc tcgtcgacgg gttgcgaaag gcgttgagga tagcaactcc 180
ggcaaactga atccagcgaa gaacatgtac aagctgtcat gggactgtgc aatggaacag 240
cagcttcagg atgccattca gtcatgccca agcgcgttcg ctggaattca aggtgttgcg 300
cagaatgtaa tgagctggtc aagctctggt ggattccccg atccatcggt aaagatagaa 360
caaacgctct ccggctggtg gagtggtgct aaaaagaacg gcgtcggccc ggacaacaaa 420
tacaacggtg gcggtctctt cgccttctct aacatggtat actccgaaac gacgaaactt 480
ggctgcgcct acaaggtttg cggcactaaa ctggcggttt cgtgcatcta taatggagtc 540
gggtacatca caaatcaacc tatgtgggag acaggtcagg cttgcaagac aggagcagac 600
tgctccactt acaagaactc aggctgcgag gatggccttt gcacgaaagg accagacgta 660
ccagaaacaa accagcagtg cccctcaaac actggaatga ctgattcagt cagagatact 720
ttcctatcgg tgcacaatga gttcaggtcg agtgttgccc gaggtctgga acccgacgct 780
ctgggcggaa atgcaccaaa agcagctaaa atgctcaaga tggtgtatga ctgtgaagta 840
gaagcatcgg ccatcagaca tggaaataaa tgcgtctatc aacattccca tggcgaagac 900
agacctggac taggagaaaa catctacaag actagtgtac tcaaattcga taagaacaaa 960
gcagccaagc aggcttcaca actctggtgg aatgagttaa aagagttcgg cgtcggccca 1020
tccaacgtcc ttaccactgc tttatggaat agacccggca tgcagattgg tcactacacc 1080
cagatggcat gggacaccac ctacaaactt ggatgtgcag ttgttttctg caatgatttc 1140
acattcggtg tttgtcagta tgggccagga ggcaattaca tgggtcatgt catctacact 1200
atgggccagc cgtgttctca gtgttcgcct ggtgctactt gcagcgtgac cgaaggcttg 1260
tgcagtgctc cttaatcagt tcttaacaat gaatatctta cagttgaaaa aaaaaaaaaa 1320
aaaaaaaa 1328

<210> SEQ ID NO 18
<211> LENGTH: 424
<212> TYPE: PRT
<213> ORGANISM: Ancylostoma caninum

<400> SEQUENCE: 18

Met Phe Ser Pro Val Ile Val Ser Val Ile Phe Thr Ile Ala Phe Cys
1 5 10 15

Asp Ala Ser Pro Ala Arg Asp Gly Phe Gly Cys Ser Asn Ser Gly Ile
20 25 30

Thr Asp Lys Asp Arg Gln Ala Phe Leu Asp Phe His Asn Asn Ala Arg
35 40 45

Arg Arg Val Ala Lys Gly Val Glu Asp Ser Asn Ser Gly Lys Leu Asn
50 55 60

Pro Ala Lys Asn Met Tyr Lys Leu Ser Trp Asp Cys Ala Met Glu Gln
65 70 75 80

Gln Leu Gln Asp Ala Ile Gln Ser Cys Pro Ser Ala Phe Ala Gly Ile
85 90 95

Gln Gly Val Ala Gln Asn Val Met Ser Trp Ser Ser Ser Gly Gly Phe
100 105 110

Pro Asp Pro Ser Val Lys Ile Glu Gln Thr Leu Ser Gly Trp Trp Ser

-continued

```
        115                 120                 125

Gly Ala Lys Lys Asn Gly Val Gly Pro Asp Asn Lys Tyr Asn Gly Gly
    130                 135                 140

Gly Leu Phe Ala Phe Ser Asn Met Val Tyr Ser Glu Thr Thr Lys Leu
145                 150                 155                 160

Gly Cys Ala Tyr Lys Val Cys Gly Thr Lys Leu Ala Val Ser Cys Ile
                165                 170                 175

Tyr Asn Gly Val Gly Tyr Ile Thr Asn Gln Pro Met Trp Glu Thr Gly
            180                 185                 190

Gln Ala Cys Lys Thr Gly Ala Asp Cys Ser Thr Tyr Lys Asn Ser Gly
        195                 200                 205

Cys Glu Asp Gly Leu Cys Thr Lys Gly Pro Asp Val Pro Glu Thr Asn
    210                 215                 220

Gln Gln Cys Pro Ser Asn Thr Gly Met Thr Asp Ser Val Arg Asp Thr
225                 230                 235                 240

Phe Leu Ser Val His Asn Glu Phe Arg Ser Ser Val Ala Arg Gly Leu
                245                 250                 255

Glu Pro Asp Ala Leu Gly Gly Asn Ala Pro Lys Ala Ala Lys Met Leu
            260                 265                 270

Lys Met Val Tyr Asp Cys Glu Val Glu Ala Ser Ala Ile Arg His Gly
        275                 280                 285

Asn Lys Cys Val Tyr Gln His Ser His Gly Glu Asp Arg Pro Gly Leu
    290                 295                 300

Gly Glu Asn Ile Tyr Lys Thr Ser Val Leu Lys Phe Asp Lys Asn Lys
305                 310                 315                 320

Ala Ala Lys Gln Ala Ser Gln Leu Trp Trp Asn Glu Leu Lys Glu Phe
                325                 330                 335

Gly Val Gly Pro Ser Asn Val Leu Thr Thr Ala Leu Trp Asn Arg Pro
            340                 345                 350

Gly Met Gln Ile Gly His Tyr Thr Gln Met Ala Trp Asp Thr Thr Tyr
        355                 360                 365

Lys Leu Gly Cys Ala Val Val Phe Cys Asn Asp Phe Thr Phe Gly Val
    370                 375                 380

Cys Gln Tyr Gly Pro Gly Gly Asn Tyr Met Gly His Val Ile Tyr Thr
385                 390                 395                 400

Met Gly Gln Pro Cys Ser Gln Cys Ser Pro Gly Ala Thr Cys Ser Val
                405                 410                 415

Thr Glu Gly Leu Cys Ser Ala Pro
            420
```

<210> SEQ ID NO 19
<211> LENGTH: 767
<212> TYPE: DNA
<213> ORGANISM: Ancylostoma caninum

<400> SEQUENCE: 19

```
cgacacaacc aacgatgtta gttcttgtac cacttttggc tctcttggct gtttctgttc      60

atggaaattc tatgagatgc ggaaataatg gaatgaccga cgaagcccgg cagaaattcc     120

tcgacgtgca caacagttac agatctatgg ttgccaaagg acaggcaaag gatgcaattt     180

cgggaaatgc tccgaaggct gccaaaatga agaaaatgat ctacgactgc aacgtcgaat     240

caactgcaat gcaaaatgcg aaaaaatgtg ttttcgccca ttcgcacagg aagggagttg     300

gcgaaaatat ttggatgtcg actgcgcgtc agatggacaa agcacaagct gctcaacagg     360
```

-continued

```
ctagtgacgg ttggttcagt gagcttgcga agtatggtgt aggccaggaa aacaagctaa    420

caacgcagtt gtggaacagg ggagttatga taggacatta cactcagatg gtctggcagg    480

agtcctacaa actcggatgt tatgtggaat ggtgttcatc gatgacctat ggtgtctgcc    540

agtacagtcc tcagggtaat atgatgaact cactcatcta cgagaaagga aacccgtgca    600

caaaagactc tgactgtggc tcgaacgcca gttgcagcgc tggggaggcg ctttgcgtcg    660

tgcgtggcta gctggacatt cccaacgtac aacagcgtta tagttaatgc aacttttctt    720

tcatcttatt gagtaaaggc attgaaaaca aaaaaaaaaa aaaaaaa                  767
```

<210> SEQ ID NO 20
<211> LENGTH: 218
<212> TYPE: PRT
<213> ORGANISM: Ancylostoma caninum

<400> SEQUENCE: 20

```
Met Leu Val Leu Val Pro Leu Leu Ala Leu Leu Ala Val Ser Val His
1               5                   10                  15

Gly Asn Ser Met Arg Cys Gly Asn Asn Gly Met Thr Asp Glu Ala Arg
            20                  25                  30

Gln Lys Phe Leu Asp Val His Asn Ser Tyr Arg Ser Met Val Ala Lys
        35                  40                  45

Gly Gln Ala Lys Asp Ala Ile Ser Gly Asn Ala Pro Lys Ala Ala Lys
    50                  55                  60

Met Lys Lys Met Ile Tyr Asp Cys Asn Val Glu Ser Thr Ala Met Gln
65                  70                  75                  80

Asn Ala Lys Lys Cys Val Phe Ala His Ser His Arg Lys Gly Val Gly
                85                  90                  95

Glu Asn Ile Trp Met Ser Thr Ala Arg Gln Met Asp Lys Ala Gln Ala
            100                 105                 110

Ala Gln Gln Ala Ser Asp Gly Trp Phe Ser Glu Leu Ala Lys Tyr Gly
        115                 120                 125

Val Gly Gln Glu Asn Lys Leu Thr Thr Gln Leu Trp Asn Arg Gly Val
    130                 135                 140

Met Ile Gly His Tyr Thr Gln Met Val Trp Gln Glu Ser Tyr Lys Leu
145                 150                 155                 160

Gly Cys Tyr Val Glu Trp Cys Ser Ser Met Thr Tyr Gly Val Cys Gln
                165                 170                 175

Tyr Ser Pro Gln Gly Asn Asn Met Asn Ser Leu Thr Tyr Glu Lys Gly
            180                 185                 190

Asn Pro Cys Thr Lys Asp Ser Asp Cys Gly Ser Asn Ala Ser Cys Ser
        195                 200                 205

Ala Gly Glu Ala Leu Cys Val Val Arg Gly
    210                 215
```

<210> SEQ ID NO 21
<211> LENGTH: 687
<212> TYPE: DNA
<213> ORGANISM: Ancylostoma caninum

<400> SEQUENCE: 21

```
ataagacagc aatgaagtcc tatcttgtga tatcagctgc gatcctcggc attgcttatg     60

ccgatgctga ttattccaag tgcccgcaaa atgaaataat gaacaacgat atgagggaaa    120

aagttacgga catgcacaac gcctacagat ccaaattcgc acgggatcat caagcttcga    180

aaatgagaaa attggtttac gactgtgcca tcgaaaaagg aatctacgag tcggatacca    240
```

-continued

```
agtgcgagat gaaaccatcg atggaggagg agaacgtaga agttatcgac ggcaacagcg    300

atgatctcac tgttatttca gaggccggta attcgtggtg gagcgagatt ttggacctga    360

aaggaaagga tgtgtacaac tccgtggaca atacatcgga aattgccaat atggcttggg    420

aaagtcatgc gaaacttggt tgcgcagttg ttgagtgctc caagaaaacc catgtagtct    480

gccgatacgg accggaagga aaaggtgaag gaaagaaaat ttacgaaaag ggcgaaacat    540

gctcacaatg cagtgattac ggacaaggtg tcacctgtga caatgacgag tgggagggat    600

tactctgctc ataatattgg aaaaacatat gtggatgatg atgttcgcaa ataaataaat    660

caattacaaa aaaaaaaaaa aaaaaaa                                         687
```

<210> SEQ ID NO 22
<211> LENGTH: 200
<212> TYPE: PRT
<213> ORGANISM: Ancylostoma caninum

<400> SEQUENCE: 22

```
Met Lys Ser Tyr Leu Val Ile Ser Ala Ala Ile Leu Gly Ile Ala Tyr
1               5                   10                  15

Ala Asp Ala Asp Tyr Ser Lys Cys Pro Gln Asn Glu Ile Met Asn Asn
            20                  25                  30

Asp Met Arg Glu Lys Val Thr Asp Met His Asn Ala Tyr Arg Ser Lys
        35                  40                  45

Phe Ala Arg Asp His Gln Ala Ser Lys Met Arg Lys Leu Val Tyr Asp
    50                  55                  60

Cys Ala Ile Glu Lys Gly Ile Tyr Glu Ser Asp Thr Lys Cys Glu Met
65                  70                  75                  80

Lys Pro Ser Met Glu Glu Glu Asn Val Glu Val Ile Asp Gly Asn Ser
                85                  90                  95

Asp Asp Leu Thr Val Ile Ser Glu Ala Gly Asn Ser Trp Trp Ser Glu
            100                 105                 110

Ile Leu Asp Leu Lys Gly Lys Asp Val Tyr Asn Ser Val Asp Asn Thr
        115                 120                 125

Asp Glu Ile Ala Asn Met Ala Trp Glu Ser His Ala Lys Leu Gly Cys
    130                 135                 140

Ala Val Val Glu Cys Ser Lys Lys Thr His Val Val Cys Arg Tyr Gly
145                 150                 155                 160

Pro Glu Gly Lys Gly Glu Gly Lys Lys Ile Tyr Glu Lys Gly Glu Thr
                165                 170                 175

Cys Ser Gln Cys Ser Asp Tyr Gly Gln Gly Val Thr Cys Asp Asn Asp
            180                 185                 190

Glu Trp Glu Gly Leu Leu Cys Ser
        195                 200
```

<210> SEQ ID NO 23
<211> LENGTH: 1689
<212> TYPE: DNA
<213> ORGANISM: Ancylostoma caninum

<400> SEQUENCE: 23

```
agaacatgat caacatccat ttcatagcgc ttgccataac ctctcttttg cctgccctat     60

ccgaagggaa accggtcgta tttgttgaac cacagtgtaa gccgaatggt tacctacaca    120

agaatacaat cgacaacaat gttcttaagc cgataaatac tcgtcgagag gctctggcca    180

agggcacgca acagaatggc tttgacccac caaacccaca aacattcttg ccaccagcga    240
```

-continued

```
cggacatgac taaactgagt tggagttgtg atcttgagca gaaggctata aaaactatca    300

acggtaactg tgtgaatccg gcaaacccaa ccaaaccgaa taacggcgaa ggattggcag    360

atgtcctcta ctacggcaac gactatgata acacggtcga aggagtgatc caaggcaatc    420

tcgaagcttg gctggtaaaa gccgatttca atgtattccc tgttaccaca aaaggtaccg    480

tcattagcta tcccacttac aatggcaaca cagatctctt ggcatactct aacttagtcc    540

ggcctaccaa tactgagata ggatgtgtac tggaaagatg tccagctaca gccaatgttc    600

caaagctagt cacgttctac tgtattttga atggaaaaaa tatcaccaac ggagaggctc    660

tctataaggg cacaactgtg aataccggag gatgcaaaga ggtcacatgc tcagcgggat    720

atgcctgtaa caacgccacc ttgctatgtg aacgtagtgc gacaacaagc tcatctacat    780

cggcaagcac atcttcatca acagcttcct caacaagttc atctatggca ataagcacat    840

cttcgtcaac aagcgcatct ggggcaacaa caacaaaagc tccttctccg caagcgcaat    900

tccccacagg gactagcact atgtgcaata ccaggcatgc ctatgctaac aggatgaccg    960

acaatctcag gaatgaatac gtaaggctgc acaacttccg aagaggctta ctcgcaaagg   1020

gagaaattcc tcagaagggt aacatatacc taccaaaggc ggctgacatg tggaaaatta   1080

gttacgactg cggcctggaa caaggagcca tagaacacgc aagccagtgt ctcacaggag   1140

ggtccggaca aagctcgaga ccaggtgtgg gagagaactt taaagtgatc ccagcggcaa   1200

gatttccgac tttcgaagat gcagcaaaaa agaccgttac tgaatggtgg aagccgattc   1260

gtaacgtgga ctacttcgga aacaacgtca acttcctccc catctatgac caagacccga   1320

tatcctcctt tacccggatg gcatgggcca caactaacaa ggtggggtgc tctatcgtaa   1380

agtgcacaac ggacaacgta tacgtaggcg tgtgccgata tagtccaatg ggtaacattg   1440

tgaacagcaa catctaccaa attgggaatc cctgcagtgt gagacctact caagcgaccg   1500

ggtgtgaccc agtcgaggga ttgtggtact aggcgcactt ttccgcactg aatggcgatt   1560

ctgttttgaa tttttgaata ttacattaat ggatgttaac aatgggtcct ttagttttct   1620

gttgttaaca agggtggtta gattggattg ggaataaatg atgcaatcgc caaaaaaaaa   1680

aaaaaaaaa                                                          1689
```

```
<210> SEQ ID NO 24
<211> LENGTH: 508
<212> TYPE: PRT
<213> ORGANISM: Ancylostoma caninum

<400> SEQUENCE: 24

Met Ile Asn Ile His Phe Ile Ala Leu Ala Ile Thr Ser Leu Leu Pro
1               5                   10                  15

Ala Leu Ser Glu Gly Lys Pro Val Val Phe Val Glu Pro Gln Cys Lys
            20                  25                  30

Pro Asn Gly Tyr Leu His Lys Asn Thr Ile Asp Asn Asn Val Leu Lys
        35                  40                  45

Pro Ile Asn Thr Arg Arg Glu Ala Leu Ala Lys Gly Thr Gln Gln Asn
    50                  55                  60

Gly Phe Asp Pro Pro Asn Pro Gln Thr Phe Leu Pro Pro Ala Thr Asp
65                  70                  75                  80

Met Thr Lys Leu Ser Trp Ser Cys Asp Leu Glu Gln Lys Ala Ile Lys
                85                  90                  95

Thr Ile Asn Gly Asn Cys Val Asn Pro Ala Asn Pro Thr Lys Pro Asn
            100                 105                 110
```

-continued

```
Asn Gly Glu Gly Leu Ala Asp Val Leu Tyr Tyr Gly Asn Asp Tyr Asp
        115                 120                 125

Asn Thr Val Glu Gly Val Ile Gln Gly Asn Leu Glu Ala Trp Leu Val
    130                 135                 140

Lys Ala Asp Phe Asn Val Phe Pro Val Thr Thr Lys Gly Thr Val Ile
145                 150                 155                 160

Ser Tyr Pro Thr Tyr Asn Gly Asn Thr Asp Leu Leu Ala Tyr Ser Asn
                165                 170                 175

Leu Val Arg Pro Thr Asn Thr Glu Ile Gly Cys Val Leu Glu Arg Cys
            180                 185                 190

Pro Ala Thr Ala Asn Val Pro Lys Leu Val Thr Phe Tyr Cys Ile Leu
        195                 200                 205

Asn Gly Lys Asn Ile Thr Asn Gly Arg Ala Leu Tyr Lys Gly Thr Thr
    210                 215                 220

Val Asn Thr Gly Gly Cys Lys Glu Val Thr Cys Ser Ala Gly Tyr Ala
225                 230                 235                 240

Cys Asn Asn Ala Thr Leu Leu Cys Glu Arg Ser Ala Thr Thr Ser Ser
                245                 250                 255

Ser Thr Ser Ala Ser Thr Ser Ser Ser Thr Ala Ser Ser Thr Ser Ser
            260                 265                 270

Ser Asn Ala Ile Ser Thr Ser Ser Ser Thr Ser Ala Ser Gly Ala Thr
        275                 280                 285

Thr Thr Lys Ala Pro Ser Pro Gln Ala Gln Phe Pro Thr Gly Thr Ser
    290                 295                 300

Thr Met Cys Asn Thr Arg His Ala Tyr Ala Asn Arg Met Thr Asp Asn
305                 310                 315                 320

Leu Arg Asn Glu Tyr Val Arg Leu His Asn Phe Arg Arg Gly Leu Leu
                325                 330                 335

Ala Lys Gly Glu Ile Pro Gln Lys Gly Asn Ile Tyr Leu Pro Lys Ala
            340                 345                 350

Ala Asp Met Trp Lys Ile Ser Tyr Asp Cys Gly Leu Glu Gln Gly Ala
        355                 360                 365

Ile Glu His Ala Ser Gln Cys Leu Thr Gly Gly Ser Gly Gln Ser Ser
    370                 375                 380

Arg Pro Gly Val Gly Glu Asn Phe Lys Val Ile Pro Ala Ala Arg Phe
385                 390                 395                 400

Pro Thr Phe Glu Asp Ala Ala Lys Lys Thr Val Thr Glu Trp Trp Lys
                405                 410                 415

Pro Ile Arg Asn Val Asp Tyr Phe Gly Asn Asn Val Asn Phe Leu Pro
            420                 425                 430

Ile Tyr Asp Gln Asp Pro Ile Ser Ser Phe Thr Arg Asn Ala Trp Ala
        435                 440                 445

Thr Thr Asn Lys Val Gly Cys Ser Ile Val Lys Cys Thr Thr Asp Asn
    450                 455                 460

Val Tyr Val Gly Val Cys Arg Tyr Ser Pro Met Gly Asn Ile Val Asn
465                 470                 475                 480

Ser Asn Ile Tyr Gln Ile Gly Asn Pro Cys Ser Val Arg Pro Thr Gln
                485                 490                 495

Ala Thr Gly Cys Asp Pro Val Glu Gly Leu Trp Tyr
            500                 505
```

<210> SEQ ID NO 25
<211> LENGTH: 1384

-continued

<212> TYPE: DNA
<213> ORGANISM: Ancylostoma caninum

<400> SEQUENCE: 25

```
atactactgc agtgtgcgtt taggagaact ctcactgcat cgaaaatgcc gaatctactc      60

ctgctgctgt ttctctcgct accaggagcg attctttcaa ccacttgtcc aggaaatgat     120

ctaacagatg ctgaacgcac actgctaact agggtgcaca attccattcg acgggaaata     180

gcgcaaggag ttgcaaacaa ctaccatggt ggtaaactgc ctgctggaaa gaacatatac     240

aggatgagat acagctgtga gctggaacag gctgctattg atgctagtca aaccttctgt     300

tccgcatcat tggaggaacc acagaaatat ggacaaaaca tccaagcata cgtcacacca     360

tctataatcg ctcgcccgaa aaacgacctt cttgaagatg cagtgaaaca atggtatctg     420

cctgttatct actacggcca gcgcgacgcg gccaacaagt ttacggatcc gcgcttgtac     480

acatttgcaa acctcgccta cgacaagaac actgcacttg gctgtcacta tgcgaaatgt     540

caaggccctg acagaatcgt cattagttgc atgtacaaca acgtcgttcc tgacaacgca     600

gtgatctacg agcctggaac tgcttgcgta aaagatgcgg actgcactac ttatcctcag     660

tccacatgca aggacagcct ttgcattatt cctacgccac atccaccaaa tccaccaaat     720

ccaccaccag caatgagtcc aaacgctgaa atgactgatg cagcacgaaa gaaggtcctc     780

ggcatgcaca actggcgcag atcgcaggtc gctctgggaa acgttcaaaa cgggaaaaat     840

gcttacaact gccccactgc aacagacatg tacaagatag aatatgattg cgacctcgag     900

aacagcgctc tagcgtatgc aaagcaatgt agtctcgttg gttcagcaga aggaactcgt     960

ccaggagaag gcgagaatgt ccacaaaggc gctctcgtaa ccgatccgga ggctgcagtt    1020

cagaccgcag ttcaagcatg gtggagtcaa atctcacaaa atggactcaa tgcacagatg    1080

aaattcactg ctttcttgaa ggacaagcct gacgctccga cagcgtttac acagatggcg    1140

tgggccaaat ccgtaaagct tggatgtgct gtctctaatt gtcaggcaga taccttcacc    1200

gtctgtagat acaaagctgc cggaaacatc gtgggcgaat tcatctatac caagggaaat    1260

gtatgcgacg cctgtaaagc cacatgcatt accgcggaag gtctttgccc aacgccttga    1320

ttttcactgg actgtttcac gaacagatca gataaatcgt ttcatcaaaa aaaaaaaaaa    1380

aaaa                                                                1384
```

<210> SEQ ID NO 26
<211> LENGTH: 424
<212> TYPE: PRT
<213> ORGANISM: Ancylostoma caninum

<400> SEQUENCE: 26

```
Met Pro Asn Leu Leu Leu Leu Leu Phe Leu Ser Leu Pro Gly Ala Ile
1               5                   10                  15

Leu Ser Thr Thr Cys Pro Gly Asn Asp Leu Thr Asp Ala Glu Arg Thr
            20                  25                  30

Leu Leu Thr Arg Val His Asn Ser Ile Arg Arg Glu Ile Ala Gln Gly
        35                  40                  45

Val Ala Asn Asn Tyr His Gly Gly Lys Leu Pro Ala Gly Lys Asn Ile
    50                  55                  60

Tyr Arg Met Arg Tyr Ser Cys Glu Leu Glu Gln Ala Ala Ile Asp Ala
65                  70                  75                  80

Ser Gln Thr Phe Cys Ser Ala Ser Leu Glu Glu Pro Gln Lys Tyr Gly
                85                  90                  95
```

-continued

```
Gln Asn Ile Gln Ala Tyr Val Thr Pro Ser Ile Ile Ala Arg Pro Lys
            100                 105                 110

Asn Asp Leu Leu Glu Asp Ala Val Lys Gln Trp Tyr Leu Pro Val Ile
        115                 120                 125

Tyr Tyr Gly Gln Arg Asp Ala Ala Asn Lys Phe Thr Asp Pro Arg Leu
    130                 135                 140

Tyr Thr Phe Ala Asn Leu Ala Tyr Asp Lys Asn Thr Ala Leu Gly Cys
145                 150                 155                 160

His Tyr Ala Lys Cys Gln Gly Pro Asp Arg Ile Val Ile Ser Cys Met
                165                 170                 175

Tyr Asn Asn Val Val Pro Asp Asn Ala Val Ile Tyr Glu Pro Gly Thr
            180                 185                 190

Ala Cys Val Lys Asp Ala Asp Cys Thr Thr Tyr Pro Gln Ser Thr Cys
        195                 200                 205

Lys Asp Ser Leu Cys Ile Ile Pro Thr Pro His Pro Pro Asn Pro Pro
    210                 215                 220

Asn Pro Pro Pro Ala Met Ser Pro Asn Ala Glu Met Thr Asp Ala Ala
225                 230                 235                 240

Arg Lys Lys Val Leu Gly Met His Asn Trp Arg Arg Ser Gln Val Ala
                245                 250                 255

Leu Gly Asn Val Gln Asn Gly Lys Asn Ala Tyr Asn Cys Pro Thr Ala
            260                 265                 270

Thr Asp Met Tyr Lys Ile Glu Tyr Asp Cys Asp Leu Glu Asn Ser Ala
        275                 280                 285

Leu Ala Tyr Ala Lys Gln Cys Ser Leu Val Gly Ser Ala Glu Gly Thr
    290                 295                 300

Arg Pro Gly Glu Gly Glu Asn Val His Lys Gly Ala Leu Val Thr Asp
305                 310                 315                 320

Pro Glu Ala Ala Val Gln Thr Ala Val Gln Ala Trp Trp Ser Gln Ile
                325                 330                 335

Ser Gln Asn Gly Leu Asn Ala Gln Met Lys Phe Thr Ala Phe Leu Lys
            340                 345                 350

Asp Lys Pro Asp Ala Pro Thr Ala Phe Thr Gln Met Ala Trp Ala Lys
        355                 360                 365

Ser Val Lys Leu Gly Cys Ala Val Ser Asn Cys Gln Ala Asp Thr Phe
    370                 375                 380

Thr Val Cys Arg Tyr Lys Ala Ala Gly Asn Ile Val Gly Glu Phe Ile
385                 390                 395                 400

Tyr Thr Lys Gly Asn Val Cys Asp Ala Cys Lys Ala Thr Cys Ile Thr
                405                 410                 415

Ala Glu Gly Leu Cys Pro Thr Pro
            420
```

<210> SEQ ID NO 27
<211> LENGTH: 1467
<212> TYPE: DNA
<213> ORGANISM: Ancylostoma caninum

<400> SEQUENCE: 27

```
cagcaatagt ccaatgaagc tcttcattct ggttttggtc gctatccttg gcattgctca      60

cgccactgat tttcaatgct ggaacttcaa atcgacggat acactgcggg aacattacct     120

caaatccatt aacaacctaa ggaagaaaat cgccgatgga tcagcggaaa acaaatcagg     180

aaagtgcccg cagggcaaga atatctacaa gctaagctgg gattgtgaat tggaactgaa     240
```

-continued

```
agcacagcaa gctgtagacc agtgcaaacc gaatgtaccc gaacccgcag gatattcgca    300

aatactaaag aaggttaaaa gcacctgcga cccaacgaag gtcctgaaga aacagataga    360

agcatggtgg actaagtccg tgaaagatgc tggagttgat aatcctccaa acaacaaaca    420

aggtttggaa gatttcgcaa agttagcaaa tggaaaggct acgaagattg gttgtgcgca    480

gaaaaactgc aacgaacagt tgtacgtggc atgtgttatt aacgaaccgg ctcctgcagt    540

gggtatgcca atctatgagg ttggagctgg atgtaattcc aaagacgatt gtacaacgta    600

tctgcagtcg aagtgcagta acaaagtatg cgtcgccggg cacccaggtg atgccaccac    660

tacaacatca acaccagcaa caacagcacc aacaacaccc acgattcctg ctggaccaac    720

aactgcgcca gctccaccac caacaactgc agctcctaca acgacgagta cgattggttc    780

gattgacaat acgatttgtc cgcaaaacca agtgatcacc gactcagtca ggctcacatt    840

cttgaatacg cacaacggac tcagatctca actcgcgcaa ggtcaaatct ttatgggaaa    900

tggcgctagg gcgcgtccgg catcgaaaat gaggaggatg gtatataact gtgatgcgga    960

atcaagcgct cgcaattcgg ccgctcagtg ccttagcagc cccggttcac ctagcggcta   1020

cactgagaac ttgcatgtta tcaacaacaa ctttgtggac cataacagtg cggctactca   1080

ggcttttaac gcatggtggt cagaaattaa cacaggatat atgcgtcagg cagagacgga   1140

aaggaatatg tactctctga gcgttggaat accaaacttc gctaaaatgg cttgggaaac   1200

caatgcacat cttggttgtg ctatagtcag atgcggtttg aacacgaacg tcgtctgccc   1260

ctactcccca aaatcggatg gaggccaaat ttacaagatg ggcccctttt gcagacgttg   1320

ccccgactac cctgggactt tttgcaacca aggactctgc tcattttaag acccgccccg   1380

atatatcttt ggggagataa ttttacgagc aataaaccaa gcgtgaagaa aaaaaaaaaa   1440

aaaaaaaaaa aaaaaaaaaa aaaaaaa                                       1467
```

```
<210> SEQ ID NO 28
<211> LENGTH: 451
<212> TYPE: PRT
<213> ORGANISM: Ancylostoma caninum

<400> SEQUENCE: 28

Met Lys Leu Phe Ile Leu Val Leu Val Ala Ile Leu Gly Ile Ala His
1               5                   10                  15

Ala Thr Asp Phe Gln Cys Trp Asn Phe Lys Ser Thr Asp Thr Leu Arg
            20                  25                  30

Glu His Tyr Leu Lys Ser Ile Asn Asn Leu Arg Lys Lys Ile Ala Asp
        35                  40                  45

Gly Ser Ala Glu Asn Lys Ser Gly Lys Cys Pro Gln Gly Lys Asn Ile
    50                  55                  60

Tyr Lys Leu Ser Trp Asp Cys Glu Leu Glu Leu Lys Ala Gln Gln Ala
65                  70                  75                  80

Val Asp Gln Cys Lys Pro Asn Val Pro Glu Pro Ala Gly Tyr Ser Gln
                85                  90                  95

Ile Leu Lys Lys Val Lys Ser Thr Cys Asp Pro Thr Lys Val Leu Lys
            100                 105                 110

Lys Gln Ile Glu Ala Trp Trp Thr Lys Ser Val Lys Asp Ala Gly Val
        115                 120                 125

Asp Asn Pro Pro Asn Asn Lys Gln Gly Leu Glu Asp Phe Ala Lys Leu
    130                 135                 140

Ala Asn Gly Lys Ala Thr Lys Ile Gly Cys Ala Gln Lys Asn Cys Asn
145                 150                 155                 160
```

-continued

Glu Gln Leu Tyr Val Ala Cys Val Ile Asn Glu Pro Ala Pro Ala Val
165 170 175

Gly Met Pro Ile Tyr Glu Val Gly Ala Gly Cys Asn Ser Lys Asp Asp
180 185 190

Cys Thr Thr Tyr Leu Gln Ser Lys Cys Ser Asn Lys Val Cys Val Ala
195 200 205

Gly His Pro Gly Asp Ala Thr Thr Thr Thr Ser Thr Pro Ala Thr Thr
210 215 220

Ala Pro Thr Thr Pro Thr Ile Pro Ala Gly Pro Thr Thr Ala Pro Ala
225 230 235 240

Pro Pro Pro Thr Thr Ala Ala Pro Thr Thr Thr Ser Thr Ile Gly Ser
245 250 255

Ile Asp Asn Thr Ile Cys Pro Gln Asn Gln Val Ile Thr Asp Ser Val
260 265 270

Arg Leu Thr Phe Leu Asn Thr His Asn Gly Leu Arg Ser Gln Leu Ala
275 280 285

Gln Gly Gln Ile Phe Met Gly Asn Gly Ala Arg Ala Arg Pro Ala Ser
290 295 300

Lys Met Arg Arg Met Val Tyr Asn Cys Asp Ala Glu Ser Ser Ala Arg
305 310 315 320

Asn Ser Ala Ala Gln Cys Leu Ser Ser Pro Gly Ser Pro Ser Gly Tyr
325 330 335

Thr Glu Asn Leu His Val Ile Asn Asn Asn Phe Val Asp His Asn Ser
340 345 350

Ala Ala Thr Gln Ala Phe Asn Ala Trp Trp Ser Glu Ile Asn Thr Gly
355 360 365

Tyr Met Arg Gln Ala Glu Thr Glu Arg Asn Met Tyr Ser Leu Ser Val
370 375 380

Gly Ile Pro Asn Phe Ala Lys Met Ala Trp Glu Thr Asn Ala His Leu
385 390 395 400

Gly Cys Ala Ile Val Arg Cys Gly Leu Asn Thr Asn Val Val Cys Pro
405 410 415

Tyr Ser Pro Lys Ser Asp Gly Gly Gln Ile Tyr Lys Met Gly Pro Phe
420 425 430

Cys Arg Arg Cys Pro Asp Tyr Pro Gly Thr Phe Cys Asn Gln Gly Leu
435 440 445

Cys Ser Phe
450

<210> SEQ ID NO 29
<211> LENGTH: 602
<212> TYPE: DNA
<213> ORGANISM: Ancylostoma caninum

<400> SEQUENCE: 29
gggtttaatt acccaagttt gagaatgatt caattgtttt tgttagcgct cgtacctatg 60
tgcatctcag tgagggaaca gtcgatagct gttaaaggac gacttttgtg tggcgatcaa 120
ccagctgcga acgtcagagt aaagttatgg gaggaagaca caggaccaga tccagatgac 180
ctactggatg caggatacac gaactccaac ggtgaattcc aactccaagg cggaacaata 240
gagacgactc ctattgaccc cgtcttgaaa atttatcatg attgcaatga cgtgactggt 300
ttcctaagcg tacctaaacc tggcagcaga aaggtgaggt tctccttacc agacaagtac 360
atcagcgatg gaatggttcc taagaaagtt atggacatcg gtgttatcaa tcttgaagtg 420

-continued

```
gaatttgaaa aggaaggacg tgaatttatc gttgactaag tgatcaataa actcatcgct    480

ttctctttct atgtaaacat ttttgttgtg aacaaatcat atggttgtac ataatccgaa    540

ctgttggttt ttcgaatact gcacaaataa agcatttctt ctaaaaaaaa aaaaaaaaaa    600

aa                                                                   602


<210> SEQ ID NO 30
<211> LENGTH: 144
<212> TYPE: PRT
<213> ORGANISM: Ancylostoma caninum

<400> SEQUENCE: 30

Met Ile Gln Leu Phe Leu Leu Ala Leu Val Pro Met Cys Ile Ser Val
1               5                   10                  15

Arg Glu Gln Ser Ile Ala Val Lys Gly Arg Leu Leu Cys Gly Asp Gln
            20                  25                  30

Pro Ala Ala Asn Val Arg Val Lys Leu Trp Glu Glu Asp Thr Gly Pro
        35                  40                  45

Asp Pro Asp Asp Leu Leu Asp Ala Gly Tyr Thr Asn Ser Asn Gly Glu
    50                  55                  60

Phe Gln Leu Gln Gly Gly Thr Ile Glu Thr Thr Pro Ile Asp Pro Val
65                  70                  75                  80

Leu Lys Ile Tyr His Asp Cys Asn Asp Val Thr Gly Phe Leu Ser Val
                85                  90                  95

Pro Lys Pro Gly Ser Arg Lys Val Arg Phe Ser Leu Pro Asp Lys Tyr
            100                 105                 110

Ile Ser Asp Gly Met Val Pro Lys Lys Val Met Asp Ile Gly Val Ile
        115                 120                 125

Asn Leu Glu Val Glu Phe Glu Lys Glu Gly Arg Glu Phe Ile Val Asp
    130                 135                 140


<210> SEQ ID NO 31
<211> LENGTH: 838
<212> TYPE: DNA
<213> ORGANISM: Ancylostoma caninum

<400> SEQUENCE: 31

cacttccagc gatgttctgt cgtgttactg tcgccgtttt gttgttggcc gtatcggcct     60

atgccggatt tttcgatgac gtcagtggca tggcctcaga tgttgggaat ttcttcacaa    120

accaattcaa caatgtgaag gatttgtttg ctggaaatca atcggaactc gagaagaaca    180

tcaatcgagt aaaggatctt ctgacggccg tcaaagaaaa ggctaagatg cttgaaccaa    240

tggccaatga tgctcagaag aagacgttat cacaggtgga caactacctc aacgaagtgc    300

aacagttcgg tgaacaggta agcaaagaag gctcggcgaa gttcgaggag aacaagggca    360

agtggcagca aatgctgaac gacatcttcg agaagggcgg tctggacggc gtgctgaagc    420

tgctcaatct gaaatctgcc ggccactgca cactcgtagc ggccatcgtc gctccagtag    480

tgctggcgtt cacccgctaa gcgccaccca ctaatcgata attgtagcct gtcacctgcc    540

gtcgatcgat aattgttgtc gcgtgtgcgt atgcttgcat ctatgtatga tgatgtgtat    600

ctatatgtga tttgtattct acttcgccgc attcagctct ggtattctga gacggattat    660

cgcttctcgc acacactcac acacacaaat aaccccccgat tatctcccga ttatcacccg    720

gttagtagat gagacataat ttccatccgt ccacatactc tacttctatc tatggtcaat    780

gtggttcttt atgtaaataa acttttccat cgaaaaaaaa aaaaaaaaaa aaaaaaaa      838
```

-continued

<210> SEQ ID NO 32
<211> LENGTH: 162
<212> TYPE: PRT
<213> ORGANISM: Ancylostoma caninum

<400> SEQUENCE: 32

Met Phe Cys Arg Val Thr Val Ala Val Leu Leu Leu Ala Val Ser Ala
1 5 10 15

Tyr Ala Gly Phe Phe Asp Asp Val Ser Gly Met Ala Ser Asp Val Gly
20 25 30

Asn Phe Phe Thr Asn Gln Phe Asn Asn Val Lys Asp Leu Phe Ala Gly
35 40 45

Asn Gln Ser Glu Leu Glu Lys Asn Ile Asn Arg Val Lys Asp Leu Leu
50 55 60

Thr Ala Val Lys Glu Lys Ala Lys Met Leu Glu Pro Met Ala Asn Asp
65 70 75 80

Ala Gln Lys Lys Thr Leu Ser Gln Val Asp Asn Tyr Leu Asn Glu Val
85 90 95

Gln Gln Phe Gly Glu Gln Val Ser Lys Glu Gly Ser Ala Lys Phe Glu
100 105 110

Glu Asn Lys Gly Lys Trp Gln Gln Met Leu Asn Asp Ile Phe Glu Lys
115 120 125

Gly Gly Leu Asp Gly Val Leu Lys Leu Leu Asn Leu Lys Ser Ala Gly
130 135 140

His Cys Thr Leu Val Ala Ala Ile Val Ala Pro Val Val Leu Ala Phe
145 150 155 160

Thr Arg

<210> SEQ ID NO 33
<211> LENGTH: 2043
<212> TYPE: DNA
<213> ORGANISM: Ancylostoma caninum

<400> SEQUENCE: 33
tcaccgcttc cgaccgatgc ttcaggaaac tacgtcaccg acgaaggaac tgtcattgag 60
aaagacgatg agggaagacc attgggaccg gatggacaag tgttgcccac cgacgaatct 120
ggaaactaca tctatcctgt cgttggaccc gatggaagcc cattgccaac tgacgagcac 180
aagcgaccaa ttcacccagt ccttggacct gatggcagcc cactgccgac agacgaatca 240
ggccatccac taggagaaga cggacagcca cttccaacag atgcttctgg cgttcctgtg 300
gataaggacg gtcagccgtt gccgacagac agcagtggac actacgtcac agttccacgt 360
gaagaagctg tcacgaagga gctaccaacg gacgagagcg gaaatgtcat ctacccagtg 420
acgaaacctg atggatcacc gcttccgacc gatgcttcag gaaactacgt caccgacgaa 480
ggaactgtca ttgagaaaga cgatgaggga agaccattgg gaccggacgg acaagtgttg 540
cccaccgacg aatccggaaa ctacatctat cctgtcgttg gacccgatgg aagccccctg 600
ccaactgacg agtacaagcg accaattcac ccagtccttg gacctgatgg cagcccactg 660
ccgacagacg aatcaggcca tccactagga gaggacggac agccacttcc aacagatgct 720
tctggcgttc ctgtggataa ggacggtcag ccgctgccga cagacagcag tggacactac 780
gtcacagttc cacgtgaaga agctgtcacg aaagagctac caacggacga gagcggaaat 840
gtcatctacc cagtgacgaa acctgatggg tcaccgcttc caaccgatgc ttccgggaac 900

-continued

```
tttattactg aagaaggact gatcattggt cccgatggtg ttgctcttcc ctacccgcgt    960

aacaggacct gctccttaaa gcaactgaag atggatatcc ttttcgcggt aagcacgaca   1020

aaagtctcga aatccacctt tgatagtatc ctgcgagcaa tatcaaagtt tgccgatgaa   1080

gtcgacttat ctcctgacgt tacccgcatt ggattagtat acggcagcaa ggacgtagtc   1140

gttccacttc cgcttggggg gtaccaagaa aaagatcata tgagggatga aattcgacgc   1200

atcgaatttt ctgatgatgg atcgcaagac tacatttctc tgtatggtcc cgccaagcaa   1260

caattcgtca tgtttcctcg agcggacagt gcgaagatcg ctatcttcct cattcaagat   1320

gaaataagtt actgcttatc cacgagaacg ttgagatgtg gttgcgctac tgctgtggat   1380

agcgattgtc gtcgaataaa caatgtccta gcggatgaca tcaaagtgtg caaggtccct   1440

gaaactgctg tagtccctac tccagttgtt catccacaag ggtcaagggc cgtctcggtc   1500

gttgtgcctc gattctttag tgctccgcca tttgacaccc acagtccgtc aaggctgaca   1560

ctgctggcag attttgctac ggagaaagaa cctctatgcg gggaacattc atttttatcc   1620

ccccagaaat ggggcaagaa tcactgtacg ttacgcattc ctctttcgat gccaggaata   1680

gatcacaaat ccgatgatca ctactactat gatgaccaga ccccattaga atccgaatat   1740

tcattggatt tgtttgggaa agcagaattg gtacgatttt tcgtacaggt caatgtggaa   1800

cgagaactgg accttgcccc cgaaacagta cgattctcgt cgcttcttcg atctaatgca   1860

gcttattaca agtctcctgg atctcgccca aacaactcca attcggcgac caaacgaagg   1920

aacagcccag ccgtcccctg atcggtgaac cccaggcttt taatgttgac aacgtttact   1980

ttctcgaact cctgctacat ttttcaaaac acaaataaaa cttttcaaaa aaaaaaaaaa   2040

aaa                                                                 2043
```

<210> SEQ ID NO 34
<211> LENGTH: 647
<212> TYPE: PRT
<213> ORGANISM: Ancylostoma caninum

<400> SEQUENCE: 34

```
Ser Pro Leu Pro Thr Asp Ala Ser Gly Asn Tyr Val Thr Asp Glu Gly
1               5                   10                  15

Thr Val Ile Glu Lys Asp Asp Glu Gly Arg Pro Leu Gly Pro Asp Gly
            20                  25                  30

Gln Val Leu Pro Thr Asp Glu Ser Gly Asn Tyr Ile Tyr Pro Val Val
        35                  40                  45

Gly Pro Asp Gly Ser Pro Leu Pro Thr Asp Glu His Lys Arg Pro Ile
    50                  55                  60

His Pro Val Leu Gly Pro Asp Gly Ser Pro Leu Pro Thr Asp Glu Ser
65                  70                  75                  80

Gly His Pro Leu Gly Glu Asp Gly Gln Pro Leu Pro Thr Asp Ala Ser
                85                  90                  95

Gly Val Pro Val Asp Lys Asp Gly Gln Pro Leu Pro Thr Asp Ser Ser
            100                 105                 110

Gly His Tyr Val Thr Val Pro Arg Glu Glu Ala Val Thr Lys Glu Leu
        115                 120                 125

Pro Thr Asp Glu Ser Gly Asn Val Ile Tyr Pro Val Thr Lys Pro Asp
    130                 135                 140

Gly Ser Pro Leu Pro Thr Asp Ala Ser Gly Asn Tyr Val Thr Asp Glu
145                 150                 155                 160

Gly Thr Val Ile Glu Lys Asp Asp Glu Gly Arg Pro Leu Gly Pro Asp
```

-continued

```
                165                 170                 175

Gly Gln Val Leu Pro Thr Asp Glu Ser Gly Asn Tyr Ile Tyr Pro Val
            180                 185                 190

Val Gly Pro Asp Gly Ser Pro Leu Pro Thr Asp Glu Tyr Lys Arg Pro
        195                 200                 205

Ile His Pro Val Leu Gly Pro Asp Gly Ser Pro Leu Pro Thr Asp Glu
    210                 215                 220

Ser Gly His Pro Leu Gly Glu Asp Gly Gln Pro Leu Pro Thr Asp Ala
225                 230                 235                 240

Ser Gly Val Pro Val Asp Lys Asp Gly Gln Pro Leu Pro Thr Asp Ser
                245                 250                 255

Ser Gly His Tyr Val Thr Val Pro Arg Glu Glu Ala Val Thr Lys Glu
            260                 265                 270

Leu Pro Thr Asp Glu Ser Gly Asn Val Ile Tyr Pro Val Thr Lys Pro
        275                 280                 285

Asp Gly Ser Pro Leu Pro Thr Asp Ala Ser Gly Asn Phe Ile Thr Glu
    290                 295                 300

Glu Gly Leu Ile Ile Gly Pro Asp Gly Val Ala Leu Pro Tyr Pro Arg
305                 310                 315                 320

Asn Arg Thr Cys Ser Leu Lys Gln Leu Lys Met Asp Ile Leu Phe Ala
                325                 330                 335

Val Ser Thr Thr Lys Val Ser Lys Ser Thr Phe Asp Ser Ile Leu Arg
            340                 345                 350

Ala Ile Ser Lys Phe Ala Asp Glu Val Asp Leu Ser Pro Asp Val Thr
        355                 360                 365

Arg Ile Gly Leu Val Tyr Gly Ser Lys Asp Val Val Val Pro Leu Pro
    370                 375                 380

Leu Gly Gly Tyr Gln Glu Lys Asp His Met Arg Asp Glu Ile Arg Arg
385                 390                 395                 400

Ile Glu Phe Ser Asp Asp Gly Ser Gln Asp Tyr Ile Ser Leu Tyr Gly
                405                 410                 415

Pro Ala Lys Gln Gln Phe Val Met Phe Pro Arg Ala Asp Ser Ala Lys
            420                 425                 430

Ile Ala Ile Phe Leu Ile Gln Asp Glu Ile Ser Tyr Cys Leu Ser Thr
        435                 440                 445

Arg Thr Leu Arg Cys Gly Cys Ala Thr Ala Val Asp Ser Asp Phe Cys
    450                 455                 460

Arg Arg Ile Asn Asn Val Leu Ala Asp Asp Ile Lys Val Cys Lys Val
465                 470                 475                 480

Pro Glu Thr Ala Val Val Pro Thr Pro Val Val His Pro Gln Gly Ser
                485                 490                 495

Arg Ala Val Ser Val Val Val Pro Arg Phe Phe Ser Ala Pro Pro Phe
            500                 505                 510

Asp Thr His Ser Pro Ser Arg Leu Thr Leu Leu Ala Asp Phe Ala Thr
        515                 520                 525

Glu Lys Glu Pro Leu Cys Gly Glu His Ser Phe Leu Ser Pro Gln Lys
    530                 535                 540

Trp Gly Lys Asn His Cys Thr Leu Arg Ile Pro Leu Ser Met Pro Gly
545                 550                 555                 560

Ile Asp His Lys Ser Asp Asp His Tyr Tyr Tyr Asp Asp Gln Thr Pro
                565                 570                 575

Leu Glu Ser Glu Tyr Ser Leu Asp Leu Phe Gly Lys Ala Glu Leu Val
            580                 585                 590
```

-continued

Arg Phe Phe Val Gln Val Asn Val Glu Arg Glu Leu Asp Leu Ala Pro
595 600 605

Glu Thr Val Arg Phe Ser Ser Leu Leu Arg Ser Asn Ala Ala Tyr Tyr
610 615 620

Lys Ser Pro Gly Ser Arg Pro Asn Asn Ser Asn Ser Ala Thr Lys Arg
625 630 635 640

Arg Asn Ser Pro Ala Val Pro
645

<210> SEQ ID NO 35
<211> LENGTH: 1262
<212> TYPE: DNA
<213> ORGANISM: Ancylostoma caninum

<400> SEQUENCE: 35
ttttattacc caagtttgag agaggctcgt gaagttggta gaaggcttac aaggatgagg 60
ctcattttac cacttgtcgc cttgataggt attggtctct cagcacatta tgaaagggac 120
tgtccatgta cgcccgaaaa attgtggctc gacgtagtgg taggtatcga cacctctatt 180
ggtatgacag aggaaggagt gacacaggtc ctcgccgatt tgtctacggt attcggagac 240
acaaaaatcg ctcaagggga agggcaccat tcccgcattg gagtcgttac atatgggctg 300
aatgccgaaa ctaggtacaa cttgactgat ttcaaatcaa cagacgatat gctggaggcg 360
atctgggata ttaagtgcag cgacgacaag tactccaatc tctttgctgg actgacgagg 420
acacaagaaa ttatgaagaa tggccgccaa ggaagactga gagcaaatgt cagatcagcc 480
attattatct acgcgagcga tttcagggaa ggcgacgtga atgacgcagt tcagctggca 540
catcagatca agatcggagg aacggatatc atcgtagttg cttttgacca aaaaggaaaa 600
gtcaatgcgc ttgaggggct ccagaagatt gcttcgcctg gtcgcctctt caagagcact 660
acgaaaaacc tagtcggtct aatccaggat gctttgtgcc agacaaactg cttttgcaaa 720
aagctctgga cgcaatacgg ggacggatct gtgaaatatg gagaatgtct aaggatcggt 780
ggaatcgacg ccaactggtt agcagctaaa aaagcatgtc agagactcat ccctggaggt 840
catctcgcca ctgagctcga cagctacaag catgacttta ttgcacgaat gttcaaggat 900
gactatagac acgagcctcc atacatgtat cacatcggac tttccttcga caaacagaag 960
aatgattact tctgggagca acccaaagat aggatgcctc tgccgctgaa ggactcacct 1020
ttccgatatt ggagtcgcgg tttccctaac cctcgggaaa aggatacttg cgtacttgca 1080
gctcaaacaa ccatactttc gcccgagatt ggctggcaga acgagcattg caccaaagtt 1140
gcaaagagat acatctgtca agtggaatca tgtgatacag acaactactg tgccaatcta 1200
taaaagtacg acaataaact gctcacctaa caagaataaa atatgacatc aaaaaaaaaa 1260
aa 1262

<210> SEQ ID NO 36
<211> LENGTH: 382
<212> TYPE: PRT
<213> ORGANISM: Ancylostoma caninum

<400> SEQUENCE: 36

Met Arg Leu Ile Leu Pro Leu Val Ala Leu Ile Gly Ile Gly Leu Ser
1 5 10 15

Ala His Tyr Glu Arg Asp Cys Pro Cys Thr Pro Glu Lys Leu Trp Leu
20 25 30

-continued

```
Asp Val Val Val Gly Ile Asp Thr Ser Ile Gly Met Thr Glu Glu Gly
        35                  40                  45

Val Thr Gln Val Leu Ala Asp Leu Ser Thr Val Phe Gly Asp Thr Lys
    50                  55                  60

Ile Ala Gln Gly Glu Gly His His Ser Arg Ile Gly Val Val Thr Tyr
65                  70                  75                  80

Gly Leu Asn Ala Glu Thr Arg Tyr Asn Leu Thr Asp Phe Lys Ser Thr
                85                  90                  95

Asp Asp Met Leu Glu Ala Ile Trp Asp Ile Lys Cys Ser Asp Asp Lys
            100                 105                 110

Tyr Ser Asn Leu Phe Ala Gly Leu Thr Arg Thr Gln Glu Ile Met Lys
        115                 120                 125

Asn Gly Arg Gln Gly Arg Leu Arg Ala Asn Val Arg Ser Ala Ile Ile
    130                 135                 140

Ile Tyr Ala Ser Asp Phe Arg Glu Gly Asp Val Asn Asp Ala Val Gln
145                 150                 155                 160

Leu Ala His Gln Ile Lys Ile Gly Gly Thr Asp Ile Ile Val Val Ala
                165                 170                 175

Phe Asp Gln Lys Gly Lys Val Asn Ala Leu Glu Gly Leu Gln Lys Ile
            180                 185                 190

Ala Ser Pro Gly Arg Leu Phe Lys Ser Thr Thr Lys Asn Leu Val Gly
        195                 200                 205

Leu Ile Gln Asp Ala Leu Cys Gln Thr Asn Cys Phe Cys Lys Lys Leu
    210                 215                 220

Trp Thr Gln Tyr Gly Asp Gly Ser Val Lys Tyr Gly Glu Cys Leu Arg
225                 230                 235                 240

Ile Gly Gly Ile Asp Ala Asn Trp Leu Ala Ala Lys Lys Ala Cys Gln
                245                 250                 255

Arg Leu Ile Pro Gly Gly His Leu Ala Thr Glu Leu Asp Ser Tyr Lys
            260                 265                 270

His Asp Phe Ile Ala Arg Met Phe Lys Asp Asp Tyr Arg His Glu Pro
        275                 280                 285

Pro Tyr Met Tyr His Ile Gly Leu Ser Phe Asp Lys Gln Lys Asn Asp
    290                 295                 300

Tyr Phe Trp Glu Gln Pro Lys Asp Arg Met Pro Leu Pro Leu Lys Asp
305                 310                 315                 320

Ser Pro Phe Arg Tyr Trp Ser Arg Gly Phe Pro Asn Pro Arg Glu Lys
                325                 330                 335

Asp Thr Cys Val Leu Ala Ala Gln Thr Thr Ile Leu Ser Pro Glu Ile
            340                 345                 350

Gly Trp Gln Asn Glu His Cys Thr Lys Val Ala Lys Arg Tyr Ile Cys
        355                 360                 365

Gln Val Glu Ser Cys Asp Thr Asp Asn Tyr Cys Ala Asn Leu
    370                 375                 380
```

```
<210> SEQ ID NO 37
<211> LENGTH: 892
<212> TYPE: DNA
<213> ORGANISM: Ancylostoma caninum

<400> SEQUENCE: 37

ggtttaatta cccaagtttg agatgaagct actcgctctt tccgctctct tcgcgctggc     60

cttcgctgct cctcgagaca agcggctagc agtgagcact atcactgtca ccggaggact    120

aggtctgtcc acgggatgcg tcgtcactgg caacgttcta tatgcaaacg gtttccgagt    180
```

-continued

```
acgtgagatt acaccatcgg agcagcaaga gttggtcaaa taccaaaacg acgtagctga    240
gtacaagacg gctctgaaac aagcaatcaa ggagcgtgag gagaaaatcc gagcccgtct    300
cgccggtaag aaggtgaagg ccgtggagtc aaccaaccaa gaggacctac cgaaaccgcc    360
acagaagccg tcattctgca caccagaaga cactacccaa ttcttcttcg aaggatgcat    420
gatccagaac aacaagatct acgtcggaaa cactttcgct cgagacctga ctcagcctga    480
aatcagcgaa ttgaaagaat tcgagaagaa attcaaggtc taccaggact acgtacagaa    540
gcaggccgaa cagcaagtga acagcctctt cggcggctct gacttcttct cggcgttgtt    600
cagcggcggt gagacgagca agccatccac gaccaccgtg gcaccagaac ttccggaaga    660
cgctcccgag cagccgccca cgccgaactt ctgcaccaga ataatctaag cctctaaatt    720
gttcgtttcg ctattggatt ggttggtttg gtgaatagcg attccgcttc ccctctcgta    780
cttacggtgt cgactagcac attagtcatg cgttgcaata tttgaacatt gtattgaggt    840
atattgtaca tttatataat aaaattatta tcttaaaaaa aaaaaaaaaa aa            892
```

<210> SEQ ID NO 38
<211> LENGTH: 228
<212> TYPE: PRT
<213> ORGANISM: Ancylostoma caninum

<400> SEQUENCE: 38

```
Met Lys Leu Leu Ala Leu Ser Ala Leu Phe Ala Leu Ala Phe Ala Ala
1               5                   10                  15

Pro Arg Asp Lys Arg Leu Ala Val Ser Thr Ile Thr Val Thr Gly Gly
            20                  25                  30

Leu Gly Leu Ser Thr Gly Cys Val Val Thr Gly Asn Val Leu Tyr Ala
        35                  40                  45

Asn Gly Phe Arg Val Arg Glu Ile Thr Pro Ser Glu Gln Gln Glu Leu
    50                  55                  60

Val Lys Tyr Gln Asn Asp Val Ala Glu Tyr Lys Thr Ala Leu Lys Gln
65                  70                  75                  80

Ala Ile Lys Glu Arg Glu Glu Lys Ile Arg Ala Arg Leu Ala Gly Lys
                85                  90                  95

Lys Val Lys Ala Val Glu Ser Thr Asn Gln Glu Asp Leu Pro Lys Pro
            100                 105                 110

Pro Gln Lys Pro Ser Phe Cys Thr Pro Glu Asp Thr Thr Gln Phe Phe
        115                 120                 125

Phe Glu Gly Cys Met Ile Gln Asn Asn Lys Ile Tyr Val Gly Asn Thr
    130                 135                 140

Phe Ala Arg Asp Leu Thr Gln Pro Glu Ile Ser Glu Leu Lys Glu Phe
145                 150                 155                 160

Glu Lys Lys Phe Lys Val Tyr Gln Asp Tyr Val Gln Lys Gln Ala Glu
                165                 170                 175

Gln Gln Val Asn Ser Leu Phe Gly Gly Ser Asp Phe Phe Ser Ala Leu
            180                 185                 190

Phe Ser Gly Gly Glu Thr Ser Lys Pro Ser Thr Thr Thr Val Ala Pro
        195                 200                 205

Glu Leu Pro Glu Asp Ala Pro Glu Gln Pro Pro Thr Pro Asn Phe Cys
    210                 215                 220

Thr Arg Ile Ile
225
```

-continued

<210> SEQ ID NO 39
<211> LENGTH: 1722
<212> TYPE: DNA
<213> ORGANISM: Ancylostoma caninum

<400> SEQUENCE: 39
gggtttaatt acccaagttt gaggatgagg gtactcctgt tactgctact tttatccatt 60
tgcgcgagcg ctggctttct agacactaaa ttcggccaga agataaagaa aactcttgac 120
aagattaaag ctgtgcttaa cggcactgca ctcatcgcga ttcgtgaaaa attcattcga 180
ctaagggaaa aaataaaagc aaagctgacg ctctctccag cacgaaaggc tatattggac 240
gaagttatga agcatatcaa aatgatcaaa aaggataaga ttcaagagaa gggcgactca 300
atcgatgaaa tcaatgaaaa gagtgcaatc ggacagttgc tgtaccaggg tgacatcgtt 360
ctgacagaaa agcaagccca gcaaattacc gaagacattg aaaatgacaa aggcgaccgc 420
gaaaaacgac aggcgttccg tgatcgcaat tatccgcgaa cattatggtc gaagggagtg 480
tactttcact ttcataggaa cgcaactcct gaagttagaa gcgtttttgt gaaaggcgca 540
aaactttgga tgaaggatac ttgcatcgac ttcttcgaaa gcaactcagc gcctgatagg 600
attcgtgtgt tcaaagagaa cggatgttgg tcgtacgttg gtaggctggg cggtgaacaa 660
gatctgtcac tgggagaagg ttgtcaatcg gttggcacag ctgcgcacga aattggccac 720
gctattggct tctaccacac tcacgcaaga catgatcgcg ataactttat tacattcaac 780
gcacaaaatg tcaagcccga ttggttggac caattcactc ttcagactcc ggcaacgaat 840
gagaactatg gaataactta cgactatgga agtatcatgc attatggtgc aaatagcgcc 900
tcgcagaacg gacgtcctac aatggttccg catgatccca aatacgtaga aactcttgga 960
tcacccataa tttccttcta tgagcttctc atgatcaaca aacactacga ctgcactaag 1020
aactgtgacc cggctacttc tgcgcagtgt aagatgggtg gcttcccaca tcctcgggat 1080
tgtacaagat gcatttgccc tagtggatat ggaggcaaac tgtgcgacca gaagccagcc 1140
ggatgcggat ctatatacca ggccaccaat cagtaccaga ccttgcacga cgaaattgga 1200
gacaagagag cgggacagag acctagagaa gacatggact tctgctatta ttggatcacg 1260
gccccaaaag gttcaaaaat cgaaatcaaa attgctggat tatcacaagg agccgctgtt 1320
gaaggatgcc agtactgggg agtagaaatc aagactcatg ccgatcaacg tcttaccggc 1380
tacaggttct gcgcaccaga agatgttgga gttagattag tgtcgaactt caacatcgta 1440
ccaataatca catacaacat attctacgcg acctatgtcg atattcagta ccgtatcgtt 1500
ggtgataatg ttggcggtcc tatgcctcag ccacaaccaa atagcaattg tgtcgacaat 1560
gaacagtgtg cgacactcgt gagaacaaag aacttctgtc agagcagatt tttcacagag 1620
tccgtcaaaa gaggtctatg tccaaagtcc agcggtttct gtcgctaact tttcagcaaa 1680
caatggaata aatgttgcac cataaaaaaa aaaaaaaaaa aa 1722

<210> SEQ ID NO 40
<211> LENGTH: 536
<212> TYPE: PRT
<213> ORGANISM: Ancylostoma caninum

<400> SEQUENCE: 40

Met Arg Val Leu Leu Leu Leu Leu Leu Leu Ser Ile Cys Ala Ser Ala
1 5 10 15

Gly Phe Leu Asp Thr Lys Phe Gly Gln Lys Ile Lys Lys Thr Leu Asp
20 25 30

-continued

```
Lys Ile Lys Ala Val Leu Asn Gly Thr Ala Leu Ile Ala Ile Arg Glu
        35                  40                  45

Lys Phe Ile Arg Leu Arg Glu Lys Ile Lys Ala Lys Leu Thr Leu Ser
    50                  55                  60

Pro Ala Arg Lys Ala Ile Leu Asp Glu Val Met Lys His Ile Lys Met
65                  70                  75                  80

Ile Lys Lys Asp Lys Ile Gln Glu Lys Gly Asp Ser Ile Asp Glu Ile
                85                  90                  95

Asn Glu Lys Ser Ala Ile Gly Gln Leu Leu Tyr Gln Gly Asp Ile Val
            100                 105                 110

Leu Thr Glu Lys Gln Ala Gln Gln Ile Thr Glu Asp Ile Glu Asn Asp
        115                 120                 125

Lys Gly Asp Arg Glu Lys Arg Gln Ala Phe Arg Asp Arg Asn Tyr Pro
    130                 135                 140

Arg Thr Leu Trp Ser Lys Gly Val Tyr Phe His Phe His Arg Asn Ala
145                 150                 155                 160

Thr Pro Glu Val Arg Ser Val Phe Val Lys Gly Ala Lys Leu Trp Met
                165                 170                 175

Lys Asp Thr Cys Ile Asp Phe Phe Glu Ser Asn Ser Ala Pro Asp Arg
            180                 185                 190

Ile Arg Val Phe Lys Glu Asn Gly Cys Trp Ser Tyr Val Gly Arg Leu
        195                 200                 205

Gly Gly Glu Gln Asp Leu Ser Leu Gly Glu Gly Cys Gln Ser Val Gly
    210                 215                 220

Thr Ala Ala His Glu Ile Gly His Ala Ile Gly Phe Tyr His Thr His
225                 230                 235                 240

Ala Arg His Asp Arg Asp Asn Phe Ile Thr Phe Asn Ala Gln Asn Val
                245                 250                 255

Lys Pro Asp Trp Leu Asp Gln Phe Thr Leu Gln Thr Pro Ala Thr Asn
            260                 265                 270

Glu Asn Tyr Gly Ile Thr Tyr Asp Tyr Gly Ser Ile Met His Tyr Gly
        275                 280                 285

Ala Asn Ser Ala Ser Gln Asn Gly Arg Pro Thr Met Val Pro His Asp
    290                 295                 300

Pro Lys Tyr Val Glu Thr Leu Gly Ile Asn Lys His Tyr Asp Cys Thr
305                 310                 315                 320

Lys Asn Cys Asp Pro Ala Thr Ser Ala Gln Cys Lys Met Gly Gly Phe
                325                 330                 335

Pro His Pro Arg Asp Cys Thr Arg Cys Ile Cys Pro Ser Gly Tyr Gly
            340                 345                 350

Gly Lys Leu Cys Asp Gln Lys Pro Ala Gly Cys Gly Ser Ile Tyr Gln
        355                 360                 365

Ala Thr Asn Gln Tyr Gln Thr Leu His Asp Glu Ile Gly Asp Lys Arg
    370                 375                 380

Ala Gly Gln Arg Pro Arg Glu Asp Met Asp Phe Cys Tyr Tyr Trp Ile
385                 390                 395                 400

Thr Ala Pro Lys Gly Ser Lys Ile Glu Ile Lys Ile Ala Gly Leu Ser
                405                 410                 415

Gln Gly Ala Ala Val Glu Gly Cys Gln Tyr Trp Gly Val Glu Ile Lys
            420                 425                 430

Thr His Ala Asp Gln Arg Leu Thr Gly Tyr Arg Phe Cys Ala Pro Glu
        435                 440                 445

Asp Val Gly Val Arg Leu Val Ser Asn Phe Asn Ile Val Pro Ile Ile
```

-continued

```
    450                 455                 460

Thr Tyr Asn Ile Phe Tyr Ala Thr Tyr Val Asp Ile Gln Tyr Arg Ile
465                 470                 475                 480

Val Gly Asp Asn Val Gly Gly Pro Met Pro Gln Pro Gln Pro Asn Ser
                485                 490                 495

Asn Cys Val Asp Asn Glu Gln Cys Ala Thr Leu Val Arg Thr Lys Asn
            500                 505                 510

Phe Cys Gln Ser Arg Phe Phe Thr Ser Ser Val Lys Arg Gly Leu Cys
        515                 520                 525

Pro Lys Ser Ser Gly Phe Cys Arg
    530                 535


<210> SEQ ID NO 41
<211> LENGTH: 850
<212> TYPE: DNA
<213> ORGANISM: Ancylostoma caninum

<400> SEQUENCE: 41

tttaattacc caagtttgag caatgaaata ctttgttctc tgcttctgcg ccttcttcgt     60

ggtcaatgct gatgaggaag acgatctacc ccgcaatcct ttgtgggacg cttacaagga    120

tgacaatggc aaatatgtga ttccgtacgt cattaacgga agttatggag aggagaaaaa    180

agttttattt gaaatgatgg acgaaatcga taagaatacc tgcgtccgct tcatacccag    240

atcgacagag caggattata tcgaaatcgt aaacagacta ggagaaggaa ccggcgctgt    300

tgtaggtaaa cctggaggga aaagcatcgt gttgttggaa tcgagcaaaa ttctaaatga    360

tccaactcct gcgcctgtaa tgcagacttt gatgaaaatc attggcttac cacctgaaca    420

cattcgacca gagaggaaag atcatatcaa gatacactgg gagaacatcg agaaaggtta    480

cgaagctttc ttcgccctct cctctgttaa gcccgatccg tacggaatac catatgatta    540

ctactccatc atgcactaca agaaggacgc ctttgccaag ccgggcacga tcacaatgga    600

aactttggat aagcgctacc aggatatcat tgggaatcaa gagaagccgt cgaagttgga    660

ttacaagaag atctgcacca agtataaatg cgatatctgc atgggtgaga agatgaagta    720

ttaaagaaag gaatgacgtt aacataagga atggttgccg atttcaacaa aacgaacgtc    780

taatacatct ggtgttgttc ctcatgttag aaatccaata aagcatttca ccgaaaaaaa    840

aaaaaaaaaa                                                           850


<210> SEQ ID NO 42
<211> LENGTH: 233
<212> TYPE: PRT
<213> ORGANISM: Ancylostoma caninum

<400> SEQUENCE: 42

Met Lys Tyr Phe Val Leu Cys Phe Cys Ala Phe Phe Val Val Asn Ala
1               5                   10                  15

Asp Glu Glu Asp Asp Leu Pro Arg Asn Pro Leu Trp Asp Ala Tyr Lys
            20                  25                  30

Asp Asp Asn Gly Lys Tyr Val Ile Pro Tyr Val Ile Asn Gly Ser Tyr
        35                  40                  45

Gly Glu Glu Lys Lys Val Leu Phe Glu Met Met Asp Glu Ile Asp Lys
    50                  55                  60

Asn Thr Cys Val Arg Phe Ile Pro Arg Ser Thr Glu Gln Asp Tyr Ile
65                  70                  75                  80

Glu Ile Val Asn Arg Leu Gly Glu Gly Thr Gly Ala Val Val Gly Lys
```

-continued

```
                85                  90                  95

Pro Gly Gly Lys Ser Ile Val Leu Leu Glu Ser Ser Lys Ile Leu Asn
            100                 105                 110

Asp Pro Thr Pro Ala Pro Val Met Gln Thr Leu Met Lys Ile Ile Gly
        115                 120                 125

Leu Pro Pro Glu His Ile Arg Pro Glu Arg Lys Asp His Ile Lys Ile
    130                 135                 140

His Trp Glu Asn Ile Glu Lys Gly Tyr Glu Ala Phe Phe Ala Leu Ser
145                 150                 155                 160

Ser Val Lys Pro Asp Pro Tyr Gly Ile Pro Tyr Asp Tyr Tyr Ser Ile
                165                 170                 175

Met His Tyr Lys Lys Asp Ala Phe Ala Lys Pro Gly Thr Ile Thr Met
            180                 185                 190

Glu Thr Leu Asp Lys Arg Tyr Gln Asp Ile Ile Gly Asn Gln Glu Lys
        195                 200                 205

Pro Ser Lys Leu Asp Tyr Lys Lys Ile Cys Thr Lys Tyr Lys Cys Asp
    210                 215                 220

Ile Cys Met Gly Glu Lys Met Lys Tyr
225                 230
```

<210> SEQ ID NO 43
<211> LENGTH: 1168
<212> TYPE: DNA
<213> ORGANISM: Ancylostoma caninum

<400> SEQUENCE: 43

```
ttaattaccc aagtttgaga atggcaacta tgctcgcggt atgtcgtttg gtcgtcttcc     60

tcaccgccgt tcacacggtg tcagcaaggg gaagacccat caacattttc gagcaaaagg    120

aaggaggaga catcacacag ctgagagaaa aagggagcgc aatgttcaac gcccttcaca    180

gaacgtcgag tctgaagtgg aacaagaggg attcagacgg gaattttgtc ataccgtaca    240

taattacagg acgctatgac cgaacggagc ggggaatatc aaggaagcaa tgaggcgcat    300

cgaggcaaat acgtgtattc gtttcaagca aagagactat gagagagact atatcgagat    360

ccagaacaaa gctggacatg gatgttacac caatgtcggt cgtgtcggtg gcagaagtat    420

actgatgctc gagtccagct tcgaggaaac atgcatggag acagaaatcg tgctgcacga    480

gttgatgcac gttgtcggtc tgtggcacga acacatgcgc cacgatcgtg acaaatacat    540

caaagtgcac tacgagaaca tcgaaaggag ttactggaac caattcgaga aagtctcacc    600

gatggaagct accacgtata acgtaccgta tgactacaaa tccgtcatgc actacgagaa    660

gtcggcattc gccagacctg gacgaatcag catggaaacg cttgatccca aatatcagaa    720

cgtcatcgga caccagaagg acgcctctcc cagtgactac cgtaagatct gcgagatata    780

ccagtgtaag aagtgcatga acggcaagat cgagatcgga ggcgactcgg actccaaccc    840

gaaaccgcca accgaggccc cagtcaccat cagaccggcg ccagaaatca acggagaatg    900

ccgcgatatg atcccgtctt tctgccgagc gttggcccgc tcgcacatga tcgactgcag    960

cttcttccat aaacaacaat gctgtgcaac ctgcgccgag ttagggcaca gggatcagga   1020

ccagggagga tggttagaac aaacaggatg gccattcgac gggctcttcc gaatattcgg   1080

acaaggaggg tggcctttca ccttcttcaa tcgctggtaa ctaatacagg tcaaataaat   1140

atttgcaaaa taaaaaaaaa aaaaaaaa                                      1168
```

<210> SEQ ID NO 44

-continued

<211> LENGTH: 366
<212> TYPE: PRT
<213> ORGANISM: Ancylostoma caninum

<400> SEQUENCE: 44

```
Met Ala Thr Met Leu Ala Val Cys Arg Leu Val Val Phe Leu Thr Ala
1               5                   10                  15

Val His Thr Val Ser Ala Arg Gly Arg Pro Ile Asn Ile Phe Glu Gln
            20                  25                  30

Lys Glu Gly Gly Asp Ile Thr Gln Leu Arg Glu Lys Gly Ser Ala Met
        35                  40                  45

Phe Asn Ala Leu His Arg Thr Ser Ser Leu Lys Trp Asn Lys Arg Asp
    50                  55                  60

Ser Asp Gly Asn Phe Val Ile Pro Tyr Ile Ile Thr Gly Arg Tyr Asp
65                  70                  75                  80

Arg Thr Glu Arg Gly Thr Ile Lys Glu Ala Asn Arg Arg Ile Glu Ala
                85                  90                  95

Asn Thr Cys Ile Arg Phe Lys Gln Arg Asp Tyr Glu Arg Asp Tyr Ile
            100                 105                 110

Glu Ile Gln Asn Lys Ala Gly His Gly Cys Tyr Thr Asn Val Gly Arg
        115                 120                 125

Val Gly Gly Arg Ser Ile Leu Met Leu Glu Ser Ser Phe Glu Glu Thr
    130                 135                 140

Cys Met Glu Thr Glu Ile Val Leu His Glu Leu Met His Val Val Gly
145                 150                 155                 160

Leu Trp His Glu His Met Arg His Asp Arg Asp Lys Tyr Ile Lys Val
                165                 170                 175

His Tyr Glu Asn Ile Glu Arg Ser Tyr Trp Asn Gln Phe Glu Lys Val
            180                 185                 190

Ser Pro Met Glu Ala Thr Thr Tyr Asn Val Pro Tyr Asp Tyr Lys Ser
        195                 200                 205

Val Met His Tyr Glu Lys Ser Ala Phe Ala Arg Pro Gly Arg Ile Ser
    210                 215                 220

Met Glu Thr Leu Asp Pro Lys Tyr Gln Asn Val Ile Gly His Gln Lys
225                 230                 235                 240

Asp Ala Ser Pro Ser Asp Tyr Arg Lys Ile Cys Glu Ile Tyr Gln Cys
                245                 250                 255

Lys Lys Cys Met Asn Gly Lys Ile Glu Ile Gly Gly Asp Ser Asp Ser
            260                 265                 270

Asn Pro Lys Pro Pro Thr Glu Ala Pro Val Thr Ile Arg Pro Ala Pro
        275                 280                 285

Glu Ile Asn Gly Glu Cys Arg Asp Met Ile Pro Ser Phe Cys Arg Ala
    290                 295                 300

Leu Ala Arg Ser His Met Ile Asp Cys Ser Phe Phe His Lys Gln Gln
305                 310                 315                 320

Cys Cys Ala Thr Cys Ala Glu Leu Gly His Arg Asp Gln Asp Gln Gly
                325                 330                 335

Gly Trp Leu Glu Gln Thr Gly Trp Pro Phe Asp Gly Leu Phe Arg Ile
            340                 345                 350

Phe Gly Gln Gly Gly Trp Pro Phe Thr Phe Phe Asn Arg Trp
        355                 360                 365
```

<210> SEQ ID NO 45
<211> LENGTH: 621
<212> TYPE: DNA

-continued

<213> ORGANISM: Ancylostoma caninum

<400> SEQUENCE: 45

```
caagtttgag catgcttcga ctagctctct tcgcggtcct cttcgcttgc gcattttcag     60

cacccaacgt tgaagtgaac aaattcgagg atattcctga gcagtacaga gaactgatcc    120

ccaaggaggt agccgaccac atcaaggcta tcactgagga ggagaagacc atcttgaagg    180

aggtgctgaa ggactacgcc aaatacaagg acgagaatga gtatttggca gcgctgaagg    240

aaaagtcacc cagcctgcac gagaaggcaa agaagttcca cgacttcatt aaggctaagg    300

tcgacgcact tggggatgaa gcaaaggcgt tcgtgaagaa agtgattgct gctgctcgca    360

aactgcacgc agagctcctt gccgggaaca aaccttctct tgaggaactg aagaacactg    420

tcaagaaata cgtggccgaa ttcgacgcgc tgaccgcagc cgcaaaagaa gatctcaaga    480

agcacttccc catcctcact tccattttca ccaacgagaa ggcaaaggcg ttgatggaca    540

agcacttgcc gaactaggtg aagcagcagt tgtttttagt cgaataaatg tttcaacttt    600

ttaaaaaaaa aaaaaaaaaa a                                              621
```

<210> SEQ ID NO 46
<211> LENGTH: 181
<212> TYPE: PRT
<213> ORGANISM: Ancylostoma caninum

<400> SEQUENCE: 46

```
Met Leu Arg Leu Ala Leu Phe Ala Val Leu Phe Ala Cys Ala Phe Ser
1               5                   10                  15

Ala Pro Asn Val Glu Val Asn Lys Phe Glu Asp Ile Pro Glu Gln Tyr
            20                  25                  30

Arg Glu Leu Ile Pro Lys Glu Val Ala Asp His Ile Lys Ala Ile Thr
        35                  40                  45

Glu Glu Glu Lys Thr Ile Leu Lys Glu Val Leu Lys Asp Tyr Ala Lys
    50                  55                  60

Tyr Lys Asp Glu Asn Glu Tyr Leu Ala Ala Leu Lys Glu Lys Ser Pro
65                  70                  75                  80

Ser Leu His Glu Lys Ala Lys Lys Phe His Asp Phe Ile Lys Ala Lys
                85                  90                  95

Val Asp Ala Leu Gly Asp Glu Ala Lys Ala Phe Val Lys Lys Val Ile
            100                 105                 110

Ala Ala Ala Arg Lys Leu His Ala Glu Leu Leu Ala Gly Asn Lys Pro
        115                 120                 125

Ser Leu Glu Glu Leu Lys Asn Thr Val Lys Lys Tyr Val Ala Glu Phe
    130                 135                 140

Asp Ala Leu Thr Ala Ala Ala Lys Glu Asp Leu Lys Lys His Phe Pro
145                 150                 155                 160

Ile Leu Thr Ser Ile Phe Thr Asn Glu Lys Ala Lys Ala Leu Met Asp
                165                 170                 175

Lys His Leu Pro Asn
            180
```

<210> SEQ ID NO 47
<211> LENGTH: 2384
<212> TYPE: DNA
<213> ORGANISM: Ancylostoma caninum

<400> SEQUENCE: 47

```
ggcacttcga catgaaggtc cttgccttag tgttactttg ggctgcaaca gccactgctc     60
```

-continued

```
tgctagacat atgtaaggag gaaatcaaga ctggaaattg tagggggggcc ttccgcaagt    120
ttggctacga tcgatgcacg aataaatgta ttccgtacac gtatggaggc tgtggagggt    180
cgagcaacat gttcgacact ttggaagaat gccaagaaaa atgtggcaag cccgaggacc    240
gctgctcaaa accactggaa agaggaatat gtctggcatc aatgaaaaga tatggctacg    300
atacaagcag taagaagtgt aaggccttca tctatggcgg atgtggcggt aacgagaaca    360
atttcgagac aatggctgag tgccgagaaa cttgcaagga cacctcttct gaagaagaat    420
cagtacctga tgcatgccta ttgccatcag aagtggggcc atgtaaagga aaagaacgtc    480
gcttctactt tgatcaaaaa cgtggcaact gcaagtcgtt cttcttcggc ggttgtggtg    540
gaaatggaaa taatttcatg accaaagcca aatgcatgga aacctgctcg aaacacatca    600
aacctgaaac agagcaagac gtctgctcac agccaattaa agctggacct tgcatggcaa    660
tgttgaaaag atatgcgtac gacaacaaga aaaagaggtg cgtgcagttt atctatggag    720
gatgtaaggg aaacaagaac aacttcgaga gcatggaaga gtgcacccgg acatgtaaga    780
aagcagtacc agagcctgag caggacacct gctcacagcc cattgaagtt ggaccttgca    840
aggcaatgtt gaaaagatat gcgtacgaca acaagaaaaa taagtgcgta cggtttatct    900
atggaggatg taagggaaac aagaacaact tcgaaagcat ggaagagtgc acccggacat    960
gtaagaaagc agtaccagag cctgagcaag acacctgctc acagcccatt gaagttggac   1020
cttgcaaggc aatgttgaaa agatatgcgt acgacaacaa gaaaaataag tgcgtgcggt   1080
ttatctatgg aggatgtaag ggaaataaga acaacttcga aagcatggaa gagtgcaccc   1140
ggacatgcaa gaaagcagta ccagagcctg aacctgagaa agagacctgc tcacagccca   1200
ttgaagttgg accttgcaag gcaatgttga aaagatatgc gtacgacaac aagaaaaata   1260
agtgcgtacg gtttatctat ggaggatgta agggaaacaa gaacaacttc gaaagcatgg   1320
aagagtgcac ccggacatgt aagaaagcag taccagagcc tgagcaagac acctgctcac   1380
agcccattga agttggacct tgcaaggcaa tgttgaaaag atatgcgtac gacaacaaga   1440
aaaataagtg cgtgcggttt atctatggag gatgtaaggg aaataagaac aacttcgaaa   1500
gcatggaaga gtgcacccgg acatgcaaga aagcagtacc agagcctgaa cctgagaaag   1560
agacctgctc tcagcccatt gaagctggtc cttgcaaggc aatggtgaga cgatttgctt   1620
acgacaacgc aaaggaaaag tgcgtagagt tcttttacgg cggatgcaaa ggaaacaaga   1680
acaacttcga aaccatggaa gattgtactt ttacgtgtga gcaacggctg gcaaagcccg   1740
agcttgagaa ggatgtgtgt tcacaaccta tcacggctgg tccttgcaga gcatcaatac   1800
cgcgatacgg ctatgattct aaaaaacgaa agtgtgtgaa gttcacctac ggaggatgca   1860
aaggaaatgg taataggttc ccgacgaaga atgaatgtga gaagacatgc aagagaggag   1920
caactggaac tacgaatcca ggaggtgaaa atgataaatg cttgctgcca attgttaccg   1980
gcccatgcaa aggaaaaaat cgtcgctatg cttacaacaa caagacagga aaatgcgtga   2040
gattcaccta tggtggttgc gggggaaacg agaacaactt caagactaag aaagactgcc   2100
aggatgcgtg cgaaaacata aatgcagcta gtccatgcac ccttcctatc gacaaaggag   2160
aaggcgactt gaatctgacc agatatggct tcaaaaatgg caagtgtgtc gcgttcaaat   2220
acggcggacg acggggaaat ctcaacaatt ttggaagcaa agccgattgc aaagaagcct   2280
gcctcaagta actacgaagc tccgctgcaa atcccagaag atcattcggt tgtctctgcc   2340
gtctatgaaa caataaagta ttaattttgt taaaaaaaaa aaaa                   2384
```

-continued

<210> SEQ ID NO 48
<211> LENGTH: 759
<212> TYPE: PRT
<213> ORGANISM: Ancylostoma caninum

<400> SEQUENCE: 48

```
Met Lys Val Leu Ala Leu Val Leu Leu Trp Ala Ala Thr Ala Thr Ala
1               5                   10                  15

Leu Leu Asp Ile Cys Lys Glu Glu Ile Lys Thr Gly Asn Cys Arg Gly
            20                  25                  30

Ala Phe Arg Lys Phe Gly Tyr Asp Arg Cys Thr Asn Lys Cys Ile Pro
        35                  40                  45

Tyr Thr Tyr Gly Gly Cys Gly Gly Ser Ser Asn Met Phe Asp Thr Leu
    50                  55                  60

Glu Glu Cys Gln Glu Lys Cys Gly Lys Pro Glu Asp Arg Cys Ser Lys
65                  70                  75                  80

Pro Leu Glu Arg Gly Ile Cys Leu Ala Ser Met Lys Arg Tyr Gly Tyr
                85                  90                  95

Asp Thr Ser Ser Lys Lys Cys Lys Ala Phe Ile Tyr Gly Gly Cys Gly
            100                 105                 110

Gly Asn Glu Asn Asn Phe Glu Thr Met Ala Glu Cys Arg Glu Thr Cys
        115                 120                 125

Lys Asp Thr Ser Ser Glu Glu Glu Ser Val Pro Asp Ala Cys Leu Leu
    130                 135                 140

Pro Ser Glu Val Gly Pro Cys Lys Gly Lys Glu Arg Arg Phe Tyr Phe
145                 150                 155                 160

Asp Gln Lys Arg Gly Asn Cys Lys Ser Phe Phe Phe Gly Gly Cys Gly
                165                 170                 175

Gly Asn Gly Asn Asn Phe Met Thr Lys Ala Lys Cys Met Glu Thr Cys
            180                 185                 190

Ser Lys His Ile Lys Pro Glu Thr Glu Gln Asp Val Cys Ser Gln Pro
        195                 200                 205

Ile Lys Ala Gly Pro Cys Met Ala Met Leu Lys Arg Tyr Ala Tyr Asp
    210                 215                 220

Asn Lys Lys Lys Arg Cys Val Gln Phe Ile Tyr Gly Gly Cys Lys Gly
225                 230                 235                 240

Asn Lys Asn Asn Phe Glu Ser Met Glu Glu Cys Thr Arg Thr Cys Lys
                245                 250                 255

Lys Ala Val Pro Glu Pro Glu Gln Asp Thr Cys Ser Gln Pro Ile Glu
            260                 265                 270

Val Gly Pro Cys Lys Ala Met Leu Lys Arg Tyr Ala Tyr Asp Asn Lys
        275                 280                 285

Lys Asn Lys Cys Val Arg Phe Ile Tyr Gly Gly Cys Lys Gly Asn Lys
    290                 295                 300

Asn Asn Phe Glu Ser Met Glu Glu Cys Thr Arg Thr Cys Lys Lys Ala
305                 310                 315                 320

Val Pro Glu Pro Glu Gln Asp Thr Cys Ser Gln Pro Ile Glu Val Gly
                325                 330                 335

Pro Cys Lys Ala Met Leu Lys Arg Tyr Ala Tyr Asp Asn Lys Lys Asn
            340                 345                 350

Lys Cys Val Arg Phe Ile Tyr Gly Gly Cys Lys Gly Asn Lys Asn Asn
        355                 360                 365

Phe Glu Ser Met Glu Glu Cys Thr Arg Thr Cys Lys Lys Ala Val Pro
    370                 375                 380
```

-continued

```
Glu Pro Glu Pro Glu Lys Glu Thr Cys Ser Gln Pro Ile Glu Val Gly
385                 390                 395                 400

Pro Cys Lys Ala Met Leu Lys Arg Tyr Ala Tyr Asp Asn Lys Lys Asn
                405                 410                 415

Lys Cys Val Arg Phe Ile Tyr Gly Gly Cys Lys Gly Asn Lys Asn Asn
            420                 425                 430

Phe Glu Ser Met Glu Glu Cys Thr Arg Thr Cys Lys Lys Ala Val Pro
        435                 440                 445

Glu Pro Glu Gln Asp Thr Cys Ser Gln Pro Ile Glu Val Gly Pro Cys
    450                 455                 460

Lys Ala Met Leu Lys Arg Tyr Ala Tyr Asp Asn Lys Lys Asn Lys Cys
465                 470                 475                 480

Val Arg Phe Ile Tyr Gly Gly Cys Lys Gly Asn Lys Asn Asn Phe Glu
                485                 490                 495

Ser Met Glu Glu Cys Thr Arg Thr Cys Lys Lys Ala Val Pro Glu Pro
            500                 505                 510

Glu Pro Glu Lys Glu Thr Cys Ser Gln Pro Ile Glu Ala Gly Pro Cys
        515                 520                 525

Lys Ala Met Val Arg Arg Phe Ala Tyr Asp Asn Ala Lys Glu Lys Cys
    530                 535                 540

Val Glu Phe Phe Tyr Gly Gly Cys Lys Gly Asn Lys Asn Asn Phe Glu
545                 550                 555                 560

Thr Met Glu Asp Cys Thr Phe Thr Cys Glu Gln Arg Leu Ala Lys Pro
                565                 570                 575

Glu Leu Glu Lys Asp Val Cys Ser Gln Pro Ile Thr Ala Gly Pro Cys
            580                 585                 590

Arg Ala Ser Ile Pro Arg Tyr Gly Tyr Asp Ser Lys Lys Arg Lys Cys
        595                 600                 605

Val Lys Phe Thr Tyr Gly Gly Cys Lys Gly Asn Gly Asn Arg Phe Pro
    610                 615                 620

Thr Lys Asn Glu Cys Glu Lys Thr Cys Lys Arg Gly Ala Thr Gly Thr
625                 630                 635                 640

Thr Asn Pro Gly Gly Glu Asn Asp Lys Cys Leu Leu Pro Ile Val Thr
                645                 650                 655

Gly Pro Cys Lys Gly Lys Asn Arg Arg Tyr Ala Tyr Asn Asn Lys Thr
            660                 665                 670

Gly Lys Cys Val Arg Phe Thr Tyr Gly Gly Cys Gly Gly Asn Glu Asn
        675                 680                 685

Asn Phe Lys Thr Lys Lys Asp Cys Gln Asp Ala Cys Glu Asn Ile Asn
    690                 695                 700

Ala Ala Ser Pro Cys Thr Leu Pro Ile Asp Lys Gly Glu Gly Asp Leu
705                 710                 715                 720

Asn Leu Thr Arg Tyr Gly Phe Lys Asn Gly Lys Cys Val Ala Phe Lys
                725                 730                 735

Tyr Gly Gly Arg Arg Gly Asn Leu Asn Asn Phe Gly Ser Lys Ala Asp
            740                 745                 750

Cys Lys Glu Ala Cys Leu Lys
        755
```

<210> SEQ ID NO 49
<211> LENGTH: 1413
<212> TYPE: DNA
<213> ORGANISM: Ancylostoma caninum -continued

<400> SEQUENCE: 49

```
ctcgcactat ttaccctagc tgtagctagc gtacacagaa ggacattcca ccacccgcgc     60
cgctatgtga agtcggtgtc gctttcgcgt caaccaacac ttcgtgaacg attgctcgga    120
actggcagtt gggaagacta tcagaaacag cgttaccact accagaagaa acttctggca    180
aagtatgcgg cgatcaaagc gacaaaactg cagtctacca atgaaattga cgagcttctt    240
cgcaactaca tggatgcgca atacttcggc accatccaaa tcggaactcc agcgcagaat    300
ttcacagtga ttttcgacac cggttcttcc aatctgtggg tgccgtccga gaaaatgcca    360
ttccacgaca tcgcgtgcat gcttcgtcac cgttatgact ccggagcatc gtcgacgtac    420
aaggaggatg gacgaaagat ggccatccag tatggcactg gctcaatgaa gggcttcatt    480
tcaaaggata atgtctgcat cgctggaatt tgcgctgaag agcaaccgtt tgctgaggca    540
acgagcgagc caggcctcac cttcatcgca gcgaagtttg atggaatcct tggcataacc    600
ttccctgaaa tctctgtgct cggagtaccg ccagtattcc acacgttcat tgaacagaag    660
aaagtgccga gcccggtgtt cgctctctgg ctcaacagaa atcctgactc ggaactcgga    720
ggtgagatca ccctcggtgg aatggacacc cgacgatacg ttgagccgat cacatggact    780
ccagtgacaa ggcgagggta ctggcagttc aagatggaca aggttcaagg aggatcaaca    840
tccattgctt gccccaatga attttctgga tgccaggcta ttgctgacac tggcacttcc    900
ctcattgctg gacctaaagc acagtcgagg gcatccagaa attcattggt gcttgagcca    960
acttatgaag gagagtacat gattccttgc gacaaggtgc ctttccctcc ccgattatcc   1020
ttcgttatcg aagcccgcac tttcaccctc aagggtgagg attacgtctt gaccgtgaaa   1080
gctggtggta aatcgatttg cctgtccggt ttcatgggaa tggacttccc agagaggatc   1140
ggagagttgt ggattcttgg ggacgttttt attggaaagt actacaccgt cttcgatgtt   1200
ggccaggccc gtcttggatt cgctcaagct aagtcagaag atggctatcc ggttggccct   1260
gctgttcgaa ggtacaacaa gttctcggag gacagcggca gtgatgagga tgatgtattc   1320
actctataag taacatgtat ccacaacttg ctctaatcct gatacgtgta ccgtgtctaa   1380
cgtgcttcca cctttgataa actgattaat ctc                                1413
```

<210> SEQ ID NO 50
<211> LENGTH: 442
<212> TYPE: PRT
<213> ORGANISM: Ancylostoma caninum

<400> SEQUENCE: 50

```
Leu Ala Leu Phe Thr Leu Ala Val Ala Ser Val His Arg Arg Thr Phe
1               5                   10                  15

His His Pro Arg Arg Tyr Val Lys Ser Val Ser Leu Ser Arg Gln Pro
            20                  25                  30

Thr Leu Arg Glu Arg Leu Leu Gly Thr Gly Ser Trp Glu Asp Tyr Gln
        35                  40                  45

Lys Gln Arg Tyr His Tyr Gln Lys Lys Leu Leu Ala Lys Tyr Ala Ala
    50                  55                  60

Ile Lys Ala Thr Lys Leu Gln Ser Thr Asn Glu Ile Asp Glu Leu Leu
65                  70                  75                  80

Arg Asn Tyr Met Asp Ala Gln Tyr Phe Gly Thr Ile Gln Ile Gly Thr
                85                  90                  95

Pro Ala Gln Asn Phe Thr Val Ile Phe Asp Thr Gly Ser Ser Asn Leu
            100                 105                 110
```

-continued

```
Trp Val Pro Ser Glu Lys Met Pro Phe His Asp Ile Ala Cys Met Leu
        115                 120                 125

Arg His Arg Tyr Asp Ser Gly Ala Ser Ser Thr Tyr Lys Glu Asp Gly
    130                 135                 140

Arg Lys Met Ala Ile Gln Tyr Gly Thr Gly Ser Met Lys Gly Phe Ile
145                 150                 155                 160

Ser Lys Asp Asn Val Cys Ile Ala Gly Ile Cys Ala Glu Glu Gln Pro
                165                 170                 175

Phe Ala Glu Ala Thr Ser Glu Pro Gly Leu Thr Phe Ile Ala Ala Lys
            180                 185                 190

Phe Asp Gly Ile Leu Gly Ile Thr Phe Pro Glu Ile Ser Val Leu Gly
        195                 200                 205

Val Pro Pro Val Phe His Thr Phe Ile Glu Gln Lys Lys Val Pro Ser
    210                 215                 220

Pro Val Phe Ala Leu Trp Leu Asn Arg Asn Pro Asp Ser Glu Leu Gly
225                 230                 235                 240

Gly Glu Ile Thr Leu Gly Gly Asn Asp Thr Arg Arg Tyr Val Glu Pro
                245                 250                 255

Ile Thr Trp Thr Pro Val Thr Arg Arg Gly Tyr Trp Gln Phe Lys Met
            260                 265                 270

Asp Lys Val Gln Gly Gly Ser Thr Ser Ile Ala Cys Pro Asn Glu Phe
        275                 280                 285

Ser Gly Cys Gln Ala Ile Ala Asp Thr Gly Thr Ser Leu Ile Ala Gly
    290                 295                 300

Pro Lys Ala Gln Ser Arg Ala Ser Arg Asn Ser Leu Val Leu Glu Pro
305                 310                 315                 320

Thr Tyr Glu Gly Glu Tyr Met Ile Pro Cys Asp Lys Val Pro Phe Pro
                325                 330                 335

Pro Arg Leu Ser Phe Val Ile Glu Ala Arg Thr Phe Thr Leu Lys Gly
            340                 345                 350

Glu Asp Tyr Val Leu Thr Val Lys Ala Gly Gly Lys Ser Ile Cys Leu
        355                 360                 365

Ser Gly Phe Met Gly Met Asp Phe Pro Glu Arg Ile Gly Glu Leu Trp
    370                 375                 380

Ile Leu Gly Asp Val Phe Ile Gly Lys Tyr Tyr Thr Val Phe Asp Val
385                 390                 395                 400

Gly Gln Ala Arg Leu Gly Phe Ala Gln Ala Lys Ser Glu Asp Gly Tyr
                405                 410                 415

Pro Val Gly Pro Ala Val Arg Arg Tyr Asn Lys Phe Ser Glu Asp Ser
            420                 425                 430

Gly Ser Asp Glu Asp Asp Val Phe Thr Leu
        435                 440
```

<210> SEQ ID NO 51
<211> LENGTH: 421
<212> TYPE: DNA
<213> ORGANISM: Ancylostoma caninum
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (353)..(353)
<223> OTHER INFORMATION: n is a, c, g, or t
<220> FEATURE:
<221> NAME/KEY: misc_feature
<222> LOCATION: (366)..(366)

-continued

```
<223> OTHER INFORMATION: n is a, c, g, or t
<220> FEATURE:
<221> NAME/KEY: misc_feature
<222> LOCATION: (394)..(394)
<223> OTHER INFORMATION: n is a, c, g, or t
<220> FEATURE:
<221> NAME/KEY: misc_feature
<222> LOCATION: (413)..(413)
<223> OTHER INFORMATION: n is a, c, g, or t

<400> SEQUENCE: 51

ttgacacagg ttcatcaaat ctctggngct cctgcatatt atgtggagga aatcgcttcg     60

aacctgaccg caacgtacaa caaggaacat gacctctact acatcgactg cagagccaat    120

gcgtctatca cgctcacaat tggccagcgc cagtacaaaa ttgaatcaaa gaacctcatc    180

attcatgtcg aagcagatac atgcatcttg gcactacatg gataccactt tctcggagca    240

acatggatct ttggtgcacc gttcataagg cagttctgta atatttatga tatgggtaac    300

aaaaggatag gattcgctca ttcgctgcag aattagcctg catttactag ttnttattcg    360

acattnttaa acaactccct caataaagta ttgngtttca aaaaaaaaaa aanaaaaaaa    420

a                                                                    421


<210> SEQ ID NO 52
<211> LENGTH: 111
<212> TYPE: PRT
<213> ORGANISM: Ancylostoma caninum

<400> SEQUENCE: 52

Leu Thr Gln Val His Gln Ile Ser Gly Ala Pro Ala Tyr Tyr Val Glu
1               5                   10                  15

Glu Ile Ala Ser Asn Leu Thr Ala Thr Tyr Asn Lys Glu His Asp Leu
            20                  25                  30

Tyr Tyr Ile Asp Cys Arg Ala Asn Ala Ser Ile Thr Leu Thr Ile Gly
        35                  40                  45

Gln Arg Gln Tyr Lys Ile Glu Ser Lys Asn Leu Ile Ile His Val Glu
    50                  55                  60

Ala Asp Thr Cys Ile Leu Ala Leu His Gly Tyr His Phe Leu Gly Ala
65                  70                  75                  80

Thr Trp Ile Phe Gly Ala Pro Phe Ile Arg Gln Phe Cys Asn Ile Tyr
                85                  90                  95

Asp Met Gly Asn Lys Arg Ile Gly Phe Ala His Ser Leu Gln Asn
            100                 105                 110


<210> SEQ ID NO 53
<211> LENGTH: 371
<212> TYPE: DNA
<213> ORGANISM: Ancylostoma caninum

<400> SEQUENCE: 53

aaggcgtatc cggaatgcgg ggagaatgag tggctcgacg actgtggaac tcagaagcca     60

tgcgaggcca agtgcaatga ggaacccccct gaggaggaag atccgatatg ccgctcacgt    120

ggttgtttat tacctcctgc ttgcgtatgc aaagacggat tctacagaga cacggtgatc    180

ggcgactgtg ttagggaaga agaatgcgac caacatgaga ttatacatgt ctgaacgaga    240

aagcaacaat aaccaaaggt tccaactctc gctctgcaaa atcgctagtt ggatgtctct    300

tttgcgtccg aatagtttta gttgatatta agtaagaact cctgctggaa agaataaagc    360

tttccaactc c                                                         371
```

-continued

<210> SEQ ID NO 54
<211> LENGTH: 77
<212> TYPE: PRT
<213> ORGANISM: Ancylostoma caninum

<400> SEQUENCE: 54

```
Lys Ala Tyr Pro Glu Cys Gly Glu Asn Glu Trp Leu Asp Asp Cys Gly
1               5                   10                  15

Thr Gln Lys Pro Cys Glu Ala Lys Cys Asn Glu Glu Pro Pro Glu Glu
            20                  25                  30

Glu Asp Pro Ile Cys Arg Ser Arg Gly Cys Leu Leu Pro Pro Ala Cys
        35                  40                  45

Val Cys Lys Asp Gly Phe Tyr Arg Asp Thr Val Ile Gly Asp Cys Val
    50                  55                  60

Arg Glu Glu Glu Cys Asp Gln His Glu Ile Ile His Val
65                  70                  75
```

<210> SEQ ID NO 55
<211> LENGTH: 1321
<212> TYPE: DNA
<213> ORGANISM: Ancylostoma ceylanicum

<400> SEQUENCE: 55

```
gttttctcct gtagtcgtca tcagtgtggt actcacagtc gccttttgcg atgcaagccc     60

agtgaaagcc agctttggct gctctaacag tgggataact gatagcgatc ggcaagcgtt    120

cctcgacttc cacaacaatg ctcggagacg agttgcgcaa ggagttgagg ataacaaatc    180

cggcaaactg aatccagcga agaacatgta taagctggac tgggactgtg agatggaaca    240

gaagctccag gatgctatcc aatcctgccc aggcggcttt gctggaattc aaggtgttgc    300

gcagaatata ataagctggt caggctccgg tggattcccg aatccatcag aaaagataaa    360

ctcaacactt gccagctggt ggggtggtgc aaaaaaacaac ggcgtcgcct cagacaacaa    420

atacactggt ggaggtcttt acgccttttc caatatggtc ttctctgaga cgacaaaact    480

cggttgcgcc tacaaggttt gcggcactaa actgacgcta tcgtgcattt ataacggaat    540

tgggtatatg acaggcgcgc caatgtggga gacaggtcag gcttgcaagg ccggagcaga    600

ctgcaccaca ttcaagaact caggttgcga agacggcctc tgcacgaaag gagcagatgt    660

ccctgagacg aaccagcagt gtccgtcaaa caccggaatg actgattcag tcagagatac    720

tttcctttca ttgcacaacg aattcaggtc gagtgttgcc cgaggtttgg aacccgatgc    780

tcttggcgga aatgcaccaa aagcatccaa aatgctcaag atggtgtacg actgtgaagt    840

agaagcatca gccatcagac atgggaataa atgcgtctac caacattctc acggcgatga    900

aagacccggc ctaggagaaa acatttacaa aaccagcatt gtcaaatttg agaagaacaa    960

agcagccaag caggcttcac aactttggtg gaacgagttg aaagagttcg gtgtcggccc   1020

atccaacatg ctcactgatg ctctctggaa caggcccaac atgcagattg gtcattacac   1080

ccagatggcc tgggagagca cctacaaact tggatgcgct gttatattct gcaatgattt   1140

cacatttggt gtttgtcagt atggaccagg aggcaattac atgaatcacc tgatctacac   1200

tattggtcaa ccatgttccg agtgtgaagc taccgccact tgcagcgtga ccgaaggatt   1260

gtgcagtgct ccttaattag tctacaataa agatgctact ttccaaaaaa aaaaaaaaaa   1320

a                                                                    1321
```

<210> SEQ ID NO 56

-continued

<211> LENGTH: 422
<212> TYPE: PRT
<213> ORGANISM: Ancylostoma ceylanicum

<400> SEQUENCE: 56

Phe Ser Pro Val Val Val Ile Ser Val Val Leu Thr Val Ala Phe Cys
1 5 10 15

Asp Ala Ser Pro Val Lys Ala Ser Phe Gly Cys Ser Asn Ser Gly Ile
20 25 30

Thr Asp Ser Asp Arg Gln Ala Phe Leu Asp Phe His Asn Asn Ala Arg
35 40 45

Arg Arg Val Ala Gln Gly Val Glu Asp Asn Lys Ser Gly Lys Leu Asn
50 55 60

Pro Ala Lys Asn Met Tyr Lys Leu Asp Trp Asp Cys Glu Met Glu Gln
65 70 75 80

Lys Leu Gln Asp Ala Ile Gln Ser Cys Pro Gly Gly Phe Ala Gly Ile
85 90 95

Gln Gly Val Ala Gln Asn Ile Ile Ser Trp Ser Gly Ser Gly Gly Phe
100 105 110

Pro Asn Pro Ser Glu Lys Ile Asn Ser Thr Leu Ala Ser Trp Trp Gly
115 120 125

Gly Ala Lys Asn Asn Gly Val Ala Ser Asp Asn Lys Tyr Thr Gly Gly
130 135 140

Gly Leu Tyr Ala Phe Ser Asn Met Val Phe Ser Glu Thr Thr Lys Leu
145 150 155 160

Gly Cys Ala Tyr Lys Val Cys Gly Thr Lys Leu Thr Leu Ser Cys Tyr
165 170 175

Asn Gly Ile Gly Tyr Met Thr Gly Ala Pro Met Trp Glu Thr Gly Gln
180 185 190

Ala Cys Lys Ala Gly Ala Asp Cys Thr Thr Phe Lys Asn Ser Gly Cys
195 200 205

Glu Asp Gly Leu Cys Thr Lys Gly Ala Asp Val Pro Glu Thr Asn Gln
210 215 220

Gln Cys Pro Ser Asn Thr Gly Met Thr Asp Ser Val Arg Asp Thr Phe
225 230 235 240

Leu Ser Leu His Asn Glu Phe Arg Ser Ser Val Ala Arg Gly Leu Glu
245 250 255

Pro Asp Ala Leu Gly Gly Asn Ala Pro Lys Ala Ser Lys Met Leu Lys
260 265 270

Met Val Tyr Asp Cys Glu Val Glu Ala Ser Ala Ile Arg His Gly Asn
275 280 285

Lys Cys Val Tyr Gln His Ser His Gly Asp Glu Arg Pro Gly Leu Gly
290 295 300

Glu Asn Ile Tyr Lys Thr Ser Ile Val Lys Phe Glu Lys Asn Lys Ala
305 310 315 320

Ala Lys Gln Ala Ser Gln Leu Trp Trp Asn Glu Leu Lys Glu Phe Gly
325 330 335

Val Gly Pro Ser Asn Met Leu Thr Asp Ala Trp Asn Arg Pro Asn Met
340 345 350

Gln Ile Gly His Tyr Thr Gln Met Ala Trp Glu Ser Thr Tyr Lys Leu
355 360 365

Gly Cys Ala Val Ile Phe Cys Asn Asp Phe Thr Phe Gly Val Cys Gln
370 375 380

Tyr Gly Pro Gly Gly Asn Tyr Met Asn His Leu Ile Tyr Thr Ile Gly

-continued 385 390 395 400

Gln Pro Cys Ser Glu Cys Glu Ala Thr Ala Thr Cys Ser Val Thr Glu
405 410 415

Gly Leu Cys Ser Ala Pro
420

<210> SEQ ID NO 57
<211> LENGTH: 740
<212> TYPE: DNA
<213> ORGANISM: Ancylostoma ceylanicum

<400> SEQUENCE: 57
gttctcgtac cacttctggt tctactggct gtttctgttg atgcaaattc cgtgagatgc 60
ggaaataatg gaatgaccga cgaggcccga cagaaattcc tcgacatgca caacggttac 120
agatcgcagg ttgccaaagg acaggccaag gatgcactct caggaaatgc accaaaagct 180
gccaaaatga agaaaatggt atatgactgt ggtgtcgaat caactgcaat gcagaatgct 240
aaaaaatgtg tcttcactca ttcgcatatg aagggacttg gcgaaaacat atggatgacg 300
actgcacgcg agatggataa agtgaaatca gctgaacagg ctagtcaggg ttggttcagt 360
gaactcgcgg aatacggtgt agggcctgaa aataagctaa caatgcagct gtggaacagg 420
ccaaatactc agattggaca ttacacgcag atggtctggc aggacaccta caaactcgga 480
tgttatgtgg aatggtgctc atctatgacc tacggcgtgt gtcagtatag ccctcaaggt 540
aacatgatga actcaatcat ctacgaaaaa ggaaacccct gcactcagga ttcggactgt 600
ggctcaaatg ccagatgcac cgctgacaag gcgctttgca tcgtgcatgg atagctgggc 660
tatcccacgg tcaacagcgc ttctactaat tagctttgct tcctctataa ataaatgcat 720
tgaaacaaaa aaaaaaaaaa 740

<210> SEQ ID NO 58
<211> LENGTH: 217
<212> TYPE: PRT
<213> ORGANISM: Ancylostoma ceylanicum

<400> SEQUENCE: 58

Val Leu Val Pro Leu Leu Val Leu Leu Ala Val Ser Val Asp Ala Asn
1 5 10 15

Ser Val Arg Cys Gly Asn Asn Gly Met Thr Asp Glu Ala Arg Gln Lys
20 25 30

Phe Leu Asp Met His Asn Gly Tyr Arg Ser Gln Val Ala Lys Gly Gln
35 40 45

Ala Lys Asp Ala Leu Ser Gly Asn Ala Pro Lys Ala Ala Lys Met Lys
50 55 60

Lys Met Val Tyr Asp Cys Gly Val Glu Ser Thr Ala Met Gln Asn Ala
65 70 75 80

Lys Lys Cys Val Phe Thr His Ser His Met Lys Gly Leu Gly Glu Asn
85 90 95

Ile Trp Met Thr Thr Ala Arg Glu Met Asp Lys Val Lys Ser Ala Glu
100 105 110

Gln Ala Ser Gln Gly Trp Phe Ser Glu Leu Ala Glu Tyr Gly Val Gly
115 120 125

Pro Glu Asn Lys Leu Thr Met Gln Leu Trp Asn Arg Pro Asn Thr Gln
130 135 140

Ile Gly His Tyr Thr Gln Met Val Trp Gln Asp Thr Tyr Lys Leu Gly
145 150 155 160

-continued

```
Cys Tyr Val Glu Trp Cys Ser Ser Met Thr Tyr Gly Val Cys Gln Tyr
                165                 170                 175

Ser Pro Gln Gly Asn Met Met Asn Ser Ile Ile Tyr Glu Lys Gly Asn
            180                 185                 190

Pro Cys Thr Gln Asp Ser Asp Cys Gly Ser Asn Ala Arg Cys Thr Ala
        195                 200                 205

Asp Lys Ala Leu Cys Ile Val His Gly
    210                 215
```

<210> SEQ ID NO 59
<211> LENGTH: 1705
<212> TYPE: DNA
<213> ORGANISM: Ancylostoma ceylanicum

<400> SEQUENCE: 59

```
gtttgaggat gagggtattc cttttagtcc tcttgttggc tatttgtgcg agcgctggtt     60

tctttgacac caagcttggt gagaaaataa agaaaacgct tggcaaaatc aaagctgcgc    120

tcaacggcac cttactcatg aaaattcgtg aaaaattcat tgcactgaga gaaaaaataa    180

aggctaagct gaagctctcc ccggcacgaa aagccctact aggcgaaatt atgaagcaca    240

ttattaaaat caaaaaggat aaaattcaag agaaaggtga ctcaatcgaa gaaatcaact    300

cgaaaagtgc tatcggagag ttgctgtacc aaggtgacat cgttctgaca aataagcaag    360

cccaggagat tgttgatgac attgagggtg atgaaaatga ccgcggaaaa cgacaggcgt    420

tccgtgatcg caactatcca cggacattat ggtcgaaggg agtgtattat tacttccatg    480

gaaacgcaac tcctgaggtg agaagcgttt tcacgaaagg cgcaagactt tggatgaaag    540

atacttgcat tgacttcttt gagagcaact cagcacccga taggattcga gttttcaaag    600

aacaaggatg ttggtcgtac gttggtagga tcgggggtca gcaagatctg tcgctgggaa    660

aaggctgtga atcggttgga acagctgcac acgaaatcgg tcatgctatt ggcttctacc    720

acactcactc aagacacgat cgcgataact tcatcacatt taacgcacaa aatgtcaagc    780

ctgattggtt ggaccaattc accaagcaga ccccggctac taatgagaac tacggaatta    840

catacgacta cggaagtatt atgcactatg gcgcaaatag cgcctctgcg aatggacagc    900

cttcaatggt tccgtttgac ccgaaatacg tagaaactct cggatcaccc ataatttcct    960

tttatgaact tctcatgatc aacaaaccct acgagtgcac caagaattgc gatccgaata   1020

cttctgcgca gtgtaagatg ggtggcttcc cacatcctcg ggattgtgga agatgcattt   1080

gtcccagtgg atatggaggc caactatgcg accagaagcc atccggatgc ggatcgatcc   1140

tccaagcgac cgctcagtac cagaacttgc acgacaaacg tggaaacgaa gcagcagggc   1200

agagacctag agaagacatg gacttctgct actactggat tacggctcca cagggttcaa   1260

gaatcgaaat caaaatcgct gatctatctc gaggagccgc tgttgatggg tgtcagtatt   1320

ggggagtaga aattaagact cacgctgacc agcgcctcac tggctacagg ttctgtgctc   1380

cagaagatgt cggacgtaca ttggtgtcga actctaacat cgtaccaata atcacataca   1440

atagatttta tgcaaccact gttgatatcc agtaccgaat cgttggtggt aatgttggcg   1500

gaccaaggcc tcagccacaa ccaaacagca attgcgtcga caatgaacag tgcgcgaccc   1560

tcatcagaac aaagaatttc tgtcagagca gatcgttcac agagtccgtc aaaagaggtc   1620

tatgtccaaa ggcatgcggt ttttgccgct aacttttcac gagacaatga aataaatatt   1680

cgcagcatca aaaaaaaaaa aaaaa                                           1705
```

-continued

```
<210> SEQ ID NO 60
<211> LENGTH: 545
<212> TYPE: PRT
<213> ORGANISM: Ancylostoma ceylanicum

<400> SEQUENCE: 60

Met Arg Val Phe Leu Leu Val Leu Leu Leu Ala Ile Cys Ala Ser Ala
1               5                   10                  15

Gly Phe Phe Asp Thr Lys Leu Gly Glu Lys Ile Lys Lys Thr Leu Gly
            20                  25                  30

Lys Ile Lys Ala Ala Leu Asn Gly Thr Leu Leu Met Lys Ile Arg Glu
        35                  40                  45

Lys Phe Ile Ala Leu Arg Glu Lys Ile Lys Ala Lys Leu Lys Leu Ser
    50                  55                  60

Pro Ala Arg Lys Ala Leu Leu Gly Glu Ile Met Lys His Ile Ile Lys
65                  70                  75                  80

Ile Lys Lys Asp Lys Ile Gln Glu Lys Gly Asp Ser Ile Glu Glu Ile
                85                  90                  95

Asn Ser Lys Ser Ala Ile Gly Glu Leu Leu Tyr Gln Gly Asp Ile Val
            100                 105                 110

Leu Thr Asn Lys Gln Ala Gln Glu Ile Val Asp Ile Glu Gly Asp Glu
        115                 120                 125

Asn Asp Arg Gly Lys Arg Gln Ala Phe Arg Asp Arg Asn Tyr Pro Arg
    130                 135                 140

Thr Leu Trp Ser Lys Gly Val Tyr Tyr Tyr Phe His Gly Asn Ala Thr
145                 150                 155                 160

Pro Glu Val Arg Ser Val Phe Thr Lys Gly Ala Arg Leu Trp Met Lys
                165                 170                 175

Asp Thr Cys Ile Asp Phe Phe Glu Ser Asn Ser Ala Pro Asp Arg Ile
            180                 185                 190

Arg Val Phe Lys Glu Gln Gly Cys Trp Ser Tyr Val Gly Arg Ile Gly
        195                 200                 205

Gly Gln Gln Asp Leu Ser Leu Gly Lys Gly Cys Glu Ser Val Gly Thr
    210                 215                 220

Ala Ala His Glu Ile Gly His Ala Ile Gly Phe Tyr His Thr His Ser
225                 230                 235                 240

Arg His Asp Arg Asp Asn Phe Ile Thr Phe Asn Ala Gln Asn Val Lys
                245                 250                 255

Pro Asp Trp Leu Asp Gln Phe Thr Lys Gln Thr Pro Ala Thr Asn Glu
            260                 265                 270

Asn Tyr Gly Ile Thr Tyr Asp Tyr Gly Ser Ile Met His Tyr Gly Ala
        275                 280                 285

Asn Ser Ala Ser Ala Asn Gly Gln Pro Ser Met Val Pro Phe Asp Pro
    290                 295                 300

Lys Tyr Val Glu Thr Leu Gly Ser Pro Ile Ile Ser Phe Tyr Glu Leu
305                 310                 315                 320

Leu Met Ile Asn Lys Pro Tyr Glu Cys Thr Lys Asn Cys Asp Pro Asn
                325                 330                 335

Thr Ser Ala Gln Cys Lys Met Gly Gly Phe Pro His Pro Arg Asp Cys
            340                 345                 350

Gly Arg Cys Ile Cys Pro Ser Gly Tyr Gly Gly Gln Leu Cys Asp Gln
        355                 360                 365

Lys Pro Ser Gly Cys Gly Ser Ile Leu Gln Ala Thr Ala Gln Tyr Gln
    370                 375                 380
```

-continued

```
Asn Leu His Asp Lys Arg Gly Asn Glu Ala Ala Gly Gln Arg Pro Arg
385                 390                 395                 400

Glu Asp Met Asp Phe Cys Tyr Tyr Trp Ile Thr Ala Pro Gln Gly Ser
                405                 410                 415

Arg Ile Glu Ile Lys Ile Ala Asp Leu Ser Arg Gly Ala Ala Val Asp
            420                 425                 430

Gly Cys Gln Tyr Trp Gly Val Glu Ile Lys Thr His Ala Asp Gln Arg
        435                 440                 445

Leu Thr Gly Tyr Arg Phe Cys Ala Pro Glu Asp Val Gly Arg Thr Leu
    450                 455                 460

Val Ser Asn Ser Asn Ile Val Pro Ile Ile Thr Tyr Asn Phe Tyr Ala
465                 470                 475                 480

Thr Thr Val Asp Ile Gln Tyr Arg Ile Val Gly Gly Asn Val Gly Gly
                485                 490                 495

Pro Arg Pro Gln Pro Gln Pro Asn Ser Asn Cys Val Asp Asn Glu Gln
            500                 505                 510

Cys Ala Thr Leu Ile Arg Thr Lys Asn Phe Cys Gln Ser Arg Ser Phe
        515                 520                 525

Thr Glu Ser Val Lys Arg Gly Leu Cys Pro Lys Ala Cys Gly Phe Cys
    530                 535                 540

Arg
545


<210> SEQ ID NO 61
<211> LENGTH: 893
<212> TYPE: DNA
<213> ORGANISM: Ancylostoma ceylanicum

<400> SEQUENCE: 61

ggtttaatta cccaagtttg agatgaagct actcgctctt tccgctctct gcgcgctggc      60

cttcgctgct ccgcgagaca agcggctagc tgtgagcact atcactgtca ctggaggact     120

aggtctctcc acgggatgtg tcgtcactgg caacgttttg tatgcaaatg gtttccgagt     180

acgcgaaatt aatccatcgg agcagcaaga gttggtcaag tatcagaacg acgtagccga     240

atataagacg gccctgaaac aagcgatcaa ggagcgagaa gagaagatcc gagcccgtct     300

cgccggcaag aaggtgaagg ccgttgagtc gaccaaagaa gaggacctgc cgaagccgcc     360

acagaagccg tcattctgca caccagaaga cactacccag ttcttctttg aaggatgcat     420

gatccagaac aacaagatct acgtcggaaa cactttcgct cgtgacctga cccaatctga     480

aatcggcgaa ctgaaggaat tcgagaagaa attcaaggtc taccaggact acgttcagaa     540

gcaggccgaa cagcaagtga acagcctctt cggcggctct gacttcttct cggcactgtt     600

cagcggcggt gagaccaagc catccacgac cactgtggca ccagaacttc ctgaagacgc     660

tcccgagcag ccgcccacgc ccaacttctg caccagaata atctaaacgt gctctgaatt     720

gtccacttag ttgttggatt ggttggtttg gtgaatagcg acttcgcttc ccctctcgta     780

cttacggtgt cgactagcac attagtcatg cgttgcaata tttgatcatt gtattaaggt     840

atattgtaca tttatataat aaaattatat ttcaactcaa aaaaaaaaaa aaa            893


<210> SEQ ID NO 62
<211> LENGTH: 227
<212> TYPE: PRT
<213> ORGANISM: Ancylostoma ceylanicum

<400> SEQUENCE: 62
```

-continued

```
Met Lys Leu Leu Ala Leu Ser Ala Leu Cys Ala Leu Ala Phe Ala Ala
1               5                   10                  15

Pro Arg Asp Lys Arg Leu Ala Val Ser Thr Ile Thr Val Thr Gly Gly
            20                  25                  30

Leu Gly Leu Ser Thr Gly Cys Val Val Thr Gly Asn Val Leu Tyr Ala
        35                  40                  45

Asn Gly Phe Arg Val Arg Glu Ile Asn Pro Ser Glu Gln Gln Glu Leu
    50                  55                  60

Val Lys Tyr Gln Asn Asp Val Ala Glu Tyr Lys Thr Ala Leu Lys Gln
65                  70                  75                  80

Ala Ile Lys Glu Arg Glu Glu Lys Ile Arg Ala Arg Leu Ala Gly Lys
                85                  90                  95

Lys Val Lys Ala Val Glu Ser Thr Lys Glu Glu Asp Leu Pro Lys Pro
            100                 105                 110

Pro Gln Lys Pro Ser Phe Cys Thr Pro Glu Asp Thr Thr Gln Phe Phe
        115                 120                 125

Phe Glu Gly Cys Met Ile Gln Asn Asn Lys Ile Tyr Val Gly Asn Thr
    130                 135                 140

Phe Ala Arg Asp Leu Thr Gln Ser Glu Ile Gly Glu Leu Lys Glu Phe
145                 150                 155                 160

Glu Lys Lys Phe Lys Val Tyr Gln Asp Tyr Val Gln Lys Gln Ala Glu
                165                 170                 175

Gln Gln Val Asn Ser Leu Phe Gly Gly Ser Asp Phe Phe Ser Ala Leu
            180                 185                 190

Phe Ser Gly Gly Glu Thr Lys Pro Ser Thr Thr Thr Val Ala Pro Glu
        195                 200                 205

Leu Pro Glu Asp Ala Pro Glu Gln Pro Pro Thr Pro Asn Phe Cys Thr
    210                 215                 220

Arg Ile Ile
225
```

<210> SEQ ID NO 63
<211> LENGTH: 407
<212> TYPE: DNA
<213> ORGANISM: Ancylostoma ceylanicum

<400> SEQUENCE: 63

```
ggttaattac ccaagtttga gaatgattca actgttgttg ttagcgctac tccctgtttg      60

catctcagtg agggaacagt cgatagcagt taaaggacgc cttctgtgcg gtgatcaacc     120

agcagcgaac gtcagagtga agttgtggga agaagacaca ggaccagatc cagatgacct     180

actggatgca ggatacacga actctaatgg tgaattccaa ctccaaggcg gaacaataga     240

gacgactccc attgatcccg tcttgaaaat ttaccatgat tgcaatgacg tgactggttt     300

tctgagcgta cctaaacctg gcagcagaaa agtgaggttc tccttaccgg acaaatacat     360

cagcgatgga atggttccta agaaagtcat ggacatcggt gttatca                   407
```

<210> SEQ ID NO 64
<211> LENGTH: 127
<212> TYPE: PRT
<213> ORGANISM: Ancylostoma ceylanicum

<400> SEQUENCE: 64

```
Met Ile Gln Leu Leu Leu Leu Ala Leu Leu Pro Val Cys Ile Ser Val
1               5                   10                  15
```

-continued

```
Arg Glu Gln Ser Ile Ala Val Lys Gly Arg Leu Leu Cys Gly Asp Gln
            20                  25                  30

Pro Ala Ala Asn Val Arg Val Lys Leu Trp Glu Glu Asp Thr Gly Pro
        35                  40                  45

Asp Pro Asp Asp Leu Leu Asp Ala Gly Tyr Thr Asn Ser Asn Gly Glu
    50                  55                  60

Phe Gln Leu Gln Gly Gly Thr Ile Glu Thr Thr Pro Ile Asp Pro Val
65                  70                  75                  80

Leu Lys Ile Tyr His Asp Cys Asn Asp Val Thr Gly Phe Leu Ser Val
                85                  90                  95

Pro Lys Pro Gly Ser Arg Lys Val Arg Phe Ser Leu Pro Asp Lys Tyr
            100                 105                 110

Ile Ser Asp Gly Met Val Pro Lys Lys Val Met Asp Ile Gly Val
        115                 120                 125


<210> SEQ ID NO 65
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 65

cttctcatga tcaacaaaca cvtacg                                          26


<210> SEQ ID NO 66
<211> LENGTH: 25
<212> TYPE: DNA
<213> ORGANISM: Artificial
<220> FEATURE:
<223> OTHER INFORMATION: Synthetic oligonucleotide primer

<400> SEQUENCE: 66

aatctaactc caacatcttc tggtg                                           25


<210> SEQ ID NO 67
<211> LENGTH: 425
<212> TYPE: PRT
<213> ORGANISM: Ancylostoma duodenale

<400> SEQUENCE: 67

Met Phe Ser Ser Val Val Val Ile Ser Val Ile Ser Thr Ile Ala Phe
1               5                   10                  15

Cys Asp Ala Ser Pro Ala Arg Ala Ser Phe Gly Cys Ser Asn Asn Gly
            20                  25                  30

Ile Thr Asp Ser Asp Arg Gln Ala Phe Leu Asp Phe His Asn Asn Ala
        35                  40                  45

Arg Arg Arg Val Ala Gln Gly Val Glu Asp Asn Lys Ser Gly Lys Leu
    50                  55                  60

Asn Pro Ala Lys Asn Met Tyr Lys Leu Glu Trp Asp Cys Lys Met Glu
65                  70                  75                  80

Gln Gln Leu Gln Asp Ala Ile Gln Ser Cys Pro Gly Gly Ser Ala Gly
                85                  90                  95

Ile Gln Gly Phe Ser Gln Asn Val Met Ser Trp Ser Asn Ser Gly Gly
            100                 105                 110

Phe Pro Asn Ser Ser Glu Lys Ile Glu Ser Thr Leu Ser Gly Trp Trp
        115                 120                 125

Ser Gly Ala Lys Asn Asn Gly Val Gly Ser Asp Asn Lys Tyr Thr Gly
    130                 135                 140
```

-continued

Gly Gly Leu Tyr Ala Phe Ser Asn Met Val Phe Ser Glu Thr Thr Lys
145 150 155 160

Ile Gly Cys Ala Tyr Lys Val Cys Gly Thr Lys Met Ala Thr Ser Cys
165 170 175

Ile Tyr Asn Gly Ile Gly Tyr Ile Thr Asn Ala Pro Met Trp Glu Thr
180 185 190

Gly Gln Ala Cys Lys Thr Gly Ala Asp Cys Ser Thr Tyr Lys Asn Ser
195 200 205

Gly Cys Glu Asp Ser Leu Cys Thr Lys Gly Ala Asp Val Pro Glu Thr
210 215 220

Asn Gln Gln Cys Pro Ser Asn Thr Gly Met Thr Asp Ser Val Arg Asp
225 230 235 240

Thr Phe Leu Ser Leu His Asn Gly Phe Arg Ser Ser Val Ala Arg Gly
245 250 255

Leu Glu Pro Asp Ala Leu Gly Gly Asn Ala Pro Lys Ala Ala Lys Met
260 265 270

Leu Lys Met Val Tyr Asp Cys Glu Val Glu Ala Ser Ala Ile Arg His
275 280 285

Gly Asn Lys Cys Val Tyr Gln His Ser Ser Gly Asn Asp Arg Pro Gly
290 295 300

Leu Gly Glu Asn Ile Tyr Lys Thr Ser Val Gln Lys Phe Glu Lys Asn
305 310 315 320

Lys Ala Ala Lys Gln Ala Ser Glu Leu Trp Trp Asn Glu Leu Arg Glu
325 330 335

Phe Gly Val Gly Pro Ser Asn Asn Leu Thr Asn Ala Leu Trp Asn Arg
340 345 350

Pro Gly Met Gln Ile Gly His Tyr Thr Gln Met Ala Trp Asp Thr Thr
355 360 365

Tyr Lys Leu Gly Cys Ala Val Val Phe Cys Asn Asp Phe Thr Phe Gly
370 375 380

Val Cys Gln Tyr Gly Pro Gly Gly Asn Tyr Met Asn His Leu Ile Tyr
385 390 395 400

Thr Met Gly Gln Pro Cys Ser Gln Cys Ala Ala Thr Ala Thr Cys Ser
405 410 415

Val Thr Glu Gly Leu Cys Ser Ala Pro
420 425

<210> SEQ ID NO 68
<211> LENGTH: 216
<212> TYPE: PRT
<213> ORGANISM: Ancylostoma duodenale

<400> SEQUENCE: 68

Met Leu Val Pro Val Ala Leu Leu Ala Leu Leu Ala Val Ala Val Glu
1 5 10 15

Gly Asn Ser Met Arg Cys Gly Asn Asn Gly Met Thr Asp Glu Ala Arg
20 25 30

Gln Glu Phe Leu Asp Val His Asn Gly Tyr Arg Ser Lys Val Ala Lys
35 40 45

Gly Gln Ala Lys Asp Ala Leu Gly Gly Asn Ala Pro Lys Ala Ala Lys
50 55 60

Met Lys Lys Met Ile Tyr Asp Cys Asn Val Glu Ser Thr Ala Met Gln
65 70 75 80

Asp Ala Lys Lys Cys Val Phe Ala His Ser His Lys Gly Leu Gly Glu

-continued

```
                85                  90                  95

Asn Ile Tyr Met Ser Thr Ala Arg Gln Met Asp Lys Ala Glu Ala Ala
            100                 105                 110

Gln Gln Ala Ser Asp Gly Trp Phe Ala Glu Leu Ala Lys Tyr Gly Val
        115                 120                 125

Gly Gln Glu Asn Lys Leu Thr Met Gln Leu Trp Asn Arg Gly Val Met
    130                 135                 140

Ile Gly His Tyr Thr Gln Met Val Trp Gln Glu Ser Tyr Lys Leu Gly
145                 150                 155                 160

Cys Tyr Val Glu Trp Cys Pro Ser Met Thr Tyr Gly Val Cys Gln Tyr
                165                 170                 175

Ser Pro Gln Gly Asn Met Met Asn Ser Ile Ile Tyr Glu Lys Gly Asn
            180                 185                 190

Pro Cys Thr Gln Asp Ser Asp Cys Gly Ser Asn Ala Lys Cys Ser Ser
        195                 200                 205

Gly Glu Ala Leu Cys Ile Val Gln
    210                 215


<210> SEQ ID NO 69
<211> LENGTH: 207
<212> TYPE: PRT
<213> ORGANISM: Necator americanus

<400> SEQUENCE: 69

Met Ser Ser Ile Thr Cys Leu Val Leu Leu Ser Ile Ala Ala Tyr Ser
1               5                   10                  15

Lys Ala Gly Cys Pro Asp Asn Gly Met Ser Glu Glu Ala Arg Gln Lys
            20                  25                  30

Phe Leu Glu Leu His Asn Ser Leu Arg Ser Ser Val Ala Leu Gly Gln
        35                  40                  45

Ala Lys Asp Gly Ala Gly Gly Asn Ala Pro Lys Ala Ala Lys Met Lys
    50                  55                  60

Thr Met Ala Tyr Asp Cys Glu Val Glu Lys Thr Ala Met Asn Asn Ala
65                  70                  75                  80

Lys Gln Cys Val Phe Lys His Ser Gln Pro Asn Gln Arg Lys Gly Leu
                85                  90                  95

Gly Glu Asn Ile Phe Met Ser Ser Asp Ser Gly Lys Ala Lys Ala Ala
            100                 105                 110

Glu Gln Ala Ser Lys Ala Trp Phe Gly Glu Leu Ala Glu Lys Gly Val
        115                 120                 125

Gly Gln Asn Leu Lys Leu Thr Gly Gly Leu Phe Ser Arg Gly Val Gly
    130                 135                 140

His Tyr Thr Gln Met Val Trp Gln Glu Thr Val Lys Leu Gly Cys Tyr
145                 150                 155                 160

Val Glu Ala Cys Ser Asn Met Cys Tyr Val Val Cys Gln Tyr Gly Pro
                165                 170                 175

Ala Gly Asn Met Met Gly Lys Asp Ile Tyr Glu Lys Gly Glu Pro Cys
            180                 185                 190

Ser Lys Cys Glu Asn Cys Asp Lys Glu Lys Gly Leu Cys Ser Ala
        195                 200                 205


<210> SEQ ID NO 70
<211> LENGTH: 31
<212> TYPE: DNA
<213> ORGANISM: Artificial
<220> FEATURE:
```

-continued

<223> OTHER INFORMATION: Synthetic oligonucleotide primer

<400> SEQUENCE: 70
ctctcgagaa aagaagccca gtaaagccag c 31

<210> SEQ ID NO 71
<211> LENGTH: 28
<212> TYPE: DNA
<213> ORGANISM: Artificial
<220> FEATURE:
<223> OTHER INFORMATION: Synthetic oligonucleotide primer

<400> SEQUENCE: 71
tgtctagagg agcactgcac aatccttc 28

<210> SEQ ID NO 72
<211> LENGTH: 27
<212> TYPE: DNA
<213> ORGANISM: Artificial
<220> FEATURE:
<223> OTHER INFORMATION: Synthetic oligonucleotide primer

<400> SEQUENCE: 72
gggaattcgg aaataatgga atgaccg 27

<210> SEQ ID NO 73
<211> LENGTH: 26
<212> TYPE: DNA
<213> ORGANISM: Artificial
<220> FEATURE:
<223> OTHER INFORMATION: Snythetic oligonucleotide primer

<400> SEQUENCE: 73
tgtctagacc atgcacgatg caaagc 26

<210> SEQ ID NO 74
<211> LENGTH: 21
<212> TYPE: DNA
<213> ORGANISM: Artificial
<220> FEATURE:
<223> OTHER INFORMATION: Synthetic oligonucleotide primer

<400> SEQUENCE: 74
gcaaatggca ttctgacatc c 21

<210> SEQ ID NO 75
<211> LENGTH: 21
<212> TYPE: DNA
<213> ORGANISM: Artificial
<220> FEATURE:
<223> OTHER INFORMATION: Synthetic oligonucleotide primer

<400> SEQUENCE: 75
tactattgcc agcattgctg c 21

<210> SEQ ID NO 76
<211> LENGTH: 678
<212> TYPE: DNA
<213> ORGANISM: Ancylostoma caninum

<400> SEQUENCE: 76
gaaaggttta attacccaag tttgaggtgt aaaaatggtc cactacaagc tgacctactt 60
caacggacgt ggcctcggcg aatgcgcgcg tcagttgttc gctcttgctg accaacaata 120
tgaggatatt cgtgttacac atgaggattt ccccgagata aaaccaaatt tgccatttgg 180

-continued

```
acaactgccg ctgcttaacg aggatggtaa agaactcgct cagtcaaacg ccatcaatcg    240

ttacctggct aggaaattcg gattcgctgg caaaacgcca tttgaggagg ctctagtgga    300

ctcgctggca gatcagatga cggactaccg tgtagaaata aaaccattcg tctatacagc    360

gtatggacat cagaaattcg gtgacctgga gacgctaaaa aaggatgtga tgcttcctgc    420

acgagacaag ttcctcggtt tcatcaccaa attcttaaag aacaacccat caggattctt    480

ggttggtgac tcggtgactt ggatagatct gttgcttgct gaacatgctt ccgacataca    540

gtcaaaggtc cccgaatacc tcgaagggtt tcctgaggtg aaggctcata tggaaaaggt    600

gcgatctatt ccgaaactga aaaaatggat cgagaccaga ccggagactc acttctgatc    660

gatacgcggg attttttc                                                  678
```

<210> SEQ ID NO 77
<211> LENGTH: 207
<212> TYPE: PRT
<213> ORGANISM: Ancylostoma caninum

<400> SEQUENCE: 77

```
Met Val His Tyr Lys Leu Thr Tyr Phe Asn Gly Arg Gly Leu Gly Glu
1               5                   10                  15

Cys Ala Arg Gln Leu Phe Ala Leu Ala Asp Gln Gln Tyr Glu Asp Ile
            20                  25                  30

Arg Val Thr His Glu Asp Phe Pro Glu Ile Lys Pro Asn Leu Pro Phe
        35                  40                  45

Gly Gln Leu Pro Leu Leu Asn Glu Asp Gly Lys Glu Leu Ala Gln Ser
    50                  55                  60

Asn Ala Ile Asn Arg Tyr Leu Ala Arg Lys Phe Gly Phe Ala Gly Lys
65                  70                  75                  80

Thr Pro Phe Glu Glu Ala Leu Val Asp Ser Leu Ala Asp Gln Met Thr
                85                  90                  95

Asp Tyr Arg Val Glu Ile Lys Pro Phe Val Tyr Thr Ala Tyr Gly His
            100                 105                 110

Gln Lys Phe Gly Asp Leu Glu Thr Leu Lys Lys Asp Val Met Leu Pro
        115                 120                 125

Ala Arg Asp Lys Phe Leu Gly Phe Ile Thr Lys Phe Leu Lys Asn Asn
    130                 135                 140

Pro Ser Gly Phe Leu Val Gly Asp Ser Val Thr Trp Ile Asp Leu Leu
145                 150                 155                 160

Leu Ala Glu His Ala Ser Asp Ile Gln Ser Lys Val Pro Glu Tyr Leu
                165                 170                 175

Glu Gly Phe Pro Glu Val Lys Ala His Met Glu Lys Val Arg Ser Ile
            180                 185                 190

Pro Lys Leu Lys Lys Trp Ile Glu Thr Arg Pro Glu Thr His Phe
        195                 200                 205
```

<210> SEQ ID NO 78
<211> LENGTH: 16
<212> TYPE: DNA
<213> ORGANISM: Artificial
<220> FEATURE:
<223> OTHER INFORMATION: Synthetic oligonucleotide primer

<400> SEQUENCE: 78

```
gctctccggc tggtgg                                                     16
```

-continued

<210> SEQ ID NO 79
<211> LENGTH: 21
<212> TYPE: DNA
<213> ORGANISM: Artificial
<220> FEATURE:
<223> OTHER INFORMATION: Synthetic oligonucleotide primer

<400> SEQUENCE: 79
ttaaggagcg ctgcacaagc c 21

<210> SEQ ID NO 80
<211> LENGTH: 28
<212> TYPE: DNA
<213> ORGANISM: Artificial
<220> FEATURE:
<223> OTHER INFORMATION: Synthetic oligonucleotide primer

<400> SEQUENCE: 80
gggaattcaa ttctatgaga tgcggaaa 28

<210> SEQ ID NO 81
<211> LENGTH: 28
<212> TYPE: DNA
<213> ORGANISM: Artificial
<220> FEATURE:
<223> OTHER INFORMATION: Synthetic oligonucleotide primer

<400> SEQUENCE: 81
tgtctagata gccagccacg acgcaaag 28

<210> SEQ ID NO 82
<211> LENGTH: 753
<212> TYPE: DNA
<213> ORGANISM: Necator americanus

<400> SEQUENCE: 82
gaaaatcaca atgatgtctt ctatcacatg tttggttctt ctctcgattg cagcgtactc 60
caaagccggt tgtcctgaca atggaatgtc agaggaagca cggcaaaaat tccttgaatt 120
gcacaattcg ttgagaagtt cggttgcatt gggacaggcc aaggatggag ctggtggaaa 180
tgccccgaaa gctgctaaga tgaagacgat ggcatacgat tgcgaagttg aaaagactgc 240
aatgaataac gcgaaacaat gtgtattcaa gcactcgcaa cctaaccaaa ggaaaggatt 300
gggagagaat atatttatgt cttcggatag cggtatggac aaagcaaagg ctgctgagca 360
ggctagcaaa gcttggttcg gcgaacttgc agaaaaagga gttggacaga atcttaagct 420
tacaggaggc ttgttcagca gaggagtcgg gcactataca cagatggtat ggcaagaaac 480
cgttaagctt ggatgctatg tggaagcgtg ctcaaatatg tgttatgtgg tgtgccagta 540
cggtcctgct ggaaatatga tgggcaagga tatctacgag aaaggagaac cgtgttcgaa 600
atgtgagaat tgcgacaagg agaagggact ctgcagtgct tgattagttg tgttcagtga 660
agctcattac gctcacatac tttaacaaat cgtagtgatc tgtagttgct ttaatattca 720
aataaacatg atgccagcaa aaaaaaaaaa aaa 753

<210> SEQ ID NO 83
<211> LENGTH: 1134
<212> TYPE: DNA
<213> ORGANISM: Necator americanus

<400> SEQUENCE: 83
gttaaagccg tgtaagcaac agggttcttt gtgatgttaa ctctcgctgc acttctgatt 60

-continued

```
tctgtttcgc tggttgagcc gacaggcata ggtgagtttc ttgctcaacc agcacctgca    120

tatgctagaa gactcacagg gcaggccctt gttgactacg tcaattcgca ccactcattg    180

tacaaggcca aatattcacc agatgctcaa gaacgcatga aatctagaat tatggatttg    240

agtttcatgg ttgatgcgga agtcatgatg gaagaaatgg accagcagga ggatatagat    300

ctcgctgttt ctttacctga aagtttcgac gctcgtgaaa aatggccaga atgtccttca    360

ataggattaa tccgtgatca gtccgccggt ggaggatgtt gggcagtatc ctcagcagag    420

gtgatgaccg acaggatctg tatacaatca aatggaacaa agcaggtgta tgtttccgaa    480

acggatatct tatcatgctg tggacaacgt tgcggtagcg ggtgtacctc aggtgtgcca    540

cgtcaagctt tcaactatgc aattcgtaaa ggtgtttgca gtggaggacc atatggaacg    600

aagggtgttt gcaaacccta tcctttctat ccatgcggct atcatgctca tctgccatat    660

tatggaccat gtccagatgg tatgtggcct acgccaacat gcgaaaaggc atgtcaatcc    720

gactatactg ttccgtacaa cgatgacagg atcttcggca gcaaaactat tgtcttgacg    780

ggagaggaaa aaattaagcg agagattttc aataacggac cattggtagc cacgtataca    840

gtttacgaag atttcgctta ttacaagaat ggaatttaca tgactggtct cggtagagcg    900

acaggcgcac atgcagtcaa aattattggc tggggtgaag aaaatggagt caagtattgg    960

ttgattgcaa actcgtggaa cactgattgg ggagagaatg gcttcttccg catgcttcgt   1020

ggaacaaacc tttgcgatat tgaactaagc gcgactggag gaacgttcaa ggtgtgaacg   1080

tgatcgaaaa gaacgatttt gaacaaaaat cttcccgtat tgtcatcaaa aaaa         1134
```

<210> SEQ ID NO 84
<211> LENGTH: 347
<212> TYPE: PRT
<213> ORGANISM: Necator americanus

<400> SEQUENCE: 84

```
Met Leu Thr Leu Ala Ala Leu Leu Ile Ser Val Ser Leu Val Glu Pro
1               5                   10                  15

Thr Gly Ile Gly Glu Phe Leu Ala Gln Pro Ala Pro Ala Tyr Ala Arg
            20                  25                  30

Arg Leu Thr Gly Gln Ala Leu Val Asp Tyr Val Asn Ser His His Ser
        35                  40                  45

Leu Tyr Lys Ala Lys Tyr Ser Pro Asp Ala Gln Glu Arg Met Lys Ser
    50                  55                  60

Arg Ile Met Asp Leu Ser Phe Met Val Asp Ala Glu Val Met Met Glu
65                  70                  75                  80

Glu Met Asp Gln Gln Glu Asp Ile Asp Leu Ala Val Ser Leu Pro Glu
                85                  90                  95

Ser Phe Asp Ala Arg Glu Lys Trp Pro Glu Cys Pro Ser Ile Gly Leu
            100                 105                 110

Ile Arg Asp Gln Ser Ala Gly Gly Gly Cys Trp Ala Val Ser Ser Ala
        115                 120                 125

Glu Val Met Thr Asp Arg Ile Cys Ile Gln Ser Asn Gly Thr Lys Gln
    130                 135                 140

Val Tyr Val Ser Glu Thr Asp Ile Leu Ser Cys Cys Gly Gln Arg Cys
145                 150                 155                 160

Gly Ser Gly Cys Thr Ser Gly Val Pro Arg Gln Ala Phe Asn Tyr Ala
                165                 170                 175

Ile Arg Lys Gly Val Cys Ser Gly Gly Pro Tyr Gly Thr Lys Gly Val
            180                 185                 190
```

-continued

```
Cys Lys Pro Tyr Pro Phe Tyr Pro Cys Gly Tyr His Ala His Leu Pro
        195                 200                 205

Tyr Tyr Gly Pro Cys Pro Asp Gly Met Trp Pro Thr Pro Thr Cys Glu
    210                 215                 220

Lys Ala Cys Gln Ser Asp Tyr Thr Val Pro Tyr Asn Asp Asp Arg Ile
225                 230                 235                 240

Phe Gly Ser Lys Thr Ile Val Leu Thr Gly Glu Glu Lys Ile Lys Arg
                245                 250                 255

Glu Ile Phe Asn Asn Gly Pro Leu Val Ala Thr Tyr Thr Val Tyr Glu
            260                 265                 270

Asp Phe Ala Tyr Tyr Lys Asn Gly Ile Tyr Met Thr Gly Leu Gly Arg
        275                 280                 285

Ala Thr Gly Ala His Ala Val Lys Ile Ile Gly Trp Gly Glu Glu Asn
    290                 295                 300

Gly Val Lys Tyr Trp Leu Ile Ala Asn Ser Trp Asn Thr Asp Trp Gly
305                 310                 315                 320

Glu Asn Gly Phe Phe Arg Met Leu Arg Gly Thr Asn Leu Cys Asp Ile
                325                 330                 335

Glu Leu Ser Ala Thr Gly Gly Thr Phe Lys Val
            340                 345
```

<210> SEQ ID NO 85
<211> LENGTH: 1177
<212> TYPE: DNA
<213> ORGANISM: Necator americanus

<400> SEQUENCE: 85

```
ttaattctta ttgctctggt ggtgacggcg ttggctcaac agccgctttc actaaaggag     60

tatctggaac agccgatacc agaggaggca gagaatcttt ccggagaagc gtttgcggag    120

tttctgaaca aacgacaatc gtttttcacg gctaagtaca cgccaaatgc tttaaacatt    180

cttaaaatgc gtgtgatgga atcgagattc ctggacaatg aagaaggtga aatgctaaaa    240

gaggaggaca tggatttcag tgaagaaatt cctgttagtt ttgatgctcg agacaaatgg    300

cccaaatgca cctccatagg atttatccgt gatcaatcac actgtggttc atgctgggca    360

gtatcgtcag cagaaacgat gtcagatcga ctctgcgtgc aatcaaacgg tacaattaag    420

gtacttctat ccgatacgga catccttgcc tgttgcccga attgtggtgc tggatgtgga    480

ggaggccaca caattcgagc gtgggaatat tttaagaaca caggcgtttg cactggcgga    540

ctatatggaa caaaggattc ctgcaaacca tacgctttct atccatgtaa agacgaaagt    600

tacggaaagt gccccaagga ttcttttcca acaccaaaat gtcgaaaaat ttgtcagtat    660

aaatacagta agaagtacgc cgacgacaaa tactacgcga attccgcata tcgaattcca    720

cagaatgaga cgtggatcaa attggagatc atgagaaacg ggcctgtgac agcatcattc    780

aggatttatc cggattttgg gttttacgaa aaaggagttt atgtgacttc aggcggaagg    840

gaactaggtg ggcacgcgat taaaatcatt ggatggggaa cggaaaaagt aaacggaact    900

gacctacctt actggttgat tgctaactct tggggtactg actggggaga gaataacggc    960

tatttccgca tacttcgcgg acaaaatcac tgccaaatag aacagaaagt tatcgccggt   1020

atgataaaag taccacaacc gaaatccgcc ggtccaccac ttcaacccaa tccttcaagc   1080

tgaaccaagt tgtagtattg tccccatcaa tccaagcatt tcttggggtg atacttttac   1140

gaataaaaac tacattataa aaaaaaaaaa aaaaaaa                            1177
```

-continued

<210> SEQ ID NO 86
<211> LENGTH: 360
<212> TYPE: PRT
<213> ORGANISM: Necator americanus

<400> SEQUENCE: 86

```
Leu Ile Leu Ile Ala Leu Val Val Thr Ala Leu Ala Gln Gln Pro Leu
1               5                   10                  15

Ser Leu Lys Glu Tyr Leu Glu Gln Pro Ile Pro Glu Glu Ala Glu Asn
            20                  25                  30

Leu Ser Gly Glu Ala Phe Ala Glu Phe Leu Asn Lys Arg Gln Ser Phe
        35                  40                  45

Phe Thr Ala Lys Tyr Thr Pro Asn Ala Leu Asn Ile Leu Lys Met Arg
    50                  55                  60

Val Met Glu Ser Arg Phe Leu Asp Asn Glu Glu Gly Glu Met Leu Lys
65                  70                  75                  80

Glu Glu Asp Met Asp Phe Ser Glu Glu Ile Pro Val Ser Phe Asp Ala
                85                  90                  95

Arg Asp Lys Trp Pro Lys Cys Thr Ser Ile Gly Phe Ile Arg Asp Gln
            100                 105                 110

Ser His Cys Gly Ser Cys Trp Ala Val Ser Ser Ala Glu Thr Met Ser
        115                 120                 125

Asp Arg Leu Cys Val Gln Ser Asn Gly Thr Ile Lys Val Leu Leu Ser
    130                 135                 140

Asp Thr Asp Ile Leu Ala Cys Cys Pro Asn Cys Gly Ala Gly Cys Gly
145                 150                 155                 160

Gly Gly His Thr Ile Arg Ala Trp Glu Tyr Phe Lys Asn Thr Gly Val
                165                 170                 175

Cys Thr Gly Gly Leu Tyr Gly Thr Lys Asp Ser Cys Lys Pro Tyr Ala
            180                 185                 190

Phe Tyr Pro Cys Lys Asp Glu Ser Tyr Gly Lys Cys Pro Lys Asp Ser
        195                 200                 205

Phe Pro Thr Pro Lys Cys Arg Lys Ile Cys Gln Tyr Lys Tyr Ser Lys
    210                 215                 220

Lys Tyr Ala Asp Asp Lys Tyr Tyr Ala Asn Ser Ala Tyr Arg Ile Pro
225                 230                 235                 240

Gln Asn Glu Thr Trp Ile Lys Leu Glu Ile Met Arg Asn Gly Pro Val
                245                 250                 255

Thr Ala Ser Phe Arg Ile Tyr Pro Asp Phe Gly Phe Tyr Glu Lys Gly
            260                 265                 270

Val Tyr Val Thr Ser Gly Gly Arg Glu Leu Gly Gly His Ala Ile Lys
        275                 280                 285

Ile Ile Gly Trp Gly Thr Glu Lys Val Asn Gly Thr Asp Leu Pro Tyr
    290                 295                 300

Trp Leu Ile Ala Asn Ser Trp Gly Thr Asp Trp Gly Glu Asn Asn Gly
305                 310                 315                 320

Tyr Phe Arg Ile Leu Arg Gly Gln Asn His Cys Gln Ile Glu Gln Lys
                325                 330                 335

Val Ile Ala Gly Met Ile Lys Val Pro Gln Pro Lys Ser Ala Gly Pro
            340                 345                 350

Pro Leu Gln Pro Asn Pro Ser Ser
        355                 360
```

<210> SEQ ID NO 87

-continued

<211> LENGTH: 1181
<212> TYPE: DNA
<213> ORGANISM: Necator americanus

<400> SEQUENCE: 87
tcgttgaggc gttatttcaa gcttctctcg cctcgatttc agattctcca attgtttcag 60
tgaatcgtgg aacagtcaat ctcacttttg tgagatccaa tgaaagctaa ttttgcgttg 120
gtcgtcgtcc ttctggcaat aaaccagtta tatgcagatg agctgcttca caaacaagag 180
tccgaacacg gacttagtgg ccaagcgctc gttgactacg ttaattcgca ccaatcactt 240
ttcaaaacag aatattcgcc aaccaatgaa caattcgtta aagcccgtat aatggacata 300
aagtatatga ctgaggctag ccacaaatat ccaagaaagg gcattaatct gaacgttgaa 360
ctccctgaaa ggtttgacgc acgtgaaaaa tggccacatt gcgcctccat cggtctcatt 420
cgcgatcact ctgcttgcgg atcgtgttgg gctgtatcgg cagcgtcggt tatgtcagat 480
cgactctgta tccagacgaa cggcacaaac cagaagatcc tttcgtcggc ggacatcctt 540
gcgtgttgtg gagaagactg tggctcagga tgcgaaggcg gttatccgat tcaggcgtac 600
ttctacctgg aaaatactgg agtatgtagt ggaggagagt atcgagaaaa gaatgtatgc 660
aaaccatatc ccttttatcc gtgtgacgga aactatggac catgccccaa ggagggtgcg 720
ttcgacactc caaagtgtcg gaaaatatgt cagttccgat atcctgttcc atacgaagaa 780
gataaagtgt ttggaaaaaa ttcacacatc cttctgcaag acaacgaggc aagaatcaga 840
caggaaattt tcataaacgg accagtggga gctaattttt acgttttcga agactttata 900
cactacaagg aagggattta taagcagaca tatgggaaat ggataggagt acatgcaatc 960
aaacttattg gttggggcac agaaaatgga acagattatt ggttggttgc taactcgtac 1020
aactacgact ggggagagaa tggcaccttc cgcattcttc gtggaactaa tcactgtttg 1080
atagaatcac aagtgatcgc aacggagatg attgtatgaa tgtctaatga acgattggtc 1140
gcatgccgat ctctgaagta aaatgtgtta atcaaaaaaa a 1181

<210> SEQ ID NO 88
<211> LENGTH: 339
<212> TYPE: PRT
<213> ORGANISM: Necator americanus

<400> SEQUENCE: 88

Met Lys Ala Asn Phe Ala Leu Val Val Val Leu Leu Ala Ile Asn Gln
1 5 10 15

Leu Tyr Ala Asp Glu Leu Leu His Lys Gln Glu Ser Glu His Gly Leu
20 25 30

Ser Gly Gln Ala Leu Val Asp Tyr Val Asn Ser His Gln Ser Leu Phe
35 40 45

Lys Thr Glu Tyr Ser Pro Thr Asn Glu Gln Phe Val Lys Ala Arg Ile
50 55 60

Met Asp Ile Lys Tyr Met Thr Glu Ala Ser His Lys Tyr Pro Arg Lys
65 70 75 80

Gly Ile Asn Leu Asn Val Glu Leu Pro Glu Arg Phe Asp Ala Arg Glu
85 90 95

Lys Trp Pro His Cys Ala Ser Ile Gly Leu Ile Arg Asp His Ser Ala
100 105 110

Cys Gly Ser Cys Trp Ala Val Ser Ala Ala Ser Val Met Ser Asp Arg
115 120 125

Leu Cys Ile Gln Thr Asn Gly Thr Asn Gln Lys Ile Leu Ser Ser Ala

-continued

```
    130                 135                 140

Asp Ile Leu Ala Cys Cys Gly Glu Asp Cys Gly Ser Gly Cys Glu Gly
145                 150                 155                 160

Gly Tyr Pro Ile Gln Ala Tyr Phe Tyr Leu Glu Asn Thr Gly Val Cys
                165                 170                 175

Ser Gly Gly Glu Tyr Arg Glu Lys Asn Val Cys Lys Pro Tyr Pro Phe
            180                 185                 190

Tyr Pro Cys Asp Gly Asn Tyr Gly Pro Cys Pro Lys Glu Gly Ala Phe
        195                 200                 205

Asp Thr Pro Lys Cys Arg Lys Ile Cys Gln Phe Arg Tyr Pro Val Pro
    210                 215                 220

Tyr Glu Glu Asp Lys Val Phe Gly Lys Asn Ser His Ile Leu Leu Gln
225                 230                 235                 240

Asp Asn Glu Ala Arg Ile Arg Gln Glu Ile Phe Ile Asn Gly Pro Val
                245                 250                 255

Gly Ala Asn Phe Tyr Val Phe Glu Asp Phe Ile His Tyr Lys Glu Gly
            260                 265                 270

Ile Tyr Lys Gln Thr Tyr Gly Lys Trp Ile Gly Val His Ala Ile Lys
        275                 280                 285

Leu Ile Gly Trp Gly Thr Glu Asn Gly Thr Asp Tyr Trp Leu Val Ala
    290                 295                 300

Asn Ser Tyr Asn Tyr Asp Trp Gly Glu Asn Gly Thr Phe Arg Ile Leu
305                 310                 315                 320

Arg Gly Thr Asn His Cys Leu Ile Glu Ser Gln Val Ile Ala Thr Glu
                325                 330                 335

Met Ile Val


<210> SEQ ID NO 89
<211> LENGTH: 1236
<212> TYPE: DNA
<213> ORGANISM: Necator americanus

<400> SEQUENCE: 89

tagataataa tctttttgca cgtcagagaa tttctttgat aaaaccacaa ttaaacaatc     60

tcagcgctgt aaacacgtgc aaaactactc gttcatttct cttcactttc cctccaaaac    120

caaacattca agagaagcat gataaccatc attaccctat tgcttatcgc ttctacagtg    180

aagtcactaa cagtggagga gtacttggcc cgaccagtgc cggaatatgc cacaaaactg    240

acaggacaag cctacgttga ctatgttaat cagcatcaat cattctacaa ggctgaatat    300

tccccgctgg ttgaacagta tgccaaagct gtgatgagat ctgagtttat gacgaagccg    360

aaccaaaatt atgtggtgaa ggacgtagat ctaaacatca atcttccaga aaccttcgac    420

gcaagggaaa aatggccaaa ctgcacatca ataaggacaa ttcgcgatca gtccaattgt    480

ggatcatgtt gggcagtatc agcggcgtcg gtaatgtcag atcgtttatg catacagtcg    540

aacggcacaa tacagtcatg ggcttctgat acggatattc tatcatgttg ctggaattgc    600

ggaatgggat gcgatggagg tagaccgttt gcggcgttct ttttcgcgat agacaatggt    660

gtatgcactg gaggaccttt cagagagcca aacgtgtgca aaccatacgc tttctatcca    720

tgcggtcgcc accaaaacca gaaatacttc ggaccttgtc caaaagagct ctggcccact    780

ccaaaatgtc ggaaaatgtg tcaactaaaa tataatgtgg cctacaaaga cgataaaatt    840

tacgggaatg atgcatacag tctccctaac aatgagacac gaatcatgca agaaattttc    900

acaaatggac ctgtagtggg atcattcagc gtgtttgctg actttgcaat ttataagaaa    960
```

-continued

```
ggagtatatg tgagtaatgg aattcagcag aatggggctc atgcagtcaa aattattggt   1020

tggggtgtgc aggatggact aaaatattgg ttgattgcta attcctggaa caatgactgg   1080

ggagacgaag gctatgtccg gttccttcgt ggagataacc actgtggaat tgaatcaagg   1140

gtggtgacag gaactatgaa agtgtaaaac aataattagt cttttcctga cgatttcaaa   1200

taaaatcttt gccactaaaa aaaaaaaaaa aaaaaa                             1236


<210> SEQ ID NO 90
<211> LENGTH: 342
<212> TYPE: PRT
<213> ORGANISM: Necator americanus

<400> SEQUENCE: 90

Met Ile Thr Ile Ile Thr Leu Leu Leu Ile Ala Ser Thr Val Lys Ser
1               5                   10                  15

Leu Thr Val Glu Glu Tyr Leu Ala Arg Pro Val Pro Glu Tyr Ala Thr
            20                  25                  30

Lys Leu Thr Gly Gln Ala Tyr Val Asp Tyr Val Asn Gln His Gln Ser
        35                  40                  45

Phe Tyr Lys Ala Glu Tyr Ser Pro Leu Val Glu Gln Tyr Ala Lys Ala
    50                  55                  60

Val Met Arg Ser Glu Phe Met Thr Lys Pro Asn Gln Asn Tyr Val Val
65                  70                  75                  80

Lys Asp Val Asp Leu Asn Ile Asn Leu Pro Glu Thr Phe Asp Ala Arg
                85                  90                  95

Glu Lys Trp Pro Asn Cys Thr Ser Ile Arg Thr Ile Arg Asp Gln Ser
            100                 105                 110

Asn Cys Gly Ser Cys Trp Ala Val Ser Ala Ala Ser Val Met Ser Asp
        115                 120                 125

Arg Leu Cys Ile Gln Ser Asn Gly Thr Ile Gln Ser Trp Ala Ser Asp
    130                 135                 140

Thr Asp Ile Leu Ser Cys Cys Trp Asn Cys Gly Met Gly Cys Asp Gly
145                 150                 155                 160

Gly Arg Pro Phe Ala Ala Phe Phe Phe Ala Ile Asp Asn Gly Val Cys
                165                 170                 175

Thr Gly Gly Pro Phe Arg Glu Pro Asn Val Cys Lys Pro Tyr Ala Phe
            180                 185                 190

Tyr Pro Cys Gly Arg His Gln Asn Gln Lys Tyr Phe Gly Pro Cys Pro
        195                 200                 205

Lys Glu Leu Trp Pro Thr Pro Lys Cys Arg Lys Met Cys Gln Leu Lys
    210                 215                 220

Tyr Asn Val Ala Tyr Lys Asp Asp Lys Ile Tyr Gly Asn Asp Ala Tyr
225                 230                 235                 240

Ser Leu Pro Asn Asn Glu Thr Arg Ile Met Gln Glu Ile Phe Thr Asn
                245                 250                 255

Gly Pro Val Val Gly Ser Phe Ser Val Phe Ala Asp Phe Ala Ile Tyr
            260                 265                 270

Lys Lys Gly Val Tyr Val Ser Asn Gly Ile Gln Gln Asn Gly Ala His
        275                 280                 285

Ala Val Lys Ile Ile Gly Trp Gly Val Gln Asp Gly Leu Lys Tyr Trp
    290                 295                 300

Leu Ile Ala Asn Ser Trp Asn Asn Asp Trp Gly Asp Glu Gly Tyr Val
305                 310                 315                 320
```

-continued

```
Arg Phe Leu Arg Gly Asp Asn His Cys Gly Ile Glu Ser Arg Val Val
                325                 330                 335

Thr Gly Thr Met Lys Val
            340


<210> SEQ ID NO 91
<211> LENGTH: 2709
<212> TYPE: DNA
<213> ORGANISM: Necator americanus

<400> SEQUENCE: 91

attttcaatg accaagctcc tcgtaagcac cgccgggttg actggcgtcg tcgcggccct     60

cttcatcact tctctggttt tcagcatcct tacatggaca cgtgtaaaaa atgacaacga    120

taacccacca agacctaagg agccactcag tcgtccagta gtgcaattgt cttcatctat    180

tcagactacc gtaaccgaaa atgtagtgac agaacccata gtgactgtgc cgacagtgtc    240

acgcaccaga gtttcggcaa aaacaatatc accgagaagt tccgcgacaa cgtcaactcg    300

aacgcttcga actctcacca caccgaaatt cgtcgcaacg gaggccgcac cgcgacgtaa    360

tcgtacgata atgtgtccga actatggagt ttcagacaac tcatacgcat accaggaagc    420

agcatcgttc attcttagtg gcctcgacga acgtgtcaat ccgtgcgaag atttctacgc    480

tttcacttgt aacaagtttc taaaagatca taaggctgaa gaacatgggg tcagtcgtta    540

cggagctata aaagaacttc aagatgcagt gaacacagaa atagttgacg ccctcttcga    600

tgtggatgtg aacgataaga agcggtcaga aacagagaga ataacgaaag cgcttctcca    660

cgactgcgtt taccacatct cgcctaatgt tccgaccgaa acaatcatta atttccttga    720

agaaattgca agaatgtttg gaggtatacc gttcctcaac cacactctaa aagaagattt    780

tgacgttttc gctgcaatgg gagaagtcga acaaaatcac gcgatgggta cgcttttcag    840

cgcaatggtt tcggtcgact acaagaagat caaacagaat tcactgttct tatcacagcc    900

tcggcttccg atgccaagag aattctacgt gcttccacag tttacgatga agcttaaaaa    960

acgtggactt caaattgctg acgttttaaa gaaatttgcc gagaagatct tagaagaacc   1020

cgataagtat agggatatga tagaaaaggc tgcgcaagat gttgtggaac tagagaggag   1080

gatcgctctg gcgtcttggg cagatgccga aatgagaaac tacgcacaac agtacaatcc   1140

ctacgatctg cccactttga aaaaggcgta tccatctgtc aaatgggaga gctatctacg   1200

tagccttttg tcaaccgtcg gtccagtcga tttttctggt ccacataaac ggctcataat   1260

ctcgcaaccg tcgtattttg ggtggttgaa tgctctcttc aatggtaacg ttgttgacga   1320

aaatacgata gtaaactata taatcacgca cttaatcttc gaagatgcgg aattccttgg   1380

tggtatattt aaagaatctg cagaggattt aaattacgtc cggtatgcgc agagaagtgg   1440

cagaggagtt gcccgagttg gaaggcaact tatgcatcaa agagatacca ggggcgaccc   1500

gaatatcccg tgcatgaatt tcatcatgac gtacatgccg tatggacctg gttatgtcta   1560

tgtaagaagc aaacagcaga gaaacgatgt tcaagcagac attaggaaac aaacagaact   1620

cgtcatcgag agctttctga atatgacttc gggcctgaag tggatgtctt cggattcgaa   1680

agaaaaagct agacagaagg ctaagggtat ggtgaggaac tacggatggc ctcaaaaact   1740

cttcggagac tttaaaagca gcgaagagat tgatgaatat cacaagaagg attatgctga   1800

aatccttgag cttaccaaga cggagaggag cagccttcga tattaccgta tgcgccgggt   1860

gctgattaaa ggatattcaa atcgcgagtc actgcgttta cttttgcagg atgcagacag   1920

gtccaatttc ctcctatcac cagcgttagt gagcgcctgg taccagccgg aaaggaactc   1980
```

-continued

```
tatcactttc ccttacgcga gcttcaatcc accgtactat agctatgaat atcctcaagc   2040

ttacaactat ggtggtcagg gtggaactgc cggtcatgag ctagtccatg gatttgacga   2100

ccaaggagtg cagttcggtc ccgatggaag tctaagtagg tgtacgtggt atgattgtgg   2160

atggatggat aaaagatcaa aagatggttt caacgacatg gcccaatgtg ttgtaacaca   2220

ttatagcact ttctgctgcc cagaacagga aggtaatata cactgcgcaa atggtgcaac   2280

cacacaaggg gaaaatattg ctgatattgg aggtgaacat gctgcataca tagcatatcg   2340

agagtacatc aaatcactag gacatgaaga gaaaagattg ccaggattag aacgatacac   2400

accaaaccag atcttttgga ttacatatgg atactcatgg tgcaggagcg taacagagga   2460

ataccttatt agtcaacttc tcaccgaccc ccacgcacca agtgcttgcc gcactaacca   2520

agtagtccaa agtatccctg cgtttggacg ggatttcggg tgctcattag gagacagaat   2580

gtatcctgca ccagagcagc gatgttcagt ttgggttcaa gagtaaatgg tcggacgaaa   2640

ctgtcggatt ttatgtttca gtcggattat aacactatca actaaacatt tcgttcaaaa   2700

aaaaaaaaa                                                           2709
```

```
<210> SEQ ID NO 92
<211> LENGTH: 878
<212> TYPE: PRT
<213> ORGANISM: Necator americanus

<400> SEQUENCE: 92

Met Thr Lys Leu Leu Val Ser Thr Ala Gly Leu Thr Gly Val Val Ala
1               5                   10                  15

Ala Leu Phe Ile Thr Ser Leu Val Phe Ser Ile Leu Thr Trp Thr Arg
            20                  25                  30

Val Lys Asn Asp Asn Asp Asn Pro Pro Arg Pro Lys Glu Pro Leu Ser
        35                  40                  45

Arg Pro Val Val Gln Leu Ser Ser Ser Ile Gln Thr Thr Val Thr Glu
    50                  55                  60

Asn Val Val Thr Glu Pro Ile Val Thr Val Pro Thr Val Ser Arg Thr
65                  70                  75                  80

Arg Val Ser Ala Lys Thr Ile Ser Pro Arg Ser Ser Ala Thr Thr Ser
                85                  90                  95

Thr Arg Thr Leu Arg Thr Leu Thr Thr Pro Lys Phe Val Ala Thr Glu
            100                 105                 110

Ala Ala Pro Arg Arg Asn Arg Thr Ile Met Cys Pro Asn Tyr Gly Val
        115                 120                 125

Ser Asp Asn Ser Tyr Ala Tyr Gln Glu Ala Ala Ser Phe Ile Leu Ser
    130                 135                 140

Gly Leu Asp Glu Arg Val Asn Pro Cys Glu Asp Phe Tyr Ala Phe Thr
145                 150                 155                 160

Cys Asn Lys Phe Leu Lys Asp His Lys Ala Glu Glu His Gly Val Ser
                165                 170                 175

Arg Tyr Gly Ala Ile Lys Glu Leu Gln Asp Ala Val Asn Thr Glu Ile
            180                 185                 190

Val Asp Ala Leu Phe Asp Val Asp Val Asn Asp Lys Lys Arg Ser Glu
        195                 200                 205

Thr Glu Arg Ile Thr Lys Ala Leu Leu His Asp Cys Val Tyr His Ile
    210                 215                 220

Ser Pro Asn Val Pro Thr Glu Thr Ile Ile Asn Phe Leu Glu Glu Ile
225                 230                 235                 240
```

-continued

```
Ala Arg Met Phe Gly Gly Ile Pro Phe Leu Asn His Thr Leu Lys Glu
                245                 250                 255

Asp Phe Asp Val Phe Ala Ala Met Gly Glu Val Glu Gln Asn His Ala
            260                 265                 270

Met Gly Thr Leu Phe Ser Ala Met Val Ser Val Asp Tyr Lys Lys Ile
        275                 280                 285

Lys Gln Asn Ser Leu Phe Leu Ser Gln Pro Arg Leu Pro Met Pro Arg
    290                 295                 300

Glu Phe Tyr Val Leu Pro Gln Phe Thr Met Lys Leu Lys Lys Arg Gly
305                 310                 315                 320

Leu Gln Ile Ala Asp Val Leu Lys Lys Phe Ala Glu Lys Ile Leu Glu
                325                 330                 335

Glu Pro Asp Lys Tyr Arg Asp Met Ile Glu Lys Ala Ala Gln Asp Val
            340                 345                 350

Val Glu Leu Glu Arg Arg Ile Ala Leu Ala Ser Trp Ala Asp Ala Glu
        355                 360                 365

Met Arg Asn Tyr Ala Gln Gln Tyr Asn Pro Tyr Asp Leu Pro Thr Leu
    370                 375                 380

Lys Lys Ala Tyr Pro Ser Val Lys Trp Glu Ser Tyr Leu Arg Ser Leu
385                 390                 395                 400

Leu Ser Thr Val Gly Pro Val Asp Phe Ser Gly Pro His Lys Arg Leu
                405                 410                 415

Ile Ile Ser Gln Pro Ser Tyr Phe Gly Trp Leu Asn Ala Leu Phe Asn
            420                 425                 430

Gly Asn Val Val Asp Glu Asn Thr Ile Val Asn Tyr Ile Ile Thr His
        435                 440                 445

Leu Ile Phe Glu Asp Ala Glu Phe Leu Gly Gly Ile Phe Lys Glu Ser
    450                 455                 460

Ala Glu Asp Leu Asn Tyr Val Arg Tyr Ala Gln Arg Ser Gly Arg Gly
465                 470                 475                 480

Val Ala Arg Val Gly Arg Gln Leu Met His Gln Arg Asp Thr Arg Gly
                485                 490                 495

Asp Pro Asn Ile Pro Cys Met Asn Phe Ile Met Thr Tyr Met Pro Tyr
            500                 505                 510

Gly Pro Gly Tyr Val Tyr Val Arg Ser Lys Gln Gln Arg Asn Asp Val
        515                 520                 525

Gln Ala Asp Ile Arg Lys Gln Thr Glu Leu Val Ile Glu Ser Phe Leu
    530                 535                 540

Asn Met Thr Ser Gly Leu Lys Trp Met Ser Ser Asp Ser Lys Glu Lys
545                 550                 555                 560

Ala Arg Gln Lys Ala Lys Gly Met Val Arg Asn Tyr Gly Trp Pro Gln
                565                 570                 575

Lys Leu Phe Gly Asp Phe Lys Ser Ser Glu Glu Ile Asp Glu Tyr His
            580                 585                 590

Lys Lys Asp Tyr Ala Glu Ile Leu Glu Leu Thr Lys Thr Glu Arg Ser
        595                 600                 605

Ser Leu Arg Tyr Tyr Arg Met Arg Arg Val Leu Ile Lys Gly Tyr Ser
    610                 615                 620

Asn Arg Glu Ser Leu Arg Leu Leu Leu Gln Asp Ala Asp Arg Ser Asn
625                 630                 635                 640

Phe Leu Leu Ser Pro Ala Leu Val Ser Ala Trp Tyr Gln Pro Glu Arg
                645                 650                 655
```

-continued

```
Asn Ser Ile Thr Phe Pro Tyr Ala Ser Phe Asn Pro Pro Tyr Tyr Ser
            660                 665                 670

Tyr Glu Tyr Pro Gln Ala Tyr Asn Tyr Gly Gly Gln Gly Gly Thr Ala
        675                 680                 685

Gly His Glu Leu Val His Gly Phe Asp Asp Gln Gly Val Gln Phe Gly
    690                 695                 700

Pro Asp Gly Ser Leu Ser Arg Cys Thr Ser Glu Gln Ile Asp Asn Trp
705                 710                 715                 720

Tyr Asp Cys Gly Trp Met Asp Lys Arg Ser Lys Asp Gly Phe Asn Asp
                725                 730                 735

Met Ala Gln Cys Val Val Thr His Tyr Ser Thr Phe Cys Cys Pro Glu
            740                 745                 750

Gln Glu Gly Asn Ile His Cys Ala Asn Gly Ala Thr Thr Gln Gly Glu
        755                 760                 765

Asn Ile Ala Asp Ile Gly Gly Glu His Ala Ala Tyr Ile Ala Tyr Arg
    770                 775                 780

Glu Tyr Ile Lys Ser Leu Gly His Glu Glu Lys Arg Leu Pro Gly Leu
785                 790                 795                 800

Glu Arg Tyr Thr Pro Asn Gln Ile Phe Trp Ile Thr Tyr Gly Tyr Ser
                805                 810                 815

Trp Cys Arg Ser Val Thr Glu Glu Tyr Leu Ile Ser Gln Leu Leu Thr
            820                 825                 830

Asp Pro His Ala Pro Ser Ala Cys Arg Thr Asn Gln Val Val Gln Ser
        835                 840                 845

Ile Pro Ala Phe Gly Arg Asp Phe Gly Cys Ser Leu Gly Asp Arg Met
    850                 855                 860

Tyr Pro Ala Pro Glu Gln Arg Cys Ser Val Trp Val Gln Glu
865                 870                 875
```

<210> SEQ ID NO 93
<211> LENGTH: 551
<212> TYPE: DNA
<213> ORGANISM: Ancylostoma caninum

<400> SEQUENCE: 93

```
gaaaagccta cgcagtcatg ctcaaactcg tcgccctagc ctgcttagct gcgatctgcc     60

tcgctcaggg tggacccgaa ggaccccctc ctttcctgaa gagtgctccc cccgagaagg    120

tgaaggaatt cgacgctctt ttcgccgatg ctggaggtct gactgatgcc cagatcgacg    180

ctaaggtcaa gggatggatc ggaaagcaga gtcaggatat ccagaacgca ttcaatgcct    240

tcgagagtga ggtgaaagcc gcccagcaac agggtgagca agctcaccag gctgctgtcg    300

ccaaattcag cgctgaagcc aaggctgccg acgccaagct caccgctatc gccaatgacg    360

cctccaagac gaatgcacag aagggagccg agatcgacgc cgttctcaag ggtcttccac    420

aaaaagtccg tgatgaaatc gagaatgcaa tgaagggata agagggcgtt gttttgtata    480

tatgaaccga taaatatgca aaataaatat ctccccttca aaaaaaaaaa aaaaaaaaaa    540

aaaaaaaaaa a                                                         551
```

<210> SEQ ID NO 94
<211> LENGTH: 147
<212> TYPE: PRT
<213> ORGANISM: Ancylostoma caninum

<400> SEQUENCE: 94

```
Met Leu Lys Leu Val Ala Leu Ala Cys Leu Ala Ala Ile Cys Leu Ala
```

-continued

```
1               5                   10                  15

Gln Gly Gly Pro Glu Gly Pro Pro Pro Phe Leu Lys Ser Ala Pro Pro
            20                  25                  30

Glu Lys Val Lys Glu Phe Asp Ala Leu Phe Ala Asp Ala Gly Gly Leu
        35                  40                  45

Thr Asp Ala Gln Ile Asp Ala Lys Val Lys Gly Trp Ile Gly Lys Gln
    50                  55                  60

Ser Gln Asp Ile Gln Asn Ala Phe Asn Ala Phe Glu Ser Glu Val Lys
65                  70                  75                  80

Ala Ala Gln Gln Gln Gly Glu Gln Ala His Gln Ala Ala Val Ala Lys
                85                  90                  95

Phe Ser Ala Glu Ala Lys Ala Ala Asp Ala Lys Leu Thr Ala Ile Ala
            100                 105                 110

Asn Asp Ala Ser Lys Thr Asn Ala Gln Lys Gly Ala Glu Ile Asp Ala
        115                 120                 125

Val Leu Lys Gly Leu Pro Gln Lys Val Arg Asp Glu Ile Glu Asn Ala
    130                 135                 140

Met Lys Gly
145


<210> SEQ ID NO 95
<211> LENGTH: 482
<212> TYPE: DNA
<213> ORGANISM: Ancylostoma ceylanicum

<400> SEQUENCE: 95

cagtcatgct caaactcgtc gccctagcct gcttagctgc tatctgcctc gctcagggtg      60

gacccgaggg accccctcct ttcctgaaga gtgctccccc cgagaaagtg aaggaattcg     120

acgctctttt cgccgatgct ggaggtctga ctgatgccca gatcgacgct aaggtcaagg     180

gatggatcgg aaagcagagc caggacatcc agaatgcatt caatgccttc gagagtgagg     240

tgaaagccgc ccagcaacag ggtgagcaag ctcaccaggc tgctgtcgcc aaattcagcg     300

ctgaggccaa ggctgccgac gccaagctca ccgctatcgc caatgacgcc tccaagacga     360

atgcgcagaa gggagccgag atcgacgccg ttctcaaggg tcttccacaa aaagtccgtg     420

atgaaatcga gaatgcaatg aagggataag agggcgttgt tttgtatata tgaaccgata     480

aa                                                                    482


<210> SEQ ID NO 96
<211> LENGTH: 147
<212> TYPE: PRT
<213> ORGANISM: Ancylostoma ceylanicum

<400> SEQUENCE: 96

Met Leu Lys Leu Val Ala Leu Ala Cys Leu Ala Ala Ile Cys Leu Ala
1               5                   10                  15

Gln Gly Gly Pro Glu Gly Pro Pro Pro Phe Leu Lys Ser Ala Pro Pro
            20                  25                  30

Glu Lys Val Lys Glu Phe Asp Ala Leu Phe Ala Asp Ala Gly Gly Leu
        35                  40                  45

Thr Asp Ala Gln Ile Asp Ala Lys Val Lys Gly Trp Ile Gly Lys Gln
    50                  55                  60

Ser Gln Asp Ile Gln Asn Ala Phe Asn Ala Phe Glu Ser Glu Val Lys
65                  70                  75                  80

Ala Ala Gln Gln Gln Gly Glu Gln Ala His Gln Ala Ala Val Ala Lys
```

-continued

```
                85                  90                  95

Phe Ser Ala Glu Ala Lys Ala Ala Asp Ala Lys Leu Thr Ala Ile Ala
            100                 105                 110

Asn Asp Ala Ser Lys Thr Asn Ala Gln Lys Gly Ala Glu Ile Asp Ala
        115                 120                 125

Val Leu Lys Gly Leu Pro Gln Lys Val Arg Asp Glu Ile Glu Asn Ala
    130                 135                 140

Met Lys Gly
145


<210> SEQ ID NO 97
<211> LENGTH: 1093
<212> TYPE: DNA
<213> ORGANISM: Ancylostoma caninum

<400> SEQUENCE: 97

tttgagatgt ggattctcgc tgcattagtg gtaacggcac ttgccgcaaa accgactacg      60

gttgaggagt tccacgctca acctatagag gagcacgtta aagacctcag tggacaagct     120

tttgttgact acatcaacga gcatcaatct ttctataggg cggaatattc accagaggcg     180

gaagcgttcg tgaaagctcg gataatggac tcgaagtatt tagtggaacc taagaaagaa     240

gaagtgctgg aggacgtata tggcaatgat ccgcctgcga gcttcgacgc tcgcacccac     300

tggcctgaat gcagatccat tggcaccatt cgtgaccagt catcatgcgg ttcatgttgg     360

gcagtatcct cagcggaagc catgtcggat gaaatatgtg ttcagtcgaa cagtacgata     420

agggtgatga tttccgactc agatatactc tcgtgctgtg gaatttcctg tggatatgga     480

tgccaaggtg gttggccgat cgaagcatac aaatggatgc aacgtgacgg tgttgttaca     540

ggtggaaaat acagacagaa gaaagtgtgc aagccgtacg ccttctatcc gtgtgggcac     600

caccaaaatg acccctacta tggaccttgc ccaggggggtt tatggcccac tccaaaatgt    660

cgaaagacgt gtcagcgaaa atacaacaag tcctaccaag aagacaagca ctttgcaacg     720

agggcctact acctcccgaa taatgaaagg aacatcaggc aagagattta caagaacgga     780

cctgtggtcg cagctttcag agtctaccag gacttcagtt attacaaaaa aggaatctat     840

gtgcacaagt ggggtggtca aacaggagca catgctgtca aagtcgttgg ttggggcaga     900

gaaaatgcaa cagattactg gctgattgcg aactcgtgga acactgactg gggagaaagc     960

ggctatttcc gtattgttcg tggaactaac gagtgcggta tcgaagcaca aatggtcggt    1020

ggagcgatga gagtgtgaaa tactcgacta tgacgccgtt ctttaatcgg ctatcgtaat    1080

gaatcattct gag                                                       1093


<210> SEQ ID NO 98
<211> LENGTH: 343
<212> TYPE: PRT
<213> ORGANISM: Ancylostoma caninum

<400> SEQUENCE: 98

Met Trp Ile Leu Ala Ala Leu Val Val Thr Ala Leu Ala Ala Lys Pro
1               5                   10                  15

Thr Thr Val Glu Glu Phe His Ala Gln Pro Ile Glu Glu His Val Lys
            20                  25                  30

Asp Leu Ser Gly Gln Ala Phe Val Asp Tyr Ile Asn Glu His Gln Ser
        35                  40                  45

Phe Tyr Arg Ala Glu Tyr Ser Pro Glu Ala Glu Ala Phe Val Lys Ala
    50                  55                  60
```

-continued

```
Arg Ile Met Asp Ser Lys Tyr Leu Val Glu Pro Lys Lys Glu Glu Val
65                  70                  75                  80

Leu Glu Asp Val Tyr Gly Asn Asp Pro Pro Ala Ser Phe Asp Ala Arg
                85                  90                  95

Thr His Trp Pro Glu Cys Arg Ser Ile Gly Thr Ile Arg Asp Gln Ser
            100                 105                 110

Ser Cys Gly Ser Cys Trp Ala Val Ser Ser Ala Glu Ala Met Ser Asp
        115                 120                 125

Glu Ile Cys Val Gln Ser Asn Ser Thr Ile Arg Val Met Ile Ser Asp
    130                 135                 140

Ser Asp Ile Leu Ser Cys Cys Gly Ile Ser Cys Gly Tyr Gly Cys Gln
145                 150                 155                 160

Gly Gly Trp Pro Ile Glu Ala Tyr Lys Trp Met Gln Arg Asp Gly Val
                165                 170                 175

Val Thr Gly Gly Lys Tyr Arg Gln Lys Lys Val Cys Lys Pro Tyr Ala
            180                 185                 190

Phe Tyr Pro Cys Gly His His Gln Asn Asp Pro Tyr Tyr Gly Pro Cys
        195                 200                 205

Pro Gly Gly Leu Trp Pro Thr Pro Lys Cys Arg Lys Thr Cys Gln Arg
    210                 215                 220

Lys Tyr Asn Lys Ser Tyr Gln Glu Asp Lys His Phe Ala Thr Arg Ala
225                 230                 235                 240

Tyr Tyr Leu Pro Asn Asn Glu Arg Asn Ile Arg Gln Glu Ile Tyr Lys
                245                 250                 255

Asn Gly Pro Val Val Ala Ala Phe Arg Val Tyr Gln Asp Phe Ser Tyr
            260                 265                 270

Tyr Lys Lys Gly Ile Tyr Val His Lys Trp Gly Gly Gln Thr Gly Ala
        275                 280                 285

His Ala Val Lys Val Val Gly Trp Gly Arg Glu Asn Ala Thr Asp Tyr
    290                 295                 300

Trp Leu Ile Ala Asn Ser Trp Asn Thr Asp Trp Gly Glu Ser Gly Tyr
305                 310                 315                 320

Phe Arg Ile Val Arg Gly Thr Asn Glu Cys Gly Ile Glu Ala Gln Met
                325                 330                 335

Val Gly Gly Ala Met Arg Val
            340
```

<210> SEQ ID NO 99
<211> LENGTH: 495
<212> TYPE: DNA
<213> ORGANISM: Ancylostoma caninum

<400> SEQUENCE: 99

```
tttaattacc caagtttgag cagcatgcca tacctcgcat tcattgtcgc actactagcc     60

tgtactgtta tgtcgggtca cggtcaaatg acgggaggat taacgaagca ggatcccaat    120

gatcctgaac acatggctag agcatggaag gccgcaaaag gcatcaatga ggacgcttct    180

aacgctggac cgtaccacat gattcctatt aagatcgtaa aggccgaatc tcaagttgtc    240

gctggagtta ggtacatatt tgaagtgctg ttcggcgaat ccacgtgtaa gaaaggacat    300

atggctgcaa ccgaactttc tgcctccaac tgtgagctga aagaaggagg aaaccgagct    360

ctatacaaag ttgagctttg ggagaagcca tgggaaaact tcgagcagtt caacgtggag    420

aagatccgaa atgttgccgc cggcgagcaa atctagccgc ttctttaaga cacctcactg    480
```

-continued cgccggcgtc tatat 495

<210> SEQ ID NO 100
<211> LENGTH: 143
<212> TYPE: PRT
<213> ORGANISM: Ancylostoma caninum

<400> SEQUENCE: 100

Met Pro Tyr Leu Ala Phe Ile Val Ala Leu Leu Ala Cys Thr Val Met
1               5                   10                  15

Ser Gly His Gly Gln Met Thr Gly Gly Leu Thr Lys Gln Asp Pro Asn
            20                  25                  30

Asp Pro Glu His Met Ala Arg Ala Trp Lys Ala Ala Lys Gly Ile Asn
        35                  40                  45

Glu Asp Ala Ser Asn Ala Gly Pro Tyr His Met Ile Pro Ile Lys Ile
    50                  55                  60

Val Lys Ala Glu Ser Gln Val Val Ala Gly Val Arg Tyr Ile Phe Glu
65                  70                  75                  80

Val Leu Phe Gly Glu Ser Thr Cys Lys Lys Gly His Met Ala Ala Thr
                85                  90                  95

Glu Leu Ser Ala Ser Asn Cys Glu Leu Lys Glu Gly Gly Asn Arg Ala
            100                 105                 110

Leu Tyr Lys Val Glu Leu Trp Glu Lys Pro Trp Glu Asn Phe Glu Gln
        115                 120                 125

Phe Asn Val Glu Lys Ile Arg Asn Val Ala Ala Gly Glu Gln Ile
    130                 135                 140

<210> SEQ ID NO 101
<211> LENGTH: 2540
<212> TYPE: DNA
<213> ORGANISM: Ancylostoma caninum

<400> SEQUENCE: 101
ttagttttgc aagggtttgg tgcaggaaac tgggatcaac ttcgagtttg ctaacgagac 60
tcttaaccga tcctcattca ccagcacctt atcgcgttct tggaacgctg cagaacttcc 120
ccgcatttaa agaagccttc aattgtccga aatcacctta cgcaccagat aaacactgta 180
acgtctgggt atcggagcta gatacatcac atggtgagcc caaggtaaaa acagagctga 240
atatagcggc gcctccacag atcactccga acgacaagga aaagtatgat gccgccaagg 300
tggccatcag tttctttcag gaatccgtca atacctctgt tgatccatgt gaagatttct 360
acaagtatgc ttgcggaaag taccaaaaag cggtctcctt ccactatgcc gacgctaaaa 420
acctcgtagc aatggctaac caattgacaa ataaggacta ccagaaagtt atcaagagct 480
caacagcatt aaccaaggag aaggcgttct tcgatgcgtg cgtagctgca acgaaagact 540
ctggtcacaa taatcagatc ctcatttcca ataattatct catgaaacga gtaaggaagt 600
tggctgacta ccttggagct gagtttacct atgcacttgg cggcagagtg gagcgactgc 660
ccaataaggt tcagctggca aacgctttgg gttacctctc ctttgaccag aacattcaaa 720
cgctggtgac acctcttgtc gacacatatt ggccagaccc gaataaagga tacacgatgt 780
tcctcgatca gaatactgca tatatgagca agactttcta ccacccggat gctttcaaaa 840
ccattaagga aaactatatt aattctgcga ctaaggtcat agaaacgttc gtaaaaactc 900
agaataaacc gattgatcct aaactcaagg ataaggtgag aggcctggtg gaatttgaac 960
aaatgatcgc gaacaagtac agcaccgatg atgacacacg ccgaatctac ttgcgatcat 1020

-continued

```
ggaatctcag aagcattagg gagctacaga accaatttgg tttcgttgat tggcaaacat   1080

atatgaagat ggttcccatg gttgcgcaaa acaaggtgca atctgcggat ttcagagttt   1140

ccgtcatgga gccgggtcag tacgccaaca tgagtcgtga ttatgctgga tttgacaaag   1200

aaaaactagt gaactacttg tttatgcgcc tgctgctatc taatgctcag tatttgccaa   1260

cctatgccag cagtttcaaa gagatgccgg aagaaccact agttcttgga cggaagcgac   1320

gcaacatcca tttctcaaaa tccgacaccc ttactgatac gcaagcgaat tgtgcaaagg   1380

tggcgaatga gctgatgatg tttgcgaatg gacgagtttt cgtcgactat gtgtatcccg   1440

acgagaaata caaggaccta ataaggagca gtgctggtgg tgtgatgcac aatgttatcc   1500

atgctttcca aagcatggtt gatcaacttg actggatgag cgaagcgaca aagagaaaag   1560

caatagaaaa gagcatgaat atcataacaa acatagcttt cccggattgg attatggaca   1620

acgcaaagtt ggacctgtat tacaaaagca tcaccttcga cccaaccaag gaaaactact   1680

acgatatttg gacaaagctt accatattca atatagaagc tcagtacaag cacttaacaa   1740

tggccacagc tgattacgaa gaattcctta tgccgccagg tattgttaat gcatggtatc   1800

agccggaatt gaatacgatc acattccccg ctggaatact tcgtcctcct tatttccatc   1860

ctgattggcc agcatcaatc aaatacggtg gaattggtct aatagcagga catgaactga   1920

ttcacggctt tgacgatcaa ggtgttcagt ggggtccaaa gggacacatc tcttacccag   1980

agaagaactg tattggatgg atggatgagc aatcaacgaa aggtttcaat cgcttggctc   2040

aatgtgtcat cgatgagtat agcacgttct gccctcttga caacaggaca tacacaccaa   2100

attgtgtgaa tggagcgcag acccaaggag agaacatcgc cgataatgga ggggtacacg   2160

cggcgttccg cgcttaccgt acacacatct ctctcaatgg accagatcca cagcttcctg   2220

acagactgtt cgggcagttc acacatgatc agctgttctt cttgaacttc gcacaggtgt   2280

ggtgcgagaa acgacgagtc gatgacagac tttaccagca gctcatggtt gaccccccact   2340

ctccagcgat gtaccgagtg ttcggtactc ttcagaacta tccggccttc agagccgcat   2400

tcaactgtcc gcttaattcg cgatacgctc ctaaggatca ttgcaatgtt tgggtgccga   2460

attatatgcc ataagaggaa gttcttcctt gaaaactacc tactcaacat aaataaagtc   2520

tgtgatttta aaaaaaaaaa                                               2540
```

<210> SEQ ID NO 102
<211> LENGTH: 823
<212> TYPE: PRT
<213> ORGANISM: Ancylostoma caninum

<400> SEQUENCE: 102

```
Ser Phe Ala Arg Val Trp Cys Arg Lys Leu Gly Ser Thr Ser Ser Leu
1               5                   10                  15

Leu Thr Arg Leu Leu Thr Asp Pro His Ser Pro Ala Pro Tyr Arg Val
            20                  25                  30

Leu Gly Thr Leu Gln Asn Phe Pro Ala Phe Lys Glu Ala Phe Asn Cys
        35                  40                  45

Pro Lys Ser Pro Tyr Ala Pro Asp Lys His Cys Asn Val Trp Val Ser
    50                  55                  60

Glu Leu Asp Thr Ser His Gly Glu Pro Lys Val Lys Thr Glu Leu Asn
65                  70                  75                  80

Ile Ala Ala Pro Pro Gln Ile Thr Pro Asn Asp Lys Glu Lys Tyr Asp
                85                  90                  95

Ala Ala Lys Val Ala Ile Ser Phe Phe Gln Glu Ser Val Asn Thr Ser
```

-continued

```
            100                 105                 110

Val Asp Pro Cys Glu Asp Phe Tyr Lys Tyr Ala Cys Gly Lys Tyr Gln
        115                 120                 125

Lys Ala Val Ser Phe His Tyr Ala Asp Ala Lys Asn Leu Val Ala Met
    130                 135                 140

Ala Asn Gln Leu Thr Asn Lys Asp Tyr Gln Lys Val Ile Lys Ser Ser
145                 150                 155                 160

Thr Ala Leu Thr Lys Glu Lys Ala Phe Phe Asp Ala Cys Val Ala Ala
                165                 170                 175

Thr Lys Asp Ser Gly His Asn Asn Gln Ile Leu Ile Ser Asn Asn Tyr
            180                 185                 190

Leu Met Lys Arg Val Arg Lys Leu Ala Asp Tyr Leu Gly Ala Glu Phe
        195                 200                 205

Thr Tyr Ala Leu Gly Gly Arg Val Glu Arg Leu Pro Asn Lys Val Gln
    210                 215                 220

Leu Ala Asn Ala Leu Gly Tyr Leu Ser Phe Asp Gln Asn Ile Gln Thr
225                 230                 235                 240

Leu Val Thr Pro Leu Val Asp Thr Tyr Trp Pro Asp Pro Asn Lys Gly
                245                 250                 255

Tyr Thr Met Phe Leu Asp Gln Asn Thr Ala Tyr Met Ser Lys Thr Phe
            260                 265                 270

Tyr His Pro Asp Ala Phe Lys Thr Ile Lys Glu Asn Tyr Ile Asn Ser
        275                 280                 285

Ala Thr Lys Val Ile Glu Thr Phe Val Lys Thr Gln Asn Lys Pro Ile
    290                 295                 300

Asp Pro Lys Leu Lys Asp Lys Val Arg Gly Leu Val Glu Phe Glu Gln
305                 310                 315                 320

Met Ile Ala Asn Lys Tyr Ser Thr Asp Asp Asp Thr Arg Arg Ile Tyr
                325                 330                 335

Leu Arg Ser Trp Asn Leu Arg Ser Ile Arg Glu Leu Gln Asn Gln Phe
            340                 345                 350

Gly Phe Val Asp Trp Gln Thr Tyr Met Lys Met Val Pro Met Val Ala
        355                 360                 365

Gln Asn Lys Val Gln Ser Ala Asp Phe Arg Val Ser Val Met Glu Pro
    370                 375                 380

Gly Gln Tyr Ala Asn Met Ser Arg Asp Tyr Ala Gly Phe Asp Lys Glu
385                 390                 395                 400

Lys Leu Val Asn Tyr Leu Phe Met Arg Leu Leu Leu Ser Asn Ala Gln
                405                 410                 415

Tyr Leu Pro Thr Tyr Ala Ser Ser Phe Lys Glu Met Pro Glu Glu Pro
            420                 425                 430

Leu Val Leu Gly Arg Lys Arg Arg Asn Ile His Phe Ser Lys Ser Asp
        435                 440                 445

Thr Leu Thr Asp Thr Gln Ala Asn Cys Ala Lys Val Ala Asn Glu Leu
    450                 455                 460

Met Met Phe Ala Asn Gly Arg Val Phe Val Asp Tyr Val Tyr Pro Asp
465                 470                 475                 480

Glu Lys Tyr Lys Asp Leu Ile Arg Ser Ser Ala Gly Gly Val Met His
                485                 490                 495

Asn Val Ile His Ala Phe Gln Ser Met Val Asp Gln Leu Asp Trp Met
            500                 505                 510

Ser Glu Ala Thr Lys Arg Lys Ala Ile Glu Lys Ser Met Asn Ile Ile
        515                 520                 525
```

-continued

```
Thr Asn Ile Ala Phe Pro Asp Trp Ile Met Asp Asn Ala Lys Leu Asp
    530                 535                 540

Leu Tyr Tyr Lys Ser Ile Thr Phe Asp Pro Thr Lys Glu Asn Tyr Tyr
545                 550                 555                 560

Asp Ile Trp Thr Lys Leu Thr Ile Phe Asn Ile Glu Ala Gln Tyr Lys
                565                 570                 575

His Leu Thr Met Ala Thr Ala Asp Tyr Glu Glu Phe Leu Met Pro Pro
            580                 585                 590

Gly Ile Val Asn Ala Trp Tyr Gln Pro Glu Leu Asn Thr Ile Thr Phe
        595                 600                 605

Pro Ala Gly Ile Leu Arg Pro Pro Tyr Phe His Pro Asp Trp Pro Ala
    610                 615                 620

Ser Ile Lys Tyr Gly Gly Ile Gly Leu Ile Ala Gly His Glu Leu Ile
625                 630                 635                 640

His Gly Phe Asp Asp Gln Gly Val Gln Trp Gly Pro Lys Gly His Ile
                645                 650                 655

Ser Tyr Pro Glu Lys Asn Cys Ile Gly Trp Met Asp Glu Gln Ser Thr
            660                 665                 670

Lys Gly Phe Asn Arg Leu Ala Gln Cys Val Ile Asp Glu Tyr Ser Thr
        675                 680                 685

Phe Cys Pro Leu Asp Asn Arg Thr Tyr Thr Pro Asn Cys Val Asn Gly
    690                 695                 700

Ala Gln Thr Gln Gly Glu Asn Ile Ala Asp Asn Gly Gly Val His Ala
705                 710                 715                 720

Ala Phe Arg Ala Tyr Arg Thr His Ile Ser Leu Asn Gly Pro Asp Pro
                725                 730                 735

Gln Leu Pro Asp Arg Leu Phe Gly Gln Phe Thr His Asp Gln Leu Phe
            740                 745                 750

Phe Leu Asn Phe Ala Gln Val Trp Cys Glu Lys Arg Arg Val Asp Asp
        755                 760                 765

Arg Leu Tyr Gln Gln Leu Met Val Asp Pro His Ser Pro Ala Met Tyr
    770                 775                 780

Arg Val Phe Gly Thr Leu Gln Asn Tyr Pro Ala Phe Arg Ala Ala Phe
785                 790                 795                 800

Asn Cys Pro Leu Asn Ser Arg Tyr Ala Pro Lys Asp His Cys Asn Val
                805                 810                 815

Trp Val Pro Asn Tyr Met Pro
            820
```

<210> SEQ ID NO 103
<211> LENGTH: 472
<212> TYPE: DNA
<213> ORGANISM: Ancylostoma caninum

<400> SEQUENCE: 103

```
acagatgaga tctctttgcc tgctgctcgc tgtggtgctt gtcgccgtcc acgcaaaaat      60

gcagaacgtc accgtcaagg ggaccaccat ctgcaacaag aagcgaatgg ccgatgtgac     120

ggtggaactg tgggagagag acaccctcga ccccaacgac ctcctcgact ccaagaagac     180

ctctagggaa ggcgagttcc tcgggaaagg tggtcagaac gaagtcggct cgattgagcc     240

attcctcaaa attacacaca cctgcaatgt caagaaaccg ggctgcaaga gaatcactga     300

gttcgacatc ccgaagtcga agatcgacac ggtctacgac atgacctacg tgacgctgga     360

tatcatttcc gcagtcgata aggagaagtg ctacatgaac gcgttgtttt ccacggcaat     420
```

-continued

```
attttgtata gacagatgaa cattccttcc gaaaaaaaaa aaaaaaaaaa aa           472
```

<210> SEQ ID NO 104
<211> LENGTH: 144
<212> TYPE: PRT
<213> ORGANISM: Ancylostoma caninum

<400> SEQUENCE: 104

```
Met Arg Ser Leu Cys Leu Leu Leu Ala Val Val Leu Val Ala Val His
1               5                   10                  15

Ala Lys Met Gln Asn Val Thr Val Lys Gly Thr Thr Ile Cys Asn Lys
            20                  25                  30

Lys Arg Met Ala Asp Val Thr Val Glu Leu Trp Glu Arg Asp Thr Leu
        35                  40                  45

Asp Pro Asn Asp Leu Leu Asp Ser Lys Lys Thr Ser Arg Glu Gly Glu
    50                  55                  60

Phe Leu Gly Lys Gly Gly Gln Asn Glu Val Gly Ser Ile Glu Pro Phe
65                  70                  75                  80

Leu Lys Ile Thr His Thr Cys Asn Val Lys Lys Pro Gly Cys Lys Arg
                85                  90                  95

Ile Thr Glu Phe Asp Ile Pro Lys Ser Lys Ile Asp Thr Val Tyr Asp
            100                 105                 110

Met Thr Tyr Val Thr Leu Asp Ile Ile Ser Ala Val Asp Lys Glu Lys
        115                 120                 125

Cys Tyr Met Asn Ala Leu Phe Ser Thr Ala Ile Phe Cys Ile Asp Arg
    130                 135                 140
```

<210> SEQ ID NO 105
<211> LENGTH: 1442
<212> TYPE: DNA
<213> ORGANISM: Ancylostoma ceylanicum

<400> SEQUENCE: 105

```
agtgccattg ccgagggatg gctcgccttg tactgttact cgcactattt accctggctg     60

tggccagcgt ccacaggagg acattccacc agccgcgtcg ttacgtgaag tcggtgtcgc    120

tttcgcgtca accaacactt cgtgaacgat tgctgggaac tggcagttgg gaggactacc    180

agaagcaacg ctatcactac cagaagaaac ttctggcaaa atatgcggca aacaaggcgt    240

cgaaactaca gtccaccaat gagattgacg agctccttcg taactatatg gatgcacaat    300

atttcggcac catccaaatc ggaactccag cgcagaattt cacagtgatt ttcgacaccg    360

gttcatccaa cctctgggtg ccgtccagga aatgcccatt ctacgacatc gcgtgcatgc    420

ttcaccaccg ctacgattct ggagcatcgt caacgtacaa ggaggatgga cgtaagatgg    480

ctattcaata tggaactggc tcaatgaagg gcttcatttc taaggataat gtctgcatcg    540

ccggaatttg tgctgtcgag caaccgtttg ccgaggcaac gagcgagcca ggcctcacgt    600

tcatcgctgc gaagttcgac ggaatccttg gcatggcctt ccctgaaatc tccgttctcg    660

gtgtaccacc agtattccac acgttcattg aacagaagaa agtgccgagc ccggtgttcg    720

ctttctggct caacagaaat cccgactcgg aactcggagg ggagatcacc ctcggtggaa    780

tggacccccg ccgatatgtt gagccgatca catggacccc agtaactcga cgaggatatt    840

ggcagttcaa gatggacaag gttcaaggag gatcaacgtc cattgcctgc cccaacggat    900

gccaggctat cgctgacact ggtacttcac tgattgccgg acctaaggct caagttgagg    960

ctatccagaa attcattggt gctgagccac ttatgaaggg agagtacatg attccctgcg   1020
```

-continued

```
acaaggtgcc ttccctcccg gagctgtcct tcgttatcga gggccggact ttcatcctca   1080

agggtgaaga ttacgtattg accgtgaaag ctggtggtaa atcgatctgc ctgtccggtt   1140

tcatgggaat ggacttcccg gagaggatcg gagagctgtg gattcttgga gacgtcttca   1200

ttggaaagta ctacactgtc ttcgatattg gccaagctcg tcttggattt gctcaggcta   1260

agtcagaaga tggctatccg gttggtcctg ctgttcgaag gtacaacaag ttctcggagg   1320

acagcgacag tgacgaggat gatgtattca ctctctaaat aacatgtatc cacaatttgc   1380

tctaatctcg atacgtgtac cgtgtctcac gtgtttccac ttttgataaa ctgattattc   1440

tg                                                                  1442
```

<210> SEQ ID NO 106
<211> LENGTH: 446
<212> TYPE: PRT
<213> ORGANISM: Ancylostoma ceylanicum

<400> SEQUENCE: 106

```
Met Ala Arg Leu Val Leu Leu Leu Ala Leu Phe Thr Leu Ala Val Ala
1               5                   10                  15

Ser Val His Arg Arg Thr Phe His Gln Pro Arg Arg Tyr Val Lys Ser
            20                  25                  30

Val Ser Leu Ser Arg Gln Pro Thr Leu Arg Glu Arg Leu Leu Gly Thr
        35                  40                  45

Gly Ser Trp Glu Asp Tyr Gln Lys Gln Arg Tyr His Tyr Gln Lys Lys
    50                  55                  60

Leu Leu Ala Lys Tyr Ala Ala Asn Lys Ala Ser Lys Leu Gln Ser Thr
65                  70                  75                  80

Asn Glu Ile Asp Glu Leu Leu Arg Asn Tyr Met Asp Ala Gln Tyr Phe
                85                  90                  95

Gly Thr Ile Gln Ile Gly Thr Pro Ala Gln Asn Phe Thr Val Ile Phe
            100                 105                 110

Asp Thr Gly Ser Ser Asn Leu Trp Val Pro Ser Arg Lys Cys Pro Phe
        115                 120                 125

Tyr Asp Ile Ala Cys Met Leu His His Arg Tyr Asp Ser Gly Ala Ser
    130                 135                 140

Ser Thr Tyr Lys Glu Asp Gly Arg Lys Met Ala Ile Gln Tyr Gly Thr
145                 150                 155                 160

Gly Ser Met Lys Gly Phe Ile Ser Lys Asp Asn Val Cys Ile Ala Gly
                165                 170                 175

Ile Cys Ala Val Glu Gln Pro Phe Ala Glu Ala Thr Ser Glu Pro Gly
            180                 185                 190

Leu Thr Phe Ile Ala Ala Lys Phe Asp Gly Ile Leu Gly Met Ala Phe
        195                 200                 205

Pro Glu Ile Ser Val Leu Gly Val Pro Pro Val Phe His Thr Phe Ile
    210                 215                 220

Glu Gln Lys Lys Val Pro Ser Pro Val Phe Ala Phe Trp Leu Asn Arg
225                 230                 235                 240

Asn Pro Asp Ser Glu Leu Gly Gly Glu Ile Thr Leu Gly Gly Met Asp
                245                 250                 255

Pro Arg Arg Tyr Val Glu Pro Ile Thr Trp Thr Pro Val Thr Arg Arg
            260                 265                 270

Gly Tyr Trp Gln Phe Lys Met Asp Lys Val Gln Gly Gly Ser Thr Ser
        275                 280                 285
```

-continued

```
Ile Ala Cys Pro Asn Gly Cys Gln Ala Ile Ala Asp Thr Gly Thr Ser
    290                 295                 300

Leu Ile Ala Gly Pro Lys Ala Gln Val Glu Ala Ile Gln Lys Phe Ile
305                 310                 315                 320

Gly Ala Glu Pro Leu Met Lys Gly Glu Tyr Met Ile Pro Cys Asp Lys
                325                 330                 335

Val Pro Ser Leu Pro Glu Leu Ser Phe Val Ile Glu Gly Arg Thr Phe
            340                 345                 350

Ile Leu Lys Gly Glu Asp Tyr Val Leu Thr Val Lys Ala Gly Gly Lys
        355                 360                 365

Ser Ile Cys Leu Ser Gly Phe Met Gly Met Asp Phe Pro Glu Arg Ile
    370                 375                 380

Gly Glu Leu Trp Ile Leu Gly Asp Val Phe Ile Gly Lys Tyr Tyr Thr
385                 390                 395                 400

Val Phe Asp Ile Gly Gln Ala Arg Leu Gly Phe Ala Gln Ala Lys Ser
                405                 410                 415

Glu Asp Gly Tyr Pro Val Gly Pro Ala Val Arg Arg Tyr Asn Lys Phe
            420                 425                 430

Ser Glu Asp Ser Asp Ser Asp Glu Asp Asp Val Phe Thr Leu
        435                 440                 445
```

<210> SEQ ID NO 107
<211> LENGTH: 582
<212> TYPE: DNA
<213> ORGANISM: Ancylostoma ceylanicum

<400> SEQUENCE: 107

```
ggtactgcag ggtttaatta cccaagtttg aggagcatgc catacctcgc attcattgtc     60

gcactactag cctgcactgt tatgtctggt cacggtcaaa tgacgggtgg attaacgaag    120

caggacccca atgatcctga gcacatggcg agagcatgga aggcggcgaa aggtatcaat    180

gaggatgcat ccaacgctgg accgtaccac atgattccca ttaagattgt caaggctgaa    240

tctcaagtcg tggctggggt tagatacata tttgaagtat tgttcggcga atcaacatgt    300

aagaaaggac atatggctgc aacagagctt tctgcctcca actgtgaact aaaagaagga    360

ggaaaccgag ctctgtataa agtggagctc tgggagaagc catgggagaa ctttgagcag    420

ttcaatgttg agaagatccg aaatgttgct gctggcgagc aaatctaacc tgcttcttta    480

agacacctca ctgaatattg aatattttgt atgtcatgta taatacgacg cgattttttt    540

tatctcacgt actttttca ctgtgacaat tgccttctct gc                       582
```

<210> SEQ ID NO 108
<211> LENGTH: 143
<212> TYPE: PRT
<213> ORGANISM: Ancylostoma ceylanicum

<400> SEQUENCE: 108

```
Met Pro Tyr Leu Ala Phe Ile Val Ala Leu Leu Ala Cys Thr Val Met
1               5                   10                  15

Ser Gly His Gly Gln Met Thr Gly Gly Leu Thr Lys Gln Asp Pro Asn
            20                  25                  30

Asp Pro Glu His Met Ala Arg Ala Trp Lys Ala Ala Lys Gly Ile Asn
        35                  40                  45

Glu Asp Ala Ser Asn Ala Gly Pro Tyr His Met Ile Pro Ile Lys Ile
    50                  55                  60

Val Lys Ala Glu Ser Gln Val Val Ala Gly Val Arg Tyr Ile Phe Glu
```

-continued

```
65                  70                  75                  80

Val Leu Phe Gly Glu Ser Thr Cys Lys Lys Gly His Met Ala Ala Thr
                85                  90                  95

Glu Leu Ser Ala Ser Asn Cys Glu Leu Lys Glu Gly Gly Asn Arg Ala
            100                 105                 110

Leu Tyr Lys Val Glu Leu Trp Glu Lys Pro Trp Glu Asn Phe Glu Gln
        115                 120                 125

Phe Asn Val Glu Lys Ile Arg Asn Val Ala Ala Gly Glu Gln Ile
    130                 135                 140


<210> SEQ ID NO 109
<211> LENGTH: 528
<212> TYPE: DNA
<213> ORGANISM: Necator americanus

<400> SEQUENCE: 109

gaaaagcctc catagtcatg ctcaagctcg ttgcactcgt ttgcctggtt gcaatctgct      60

tcgctcaggg accacaagga ccccctccgt tcctgcaaag tgctccagcg gctgttcaac     120

aagacttcga caagctcttc gtcaatgctg gctccaagac tgatgcagaa atcgacaaaa     180

tggtccaaga ttgggttggc aaacaagatg catccatcaa gaccgcattc gatgcgttcg     240

tgaaggaagt gaaagccgct caagcgcaag gtgaagctgc ccatcaggct gctatcgcca     300

agttcagcgc agaggccaaa gcggctgatg ccaagctgag cgcaattgcg aacgacaggt     360

cgaagacaaa cgcgcaaaag ggagctgaga tcgactcggt actcaaggga cttcctccaa     420

atgtccgcac agagatcgaa aacgccatga aaggataaga agtctctatt ttgtatatat     480

gaaccgataa atatgcacaa taaaaaaaaa aaaaaaaaaa aaaaaaaa                  528


<210> SEQ ID NO 110
<211> LENGTH: 146
<212> TYPE: PRT
<213> ORGANISM: Necator americanus

<400> SEQUENCE: 110

Met Leu Lys Leu Val Ala Leu Val Cys Leu Val Ala Ile Cys Phe Ala
1               5                   10                  15

Gln Gly Pro Gln Gly Pro Pro Pro Phe Leu Gln Ser Ala Pro Ala Ala
            20                  25                  30

Val Gln Gln Asp Phe Asp Lys Leu Phe Val Asn Ala Gly Ser Lys Thr
        35                  40                  45

Asp Ala Glu Ile Asp Lys Met Val Gln Asp Trp Val Gly Lys Gln Asp
    50                  55                  60

Ala Ser Ile Lys Thr Ala Phe Asp Ala Phe Val Lys Glu Val Lys Ala
65                  70                  75                  80

Ala Gln Ala Gln Gly Glu Ala Ala His Gln Ala Ala Ile Ala Lys Phe
                85                  90                  95

Ser Ala Glu Ala Lys Ala Ala Asp Ala Lys Leu Ser Ala Ile Ala Asn
            100                 105                 110

Asp Arg Ser Lys Thr Asn Ala Gln Lys Gly Ala Glu Ile Asp Ser Val
        115                 120                 125

Leu Lys Gly Leu Pro Pro Asn Val Arg Thr Glu Ile Glu Asn Ala Met
    130                 135                 140

Lys Gly
145
```

-continued

<210> SEQ ID NO 111
<211> LENGTH: 1672
<212> TYPE: DNA
<213> ORGANISM: Necator americanus

<400> SEQUENCE: 111
gaaaggttta attacccaag tttgaggatg aagattgccc tggttgttct gctgttagtc 60
gcctacgcaa attctgcgga catcttcaga actgaatttg gagctaaaat aaaagcagag 120
gcggataaaa gtaagacgaa actaaatatc tcctctcttc ttcaagtccg tgggaaattc 180
ctcaagttaa gacaacagat caaggagagc ttagctctga ccccggaacg aaaagagttg 240
ttgcataagt tgatgcagaa attagtacac atcaaaaagg atcatgttca taagggtggt 300
gactcaatcg atgaaatcaa taagaaggtt ggaatgtcag atctgctcta cgatggtgat 360
atggttctaa cgaaagagca agccgaggaa atggttagcg atatcgacgg aagtggaagc 420
aaccgtgcaa agcgtcaagc gtatcgtaac aaactttatc cgaaaacact ttggaccgat 480
ggagttatct attatttcca tcctagtgca acgaatagca tgcgaagtgt gttcctgaaa 540
gcagcaaaag aatggagctc tcaaacgtgt atcgatttcc atgaggatgt ggttggaatg 600
ggcccaaaca ggatcaaggt tttcaaagag aaaggttgtt ggtcgatggt tggacgactc 660
cctcgtccac aggagctttc gttgggaaga ggatgtgata cgattgccac agcacaacac 720
gagatcggcc atgcgctggg attcttccac cagcaggcta gacacgatcg cgatgactac 780
attgtattta attcagagaa tgtagtgccg cgatatctgg atcaattcaa gaaacagagc 840
aaagaaacaa acgataatta cggattaact tatgattacg gaagcaccat gcagtacgga 900
tcgaccagcg gatcccaaaa tggaaaacct acaatggtgc caaaagatcc taaatatata 960
gaaaccctgg gatcaccttt cattgcattc tacgatttac tggcaataaa tacgcactac 1020
aaatgtcttg agaaatgcga taataatggg gcacaatgca aaatgggtgg attccctaat 1080
ccaagagatt gctcaaaatg catttgtccc agtggatacg gtggcgctac atgtgaccag 1140
aaacctgaag gatgtggtga agtacttgaa gcaacgaagg aggctaaaac cctcaaaagt 1200
gaaattggag ataaaagtgc aggagatgag gacagagagg acatgaccaa gtgttactat 1260
tggatcaagg caccggaagg atcgaaagtt gaggttaaga tcgtaaacct agctaaaggt 1320
cttgccattg atggatgcag atattggggt gtggaaatta aaactcagga ggatcaacgt 1380
gcttccggat acagattctg cgctcccgaa gatgctggcg tcactttgga gtcgcactcg 1440
aatattgtcc ctataatagc gttcaataga cacggctcta ctgaatttga attacagtac 1500
cgaatcgtat aattctgcgt gaccaacgct tctcctaaga gacgagaaag ttctgcaaca 1560
atactttatt catgtataac aatataggag agtttttctt agtagaagta ctttctttgt 1620
tggttctcca gaaataaacg atttccatgc aaaaaaaaaa aaaaaaaaaa aa 1672

<210> SEQ ID NO 112
<211> LENGTH: 494
<212> TYPE: PRT
<213> ORGANISM: Necator americanus

<400> SEQUENCE: 112

Met Lys Ile Ala Leu Val Val Leu Leu Leu Val Ala Tyr Ala Asn Ser
1 5 10 15

Ala Asp Ile Phe Arg Thr Glu Phe Gly Ala Lys Ile Lys Ala Glu Ala
20 25 30

Asp Lys Ser Lys Thr Lys Leu Asn Ile Ser Ser Leu Leu Gln Val Arg
35 40 45

-continued

```
Gly Lys Phe Leu Lys Leu Arg Gln Gln Ile Lys Glu Ser Leu Ala Leu
    50                  55                  60

Thr Pro Glu Arg Lys Glu Leu Leu His Lys Leu Met Gln Lys Leu Val
65                  70                  75                  80

His Ile Lys Lys Asp His Val His Lys Gly Gly Asp Ser Ile Asp Glu
                85                  90                  95

Ile Asn Lys Lys Val Gly Met Ser Asp Leu Leu Tyr Asp Gly Asp Met
            100                 105                 110

Val Leu Thr Lys Glu Gln Ala Glu Glu Met Val Ser Asp Ile Asp Gly
        115                 120                 125

Ser Gly Ser Asn Arg Ala Lys Arg Gln Ala Tyr Arg Asn Lys Leu Tyr
    130                 135                 140

Pro Lys Thr Leu Trp Thr Asp Gly Val Ile Tyr Tyr Phe His Pro Ser
145                 150                 155                 160

Ala Thr Asn Ser Met Arg Ser Val Phe Leu Lys Ala Ala Lys Glu Trp
                165                 170                 175

Ser Ser Gln Thr Cys Ile Asp Phe His Glu Asp Val Val Gly Met Gly
            180                 185                 190

Pro Asn Arg Ile Lys Val Phe Lys Glu Lys Gly Cys Trp Ser Met Val
        195                 200                 205

Gly Arg Leu Pro Arg Pro Gln Glu Leu Ser Leu Gly Arg Gly Cys Asp
    210                 215                 220

Thr Ile Ala Thr Ala Gln His Glu Ile Gly His Ala Leu Gly Phe Phe
225                 230                 235                 240

His Gln Gln Ala Arg His Asp Arg Asp Asp Tyr Ile Val Phe Asn Ser
                245                 250                 255

Glu Asn Val Val Pro Arg Tyr Leu Asp Gln Phe Lys Lys Gln Ser Lys
            260                 265                 270

Glu Thr Asn Asp Asn Tyr Gly Leu Thr Tyr Asp Tyr Gly Ser Thr Met
        275                 280                 285

Gln Tyr Gly Ser Thr Ser Gly Ser Gln Asn Gly Lys Pro Thr Met Val
    290                 295                 300

Pro Lys Asp Pro Lys Tyr Ile Glu Thr Leu Gly Ser Pro Phe Ile Ala
305                 310                 315                 320

Phe Tyr Asp Leu Leu Ala Ile Asn Thr His Tyr Lys Cys Leu Glu Lys
                325                 330                 335

Cys Asp Asn Asn Gly Ala Gln Cys Lys Met Gly Gly Phe Pro Asn Pro
            340                 345                 350

Arg Asp Cys Ser Lys Cys Ile Cys Pro Ser Gly Tyr Gly Gly Ala Thr
        355                 360                 365

Cys Asp Gln Lys Pro Glu Gly Cys Gly Glu Val Leu Glu Ala Thr Lys
    370                 375                 380

Glu Ala Lys Thr Leu Lys Ser Glu Ile Gly Asp Lys Ser Ala Gly Asp
385                 390                 395                 400

Glu Asp Arg Glu Asp Met Thr Lys Cys Tyr Tyr Trp Ile Lys Ala Pro
                405                 410                 415

Glu Gly Ser Lys Val Glu Val Lys Ile Val Asn Leu Ala Lys Gly Leu
            420                 425                 430

Ala Ile Asp Gly Cys Arg Tyr Trp Gly Val Glu Ile Lys Thr Gln Glu
        435                 440                 445

Asp Gln Arg Ala Ser Gly Tyr Arg Phe Cys Ala Pro Glu Asp Ala Gly
    450                 455                 460
```

-continued

```
Val Thr Leu Glu Ser His Ser Asn Ile Val Pro Ile Ile Ala Phe Asn
465                 470                 475                 480

Arg His Gly Ser Thr Glu Phe Glu Leu Gln Tyr Arg Ile Val
                485                 490
```

<210> SEQ ID NO 113
<211> LENGTH: 759
<212> TYPE: DNA
<213> ORGANISM: Necator americanus

<400> SEQUENCE: 113

```
acttcaagcg atgttccgtc ctgctactgc cgtccttcta ttgttggccg cgtccagcac     60

atttgctgga tttttcgatg atgttggagg cttacccagt ggtgtgggag attttttcac    120

aaagcagttc aacaatgtga aggatctttt tgctaaagat caagatactc ttgagaagaa    180

tatcaatctg gtaaaggatc tattgattgc cattaaggag aaggctaaga tgctggaacc    240

gatggccaac gaggctcaga agaagacatt agggcaggtg gacaactatc tcaatgaagt    300

tcaacagttc ggcgatcagg tagccaagga gggttctacg aaatttgagg agaacaaagg    360

gaaatggcag caaatgttga acgatatctt cgagaaaggt ggactggaca gcgtgatgaa    420

gttgctcaat ctgaagtccg gcggtcgctg cacgttagcc gctgcactcg tcgctcccgt    480

tgtgctcgcg ctcatccgct aattcacttc taccgccgcc gactactgta gtttaccctg    540

tgcctgtgtg tgatatgtgg atttgtgcat gatgtgtatc tatgatttgt gatttatttt    600

tctcttgtac ttccatgaat tcagctctgg tattctgaga cggaccaaca tctccgcagt    660

actttttgt attgttatca tcaccgtaat cctgtgactg gcgtaaaatg tttagttttc    720

cgataaaata catttcgaaa aaaaaaaaaa aaaaaaaaa                           759
```

<210> SEQ ID NO 114
<211> LENGTH: 163
<212> TYPE: PRT
<213> ORGANISM: Necator americanus

<400> SEQUENCE: 114

```
Met Phe Arg Pro Ala Thr Ala Val Leu Leu Leu Leu Ala Ala Ser Ser
1               5                   10                  15

Thr Phe Ala Gly Phe Phe Asp Asp Val Gly Gly Leu Pro Ser Gly Val
            20                  25                  30

Gly Asp Phe Phe Thr Lys Gln Phe Asn Asn Val Lys Asp Leu Phe Ala
        35                  40                  45

Lys Asp Gln Asp Thr Leu Glu Lys Asn Ile Asn Leu Val Lys Asp Leu
    50                  55                  60

Leu Ile Ala Ile Lys Glu Lys Ala Lys Met Leu Glu Pro Met Ala Asn
65                  70                  75                  80

Glu Ala Gln Lys Lys Thr Leu Gly Gln Val Asp Asn Tyr Leu Asn Glu
                85                  90                  95

Val Gln Gln Phe Gly Asp Gln Val Ala Lys Glu Gly Ser Thr Lys Phe
            100                 105                 110

Glu Glu Asn Lys Gly Lys Trp Gln Gln Met Leu Asn Asp Ile Phe Glu
        115                 120                 125

Lys Gly Gly Leu Asp Ser Val Met Lys Leu Leu Asn Leu Lys Ser Gly
    130                 135                 140
```

-continued

```
Gly Arg Cys Thr Leu Ala Ala Ala Leu Val Ala Pro Val Val Leu Ala
145                 150                 155                 160

Leu Ile Arg
```

HOOKWORM VACCINE

This application claims priority to International patent application PCT/US02/33106 (filed 17 Oct. 2002, of which it is a continuation-in-part), and to U.S. provisional patent application 60/329,533 (filed 17 Oct. 2001), 60/332,007 (filed 23 Nov. 2001) 60,375,404 (filed 26 Apr. 2002), and 60/505,848 (filed 26 Sep. 2003). The entire contents of each application to which priority is claimed is hereby incorporated by reference.

This invention was made in part by funds from government grants: Tropical Medicine Research Center (TMRC) grant from the National Institutes of Health P50 A1-39461 and A1-32726. The United States government may have rights in this invention.

BACKGROUND OF THE INVENTION

1. Field of the Invention

The invention generally relates to a vaccine for hookworm. In particular, the invention provides vaccines based on parasite-derived antigens.

2. Background of the Invention

Hookworm infection is a significant public health concern in developing countries around the world, causing enteritis, intestinal blood loss, anemia, developmental delays, and malnutrition. It is estimated that there are more than one billion cases of human hookworm infection worldwide, with 194 million cases in China alone (Hotez et al. 1997). In some regions of China such as Hainan Province in the South China Sea more than 60 percent of the population harbors hookworms (Gandhi et al. 2001).

Most of the pathology caused by hookworm results from the adult stages of the parasite in the human intestine. The attachment of adult *Ancylostoma* and *Necator* hookworms to the mucosa and submucosa of the vertebrate small intestine is one of the best-defined examples of host-parasite relationships in all of parasitology. Comprised of several cubic millimeters of host mucosal and submucosal tissue lodged in the buccal capsule of the parasite, it is possible to actually touch the host-parasite relationship at necropsy or autopsy (Kalkofen, 1970; Kalkofen, 1974).

The dog hookworm *Ancylostoma caninum* is a major cause of morbidity and mortality in dogs throughout the world including subtropical regions of North America. Hookworm-associated blood loss leading to severe anemia and even death can occur in dogs between 2 and 3 weeks after a single primary infection (Soulsby, 1982; Jones and Hotez, 2002). Significantly, *A. caninum* has also been recently identified as an important human pathogen. Zoonotic infection with one adult *A. caninum* parasite can result in eosinophilic enteritis syndrome, an inflammatory condition of the intestine in response to invasion by the parasite (Prociv and Croese, 1990). The pathogenesis of *A. caninum* infection is associated with the intestinal blood loss that occurs during adult worm attachment and feeding in the mammalian small intestine (Kalkofen, 1970; Kalkofen, 1974).

Current efforts for the treatment and control of hookworm infestations are limited to periodic removal of adult hookworms from patients with anthelmintics. This approach has several limitations, including rapid reinfection following treatment, requiring multiple visits, and the eventual development of anthelmintic resistant strains of hookworms following several years of heavy anthelmintic treatments (Savioli et al. 1997; Geerts and Gryseels, 2000). Thus, it would be of great benefit to have available additional methods for both treating and preventing hookworm infection in mammals. For example, it would be highly advantageous to have available vaccines to treat or prevent hookworm infection.

SUMMARY OF THE INVENTION

The present invention provides preparations for eliciting an immune response against hookworm. The preparations contain various hookworm antigens which have been identified as useful for eliciting an immune response. These preparations may be used as vaccines against hookworm in mammals, for example, in humans. As a result of the administration of the preparations, the vaccinated mammal may develop an immune response against hookworm which causes immunity to infection by the parasite, or may display a lower worm burden, decreased blood loss, or a decrease in size of parasitizing hookworms. To that end, the invention provides a composition comprising a recombinant or synthetic antigen or a fragment thereof derived from hookworm, and a pharmacologically acceptable carrier. The recombinant or synthetic antigen may display at least about 80% identity to an antigen such as ASP-1, ACE, CTL, APR-1, APR-2, TMP, MEP-1, MEP-2, ASP-1, ASP-2, ASP-3, ASP-4, ASP-5, ASP-6, TTR-1, TTR-2, 103 (also referred to as SAA-1), 16, VWF, CTL, API, MTP-1, MTP-2, MTP-3, FAR-1, KPI-1, APR-1, APR-2, AP, ASP-1, ASP-2, API, CP-1, CP-2, CP-3, CP-4, CYS, and GST. In preferred embodiments, the antigen is ASP-1, ASP-2, MTP-1, 103 (SAA), 16, GST, TMP, MEP-1, APR or CP-2. The antigens may be derived from a hookworm from species such as *Necator americanus, Ancylostoma caninum, Ancylostoma ceylanicum*, and *Ancylostoma duodenale.*

The invention also provides a method of eliciting an immune response to hookworm in a mammal. The method includes the step of administering to the mammal an effective amount of a composition comprising a recombinant or synthetic antigen (or a fragment of the antigen) derived from hookworm, and a pharmacologically acceptable carrier. The recombinant or synthetic antigen may display at least about 80% identity to an antigen such as ASP-1, ACE, CTL, APR-1, APR-2, TMP, MEP-1, MEP-2, ASP-1, ASP-2, ASP-3, ASP-4, ASP-5, ASP-6, TTR-1, TTR-2, 103 (also referred to as SAA-1), 16, VWF, CTL, API, MTP-1, MTP-2, MTP-3, FAR-1, KPI-1, APR-1, APR-2, AP, ASP-1, ASP-2, API, CP-1, CP-2, CP-3, CP-4, CYS, and GST. In preferred embodiments, the antigen is ASP-1, ASP-2, MTP-1,103 (SAA), 16, GST, TMP, MEP-1, APR, or CP-2. The antigens may be derived from a hookworm from species such as *Necator americanus, Ancylostoma caninum, Ancylostoma ceylanicum*, and *Ancylostoma duodenale.*

The invention further provides a method of vaccinating a mammal against hookworm. The method includes the step of administering to the mammal an effective amount of a composition comprising a recombinant or synthetic antigen (or a fragment of the antigen) derived from hookworm and a pharmacologically acceptable carrier. The recombinant or synthetic antigen may display at least about 80% identity with an antigen such as ASP-1, ACE, CTL, APR-1, APR-2, TMP, MEP-1, MEP-2, MTP-1, ASP-1, ASP-2, ASP-3, ASP-4, ASP-5, ASP-6, TTR-1, TTR-2, 103 (also referred to as SAA-1), 16, VWF, CTL, API, MTP-1, MTP-2, MTP-3, FAR-1, KPI-1, APR-1, APR-2, AP, ASP-1, ASP-2, MTP-1, API, CP-1, CP-2, CP-3, CP-4, CYS, and GST. In preferred embodiments, the antigen is ASP-1, ASP-2, MTP-1, 103 (SAA), 16, GST, TMP, MEP-1, APR, or CP-2. The antigens may be derived from a hookworm from species such as

*Necator americanus, Ancylostoma caninum, Ancylostoma ceylanicum*, and *Ancylostoma duodenale.*

The invention further provides a composition comprising a recombinant or synthetic antigen (or a fragment of the antigen) derived from hookworm. The recombinant or synthetic antigen display at least about 80% identity with an antigen such as ASP-1, ACE, CTL, APR-1, APR-2, TMP, MEP-1, MEP-2, ASP-1, ASP-2, ASP-3, ASP-4, ASP-5, ASP-6, TTR-1, TTR-2, 103 (also referred to as SAA-1), 16, VWF, CTL, API, MTP-1, MTP-2, MTP-3, FAR-1, KPI-1, APR-1, APR-2, AP, ASP-1, ASP-2, API, CP-1, CP-2, CP-3, CP-4, CYS, and GST. The composition further comprises a pharmacologically acceptable carrier. In preferred embodiments, the antigen is ASP-1, ASP-2, MTP-1, 103 (SAA), 16, GST, TMP, MEP-1, APR, or CP-2. The antigens may be derived from a hookworm from species such as *Necator americanus, Ancylostoma caninum, Ancylostoma ceylanicum*, and *Ancylostoma duodenale.*

The invention further provides a vaccine comprising a recombinant or synthetic antigen (or a fragment of the antigen) derived from hookworm. The recombinant or synthetic antigen displays at least about 80% identity with an antigen such as ASP-1, ACE, CTL, APR-1, APR-2, TMP, MEP-1, MEP-2, ASP-1, ASP-2, ASP-3, ASP-4, ASP-5, ASP-6, TTR-1, TTR-2, 103 (also referred to as SAA-1), 16, VWF, CTL, API, MTP-1, MTP-2, MTP-3, FAR-1, KPI-1, APR-1, APR-2, AP, ASP-1, ASP-2, API, CP-1, CP-2, CP-3, CP-4, CYS, and GST. The vaccine further comprises a pharmacologically acceptable carrier. In preferred embodiments, the antigen is ASP-1, ASP-2, MTP-1, 103 (SAA), 16, GST, TMP, MEP-1, APR, or CP-2. The antigens may be derived from a hookworm from species such as *Necator americanus, Ancylostoma caninum, Ancylostoma ceylanicum*, and *Ancylostoma duodenale.*

The present invention further provides a composition for eliciting an immune response comprising a recombinant or synthetic antigen (or a fragment of the antigen) derived from hookworm. The recombinant or synthetic antigen displays at least about 80% identity with an antigen selected from the group consisting of ASP-1, ACE, CTL, APR-1, APR-2, TMP, MEP-1, MEP-2, ASP-1, ASP-2, ASP-3, ASP-4, ASP-5, ASP-6, TTR-1, TTR-2, 103 (also referred to as SAA-1), 16, VWF, CTL, API, MTP-1, MTP-2, MTP-3, FAR-1, KPI-1, APR-1, APR-2, AP, ASP-1, ASP-2, API, CP-1, CP-2, CP-3, CP-4, CYS, and GST. The composition further comprises a pharmacologically acceptable carrier. In preferred embodiments, the antigen is ASP-1, ASP-2, MTP-1, 103 (SAA), 16, GST, TMP, MEP-1, APR, or CP-2. The antigens may be derived from a hookworm from species such as *Necator americanus, Ancylostoma caninum, Ancylostoma ceylanicum*, and *Ancylostoma duodenale.*

The invention further provides a method for enabling vaccination of a patient against parasite derived infectious diseases. The method includes the steps of treating hookworm infection to a degree sufficient to increase lymphocyte proliferation, and vaccinating the patient against an infectious disease such as HIV, tuberculosis, malaria, measles, tetanus, diphtheria, pertussis, or polio.

The present invention also provides a method for enabling hookworm vaccination. The method includes the steps of chemically treating a hookworm infected patient to ameliorate hookworm infection, and vaccinating the patient with a recombinant or synthetic antigen (or a fragment of the antigen) derived from hookworm after amelioration of hookworm infection. In the method, the hookworm infection may be completely eradicated by treatment, or may be lessened to such an extent that hookworm vaccination is effective. The recombinant or synthetic antigen may display at least about 80% identity with an antigen such as ASP-1, ACE, CTL, APR-1, APR-2, TMP, MEP-1, MEP-2, ASP-1, ASP-2, ASP-3, ASP-4, ASP-5, ASP-6, TTR-1, TTR-2, 103 (also referred to as SAA-1), 16, VWF, CTL, API, MTP-1, MTP-2, MTP-3, FAR-1, KPI-1, APR-1, APR-2, AP, ASP-1, ASP-2, API, CP-1, CP-2, CP-3, CP-4, CYS, and GSTThe antigens may be derived from a hookworm from species such as *Necator americanus, Ancylostoma caninum, Ancylostoma ceylanicum*, and *Ancylostoma duodenale.*

The present invention also provides a method for reducing blood loss in a patient infected with hookworm. The method includes the step of administering to the patient a composition comprising a recombinant or synthetic antigen (or a fragment of the antigen) derived from hookworm, and a pharmacologically acceptable carrier.

The present invention also provides a method for reducing hookworm size in a patient infected with hookworm. The method includes the step of administering to the patient a composition comprising a recombinant or synthetic antigen (or a fragment of the antigen) derived from hookworm, and a pharmacologically acceptable carrier.

The invention further provides a method of reducing hookworm burden in a patient infected with hookworm. The method comprises the step of administering to the patient a composition comprising a recombinant or synthetic antigen (or a fragment of the antigen) derived from hookworm, and a pharmacologically acceptable carrier.

The present invention also provides the following nucleic acid and amino acid sequences: SEQ ID NO: 11, SEQ ID NO: 12, SEQ ID NO: 13, SEQ ID NO: 14, SEQ ID NO: 15, SEQ ID NO: 16, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 47, SEQ ID NO: 48, SEQ ID NO: 49, SEQ ID NO: 50, SEQ ID NO: 51, SEQ ID NO: 52, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63 and SEQ ID NO: 64.

BRIEF DESCRIPTION OF THE DRAWINGS

FIGS. 1A and B. Na-ASP-1: A, cDNA (SEQ ID NO: 1) and B, deduced amino acid sequence (SEQ ID NO: 2). GeneBank accession # AF079521.

FIGS. 2A and B. Na-ACE: A, cDNA (SEQ ID NO: 3) and B, deduced amino acid sequence (SEQ ID NO: 4). GeneBank accession # AF536813.

FIGS. 3A and B. Na-CTL: A, cDNA (SEQ ID NO: 5) and B, deduced amino acid sequence (SEQ ID NO: 6).

FIGS. 4A and B. Na-APR-1: A, cDNA (SEQ ID NO: 7) and B, deduced amino acid sequence (SEQ ID NO: 8).

FIGS. 5A and B. Na-APR-2: A, cDNA (SEQ ID NO: 9) and B, deduced amino acid sequence (SEQ ID NO: 10).

FIGS. 6A and B. Ac-TMP: A, cDNA (SEQ ID NO: 11) and B, deduced amino acid sequence (SEQ ID NO: 12).

FIGS. 7A and B. Ac-MEP-1: A, cDNA (SEQ ID NO: 13) and B, deduced amino acid sequence (SEQ ID NO:14). GeneBank accession # AF273084.

FIGS. 8A and B. Ac-MTP-1: A, cDNA (SEQ ID NO: 15) and B, deduced amino acid sequence (SEQ ID NO: 16). GeneBank accession # AY036056.

FIGS. 9A and B. Ac-ASP-1: A, cDNA (SEQ ID NO: 17) and B, deduced amino acid sequence (SEQ ID NO: 18). GeneBank accession # AF 132291.

FIGS. 10A and B. Ac-ASP-2: A, cDNA (SEQ ID NO: 19) and B, deduced amino acid sequence (SEQ ID NO: 20). GeneBank accession # AF089728.

FIGS. 11A and B. Ac-ASP-3: A, cDNA (SEQ ID NO: 21) and B, deduced amino acid sequence (SEQ ID NO: 22).

FIGS. 12A and B. Ac-ASP-4: A, cDNA (SEQ ID NO: 23) and B, deduced amino acid sequence (SEQ ID NO: 24).

FIGS. 13A and B. Ac-ASP-5: A, cDNA (SEQ ID NO: 25) and B, deduced amino acid sequence (SEQ ID NO: 26).

FIGS. 14A and B. Ac-ASP-6: A, cDNA (SEQ ID NO: 27) and B, deduced amino acid sequence (SEQ ID NO: 28).

FIGS. 15A and B. Ac-TTR-1: A, cDNA (SEQ ID NO: 29) and B, amino acid sequence (SEQ ID NO:30) deduced from nucleotides 25-531.

FIGS. 16A and B. Ac-103: A, cDNA (SEQ ID NO: 31) and B, amino acid sequence (SEQ ID NO: 32).

FIGS. 17A and B. Ac-VWF: A, cDNA (SEQ ID NO: 33) and B, amino acid sequence (SEQ ID NO: 34).

FIGS. 18A and B. Ac-CTL: A, cDNA (SEQ ID NO: 35) and B, amino acid sequence (SEQ ID NO: 36).

FIGS. 19A and B. Ac-API-1: A, cDNA (SEQ ID NO: 37) and B, amino acid sequence (SEQ ID NO: 38) deduced from nucleotides 23-706.

FIGS. 20A and B. Ac-MTP-1: A, cDNA (SEQ ID NO: 39) and B, amino acid sequence (SEQ ID NO: 40).

FIGS. 21A and B. Ac-MTP-2: A, cDNA (SEQ ID NO: 41) and B, amino acid sequence (SEQ ID NO: 42).

FIGS. 22A and B. Ac-MTP-3: A, cDNA (SEQ ID NO: 43) and B, amino acid sequence (SEQ ID NO: 44).

FIGS. 23A and B. Ac-FAR-1: A, cDNA (SEQ ID NO: 45) and B, amino acid sequence (SEQ ID NO: 46). GeneBank Acession # AF529181

FIG. 24A-C. Ac-KPI-1: A and B, cDNA (SEQ ID NO: 47) and C, amino acid sequence (SEQ ID NO: 48) deduced from nucleotides 12-2291.

FIGS. 25A and B. Ac-APR-1: A, cDNA (SEQ ID NO: 49) and B, amino acid sequence (SEQ ID NO: 50).

FIGS. 26A and B. Ac-APR-2: A, partial cDNA sequence (SEQ ID NO: 51) and B, partial amino acid sequence (SEQ ID NO: 52).

FIGS. 27A and B. Ac-AP: A, cDNA (SEQ ID NO: 53) and B, amino acid sequence (SEQ ID NO: 54).

FIGS. 28A and B. Ay-ASP-1: A, cDNA (SEQ ID NO: 55) and B, amino acid sequence (SEQ ID NO: 56).

FIGS. 29A and B. Ay-ASP-2: A, cDNA (SEQ ID NO: 57) and B, amino acid sequence (SEQ ID NO: 58).

FIGS. 30A and B. Ay-MTP-1: A, cDNA (SEQ ID NO: 59) and B, amino acid sequence (SEQ ID NO: 60).

FIGS. 31A and B. Ay-API-1: A, cDNA (SEQ ID NO: 61) and B, amino acid sequence (SEQ ID NO: 62) deduced from nucleotides 23-703.

FIGS. 32A and B. Ay-TTR: A, partial cDNA (SEQ ID NO: 63) and B, partial amino acid sequence (SEQ ID NO: 64).

FIG. 42. Alignment of deduced amino acid sequences of *Ancylostoma*-secreted protein (ASP)-1 derived from different species of third-stage hookworm larvae. Sequences were aligned by use of CLUSTAL W software and were prepared for display by use of BOXSHADE software. Black boxes, identical amino acids; gray boxes, similar amino acids; asterisks, amino acids common to every sequence; and arrows, cysteines conserved in all ASPs. Names and GenBank accession nos. are as follows: Ay (*A. ceylanicum*)-ASP-1 (SEQ ID NO: 56), AAN11402; Ac (*A. caninum*)-ASP-1 (SEQ ID NO: 18), AAC47001; Ad (*A. duodenale*)-ASP-1, AAD13339 (SEQ ID NO: 67); and Na (*Necator americanus*)-ASP-1 (SEQ ID NO: 2), AAD13340. The amino acid sequence identities between Ay-ASP-1 and other hookworm ASP-1 proteins are shown at the end of sequence.

FIGS. 43A and B. A, Alignment of deduced amino acid sequences of *Ancylostoma*-secreted protein (ASP)-2 derived from different species of third-stage hookworm larvae. Sequences were aligned by use of CLUSTAL W software and were prepared for display by use of BOXSHADE software. Black boxes, dentical amino acids; gray boxes, similar amino acids; asterisks, amino acids common to every sequence; and arrows, cysteines conserved in all ASPs. The names and GenBank accession nos. are as follows: Ay (*A. ceylanicum*)-ASP-2 (SEQ ID NO: 58), AAP41953; Ac (*A. caninum*)-ASP-2 (SEQ ID NO: 20), AAC35986; Ad (*A. duodenale*)ASP-2 (SEQ ID NO: 68), AAP41951; and Na (*Necator americanus*)-ASP-2 (SEQ ID NO: 69), AAP41952. The amino acid sequence identities between Ay-ASP-2 (SEQ ID NO: 58) and other hookworm ASP-2 proteins are shown at the end of sequence. B, cDNA sequence of Na-ASP-2 (SEQ ID NO: 82).

FIG. 57A-C. A, cDNA sequence of *A. caninum* GST (SEQ ID NO: 76) and B, corresponding amino acid sequence (SEQ ID NO: 77). C, alignment of coding region and amino acid sequence. Amino acids 1-19 are signal peptide.

FIGS. 61A and B. Na-CP-2: A, cDNA (SEQ ID NO: 83) and B, amino acid sequence (SEQ ID NO: 84).

FIGS. 62A and B. Na-CP-3: A, cDNA (SEQ ID NO: 85) and B, amino acid sequence (SEQ ID NO: 86).

FIGS. 63A and B. Na-CP-4: A, cDNA (SEQ ID NO: 87) and B, amino acid sequence (SEQ ID NO: 88).

FIGS. 64A and B. Na-CP-5: A, cDNA (SEQ ID NO: 89) and B, amino acid sequence (SEQ ID NO: 90).

FIGS. 65A and B. Na-MEP-1: A, cDNA (SEQ ID NO: 91) and B, amino acid sequence (SEQ ID NO: 92).

FIGS. 66A and B. Ac-16: A, cDNA (SEQ ID NO: 93) and B, amino acid sequence (SEQ ID NO: 94).

FIGS. 67A and B. Ay-16: A, cDNA (SEQ ID NO: 95) and B, amino acid sequence (SEQ ID NO: 96).

FIGS. 68A and B. Ac-CP-1: A, cDNA (SEQ ID NO: 97) and B, amino acid sequence (SEQ ID NO: 98).

FIGS. 69A and B. Ac-Cys: A, cDNA (SEQ ID NO: 99) and B, amino acid sequence (SEQ ID NO: 100).

FIGS. 70A and B. Ac-MEP-2: A, cDNA (SEQ ID NO: 101) and B, amino acid sequence (SEQ ID NO: 102).

FIGS. 71A and B. Ac-TTR-2: A, cDNA (SEQ ID NO: 103) and B, amino acid sequence (SEQ ID NO: 104).

FIGS. 72A and B. Ay-APR-1: A, cDNA (SEQ ID NO: 105) and B, amino acid sequence (SEQ ID NO: 106).

FIGS. 73A and B. Ay-CYS: A, cDNA (SEQ ID NO: 107) and B, amino acid sequence (SEQ ID NO: 108).

FIGS. 74A and B. Na-16: A, cDNA (SEQ ID NO: 109) and B, amino acid sequence (SEQ ID NO: 110).

FIGS. 75A and B. Na-MTP-1: A, cDNA (SEQ ID NO: 111) and B, amino acid sequence (SEQ ID NO: 112).

FIGS. 76A and B. Na-103 (SAA-1): A, cDNA (SEQ ID NO: 113) and B, amino acid sequence (SEQ ID NO: 114).

DETAILED DESCRIPTION OF THE PREFERRED EMBODIMENTS OF THE INVENTION

Figure 33A:
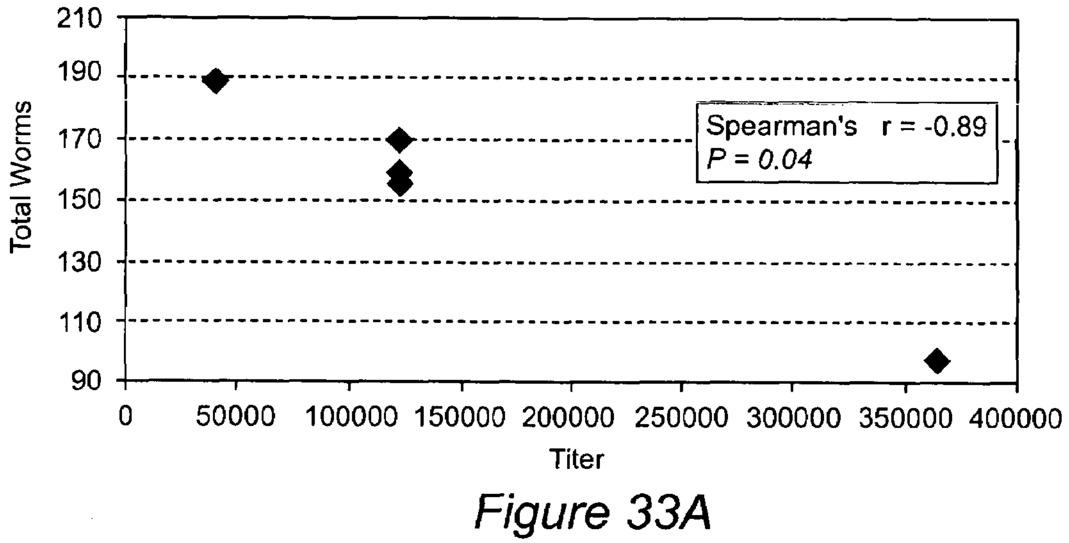
FIGS. 33A and B. Spearman rank order correlations between hookworm burden and anti-MTP-1 antibody titer. A) total worms; B) median EPG.

The present invention provides compositions for use in eliciting an immune response to hookworm in a mammal. Such compositions may be utilized as vaccines for use in the treatment and/or prevention of hookworm infection. The vaccines comprise purified preparations of antigens which are derived from hookworm, and a pharmacologically acceptable carrier. By "derived from" we mean that the antigen is a biomolecule that originated from (i.e. was isolated from) a hookworm. For example, the antigen may be a protein, a polypeptide, or an antigenic fragment of a protein, or polypeptide, which constitutes part of a hookworm organism. Typically, such an antigen is isolated and at least partially purified from a hookworm by methods which are well known to those of skill in the art (for example, see Examples section below). When manufactured for use in eliciting an immune response or as a vaccine, such antigens may be "synthetic" i.e. obtained synthetically (e.g. by peptide synthesis in the case of polypeptides and protein fragments), or "recombinant" i.e. obtained by genetic engineering techniques (e.g. by production in a host cell which harbors a vector containing DNA which encodes the antigen). Those of skill in the art will recognize that many such suitable expression systems are available, including but not limited to those which employ *E. coli*, yeast (e.g. *Pichia pastoris*), baculovirus/insect cells, plant cells, and mammalian cells, and. In preferred embodiments of the invention, the antigens are expressed in a yeast or baculovirus/insect cell expression system.

Examples of specific antigens, their amino acid primary sequences, and nucleic acid sequences which encode them are given herein. For ease of reference, Table I lists some exemplary antigens and their corresponding SEQ ID NOS. However, those of skill in the art will recognize that many variants of the sequences presented herein may exist or be constructed which would also function as antigens in the practice of the present invention. For example, with respect to amino acid sequences, variants may exist or be constructed which display: conservative amino acid substitutions; non-conservative amino acid substitutions; truncation by, for example, deletion of amino acids at the amino or carboxy terminus, or internally within the molecule; or by addition of amino acids at the amino or carboxy terminus, or internally within the molecule (e.g. the addition of a histidine tag for purposes of facilitating protein isolation, the substitution of residues to alter solubility properties, the replacement of residues which comprise protease cleavage sites to eliminate cleavage and increase stability, the addition or elimination of glycosylation sites, and the like, or for any other reason). Such variants may be naturally occurring (e.g. as a result of natural variations between species or between individuals); or they may be purposefully introduced (e.g. in a laboratory setting using genetic engineering techniques). All such variants of the sequences disclosed herein are intended to be encompassed by the teaching of the present invention, provided the variant antigen displays sufficient identity to the described sequences. Preferably, identity will be in the range of about 50 to 100%, and more preferably in the range of about 75 to 100%, and most preferably in the range of about 80 to 100% of the disclosed sequences. The identity is with reference to the portion of the amino acid sequence that corresponds to the original antigen sequence, i.e. not including additional elements that might be added, such as those described below for chimeric antigens.

TABLE I

Hookworm antigens, description, and corresponding SEQ ID NOS.

| Source | Antigen | Description | SEQ ID NOs. /. cDNA (Accession No.) | SEQ ID NOs. /. open reading frame (Accession No.) |
|---|---|---|---|---|
| *Necator americanus* | | | | |
| | Na-ASP-1 | secreted protein | SEQ ID NO: 1 (AF079521) | SEQ ID NO: 2 (AAD13340) |
| | Na-ASP-2 | secreted protein | SEQ ID NO: 82 (AY288089) | SEQ ID NO: 69 (AAP41952) |
| | Na-ACE | cholinesterase | SEQ ID NO: 3 (AF36813) | SEQ ID NO: 4 (AAN05636) |
| | Na-CTL | C-lectin | SEQ ID NO: 5 | SEQ ID NO: 6 |
| | Na-APR-1 | aspartic protease | SEQ ID NO: 7 | SEQ ID NO: 8 |
| | Na-APR-2 | aspartic protease | SEQ ID NO: 9 | SEQ ID NO: 10 |
| | Na-CP-2 | cysteine protease | SEQ ID NO: 83 | SEQ ID NO: 84 |
| | Na-CP-3 | cysteine protease | SEQ ID NO: 85 | SEQ ID NO: 86 |
| | Na-CP-4 | cysteine protease | SEQ ID NO: 87 | SEQ ID NO: 88 |
| | Na-CP-5 | cysteine protease | SEQ ID NO: 89 | SEQ ID NO: 90 |
| | Na-MEP-1 | metallo-endopeptidase | SEQ ID NO: 91 | SEQ ID NO: 92 |

TABLE I-continued

| Hookworm antigens, description, and corresponding SEQ ID NOS. | | | SEQ ID NOs. /. | |
|---|---|---|---|---|
| Source | Antigen | Description | cDNA (Accession No.) | open reading frame (Accession No.) |
| | Na-MTP-1 | astacin protease | SEQ ID NO: 111 | SEQ ID NO: 112 |
| | Na-103 (SAA-1) | surface protein | SEQ ID NO: 113 | SEQ ID NO: 114 |
| | Na-16 | surface-associated antigen | SEQ ID NO:109 | SEQ ID NO:110 |
| *Ancylostoma duodenale* | | | | |
| | Ad-ASP-1 | secreted protein | (AF077402) | SEQ ID NO: 67 (AAD13339) |
| | Ad-ASP-2 | secreted protein | (AY288088) | SEQ ID NO: 68 (AAP41951) |
| *Ancylostoma caninum* | | | | |
| | Ac-TMP | met protease inhibitor | SEQ ID NO: 11 (AF372651) | SEQ ID NO: 12 (AAK58952) |
| | Ac-MEP-1 | metallo-endopeptidase | SEQ ID NO: 13 (AF273084) | SEQ ID NO: 14 (AAG29103) |
| | Ac-MEP-2 | metallo-endopeptidase | SEQ ID NO:101 | SEQ ID NO:102 |
| | Ac-MTP-1 | astacin protease | SEQ ID NO: 15 (AY036056) | SEQ ID NO: 16 (AAK62032) |
| | Ac-ASP-1 | secreted protein | SEQ ID NO: 17 (AF132291) | SEQ ID NO: 18 (AAD31839) |
| | Ac-ASP-2 | secreted protein | SEQ ID NO: 19 (AF089728) | SEQ ID NO: 20 (AAC35986) |
| | Ac-ASP-3 | secreted protein | SEQ ID NO: 21 (AY217004) | SEQ ID NO: 22 (AA063575) |
| | Ac-ASP-4 | secreted protein | SEQ ID NO: 23 (AY217005) | SEQ ID NO: 24 (AA063576) |
| | Ac-ASP-5 | secreted protein | SEQ ID NO: 25 (AY217006) | SEQ ID NO: 26 (AA063577) |
| | Ac-ASP-6 | secreted protein | SEQ ID NO: 27 (AY217007) | SEQ ID NO: 28 (AA063578) |
| | Ac-TTR-1 | transthyretin | SEQ ID NO: 29 | SEQ ID NO: 30 |
| | Ac-TTR-2 | transthyretin | SEQ ID NO: 103 | SEQ ID NO: 104 |
| | Ac-103 (SAA-1) | surface protein | SEQ ID NO: 31 (AY462062) | SEQ ID NO: 32 (AAR25200) |
| | Ac-VWF | surface lectin | SEQ ID NO: 33 | SEQ ID NO: 34 |
| | Ac-CTL | C-lectin | SEQ ID NO: 35 | SEQ ID NO: 36 |
| | Ac-API | aspartyl protease inhibitor | SEQ ID NO: 37 | SEQ ID NO: 38 |
| | Ac-MTP-1 | astacin protease | SEQ ID NO: 39 | SEQ ID NO: 40 |
| | Ac-MTP-2 | astacin protease | SEQ ID NO: 41 | SEQ ID NO: 42 |
| | Ac-MTP-3 | astacin protease | SEQ ID NO: 43 | SEQ ID NO: 44 |
| | Ac-FAR-1 | retinol binding | SEQ ID NO: 45 | SEQ ID NO: 46 |

TABLE I-continued

Hookworm antigens, description, and corresponding SEQ ID NOS.

| Source | Antigen | Description | SEQ ID NOs. /. cDNA (Accession No.) | SEQ ID NOs. /. open reading frame (Accession No.) |
|---|---|---|---|---|
| | Ac-KPI-1 | protease inhibitor | SEQ ID NO: 47 | SEQ ID NO: 48 |
| | Ac-APR-1 | aspartic protease | SEQ ID NO: 49 | SEQ ID NO: 50 |
| | Ac-APR-2 | pepsinogen | SEQ ID NO: 51 | SEQ ID NO: 52 |
| | Ac-AP | anticoagulant | SEQ ID NO: 53 | SEQ ID NO: 54 |
| | Ac-CP-1 | cysteine protease | SEQ ID NO: 97 | SEQ ID NO: 98 |
| | Ac-CP-2 | cysteine protease | (U18912) | (AAC46878) |
| | Ac-CYS | cystatin | SEQ ID NO: 99 | SEQ ID NO: 100 |
| | Ac-GST | glutathione S transferase | SEQ ID NO: 76 | SEQ ID NO: 77 |
| | Ac-16 | surface-associated antigen | SEQ ID NO: 93 | SEQ ID NO: 94 |
| *Ancyclostoma ceylanicum* | | | | |
| | Ay-ASP-1 | secreted protein | SEQ ID NO: 55 (AY136548) | SEQ ID NO: 56 (AAN11402) |
| | Ay-ASP-2 | secreted protein | SEQ ID NO: 57 (AY288090) | SEQ ID NO: 58 (AAP41953) |
| | Ay-MTP-1 | astacin protease | SEQ ID NO: 59 (AY136547) | SEQ ID NO: 60 (AAN11401) |
| | Ay-API-1 | aspartyl protease inhibitor | SEQ ID NO: 61 | SEQ ID NO: 62 |
| | Ay-TTR | transthyretin-like | SEQ ID NO: 63 | SEQ ID NO: 64 |
| | Ay-16 | surface-associated antigen | SEQ ID NO: 95 | SEQ ID NO: 96 |
| | Ay-APR-1 | aspartic protease | SEQ ID NO: 105 | SEQ ID NO: 106 |
| | Ay-CP-2 | cysteine protease | (AF522068) | (AAM82155) |
| | Ay-CYS | cystatin | SEQ ID NO:107 | SEQ ID NO:108 |

The invention also encompasses chimeric antigens, for example, antigens comprised of the presently described amino acid sequences plus additional sequences which were not necessarily associated with the disclosed sequences when isolated but the addition of which conveys some additional benefit. For example, such benefit may be utility in isolation and purification of the protein, (e.g. histidine tag, GST, and maltose binding protein); in directing the protein to a particular intracellular location (e.g. yeast secretory protein); in increasing the antigenicity of the protein (e.g. KHL, haptens). All such chimeric constructs are intended to be encompassed by the present invention, provided the portion of the construct that is based on the sequences disclosed herein is present in at least the indicated level of homology.

Those of skill in the art will recognize that it may not be necessary to utilize the entire primary sequence of a protein or polypeptide in order to elicit an adequate antigenic response to the parasite from which the antigen originates. In some cases, a fragment of the protein is adequate to confer immunization. Thus, the present invention also encompasses antigenic fragments of the sequences disclosed herein, and their use in vaccine preparations. In general, such a fragment will be at least about 10-13 amino acids in length. Those of skill in the art will recognize that suitable sequences are often hydrophilic in nature, and are frequently surface accessible.

Likewise, with respect to the nucleic acid sequences disclosed herein, those of skill in the art will recognize that many variants of the sequences may exist or be constructed which would still function to provide the encoded antigens or desired portions thereof. For example, due to the redundancy of the genetic code, more than one codon may be used to code for an amino acid. Further, as described above, changes in the primary sequence of the antigen may be desired, and this would necessitate changes in the encoding nucleic acid sequences. In addition, those of skill in the art will recognize that many variations of the nucleic acid sequences may be constructed for purposes related to cloning strategy, (e.g. for ease of manipulation of a sequence for insertion into a vector, such as the introduction of restriction enzyme cleavage sites, etc.), for purposes of modifying transcription (e.g. the introduction of promoter or enhancer sequences, and the like), or for any other suitable purpose. All such variants of the nucleic acid sequences disclosed herein are intended to be encompassed by the present invention, provided the sequences display about 50 to 100% identity to the original sequence and preferably, about 75 to 100% identity, and most preferably about 80 to 100% identity. The identity is with reference to the portion of the nucleic acid sequence that corresponds to the original sequence, and is not intended to cover additional elements such as promoters, vector-derived sequences, restriction enzyme cleavage sites, etc. derived from other sources.

The antigens of the present invention may be derived from any species of hookworm, examples of which include but are not limited to *Necator americanus, Ancylostoma caninum, Ancylostoma ceylanicum* and *Ancylostoma duodenale.*

Examples of suitable hookworm antigens include but are not limited to Na-ASP-1, Na-ACE, Na-CTL, Na-APR-1, NA-APR-2, Ac-TMP, Ac-MEP-1, Ac-MTP-1, Ac-ASP-1, Ac-ASP-2, Ac-ASP-3, Ac-ASP-4, Ac-ASP-5, Ac-ASP-6, Ac-TTR-1, Ac-103, Ac-VWF, Ac-CTL, Ac-API, Ac-MTP-1, Ac-MTP-2, Ac-MTP-3, Ac-FAR-1, Ac-KPI-1, Ac-APR-1, Ac-APR-2, Ac-AP, Ay-ASP-1, Ay-ASP-2, Ay-MTP-1, Ay-API, and Ay-TTR.

In some embodiments of the invention, the antigenic entity is an activation associated secretory protein, examples of which include but are not limited to Na-ASP-1, Ac-ASP-3, Ac-ASP-4, Ac-ASP-5, Ac-ASP-6, Ay-ASP-1, and Ay-ASP-2.

In other embodiments of the invention, the antigenic moiety is a protease, examples of which include but are not limited to metalloproteases (e.g. Ac-MTP-2, Ac-MTP-3; cysteine proteases; aspartic proteases (e.g. Ac-APR-1 and Ac-APR-2); and serine proteases.

In yet other embodiments of the invention, the antigen may be a lectin (e.g. Na-CTL, Ac-CTL).

In other embodiments of the invention, the antigen may be a protease inhibitor (e.g. Ac-API-I, Ay-API-1, Ac-AP, Ac-KPI-1).

In a preferred embodiment, the antigen utilized in the practice of the present invention is Ac-TMP, the DNA encoding sequence of which is given in FIG. 6A (SEQ ID NO: 11), and the amino acid sequence of which is given in FIG. 6B (SEQ ID NO: 12).

In another preferred embodiment, the antigen utilized in the practice of the present invention is Ac-MEP-1, the DNA encoding sequence of which is given in FIG. 7A (SEQ ID NO: 13, and the amino acid sequence of which is given in FIG. 7B (SEQ ID NO: 14).

In another preferred embodiment, the antigen utilized in the practice of the present invention is Ac-MTP-1, the DNA encoding sequence of which is given in FIG. 8A (SEQ ID NO: 15, and the amino acid sequence of which is given in FIG. 8B (SEQ ID NO: 16).

Other preferred antigens include but are not limited to Na-CTL (SEQ ID NOS. 5-6); Na-APR-1 (SEQ ID NOS. 7-8); Na-APR-2 (SEQ ID NOS. 9-10); Ac-TMP (SEQ ID NOS. 11-12); Ac-ASP-3 (SEQ ID NOS. 21-22); Ac-ASP-4 (SEQ ID NOS. 23-24); Ac-ASP-5 (SEQ ID NOS. 25-26); Ac-ASP-6 (SEQ ID NOS. 27-28); Ac-TTR-1 (SEQ ID NOS. 29-30); Ac-TTR-2 (SEQ ID NOS. 103-104) Ac-103 (SAA-1) (SEQ ID NOS. 31-32); Ac-VWF (SEQ ID NOS. 33-34); Ac-CTL (SEQ ID NOS. 35-36); Ac-API-1 (SEQ ID NOS. 37-38); Ac-MTP-1 (SEQ ID NOS. 39-40); Ac-MTP-2 (SEQ ID NOS. 41-42); Ac-MTP-3 (SEQ ID NOS: 43-44); Ac-KPI-1 (SEQ ID NOS: 47-48); Ac-APR-1 (49-50); Ac-APR-2 (SEQ ID NOS: 51-52); Ay-ASP-1 (SEQ ID NOS: 55-56); Ay-ASP-2 (SEQ ID NOS: 57-58); Ay-MTP-1 (SEQ ID NOS: 59-60); Ay-API-1 (SEQ ID NOS: 61-62); Ay-TTR (SEQ ID NOS: 63-64); Na-ACE (SEQ ID NOS: 3 and 4); Na-ASP-1 (SEQ ID NOS: 1 and 2); Ac-MEP-1 (SEQ ID NOS: 13-14);

Other preferred antigens for use in the practice of the present invention include Ad-ASP-1 (protein, SEQ ID NO: 67); Ad-ASP-2 (protein, SEQ ID NO: 68); Na-ASP-2 (protein, SEQ ID NO: 69; nucleotide, SEQ ID NO: 82); CP-2 antigens, e.g. Ac-CP-2 (Genebank Accession # U18912); Na-CP-2 (SEQ ID NOS: 83-84); Na-CP-3 (SEQ ID NOS: 85-86); Na-CP-4 (SEQ ID NOS: 87-88); Na-CP-5 (SEQ ID NOS: 89-90); Ac-CP-1 (SEQ ID NOS: 97-98); Ac-CP-2; Ay-CP-2; GST antigens, e.g. Ac-GST (protein SEQ ID NO: 77, nucleotide SEQ ID NO: 76); Na-MEP-1 (SEQ ID NOS: 91-92); Na-MTP-1 (SEQ ID NOS: 111-112); Na-103 (SAA-1) (SEQ ID NOS: 113-114); Na-16 (SEQ ID NOS: 109-110; Ac-MEP-2 (SEQ ID NOS: 101-102); Ac-CYS (SEQ ID NOS: 99-100); Ay-CYS (SEQ ID NOS: 107-108); Ac-16 (SEQ ID NOS: 93-94); Ay-16 (SEQ ID NOS: 95-96); Ay-APR-1 (SEQ ID NOS: 105-106).

The present invention provides compositions for use in eliciting an immune response which may be utilized as a vaccine against hookworm. By "eliciting an immune response" we mean that an antigen stimulates synthesis of specific antibodies at a titer of about >1 to about $1\times10^6$ or greater. Preferably, the titer is from about 10,000 to about $1\times10^6$ or more, and most preferably, the titer is greater than $1\times10^6$, and/or cellular proliferation as measured by, for example, $^3$H thymidine incorporation. By "vaccine" we mean an antigen that elicits an immune response that results in a decrease in hookworm burden of a least about 30% in an organism in relation to a non-vaccinated (e.g. adjuvant alone) control organism. Preferably, the level of the decrease is about 50%, and most preferably, about 60 to about 70% or greater.

The present invention provides compositions for use in eliciting an immune response which may be utilized as a vaccine against hookworm. The compositions include a substantially purified hookworm antigen or variant thereof as described herein, and a pharmacologically suitable carrier. The preparation of such compositions for use as vaccines is well known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. In addition, the composition may contain other adjuvants. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of hookworm antigen in the formulations may vary. However, in general, the amount in the formulations will be from about 1-99%.

The vaccine preparations of the present invention may further comprise an adjuvant, suitable examples of which include but are not limited to Seppic, Quil A, Alhydrogel, etc.

The preparations of the present invention may contain a single hookworm antigen. Alternatively, more than one hookworm antigen may be utilized in a preparation, i.e. the preparations may comprise a "cocktail" of antigens. In a preferred embodiment, such a cocktail will contain two or more antigens, and will be a combination of a larval stage antigen and an adult stage antigen. Examples of suitable larval stage antigens include but are not limited to ASP-2, MTP-1, 103 (SAA-1), 16 and GST. Examples of suitable adult stage antigens include but are not limited to APR-1, CP-2, GST, MEP-1, APR-2, and TMP. GST is an antigen that is present at both the larval and adult stage. The antigens utilized in the cocktail may be from any species. However, in preferred embodiments of the invention, the antigens will be antigens derived from a human hookworm source such as Na-Asp-2, Na-APR-1, Na-CP-2, Na-GST, Na-MEP-1, Ad-Asp-2, Ad-APR-1, Ad-CP-2, Ad-GST, Ad-MEP-1, Na-MTp-1, Ad-MTP-1, Na-103 (Na-SAA), Ad-103 (Ad-SAA-1), Na-16, and Ad-16. Preferably, the cocktail will contain at least two antigens derived from a human hookworm source, at least one larval stage and at least one adult stage, such as, for example, either Na- or Ad-: Asp-2 APR-1; Asp-2 and CP-2; Asp-2 and GST; Asp-2 and MEP-1.

The present invention also provides a method of eliciting an immune response to hookworm and methods of vaccinating a mammal against hookworm. By eliciting an immune response, we mean that administration of the antigen causes the synthesis of specific antibodies (at a titer in the range of 1 to $1\times10^6$, preferably $1\times10^3$, more preferable in the range of about $1\times10^3$ to about $1\times10^6$, and most preferably greater than $1\times10^6$) and/or cellular proliferation, as measured, e.g. by $^3$H thymidine incorporation. The methods involve administering a composition comprising a hookworm antigen in a pharmacologically acceptable carrier to a mammal. The vaccine preparations of the present invention may be administered by any of the many suitable means which are well known to those of skill in the art, including bu not limited to by injection, orally, intranasally, by ingestion of a food product containing the antigen, etc. In preferred embodiments, the mode of administration is subcutaneous or intramuscular.

The present invention provides methods to elicit an immune response to hook worn and to vaccinate against hookworm in mammals. In one embodiment, the mammal is a human. However, those of skill in the art will recognize that other mammals exist for which it would also be of benefit to vaccinate against hookworm, i.e. the preparations may also be used for veterinary purposes. Examples include but are not limited to companion "pets" such as dogs, cats, etc.; food source, work and recreational animals such as cattle, horses, oxen, sheep, pigs, goats, and the like.

Those of skill in the art will recognize that, in general, in order to vaccinate (or elicit an immune response in) a species of interest (e.g. humans) against hookworm, the antigen which is utilized will be derived from a species of hookworm which parasitizes the species of interest. For example, in general, antigens from *Necator americanus* may be preferred for the immunization of humans, and antigens from *Ancylostoma caninum* may be preferred for the immunization of dogs. However, this may not always be the case. For example, *Ancylostoma caninum* is known to parasitize humans as well as its primary canine host. Further, cross-species hookworm antigens may sometimes be highly effective in eliciting an immune response in a non-host animal, i.e. in an animal that does not typically serve as host for the parasite from which the antigen is derived. Rather, the measure of an antigen's suitability for use in an immune-stimulating or vaccine preparation is dependent on its ability to confer protection against invasion and parasitization by the parasite as evidenced by, for example, hookworm burden reduction or inhibition of hookworm associated blood loss (e.g. as measured by hematocrit and/or hemoglobin concentration. For example, for use in a vaccine preparation, an antigen upon administration results in a reduction in worm burden of at least about 30%, preferably at least about 50%, and most preferably about 60 to about 70%.

In one embodiment of the present invention, a method for enabling vaccination of a patient against infectious diseases is provided. The method involves chemically treating hookworm infection to a degree sufficient to increase lymphocyte proliferation, followed by vaccinating the patient against said infectious disease. The method is based on evidence provided in Example 10 which shows that hookworm infestation causes anergy to hookworm and possibly other antigen stimulation. Therefore, by chemically treating hookworm infected patients prior to vaccination against hookworm or any infectious agent, the response to the vaccination will be improved. Examples of infectious diseases against which vaccination outcomes may be improved include but are not limited to HIV, tuberculosis, malaria, and routine childhood vaccinations (e.g. measles, tetanus, diphtheria, pertussis, polio, and the like).

Examples of agents with which hookworm may be chemically treated include but are not limited to albendazole and other anthelmintic drugs.

Certain of the antigens described herein may also be useful in the vaccination against other parasites, for example (including but not limited to) *Schistosoma* sp and soil transmitted parasites such as *Ascaris* sp and *Trichuris* sp. This may be due to the potential cross reactivity between the hookworm antigens and antigens from these species.

Certain of the antigens described herein may also be useful in the treatment of other neoplastic, autoimmune, and cardiovascular conditions, as well as for the treatment of pro-inflammatory states. Such uses of other hookworm antigens have been described in, for example, U.S. Pat. No. 5,427,937 to Capello et al. and U.S. Pat. No. 5,753,787 to Hawdon.

The present invention also provides the following nucleic acid and amino acid sequences: SEQ ID NO: 11, SEQ ID NO: 12, SEQ ID NO: 13, SEQ ID NO: 14, SEQ ID NO: 15, SEQ ID NO: 16, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 47, SEQ ID NO: 48, SEQ ID NO: 49, SEQ ID NO: 50, SEQ ID NO: 51, SEQ ID NO: 52, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, and SEQ ID NO: 64. The sequences represent cDNA sequences and the amino acid sequences (open reading frames) which they encode.

While the sequences themselves are being claimed, other sequences with a high level of identity in comparison to those described are also contemplated, e.g. sequences having at least about 65 to 100% identity, or preferably about 75 to 100% identity, or most preferably at least about 80 to 100% identity, to the sequences that are given.

In particular, the sequences for Ac-APR-2 (SEQ ID NOS: 51 and 52) and Ay-TTR-1 (SEQ ID NOS: 63 and 64) are partial sequences which represent the majority of the antigen sequence. Thus, the present invention encompasses the entire Ac-APR-2 antigen and the entire Ay-TTR-1 antigen.

Further, those of skill in the art will recognize that the Ay-TTR-1 and Ay-TTR-2 antigens which are provided in the present application are representative of the Ay-TTR family of antigens present in many species of nematodes. As such, an Ay-TTR antigen from any nematode is intended to be encompassed by the present invention. In particular, any Ay-TTR antigen derived from a hookworm species including but not limited to *Necator americanus, Ancylostoma caninum, Ancylostoma ceylanicum*, and *Ancylostoma duodenale*, are encompassed.

Additional sequences that are provided by the present invention include: SEQ ID NO: 76 and SEQ ID NO: 77, representing Ac-GST cDNA and corresponding amino acid sequence, respectively; SEQ ID NO: 83 and SEQ ID NO: 84, representing Na-CP-2 cDNA and corresponding amino acid sequence, respectively; SEQ ID NO: 85 and SEQ ID NO: 86, representing Na-CP-3 cDNA and corresponding amino acid sequence, respectively; SEQ ID NO: 87 and SEQ ID NO: 88, representing Na-CP-4 cDNA and corresponding amino acid sequence, respectively; SEQ ID NO: 89 and SEQ ID NO: 90, representing Na-CP-5 cDNA and corresponding amino acid sequence, respectively; SEQ ID NO: 91 and SEQ ID NO: 92, representing Na-MEP-1 cDNA and corresponding amino acid sequence, respectively; SEQ ID NO: 93 and SEQ ID NO: 94, representing Ac-16 cDNA and corresponding amino acid sequence, respectively; SEQ ID NO: 95 and SEQ ID NO: 96, representing Ay-16 cDNA and corresponding amino acid sequence, respectively; SEQ ID NO: 97 and SEQ ID NO: 98, representing Ac-CP-1 cDNA and corresponding amino acid sequence, respectively; SEQ ID NO: 99 and SEQ ID NO: 100, representing Ac-CYS cDNA and corresponding amino acid sequence, respectively; SEQ ID NO: 101 and SEQ ID NO: 102, representing Ac-MEP-2 cDNA and corresponding amino acid sequence, respectively; SEQ ID NO: 103 and SEQ ID NO: 104, representing Ac-TTR-2 cDNA and corresponding amino acid sequence, respectively; SEQ ID NO: 105 and SEQ ID NO: 106, representing Ay-APR-1 cDNA and corresponding amino acid sequence, respectively; SEQ ID NO: 107 and SEQ ID NO: 108, representing Ay-Cys cDNA and corresponding amino acid sequence, respectively; SEQ ID NO: 109 and SEQ ID NO: 110, representing Na-16 cDNA and corresponding amino acid sequence, respectively; SEQ ID NO: 111 and SEQ ID NO: 112, representing Na-MTP-1 cDNA and corresponding amino acid sequence, respectively; and SEQ ID NO: 113 and SEQ ID NO: 114, representing Na-SAA-1 cDNA and corresponding amino acid sequence, respectively.

EXAMPLES

Example 1

Molecular Cloning and Purification of Ac-TMP

Materials and Methods

Immunoscreening of adult *A. caninum* library Preparation of anti-*A. caninum* secretory product antibody. One hundred living adult stage *Ancylostoma caninum* hookworms were recovered from the intestines of an infected dog, at necropsy (6 weeks post-infection), as described previously (Hotez and Cerami, 1983). The adult worms were washed three times in sterile PBS, then maintained in 15 ml RPM 1640 containing 25 mM HEPES, 100 units/ml of ampicillin and 100 μg/ml streptomycin at 37C (5% $CO_2$) for 24 hours. The supernatant was collected, concentrated with PEG6000, and dialyzed against 1 L phosphate buffered saline (pH 7.2) overnight at 4° C. Following dialysis, the secreted products were centrifuged at 10,000×g for 10 min, and the supernatant was recovered.

A rabbit was immunized by subcutaneous injection with the hookworm-secreted proteins (400 ug) emulsified with complete Freund's adjuvant. Subsequently, the rabbit was immunized at two week intervals with the same quantity of hookworm secreted proteins emulsified with incomplete Freund's adjuvant for a total of three immunizations. The final bleed was obtained 10 days after the final immunizations, and the serum was separated from whole blood and stored at −20° C.

Construction of the cDNA expression ZapII (Stratagene, La Jolla Calif.) library was reported previously (Capello et al., 1996)). An estimated $5\times10^5$ plaques were screened with the rabbit anti-*A. caninum* adult secretory product antibody according to manufacturer's instructions. Briefly, $5\times10^4$ plaques were plated on an LB agar plate. *A. caninum* antigen expression was induced by covering the plaques with nitrocellulose membranes soaked with 10 mM IPTG. Four hours after incubation at 37° C., the membranes were lifted, blocked with 5% non-fat milk in PBS, and then incubated with the rabbit antibody (1:500 dilution) for 1 hour at 24° C. The membranes were washed three times with PBS buffer containing 0.1% Tween-20 (PBS-Tween) and then incubated with horseradish peroxidase conjugated goat anti-rabbit IgG (Sigma) at a 1:1000 dilution at 24° C. for another hour. The membranes were washed again three times with PBS-Tween and then developed with 3,3'-diaminobenzidine (DAB) substrate and hydrogen peroxide. The putative positive clones were scored and isolated for secondary screening.

The immunopositive clones were excised into pBluscript phage according to manufacturer's instructions (Stratagene), Phagemid DNA was extracted using the alkaline lysis method (Qiagen) and double strand sequencing was performed using flanking vector primers ($T_3$ and $T_7$). Nucleotide and deduced amino acid sequences were compared to existing sequences in GenBank by BLAST searching. ESEE 3.1 software was used for sequence analysis.

Reverse Transcription Polymerase Chain Reaction (RT-PCR) Amplification.

RT-PCR was used to determine the developmental stage specificity of Ac-tmp mRNA transcription. *A. caninum* eggs, L1 and L2 larval stages, and L3 infective larvae were obtained as described previously (Hawdon et al, 1999). The total RNA was isolated from each life history stage using TRIzol reagent (GIBCO BRL). Single-strand cDNA was synthesized using oligo d(T) primer and MMLV-RT(GIBCO BRL). Specific primers (TIMP3'-1HR and TIMP5'-2ER based on the sequence of Ac-tmp from 60 bp to 440 bp were used to amplify the Ac-tmp cDNA. PCR reaction parameters were comprised of 94° C. denaturing for 1 min, 55° C. annealing for 1 min, 72C extension for 2 min. A total 30 cycles were performed.

Purification of Ac-TMP natural product. Optimization of semi-preparative reverse phase chromatographic conditions for the fractionations of *A. caninum* adult secretory products was carried out on a 510 HPLC system (Waters), equipped with a 490 E multiwavelength detector with a semi-preparative flow-cell, set at 214, 280, 260 and 254 mm and a 250 mm×4.6 I.D. YMC-Pack Protein-RP, 200Å, 5 μm $C_4$ Column (Waters). The adult *A. caninum* secretory products used as starting material were collected over 15 hr from 1260 adult hookworms in 15 ml RPMI 1640 containing 25 mM HEPES, 100 units/ml ampicillin, 100 μg/ml streptomycin and 100 μg/ml gentamicin at 37° C. The supernatant was concentrated by ultrafiltration in a Centricon-3 microconcentrator (Amicon) to 0.3 vol. before centrifugation for 1 hr at 7,500×g. Approximately 0.6 mg of the parasite secretory protein was chromatographed. Eluent A was 0.01% Trifluoroacetic acid (TFA) in water, and eluent B was 0.01% TFA in acetonitrile. A 40-min linear aradient from 0-80% B was run at a flow-rate of 1 ml/min. Fractions of 0.5 min were collected, lyophilized, and were used for further purification and analysis by SDS-PAGE (Laemmli, 1970). For SDS-PAGE, 2 μl of secretory products as well as the 10 μl of HPLC isolated fraction number 51 were mixed with the same volume of 2×SDS-PAGE sample buffer (4% SDS, 2.5% 2-mercapto ethanol, 15% glycerol) and boiled for 5 min. The samples were run on a 4-20% gradient SDS-PAGE gel at 100 V for 2 hours. The gel was stained with silver according to manufacturer's instruction (BIO-RAD).

RP-HPLC of Fraction 51, the fraction that contained the most abundant *A. caninum* secretory protein from the semi-preparative separation, was carried out on a 510 HPLC system equipped as described above using a 250 mm.×3.0 I.D. YMC protein RP, 200 A, 5 μm C4 column. Eluent A was 0.01% TFA in water, and B was 0.01% TFA in acetonitrile. A 30-min linear gradient from 0-60% B was run at a flow-rate of 1 ml/min. Fractions of 0.5 min were collected and lyophilized. The major protein peak collected from this separation was subjected to amino acid sequence analysis and SDS-PAGE (Laemmli, 1970). Amino acid sequence analysis based on the Edman degradation of protein was performed on precise 494 model protein sequencer (Applied Biosystems) equipped with a 785A programmable detector and a 140C pump system, by ProSeq, Inc. (Boxford Mass.). The sequencer products were identified using standard precise 610A software.

To confirm that the N-terminal sequence corresponded to Ac-TMP, degenerate oligonucleotide primers were synthesized in both orientations that corresponding to the partial N-terminal peptides sequence of fraction number 51. Paired flanking degenerate vector primers were used to amplify the product from DNA obtained from the adult cDNA library constructed in ZapII. The "hot start" PCR conditions were 10 mM Tris-HCl (pH 8.5) containing 50 mM KCl, 2.0 mM $MgCl_2$, 0.2 mM of each dNTP, and 1 μl cDNA library, in 20 μl reaction. The reactions were heated at 94° C. for 5 min, then lowered to 85° C. for 5 min, then 1 unit of Taq DNA polymerase (GIBCO BRL) was added. This was followed by 30 cycles of 1 min of denaturation at 94° C., 1 min of annealing at 55° C., and 2 min of extension at 72° C. The PCR products were run on an agarose gel and stained with ethidium bromide. The PCR products were gel purified with the QIAEX II Gel Extraction kit (Qiagen, Valencia, Calif.), and sequenced.

Results for Example 1

Ac-TMP cDNA. Ac-TMP cDNA was cloned from an adult hookworm cDNA library by immunoscreening with rabbit antibody directed against whole *A. caninum* adult secretory products. Two positive identical clones were isolated. The full-length cDNA consists of 559 bps (SEQ ID NO: 11) encoding an open reading frame (ORF) of 140 amino acids (SEQ ID NO: 12) and a poly-A tail at the 3' end. The predicted ORF has a calculated molecular weight of 16,100 daltons and a theoretical pI of 7.55. There is a hydrophobic signal peptide sequence with a signal peptidase cleavage site between amino acids 16 and 17. Ac-TMP has a signature N terminal Cys-X-Cys sequence immediately following the signal peptide. One putative N linked glycosylation site (N-X-T) exists between amino acids 119 and 122 (FIG. 6B).

GenBank database searching revealed that the predicted amino acid sequence of this molecule shares 33 percent identity and 50 percent similarity to the N-terminal domain of human tissue inhibitor of metalloproteinase 2 (TIMP-2). Both Ac-TMP and a putative TIMP from the free-living nematode *Caenorhabditis elegans* are comprised of a single domain and lack a second, C-terminal domain that is characteristic of vertebrate TIMPs (data not shown). RT-PCR amplification. To identify the life-history stage specific expression of Ac-TMP, mRNAs were extracted from different developmental stages of *A. caninum* and reverse transcribed to cDNA with Ac-TMP specific primers. RT-PCR produced a 380 bp specific band that was only amplified from adult cDNA. No amplification was seen from the cDNA of eggs, Li-L2 and L3 life history stages. Amplification of *A. caninum* genomic DNA revealed two bands suggestive of a possible intron or the existence of a second, related Ac-TMP gene (data not shown).

Identification of Ac-TMP in secretory products of *A. caninum* adult worm. To confirm that Ac-TMP is released by adult *A. caninum* hook-worms, the protein was identified in and purified from parasite secretory products via RP-HPLC. Each of the major peaks were subjected to amino acid sequence analysis as part of a larger *A. caninum* proteomics study (data not shown). The peak of protein corresponding to "Fraction 51" was selected for further study and re-chromatographed. Fraction 51 was comprised of one predominant band after silver staining that migrated with an apparent molecular weight of Mr=16,000. The N-terminal peptide sequence (20 amino acids) of this fraction was an identical match with the sequence of the predicted ORF of Ac-TMP after the predicted signal peptidase cleavage site. Based on the calculated area under the curve of HPLC peak 51 relative to the total area of the entire secretory product profile, Ac-TMP was determined to comprise approximately 6.3 percent of the total *A. caninum* secretory products. This identified the molecule as one of the most abundant proteins released by adult *A. caninum*. The abundance of Ac-TMP in hookworm secretory products was confirmed by visual inspection on SDS-PAGE. Paired degenerate primers based on the sequence of the first seven amino acids were used to construct PCR products from the adult hookworm cDNA library. DNA sequence of the PCR products confirmed the identity to Ac-TMP cDNA (data not shown).

This example demonstrates that TMP is the most abundant protein secreted by hookworms and that the protein has been cloned and expressed, and the recombinant protein isolated.

Example 2

Molecular Cloning and Characterization of Ac-mep-1

Materials and Methods.

Parasites. *A. caninum* parasites were maintained in beagles as described previously (Schad 1982). Third stage infective larvae (L3) were isolated from charcoal coprocultures and stored in BU buffer (Hawdon et al. 1995). Adult *A. caninum* worms were collected from infected dogs upon necropsy. These worms were washed three times in PBS, snap frozen in liquid nitrogen, and stored at −80□C.

Nucleic acids Genomic DNA was isolated from adult *A. caninum* by standard methods (Ausubel et al. 1993). *A. caninum* RNA was isolated by grinding previously frozen (−80 □C) adult worms in the presence of Trizol reagent (Gibco BRL) and following manufacturers protocol. cDNA was prepared from RNA by the ProSTAR First Strand RTPCR Kit (Stratagene) according to the manufacturer's instructions.

*A. caninum* genomic and cDNA libraries An *A. caninum* genomic DNA library was constructed as follows: 30 ug *A. caninum* genomic DNA was partially digested (37 □C for 5 min) by 8 U Sau3A restriction enzyme (NEB) in a 100 ul volume with recommended buffer. The digested DNA was then ethanol precipitated and pelleted by standard methods. The resulting pellet was dried, dissolved in water, and ligated into the Lambda-FIXII vector (Stratagene) according to manufacture's protocol. This ligation reaction was then packaged with Gigapack Gold packaging extract (Stratagene) and amplified. An *A. caninum* adult cDNA library was constructed previously (Capello et al. 1996) in lambda ZAPII (Stratagene) vector.

Metalloprotease cloning Cloning the Ac-mep-1 cDNA began with PCR on adult hookworm library cDNA using a degenerate primer and oligo-dT. A degenerate primer was designed against a conserved sequence containing the zinc binding motif observed in an BLAST alignment of two hypothetical zinc metalloprotease genes from *C. elegans* (GenBank™ accession numbers T22668 and Q22523) The reaction conditions were as follows: 85 ng template DNA, 1× thermophillic DNA buffer (Promega), 2.5 mM MgCl2, 0.2 mM dNTP's, 2 uM each primer, 1 U taq DNA polymerase (Promega), in 20 μl total volume. The reactions were cycled at 94° C. for 1 min, 55C for 1 min, and 72C for 1 min 35 times. This PCR yielded a fragment which when cloned (pGEM-T, Promega) and sequenced represented 458 bp (including 21 residues of the poly A tail) of the 3 Ac-mep-1 cDNA (Clone MP-1). Utilizing the MP-1 as the basis for specific primer design additional sequence of Ac-mep-1 (Clone MP-2) was identified by PCR on library DNA with T3 (vector) and MEP-R1 gene specific primers. Reactions were conducted on serial dilutions of library DNA until a unique product was amplified and then cloned. Reaction conditions were as described above.

In a similar clone MP-3 was amplified with T3 and MEP-R2 primers. The 5'-RACE kit from GibcoBRL was employed to identify the 5' end of Ac-mep-1. Briefly, first strand cDNA was produced in a reverse transcription reaction with the Ac-mep-1 specific primer RACE-R1 on freshly prepared RNA. This cDNA was then poly C tailed at its 3' end with terminal deoxytransferase and used as template in a PCR reaction with anchor primer AAP (GibcoBRL) and gene specific reverse primer MEP-R2. The resulting products were diluted and used as template in a hemi-nested PCR reaction with anchor primer UAP (GibcoBRL) and gene specific primer MEP-R3. The PCR product generated was cloned and termed MP-4.

More 5' sequence was identified from a genomic DNA clone (G-MEP) of Ac-mep-1 like sequence. Multiple clones were sequenced to confirm the Ac-mep-1 cDNA and the full length coding region of Ac-mep-1 was PCR amplified (clone FL-1) under the conditions described above as a single fragment utilizing suitable primers.

Sequence analysis Alignment of the partial Ac-mep-1 clones was conducted using MEGALIGN software from DNASTAR Inc. (version 3.7.1). BLAST analysis of the initial sequences used for degenerate primer design and the predicted open reading frame (ORF) of Ac-mep-1 was conducted using the National Center for Biotechnology Information BLAST utility. Sequence analysis of Ac-mep-1 was conducted using the Curatools sequence analysis utility (Curagen Corp., New Haven, Conn.). The FGENESH gene finder utility (CGG WEB server (genomic.sanger.ac.uk) with settings to analyze *C. elegans* DNA was utilized for gene predictions from the genomic DNA clone G-MEP. Identification of potential exon sequences in GMEP was accomplished with the Wise2 sequence analysis utility (sanger.ac.uk/Software Wise2/).

Northern blotting Northern blot analysis was conducted on Trizol (GibcoBRL) isolated total RNA from ten adult worms. This RNA was fractionated on a 1.2% formaldehyde gel and blotted to Hybond-N membrane (Amersham) by standard methods. The blot was probed with a $^{32}P$ random prime labeled DNA fragment representing bp 780-2688 of the Ac-mep-1 cDNA.

Developmental RT-PCR RT-PCR was used to investigate Ac-mep-1 transcription in *A. caninum* life history stages. For these reactions cDNA from egg, L1, non-activated and activated L3 and adult worms were tested with Ac-mep-1 specific primers MEP-F1 and MEP-R1. The quality if these cDNAs was verified in separate reactions using primers PKA-F and PKA-R, which are specific for *A. caninum* protein kinase A (Hawdon et al. 1995). The reaction conditions were identical to those defined in Section 2.4.

Anti-Ac-mep-1 antibody A cDNA fragment representing 610 amino acids from the C-terminal portion of Ac-mep-1 was amplified from the adult *A. caninum* cDNA lambda library by PCR using suitable primers. This fragment was T/A cloned into pGEM (Promega) from which it was cloned into pET28c expression vector (Novagen) at the HindIII site by standard methods (Sambrook and Russell, 2001). Bacterial protein expression of truncated Ac-mep-1 (tAc-MEP-1) was induced by the addition of 1 mM IPTG to a culture of BL21 (DE3)PlysS (Stratagene) cells transformed with the tAc-MEP-1/pET28c construct.

The expressed protein was insoluble. In order to purify tAc-mep-1 the induced cell pellets were frozen (BL21(DE3) PlysS cells lyse after freezing), resuspended in one-tenth vol. of 50 mM tris pH 8.0, 2 μM EDTA, sonicated until no longer viscous and then centrifuged at 12, 000×g for 15 min (Sorvall RC5B, GSA rotor). The resulting pellet was resuspended in 15 ml 1% SDS, 0.5% B-mercaptoethanol, sonicated, boiled for 5 min, and then incubated at room temperature for 2 h. Undissolved debris was removed by repeat centrifugation. The supernatant was dialyzed exhaustively against phosphate buffered saline (pH 7.4) to remove the BME. The protein was purified on HisBind (Novagen) nickel resin affinity column according to the manufacturer's protocol without denaturant. Groups of five male Balb/c mice (6-week-old) were immunized intraperitoneally with 20 ug of alum-precipitated tAc-MEP-1 or alum alone as control. The mice were subsequently boosted twice at 2-week intervals. One week after the third and final immunization, sera was collected, pooled, and used as a primary antibody in the western blot and immunostaining analysis.

Western blotting Proteins separated by 10% SDS-PAGE were transferred to methanol charged Immobilon-P PVDF membranes (Millipore) in transfer buffer (39 mM glycine, 48 mM tris base, 0.037% SDS, pH 8.3) for 18 h at 30V. The membrane was blocked in 5% nonfat milk in PBS (blocking buffer), for 1 h at room temperature (RT) with gentle shaking and incubated with *E. coli* absorbed primary mouse anti-tAc-MEP-1 antibody (1:1500) diluted in blocking buffer for 1 h at RT. The membrane was then washed three times in blocking buffer (10 min each), and incubated for 1 h at RT with horseradish peroxidase-conjugated goat anti-mouse IgG secondary antibody (1:5000) in blocking buffer with shaking. Finally, the membrane was washed three times in PBS for 15 min and developed with Renaissance (NEN Life Science Products) chemiluminescent reagents.

Immunolocalization Adult *A. caninum* worms were paraffin embedded and sectioned by standard methods. In situ immunolocalization of Ac-MEP-1 was accomplished by incubating de-parrafinized worm sections in a 1:100 dilution (in PBS, pH 7.4) of mouse anti-tAc-MEP-1 or control sera (see above) for 1 h at RT. The sections were washed three times in PBS and incubated in a 1:200 dilution of goat anti-mouse IgG at 25° C. for 1 h followed by washing in PBS (three times). Sections were then visualized with a Olympus IX-50 inverted fluorescence microscope (U-MWIG filter) and photographed.

Results for Example 2 cDNA structure of Ac-mep-1 The cloning strategy employed in obtaining the complete coding sequence of Ac-mep-1 was as follows: About 2.6 kb of the Ac-mep-1 transcript was identified by sequencing degenerate PCR clone MP-1, PCR derived clones MP-2, MP-3 and the 5' RACE clone MP-4. Although there was a methionine codon close to the 5' end of the RACE product, this codon was preceded by 58 in-frame amino acids that contained no stop, suggesting that MP-4 did not represent the actual 5' end of Ac-mep-1. In addition, we have been unable to obtain a cDNA clone (by PCR) that included a spliced leader sequence. Therefore, G-MEP, a genomic DNA clone of Ac-mep-1 like sequence (98.7% exon identity), was examined with a gene prediction program for *C. elegans* DNA and a different potential transcription start site than was identified by 5' RACE was identified. This prediction extended 158 bp beyond the 5' RACE sequence and increased the deduced coding region by 91 amino acids. Utilizing this prediction the entire coding region of Ac-mep-1 was amplified as a single product of 2.7 kb product and the clone was confirmed by partially sequencing both its ends. The total length of the Ac-mep-1 transcript is ~2.8 kb as verified by Northern blot (non-coding portions of the 5' and 3' ends were not amplified in the full length PCR). The deduced amino acid sequence of this transcript encodes a single ORF of 870 amino acids with four potential N-linked glycosylation sites (predicted pI=5.5, m.w.=98.7 kDa). The N-terminal amino acids of Ac-MEP-1 comprise a hydrophobic signal peptide sequence with a predicted cleavage after residue 22 (see FIG. 7B). Two signature zinc-binding motifs characteristic of the Endopeptidase 24.11 family of metalloproteases (Hooper, 1994) were identified.

Ac-mep-1 is 66% similar and 48% identical to a metalloprotease (Hc-MEP1b) from the related trichostrongyle blood feeding nematode *H. contortus*. It is also equally similar to a metalloprotease (T25B6.2) from the non-parasitic nematode *C. elegans* (Gen-Bank™ T28906). Fourteen cysteine residues are highly conserved between these three molecules. Two additional cysteines (only one is conserved) are present in both Ac-MEP-1 and Hc-MEP1b.

Northern blot and developmental analysis of Ac-mep-1 expression Northern blot analysis reveals a single mRNA transcript of approximately 2.8 kb in adult hookworm mRNA (not shown). RT-PCR was employed to investigate the developmental specificity of Ac-mep-1 transcription. Of the cDNAs tested it was possible to identify transcription only in the adult stage of the parasite and not in hookworm eggs, L1 or activated and non-activated L3 larvae. In contrast, positive control PCR conducted on the same cDNAs with primers specific for *A. caninum* protein kinase A revealed amplification from all template cDNAs. Thus, Ac-mep-1 appears to be expressed exclusively in adult worms.

Western blot analysis and immunolocalization of Ac-mep-1 in adult worm sections By western blotting, the mouse anti-MEP-1 antiserum strongly recognizes adult *A. caninum* proteins of ~90 and 100 kDa. Immunohistochemical analysis of adult worm sections localizes Ac-mep-1 to the microvillar surface of the hookworm gut. The antiserum reacts strongly to the gut microvilli in sections of adult worm as compared with sections incubated with control sera. Weaker staining in the tegument of the adult worm was also occasionally noted. Although the function of Ac-MEP-1 is not known, its location along the microvillar surface of the parasite gut would suggest that the enzyme is in direct contact with the blood meal, and may, therefore, have a role in nutrient digestion.

This example demonstrates that MEP-1 is an important enzyme which allows hookworms to digest blood, and therefore is an attractive vaccine target. The recombinant MEP-1 protein has been cloned and expressed.

Example 3

AC-MTP Antigen Studies

Infective third-stage *Ancylostoma* hookworm larvae (L3) release a zinc-dependent metalloprotease that migrates with an apparent molecular weight of 50 kDa (Hawdon et al 1995a). The enzyme is released specifically in response to stimuli that induce feeding and development in the L3 (Hawdon et al, 1995b), and probably functions either in parasite skin and tissue invasion or ecdysis (Hotez et al, 1990). Because of its role in parasite-derived tissue invasion and molting, an anti-enzyme antibody response directed against Ac-MTP-1 might block larval migrations and parasite entry into the intestine. Ac-MTP-I is stage specific, and released by hookworm L3activated under hostlike conditions to resume feeding in vitro. Release of Ac-MTP-I during activation makes this molecule an attractive vaccine target.

Example 3A

Isolation of a cDNA from an *A. Caninum* L3Expression Library that Encodes a Zinc-Metalloprotease (Ac-mtp-1) of the Astacin Family Material and Methods Antisera: Sera used for immunoscreening of the *A. caninum* L3 expression library were collected from 5 residents of Nanlin county in Anhui Province, China, under an IRB-approved human investigations protocol. *Ancylostoma duodenale* is the predominant hookworm in this region, with a ratio of *A. duodenale* to *Necator americanus* of greater than 20:1 based on the recovery of larval and adult hookworms from infected patients (Yong et al. 1999). Sera were obtained from Anhui residents who had high titers of circulating antibodies to *A. caninum* L3 whole lysate antigens, as described elsewhere (Xue et al., 2000). Two of the residents were hookworm egg-negative, whereas the remaining 3 harbored quantitative fecal egg counts of less than 400 eggs per gram of feces. Because of their high antibody titer and low intensity of infection, these individuals were considered putatively resistant, and their sera were pooled and used for immunoscreening. Negative control sera were collected from college students in Shanghai.

Expression library screening: An *A. caninum* (Baltimore strain) L3 cDNA library constructed in X ZapII (Stratagene, La Jolla, Calif.) (Hawdon et al. 1995) was screened using the pooled antisera according to the manufacturer's instructions. Briefly, $5\times10^4$ plaques were induced to express protein by applying a nitrocellulose membrane soaked in 10 mM IPTG for 4 hr at 37 C. Following incubation, the membrane was incubated in 5% non-fat dry milk in PBS for 1 hr. The blocked membrane was incubated with a 1:100 dilution of pooled human sera in PBS for 1 hr at 22 C, washed 3 times in PBS for 10 min at 22 C, and incubated with a 1:1000 dilution of horseradish peroxidase conjugated anti-human IgG (Sigma, St. Louis Mo.). The membrane was developed with substrate of 3,3'-diaminobenzidine (DAB) and 0.015% hydrogen peroxide. Positive plaques were subjected to several rounds of plaque purification by re-plating and rescreening. Plasmids were rescued by in vivo excision (Short and Sorge, 1992) and both strands sequenced using primers complementary to flanking vector sequence. Nucleotide and deduced amino acid sequences were compared to existing sequences in the GeneBank database by BLAST searching (Altschul et al., 1997).

Cloning of full-length Ac-MTP cDNA: All of the positive clones isolated were truncated at the 5' end. To obtain the 5' end, a PCR using a gene specific primer P I and a primer corresponding to the conserved nematode spliced leader was used to amplify the 5' end from first strand cDNA of *A. caninum* L3. Twenty μL reactions containing 100 ng of each primer, 1 U of Taq polymerase (Promega, Madison Wis.), and 1 μL of cDNA was denatured for 2 min at 95 C, followed by 30 cycles of 1 min at 94 C, 1 min at 55 C, and 2 min at 72 C. Amplicons were gel purified and cloned into pGEM Easy-T vector (Promega, Madison, Wis.) by standard methods.

Stage Specificity: The stage-specificity of mtp-1 transcription was determined by RT-PCR (Hawdon et al, 1995). *A. caninum* eggs were isolated from the feces of infected dogs by sucrose floatation (Nolan et al., 1994), axenized by treatment with NaOCl, and plated on nematode growth medium agar plates (Sulston et al. 1988). Following incubation at 26 C for 24-30 h, the hatchlings (mixed $L_1/L_2$) were washed from the plates with BU buffer (Hawdon and Schad, 1991) and snap-frozen in a dry ice/ethanol bath. Unhatched eggs were also snap frozen to make cDNA. *A. caninum* adults were collected from the small intestine of an infected dog at necropsy. RT-PCR was performed on *A. caninum* eggs, mixed $L_1/L_2$ serum-stimulated and non-stimulated $L_3$ (see below), and adult *A. caninum* samples as follows. Samples were ground to a powder in a pre-chilled (liquid $N_2$) mortar, and total RNA isolated using the TRIzol reagent (Life Technologies, Gaithersburg, Md.) according to the manufacturer's instructions. The RNA was treated with 10 U DNAse 1 (RNase free, Boehringer Mannheim, Indianapolis, Ind.) and re-extracted with TRIzol. Total egg RNA was isolated by mechanical disruption with glass beads in the presence of TRIzol using a BeadBeater machine (BioSpec, Bartlesville, Okla.), DNAse treated, and re-extracted as above. First strand cDNA was synthesized from each sample in a 50 μL reaction containing 50 mM Tris HCl, pH 8.3, 75 mM KCl, 3 mM $MgCl_2$, 10 mM DTT, 500 ng oligo(dT) primer, 1 μg of total RNA, and 200 U of Moloney murine leukemia virus reverse transcriptase (Life Technologies) at 37 C for 1 hr. The reaction was incubated at 94° C. for 5 min, and brought to 100 μL with $dH_2O$. One μL of the first strand cDNA was used in a PCR with primers MTP5'-I(5'-CTTCTCATGATCAACAAACACTACG) SEQ ID NO: 65 and MTP3'-1 (5'AATCTAACTCCAACATCTTCTG-GTG) SEQ ID NO: 66. The reaction was cycled 30 times for 1 min at 94 C, 1 min at 55 C, and 1 min at 72 C. Amplicons were separated by agarose gel electrophoresis and visualized by staining with ethidium bromide.

Expression and Purification of Recombinant Protein: The full-length Ac-mtp-1 cDNA was cloned in-frame in the expression vector pET28 (Novagen) and transformed into competent BL-21 *E. coli* cells using standard techniques. Expression of the recombinant protein, containing 6 vector-encoded histidine residues (His-Tag) at the 5' end, was induced by the addition of 1 mM IPTG for 3 hours at 37° C. One ml of cells expressing rMTP-1 were sedimented by centrifugation at 5000×g for 5 min, the supernatant discarded, and the cells lysed in 100 mls of TE (pH 8.0) containing 100 μg/ml lysozyme and 0.1% Triton X-100. After incubation at 30° C. for 20 min, the sample was sonicated (power level 2-3, 20-30% duty cycle) on ice for 10 bursts of 5 sec each until the sample was no longer viscous. Soluble and insoluble cell fractions were separated by electrophoresis in a 12% SDS-PAGE under reducing conditions, and the resolved proteins visualized with Cooomassie blue staining. For purification of rMTP-1, a cell pellet from 2 l of induced bacterial culture was suspended in 60 ml of 1.0% SDS, 0.5% 2-mercaptoethanol, boiled for 5 min, and cooled to room temperature. The extract was dialyzed against 2 liters of 0.1% SDS in PBS for 48 hr with 2 changes of buffer, and applied to a 10 ml HisBind nickel resin column (Novagen). Chromatography was conducted according to the manufacturer's instruction except that 0.1% SDS was added to all buffers.

In an effort to increase solubility and investigate the domain structure of MTP-1, 3 constructs lacking the amino HisTag sequences were made by PCR. The full length Ac-MTP cDNA (1-1642 bp), the cDNA without the 5'-propeptide (408-1642 bp), and the putative catalytic domain (408-1101 bp) were cloned in frame into pET28 at the upstream NcoI site, thereby removing the HisTag coding sequence from the vector. The recombinant proteins were expressed under the same conditions as described above. Antiserum Production Anti-rMTP polyclonal antiserum. was obtained by immunizing BABL/C mice with purified rMTP. Twenty μg of column purified rMTP was co-precipitated with alum (Ghosh et al. 1996) and injected subcutaneously. Additional boosts with alum precipitated rMTP (20 μg each) were administered at 3, 6, and 9 weeks.

Mouse antiserum was adsorbed against bacterial lysates of *E. coli* strain BL21 to remove antibodies reacting with bacterial proteins. Twenty-five ml of induced cells were centrifuged, dissolved in 25 mls of 2× sample buffer (100 mM Tris, pH 6.8, 2% SDS, 2.5% 2-mercaptoethanol, and centrifuged at 12,000×g for 10 min. Nitrocellulose membranes (4 cm×8 cm) were soaked in the supernatant for 20 min, followed by incubation in transfer buffer (48 mM Tris, 39 mM glyine, 0.037% SDS, 20% methanol) for 30 min. The membranes were washed 3 times in PBS containing 0.1% Tween-20 and incubated with a 1:100 dilution of the mouse antiserum for 1 hr at 22 C. The incubation was repeated 2 times with fresh membranes. To confirm specificity of the antibody, an aliquot of the adsorbed mouse antiserum was adsorbed a second time against bacterial lysates of BL21 (DE3) cells expressing full length rMTP-1. The adsorbed antiserum was used for Western blotting.

In vitro activation of L3 and collection of ES products: *A. caninum* $L_3$ were activated under host-like conditions as described previously (Hawdon et al, 1999). Briefly, L3 collected from coprocultures were decontaminated with 1% HClin BU buffer (Hawdon and Schad, 1991) for 30 min at 22 C. Approximately 5000 $L_3$ were incubated at 37 C, 5% $CO_2$ for 24 hr in 0.5 ml $RPM_{1640}$, tissue culture medium supplemented with 25 mM HEPES pH 7.0, and antibiotics (Hawdon et al., 1999) in individual wells of 24-well tissue culture plates. L3 were activated to resume feeding by including 15% (v/v) of a<10 kD ultrafiltrate of canine serum and 25 mM S-methyl-glutathione (Hawdon et al, 1995). Non-activated $L_3$ were incubated in RPMI without the stimuli. The percentage of feeding larvae was determined as described (Hawdon et al, 1996).

Medium containing activated and non-activated $L_3$ were transferred to separate microcentrifuge tubes and centrifuged for 5 min at 14,000 rpm. Supernatants from identical treatment groups were pooled, filtered through a 0.45 μm syringe filter to remove any $L_3$ and cast cuticles, and stored at −20 C. Prior to electrophoresis, the supernatants were concentrated by ultrafiltration using Centricon 10 cartridges (Amicon, Beverley, Mass.). Concentrated ES were washed with 1 ml of BU, ultrafiltered, and lyophilized.

To collect adult ES, 1260 adult worms were incubated in $RPM_{1640}$, tissue culture medium (Hawdon et al., 1999) for 15 hrs at 37 C, 10% $CO_2$. The supernatant was concentrated 3-fold by ultrafiltration in Centricon 3 spin columns.

Western blotting: Lysates of bacterial cells expressing rMTP-1 fusion proteins and lyophilized ES products were re-suspended in 2×SDS-PAGE sample buffer (4% SDS, 5% 2-mercaptoethanol, 15% glycerol) and separated on a 4-20% gradient SDS-PAG (Invitrogen, Carlsbad, Calif.). Separated proteins were transferred to a polyvinylidene fluoride membrane (Millipore, Bedford, Mass.) by electroblotting at 25V for 1 hr (Towbin et al., 1979). The membrane was blocked with 5% non-fat dry milk in wash buffer (PBS, pH 7.4, 0.1% Tween 20) for 1 hour at 22 C. The blocked membrane was incubated for 1 hr at 22 C with a 1:5000 dilution of mouse rMTP antisermn which has been preabsorbed against bacterial lysates expressing full length rMTP. The membrane was washed 3 times with wash buffer for 10 min at 24° C., followed by incubation with a 1:5000 dilution of horseradish peroxidase-conjugated goat anti-mouse Ig (Boehringer Mannheim, Indianapolis, Ind. for 1 hour at 22° C. Bands were visualized using chemiluminescent detecting reagents (ECL+, Amersham. Pharmacia Biotech, Piscataway, N.J.).

Results for Example 3A.

Cloning of *A. caninum* MTP cDNA An *A. caninum* L3 cDNA expression library was screened using pooled sera with high anti-hookworm L3 titer collected from human patients in endemic regions of China. Twelve positive clones were identified, 6 of which were identical as determined by DNA sequencing. Each clone contained a 3'poly-A tail, but was truncated at the 5' end. The 5' end was isolated from *A. caninum* $L_3$ cDNA by PCR using a primer derived from the nematode spliced leader (Hawdon et al., 1995; Bektech et al., 1988) together with the gene-specific primers P1.

The full length cDNA, without the poly(dA) tail, is 1703 bp (see FIG. 8A, SEQ ID NO: 15) and encodes a 547 amino acid open reading frame (see FIG. 8B, SEQ ID NO: 16) with a calculated molecular weight of 61,730 and a pI of 8.72. The ATG start codon begins 2 nt downstream from the end of the spliced leader sequence, resulting in a total of 23 untranslated nt at the 5' end of the Ac-mtp-1 cDNA. A TAA stop codon is located at nt 1666-1668, followed by a 35 bp 3' UTR containing an AATAAA polyadenylation signal (Blumenthal and Steward, 1997) 12 bp upstream (bases 1687-1692) from the poly(da) tail. Amino acids 1 through 16 of the deduced protein sequence are predicted to represent a hydrophobic signal peptide, with a potential cleavage site between Ala,6 and Gly,7 (Nielson et al, 1995). The deduced sequence contains 2 potential N-linked glycosylation sites (N—X—S/T) at Asn39 and Asn159.

A BLAST search (Altschul et al., 1997) of GenBank using the Ac-MTP-1 predicted amino acid sequence indicated significant homology to members of a family of zinc metalloproteinases called the astacins (Bond and Benyon, 1995), named for the digestive protease astacin from the crayfish *Astacus astacus*. A search of the protein structure databases (Apweiler et al, 2000) with the Ac-MTP-1 deduced amino acid sequence revealed the presence of characteristic astacin fingerprints, including the extended zinc binding domain and a conserved Met turn located 37 amino acids downstream. The catalytic domain containing the zinc binding site is followed by a domain with homology to epidermal growth factor (EGF), from amino acids 334 to 368. From amino acids 374 to 484 is a domain with weak homology to the CUB domain, named for its occurrence in complement subcomponents Clr/Cls, embryonic sea urchin protein Uegf, and BMP-1. The EGF and CUB domains are common in astacin metalloproteinases, and are believed to be involved in protein-protein interactions (Bond and Benyon, 1995).

Following the N-terminal signal peptide is a 119 amino acid, helix-rich pro-peptide domain. The C-terminal end of the propeptide domain contains a 4 basic amino acid sequence (R-E-K-R) from amino acids 132 to 135 that is a potential recognition site for furin or other trypsin-like processing enzymes (Bond and Benyon, 1995). Proteolysis at this site would activate Ac-MTP-I to a putative 412 amino acid processed form with a calculated MW of 46419 and a pI of 8.04.

RT-PCR analysis of stage specificity: The stage-specificity of Ac-mtp-1 expression was investigated by qualitative RT-PCR of cDNA from several developmental stages of *A. caninum*. Ac-mtp-1 specific primers were designed to amplify a 434 bp portion of the Ac-mtp-1 cDNA corresponding to nt 985-1419 of the complete sequence. The product of the predicted size was amplified from both non-activated and activated $L_3$ cDNA, but not from *A. caninum* egg or $L_1/L_2$ mixed stage cDNA. A band of lesser intensity was seen in adult cDNA. A longer fragment was amplified from genomic DNA, indicating that the primers spanned an intron, and confirming that the amplicons from the cDNAs were derived from amplification of cDNA rather than contaminating genomic DNA. Control primers that amplify a portion of the constitutively expressed *A. caninum* protein kinase A catalytic subunit (Hawdon et al., 1995) successfully amplified product from all DNA samples, indicating that amplifiable template was present.

Expression of recombinant MTP and immunoblotting: Recombinant MTP-1 was produced in *E. coli*, purified by Ni column chromatography, and used to immunize BALB/c mice for the production of specific antiserum. The antiserum was adsorbed against *E. coli* lysates and used to determine if Ac-MTP-1 is secreted by *A. caninum* $L_3$ in vitro. ES products from 10,000 non-activated (non-feeding) and activated (feeding) $L_3$ were analyzed by Western blotting using the rMTP-1 antiserum. The antiserum recognizes both the full length and processed (i.e. without the pro-peptide domain) forms of rMTP-1 expressed in *E. coli* BL21 (DE3) cells but fails to recognize any bands in lysates of induced cells containing the vector alone.

The rMTP antiserum recognized bands of MW, of 47.5 and 44.5 in the ES products of 10,000 *A. caninum* L3 that had been activated to resume feeding in vitro. The antiserum failed to recognize any bands in ES from 10,000 non-activated $L_3$ in culture medium alone, or in adult *A. caninum* ES products or worm lysates (not shown). A slower migrating band in activated ES has a MW similar to that of the processed form of rMTP (47.5 versus 46.5), indicating that *A. caninum* $L_3$ release processed MTP-1 during in vitro activation. The lower MW band was also recognized by pre-immune mouse serum (not shown), suggesting that the antiserum recognized a protein unrelated to Ac-MTP-1. To confirm that this recognition was non-specific, the mouse antiserum was adsorbed against BL21 (DE3) cells expressing full length MTP-1 and used to probe the Western blot. Adsorbed antiserum failed to recognize any rMTP-1, but recognized a band of MWr=44.5 in activated ES products, suggesting that recognition of the lower MW band by the antiserum is non-specific.

Recombinant MTP-1 was recognized by the pooled sera used to screen the library, but sera from individuals living in a non-endemic area (Shanghai) failed to recognize rMTP-1 (not shown).

Example 3B

Isolation and Characterization of a MTP-1 cDNA

Serum from hookworm-infected patients in China was used as a probe to carry out the isolation and characterization of a cDNA from an *A. caninum* L3 expression library that encodes a zincmetalloprotease (Ac-mtp-1) of the astacin family. An *A. caninum* (Baltimore strain) L3 cDNA expression library constructed in 1 ZapII (Stratagene, La Jolla, Calif.) (Hawdon et al., 1995) was screened according to the manufacturer's instructions using pooled antisera from patients in Anhui Province, China, where *A. duodenale* is the predominant hookworm species (Yong et al., 1999). Sera from patients with low fecal egg counts and high titers of circulating antibodies to *A. caninum* L3 whole lysate antigens, suggesting that they might be resistant to hookworm infection, were used. Six identical, truncated clones were recovered following plaque purification. The 5' end was isolated from *A. caninum* L3 cDNA by nested PCR using the nematode spliced leader sequence together with two gene-specific primers (Hawdon et al., 1995), and two independent 5' end clones were sequenced.

Results from Example 3B.

The amplified sequence is believed to represent the complete 5' end of the transcript because the predicted ATG start codon is the first methionine following the spliced leader, the first 16 deduced amino acids encode a signal peptide characteristic of secreted proteins (Nielson et al., 1997), and alignments with similar metalloproteases suggest that this is the complete amino acid sequence. The full length cDNA, without the poly(dA) tail, is 1703 bp and encodes a 547 amino acid open reading frame with a calculated molecular weight of 61,730 and a pI of 8.72. Amino acids 1 through 16 of the deduced protein sequence are predicted to represent a hydrophobic signal peptide, with a potential cleavage site between Ala16 and Gly17 (Nielson et al., 1997). The protein sequence contains two potential N-linked glycosylation sites (NX-S/T) at Asn39 and Asn159. A BLAST search (Altschul et al., 1997) of GenBank using the Ac-MTP-1 predicted amino acid sequence indicated significant homology to members of a family of zinc metalloproteinases called the astacins (Bond and Beynon, 1995), named for a digestive protease from the crayfish *Astacus astacus*. Members of this family are characterized by a short-terminal signal peptide that targets them for secretion, followed by a pro-peptide, and a catalytic domain containing the characteristic zinc-binding region and 'Met turn'. Unlike astacin, most other members of the family contain C-terminal domains, including variable numbers of EGF and CUB domains (Bond and Beynon, 1995). A search of the protein structure databases (Apweiler et al, 2000) with the Ac-MTP-1 deduced amino acid sequence revealed the presence of characteristic astacin fingerprints, including an extended zinc binding region, and a conserved Met turn located 37 amino acids downstream. The catalytic domain containing the zinc binding site is followed by a domain with homology to epidermal growth factor (EGF), from amino acids 334 to 368. From amino acids 374 to 484 is a domain with weak homology to the CUB domain, named for its occurrence in complement subcomponents Clr/Cls, embryonic sea urchin protein Uegf, and BMP-I (Bork and Beckman, 1993).

Astacin metalloproteinases are synthesized as inactive proenzymes. Removal of the pro-peptide by a processing enzyme activates the enzyme (Bond and Beynon, 1995). Ac-MTP-1 contains a 119 amino acid N-terminal domain with a predicted four amino acid recognition site ($R_{132}$ $E_{133}$ $K_{134}$ $R_{135}$) for a trypsin- or furin-type processing enzyme at its C-terminus (Bond and Beynon, 1995). Proteolysis at this site would activate Ac-MTP-1 to a putative 412 amino acid processed form with a calculated MW of 46,419 and a pI of 8.04. The pro-peptide is also predicted to contain four amphipathic α-helices separated by a short linker region (amino acids 23-86) (Kelley et al., 2000).

The stage-specificity of Ac-mtp-1 expression was investigated by qualitative RT-PCR of cDNA from several developmental stages of *A. caninum*. Specific primers were designed to amplify a 434 bp portion of the Ac-mtp-1 cDNA corresponding to nucleotides 985-1419 of the complete sequence. A product of the predicted size was amplified from both non-activated and activated L3 cDNA, but not from *A. caninum* egg or L1/L2 mixed stage cDNA, indicating that Ac-mtp-1 is expressed primarily in the L3 stage. A band of lesser intensity was seen in adult cDNA. Although this band was weak, conclusions regarding the amount of gene expression are not possible, as the RT-PCR is qualitative only. However, a Western blot of adult lysates using mouse anti-rMTP serum failed to recognize any proteins in adult ES or lysates (not shown). This suggests that expression of Ac-MTP-1 is restricted to the L3 stage, and that the message present in the adult stages is untranslated or possibly partially degraded.

Recombinant MTP-1 was produced in *Escherichia coli*, purified by Ni column chromatography, and used to immunize BALB/c mice for the production of specific antiserum. The antiserum was adsorbed against *E. coli* lysates and used to determine if Ac-MTP-1 is secreted by *A. caninum* L3 in vitro. ES products collected from 10,000 non-activated (non-feeding) and activated (feeding) L3 (Hawdon and Schad, 1993) were analyzed by Western blotting using the rMTP-1 antiserum. The antiserum recognizes both the full length and processed (i.e. without the pro-peptide domain) forms of rMTP-1 expressed in *E. coli* BL21(DE3) cells, but fails to recognize any bands in lysates of induced cells containing the vector alone. A lower MW band was observed and is similar in size to the processed rMTP (i.e. lacking the pro-sequence), suggesting that some of the rMTP expressed in *E. coli* undergoes in vitro cleavage at the C-terminal end of the pro-peptide. This is probably the result of autocatalytic cleavage, although non-specific cleavage by a bacterial protease is also a possibility. Autocatalysis might also represent the physiological activation mechanism of Ac-MTP-1 in vivo.

The rMTP antiserum recognized bands of Mr of 47.5 and 44.5 in the ES products of 10,000 *A. caninum* L3 that had been activated to resume feeding in vitro. The antiserum failed to recognize any specific bands in ES from non-activated L3, in culture medium alone, or in adult *A. caninum* ES products or worm lysates (not shown). A slower migrating band in activated ES had a Mr similar to that of the processed form of rMTP (47.5 vs. 46.5), indicating that *A. caninum* L3 release processed MTP-1 during in vitro activation. Furthermore, MTP-1 is released only in response to stimuli that activate L3 to resume feeding, and therefore, most likely functions at some stage of the infective process (Hawdon et al., 1996). The metalloproteolytic activity described previously was also released specifically during activation, and was of similar molecular size (Hawdon et al., 1995), suggesting that Ac-MTP-1 might be responsible for at least a portion of this activity.

A lower MW band (Mr 44.5 kDa) in activated ES products was also recognized by pre-immune mouse serum (not shown), suggesting that the antiserum recognized a protein unrelated to Ac-MTP-1. To confirm that this recognition was non-specific, the mouse antiserum was adsorbed against *E. coli* cells expressing full length MTP-1 and used to probe the Western blot. Adsorbed antiserum failed to recognize any rMTP-1, but recognized a band of Mr 44.5 in activated ES products, suggesting that recognition of the lower MW band by the antiserum is non-specific. Recombinant MTP-1 was recognized by the pooled sera used to screen the library, but sera from individuals living in a non-endemic area (Shanghai) failed to recognize rMTP-1 (not shown).

While the exact function of Ac-MTP-1 is unknown, the stage specificity of expression and the specific release during activation suggest a critical role in the infective process. Thus, interruption of Ac-MTP-1 function in vivo offers a useful strategy for the development of a vaccine to control hookworm disease.

This example demonstrates that MTP-1 is an important enzyme used by the hookworm parasite for invasion, and the protein is an immunodominant antigen because it is recognized by serum from patients with low hookworm burden despite repeated exposure to hookworm. MTP is therefore an attractive candidate for a vaccine antigen.

Example 3C

Canine Vaccine Trials with Ac-MTP-1 Antigen

To test whether Ac-MTP-1 could be an effective vaccine, two groups of five (5) purpose-bred male beagles 8+1 wk of age were vaccinated either with the recombinant (expressed and isolated from *Escherichia coli*) fusion protein formulated with AS02A adjuvant, or adjuvant alone. The composition of AS02A, which has been successfully used in several malaria vaccine clinical studies, is described elsewhere (Lalvani et al, 1999; Bojang et al, 2001; Kester et al, 2001). Details of the animal husbandry and housing conditions were reported previously (Hotez et al, 2002a). The recombinant fusion protein containing a polyhistidine tag was purified from washed *E. coli* inclusion bodies that were solubilized in 6 M guanidine-HCl in 10 mM Tris HCl, pH 8.0. The solubilized inclusion bodies were processed in 5-10 ml batches by gel filtration chromatography (Sephacryl S-300, 26/60 gel filtration column [Amersham Pharmacia] pre-equilibrated in a buffer containing 0.1 NaH2PO4, 10 mM Tris-HCl and 6 M guanidine) at room temperature (flow rate of 2 ml/minute). Selected fractions containing Ac-MTP-1 (as determined by analysis on sodium dodecyl sulfate-polyacrylamide gel electrophoresis [SDS-PAGE]) were pooled, refolded according to the method of Singh et al (2001), and then loaded onto a 5 ml Hi-Trap IMAC column (Amersham Pharmacia) charged with $ZnCl_2$ and equilibrated in 50 mM sodium phosphate pH 7.2, 1 M urea, and 0.5 M NaCl. The column was subsequently washed with 15 column volumes of equilibration buffer, and the bound protein was eluted with 50 mM sodium phosphate pH7.2, 1 M urea, 0.5 M NaCl, and 50 mM ethylenediamine tetraacetic acid (EDTA). Eluted samples containing protein were pooled and dialyzed against 10 mM Tris-HCl pH 8.0, 5% glycerol, 1 mM dithiothreitol, and 2 mM EDTA. The purified recombinant Ac-MTP-1 did not exhibit enzymatic activity (data not shown).

The recombinant Ac-MTP-1 fusion protein was mixed with SBAS2 adjuvant and administered to each of five dogs in four intramuscular injections on days 1, 4, 43, and 50. Each dog received approximately 140 μg of recombinant fusion protein and 0.5 ml of AS02A per dose. Five dogs were also injected intramuscularly with AS02A on the same schedule. Following immunization, blood was collected weekly by venipuncture and the serum was separated and stored frozen at −20° C. Antigen-specific canine IgG2 and IgE antibodies were measured by indirect enzyme-linked immunosorbent assay (ELISA) as described previously (Hotez et al, 2002a). Immunoblotting of secretory products from nonactivated L3 and L3 activated under host stimulatory conditions was done as described previously (Zhan et al, 2002) using pooled sera from the Ac-MTP-1-vaccinated dogs. Fourteen days following the final immunization, each dog in the study was subcutaneosly infected with 500 *A. caninum* L3. The origin of the hookworm strain used for the study is described elsewhere (Hotez et al., 2002c). Validation of the hookworm species used in the study was confirmed by a polymerase chain reaction followed by restriction fragment length polymorphism (Hawdon, 1996). Following infection, the dogs were bled weekly by venipuncture to obtain a complete blood count (CBC). Serum chemistries were also obtained at the end of the vaccination schedule and prior to necropsy. Quantitative hookworm egg counts (McMaster technique) on each dog were obtained 3 days per wk beginning on day 12 post-infection (PI). Five wk post-infection, the dogs were killed by intravenous barbituate injection, and the adult hookworms were recovered and counted from the small and large intestines at necropsy (Hotez et al., 2002c). The statistical significance of differences between adult hookworm burdens was determined using the Anova test, as were differences in hematological parameters and in quantitative hookworm egg counts. Comparisons of hookworm burden and egg counts with antibody titers were measured using Spearman rank order (nonparametric) correlations.

SDS-PAGE analysis of the Ac-MTP-1 recombinant fusion proteins followed by Coomassie blue staining revealed that the protein migrates with an apparent MW of 61 kDa—the predicted mass of the proenzyme. Also present is a triplet of bands that migrate with a lower apparent molecular weight, which probably corresponds to the partially processed Ac-MTP-1. Following immunization, each of the vaccine-recipient dogs developed high titers of IgG2 anti-Ac-MTP-1-specific antibody ranging between 1:40,500 and 1:364,500; the anti-Ac-MTP-1-specific IgE antibody responses ranged between 1:500 and 1:1,500. Sera from the vaccinated dogs recognized a triplet of closely migrating proteins with the predicted molecular weight of the proenzyme and processed form of Ac-MTP-1 in secretory products of host-activated L3, but not in those of non-activated L3. The additional bands may also correspond to other related metalloproteases secreted by *A. caninum* L3; at least 3 closely related expressed sequence tags from *A. caninum* L3 were found in a dbEST database (ncbi.nim.nih.gov/dbEST/index.html).

Figure 33B:
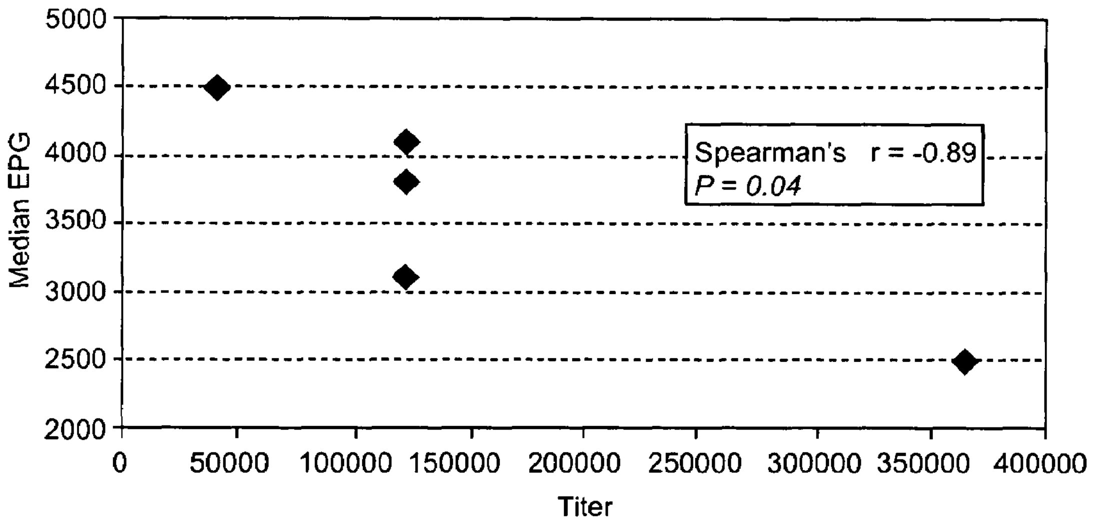

Overall, there were no statistically significant differences in the number (mean+standard deviation) of adult hookworms recovered from the vaccinated dogs (154+34 hookworms) compared to the number of adult hookworms recovered from control dogs (143+30 hookworms). However, as shown in FIG. 33A there was a statistically significant reduction in the number of adult hookworms recovered from the intestines of vaccinated dogs that had high anti-*A. caninum* IgG2 antibody titers. The Spearman correlation between antibody titers and adult hookworm burden was −0.89 (P=0.04). The number of hookworms recovered from the dog with the highest antibody titer (98 hookworms) was equivalent to a 50 percent reduction in worm burden compared to the number of adult hookworms recovered from the dog with the lowest antibody titer (189 hookworms). An identical relationship was noted between IgG2 antibody titers and median quantitative egg counts (FIG. 33B).

These studies suggest that Ac-MTP-1 might offer downstream promise as an anti-hookworm vaccine antigen.

Example 4

Canine Vaccine Trials with Ac-TMP, Ac-AP, and Ac-APR-1 Antigens

To evaluate whether antibodies directed against parasite enzymes and enzyme inhibitors have therapeutic potential for ancylostomiasis, canine vaccine trials employing recombinant fusion proteins that encode adult *A. caninum* proteases or protease inhibitors were conducted. Because small quantities of proteins are available from living hookworms, testing these molecules as vaccine candidates requires recombinant vector expression in prokaryotic or eukaryotic host systems, followed by canine immunization with the purified recombinant fusion protein.

Material and Methods for Example 4.

Study dogs and animal husbandry: Following protocol approval by The George Washington University Institutional Animal Care and Use Committee (IACUC), purpose bred, parasite naïve, male beagles 8±1 week of age were purchased, identified by ear tattoo, and maintained in the AALAC (Association for Assessment and Accreditation of Laboratory Animal Care) accredited George Washington University Animal Research Facility. The dogs were housed in a room dedicated for the study, at a room temperature of 70±4° F., with 10-15 air changes per hour comprised of 100 percent fresh air, and 12 hr light cycles alternating with 12 hr dark cycles. The airflow and timer functions were monitored daily. The dogs were fed on a diet of Teklad Certified Dog Chow #8727, supplemented with a canned soft diet in the event of anorexia. The drinking water was piped from a filter plant and delivered via automatc water system; water analysis was performed by the U.S. Army Corps of Engineers. Water from the facilities automatic system is cultured for bacteria and fungi annually. The pens were flushed daily and sanitized every two weeks. Dogs within a given study group were permitted to live together and socialize prior to the hookworm larval challenge, but were caged individually post-infection. All dogs were quarantined for approximately one week before beginning the vaccine trial. Prior to vaccination a complete blood count (CBC), serum chemistries, and a pre-vaccination serum sample were obtained.

Vaccine study design and sample size: The vaccine trial was designed to test three different antigens, each formulated with alum, as well as an alum adjuvant control. A total of 24 dogs were randomly assigned into four groups comprised of 6 dogs each. The canine sample size was selected on the ability to detect a 40-50 percent reduction in the numbers of adult hookworms in the small intestines of the vaccinated group relative to control dogs, at a statistical power of 80 percent (alpha=0.05, two-tailed). The data were derived from the mean and standard deviation of adult hookworms previously recovered from age-matched dogs infected with 400 *A. caninum* $L_3$ (Hotez et al, 2002).

Recombinant Antigens: Each group of 6 dogs was vaccinated with recombinant hookworm proteins expressed as fusion proteins either in *Escherichia coli* or in an insect cell line with baculovirus. Ac-AP (Cappello et al, 1995; 1996) and Ac-TMP, were expressed in *E. coli* as pET 28 (Novagen) fusion proteins containing a polyhistidine tag (Cappello et al, 1996). Ac-APR-1 (Harrop et al, 1996) was expressed in a baculovirus pBacPAK6 vector (Clontech), modified to contain a polyhistidine-encoding sequence and additional restriction enzyme sites (Brindley et al, 2001). Recombinant Ac-AP and Ac-TMP fusion proteins were then purified by nickel affinity chromatography, followed by a second step of purification. In the case of Ac-AP (Cappello et al, 1995; 1996), the recombinant protein was purified by mono-S (Amersham-Pharmacia) ion exchange chromatography, while Ac-TMP (Zhan et al, 2002) was purified by superdex 75 (Amersham-Pharmacia) gel filtration chromatography. Ac-APR-1 (Harrop et al, 1996) was purified by substrate affinity chromatography using pepstatin agarose (Brindley et al, 2001). The antigen stock protein concentration was determined by Pierce Micro BCA assay (Pierce Chemicals) or by the absorbance of the sample at 289 nm using an extinction coefficient that was calculated from the deduced amino acid composition of the fusion protein. The amount of alum adsorbed protein in each dose of antigen was measured by the Pierce Micro BCA assay using a bovine serum albumin standard. The relative purity of each of the antigens relative to contaminating *E. coli* or insect cell proteins was determined by analysis on sodium dodecyl sulfate polyacrylamide gel electrophoresis (SDS-PAGE).

Adjuvant formulations: Recombinant Ac-TMP and Ac-APR fusion proteins were alum precipitated with a combination of aluminum potassium sulfate dodecahydrate and sodium bicarbonate as described previously (Ghosh et al, 1996). The method requires the precipitation of an aqueous solution of the protein with aluminum salt under alkaline conditions, followed by centrifugation and washing (Ghosh and Hotez, 1999). Using this method, recombinant Ac-AP fusion protein was not detected in the alum precipitate. Therefore, the first two doses of Ac-AP were administered without adjuvant. However, the final two doses of Ac-AP were adsorbed to an amorphous, non-crystalline calcium phosphate gel.

Canine Immunizations: A four-dose immunization schedule was selected (Table II). Each of the dogs was vaccinated by subcutaneous immunization at two sites in the shoulder, through a 22 gauge needle. The volume of the injections ranged between 0.5 and 1.0 ml. Four doses of each antigen were administered over a 38-day period. The first two injections (primary immunization) were administered on days 1 and 4, and the final two immunizations (boosts) were administered on days 34 and 38. Dogs in the control group were injected with an equivalent amount of alum.

TABLE II

Antigen quantities and adjuvants used for each canine vaccination.

| | Ac-AP | Ac-TMP | Ac-APR-1 | Alum |
|---|---|---|---|---|
| Dose 1 (day 1) | 100 μg | 71 μg | 12.5 μg | — |
| Adjuvant | None | Alum | Alum | Alum |
| Dose 1 (day 1) | 100 μg | 71 μg | 12.5 μg | — |
| Adjuvant | None | Alum | Alum | Alum |
| Dose 1 (day 1) | 180 μg | 61 μg | 95 μg | — |
| Adjuvant | Calcium phosphate | Alum | Alum | Alum |
| Dose 1 (day 1) | 273 μg | 69 μg | 86 μg | — |
| Adjuvant | Calcium phosphate | Alum | Alum | Alum |

Canine antibody measurements: Blood was collected weekly by venipuncture and the serum was separated and stored frozen at −20° C. Antigen-specific canine IgG1 antibodies were measured by indirect enzyme-linked immunosorbent assay (ELISA). Other IgG subclasses were not measured due to the unavailability of suitable high-quality canine-specific reagents. The optimal concentrations of sample sera and enzyme-linked detection antibody were determined by checkerboard titrations. Optimal antigen concentrations were determined by using a saturation technique. NUNC Maxisorp F96 certified plates (Rosklide, Denmark; Batch no. 045638) were coated with 0.1 ml per well of antigen in 0.05M carbonate bicarbonate buffer (pH 9.6). Sealed plates were incubated overnight (ON) at 4 C and then washed 3 times with PBS (pH 7.2) using a DYNEX Opsys plate washer (Chantilly, Va.). The plates were treated for 1.5 hours with 0.25 ml per well of 0.15M PBS (pH 7.2) containing 0.5% Tween 20 (PBS-Tween 20) at room temperature (RT), decanted, and blotted on paper towels. Various serial dilutions of test sera were prepared in 0.1 ml PBS-Tween 20 and incubated ON at 4 C. After washing, 0.1 ml of anti-canine IgG1 conjugated to alkaline phosphatase (Bethyl Laboratories, Montgomery, Tex.) at a dilution of 1:1000 were added to each well. After 1.5 hours at RT, the plates were washed 10 times with PBS-Tween 20, before 0.1 ml of 2.5 mM of para-nitro phenylphosphate (Sigma St. Louis, Mo.) in a solution of 10 mM diethanolamine (Sigma, St. Louis, Mo.) and 0.5 mM magnesium chloride (Sigma, St. Louis, Mo.) (pH 9.5) were added to each well. The plates were incubated in the dark for 30 minutes and read at a wavelength of 405 nm on a SpectraMax 240 PC reader (Molecular Devices, Sunnyvale, Calif.) with SOFTmax Pro software (Molecular Devices, Sunnyvale, Calif.). The mean optical density of control canine sera was used as a baseline. The last serum dilution greater than 3 times above baseline was considered the titration endpoint. The geometric mean of these endpoints was calculated for the six canines from each group.

Canine hookworm infections and parasite recovery: Fourteen days following the final immunization, each dog in the study was orally infected with 400 *A. caninum* $L_3$ administered in a gelatin capsule. The origin of the hookworm strain used for the study is described elsewhere (Hotez et al, 2002). Validation of the hookworm species used in the study was confirmed by a polymerase chain reaction followed by restriction fragment length polymorphism (Hawdon, 1996). Following infection, the dogs were bled weekly by venipuncture in order to obtain a complete blood count (CBC). Serum chemistries were also obtained at the end of the vaccination schedule and prior to necropsy. Quantitative hookworm egg counts (McMaster technique) on each dog were obtained three days per week beginning on day 12 post-infection. Five weeks post-infection, the dogs were euthanized by intravenous barbituate injection, and the adult hookworms were recovered and counted from the small and large intestines at necropsy (Hotez et al, 2002). The sex of each of the adult hookworms was determined by visual inspection. The necropsies were performed over a period of three days when 8 dogs per day (two dogs from each of the four groups) were euthanized. Approximately 1-2 cm of small intestine was separated and placed into formalin for future histopathological analysis.

Statistical methods: The percentage reduction or increase in adult hookworm burden in the vaccinated group was expressed relative to the control group by the following formula:

$$\frac{\left(\begin{array}{c}\text{mean hookworms in control group} - \\ \text{mean hookworms in vaccinated group}\end{array}\right)}{(\text{mean hookworms in control group})} \times 100$$

The statistical significance of differences in adult hookworm burdens was determined using nonparametric tests; the Kruskal-Wallis with Dunn procedures, and Mann-Whitney U tests. Differences between groups in hematological parameters and in quantitative hookworm egg counts were assessed by the ANOVA test. When more than two tests were computed on the same variable, the level of significance was adjusted for the number of tests. The sex differences of the adult hookworms recovered were statistically compared by the Wilcoxon-Signed Ranks test for two dependent groups. Differences were considered statistically significant if the calculated P value was equal to or less than 0.10 (two sided) or −0.05 (one sided).

Results for Example 4.

Adult *A. caninum* antigens: Three recombinant *A. caninum* antigens were selected for canine vaccinations. Two of them, Ac-AP and Ac-TMP are protease inhibitors secreted only by adult stage hookworms. Ac-AP is a 91 amino acid factor Xa inhibitor anticoagulant (Cappello et al, 1995; 1996), and Ac-TMP is a 140 amino acid putative tissue inhibitor of metalloproteinase, and the most abundant protein secreted by *A. caninum*. The third antigen selected, was Ac-APR-1, a 422 amino acid aspartic acid cathepsin (Harrop et al, 1996). SDS-PAGE analysis of the recombinant fusion proteins followed by Coomassie blue staining was carried out. As expected, the recombinant fusion proteins Ac-APR-1 and Ac-TMP migrated on SDS-PAGE with apparent molecular weights of $M_r$=45,000 and 18,000, respectively. The predicted molecular mass of Ac-AP expressed as a pET 28 fusion protein with an N-terminal polyhistidine tag is 12,191 Da (Cappello, 1996). On SDS-PAGE, the recombinant Ac-AP fusion protein was visualized as a band with a predominant Mr of 22,000 and a minor band that migrates at approximately 15,000 Da. This observation may correspond to polypeptide oligomer formation. This was shown previously to occur during purification of the Ac-AP natural product (Cappello et al, 1995). Factor Xa inhibitory activity, DNA sequence analysis of the pET 28 plasmid encoding the recombinant Ac-AP fusion protein, and amino terminal peptide sequence analysis by Edman degradation of the 22 kDa band confirmed the identity of the gene product (data not shown).

Canine antibody responses. A canine vaccination schedule was selected that provided for a primary immunization to be administered in two subcutaneous doses over an initial 4-day period (day 1 and day 4), followed by two subsequent subcutaneous immunization boosts that were administered beginning 30 days after the primary immunizations (day 34 and day 38). Ac-TMP and Ac-APR-1 were injected as alum-precipitated proteins. In contrast, Ac-AP did not form a precipitate with alum. Therefore, for the first two doses, Ac-AP was administered subcutaneously without adjuvant. However, during the 30-day time period between the second and third immunization, a protocol that employed calcium phosphate gel was shown to effectively precipitate Ac-AP (data not shown). For that reason, calcium phosphate was selected as the adjuvant for the final two immunizing doses of Ac-AP.

Figure 34A:
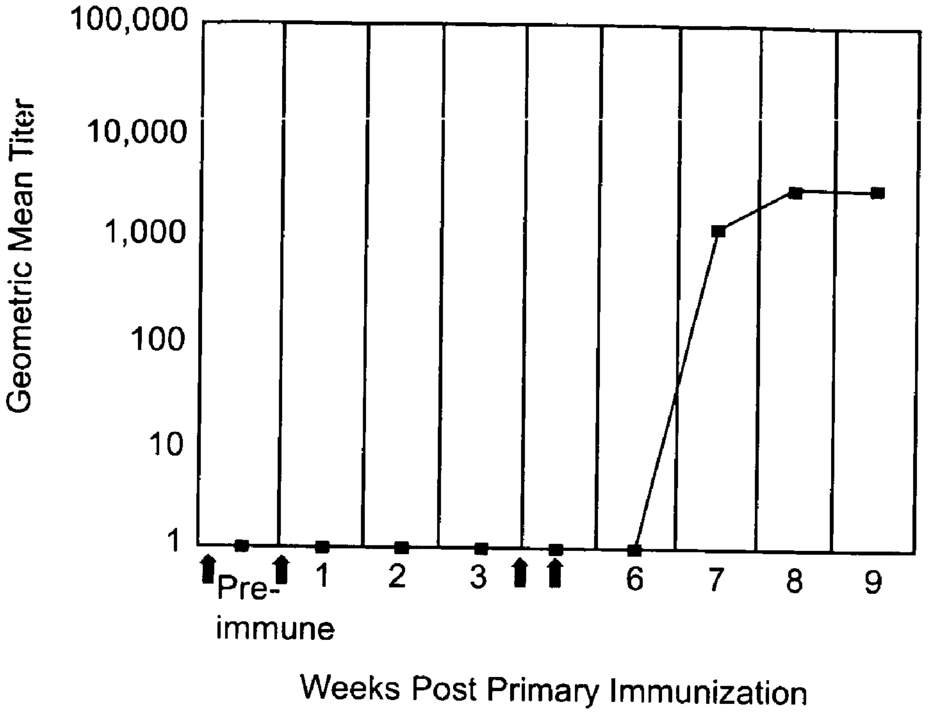
FIG. 34A-C. Antigen-specific geometric mean IgG1 antibody titers in dogs vaccinated with *A. caninum* recombinant fusion proteins as a function of time. Geometric means were calculated for a total of 6 dogs in each group, except for Ac-AP in which only a single dog developed an antigen-specific antibody response. The arrows denote timed vaccinations. (A) Anti-Ac-APR-1 responses (n=6). (B) Anti-Ac-TMP responses (n=6). (C) Anti-Ac-AP responses (n=1).
Figure 34B:
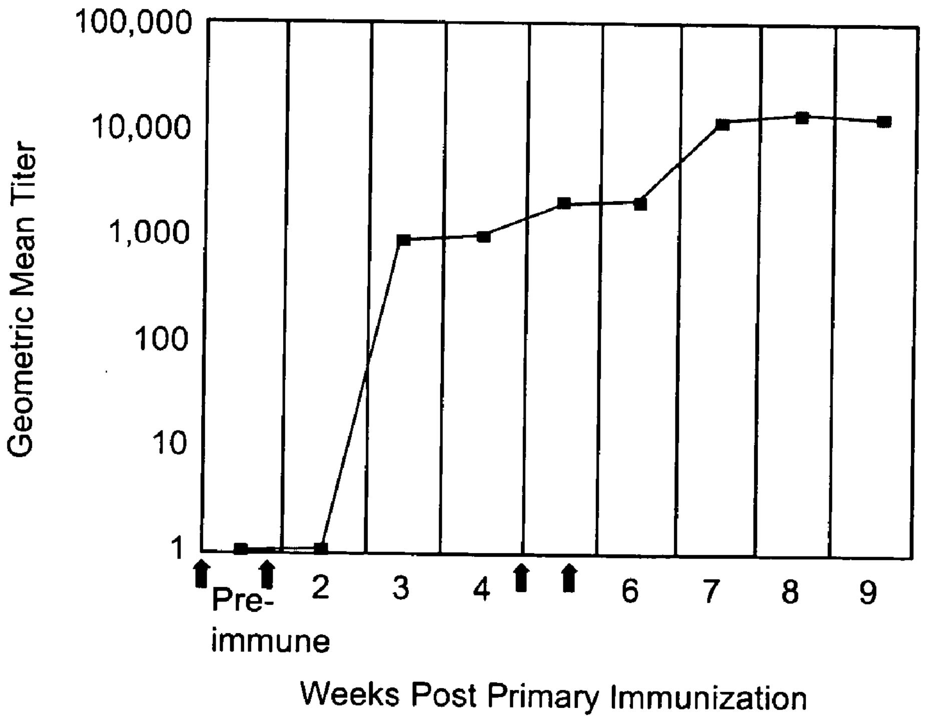
Figure 34C:
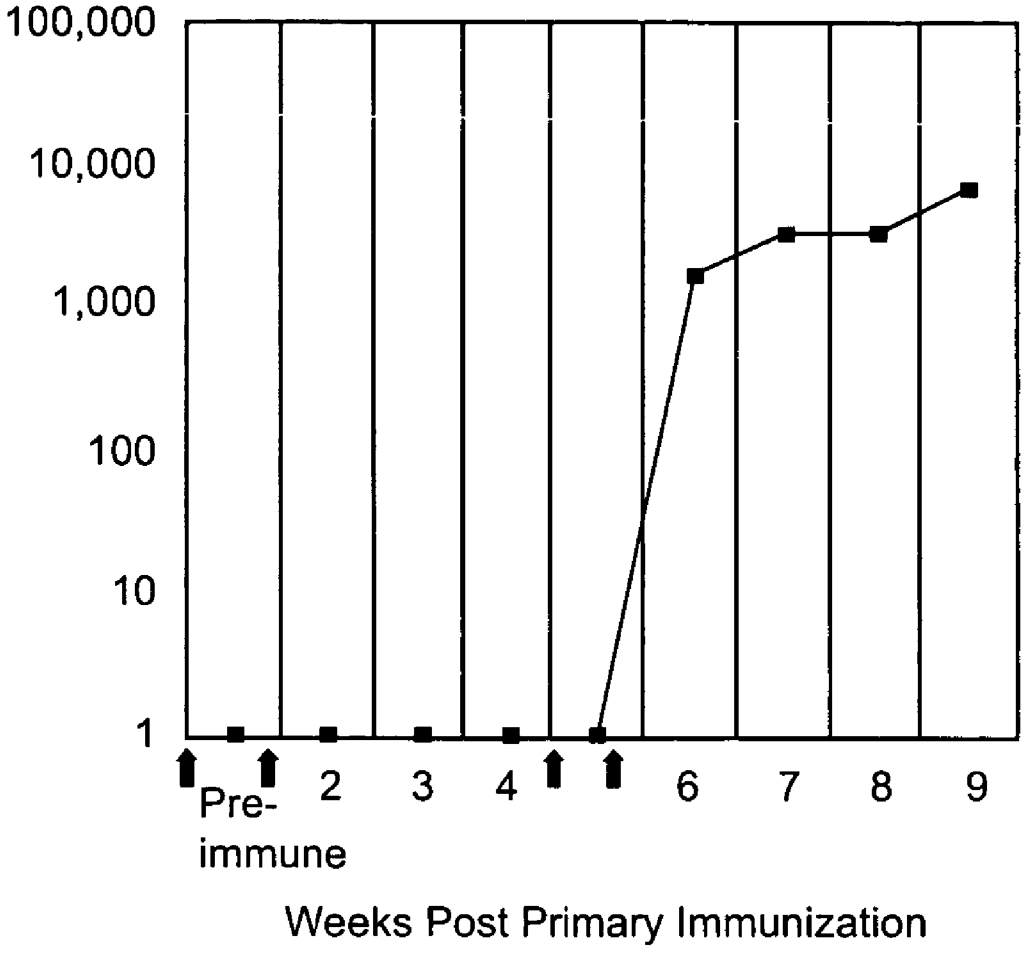

Geometric mean IgG1 antibody titers to the three vaccine antigens are shown in FIG. 34A-C. Among the dogs vaccinated against Ac-APR-1 (FIG. 34A), there was a rise in antigen-specific IgG1 following the final two immunization boosts at approximately 6 weeks after the primary immunization. In contrast, anti-Ac-TMP IgG1 antibody responses were more robust (FIG. 34B), and began to increase 2 weeks following the primary immunization, prior to the third and fourth doses. Following the final two boosts there was a second increase in anti-Ac-TMP antibody titer that exceeded 1:10,000. Five of the six dogs vaccinated against Ac-AP failed to respond immunologically to the antigen. As shown in FIG. 34C, the single canine who responded to Ac-AP vaccination exhibited an antigen-specific antibody response following the final two doses.

Adult *A. caninum* hookworm recovery from the small intestine. The numbers of adult *A. caninum* hookworms recovered from the small intestines of the vaccinated dogs is shown in Table III. Hookworm burden reductions in the vaccinated dogs relative to dogs injected with alum alone ranged between 4.5 to 18 percent. The above reduction was not sufficient to show statistical significance between groups (Kruskal-Wallis test, P=0.19). However, the probability (P) of 18 percent reduction in the number of hookworms recovered from the small intestines of the dogs vaccinated with Ac-APR-1 (the biggest reduction in one group) was less than 0.05 by the Dunn procedure, and 0.03 by Mann-Whitney U one sided test. Dogs vaccinated against Ac-TMP also exhibited a reduction in the adult hookworm burden (10.8 percent) although this was not statistically significant. The five dogs that did not exhibit an antibody response against Ac-AP, also exhibited no significant hookworm burden reduction. However, the single dog with a significant anti-Ac-AP antibody response, exhibited a 34.7 percent reduction in adult hookworm burden. As shown in Table III, data did not provide sufficient evidence for statistically significant reductions in quantitative hookworm egg counts between the vaccinated and control dogs. Similarly, vaccination did not affect the hematological parameters of the dogs, including hematocrit, hemoglobin, white blood cell count, and eosinophilia (data not shown). As expected, the challenge dose of hookworm used in this study did not produce anemia in the control alum-injected dogs (data not shown). Adult *A. caninum* hookworm recovery from the colon.

TABLE III

Reduction of adult hookworms in the small intestines of vaccinated relative to alum-injected dogs.

| Experimental group | Dogs No. | WORMS Mean | SD | Median | % Decrease |
|---|---|---|---|---|---|
| Control | 6 | 176 | 22 | 180 | |
| Ac-AP | 5 | 168 | 36 | 170 | 4.5 |
| Ac-AP* | 1 | 115 | | 115 | 34.7 |
| Ac-TMP | 6 | 157 | 26 | 161 | 10.8 |
| Ac-APR-1 | 6 | 144 | 31 | 138 | 18** |

*Positive immune response
**P < 0.05 (Dunn procedure)

Whereas there was a reduction in the numbers of adult hookworms recovered from the small intestines of vaccinated dogs, there was a corresponding increase in the number of adult hookworms that were recovered from the colon (Table IV).

TABLE IV

Increase of adult A caninum hookworms in the colons of vaccinated dogas relative to alum-injected dogs.

| Experimental group | Dogs No. | WORMS Mean | SD | Median | % Increase |
|---|---|---|---|---|---|
| Control | 4 | 6 | 8 | 4 | |
| Ac-AP | 5 | 17 | 17 | 14 | 183 |
| Ac-AP* | 1 | 71 | | 71 | 1083 |
| Ac-TMP | 4 | 36 | 11 | 32 | 500** |
| Ac-APR-1 | 5 | 24 | 11 | 27 | 300** |

*Positive immune response
**P < 0.05 (Dunn procedure)

The increase in the number of adult hookworms recovered from the large intestines was statistically significant (Kruskal-Wallis test, P=0.07). The dogs vaccinated with either Ac-TMP (500 percent increase) or Ac-APR-1 (300 percent increase), exhibited a statistically significant increase relative to the dogs injected with alum (Dunn procedure, P<0.05). Dogs that were vaccinated with Ac-AP but did not exhibit an antigen-specific antibody response did not have a statistically significant increase in the number of adult hookworms recovered from the colon. However, the single dog with a significant anti-Ac-AP antibody response exhibited a 1083 percentage increase in the number of adult hookworms in its colon.

Overall, there were no statistically significant differences between the vaccinated and control dogs with respect to the total numbers of adult hookworms recovered from small and large intestines combined (data not shown). Instead, antibody responses to the recombinant hookworm antigens resulted in significant migration of adult hookworms away from the small intestine and into the colon. The ratio of adult hookworms in the small intestine relative to the colon decreased from 43.9 in the alum-injected dogs down to ratios between 6.6 and 7.3 in the Ac-TMP and Ac-APR-1 vaccinated dogs, respectively. The single dog exhibiting an anti-Ac-AP antibody response had a small intestine to colon hookworm burden ratio of 1.6, indicating that almost one-half of this dog's hookworm burden had shifted to the colon.

Figure 35:
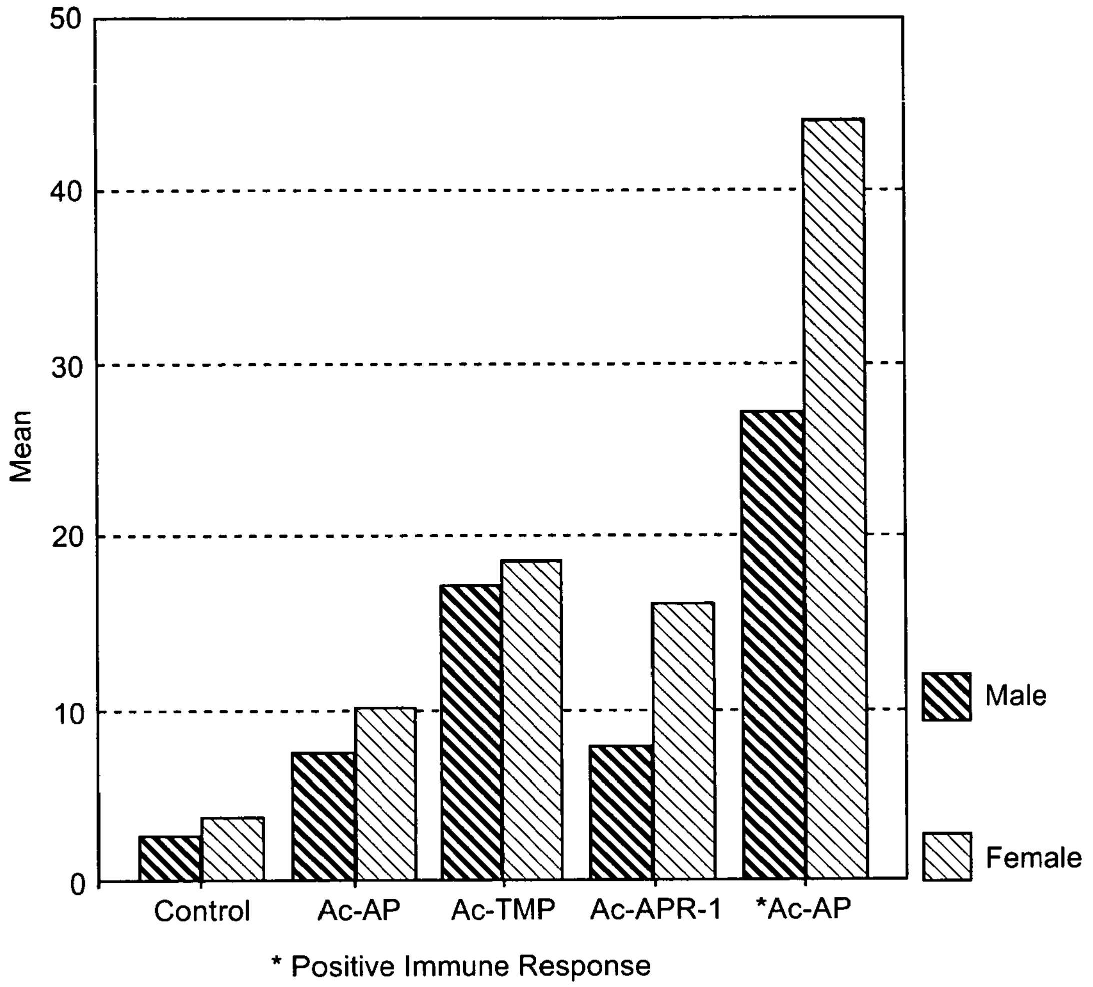
FIG. 35. Female and male adult *A. caninum* hookworms recovered from the colons of either vaccinated or alum-injected dogs.

Sex-dependent differences. Hookworms of either sex did not migrate away from the small intestine and into the colon in equal numbers. As shown in FIG. 35, it was more common to recover female adult hookworms from the colon than males. The greater numbers of female hookworms residing in the colon was statistically significant for dogs vaccinated with Ac-APR-1 (P=0.04) and Ac-AP (P=0.06). Male hookworms were more likely than female hookworms to be recovered from the small intestines, although the differences were not statistically significant. Sex determinations were not made on the hookworms attached to a 1-2 cm segment of small intestine that was saved for histopathological analysis. The mean number of hookworms in this segment ranged between 5 and 6 worms. This small number of worms did not contribute significantly to the sex-dependent difference score (data not shown).

This example demonstrates that it is feasible to vaccinate mammals with recombinant fusion proteins to elicit an antigen specific response, and that the antibody response is associate either with a hookworm burden reduction in the gut or in a shift in hookworm habitat in the gut.

Example 5

Canine Vaccine Trials of Ac-MTP-1 and Ac-TTR

Example 5

A. Antibody Titers and Hookworm Reduction

*E. coli* derived antigens Ac-MTP-1 and Ac-TTR were tested in vaccine trials in dogs. Antigens were administered with adjuvant SBAS2. The vaccinated animals exhibited high levels of canine IgG2 antigen-specific antibodies, and a modest increase in antigen-specific IgE. Subsequently the dogs were challenged by subcutaneous injection of L3 hookworm larvae.

Figure 36A:
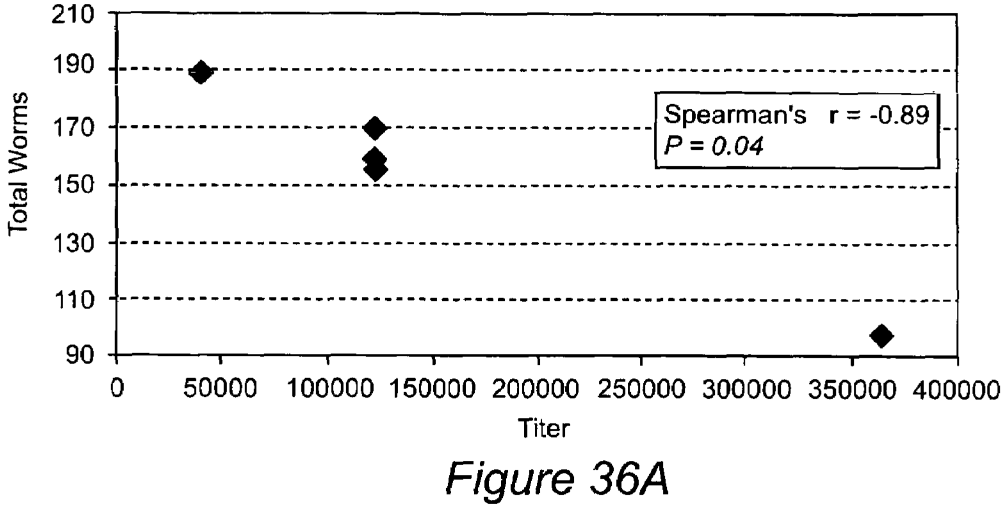
FIGS. 36A and B. Spearman rank order correlations between hookworm burden and anti-MTP-1 antibody titer FIGS. 37A and B. A) Relationship between anti-TTR IgE antibodies and hookworm burden reductions; B) Relationship between anti-TTR IgG1 antibodies and hookworm burden reductions FIGS. 38A and B. HV-4 Canine hemoglobin (B) and hematocrit (A) changes following L3 challenge FIG. 39. Statistically significant reduction in worm size (between 1 and 2 mm) among the TTR vaccinated group relative to the adjuvant control group.
Figure 36B:
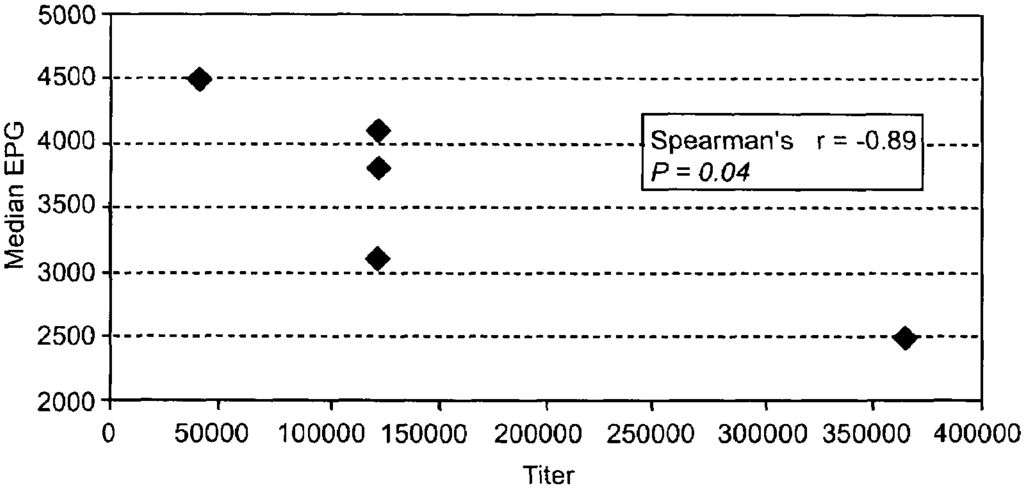

As shown in FIGS. 36A and B, there was a statistically significant reduction in the number of adult hookworms recovered from the intestines of vaccinated dogs that had high anti-*A. caninum* IgG2 anti-MTP-1 antibody titers. The Spearman correlation between antibody titers and adult hookworm burden was −0.89 (P=0.04). The number of hookworms recovered from the dog with the highest antibody titer (98 hookworms) was equivalent to a 50 percent reduction in worm burden compared to the number of adult hookworms recovered from the dog with the lowest antibody titer (189 hookworms). An identical relationship was noted between IgG2 antibody titers and median quantitative egg counts.

SDS-PAGE analysis of the Ac-MTP-1 recombinant fusion proteins followed by Coomassie blue staining revealed that the protein migrates with an apparent MW of 61 kDa—the predicted mass of the proenzyme. Also present is a triplet of bands that migrate with a lower apparent molecular weight, which probably corresponds to the partially processed Ac-MTP-1. Following immunization, each of the vaccine-recipient dogs developed high titers of IgG2 anti-Ac-MTP-1-specific antibody ranging between 1:40,500 and 1:364,500; the anti-Ac-MTP-1-specific IgE antibody responses ranged between 1:500 and 1:1,500. Sera from the vaccinated dogs recognized a triplet of closely migrating proteins with the predicted molecular weight of the proenzyme and processed form of Ac-MTP-1 in secretory products of host-activated L3, but not in those of non-activated L3.

Figure 37A:
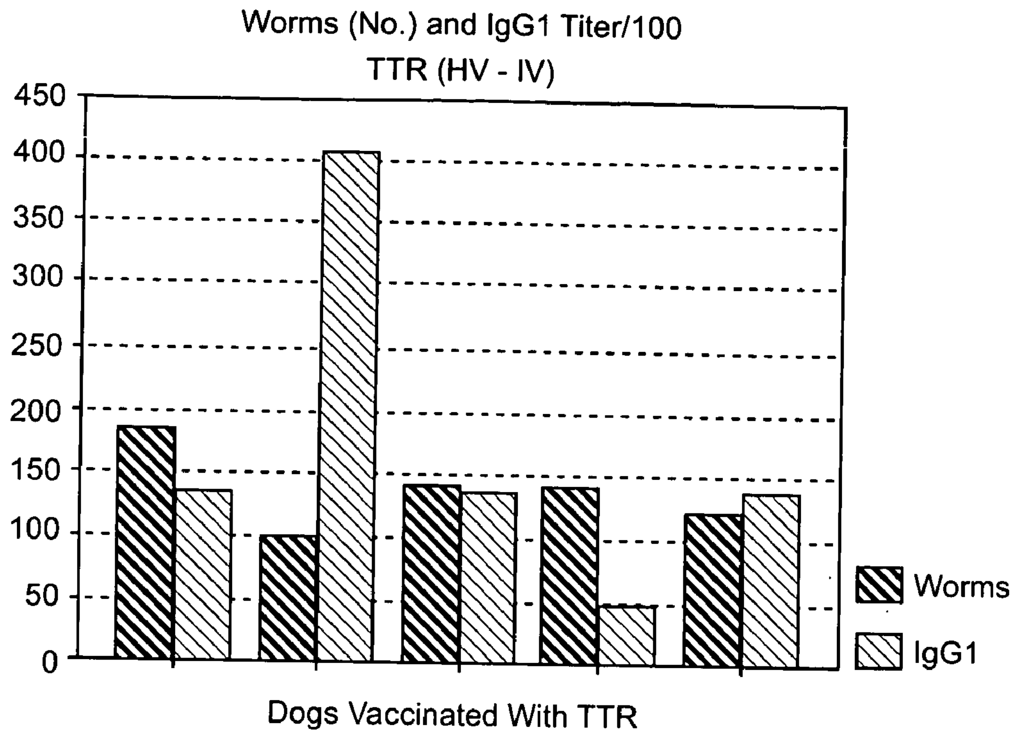
Figure 37B:
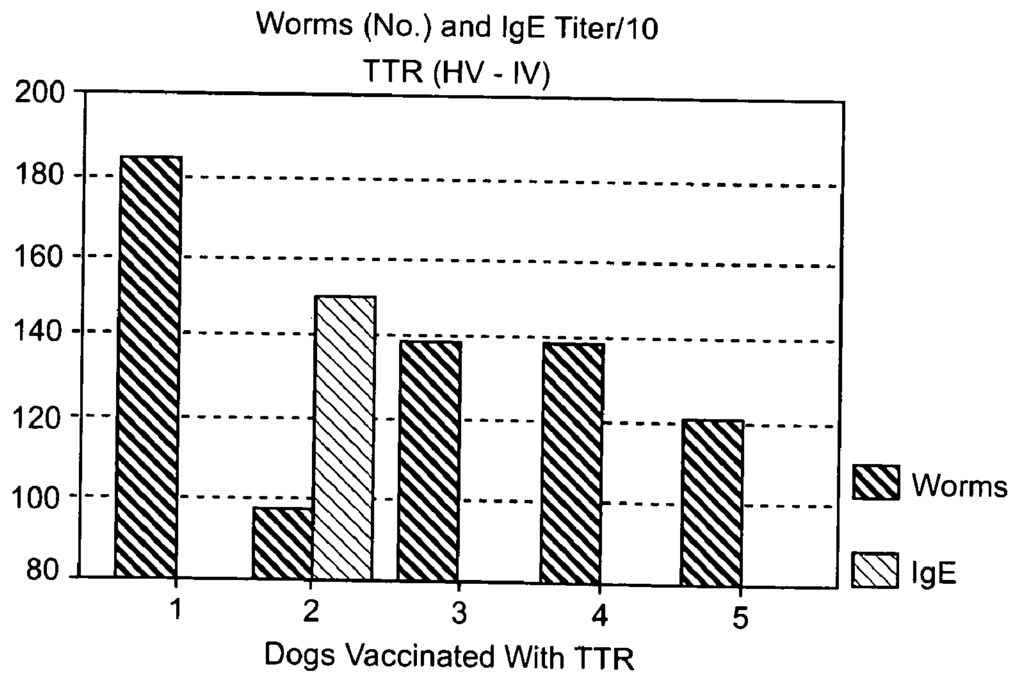

With respect to the use of the TTR antigen, as can be seen in FIGS. 37A and B, one dog with high IgE and IgG1 antibody to TTR exhibited reduced (6%) hookworm burden.

This example demonstrates that vaccination of mammals with either MTP or with TTR elicit a protective antibody response, and that with high antibody titers a reduction in worm burden is observed.

Example 5B

Figure 38A:
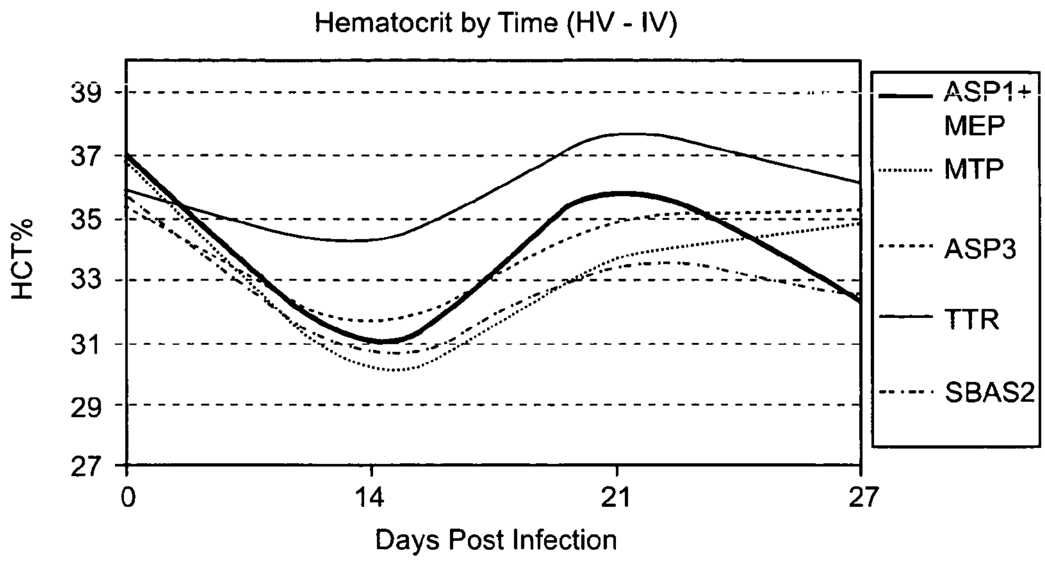
Figure 38B:
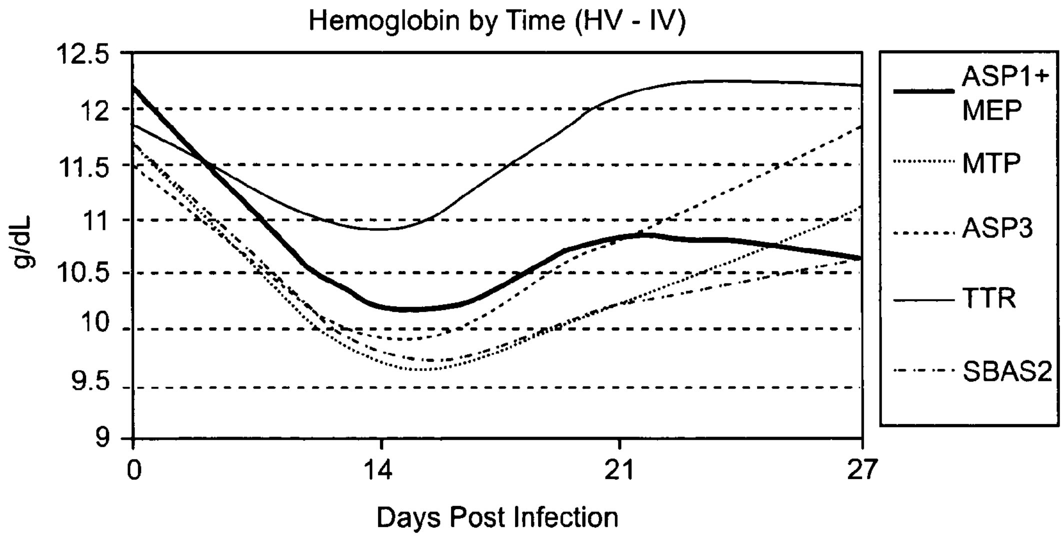

Protection Against Blood Loss and Decrease in Hookworm Size Due to Vaccination with Hookworm Antigen Animals were also tested to ascertain whether vaccination with hookworm antigens protected against blood loss. Vaccination with Ac-TTR was shown to confer significant protection against blood loss (FIGS. 38A and B). Using the Mann-Whitney test, the differences in both hemoglobin (38B) concentration (P=0.036) and hematocrit (38A) concentration (P=0.009) between the TTR and adjuvant control groups were statistically significant.

Figure 39:
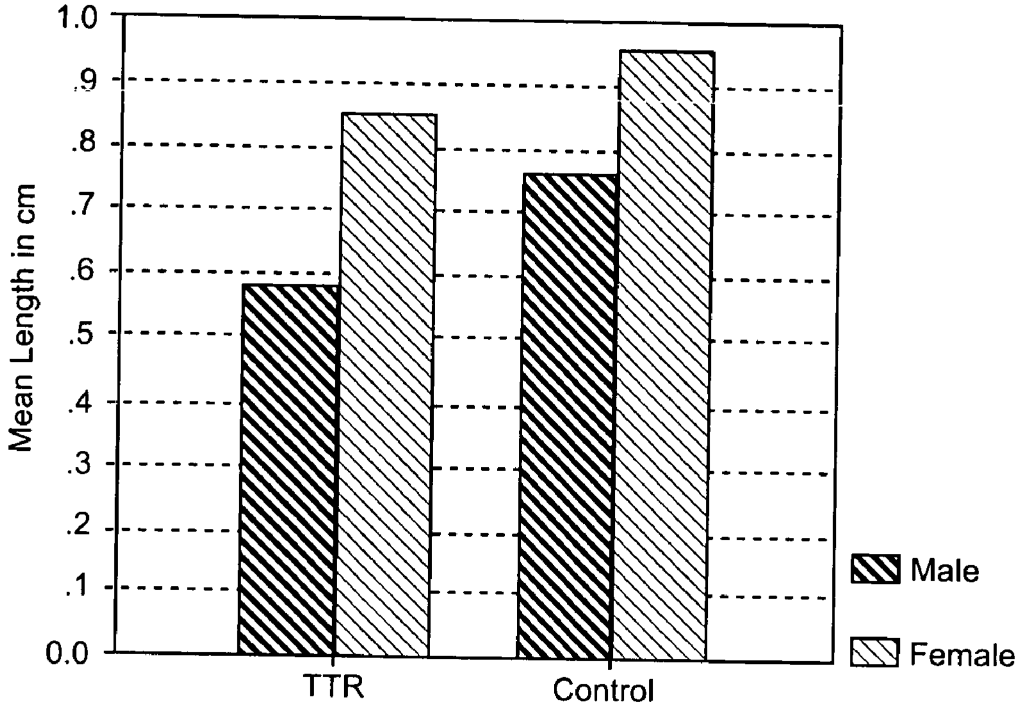

Further, the differences in hemoglobin concentration translated to a statistically significant reduction in worm size. Data was collected using an imaging system based on scans of the worms recovered from a host. Worms were photographed with a CoolSnapPro digital camera (Media Cybernetics), and the images measured in ImagePro Software using a macro to determine worm length (in mm) compared between treatments. As shown in FIG. 39 there was a statistically significant reduction in worm size (between 1 and 2 mm) among the TTR vaccinated group relative to the adjuvant control group.

This example demonstrates that vaccination with TTR, in addition to reducing worm burden, will also reduce blood loss.

Example 6

Chimeric Hookworm Antigens

The protective effect of two different hepatitis B core particles expressing a peptide epitope that corresponds to amino acids 291-303 of Na-ASP-1 (also found in Ac-ASP-1) were investigated. Previously by investigation of relative hydropathy (hydrophobicity and hydrophilicity) of the predicted amino acid sequence of Na-ASP-1 and Ac-ASP-1 it was discovered that both molecules exhibit a hydrophilic sequence that modeling predicted could represent a looped-out region of the molecule. Covalent attachment of the peptide to KLH (keyhole limpet hemocyanin) confirmed that the chimeric molecule could protect mice against challenge infections.

Two different chimeric molecules expressing ASP-1 were constructed. ICC-1546 expresses ASP-1 amino acids 291-303 as a “looped out” tethered structure, whereas ICC-1564 expresses the same peptide as an N-terminal structure. Previous studies had demonstrated that mouse anti-L3 antibody recognizes ICC-1546, but not ICC-1564.

The antigenic chimeras were administered as described above with alhydrogel as adjuvant. DSM (detergent solubilized membrane extract of adult *A. caninum*) served as a negative control. Larval challenge was carried out by subcutaneous injection of L3 stage larvae.

The results showed that vaccination of dogs with either particle produced high levels of anti-particle antibody. Most of the antibody was directed against the hepatitis core antigen constituent. However, in one dog vaccinated with ICC-1546, there was a high level of anti-ASP-1 (and antipeptide) antibody. This dog exhibited a significant reduction in hookworm burden (Table V).

TABLE V

| Comparison of Anti-ASP-1 antibody and hookworm burden | | | |
|---|---|---|---|
| ICC 1546 | Total Hookworms | Anti-ASP-1 IgG1 | IgG2 |
| A1 | 139 | 1:800 | 0 |
| A2 | 181 | 1:800 | 0 |
| A3 | 170 | 1:200 | 0 |
| A4 | 180 | 1:800 | 0 |
| A5 | 118 | 1:1,600 | 1:1,600 |
| Average A | 158 | | |
| ICC 1564 | Total Hookworms | Total Hookworms | IgG2 |
| B1 | 135 | 1:100 | 0 |
| B2 | 143 | 1:100 | 0 |
| B3 | 206 | 1;200 | 0 |
| B4 | 195 | 1:800 | 0 |
| B5 | 217 | 1:400 | 0 |
| Average B | 179 | | |
| Alum | Total Hookworms | Total Hookworms | Total Hookworms |
| D1 | 176 | 0 | 0 |
| D2 | 150 | 0 | 0 |
| D3 | 161 | 0 | 0 |
| D4 | 241 | 0 | 0 |
| D5 | 255 | 0 | 0 |
| Average D | 191 | | |

This example demonstrates that high antibody titers to a specific epitope associated with ASP-1 will result in reduced worm burden.

Example 7

Antigen Expression in Baculovirus/Insect Cells and Yeast

Expression of hookworm antigens in eukaryotic expression systems, such as baculovirus/insect cells and the yeast *Pichia pastoris*, have been carried out to afford maximum opportunities for obtaining soluble and bioactive recombinant proteins.

A. Expression in *Pichia Pastoris*

The antigens Na-ASP-1, Ac-TTR, Ac-API, and Ay-ASP-2 have been successfully expressed with *Pichia* fermentation systems. Antigens were isolated with polyhistidine tags for ease of isolation.

B. Expression in Baculovirus/Insect Cell System

Antigens Na-CTL, Ac-MEP-1, Ac-ASP-2 and Ac-MTP-1 have been successfully expressed in a baculovirus/insect cell expression system. Antigens were isolated with polyhistidine tags for ease of isolation.

Example 8

Cloning of cDNAs of *A. Ceylanicum* Orthologous Antigens Ay-ASP-1, Ay-ASP-2 and Ay-MTP Orthologous antigens from the hamster parasite hookworm *A. ceylanicum* were successfully cloned following the construction of an *A. ceylanicum* larval cDNA library.

The *A. ceylanicum* orthologue of ASP-1 was cloned by screening the *A. ceylanicum* L3 cDNA library using a 900 bp $^{32}$P-labeled Ac-ASP1 cDNA fragment as a probe. Screening of approximately 500,000 clones resulted in 85 positive clones. Of these 21 clones were sequenced of which 19 encoded identical cDNAs. No other orthologues of ASP-1 were found. The clones exhibited 85% identity and 92% similarity with Na-ASP-1.

By screening approximately 100,000 plaques of the *A. ceylanicum* L3 cDNA library using a 600 bp $^{32}$P-labeled Ac-asp-2 cDNA fragment as a probe, 30 positive clones were obtained, of which 10 were sequenced and found to be identical to Ay-ASP-2 predicted ORFs (orthologous clones).

By screening approximately 500,000 *A. ceylanicum* L3 cDNA library using a 590 bp $^{32}$P-labeled Ac-MTP cDNA fragment as a probe, 700 positive clones were obtained and 8 sequenced. Seven of the 8 encoded Ay-MTP-1, while one other encoded a putative isoform (Ay-MTP-2).

This example demonstrates that there is a high degree of similarity between antigens from *A. caninum* and *A. ceylanicum* hookworm species, and the data suggests a high degree of identity (>80%) amongst most of hookworm antigens.

Example 9

Immunolocalization

Immunolocalization of some of the major vaccine antigens was carried out in sections of adult hookworms. The immunolocalizations were determined to be as follows: Ac-103 as a hookworm surface antigen, Ac-FAR-1 and Ac-API as components of the pseudocoelomic fluid, (Ac-API is also a pharyngeal protein), Ac-CP-1 as an amphibian gland protein, Ac-TMP in the excretory glands, and ASP-3 as an amphibian and esophageal protein. In addition the total proteins of the hookworm ES products localized to amphibian and excretory glands, and to the brush border membrane of the hookworm alimentary canal.

This example demonstrates that many of the hookworm antigens are exposed either on the surface of the worm or secreted by worm and are therefore susceptible to targeting by host antibodies or host immunocompetent cells.

Example 10

Human Investigations Conducted in Minas Gerais State, Brazil

It has been previously reported that in China and elsewhere, human hookworm infection exhibits a unique epidemiology compared with the other soil-transmitted helminthiases (e.g., ascariasis and trichuriasis) and schistosomiasis (Gandhi et al, 2001). Whereas the prevalence and intensity of these other helminth infections peak during childhood and adolescence and subsequently decline into adulthood, the prevalence and intensity of hookworm infection increases with age. In many Chinese and Brazilian villages (and presumably elsewhere) middle aged and even elderly residents exhibit the most severe infections.

Figure 40:
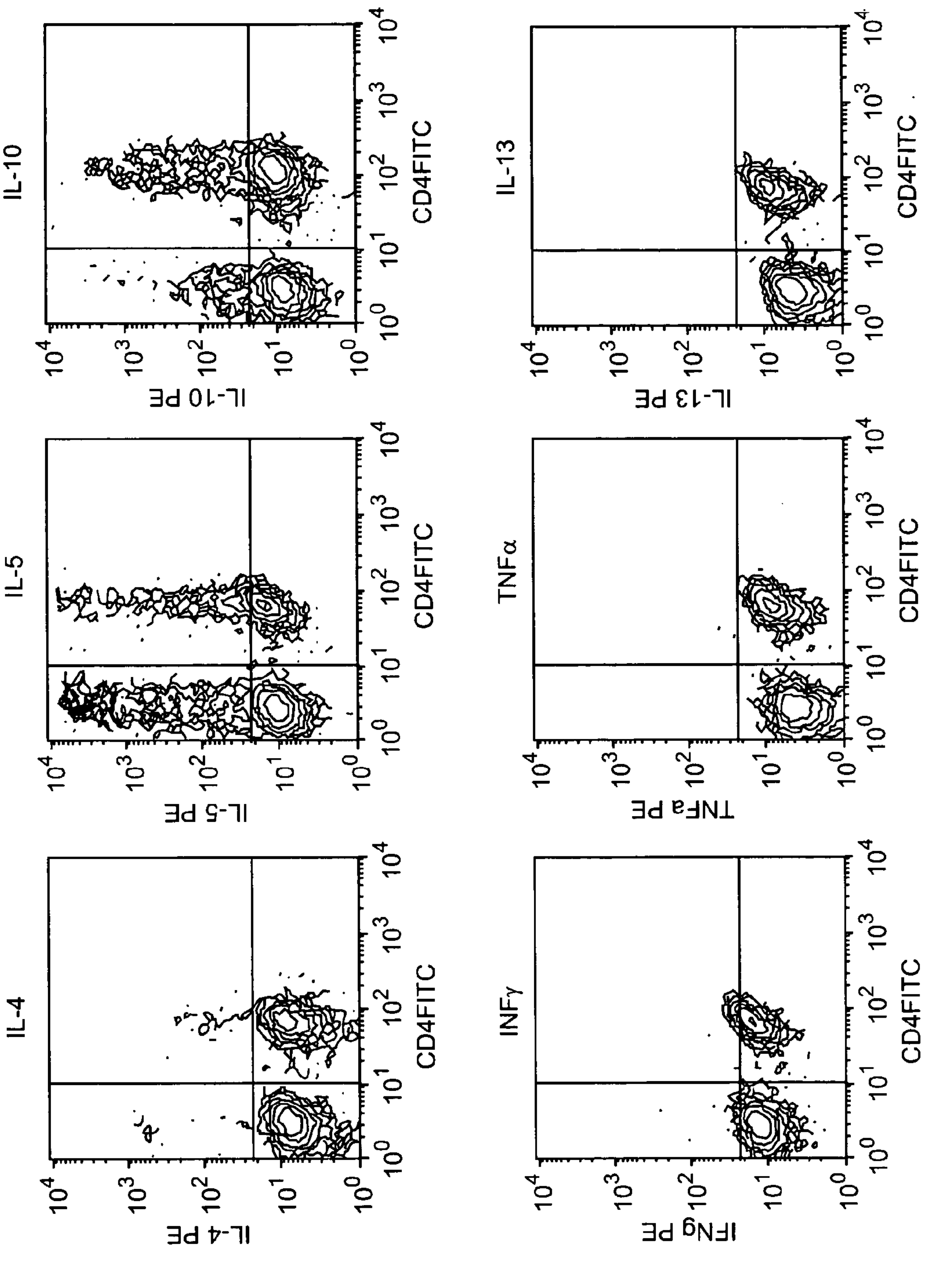
FIG. 40. CD4+lymphocytes from hookworm-infected (egg positive) individual post-stimulation with *Ancylostoma* L3 antigen.
Figure 41:
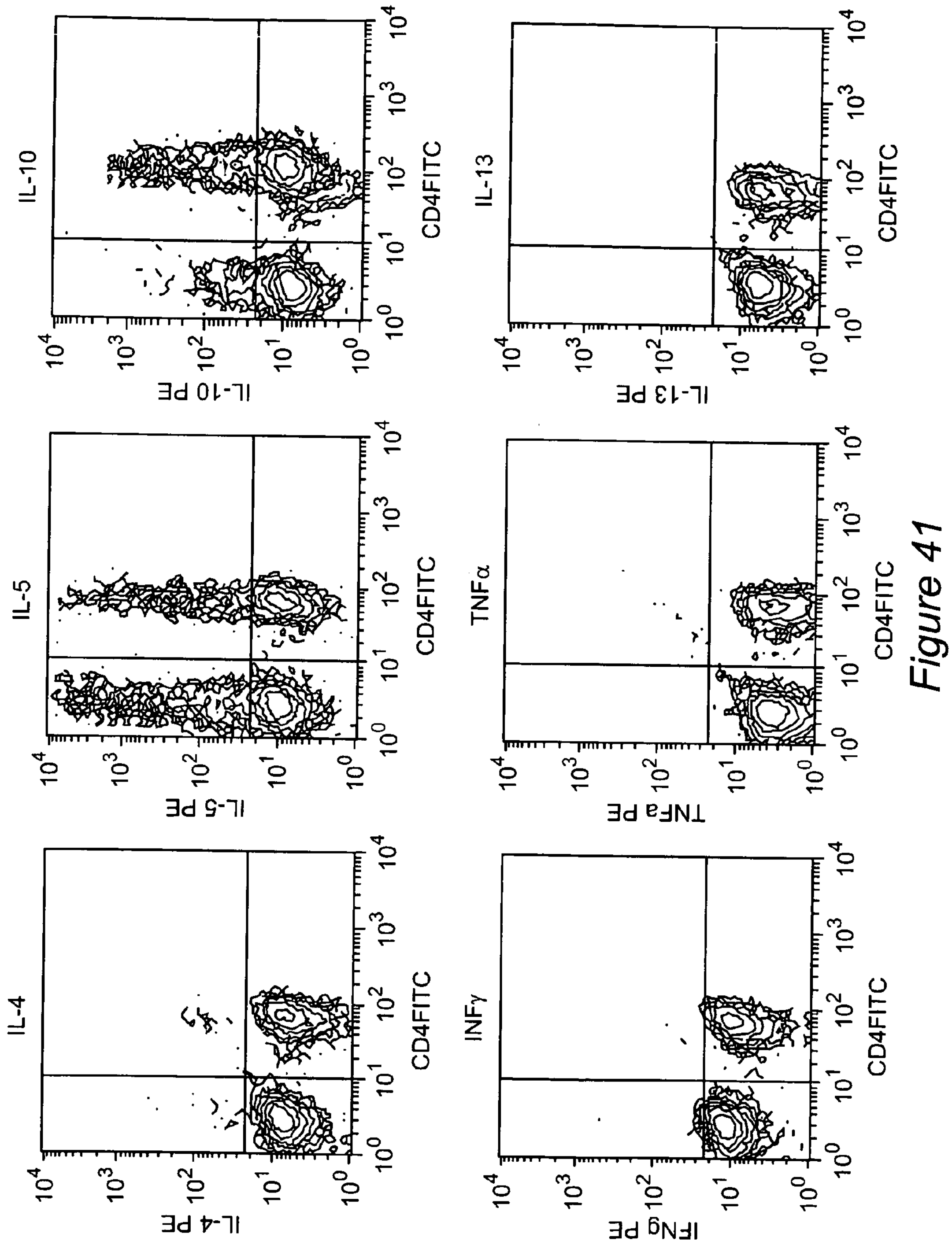
FIG. 41. CD4+lymphocytes from hookworm-infected (egg positive) individual post-stimulation with *Pichia*-expresses recombinant Na-ASP-1.

The underlying immunological mechanisms accounting for this observation has been investigated. Shown in FIGS. 40 and 41, CD-4+lymphocytes were gated from the whole blood of hookworm infected residents and stimulated with either L3 soluble hookworm antigen FIG. 40) or *Pichia*-expressed recombinant Na-ASP-1 (FIG. 41). Host cytokine production was measured by an intracellular cytokine staining technique. Both antigens stimulated high levels of IL-10 and IL-5, but not IL-4. IL-10 is a strong immunomodulator with downregulatory, anti-inflammatory properties, and IL-4 is associated with antibody production and TH-2 type immunity. The findings suggest that hookworm infected individuals might be anergic to hookworm and possibly other antigen stimulation.

In contrast, it was shown that individuals treated for hookworm produce IL-4. This observation indicates that removal of hookworms from the intestine helps to reconstitute a patient's immunity. This is a critical observation since it suggests that in the absence of treatment a recombinant hookworm vaccine may be unlikely to function as a therapeutic vaccine in patients who are actively infected, and that anthelmintic chemotherapeutic treatment may be necessary prior to vaccination.

Further, these observations also suggest that hookworm infection might thwart otherwise successful vaccinations against such etiological agents as HIV and malaria. In regions of Subsaharan Africa where hookworm overlaps with HIV and malaria, it may become essential to monitor a study participant's hookworm status prior to HIV or malaria vaccination, and to treat those that are found to be actively infected prior to immunization.

REFERENCES

Altschul S F, Madden T L, Schaeffer A A, Zhang J, et al. 1997. Gapped BLAST and PSI-BLAST: a new generation of protein database search programs. *Nucl Acids Res* 25:3389-402.

Apweiler R, Attwood T K, Bairoch A, Bateman A, et al. 2000. InterPro* an integrated documentation resource for protein families, domains and functional sites. *Bioinformatics* 16:1145-50.

Ausubel F M, Brent R, Kingston R E, Moore D D, Seidman J G, Struhl K, editors. Current Protocols in Molecular Biology. New York: Wiley, 1993.

Bektesh S, Van Doren K, Hirsh D. Presence of the *Caenorhabdifis elegans* spliced leader on different mRNAs and in different genera of nematodes. Genes Devel 1988; 2: 1277-83.

Blumenthal T, Steward K, RNA processing and gene structure. In: Riddle D L, Blumenthal T, Meyer B J, Priess J R, editors. *C elegans* 11. Plainview: Cold Spring Harbor Laboratory Press, 1997; 33:117-45.

Bojang, K. A., P. J. Milligan, M. Pinder, L. Vigneron, A. Alloueche, K. E. Kester, W. R. Ballou, D. J. Conway, W. H. Reece, P. Gothard, L. Yamuah, M. Delchambre, G. Voss, B. M. Greenwood, A. Hill, K. P. McAdam, N. Tornieporth, J. D. Cohen, T. Doherty; RTS, S Malaria Vaccine Trial Team. 2001. Lancet 358:1927-34.

Bond J S, Beynon R J. 1995. The astacin family of metalloendopeptidases. *Prot Sci* 4:1247-61.

Bork P, Beckmann G. 1993. The CUB domain. A widespread module in developmentally regulated proteins. *J Mol Biol* 231:53945.

Capello M, Hawdon J M, Jones B F, Kennedy P W and Hotez P J 1996. cloning and expression of *Ancylostonia caninum* anticoagulant peptide (AcAP) *Mol. Biochem. Parasitol* 80:113-117.

Gandhi N S, Chen J Z, Khoshnood K, Xin FY, Li S W, Liu Y R, Zhan B, Xue H C, Tong J, Wansz Y, Wang W S, He D X, Chen C, Xiao S H, Hawdon T M, Hotez P J. 2001. Epidemiology of *Necator americanus* hook-worm infections in Xiulongkan Village, Hainan Province, China: high prevalence and intensity among, middle aged and elderly residents. *J Parasitol.* 87: in press.

Geerts S, Gryseels B. 2000. Drug resistance in human helminths: current situation and lessons from livestock. *Clin Microbiol Rev;*13:20 22.

Ghosh K, Hawdon J, Hotez P. Vaccination with alum-precipitated recombinant, 4ncylostoma-secreted protein I protects mice against challenge infections with infective hookworm (4ncylostoma caninum) larvae. J Infect Dis 1996; 174: 1380-3.

Hawdon J M, Hotez P J. 1996. Hookworm: developmental biology of the infectious process. *Curr Opin Genet Dev* 6:618-23.

Hawdon J M, Schad G A. 1993. *Ancylostoma caninum*: glutathione stimulates feeding in third-stage larvae by a sulfhydryl-independent mechanism. *Exp Parasitol* 77:489-91.

Hawdon, J M, Narasimhan, S, Hotez P J 1999. *Ancylostoma* secreted protein 2 (Asp-2) Cloning and characterization of a second member of a novel family of nematode secreted proteins from *Ancylostoma caninum. Mol. Biochem Parasitol.* 99: 140-65.

Hawdon J M, Jones B F, Hotez P J. 1995b. Cloning and characterization of a cDNA encoding the catalytic subunit of a cAMP-dependent protein kinase from *Ancylostoma caninum* third-stage infective larvae. *Mol Biochem Parasitol* 69:127-30.

Hawdon J M, Jones B F, Hoffman D R, Hotez P J. Cloning and characterization of *Ancylostoma* secreted protein: a novel protein associated with the transition to parasitism by infective hookworm larvae. J Biol Chem 1996; 271: 6672-8.

Hawdon J M, Jones B F, Perregaux M A, Hotez P J.1995a. *Ancylostoma caninum*: metalloprotease release coincides with activation of infective larvae in vitro. *Exp Parasitol* 80:205-11.

Hawdon J M, Schad G A. Long-term storage of hookworm infective larvae in buffered saline solution maintains larval responsiveness to host signals. J Helm Soc Wash 1991; 58: 140-2.

Hawdon, J. M. 1996. Differentiation between the human hookworms *Ancylostoma duodenale* and *Necator americanus* using PCR-RFLP. Journal of Parasitology 82:642-647.

Hooper N M. Families of zinc metalloproteases. FEBS Lett 1994;354:1-6.

Hotez P, B. Zhan, J. Qun, J. M. Hawdon, H. A. Young, S. Simmens, R. Hitzelberg, and B. C. Zook. 2002c. Natural history of primary canine hookworm infections following 3 different oral doses of third-stage infective larvae of *Ancylostoma caninum*. Comparative Parasitology 69:72-80.

Hotez P J, Feng Z, Xu L Q, Chen M G, Xiao S H, Liu S X, Blair D, McManus D P, Davis G M. 1997. Emerging and reemerging helminthiases and the public health of China. *Emerg. Infect. Dis.* 3:303-10.

Hotez P J and Cerami, A. 1983 Secretion of a proteolytic anticoagulant by *Ancylcostoma* hookworms. J. Exp. Med. 15: 1594-1603.

Hotez P., J. Ashcom, B. Zhan, J. Bethony, A. Williamson, J. M. Hawdon, J. J. Feng, A. Dobardzic, I. Rizo, J. Bolden, J. Qun, Y. Wang, R. Dobardzic, S. Chung-Debose, M. Crowell, B. Datu, A. Delaney, D. Dragonovski, J. Yang, Y. Y. Liu, K. Ghosh, A. Loukas, W. Brandt, P. K. Russell, and B. C. Zook. 2002a. Effect of vaccinations with recombinant fusion proteins on *Ancylostoma caninum* habitat selection in the canine intestine. Journal of Parasitology 88: in press.

Jones, B F, Hotez P J. 2002. *Molecular & Biochemical Parasitology* 119: 107-116

Kalkofen U P. 1974. Intestinal trauma resulting from feeding activities of *Ancylostoma caninum. Am. J. Trop. Med. Hyg.* 23:1046-53.

Kalkofen U P. 1970. Attachment and feeding behavior of *Ancylostoma caninum, Z. Parasitenkd.* 33:339-354.

Kelley L A, MacCallum R M, Sternberg M J. 2000. Enhanced genome annotation using structural profiles in the program 3D-PSSM. *J Mol Biol* 299:499-520.

Kester, K. E., D. A>McKinney, N. Tornieporth, C. F. Ockenhouse, D. G. Heppner, T. Hall, U. Krzych, M. Delchambre, G. Voss, M. G. Dowler, J. Palensky, J. Wittes, J. Cohen, W. R. Ballou; RTS,S Malaria Vaccine Evaluation Group. 2001. Journal of Infectious Diseases 183:640-7.

Laemmli U K. 1970. Cleavage of structural proteins during the assembly of the head of bacteriophage T4 *Nature* (London) 227:680-5

Lalvani, A., P. Moris, G. Voss, A. A. Pathan, K. E. Kester, R. Brookes, E. Lee, M. Koustsoukos, M. Plebanski, M. Delchambre, K. L. Flanagan, C. Carton, M. Slaoui, C. Van Hoecke, W. R. Ballou, A. V. Hill, J. Cohen. 1999. Potent induction of focused Thl-type cellular and humoral immune responses by RTS,S/SBAS2, a recombinant *Plasmodium falciparum* malaria vaccine. Lancet 180: 1656-64.

Nielsen H, Engelbrecht J, Brunak S, von Heijne G. 1997. Identification of prokaryotic and eukaryotic signal peptides and prediction of their cleavage sites. *Protein Eng* 10:1-6.

Nolan T J, Bhopale V, Megyeri Z, Schad G A. Cryopreservation of human hookworms. J Parasitol 1994; 80: 648-50.

Prociv P, Croese J. 1990. Human eosinophilic enteritis caused by dog hookworm *Ancylostoma caninum. Lancet* 335:1299-302.

Sambrook J, Russel D W. Molecular Cloning, A laboratory Manual, third ed. Cold Spring Harbor, N.Y.: Cold Spring Harbor Laboratory Press, 2001.

Savioli L, Bundy D, Albonico M, Renganathan E. 1997. Anthelmintic resistance in human helminths: learning from the problems with worm control in livestock* reply. *Parasitol Today* 13:156.

Schad G. Arrested development of *Ancylostoma caninum* in dogs: Influence of photoperiod and temperature on induction of a potential to arrest. In: Meerovitch E, editor. Aspects of Parasitology: A Festschriff Dedicated to the Fiftieth Anniversary of the Institute of Parasitology of McGill University. Montreal: McGill University, 1982: 361-91.

Short J M, Sorge J A. In vivo excision properties of bacteriophage lambda ZAP expression vectors. Meth Enzymol 1992; 216: 495-508.

Singh, S., K. Pandey, R. Chattopadhayay, S. S. Yazdani, A. Lynn, A. Bharadwaj, A. Ranjan, and C. Chitnis. 2001. Biochemical, biophysical, and functional characterization of bacterially expressed and refolded receptor binding domain of *Plasmodium vivax* duffy-binding protein. Journal of Biological Chemistry 276:17111-17116.

Soulsby E. Helminths, Arthropods and Protoza of Domesticated Animals, 7th ed. Philadelphia: Lea and Febiger, 1982.

Sulston J, Hodgkin J, Methods. In: Wood W B, editors. The Nematode *Caenorhabdifis elegans.* Cold Spring Harbor: Cold Spring Harbor Laboratory, 1988; 587-606.

Towbin H, Staehelin T, Gordon J. Electrophoretic transfer of proteins from polyacrylamide gels to nitrocellulose sheets: procedure and some applications. Proc Natl Acad Sci USA 1979; 76: 4350.

Xue H C, Wang Y, Xiao SH, Liu S, et al. Epidemiology of human ancylostomiasis among rural villagers in Nanlin County (Zhongzhou Village), Anhui Province, China: 11. Seroepidemiological studies of the age relationships of serum antibody levels and infection status. Southeast Asian J Trop Med Public Health 2000; 3 1: in press.

Yong W, Guangjin S, Weitu W, Shuhua X, et al. 1999. Epidemiology of human ancylostomiasis among rural villagers in Nanlin County (Zhongzhou village), Anhui Province, China: age-associated prevalence, intensity and hookworm species identification. *Southeast Asian J Trop Med Public Health* 30:692-7.

Example 11

Cloning, Yeast Expression, Isolation and Vaccine Testing of Recombinant *Ancylostoma*-Secreted Protein (ASP)-1 and ASP-2 from *Ancylstoma Ceylanicum*

An estimated 740 million people in the developing countries of the tropics and subtropics are infected with the hookworm *Necator americanus* or *Ancylostoma duodenale* [1]. The highest prevalence of hookworm infection occurs in impoverished rural areas of sub-Saharan Africa, Southeast Asia, China, Brazil, and Central America [1, 2]. In some of these regions, up to 57% of the moderate and severe iron deficiency anemia (IDA) is attributable to hookworm infection [3-5], which results from parasite-induced blood loss and hemoglobin digestion [6-8]. IDA accounts for huge numbers of disability-adjusted life-years lost in developing countries; some studies rank IDA among the top 15 causes of global disease burden [9, 10]. Because it is linked to a major etiology of IDA, hookworm infection is considered, in terms of DALYs, to be one of the most important parasitic diseases of humans, possibly second only to malaria [11]. At present, the major approach to hookworm control relies on frequent and periodic dewormings through the administration of albendazole and other anthelmintic drugs. There has been significant interest by the World Health Organization (WHO) and other international organizations in conducting such interventions on a large scale [12], particularly for school-aged children, who might otherwise suffer from the physical and intellectual growth retardation effects of hookworm and other soil-transmitted helminths (STHs) [13-15].

However, unlike other STH infections (e.g., *ascariasis* and trichuriasis), there is an emerging body of evidence suggesting that the peak prevalence and intensity of hookworm frequently occurs among adult populations [16-18], including high rates of hookworm infection among pregnant women, in whom hook-worm-induced IDA results in adverse consequences for both the mother and the unborn fetus [19]. Therefore, the school-based anthelmintic chemotherapy programs now being pro-posed by WHO and other international health agencies to control STH infections might fail to target hookworm. Moreover, hookworm reinfection often occurs within just a few months after anthelmintic treatment [20]. This feature of human hookworm infection would also thwart the success of mass chemotherapy initiatives.

As an alternate or complementary approach to hookworm control, efforts are under way to develop a vaccine [11]. On the basis of previous success with trickle doses of third-stage infective hookworm larvae (L3) or L3 attenuated by ionizing radiation (irL3) [21], vaccine development efforts have targeted the major antigens secreted by hookworm L3 at entry into the host [22]. The most abundant antigens released by hookworm L3 by host stimulation with serum have now been cloned from the dog hookworm *A. caninum*, including a zinc metalloprotease of the astacin class [23] and 2 *Ancylostoma*-secreted proteins (ASP-1 and ASP-2) that belong to the pathogenesis-related protein (PRP) superfamily [22, 24-25]. To test whether these antigens protect laboratory animals against challenge infections, we have adopted a parallel strategy of testing them as immunogens in dogs challenged with *A. caninum* and in hamsters challenged with *A. ceylanicum*. Both systems offer unique advantages and disadvantages [11]. Here, we report the cloning and yeast expression of asp-1 and asp-2 cDNAs from *A. ceylanicum*, the isolation of the recombinant macromolecules, and their vaccine testing in hamsters. We report that vaccination of hamsters with recombinant ASP-2 formulated with the adjuvant Quil A results in protection, as evidenced by reduction in hookworm burden, hookworm size, and spleen size, compared with those in control hamsters vaccinated with Quil A alone.

Materials and Methods for Example 11.

Cloning of asp-1 and asp-2 cDNAs from *A. Ceylanicum*

To construct an *A. ceylaninum* L3 cDNA library, L3 of *A. ceylanicum* were obtained from coprocultures of a donor dog infected with *A. ceylanicum*. Total RNA was exacted from *A. ceylanicum* L3 by use of the TRIzol reagent (GIBCO BRL), and mRNA was isolated by use of oligo dT affinity chromatography (Oligotex mRNA Mini Kit; Qiagen). A 1 ZAPII cDNA library was constructed according to the manufacturer's instructions (Stratagene). Products of the polymerase chain reaction (PCR) from *A. caninum* cDNA and asp-specific primers were used as heterologous probes to screen the *A. ceylanicum* library [24, 25]. The species derivation of each hookworm reagent was abbreviated as follows: Ac, *A. caninum*; Ad, *A. duodenale*; Ay, *A. ceylanicum*; and Na, *N. americanus*. Specific primers for Ac-asp-1 DNA (Ac-asp-1 F1: 5-GCTCTCCGGCTGGTGG-3 (SEQ ID NO: 78) and Ac-asp-1 R1: 5-TTAAGGAGCGCTGCACAAGCC-3 (SEQ ID NO: 79)) were used to amplify Ac-asp-1 cDNA (366-1275 bp). Specific primers for *A. caninum* asp-2 DNA (Ac-asp-2 F1: 5-GGGAATTCAATTCTATGAGATGCGGAAA-3 (SEQ ID NO: 80) and Ac-asp-2 R1: 5-TGTCT-AGATAGCCACGCACGACGCAAA G-3 (SEQ ID NO: 81)) were used to amplify Ac-asp-2 cDNA (66-668 bp). The first-strand *A. caninum* L3 cDNA reverse transcribed from *A. caninum* L3 total RNA was used as a template. The PCR products were labeled randomly with a $^{32}$ [P]-dCTP by use of a Rediprime labeling kit (Amersham). The radiolabeled 909-bp Ac-asp-1 fragment and the 602-bp Ac-asp-2 fragment were used as probes to screen the *A. ceylanicum* L3 cDNA library. Approximately $1\times10^5$ plaques of the *A. ceylanicum* L3 cDNA library were plated on 2 NZY agar plates. Plaque DNA was transferred to positively charged nylon membranes. After denaturation with alkali and stabilization by baking for 2 h at 80° C., the membranes were prehybridized for 2 h at 65° C. and then hybridized for 16 h in a solution of Rapid-hyb buffer (Amersham). Positive plaques were rescreened once, and the single positive clones were in vivo excised to phagemids by use of a helper phage (Stratagene). Double-strand sequencing was performed on the phagemid DNA by use of the generic vector primers T3 and T7. Sequence editing, alignments, and comparisons were performed by use of Eyeball Sequence Editor software (version 1.09e).

Subcloning into *Pichia Pastoris* cDNA fragments encoding Ay-ASP-1 and Ay-ASP-2 (except for the predicted signal sequence) were amplified from pBluescript phagemids by use of specific primers for Ay-asp-1 (SEQ ID NO: 55): (Ay-asp-1) F1: 5-CTCTCGAGAAAAGAAGCCCAGTAAAGCCAGC-3 (SEQ ID NO: 70) and Ay-asp-1 R1: 5-TGTCTAGAGGAGCAC TGCACAATC-CTT C-3) (SEQ ID NO: 71) and Ay-asp-2 (SEQ ID NO: 57) (Ay-asp-2 F1: 5-GGGAATTCGGAAATAATGG AATGACCG-3 (SEQ ID NO: 72) and Ay-asp-2 R1: 5-TGTCTAGACCATGCACG-ATGCAAA GC-3) (SEQ ID NO: 73). The PCR products were then cloned into the eukaryotic expression vector pPICZαA (Invitrogen) by use of XhoI/XbaI sites for Ay-asp-1 and EcoRI/XbaI sites for Ay-asp-2 (SEQ ID NO: 57). The correct open-reading frame (ORF) was confirmed by sequencing that used the vector flanking primers corresponding to the regions encoding the a-factor and 3' AOX1. The recombinant plasmids were linearized by use of SacI digestion and were transformed into the *P. pastoris* X33 strain by eletroporation, according to the manufacturer's instructions (Invitrogen). The transformants were selected on zeocin-resistant YPDA plates and identified by PCR amplification using the Ay-asp-1- and Ay-asp-2-specific primers (Ay-asp-1 F1/Ay-asp-1 R1 and Ay-asp-2 F1/Ay-asp-2 R1, respectively).

Fermentation and Expression of Ay-ASP-1 (SEQ ID NO: 56) and Ay-ASP-2 (SEQ ID NO: 58)

A culture inoculum was prepared from *P. pastoris* cells containing either the Ay-asp-1 or Ay-asp-2 gene in pPICZaA (In-vitrogen). The inoculum was prepared in 2 stages. In the first stage, 50 mL of buffered-complex glycerol medium with yeast (0.1 moVL potassium phosphate buffer [pH 6.0] containing 1% [wt/vol] yeast extract, 2% [wt/vol] peptone, 1.34% [wt/vol] yeast nitrogen base without amino acids, 1% [vol/vol] glycerol, and $4\times10^{-5}$% d-biotin) in a 250-mL flask was inoculated with *P. pastoris* cells and grown for 24-36 h at 30° C., to a final OD600 nm of 10-20. In the second stage, 100 mL of buffered-complex glycerol medium without yeast extract was inoculated in a 500-mL shaker flask with 5-10 mL of *P. pastoris* cells from the first-stage culture and grown for 0.16 h at 30° C., to a final OD600 nm of 15-20. A Bioflo 3000 fermentor (New Brunswick Scientific), with a working volume of 5 L, was used for scale-up fermentation. Growth of *P. pastoris* in the fermentor was divided into glycerol and methanol phases.

Glycerol phase. Approximately 50 mL of the shaker flask culture of *P. pastoris* cells was used to inoculate 2 L of heat-sterilized basal salt media (BSM) containing 2.5 mL/L filter-sterilized trace element (PTM1) solution. Each liter of BSM contained 0.93 g of $CaSO_4$, $2H_2O$, 18.2 g of $K_2$ $SO_4$, 14.9 g of $MgSO_4$, $7H_2O$, 4.13 g of KOH, 11.35 mL of 85% $H_3PO_4$, and 40 g of glycerol. The pH of the BSM was adjusted to 5.0 with 29% ammonium hydroxide. Dissolved oxygen was maintained above 35% throughout the fermentation. At 21-24 h into the initial glycerol phase (when a sharp increase in the percentage of dissolved oxygen was observed), 50% (vol/vol) glycerol was introduced into the cell culture media at a set flow rate of 15 g/L1 h for 6 h. The pH of the cell culture media was then increased linearly from 5.0 to 6.0 by adding 29% ammonium hydroxide. The temperature was decreased linearly from 30° C. to 26° C. over a 2-h period before the completion of this phase. Antifoam 204 (Sigma) was also added. Methanol phase. The methanol phase was initiated when the wet cell weight reached 225-250 g/L. Methanol was added at an initial flow rate of 1 mL/L/h, increasing to 9.0 mL/L/h over an 8-h period, and then subsequently maintained at a flow rate of 9.0 mL/L/h for 87 h. The wet cell weight was ~465 and 479 g/L for cells expressing Ay-ASP-1 (SEQ ID NO: 56) and Ay-ASP-2, (SEQ ID NO: 58) respectively.

Purification and Biochemical Characterization of Ay-ASP-1 and Ay-ASP-2

The cells were harvested, and supernatant was collected by centrifugation (8650 g for 20 min at 4C) by use of a Beckman JA-10 rotor (Beckman Instruments). The supernatant was then centrifuged a second time, to remove traces of cells and debris. Approximately 1.6 L of supernatant was filtered through a 0.8-m mol membrane (Fisher Scientific) and was concentrated to 200 mL by ultrafiltration by use of a 10,000 MWCO membrane (Pall Corporation); 2 L of binding buffer (20 mmol/L Tris-HCl, 5 mmol/L imidazole, and 0.5 mol/L NaCl [pH 7.9]) was added to the concentrated supernatant. The modified supernatant was then concentrated again to 200 mL by ultrafiltration, and the recombinant protein was isolated by immobilized metal ion affinity chromatography (IMAC) by use of a 1.25-mL pre-packed HisBind column (Novagen). The columns were washed with 8 mL of HisBind buffer (20 mmol/L Tris-HCl [pH 7.9] containing 0.5 mol/L NaCl), and the recombinant proteins were eluted with a stepwise gradient of the HisBind buffer containing 5 mmol/L, 20 mmol/L, 60 mmol/L, and 1.0 mol/L imidazole, as recommended by the manufacturer. The column eluates were analyzed by SDS-PAGE by use of 4%-20% Tris-glycine gels (Invitrogen) and were stained with Coomassie brilliant blue R-250 (CBB). The column fractions containing the purified Ay-ASP-1 (SEQ ID NO: 56) and Ay-ASP-2 (SEQ ID NO: 58) were identified by Western blot by use of an antihistidine tag monoclonal antibody (Novagen), goat antimouse IgG secondary antibody conjugated to horseradish peroxidase (ICN Biomedical), and the chemiluminescent detection system ECL+plus (Amersham Biosciences). Fractions containing purified Ay-ASP-1 (SEQ ID NO: 56) and Ay-ASP-2 (SEQ ID NO: 58) were concentrated by use of Amicon Ultra centrifugal filter devices (Millipore Corporation) with 30,000 and 10,000 molecular-weight cutoffs, respectively, and were desalted by use of PD-10 Columns (Amersham). Protein concentrations were determined by use of the BCA assay (Pierce) and also by SDS-PAGE using known quantities of bovine serum albumin as a control.

N-terminal sequencing. SDS-PAGE analysis of Ay-ASP-1 (SEQ ID NO: 56) and Ay-ASP-2 (SEQ ID NO: 58) was performed on a 4%-20% gradient gel transferred to a polyvinyldene fluoride (immobilon-P) membrane (Millipore) at 250 mA for 1 h. The membrane was dried on filter paper for 15 min, soaked in 100% methanol, washed 5 times for 5 min/wash in MQ water (ultrapure water purified using the Milli-Q Water System; Millipore), and then stained with CBB. After drying, the visible bands were cut out, and—terminal amino acid sequences were obtained by Edman degradation, by use of a PE Biosystems 494 protein sequencer, at the Protein Chemistry Core Facility, Howard Hughes Medical Institute of Columbia University (New York, N.Y.).

Irradiation of L3

Live *A. ceylanicum* L3 were irradiated with 40,000 rad in a Shepherd Mark IV Cesium 137 irradiator, model 25. To obtain homogeneity of irradiation exposure, a low exposure rate (but without an attenuator) and a moving turntable were used. The decay factor was considered while calculating the time of exposure. The irL3 were inspected by microscopy to ensure that they were actively motile and viable before and after irradiation.

Hamster Vaccinations, Measurement of Anti-ASP Immune Responses, and Parasite Challenge Three-week-old male golden Syrian hamsters (*Mesocricetus auratus*) were vaccinated by intramuscular injection with 25 m g of either Ay-ASP-1 (SEQ ID NO: 56) or Ay-ASP-2 (SEQ ID NO: 58), each formulated with either Montanide ISA-720 (Seppic) or Quil A (Brenntag Biosector). To formulate each recombinant antigen with Quil A, 25 m g of the recombinant fusion protein was mixed, in a total volume of 95 m L, with 25 m g of Quil A, which was dissolved in 100 m L of PBS (pH 7.4). To formulate each recombinant antigen with Montanide ISA-720, 25 m g of the recombinant fusion protein was mixed, in a total volume of 60 m L, with 140 m L of Montanide ISA-720 and was shaken gently for 10 min at room temperature. The final volume was 200 m L for each antigen preparation per hamster. There were 10 hamsters in each group. The antigens were administered intramuscularly every 3 weeks on days 0, 21, and 42. An additional group of 10 hamsters was vaccinated by oral vaccination with 100 irL3 in 300 m L of PBS by use of the same vaccination schedule used for the other hamsters.

Eight days after the final vaccination, the hamsters were bled retro-orbitally, and their IgG antibody responses to each of the recombinant antigens were measured by ELISA, as described elsewhere [31], by use of anti-hamster IgG conjugated with horseradish peroxidase (Rockland) as a secondary antibody. ELISA plates were developed with o-phenylenediamine substrate. Serum antibody titers were determined by measuring the last dilution that resulted in 3 SD above background. On day 56 after the initial vaccination (14 days after the final vaccination), each hamster was infected orally with 100 *A. ceylanicum* L3. The larvae were introduced directly into the stomach by use of a gavage tube.

Measurement of Hookworm Burden, Hookworm Size, and Host Spleen Size

The hamsters were killed at days 19-21 after infection, and the intestines and spleens were removed. The spleens were weighed, fixed in formalin, and examined histologically. The adult hook-worms in the intestines were removed, placed in triethanolamine and formalin fixative [26], and counted. Worm lengths were determined digitally as follows: preserved worms were photographed by use of a Cool Snap Pro CCD monochrome camera (Media Cybernetics) attached to a computer running Image Pro Plus software (version 4.1.0.0; Media Cybernetics). A macro was written to automatically determine the object endpoints and draw a "backbone" on the image of the worm. This allowed us to measure worms that were coiled or curved. The length of the digital line was determined automatically by use of the size (length) command in the software package. The software was calibrated by photographing a ruler at the same focal depth as the worms, and the lengths were expressed in centimeters. The measurements were exported to Microsoft Excel spread-sheets, and measurements derived from spurious images, such as debris or partial worms, were removed before analysis.

Statistical Methods

Hookworm burden reduction (vaccine protection) was defined as P=(AWC−AW I)/AWC, where P (protection) is expressed as percentage, AWC is the number of adult worms in the unvaccinated control hamsters (injected with adjuvant alone), and AWI is the number of adult worms in the hamsters vaccinated with recombinant antigen or irL3 [27]. The statistical significance of differences in adult hookworm burdens was determined by use of the Kruskal-Wallis and the Mann-Whitney U nonparametric tests. Mean spleen weights were compared by use of 1-way analysis of variance. After we determined that differences existed among the means, the Bonferroni post hoc test was used to determine which means differed. Mean lengths of adult worms were compared by use of the t test for 2 independent groups, assuming equal variances (Levene's test). Spleen weights and circulating hemoglobin were correlated by use of the Spearman's correlation. Differences were considered to be statistically significant if the calculated P<0.05.

Results for Example 11.

Cloning of Ay-asp-1 and Ay-asp-2. From $1\times10^5$ plaques screened for Ay-asp-1, 85 positive clones were obtained. A total of 21 positive clones were subjected to DNA sequencing. Of these, 19 sequences were identical, each encoding an ORF with homology to Ac-asp-1 (SEQ ID NO: 55) (designated as Ay-asp-1). The Ay-asp-1 cDNA included 1322 bp, with a 3 poly(A) tail, but lacked a 5' initiation codon. The Ay-asp-1 cDNA encodes a predicted ORF of 424 aa that lacked 1 aa (Met) at the N-terminus, compared with Ac-ASP-1 (SEQ ID NO: 56). The predicted ORF of Ay-ASP-1 (SEQ ID NO: 56) has a calculated molecular weight of 45,748.46 Da and a predicted pI of 6.03. Two putative N-linked glycosylation sites were detected at Asn residues 58 and 120. Amino acid sequence comparisons among ASP-1 molecules from different species of hookworm larvae revealed that Ay-ASP-1 (SEQ ID NO: 56) exhibited 86% identity to Ad-ASP-1 (SEQ ID NO: 67) and 85% identity to both Ac-ASP-1 (SEQ ID NO: 18) and Na-ASP-1 (SEQ ID NO: 2) [28] (FIG. 42).

From $1\times10^3$ plaques screened for Ay-asp-2, (SEQ ID NO: 57) 30 positive clones were obtained. A total of 10 were subjected to DNA sequencing. The sequences of these 10 clones were identical and encoded an ORF with close identity to the single-domain Ac-asp-2 (SEQ ID NO: 57) cDNA cloned previously from *A. caninum* [25]. The Ay-asp-2 cDNA included 740 bp, with a 3 poly(A) tail, but lacked a 5 initiation codon. The cDNA encoded an ORF of 217 aa that lacked 2 aa at the N-terminus, on the basis of its alignment with Ac-ASP-2 (SEQ ID NO: 20). The first 20 aa comprised a hydrophobic signal peptide sequence without an N-terminal Met. The predicted ORF of Ay-ASP-2 had a calculated molecular weight of 24,006 Da and a predicted pI of 8.04. No putative N-linked glycosylation site was detected in the sequence. The amino acid sequence comparison among ASP-2 molecules from different species of hookworm larvae revealed that Ay-ASP-2 (SEQ ID NO: 58) exhibited 83% identity to both Ac-ASP-2 (SEQ ID NO: 20) and Ad-ASP-2 (SEQ ID NO: 68) and 61% identity to Na-ASP-2 (SEQ ID NO: 69) (FIG. 43A). One additional amino acid (Pro) is inserted into residue 140 of Ay-ASP-2 (SEQ ID NO: 58), compared with other hookworm ASP-2 molecules. The placement of all cysteines was conserved among the ASP-1 and ASP-2 molecules. The cDNA sequence of Na-ASP-2 (SEQ ID NO: 82) is presented in FIG. 43B.

Expression, purification, and biochemical characterization of recombinant Ay-ASP-1 and Ay-ASP-2. Both recombinant fusion proteins were secreted by *P. pastoris* during fermentation. The yields of Ay-ASP-1 (SEQ ID NO: 56) and Ay-ASP-2 (SEQ ID NO: 58) were 6 and 1 mg/L, respectively. In addition to the ORF, the recombinant Ay-ASP-1 (SEQ ID NO: 56) and Ay-ASP-2 (SEQ ID NO: 58) fusion proteins each contained C-terminal myc and histidine tags. N-terminal amino acid sequencing by Edman degradation of Ay-ASP-1 (SEQ ID NO: 56) identified a SPVKA sequence (data not shown), which is the predicted N-terminus following signal peptide removal. The Ay-ASP-2 (SEQ ID NO: 58) N-terminus comprised an EAEAEF expressed from the vector sequence flanking an EcoR1 site. This was also confirmed by Edman degradation (data not shown). The predicted molecular mass of the recombinant Ay-ASP-1 (SEQ ID NO: 56) and Ay-ASP-2 (SEQ ID NO: 58) fusions proteins, which contained these additional sequences, were 46,508 (428 aa) and 25,228 (225 aa) Da, respectively. SDS-PAGE analyses of the *Pichia*-expressed recombinant proteins during purification by IMAC showed that Ay-ASP-1 (SEQ ID NO: 56) and Ay-ASP-2 (SEQ ID NO: 58) migrated on SDS-PAGE with apparent molecular weights of 48 kDa and 30 kDa, respectively (not shown).

Figure 44:
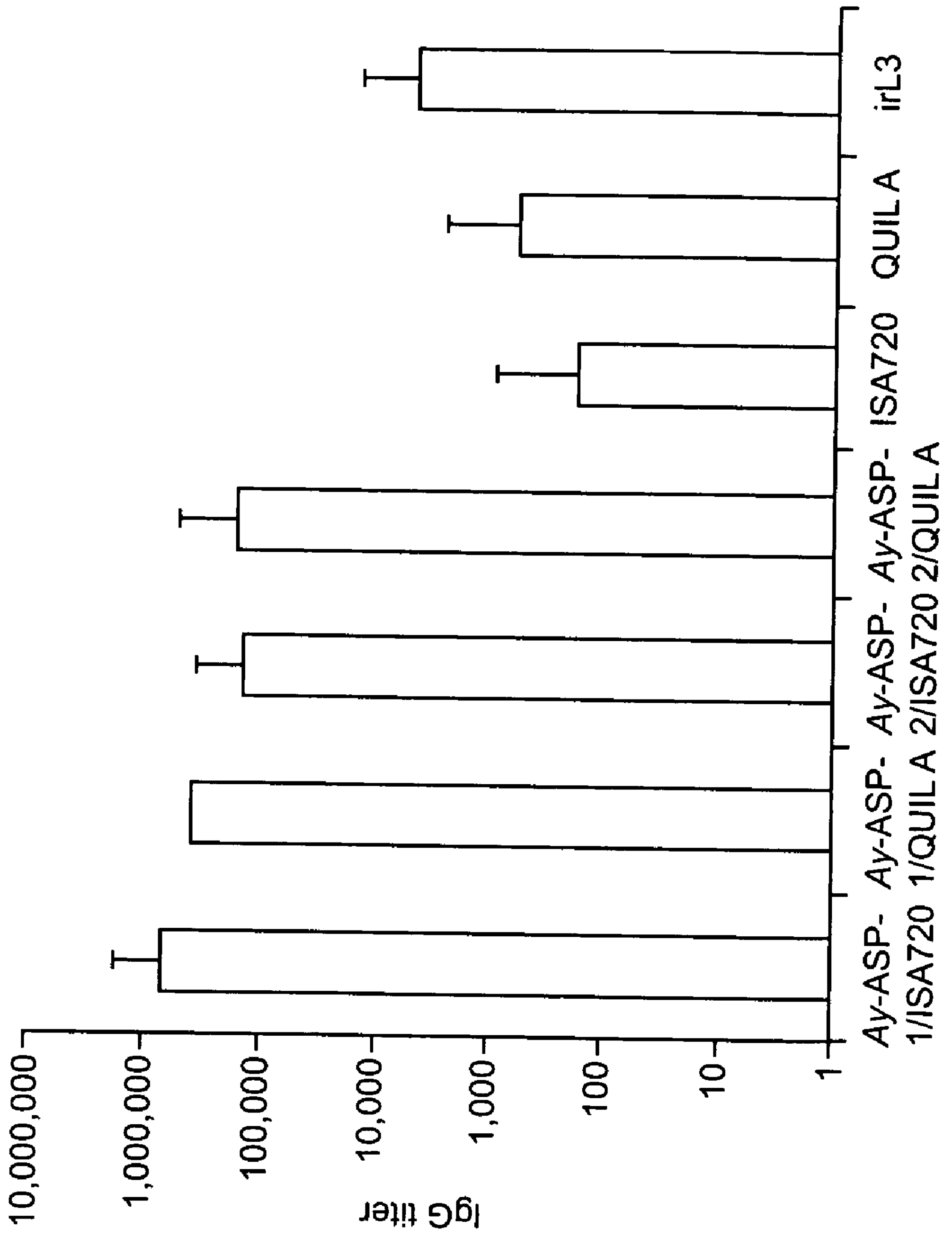
FIG. 44. Total IgG titers (geometric) in serum from golden Syrian hamsters vaccinated with Ay (*Ancylostoma ceylanicum*)-ASP-1 (SEQ ID NO: 56) mean SD (*Ancylostoma*-secreted protein) and Ay-ASP-2 (SEQ ID NO: 58) formulated with either Quil A or Montanide ISA-720 as adjuvant. Serum samples were obtained 8 days after the final vaccination (see Materials and Methods). Vaccinations with radiation-attenuated *A. ceylanicum* third-stage infective larvae (irL3) are included as a positive control (hamsters/group). Antibody titers were determined by measuring the last dilution that resulted in 3 SD above n p 10 background.

Hamster immune responses to vaccination. The prechallenge IgG antibody titers in response to 3 vaccinations with ASP-1 or ASP-2 formulated with either Quil A or Montanide ISA-720 and 2 vaccinations with irL3 are shown in FIG. 44. In response to the ASP vaccination series, hamsters developed high anti-ASP-1 (1: 364,500) and anti-ASP-2 IgG (1: 135,609) titers when Quil A was used as the adjuvant and high anti-ASP-1 (1: 631,333) and anti-ASP-2 IgG (1: 135, 609) titers when Montanide ISA-720 was used as the adjuvant, but only modest anti-L3 (1: 4500) titers. Because of the absence of commercially available antihamster secondary antibodies, no other immunoglobulin classes or subclasses were measured.

Vaccination and challenge with *A. ceylanicum* L3. After oral challenge with 100 A. *ceylanicum* L3, statistically significant reductions in adult hookworm burden were noted among the hamsters vaccinated with either irL3 (58% reduction; P<0.001) or Ay-ASP-2 (SEQ ID NO: 58) formulated with Quil A (32%; P=0.025) (table VI).

TABLE VI

Hookworm burden reductions in hamsters after vaccination with Quil A alone (control group), recombinant Ay (*Ancylostoma ceylanicum*)-ASP-1 (SEQ ID NO: 56) *Ancylostoma*-secreted protein-1) formulated with Quil A, Ay-ASP-2 (SEQ ID NO: 58) formulated with Quil A, or irradiated *A. ceylanicum* third-stage infective larvae (L3), followed by *A. ceylanicum* L3 challenge.

| Groups | Adult hookworms, mean ± SD | Reduction relative to Quil A-injected hamsters, % | P, one-sided |
|---|---|---|---|
| Quil A alone | 55.8 ± 12.1 | — | — |
| Ay-ASP-1 formulated with Quil A | 44.4 ± 20.7 | 21 | .16 |
| Ay-ASP-2 formulated with Quil A | 37.9 ± 19.8 | 32 | .025 |
| Irradiated L3 | 23.4 ± 16.4 | 58 | <.001 |

Statistically significant protection was not observed in hamsters vaccinated with Ay-ASP-1 (SEQ ID NO: 56) formulated with Quil A or with either ASP molecule formulated with the adjuvant Montanide ISA-720 (data not shown). In addition to reducing hookworm burden, as shown in table VII, vaccination with Ay-ASP-2 (SEQ ID NO: 58) formulated with Quil A reduced the size of the hook-worms by 14%, relative to that of the hookworms recovered from hamsters vaccinated with Quil A alone (P<0.001).

TABLE VII

Comparison of the mean lengths of hookworms recovered from hamsters after vaccination with Quil A alone (control group), recombinant Ay (*Ancylostoma ceylani-cum*)-ASP-1 (SEQ ID NO: 56) (*Ancylostoma*-secreted protein-1) formulated with Quil A, Ay-ASP-2 (SEQ ID NO: 58) formulated with Quil A, or irradiated *A. ceylanicum* third-stage infective larvae (L3), followed by *A. ceylanicum* L3 challenge.

| Group | No. of worms | Length, mean ± SD, cm | Reduction in worm length, % | P |
|---|---|---|---|---|
| Quil A alone | 464 | 0.50 ± 0.18 | — | — |
| Ay-ASP-1 (SEQ ID NO: 56) formulated with Quil A | 424 | 0.50 ± 0.17 | 0 | .99 |
| Ay-ASP-2 (SEQ ID NO: 58) formulated with Quil A | 310 | 0.43 ± 0.18 | 14 | <.001 |
| Irradiated L3 | 217 | 0.47 ± 0.19 | 6 | 0.18 |

The hamsters vaccinated with either Ay-ASP-2 (SEQ ID NO: 58) formulated with Quil A or irL3 experienced statistically significant reductions in host spleen size, compared with hamsters vaccinated with Quil A alone (table VIII). After host blood loss in hamsters infected with heavy hookworm burdens, the spleen expanded in size because of an influx of hematopoietic cells replacing lymphoid tissue. The extramedullary hematopoiesis was characterized by a pre-dominance of erythroblastic cells with deep blue cytoplasm and megakaryocytes (not shown). The spleens exhibited a statistically significant negative correlation ($r=-0.5$; $P<0.01$) with host circulating hemoglobin levels. In contrast, there were no statistically significant differences in splenic weights between hamsters vaccinated with both ASPs formulated with Montanide ISA-720 or with Montanide ISA-720 adjuvant alone (data not shown). As shown in table IX, hamsters vaccinated with either irL3 or ASP-1 formulated with Quil A also experienced less loss of body weight than did hamsters vaccinated with Quil A alone.

TABLE VIII

Weights of spleens recovered from hamsters after vaccination with Quil A alone (control group), recombinant Ay (*Ancylostoma ceylanicum*)-ASP-1 (SEQ ID NO: 56) (*Ancylostoma*-secreted protein-1) formulated with Quil A, Ay-ASP-2 (SEQ ID NO: 58) formulated with Quil A, or irradiated *A. ceylanicum* third-stage infective larvae (L3), followed by *A. ceylanicum* L3 challenge.

| Group | Spleen weight, mean ± SD, g | P |
|---|---|---|
| Quil A alone | 0.61 ± 0.07 | — |
| Ay-ASP-1 (SEQ ID NO: 56) formulated with Quil A | 0.52 ± 0.09 | .36 |
| Ay-ASP-2 (SEQ ID NO: 58) formulated with Quil A | 0.46 ± 0.14 | .025 |
| Irradiated L3 | 0.40 ± 0.09 | <.001 |

TABLE IX

Body-weight reductions of hamsters vaccinated with Quil A alone (control group), recombinant Ay (*Ancylostoma ceylanicum*)-ASP-1 (SEQ ID NO: 56) (*Ancylostoma*-secreted protein-1) formulated with Quil A, Ay-ASP-2 (SEQ ID NO: 58) formulated with Quil A, or irradiated *A. ceylanicum* third-stage infective larvae (L3).

| Group | Mean (median) ± SD, g | P |
|---|---|---|
| Quil A alone | 17.8 (17.0) ± 4.4 | — |
| Ay-ASP-1 (SEQ ID NO: 56) formulated with Quil A | 17.8 (16.6) ± 4.9 | .94 |
| Ay-ASP-2 (SEQ ID NO: 58) formulated with Quil A | 15.5 (14.3) ± 9.2 | .27 |
| Irradiated L3 | 10.8 (12.4) ± 4.9 | .006 |

NOTE.
Body weights were measured at necropsy and were compared with body weights at the time of experimental infection with L3.

Discussion for Example 11.

In studies performed during the 1960s, irL3 were shown to induce high levels of protective immunity in dogs, as evidenced by reduced hookworm burden and size and diminished blood loss [29]. These observations provided the basis for a commercial dog antihookworm vaccine that was marketed in Florida in 1973 and then in the eastern United States in 1974 [30]. The irL3 vaccine was later removed from commercial production because of its high cost and the requirement that the irL3 needed to maintain viability in order to release hookworm antigens [11, 21, 30]. Because administration of living L3 is not a viable strategy for human antihookworm vaccine development, an alternative approach might be to vaccinate animals with antigens secreted by living larvae; this, in turn, relies on the identification of the major L3 antigens secreted by the parasite at host entry and on cloning of the corresponding genes to produce recombinant proteins [11]. The results presented here have demonstrated that, in hamsters, recombinant ASP-2 derived from *A. ceylanicum* L3 elicits levels of protection comparable to levels elicited by irL3.

Both asp-1 and asp-2 cDNAs were expressed in methanol by *P. pastoris*. The rationale for selecting yeast as an expression vector is that previous attempts to express asp cDNAs in *Escherichia coli* resulted in the production of expressed recombinant proteins in inclusion bodies. The *E. coli*—expressed proteins could not be refolded or solubilized. We and others have determined that *E. coli* fails to express proteins of the PRP superfamily in soluble form [11,31], most likely because their high cysteine content causes improper protein folding secondary to aberrant disulfide bond formation [11]. For instance, ASP-1 is a 45-kDa molecule containing 20 cysteines and 10 disulfide bonds in 2 PRP domains [24], whereas ASP-2 is a 24-kDa molecule containing 10 cysteines and 5 disulfide bonds in a single PRP domain [22, 25]. Other investigators have reported similar difficulties in expressing PRP superfamily proteins in prokaryotic systems [31].

One advantage of using *P. pastoris*, as opposed to other eukaryotic expression systems, such as insect and mammalian cells, is the comparatively high yields obtained from the yeast system, which allows recombinant proteins to be expressed at relatively low cost. It is anticipated that cost will be an important factor in the manufacture of human antihookworm vaccines targeted for the poorest of the poor in developing countries [32].

The ASPs were tested in laboratory hamsters challenged with *A. ceylanicum*. Although *A. ceylanicum* is considered to be only a minor cause of hookworm in humans, it has been adapted for use in studying the pathobiology of animal hookworm infections. Among the benefits of studying *A. ceylanicum* in hamsters is that heavy infections cause host blood loss leading to anemia [33]. This makes it possible to determine whether vaccination helps to reduce blood loss, as well as hookworm burden. Because the spleen increases in size and weight with extramedullary hematopoiesis caused by blood loss and anemia, the organ can be measured as a surrogate for measuring blood loss. However, the hamster model also suffers from some disadvantages for purposes of vaccine development. First, the hookworm is not a natural parasite of hamsters, and, second, there are very few immunological reagents to study the host immune response to either vaccination or infection. ASP-2 is the first recombinant vaccine antigen that has been shown to protect a permissive host (a host in which L3 complete their development to the adult stages) against hookworm at a level comparable to irL3. This molecule exhibits a high degree of amino acid similarity to Hc24, a protective antigen isolated from the trichostrongyle *Haemonchus contortus* [34-35], as well as a single-domain ASP protective antigen from *Ostertagia ostertagi [*36] and *Onchocerca volvulus [*37-38]. In sheep, Hc24-induced protection is dependent on antigen-specific host IgE [35]. The absence of hamster-specific immunological reagents made it impossible to measure antigen-specific IgE titers, although the antigen-specific IgG titers exceeded 1: 100,000 in the present study. In contrast, ASP-1 did not elicit comparable protection in hamsters, even though it elicited a strong immune response. The modest level of protection was disappointing, given that a fusion protein composed of a histidine tag and aa 96-428 of *A. caninum* ASP-1 was effective at blocking *A. caninum* L3 migrations in mice, when it was used as a vaccine with alum [39-41]. The basis for this difference is under investigation.

The differences in protection noted between ASP-2 formulated with Quil A and ASP-2 formulated with Montanide ISA-720 are also under study. Quil A is a derivative of saponin and was chosen because it has been used successfully as an adjuvant for recombinant schistosome proteins in mice and water buffaloes [42, 43]. Montanide ISA-720 was chosen because of its previous use as an adjuvant in experimental human malaria vaccines [44, 45]. Without the benefit of available immunological reagents, however, it will be difficult to determine the qualitative differences in the immune response profiles of these 2 adjuvant formulations in hamsters.

Because of the success of the ASP-2 homologue Hc24 in sheep and, in the present study, in hamsters, ASP-2 will be considered further for development and pilot manufacture of clinical-grade recombinant protein. Parallel studies have demonstrated that a small subset of humans living in regions of China and Brazil where hookworm is endemic acquire naturally circulating anti-ASP-2 antibodies. Early indications are that these individuals exhibit low hookworm burdens and are resistant to reinfection (date not shown). Moreover, in preliminary data from our laboratory, we have found some protection against *A. caninum* infections in dogs vaccinated with recombinant *A. caninum* ASP-2 (authors' unpublished data). Together with the results reported here, these data will be used to justify moving forward to human phase 1 clinical trials with Na-ASP-2 (SEQ ID NO: 69) as a lead vaccine candidate.

References for Example 11

1. de Silva N, Brooker S, Hotez P, Montresor A, Engels D, Savioli L. Soil-transmitted helminth infections: updating the global picture. Trends Parasitol 2003; 19:547-51.
2. Hotez P J. China's hookworms. China Q 2002; 172:1029-41.
3. Stoltzfus R J, Chwaya H M, Tielsch J M, Schulze K J, Albonico M, Savioli L. Epidemiology of iron deficiency anemia in Zanzibari schoolchildren: the importance of hookworms. Am J Clin Nutr 1997; 65:153-9.
4. Stoltzfus R J, Dreyfuss M L, Chwaya H M, Albonico M. Hookworm control as a strategy to prevent iron deficiency. Nutr Rev 1997; 55:223-32.
5. Dreyfuss M L, Stoltzfus R J, Shrestha J B, et al. Hookworms, malaria and vitamin A deficiency contribute to anemia and irondeficiency among pregnant women in the plains of Nepal. J Nutr 2000; 130:2527-36.
6. Williamson A L, Brindley P J, Abbenante G, et al. Cleavage of hemoglobin by hookworm cathepsin D aspartic proteases and its potential contribution to host-specificity. FASEB J 2002; 16:1458-60.
7. Williamson A L, Brindley P J, Abbenante G, et al. Hookworm aspartic protease, Na-APR-2, cleaves human hemoglobin and serum proteins in a host-specific fashion. J Infect Dis 2003; 187:484-94.
8. Williamson A L, Brindley P J, Knox DP, Hotez P J, Loukas A. Digestive proteases of blood-feeding nematodes. Trends Parasitol 2003; 19: 417-23.
9. Murray C J L, Lopez A D. The global burden of disease. Global Burden of Disease and Injury Series. Geneva: World Health Organization, 1996.
10. World Health Organization (WHO). World Health Report 2002. Geneva: WHO, 2002.
11. Hotez P J, Zhan B, Bethony J M, et al. Progress in the development of a recombinant vaccine for human hookworm disease: the Human Hookworm Vaccine Initiative. Int J Parasitol 2003; 33:1245-58.
12. Albonico M, Crompton D W, Savioli L. Control strategies for human intestinal nematode infections. Adv Parasitol 1999; 42:277-341.
13. Hotez P J. Hookworm disease in children. Pediatr Infect Dis J 1989;8: 516-20.
14. Sakti H, Nokes C, Hertanto W S, et al. Evidence for an association between hookworm infection and cognitive function in Indonesian school children. Trop Med Int Health 1999; 4:322-34.
15. Stephenson L S, Latham M C, Kurz KM, Kinoti S N, Brigham H. Treatment with a single dose of albendazole improves growth of Kenyan schoolchildren with hookworm, *Trichuris trichiura*, and *Ascaris lumbricoides* infection. Am J Trop Med Hyg 1989; 41:78-87.
16. Bundy DAP. Is the hookworm just another geohelminth? In: Schad G A, Warren K S, eds. Hookworm disease, current status and new directions. London: Taylor & Francis, 1990:147-64.
17. Gandhi N S, Chen J Z, Koshnood K, et al. Epidemiology of *Necator americanus* hookworm infections in Xiulongkan Village, Hainan Province, China: high prevalence and intensity among middle-aged and elderly residents. J Parasitol 2001; 87:739-43.
18. Bethony J, Chen J Z, Lin S X, et al. Emerging patterns of hookworm infection: influence of aging on the intensity of *Necator* infection in Hainan Province, People's Republic of China. Clin Infect Dis 2002; 35:1336-44.
19. Bundy D A, Chan M S, Savioli L. Hookworm infection in pregnancy. Trans R Soc Trop Med Hyg 1995; 89:521-2.

20. Albonico M, Smith P G, Ercole E, et al. Rate of reinfection with intestinal nematodes after treatment of children with mebendazole or albendazole in a highly endemic area. Trans R Soc Trop Med Hyg 1995; 89:538-41.

21. Hotez P, Ghosh K, Hawdon J M, et al. Experimental approaches to the development of a recombinant hook-worm vaccine. Immunol Rev 1999; 171:163-71.

22. Hawdon J M, Hotez P J. Hookworm: developmental biology of the infectious process. Curr Opin Genet Dev 1996; 6:618-23.

23. Zhan B, Hotez P J, Wang Y, Hawdon J M. A developmentally regulated metalloprotease secreted by host-stimulated *Ancylostoma caninum* third-stage infective larvae is a member of the astacin family of proteases. Mol Biochem Parasitol 2002; 120:291-6.

24. Hawdon J M, Jones BF, Hoffman D, Hotez P J. Cloning and expression of *Ancylostoma* secreted protein: a polypeptide associated with the transition to parasitism by infective hookworm larvae. J Biol Chem 1996; 271:6672-8.

25. Hawdon J M, Narasimhan S, Hotez P J. *Ancylostoma* secreted protein 2: cloning and characterization of a second member of a family of nematode secreted proteins from *Ancylostoma caninum*. Mol Biochem Parasitol 1999; 99:149-65.

26. Courtney W D, Polley D, Miller V L. TAF, an improved fixative in nematode technique. Plan Disease Reporter 1995; 39:570-1.

27. Hotez P J, Ashcom J, Zhan B, et al. Effect of recombinant fusion protein vaccinations on *Ancylostoma caninum* adult hookworm habitat selection in the canine intestine. J Parasitol 2002; 88:684-90.

28. Bin Z, Hawdon J, Qiang S, et al. *Ancylostoma* secreted protein 1 (ASP-1) homologues in human hookworms. Mol Biochem Parasitol 1999; 98:143-9.

29. Miller T A. Vaccination against the canine hookworm diseases. Adv Parasitol 1971; 9:153-83.

30. Miller T A. Industrial development and field use of the canine hook-worm vaccine. Adv Parasitol 1978; 16:333-42.

31. Monsalve R I, Lu G, King T P. Expression of recombinant venom al-lergen, antigen 5 of yellowjacket (*Vespula vulgaris*) and paper wasp (*Polistes annulares*), in bacteria or yeast. Protein Expr Purif 1999; 16: 410-6.

32. Hotez P J. Vaccines as instruments of foreign policy. EMBO Rep 2001;2: 862-8.

33. Bungiro R D Jr, Greene J, Kruglov E, Cappello M. Mitigation of hook-worm disease by immunization with soluble extracts of *Ancylostoma ceylanicum*. J Infect Dis 2001; 183:1380-7.

34. Schallig H, van Leeuwen M A, Cornelissen A W. Protective immunity induced by vaccination with two *Haemonchus contortus* excretory secretory proteins in sheep. Parasite Immunol 1997; 19:447-53.

35. Kooyman F N, Schallig H D, van Leeuwen M A, et al. Protection in lambs vaccinated with *Haemonchus contortus* antigens is age related, and cor-relates with IgE rather than IgG1 antibody. Parasite Immunol 2000; 22:13-20.

36. Geldhof P, Vercauteren I, Gevaert K, et al. Activation associated secreted proteins are the most abundant antigens in a host protective fraction from *Ostertagia ostertagi*. Mol Biochem Parasitol 2003; 128:111-4.

37. Lustigman S, James E R, Tawe W, Abraham D. Towards a recombinant antigen vaccine against *Onchocerca volvulus*. Trends Parasitol 2002; 18: 135-41.

38. Lustigman S, MacDonald A J M, Abraham D. CD4+ dependent immunity to *Onchocerca volvulus* third-stage larvae in humans and the mouse vaccination model: common ground and distinctions. Int J Parasitol 2003; 33:1161-71.

39. Ghosh K, Hawdon J M, Hotez P J. Vaccination with alum-precipitated ASP-1 protects mice against challenge infections with infective hook-worm (*Ancylostoma caninum*) larvae. J Infect Dis 1996; 174:1380-3.

40. Ghosh K, Hotez P J. Antibody-dependent reductions in mouse hook-worm burden after vaccination with *Ancylostoma caninum* secreted protein 1. J Infect Dis 1999; 180:1674-8.

41. Sen L, Ghosh K, Bin Z, et al. Hookworm burden reductions in BALB/c mice vaccinated with *Ancylostoma* secreted protein I (ASP-1) from *Ancylostoma duodenale, A. caninum* and *Necator americanus*. Vaccine 2000; 18:1096-102.

42. McManus D P, Wong J Y, Zhou J, et al. Recombinant paramyosin (rec-Sj-97) tested for immunogenicity and vaccine efficacy against *Schistosoma japonicum* in mice and water buffaloes. Vaccine 2001; 20:870-8.

43. Zhou J, Waine G J, Zheng Q, Zeng X, Yi X, McManus DP. B-cell epitopes recognized by Chinese water buffaloes (*Bos buffelus*) on the 22 kDa tegumental membrane-associated antigen (Sj-22) of the Asiatic blood-fluke, *Schistosoma japonicum*. Vet Re s 1999; 30:427-32.

44. Saul A, Lawrence G, Smillie A, et al. Human phase I vaccine trials of 3 recombinant asexual stage malaria antigens with Montanide ISA 720 adjuvant. Vaccine 1999; 17:3145-59.

45. Genton B, Al-Yaman F, Anders R, et al. Safety and immunogenicity of a three-component blood-stage malaria vaccine in adults living in an endemic area of Papua New Guinea. Vaccine 2000; 18:2504-11.

Example 12

Antibodies Against a Secreted Protein from Hookworm Larvae Reduce the Intensity of Infection in Humans and Laboratory Animals An estimated 740 million people are infected with the hookworms *Necator americanus* or *Ancylostoma duodenale* in the tropics and subtropics[1]. New data employing disability adjusted life years (DALYs) reveals that hookworm disease outranks African trypanosomiasis, schistosomiasis, dengue, Chagas disease, and leprosy in terms of disease burden[2]. The major approach to hookworm control currently relies on periodic deworming through the administration of benzimidazole anthelmintic drugs. However, rapid re-infection after anthelmintic treatment[3] and the diminishing efficacy of benzimidazoles with repeated use[4] have made the successful development of an anti-hookworm vaccine an urgent public health need.

The development of a hookworm vaccine requires an understanding of how protective immune responses are generated, both in individuals from endemic areas and laboratory animals under experimental conditions. Human and animal studies of helminth infections have established the importance of antibody-mediated protection, especially the protective role of parasite-specific IgE 5. For example, specific IgE against helminth antigens associates with reduced infection intensities (quantitative egg counts) to human infections with *Schistosoma*[6,7], *Trichuris*[8] and *Ascaris*[9].

Individuals with high levels of total and parasite-specific IgE had fewer and less fecund hookworms[10,11]. In laboratory animals, IgE mediates resistance to experimental schistosome infections in baboons[12], nematode infections of sheep and cattle[13,14] and nematode parasites of rodents[15]. Although the exact mechanisms by which IgE mediates protection are not known, it is thought to target degranulation of mast cells, basophils and eosinophils against the parasite[5].

With human and animal studies having established the importance of IgE-mediated protection against helminth parasites, we sought to identify antigens that elicit a strong, but not harmful, IgE response for the development of an effective hookworm vaccine. Based on the success of vaccinating laboratory animals with irradiated hookworm larvae[16,17], we examined the antibody responses of individuals living in hookworm endemic areas against the most abundant antigens released by infective larval stages (L3) of hookworms, the *Ancylostoma* Secreted Proteins (ASPs). The ASPs belong to the pathogenesis related protein (PRP) superfamily[18,19], and both ASP-1 and ASP-2 have been shown to be protective in rodent models of hookworm infection[20,21].

Cross-sectional studies from *N. americanus* endemic areas in Brazil and China, showed that the presence of IgE against ASP-2 associated with reduction in the intensity of infection. Subsequently, the protective role of ASP-2 in a canine experimental model of hookworm infection was confirmed. These parallel findings in humans and canines suggest that the presence of antibodies against ASP-2 results in a marked reduction in infection intensity, thus providing the strongest support yet for the development of an effective recombinant vaccine against human hookworm infection.

Results for Example 12.

Hookworm Infection Prevalence and Intensities in Brazil and China

Figure 45:
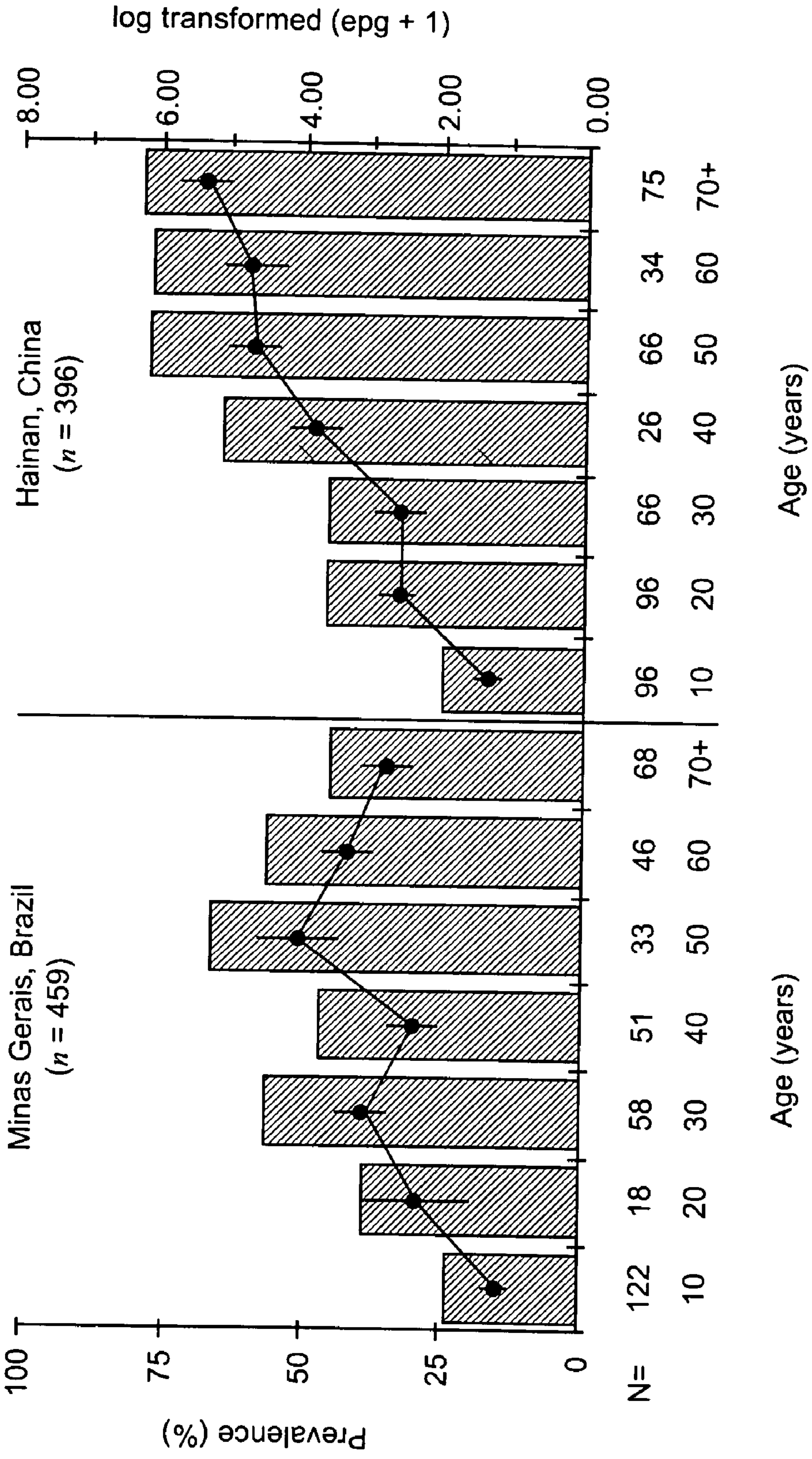
FIG. 45. The relationship between age and prevalence (bars) and log transformed eggs per gram of feces (lnepg) (●) in people infected with *Necator americanus* in Minas Gerais, Brazil (n=495) and Hainan Province, China (n=396). Lines represent standard error of the mean for lnepg.

The prevalence (95% Confidence interval [CI]) of *N. americanus* infection in the Brazilian sample was 62% (58, 66%; n=245), with a mean (95% CI) epg of 301 (222, 350). The prevalence (95% CI) of *N. americanus* infection in the China sample 6 was 56% (51, 60%; n=257), with a mean (95% CI) epg of 971 (639, 1304). FIG. 45 shows that the middle-age and elderly age strata have the highest prevalence and intensity of infection in both samples.

Infected People Generate Heterogeneous Antibody Responses to Crude Hookworm Extracts Sera from each blood sample were assayed for antibodies of each isotype to preparations of *A. caninum* crude antigen extracts, including third stage larval extract (L3E), adult extract (AE), and adult excretory/secretory (ES) products. L3 ES products were not available in sufficient quantities for serological analyses. *Necator* infected individuals produced all four IgG subclasses (IgG1, IgG2, IgG3, and IgG4) and IgE against *A. caninum* L3E, AE, and adult ES (data not shown). There was no association between levels of these antibodies and the age, sex, or intensity of infection in either study sample. A marked heterogeneity characterized the levels of antibody isotype produced to the crude antigen preparations among individuals of the same age, sex, and gender (not shown).

Expression of Recombinant, Secreted ASP-2 in Insect Cells

Figure 46:
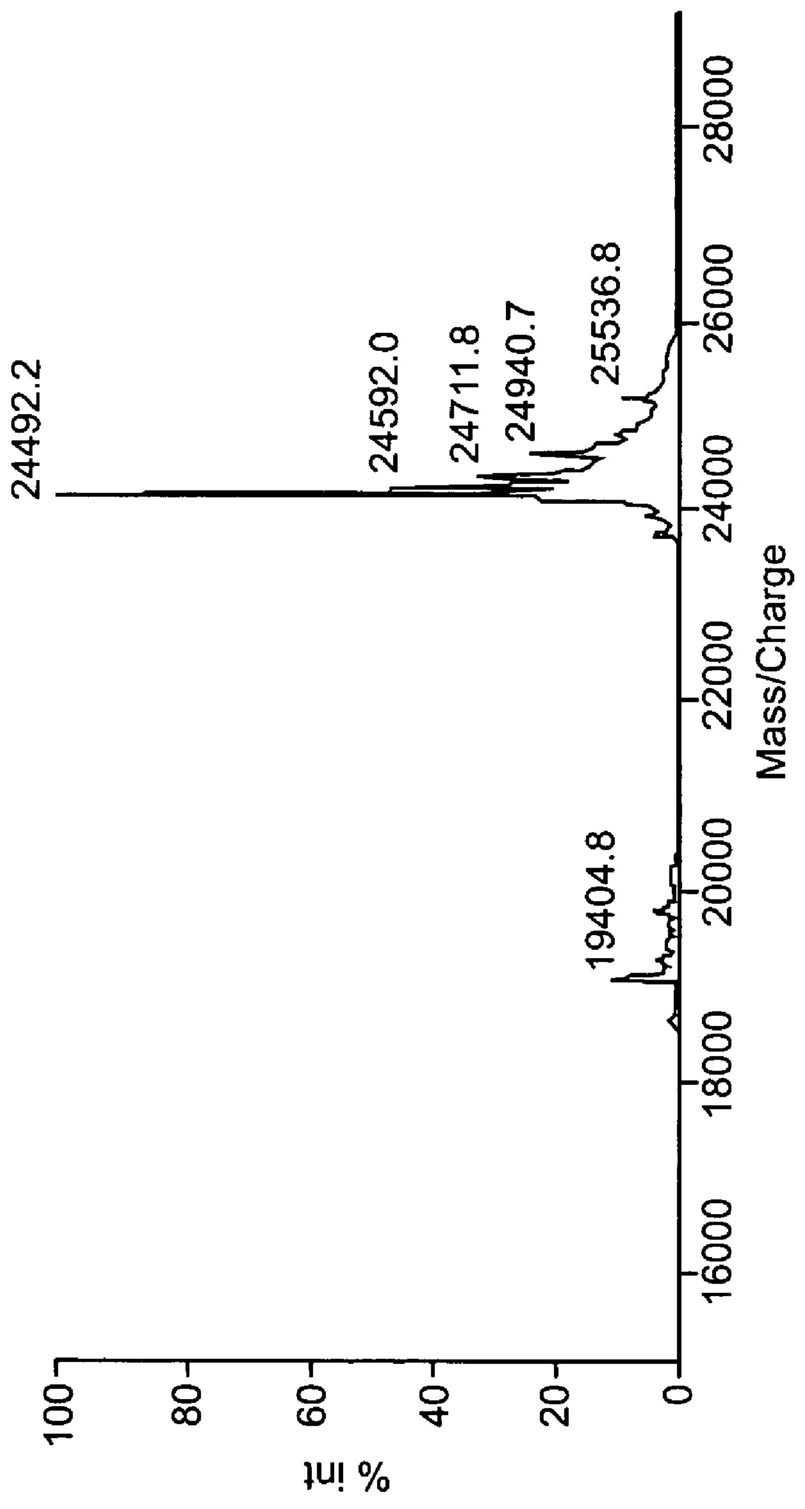
FIG. 46. Secretion, purification and biochemical analysis of recombinant Ac-ASP-2 (SEQ ID NO: 20) expressed in Sf9 insect cells. The purified protein displayed a mass of 24,492 da (major species) by mass spectroscopy with smaller quantities of minor species observed between 24,592 and 25,537 da FIG. 47. The distribution of anti-ASP-2 serum antibody isotypes from people in hookworm-endemic areas of Hainan Province, China (n=222) and Minas Gerais, Brazil (n=285) Antibody isotypes not shown here were not detected against ASP-2. Restriction in the antibody subclass response to ASP-2.
Figures 47A, 47B:
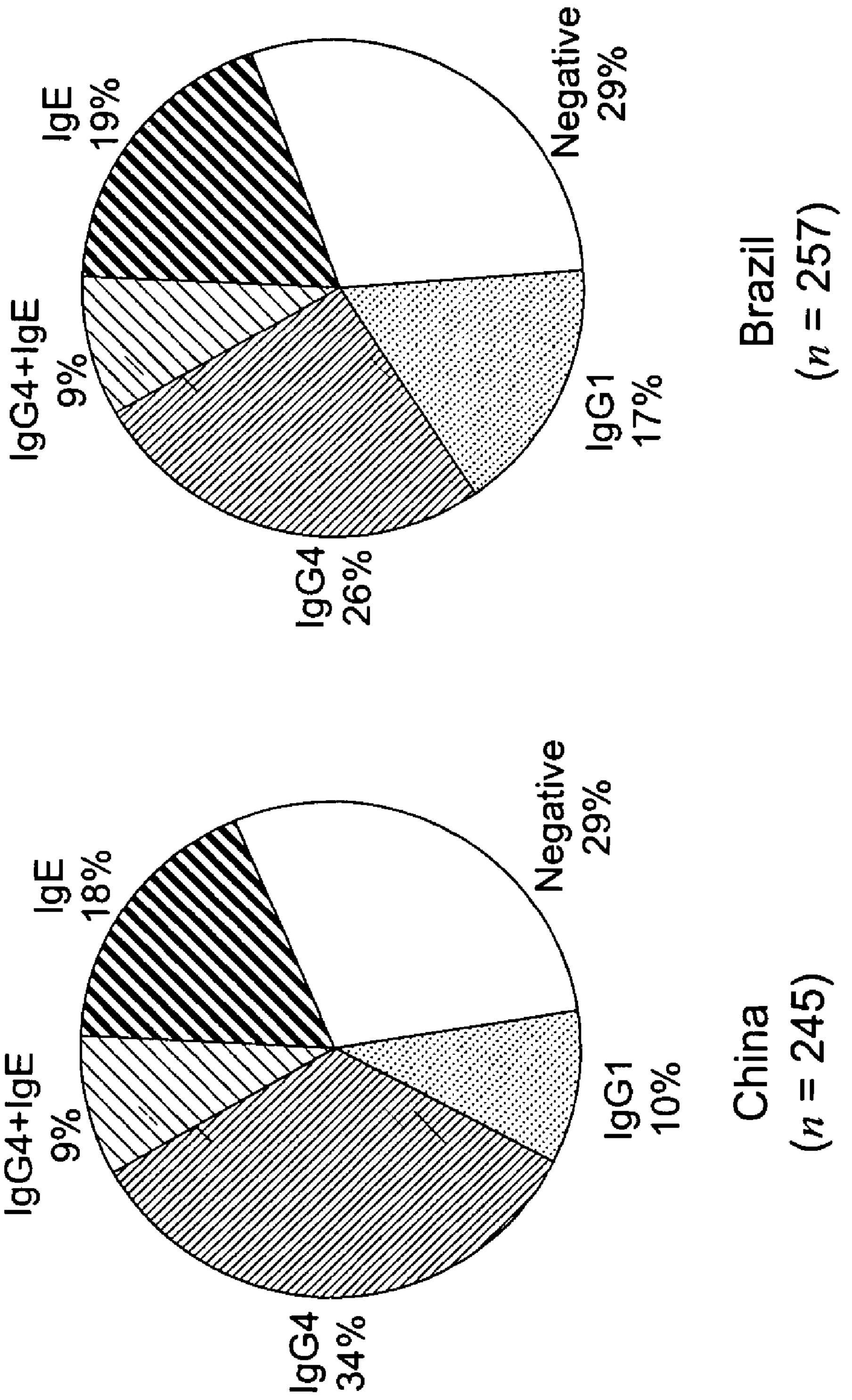

Ac-ASP-2 (SEQ ID NO: 20) was secreted a concentration of approximately 2 mg.L −1 by Sf9 cells into culture medium. The protein was purified using nickel-NTA agarose and resolved as two closely migrating bands of 24-25 kDa (not shown). Both bands were recognized by monoclonal antibodies raised to the vector-derived, C-terminal V5 and His epitopes (not shown). The five N-terminal amino acids were sequenced from both bands and they were identical: G-M-R-N-S (SEQ ID NO: 115) where G-M-R is derived from the restriction site in the cloning vector, and N-S are the first two amino acids of mature7 (processed) Ac-ASP-2 (SEQ ID NO: 20). Mass spectroscopy revealed the molecular weight of the major peak to be 24,492.2 Da (FIG. 46); this is in agreement with the predicted molecular weight of the secreted fusion protein (25,439.9 Da) in the absence of glycosylation. Ac-ASP-2 (SEQ ID NO: 20) was predicted to contain one N-linked glycosylation site at Asn-204, and treatment of the recombinant protein with PNGaseF removed the majority of protein that resolved in the upper band (data not shown). O-glycosidase treatment did not have an effect on the apparent molecular weight of recombinant Ac-ASP-2 (SEQ ID NO: 20). Rabbit antiserum raised to ASP-2 recognized the recombinant antigen as well as a protein of the expected size in L3 extracts from *N. americanus* (not shown), indicating that *N. americanus* L3 produce a protein with immunologic similarity to Ac-ASP-2 (SEQ ID NO: 20). A molecular model of Ac-ASP-2 (SEQ ID NO: 20) based on the known structure of a PRP family member (Ves v 5 from the yellow jacket) showed that the two sequences shared significant identity in fold, despite only 26% identity at the primary sequence level (not shown). ASP-2 retained the general α, β, α core sandwich fold displayed by PRPs 22.

IgE Against ASP-2 Associates with Reducedfecal Egg Counts in Infected People

*Necator*-infected individuals were classified into one of five profiles based on the predominant isotype response to recombinant ASP-2: (1) no isotype, (2) IgG1 only, (3) IgG4 only, (4) IgE only, or (5) combined IgG4 and IgE. FIG. 4*a* graphically represents the relative proportions of each antibody isotype profile from both endemic areas. The largest group consisted of infected individuals who either failed to mount an antibody response to ASP-2 (29% in both areas) or mounted an IgG4 response (34% in China and 26% in Brazil). Individuals who mounted only an IgE response to ASP-2 constituted 18% of the Chinese sample and 19% of the Brazilian sample. The 8 combined IgG4 and IgE response was consistently the smallest group (9%). As shown in immunoblots (not shown), individuals who mounted an IgE response to ASP-2 did not mount an IgG1 response. Individuals who mounted an IgG1 response did not mount an IgE response (not shown). We did not observe an IgG2 or IgG3 response to ASP-2 in the serum of any individual.

Figure 48B:
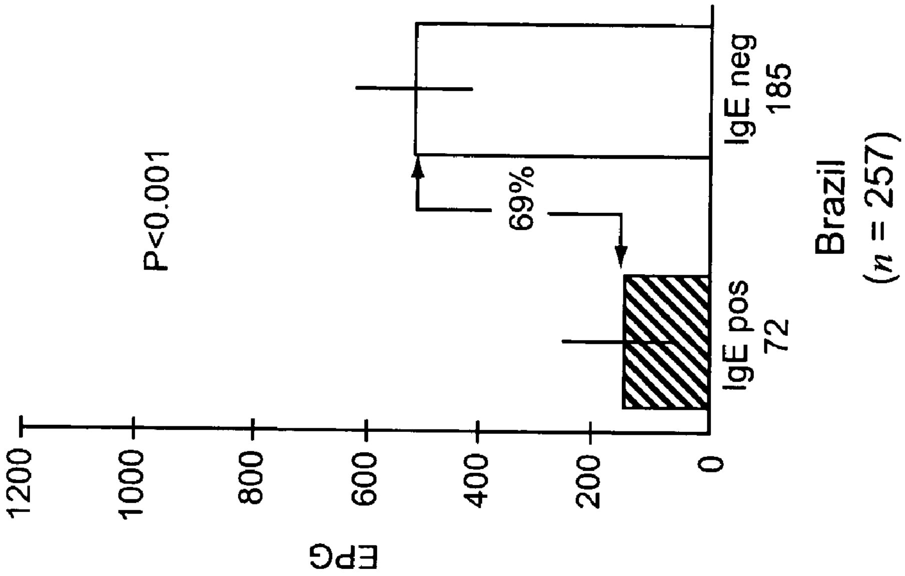
FIG. 48. The relationship between antibody isotype responses to ASP-2 and intensity of infections with *Necator americanus*. The relationship between individuals with IgE (IgE-pos) or without IgE (IgE-neg) against ASP-2 and fecal egg counts in samples from Hainan Province, China (a) and Minas Gerais, Brazil (b). Bars indicate 95% confidence intervals for the mean fecal egg counts. P values and percentages indicate differences in mean fecal egg counts between IgE-positive and IgE-negative groups.
Figure 48A:
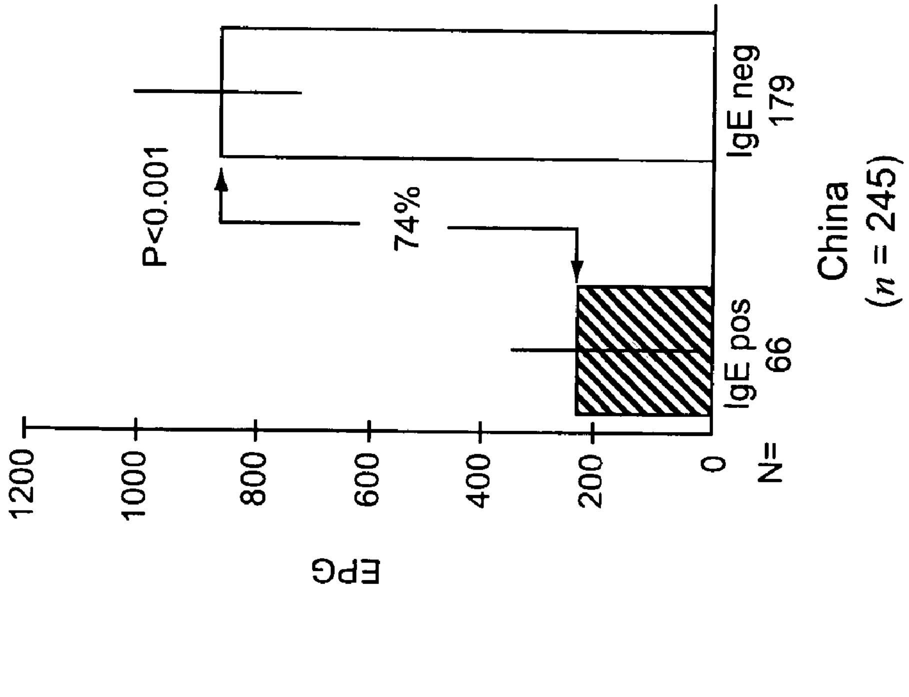

Infected individuals who were positive for IgE against Ac-ASP-2 (SEQ ID NO: 20) from China (FIG. 48*a*) and Brazil (FIG. 48*b*) had marked (74% and 69%, respectively) and significantly (P<0.001 for both) reduced fecal egg counts compared to infected individuals who did not produce IgE against ASP-2. It should be emphasized that the presence or absence of an IgE response to ASP-2, and not the quantitative nature of the response, was associated with a significant reduction in infection intensity.

Individuals who were positive for both IgG4 and IgE to ASP-2 also had reduced (30% for China and 25% for Brazil) but not significantly (P=0.123) different fecal egg counts. Sera from patients from both endemic areas were also assayed for the antibody isotype response to ASP-1, a heterodimeric protein with a duplicated PRP domain (compared with ASP-2 which has a single PRP domain). While a vigorous and heterogenous antibody isotype response was detected for IgG1, IgG3, IgG4, and IgE to ASP-1, there was no association between these responses and infection intensity, age, gender or the antibody response to crude hookworm extracts (not shown).

Figure 49:
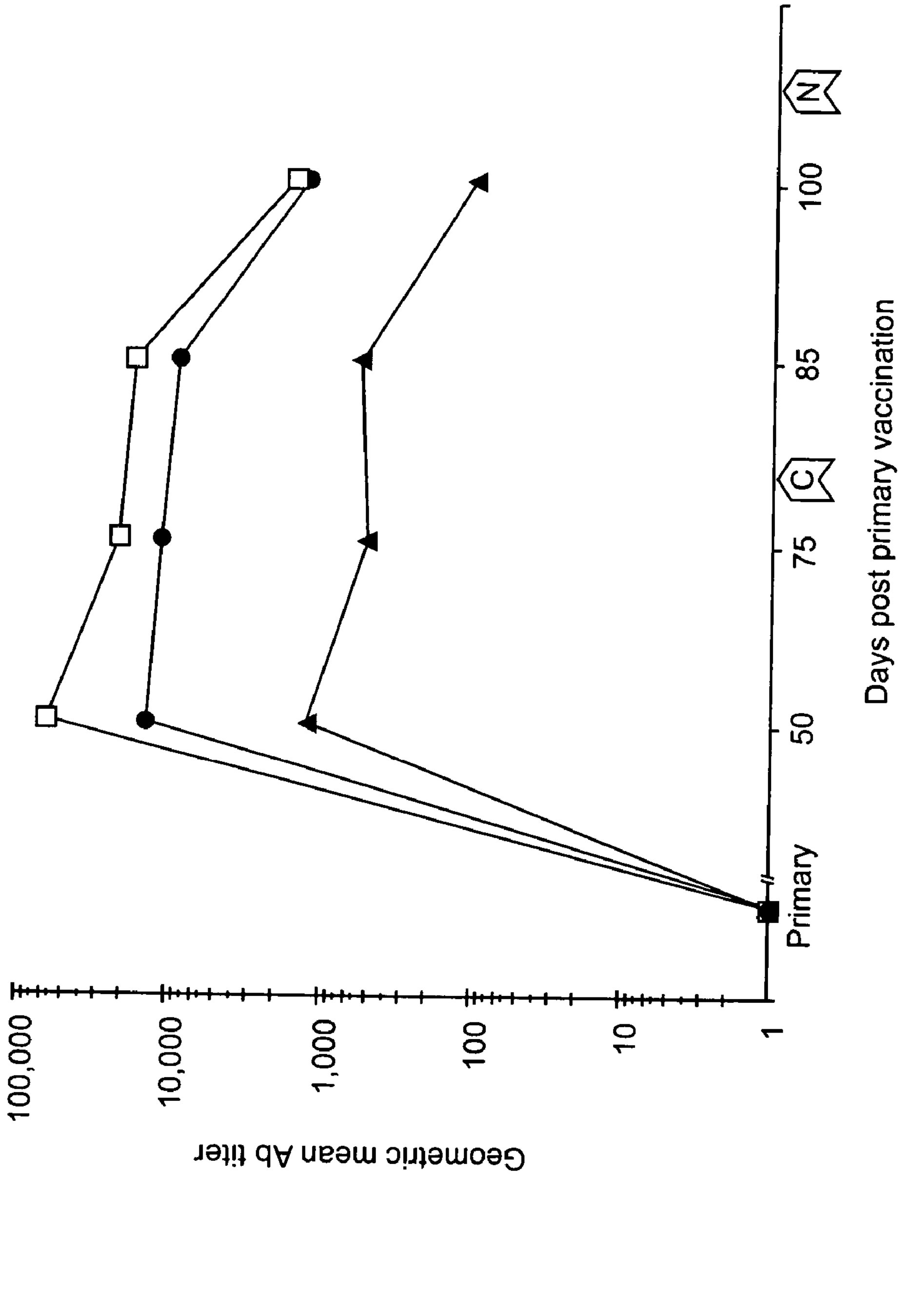
FIG. 49. Canine anti-ASP-2 antibodies induced by vaccination recognize recombinant and parasite-derived ASP-2. Geometric mean titers of the IgG1 (□), IgG2 (●) and IgE (▲) antibody responses against ASP-2 in canines vaccinated with recombinant ASP-2 The control group was vaccinated with AS03 adjuvant only and had no titers (data not shown). The letter C inside a gray arrow refers to larval challenge; the letter N inside a gray arrow refers to necropsy. Individual dogs (A-E) vaccinated with recombinant ASP-2 generated antibodies at day 75 (before larval challenge) that immunoprecipitated native ASP-2 from L3 extracts.

Vaccination of Dogs with Recombinant Ac-ASP-2 (SEQ ID NO: 20) Confers Protection Against Hookworm Infection Canines immunized with recombinant Ac-ASP-2/AS03 produced strong IgG1 and IgG2 antibody titers to recombinant Ac-ASP-2 (SEQ ID NO: 20)(FIG. 49). The IgE titers to Ac-ASP-2 (SEQ ID NO: 20) in the test canines were one log lower than the IgG1 and IgG2 titers. Dogs immunized with AS03 adjuvant alone did not generate detectable antibody responses to Ac-ASP-2 (SEQ ID NO: 20) prior to larval challenge. Sera from dogs vaccinated with recombinant ASP-2 immunoprecipitated native ASP-2 from biotinylated *A. caninum* extracts (L3E) (not shown), while sera from animals immunized with adjuvant alone did not precipitate any L3E proteins.

Figures 50A, 50B, 50C:
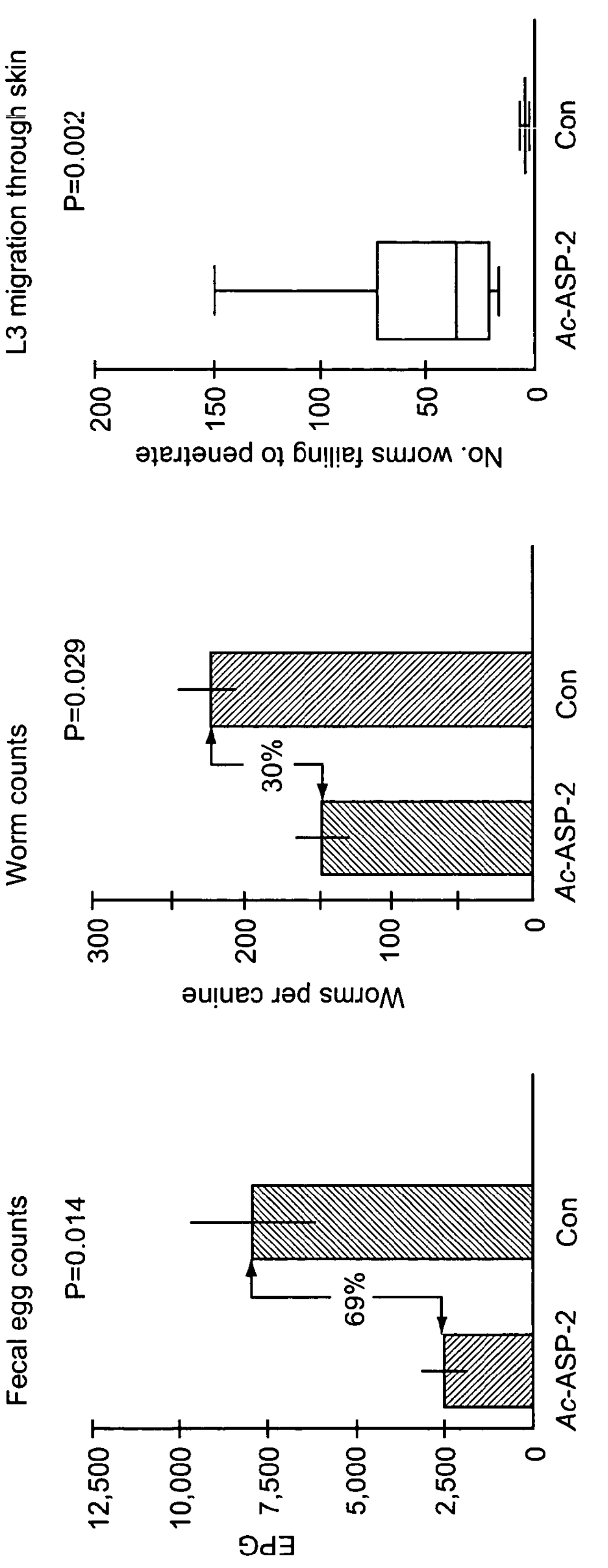
FIG. 50. Vaccination of dogs with recombinant ASP-2 provides protection against hookworm infection. Fecal egg counts for canines vaccinated with ASP-2 or the adjuvant AS03 alone (con) (a). Comparison of adult worms retrieved during necropsy from the colon and small intestine of canines vaccinated with ASP-2/AS03 and AS03 alone (con) (b). Bars indicate standard error of the mean for each group. Sera from dogs immunized with ASP-2 partially inhibited migration of *A. caninum* third stage larvae through canine skin in vitro (c). There was a 30% reduction (P=0.02) in the numbers of L3 that penetrated canine skin when L3 were first incubated in sera from vaccinated dogs compared to control animals. Values for inhibition assays are raw data.

We observed a marked (69%) and significant (P=0.025) reduction in fecal egg counts in animals vaccinated with ASP-2 compared with control animals (FIG. 50*a*). We also observed a marked (30%) and statistically significant (P=0.044) reduction in adult worms retrieved during necropsy from the colon and small intestine of animals vaccinated with ASP-2 (FIG. 50*b*).

Sera from dogs immunized with ASP-2 but not control sera interfered with migration (30% reduction) of *A. caninum* L3 through canine skin in vitro (FIG. 50*c*). There was a strong association (r 2=0.86; P=0.037) between adult worm burden in the intestine and the inhibitory effect of serum from vaccinated canines on the ability of *A. caninum* L3 to penetrate canine skin in vitro (not shown).

Discussion for Example 12.

Here we show that individuals who mount an IgE response to ASP-2 have markedly reduced intensity of hookworm infection. Vaccination of dogs with recombinant ASP-2 also resulted in protection as measured by reduced fecal egg counts and decreased worm burdens. Finally, sera from dogs vaccinated with ASP-2 reduced the ability of *A. caninum* L3 to migrate through canine skin in vitro. This is the first study to observe an association between an antibody response to a recombinant antigen and a reduction in intensity of both human and animal hookworm infections.

The ASPs are cysteine rich secretory proteins (CRISPs) belonging to the PRP superfamily[22]. All parasitic nematodes investigated to date, including the major species of animals[18,19,23-25] and humans[26-28], secrete PRPs. Available data suggest that the PRPs play diverse roles in nematode parasitism by binding to host cells. For example, nematode PRPs interfere with neutrophil recruitment by binding to integrins[29], combat hemostasis by binding to platelets and inhibiting their activation[30], and elicit angiogenesis in vitro[27]. The observation that hookworm ASP-2 is released by L3 after their stimulation with serum suggests its importance during the early stages of host larval invasion[19,31]. Therefore, specific antibody responses against ASP-2 might interrupt the physiologic function of this nematode PRP.

ASPs are the most abundant antigens recognized in host protective fractions of secretory products from nematode parasites of sheep[14] and cattle[23]. In the former study, protection was mediated by antigen-specific IgE. We now show that IgE against hookworm ASP-2 is associated with reduced infection intensity in humans. Our findings are consistent with other studies on the role of IgE in immunity to *N. americanus*[10].

Based upon the observation that sera from canines vaccinated with ASP-2 inhibited *A. caninum* L3 entry through skin in vitro, we strongly suspect that antibodies may be working to reduce the number of L3 that ultimately enter the gastrointestinal tract by first targeting them during cutaneous entry. Two convergent lines of evidence further support this theory. First, asp-2 mRNA is transcribed only by the L3 stage and ASP-2 protein is released by L3 only under host stimulatory conditions[19]. Therefore, ASP-2 functions during the larva's transition from the external environment to parasitism upon entry into the host[19,31]. In addition, natural and experimental infections with schistosomes suggests that IgE is an important component in the elimination of penetrating larvae[12].

The effects of anti-ASP-2 antibody may also extend beyond direct damage to invading larvae. Dogs vaccinated with ASP-2 had a marked reduction in adult worm fecundity, and hamsters vaccinated with the *Ancylostoma ceylanicum* orthologue of ASP-2 exhibited marked reduction in both adult worm burdens and worm size[21]. ASP-2 protein is not detected in adult parasites, however the anti-fecundity effect of vaccination with ASP-2 may be attributed to immunologic damage caused to L3 that go on to mature to adulthood. As larvae mature, sexual organogenesis occurs; if larvae are damaged or immunologically attenuated, some might be expected to reach maturity but in a compromised state, e.g., sterile or sexually immature. This is consistent with the observation that some radiation-attenuated helminth larvae develop into sterile adult worms[32]. Therefore, it is likely that the anti-fecundity effect induced by vaccination with ASP-2 is a result of both fewer worms reaching adulthood in the intestine, as well as a compromised reproductive capacity of those parasites that finally reach the gut.

The major clinical manifestations of hookworm disease are the consequences of iron deficiency, anemia and hypoalbuminemia, which develop when blood loss exceeds host iron and protein intake and reserves[33]. By these mechanisms, hookworm is increasingly recognized as a major global cause of iron-deficiency anemia, the world's most important nutritional deficiency[34]. Hookworm fecal egg counts correlate positively with host blood loss, and negatively with circulating hemoglobin concentration and iron status[35]. Therefore, the observation that anti-ASP-2 antibodies associate with reduced fecal egg counts and worms burdens has important clinical implications, and support the development of ASP-2 as a hookworm vaccine.

ASP-2 fulfills many of the criteria required for an efficacious hookworm vaccine. The optimal vaccine would have the following features: (1) it would decrease the number of L3 that reach the gastrointestinal tract; (2) it would prevent development of L3 into blood-feeding adult hookworms, and (3) it would block the survival and fecundity of adult hookworms[34,36]. Achieving all three goals will likely require a combination vaccine comprised of ASP-2 from the L3, in addition to an essential proteolytic enzyme for adult hookworm blood-feeding[37,38]. Development, manufacture, and clinical testing of such a combination vaccine are in progress[36].

Materials AND Methods for Example 12.

Patient Sample

The village of Daocong is located on the north of Hainan Island, China. Five hundred and ninety-one individuals were registered with the Daocong village administration. Three inclusion criteria were applied to the sample: (1) continuous residence in the endemic area over the last two years, (2) willing and able to comply with the study protocol Including blood and fecal samples); and (3) no prior treatment for hookworm during the previous two years as determined by survey. Three-hundred and ninety-six (67%) met all inclusion criteria. The 195 individuals not participating in the study did not differ by age (P=0.30), gender (P=0.35), occupation (P=0.43), or area of residence within the village (P=0.40). All research was performed in accordance with the ethical standards of the Yale University Human Investigations Committee (protocol 10932), the Internal Review Board (IRB) of the George Washington University Medical Center (protocol 080004), and the Institute of Parasitic Diseases through a single project assurance from the National Institutes of Health. Each house was assigned a unique household identification number (HHID) and each resident a unique personal identity number (PID). Individuals excluded from the analysis received a fecal examination and were treated for any diagnosed helminth infection.

Five hundred and twenty one individuals were enumerated in the study area of Virgem das Gracas is located in Minas Gerais State, Brazil. All research was performed in accordance with the Ethics Committee of the Centro de Pesquisas de Rene Rachou, FIOCRUZ, Belo Horizonte, Minas Gerais, Brazil (06-2002 and 02-2002) and the IRB of the George Washington University Medical Center (090303EX). At this time, each house was assigned a unique HHID and each resident a unique PID. The 3 inclusion criteria applied to the Hainan study sample were also applied here. Four-hundred and fifty-nine (88%) individuals met all three inclusion criteria. The 62 individuals not participating in the study did not differ by age (P=0.66), gender (P=0.33), occupation (P=0.21), or area of residence within the village (P=0.22). Each house was assigned a unique household identification number (HHID) and each resident a unique personal identity number (PID). Individuals excluded from the analysis received a fecal examination and were treated for any diagnosed helminth infection. Sera from 30 volunteers from a non-*Necator* endemic area in Minas Gerias, Brazil, who were egg-negative at the time of blood draw, were pooled and used as an "endemic negative control" on each ELISA plate. Sera from 28 volunteers from the United States were pooled and used as a "non-endemic negative control" on each ELISA plate.

Recombinant Protein Expression

Recombinant Ac-ASP-2 (SEQ ID NO: 20) was expressed in *Spodpotera frugiperda* Sf9 insect cells using the pMIB-V5/His expression system (Invitrogen, Carlsbad, Calif.). The entire ASP-2 open reading frame (GenBank accession number AF 089728) minus the N-terminal signal peptide (from Asn-18 to the C-terminal Gly-218) was cloned into pMIB-V5/HisA using the SphI and XbaI restriction sites so that the recombinant ASP-2 was fused in-frame with the vector-derived N-terminal melittin signal peptide and C-terminal V5 and 6-His epitopes. Sf9 cells were grown in Excell 420 medium (JRH Bioscience, Lenexa, Kans.) and transfected with ASP-2 plasmid midi-prep (Qiagen, Valencia, Calif.) and Genejammer transfection reagent (Stratagene, La Jolla, Calif.) according to the manufacturer's instructions. Transfected cells were selected using Blasticidin S (Cayla, Toulouse, France) at a final concentration of 25 $\mu g.ml^{-1}$ in 6 well plates and maintained in 10 $\mu g.ml^{-1}$ blasticidin after selection. Selected cells were transferred successively from adherent populations to shaker flasks according to the manufacturer's instructions (Invitrogen). Stably selected cells in log phase were then used to seed a total of 4 liters of Excel 420 medium to a final cell density of $1.0\times10^6$ cells per ml in a Bioflo 10 bioreactor (New Brunswick Scientific, Edison, N.J.) with a 7.5 liter vessel. The cells were maintained at a temperature of 27□C. and stirred at 70 rpm in the presence of 55-80% dissolved $O_2$. pH was not adjusted and remained between 6.1-6.4. Cells were grown until a cell density of $1.0\times10^7$ cells per ml was attained. Supernatant was harvested by centrifugation at 4,000×g and concentrated 10-fold by ultrafiltration using a 10 kDa cut-off ultrasette membrane (Pall Corporation) and peristaltic pump. Concentrated supernatant containing recombinant ASP-2 was buffer-exchanged into milliQ H2O followed by binding buffer (0.05M $NaH_2PO_4$, 0.3M NaCl, 10 mM imidazole, pH 8.0) before being applied to a nickel-NTA agarose column (Novagen, EMD Biosciences, Darmstadt, Germany) with a settled bed volume of 2.0 ml. The column was washed with 10 volumes of binding buffer followed by 5 column volumes each of 20, 40 and 60 mM imidazole in binding buffer. Proteins were eluted in 5 column volumes of 250 mM imidazole in binding buffer. Fractions were assessed for recombinant protein and resulting purity by SDS-PAGE using pre-cast 4-20% Tris-glycine gradient mini gels (Invitrogen) stained with Coomassie Brilliant Blue (CBB). Fractions containing purified protein were pooled, concentrated and buffer-exchanged into PBS, pH 7.2 at 4° C. Protein concentration was determined using a micro BCA kit (Pierce, Rockford, Ill.).

Molecular Modeling

The predicted structure of Ac-ASP-2 (SEQ ID NO: 20) was determined by modeling the amino acid sequence against all coordinates in the RCSB Protein Data Bank using the first-approach mode in Swiss-Model. Pdb files generated were refined and viewed using Swiss-PdbViewer 3.7.

Biochemical Analyses of Recombinant Ac-ASP-2

Recombinant Ac-ASP-2 (SEQ ID NO: 20) (2.0 μg) was transferred to PVDF membrane, stained with CBB, destained and rinsed extensively in distilled H2O before being submitted for Edman degradation at Columbia University Protein Core Facility, NY. Molecular weight determinations and purity were determined by Matrix-Assisted Laser Desorption Ionization, Time of Flight (MALDI-TOF) spectroscopy using an AXIMA-16 CFR instrument (Kratos Analytical Inc., Chestnut Ridge, N.Y.) by Dr Paolo Lecchi at The George Washington University Proteomics facility. The glycosylation status of recombinant Ac-ASP-2 was assessed using an Enzymatic CarboRelease kit (QA-Bio, San Mateo, Calif.) under denaturing conditions to remove any N-linked and O-linked oligosaccharides.

Production of Rabbit Anti-Ac-ASP-2 Serum and Western Blotting

Ac-ASP-2 (SEQ ID NO: 20) was formulated with Freund's Complete Adjuvant (first immunization) and Freund's Incomplete Adjuvant (second-fourth immunizations) using standard procedures. An antiserum against formulated Ac-ASP-2 (SEQ ID NO: 20) was raised in a rabbit by immunizing with 150 μg of recombinant protein per dose. The rabbit was immunized four times at 3 weekly intervals. Blood was drawn before the first and one week after the final immunization and sera were recovered. Western blotting was used to determine the antigenicity of recombinant Ac-ASP-2 (SEQ ID NO: 20) and to identify the protein in L3 extracts of *N. americanus*. Twenty-five nanograms of recombinant protein or 1.0 μg of larval extracts were separated on a 4-20% gradient SDS polyacrylamide gel and subsequently transferred to PVDF membrane. After transfer, the membrane was blocked with 5% non-fat dry milk in TBS/0.05% Tween-20 (TBST) overnight, and then probed with a 1:20,000 dilution of rabbit serum (pre- and post-vaccination) for one hour. After three washes with TBST, the membrane was incubated with horseradish peroxidase-conjugated goat anti-rabbit IgG (heavy and light chains) for one hour. Bands were visualized using ECL plus enhanced chemiluminescence (Amersham Biosciences, Piscataway, N.J.).

Parasitological Methods

The presence of intestinal nematode eggs was determined by saline float. In the case of a positive fecal sample, 3 subsequent fecal samples were taken over the course of 3 days. Two slides from each day's fecal sample were prepared within 24 hours of receipt using the Kato-Katz thick smear technique. Hookworm species (*A. duodenale* or *N. americanus*) were determined by morphological identification of third stage larvae reared from eggs by coproculture[39].

Indirect ELISA.

Serum samples were obtained from whole blood collected into siliconized tubes. Serum was separated by centrifugation at 800×g for 10 min; the resulting serum supernatant was transferred to sterile 1 mL tubes and stored at −80° C. An indirect ELISA was then used to study isotype responses of participants to three crude *A. caninum* antigen preparations. Nunc Maxisorp Surface 96 well plates (Nalge Nunc International, Rochester, N.Y.) were coated with 0.5 μg/well of crude antigen preparation in 20 mM sodium bicarbonate/27 mM sodium carbonate, pH 9.6 and stored overnight at 4° C. For IgG2 assays, 96-well plates were adsorbed overnight at room temperature with 100 μl/well of Poly-L-lysine at 1 $\mu g.mL^{-1}$ in 50 mM sodium carbonate, pH 9.0. Plates were then washed with PBS and crude antigen added and incubated in the manner described above. Plates were washed 5 times with PBS, pH 7.2, and then blocked for 1 h with PBS containing 1% fetal calf serum. Plates were washed 5 times with PBST. Serum samples were diluted 1:100 in PBST, and 100 μL/well was added in duplicate. Plates were incubated overnight at 4° C. and then washed 5 times with PBST as before. One hundred μL of the following dilutions of horseradish peroxidase-conjugated anti-human antibodies (Zymed, San Francisco, 18 CA) were added to each well: 1:5,000 of IgG1; 1:1,000 of IgG2, IgG3 and IgG4; and 1:800 of IgE. The plates were incubated for 1 h at RT and then washed 10 times with PBST. One hundred μAL per well of Ortho-Phenylenediamine (OPD, Sigma-Aldrich, St Louis, Mo.) containing 0.03% hydrogen peroxide was then added. Plates were developed for 30 minutes in the dark. The reaction was stopped with 50 μL per well of 30% $H_2SO_4$ and the Optical Density (OD) measured at 492 nm on an automated ELISA reader (Molecular Devices, Sunnyvale, Calif.). We considered sera to be positive for an isotype response to a defined antigen when the OD reading for the isotype against Ac-ASP-2 was 3 SD above the combined mean OD of the USA and Brazil controls. Assays were standardized according to previously described methods[40]. Sera used in the IgE-ELISA were not de-adsorbed for other isotypes because of the observation that people who produced IgE did not produce IgG 1 and vice versa.

Data Entry and Statistical Methods for Human Studies

All research on human subjects was conducted by trained personnel by the standards of Good Clinical Practices. Data from case report forms were double-entered into an Excel file and then transferred to SPSS 10.00. Conflicts in double entry of data were resolved by referring to source documents. Student's t-test was used to determine significant differences in means for normally distributed continuous variables for two independent effects. ANOVA was used to test the mean differences of continuous variables when an effect consisted of more than one group (e.g., 10-year age intervals). Bonferroni post hoc tests, with a significance level of 0.05, were used for multiple pair-wise testing normally distributed continuous variables. A chi-square test was used to test the significance of proportions of egg positive and negative individuals. A Pearson product moment correlation was used for all19 correlations among normally distributed variables. Spearman correlation coefficient was used as a nonparametric measure of correlation between ordinal variables. For all of the cases, the values of each of the variables were ranked from smallest to largest, and the Pearson correlation coefficient was computed on the ranks. Before calculating a correlation coefficient, data were screened for outliers.

Animal Husbandry and Vaccination

The test and control animals were purpose bred, parasite naïve male beagles 56±4 days of age (body weights equal to or exceeded 2.5 kg, hematocrit equal to or exceeded 28.0, WBC did not exceed $20\times10^6$) on arrival. All dogs in a trial were purchased from the same vendor (Marshall Farms, North Rose, N.Y.), identified by ear tattoo, and maintained in the George Washington University Animal Research Facility as previously described[37]. The experiments were conducted according to a protocol approved by the George Washington University Animal Care and Use Committee. Dogs were housed in groups for approximately one month and 1 to 3 animals per cage thereafter; controls were housed identically to test animals. Following larval challenge, all dogs were individually housed. A serum sample was obtained from each dog before the first and after each subsequent vaccination.

Crude Hookworm Antigen Preparation.

*A. caninum* L3 were harvested and homogenized to generate soluble extracts (L3E) as previously described[41]. Adult *A. caninum* ES proteins and somatic extracts (AE) were prepared as previously described[25,42]. *N. americanus* L3 were harvested and soluble extracts prepared as described elsewhere. Protein concentrations were measured using the BCA protein assay kit (Pierce).

Vaccine Study Design and Antigen-Adjuvant Formulation

This study was conducted and reported in compliance with the intent of the Good Laboratory Practice Regulations (F.R. Vol. 43, No. 247, pp. 60013-60025, Dec. 22, 1978 and subsequent amendments). The study was audited by Quality Assurance while in progress to assure compliance with GLP regulations, adherence to the protocol and standard operating procedures. The data and final report were audited by Quality Assurance to assure that the report accurately described study conduct and results. The vaccine trial was designed to test Ac-ASP-2 formulated with Adjuvant System 03 (AS03) 44 obtained from GlaxoSmithKline. The rationale for selecting AS03 as an adjuvants is discussed elsewhere 37. The ten purpose bred beagles were randomized into two arms: immunized with Ac-ASP-2 (SEQ ID NO: 20) or adjuvant only (control). To make six doses of Ac-ASP-2 (SEQ ID NO: 20) formulated with AS03, 600 μg of recombinant protein (0.3 ml of Ac-ASP-2 (SEQ ID NO: 20) at a concentration of 2 $mg.ml^{-1}$) was mixed with 1.2 ml of 20 mM Tris-HCl, 0.5 M NaCl, pH 7.9 and 1.5 ml of AS03; the contents of the tube were vortex mixed for 30 seconds then shaken at low speed for 10 minutes. Dogs were immunized with 100 μg of formulated antigen in a final volume of 0.5 ml. AS03 only control was prepared as described above, with PBS included instead of Ac-ASP-2 (SEQ ID NO: 20). Formulation of GSK adjuvants were conducted according to the protocol provided by GSK. All injections were performed intramuscularly (IM). Test and control articles were prepared on the day of injection.

Hookworm Infections and Parasite Recovery

*A. caninum* larvae were cultured from eggs collected in the feces of infected dogs. All hookworms in the infective challenge were approximately equal age (17±7 days post hatching). The species identity of the infective larvae were validated using PCR 45. All dogs were infected by the footpad method with the same dose of 500 L3 of *A. caninum* 37. Larval challenge occurred on one of three consecutive days (at age 120±9 days). Fourteen-sixteen days after the final immunization, dogs were anesthetized using a combination of ketamine and xylazine (20 $mg.kg^{-1}$ and 10 $mg.kg^{-1}$ respectively), and 500 *A. caninum* L3 in a final volume of 50 μl were applied to the footpad.

Canine Immunizations and Antibody Measurements

Beagles were immunized with formulated Ac-ASP-2 (SEQ ID NO: 20) as previously described[37]. The vaccines were administered IM three times beginning at age 62±4 days. Boosts were administered to the dogs at intervals of 21 days. Blood was drawn at least once every 21 days and serum was separated from cells by centrifugation. Each animal's specific antibody response was evaluated by indirect ELISA using serum taken prior to the infective challenge[37]. Recombinant Ac-ASP-2 (SEQ ID NO: 20) was coated onto microtiter plates at a concentration of 5 $\mu ml^{-1}$. Dog sera were titrated between 1:100 and 1:$2\times10^6$ to determine endpoint titers. Anti-canine IgG1, IgG2 and IgE antibodies conjugated to horse-radish peroxidase (Bethyl Laboratories, Montgomery, Tex.) were used at a dilution of 1:1,000.

L3 Skin Penetration Assays

Live *A. caninum* L3 were incubated with sera (neat) from immunized dogs then L3 were placed on canine skin to observe whether serum antibodies interfered with the penetration of skin in vitro[46]. Briefly, fresh skin from the ear of a dog was shaved, and approx. 4 cm 2 section of skin was stretched and sandwiched between 2×20 mL syringe barrels that were clamped together with bulldog clips. The lower syringe was filled to the top with PBS so that the buffer was in contact with the underside of the skin. One milliliter of PBS was placed on the skin for 15 min to check integrity of the skin. L3 (300 L3/group) were then incubated in 0.05 ml of PBS, pH 7.2, or undiluted serum from different vaccinated or control dogs for 30 min at 37° C. Each group of L3 were then placed on the upper side of the skin (added to the 1.0 ml of PBS already present) and allowed to migrate for 30 min at RT. L3 that remained on the surface of the skin were collected and counted, by removing the remaining liquid with a pipette and washing the skin with 2 volumes of PBS. Each assay was performed in triplicate.

References for Example 12

1. de Silva, N. R. et al. Soil-transmitted helminth infections: updating the global picture. *Trends Parasitol* 19, 547-51 (2003).
2. WHO. The world health report 2002. Reducing risks, promoting healthy life. (2002).
3. Albonico, M. et al. Rate of reinfection with intestinal nematodes after treatment of children with mebendazole or albendazole in a highly endemic area. *Trans R Soc Trop Med Hyg*[89], 538-41 (1995).
4. Albonico, M. et al. Efficacy of mebendazole and levamisole alone or in combination against intestinal nematode infections after repeated targeted mebendazole treatment in Zanzibar. *Bull World Health Organ* 81, 343-52 (2003).
5. Garraud, O., Perraut, R., Riveau, G. & Nutman, T. B. Class and subclass selection in parasite-specific antibody responses. *Trends Parasitol* 19, 300-4 (2003).
6. Hagan, P., Blumenthal, U. J., Dunn, D., Simpson, A. J. & Wilkins, H. A. Human IgE, IgG4 and resistance to reinfection with *Schistosoma haematobium. Nature* 349, 243-5 (1991).
7. Dunne, D. W. et al. Immunity after treatment of human schistosomiasis: association between IgE antibodies to adult worm antigens and resistance to reinfection. *Eur J Immunol* 22, 1483-94 (1992).
8. Faulkner, H. et al. Age- and infection intensity-dependent cytokine and antibody production in human trichuriasis: the importance of IgE. *J Infect Dis* 185, 665-72 (2002).
9. McSharry, C., Xia, Y., Holland, C. V. & Kennedy, M. W. Natural immunity to *Ascaris lumbricoides* associated with immunoglobulin E antibody to ABA-1 allergen and inflammation indicators in children. *Infect Immun* 67, 484-9 (1999).
10. Pritchard, D. I., Quinnell, R. J. & Walsh, E. A. Immunity in humans to *Necator americanus*: IgE, parasite weight and fecundity. *Parasite Immunol* 17, 71-5 (1995).
11. Loukas, A. & Prociv, P. Immune responses in hookworm infections. *Clin Microbiol Rev* 14, 689-703 (2001).
12. Nyindo, M. et al. Role of adult worm antigen-specific immunoglobulin E in acquired immunity to *Schistosoma mansoni* infection in baboons. *Infect Immun* 67, 636-42 (1999).
13. Huntley, J. F. et al. IgE responses in the serum and gastric lymph of sheep infected with *Teladorsagia circumcincta. Parasite Immunol* 20, 163-8 (1998).
14. Kooyman, F. N. et al. Protection in lambs vaccinated with *Haemonchus contortus* antigens is age related, and correlates with IgE rather than IgG1 antibody. *Parasite Immunol* 22, 13-20 (2000).
15. Negrao-Correa, D., Adams, L. S. & Bell, R. G. Variability of the intestinal immunoglobulin E response of rats to infection with *Trichinella spiralis, Heligmosomoides polygyrus* or *Nippostrongylus brasiliensis. Parasite Immunol* 21, 287-97 (1999).
16. Girod, N., Brown, A., Pritchard, D. I. & Billett, E. E. Successful vaccination of BALB/C mice against human hookworm (*Necator americanus*): the immunological phenotype of the protective response. *Int J Parasitol* 33, 71-80 (2003).
17. Miller, T. A. Persistence of immunity following double vaccination of pups with x-irradiated *Ancylostoma caninum* larvae. *J. Parasitol.* 51, 705-11 (1965).
18. Hawdon, J. M., Jones, B. F., Hoffman, D. R. & Hotez, P. J. Cloning and characterization of *Ancylostoma*-secreted protein. A novel protein associated with the transition to parasitism by infective hookworm larvae. *J Biol Chem* 271, 6672-8 (1996).
19. Hawdon, J. M., Narasimhan, S. & Hotez, P. J. *Ancylostoma* secreted protein 2: cloning and characterization of a second member of a family of nematode secreted proteins from *Ancylostoma caninum. Mol Biochem Parasitol* 99, 149-65 (1999).
20. Ghosh, K., Hawdon, J. & Hotez, P. Vaccination with alum-precipitated recombinant *Ancylostoma*-secreted protein 1 protects mice against challenge infections with infective hookworm (*Ancylostoma caninum*) larvae. *J Infect Dis* 174, 1380-3 (1996).

21. Goud, G. N. et al. Cloning, Yeast Expression, Isolation and Vaccine Testing of Recombinant *Ancylostoma* secreted protein 1 (ASP-1) and ASP-2 from *Ancylostoma ceylanicum. J Infect Dis* in press (2003).

22. Henriksen, A. et al. Major venom allergen of yellow jackets, Ves v 5: structural characterization of a pathogenesis-related protein superfamily. *Proteins* 45, 438-48 (2001).

23. Geldhof, P. et al. Activation-associated secreted proteins are the most abundant antigens in a host protective fraction from *Ostertagia ostertagi. Mol Biochem Parasitol* 128, 111-4 (2003).

24. Sharp, P. & Wagland, B. M. Nematode Vaccine. (Biotech Australia Pty Limited, USA, 1998).

25. Zhan, B. et al. Molecular characterisation of the *Ancylostoma*-secreted protein family from the adult stage of *Ancylostoma caninum. Int J Parasitol* 33, 897-907 (2003).

26. Lustigman, S., James, E. R., Tawe, W. & Abraham, D. Towards a recombinant antigen vaccine against *Onchocerca volvulus. Trends Parasitol* 18, 135-41 (2002).

27. Lustigman, S., MacDonald, A. J. & Abraham, D. CD4+-dependent immunity to *Onchocerca volvulus* third-stage larvae in humans and the mouse vaccination model: common ground and distinctions. *Int J Parasitol* 33, 1161-71 (2003).

28. Murray, J., Gregory, W. F., Gomez-Escobar, N., Atmadja, A. K. & Maizels, R. M. Expression and immune recognition of *Brugia malayi* VAL-1, a homologue of vespid venom allergens and *Ancylostoma* secreted proteins. *Mol Biochem Parasitol* 118, 89-96 (2001).

29. Moyle, M. et al. A hookworm glycoprotein that inhibits neutrophil function is a ligand of the integrin CD11b/CD18. *J. Biol. Chem.* 269, 10008-15 (1994).

30. Del Valle, A., Jones, B. F., Harrison, L. M., Chadderdon, R. C. & Cappello, M. Isolation and molecular cloning of a secreted hookworm platelet inhibitor from adult *Ancylostoma caninum. Mol Biochem Parasitol* 129, 167-77 (2003).

31. Hawdon, J. M. & Hotez, P. J. Hookworm: developmental biology of the infectious process. *Curr Opin Genet Dev* 6, 618-23 (1996).

32. Miller, T. A. Comparison of the immunogenic efficiencies of normal and x-irradiated *Ancylostoma caninum* larvae in dogs. *J Parasitol* 52, 512-9 (1966).26

33. Stoltzfus, R. J., Dreyfuss, M. L., Chwaya, H. M. & Albonico, M. Hookworm control as a strategy to prevent iron deficiency. *Nutr Rev* 55, 223-32 (1997).

34. Hotez, P. J. et al. Current concepts: Hookworm infection. *New Eng J Med* in press(2004).

35. Stoltzfus, R. J. et al. Epidemiology of iron deficiency anemia in Zanzibari schoolchildren: the importance of hookworms. *Am J Clin Nutr* 65, 153-9 (1997).

36. Hotez, P. J. et al. Progress in the development of a recombinant vaccine for human hookworm disease: The Human Hookworm Vaccine Initiative. *Int J Parasitol* 33, 1245-58 (2003).

37. Loukas, A. et al. Vaccination of dogs with a recombinant cysteine protease from the intestine of canine hookworms diminishes fecundity and growth of worms. *J Infect Dis* in press(2004).

38. Williamson, A. L., Brindley, P. J., Knox, D. P., Hotez, P. J. & Loukas, A. Digestive proteases of blood-feeding nematodes. *Trends Parasitol* 19, 417-23 (2003).

39. Pawlowski, Z., Karlewiczowa, R. & Rauhut, W. Usefulness of the Harada-Mori and Dancescu methods in diagnosing hookworm infections. *Wiad Parazytol* 17, 59-63 (1971).

40. Bethony, J. et al. Familial resemblance in humoral immune response to defined and crude *Schistosoma mansoni* antigens in an endemic area in Brazil. *J Infect Dis* 180, 1665-73 (1999).

41. Zhan, B., Hotez, P. J., Wang, Y. & Hawdon, J. M. A developmentally regulated metalloprotease secreted by host-stimulated *Ancylostoma caninum* third-stage infective larvae is a member of the astacin family of proteases. *Mol Biochem Parasitol* 120, 291-6 (2002).

42. Loukas, A., Croese, J., Opdebeeck, J. & Prociv, P. Detection of antibodies to secretions of *Ancylostoma caninum* in human eosinophilic enteritis. *Trans R Soc Trop Med Hyg* 86, 650-3 (1992).

43. Carr, A. & Pritchard, D. I. Antigen expression during development of the human hookworm, *Necator americanus* (Nematoda). *Parasite Immunol* 9, 219-34 (1987).

44. Stoute, J. A. et al. A preliminary evaluation of a recombinant circumsporozoite protein vaccine against *Plasmodium falciparum* malaria. RTS,S Malaria Vaccine Evaluation Group. *N Engl J Med* 336, 86-91 (1997).

45. Zhan, B., Li, T., Xiao, S., Zheng, F. & Hawdon, J. M. Species-specific identification of human hookworms by PCR of the mitochondrial cytochrome oxidase I gene. *J Parasitol* 87, 1227-9 (2001).

46. Williamson, A. L. et al. Hookworm aspartic protease, Na-APR-2, cleaves human hemoglobin and serum proteins in a host-specific fashion. *J Infect Dis* 187, 484-94 (2003).

Example 13

Vaccination of Dogs with a Recombinant Cysteine Protease from the Intestine of Canine Hookworms Diminishes Fecundity and Growth of Worms Hookworms digest blood-derived hemoglobin using a range of mechanistically distinct proteases, and preliminary data suggested that Ac-CP-2, a cathepsin B cysteine protease [6] from *A. caninum* might be involved in this pathway [15]. With a view to eventually vaccinating people against human hookworm disease, we decided to immunize dogs against the canine hookworm, *A. caninum*, with catalytically active recombinant Ac-CP-2 to determine whether vaccinated animals were protected against hookworm disease. We show that the cathepsin B-like protease, Ac-CP-2 is secreted as a proteolytically active enzyme by the yeast *Pichia pastoris* and that the enzyme is expressed in the intestinal lumen of blood-feeding adult hookworm parasites. Vaccination of dogs with Ac-CP-2 formulated with several discrete adjuvants resulted in reduced fecal egg counts and decreased sizes of female and male worms. Moreover, the number of female hookworms present in the intestines of vaccinated dogs was significantly reduced relative to control dogs. Antibodies generated by vaccinated dogs bound to the intestinal lumen and intestinal contents of hookworms recovered from those dogs, and interfered with proteolytic function of the recombinant Ac-CP-2 enzyme in vitro.

Materials and Methods for Example 13.

Expression of Recombinant Ac-CP-2 in *Pichia Pastoris*

The entire open reading frame encoding the pro-enzyme of Ac-CP-2 (spanning Ala-12 to the C-terminal Val-340) excluding the predicted signal peptide was cloned into the expression vector pPIC-Zα using the XbaI and XhoI sites. Colonies were selected from transformed cells and suspension cultures were grown in flasks then transferred to a Bioflo 3000 fermentor (New Brunswick Scientific) utilizing a 5 liter vessel as described [1]. The recombinant protein was secreted into culture medium and affinity purified on nickel-agarose as described [1].

Assessment of Catalytic Activity and Glycosylation of Recombinant Ac-CP-2

Purified, recombinant Ac-CP-2 was assessed for proteolytic activity using the fluorogenic peptidyl substrate Z-Phe-Arg-aminomethyl coumarin (AMC) (Bachem) [2]. The pH optimum of Ac-CP-2 was assessed using Z-Phe-Arg-AMC at different pH values according to published protocols [3]. The cysteine protease inhibitor E64 was included in some assays at a final concentration of 5 μM. Recombinant Ac-CP-2 was treated with PNGase F and O-glycosidase, according to the manufacturer's instructions (Enzymatic CarboRelease kit, QA-Bio), under denaturing conditions to remove any N-linked and O-linked oligosaccharides.

Animal Husbandry and Vaccination

Purpose-bred, parasite naive, male beagles aged 8±1 wk were purchased from Marshall farms, identified by ear tattoo, and maintained in the George Washington University Animal Research Facility as previously described [4]. The experiments were conducted according to a protocol approved by the University Animal Care and Use Committee. Before the first vaccination and after each subsequent one, a serum sample was obtained from each dog.

Vaccine Study Design and Antigen-Adjuvant Formulation

The vaccine trial was designed to test Ac-CP-2 formulated with 4 different adjuvants. ASO3 and ASO2 were obtained from GlaxoSmithKline and ISA 70 was obtained from SEPPIC, Inc. Alum was prepared as described [5]. To make six doses of Ac-CP-2 formulated with ASO3, 600 μg of recombinant protein (0.3 ml of Ac-CP-2 at a concentration of 2 $mg.ml^{-1}$) was mixed with 1.2 ml of 20 mM Tris-HCl, 0.5 M NaCl, pH 7.9 and 1.5 ml of ASO3; the contents of the tube were vortex mixed for 30 seconds then shaken at low speed for 10 minutes. Dogs were immunized with 100 μg of formulated antigen in a final volume of 0.5 ml. To make six doses of Ac-CP-2 formulated with AS02, 600 μg of recombinant protein (0.3 ml of Ac-CP-2 at a concentration of 2 $mg.ml^{-1}$) was mixed with 0.9 ml of 20 mM Tris-HCl, 0.5 M NaCl, pH 7.9 and 1.8 ml of ASO2; the contents of the tube were vortex mixed for 30 seconds then shaken at low speed for 10 minutes. Dogs were immunized with 100 μg of formulated antigen in a final volume of 0.5 ml. To make six doses of Ac-CP-2 formulated with ISA 70, 600 μg of recombinant protein (0.3 ml of Ac-CP-2 at a concentration of 2 $mg.ml^{-1}$) was mixed with 1.66 ml of ISA 70; the contents of the tube were vortex mixed for 30 seconds then shaken at low speed for 10 minutes. Dogs were immunized with 100 μg of formulated antigen in a final volume of 0.327 ml. To make six doses of Ac-CP-2 formulated with alum, 600 μg of recombinant protein (0.3 ml of Ac-CP-2 at a concentration of 2 $mg.ml^{-1}$) was mixed with 0.135 ml of 1M NaHCO3; 0.3 ml of $AlK(SO_4)_2$ $12H_2O$ [5] was added to initiate precipitation. Precipitate was collected by centrifugation at 14,000 rpm for 10 mins. The supernatant was collected and the precipitation was repeated; the supernatant was collected and assayed for non-precipitated protein using a BCA protein assay (Pearce). The two precipitates were pooled, washed with PBS and resuspended in 3 ml of the supernatant and dogs were immunized with 100 μg of formulated antigen in a final volume of 0.5 ml. Alum only control was prepared as described above, with PBS included instead of Ac-CP-2.

Canine Immunizations and Antibody Measurements

Beagles were immunized with formulated Ac-CP-2 as previously described [4]. The study regimen used is shown along the X-axis of FIG. 2. The vaccines were administered intramuscularly three times beginning at age 62+/−4 days. Boosts were administered to the dogs at intervals of 21 days. Blood was drawn at least once every 21 days and serum was separated from cells by centrifugation. Enzyme-linked immunosorbent assays (ELISA) were performed as previously described [4]. Recombinant Ac-CP-2 was coated onto microtiter plates at a concentration of $\mu g.ml^{-1}$. Dog sera were titrated between 1:100 and 1:2×10 6 to determine endpoint titers. Anti-canine IgG1, IgG2 and IgE antibodies conjugated to horse-radish peroxidase (Bethyl Laboratories) were used at a dilution of 1:1,000.

Hookworm Infections and Parasite Recovery

Fourteen-sixteen days after the final immunization, dogs were anesthetized using a combination of ketamine and xylazine (20 mg/kg and 10 mg/kg respectively) and 500 *A. caninum* L3 in a final volume of 50 μL were applied to the footpad. After applying L3, the foot was wrapped in parafilm, gauze padding and packaging tape in that order to ensure that L3 did not escape from the site of application. Dogs were monitored for 3 hours after which the parafilm, gauze and tape were removed. The site of L3 application was rinsed with saline and any remaining L3 that had not penetrated were counted. Quantitative hookworm egg counts (McMaster technique) were obtained for each dog 3 days per week beginning on day 13-15 post-infection. Four weeks post-infection, the dogs were killed by intravenous injection of barbiturate, and adult hookworms were recovered and counted from the small and large intestines at necropsy [4]. The sex of each adult worm was determined and worm lengths were measured as described elsewhere [61Approximately 1-2 cm lengths of the small intestine were removed and stored in formalin for future histopathological analysis.

Statistical Methods

The percentage reduction or increase in adult hookworm burden in the vaccinated groups was expressed relative to the control group as described elsewhere [4]. The statistical significance of differences in adult hookworm burdens was determined using nonparametric tests: the Kruskal-Wallis test with Dunn procedures, and Mann-Whitney U-tests. Differences between groups in quantitative hookworm egg counts and worm lengths were assessed by the ANOVA test. Once determined the differences among the means of groups were determined, a Dunnet post hoc multiple comparison t test was used to compare the vaccine treatment groups against the control group. The sex differences of the adult hookworms recovered were statistically compared using the Wilcoxon-Signed Ranks test for 2 dependent groups. Differences were considered statistically significant if the calculated P value was equal to or less than 0.10 (2-sided) or −0.05 (1-sided).

Immunohistochemistry

Adult hookworms recovered from vaccinated dogs were fixed, sectioned and probed with various sera and Cy3-conjugated secondary antibodies (BD Biosciences) as previously described [7]. Sera from vaccinated dogs and Cy3-conjugated anti-dog IgG were diluted 1:500. Some sections were probed with rabbit anti-Ac-CP-1 serum [6] followed by Cy3-conjugated anti-rabbit IgG; both antibodies were diluted 1:500.

Effect of Anti-Ac-CP-2 IgG on Proteolytic Activity

Canine IgG was purified from sera of vaccinated dogs using protein A-agarose (Amersham Biosciences) as previously described [8]. Purified IgG (10-500 ng) was incubated with 1.0 μg of recombinant Ac-CP-2 for 45 mins prior to assessing proteolytic activity as described above.

Results for Example 13.

Secretion of Catalytically Active, Glycosylated Ac-CP-2 by *P. pastoris*

Figure 51:
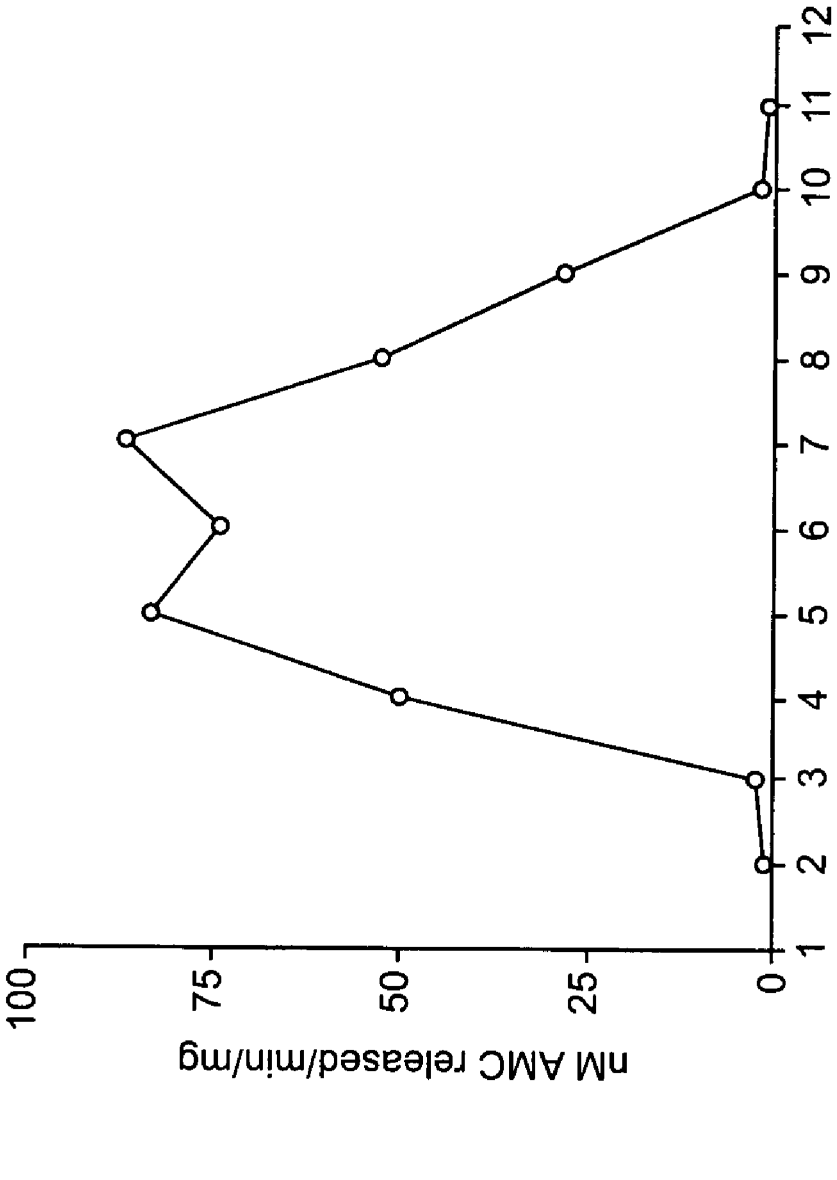
FIG. 51. pH profile of the catalytic activity of recombinant Ac-CP-2 against the substrate Z-Phe-Arg-AMC.

Ac-cp-2 cDNA (GenBank accession number U18912) was cloned and reported by Harrop and colleagues [6]. We expressed recombinant Ac-CP-2 as a secreted fusion protein in *P. pastoris* with a yield of 35 $mg.L^{-1}$. Secretion was mediated by the α-mating factor signal peptide derived from the pPIC-Z α vector. The protein was purified from *P. pastoris* culture supematant using nickel-agarose [20]. The purified protein migrated with an apparent molecular size of 48 kDa (not shown). This was higher than the predicted size of the pro-enzyme (41.8 kDa) and processed, mature enzyme (32.1 kDa) factoring in the C-terminal myc and His tags and—terminal EAEAEF (SEQ ID NO: 116) motifs (introduced by the choice of restriction sites used in cloning of the construct). N-linked glycosylation of the 5 predicted sites in Ac-CP-2 probably accounted for some of the discrepancy between the predicted and observed molecular sizes. Deglycosylation with PNGaseF reduced the apparent molecular mass of recombinant Ac-CP-2 by 5-10 kDa although numerous bands within this size range were apparent (not shown), probably corresponding to partially deglycosylated proteins. N-terminal amino acid sequencing of the major secreted protein by Edman degradation showed the N-terminal residue to be Glu-13, suggesting that some post-translational processing of the pro-region had occurred. However, this did not correspond with the predicted cleavage site of the pro-region from the mature enzyme (Asp-81-Asp-82 using the numbering scheme of the fusion protein presented here). Although this is only a predicted cleavage site based on the known cleavage site of the pro-region of other related enzymes [9], it is unlikely that Glu-13 is the N-terminal residue of the native, secreted protease. Difficulty in obtaining sufficient quantities of native, hookworm-derived Ac-CP-2 precluded N-terminal sequence information for comparison. Nonetheless, numerous faint bands with molecular sizes ranging from 30-40 kDa appeared when the purified recombinant Ac-CP-2 was stained with silver (not shown), suggesting that a small quantity of the recombinant protein was correctly processed to yield the mature form of the enzyme. This was further confirmed by the catalytic activity seen when recombinant Ac-CP-2 was incubated with Z-Phe-Arg-AMC (FIG. 51). A broad pH range was observed with activity detected between pH 4-8 with optimal catalysis between pH 5 and pH 7. Addition of the cysteine protease inhibitor, E64, to a final concentration of 5 μM completely ablated cleavage of the peptide substrate (not shown). Moreover, other recombinant proteins (non-proteolytic) expressed and purified in an identical fashion in our laboratory did not cleave Z-Phe-Arg-AMC (not shown).

Recombinant Ac-CP-2 is Immunogenic in Dogs

Figure 52A:
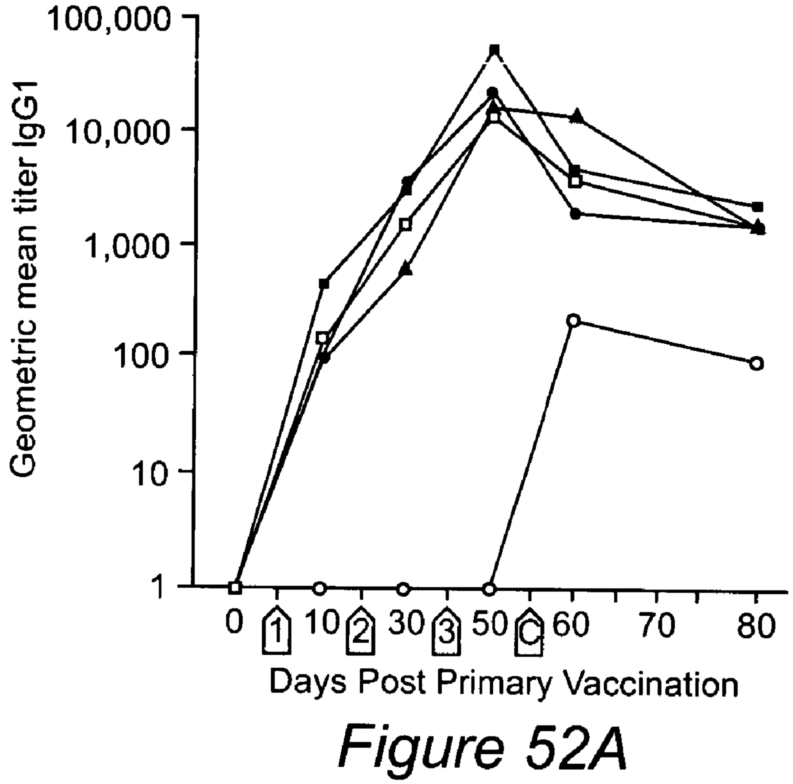
FIG. 52. The geometric mean titers of the IgG1(A) and IgG2 (B) antibody responses of vaccinated dogs against recombinant Ac-CP-2 formulated with AS03 (■), AS02 (●), ISA70 (□), alum (▲) or alum alone without CP-2 (○). Open arrows on the X-axis indicate the days of vaccination (numbers inside) and larval challenge (C).
Figure 52B:
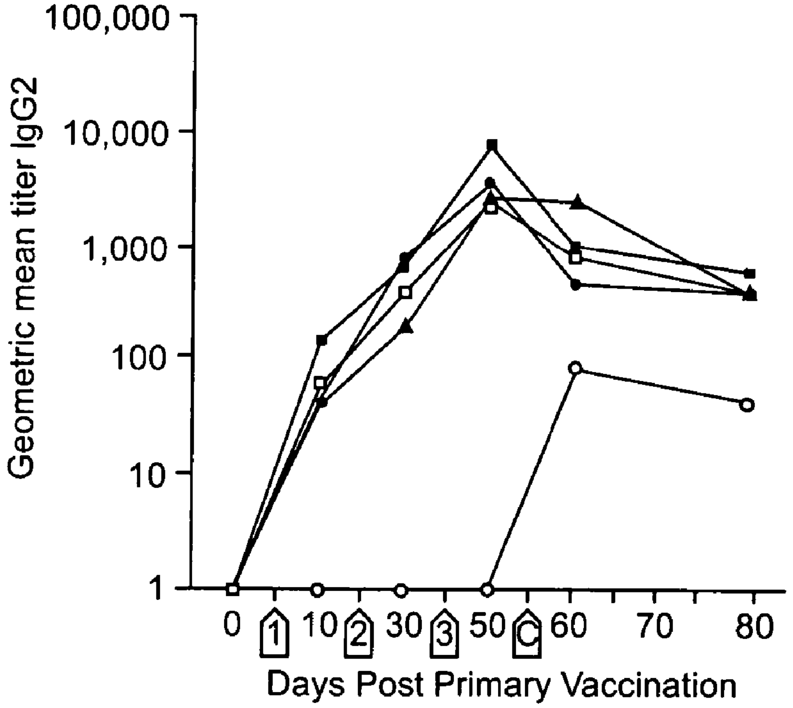

Dogs immunized with recombinant Ac-CP-2 formulated with different adjuvants produced IgG1 and IgG2 antibody responses as measured by ELISA using the recombinant protein (FIG. 52). IgE titers were low (<1,500) and are not discussed further. The maximum IgG1 titers (geometric mean=50,452) were induced by formulating Ac-CP-2 with ASO3. The maximum IgG2 titers (geometric mean=78,294) were induced by formulating Ac-CP-2 with ASO2. Dogs immunized with adjuvant alone did not generate detectable immune responses until larval challenge, suggesting that antibodies to Ac-CP-2 (or a similar protease) are induced during natural infection with the parasite. Ac-cp-2 mRNA was not identified from more than 9,000 expressed sequence tags generated from serum-stimulated (induced to feed) *A. caninum* L3 implying that the mRNA and protein are only expressed in the adult-blood feedingstages. The increase in anti-Ac-CP-2 antibody titers in control dogs after L3 challenge (but before worms would have matured to adulthood) is likely due to secretion of antigenically related cysteine proteases by L3; the closest homolog of Ac-CP-2 from *A. caninum* L3 cDNAs (EST pb58a11.yl) shared 64% identity at the amino acid level. ASO2 and ASO3 adjuvants induced the greatest antibody responses, especially of the IgG2 subclass. ISA 70 and alum induced much weaker responses although the general pattern and duration of responses were similar to those induced by the ASO adjuvants.

Vaccination with Ac-CP-2 Decreases Fecundity of Female Hookworms

Figure 53:
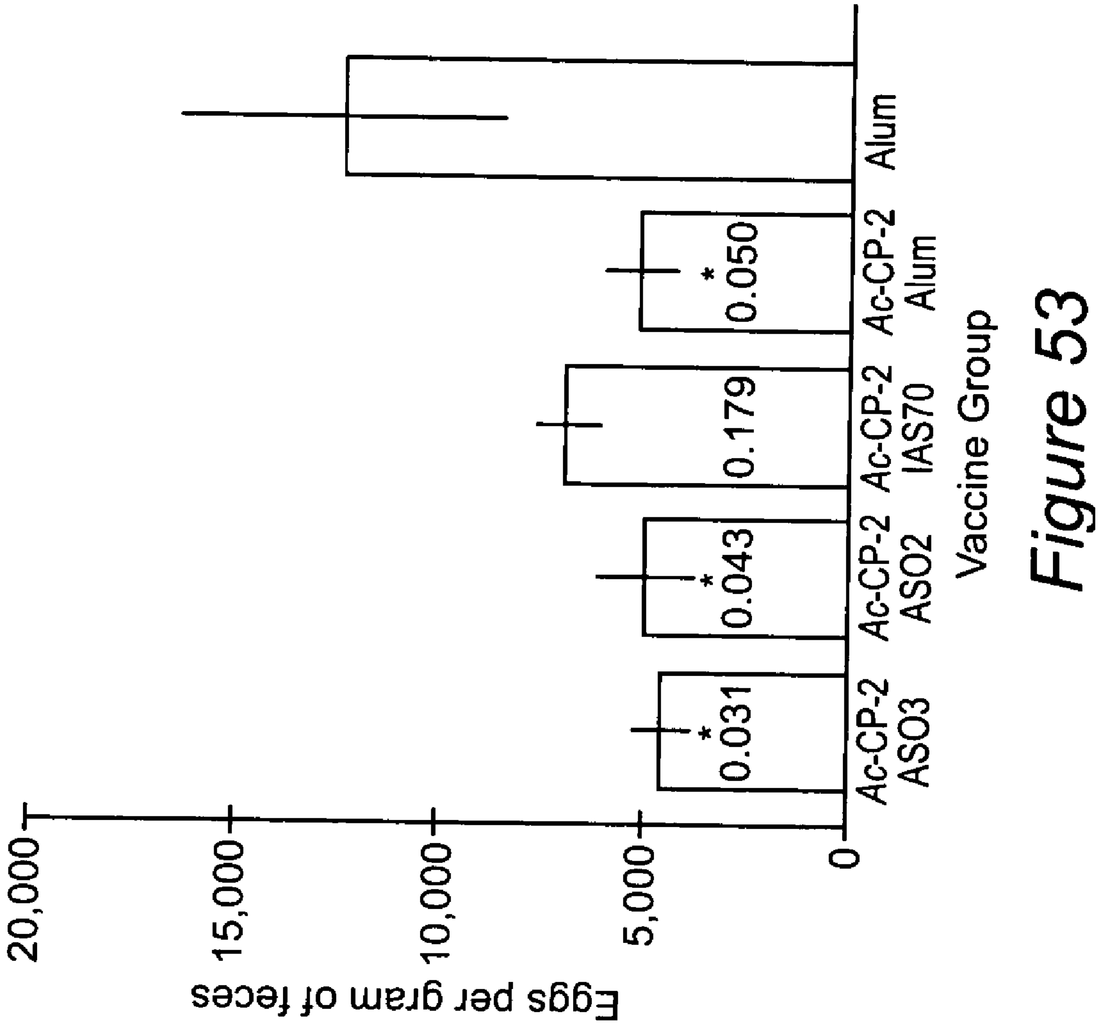
FIG. 53. The geometric mean egg counts from dogs immunized with Ac-CP-2 formulated with different adjuvants or alum alone (control). The error bars refer to standard error of the mean. The numbers within the bars refer to the P-value of a Dunnett (Post Hoc) test, a pairwise multiple comparison t test that compares a set of treatments against a single control mean.

Dogs rapidly develop age- and exposure-related immunity to *A. caninum* [10]. We therefore observed egg counts from vaccinated animals up to 3 weeks post-challenge. At 3 weeks after larval challenge, a significant decrease in egg counts was observed in dogs vaccinated with Ac-CP-2 formulated with either ASO2, ASO3 or alum compared with dogs that were vaccinated with alum alone ($P \leqq 0.05$) (FIG. 53). Statistically significant differences between mean adult male worm burdens of dogs vaccinated with Ac-CP-2 and adjuvant alone were not seen (Table X). The greatest number of female worms was recovered from dogs immunized with alum alone (mean=131); the smallest number of female worms was recovered from dogs immunized with Ac-CP-2/ASO3 (mean=104). While the decrease in worm burdens in the latter group was noteworthy, the differences were not statistically significant.

TABLE X

Mean adult worm numbers recovered from the small and large intestines of dogs immunized with Ac-CP-2 formulated with different adjuvants or adjuvant alone.

| | Small intestine | | Large intestine | |
|---|---|---|---|---|
| Group | Male | Female | Male | Female |
| Ac-CP-2/ASO3 | 107 | 111 | 8 | 9 |
| Ac-CP-2/ASO2 | 109 | 104 | 7 | 11 |
| Ac-CP-2/ISA70 | 113 | 116 | 7 | 8 |
| Ac-CP-2/alum | 125 | 120 | 4 | 6 |
| Alum | 105 | 131 | 6 | 9 |

Vaccination with Ac-CP-2/ASO2 Resulted in a Lower Proportion of Female Worms

Figure 54:
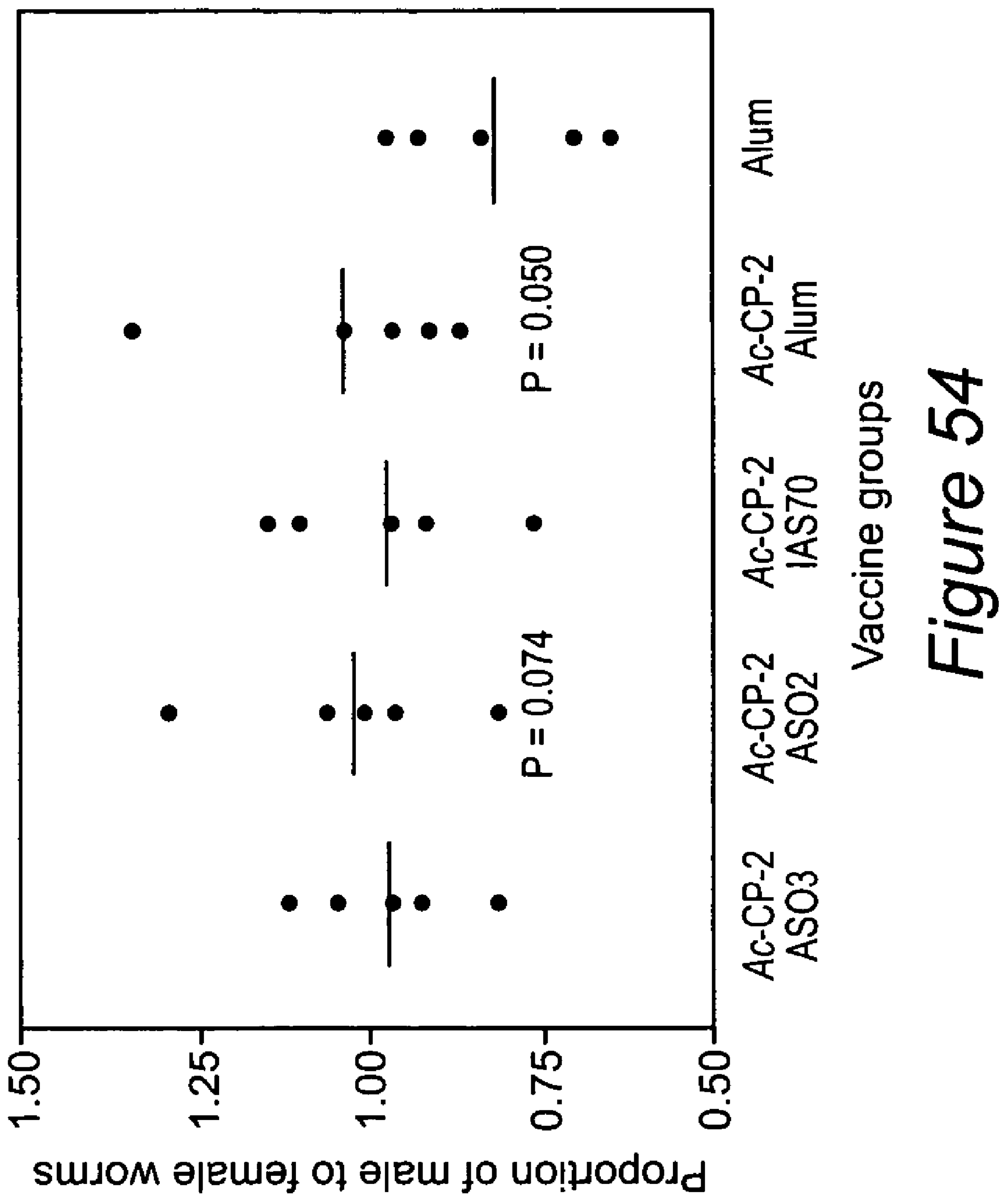
FIG. 54. The proportions of male to female worms recovered from dogs immunized with Ac-CP-2 formulated with different adjuvants or alum adjuvant alone. Individual proportions are shown for each dog and the mean value for each group is denoted by a bar. Where the proportions were significantly different (P<0.1 using a Wilcoxon-Signed Ranks test) between vaccine and control groups, P values are denoted beneath the mean.

Comparison of the proportions of male to female worms revealed that worms recovered from dogs vaccinated with Ac-CP-2/alum (P=0.05) and Ac-CP-2/ASO2 (P=0.074) had more male worms than female worms when compared with worms recovered from dogs immunized with adjuvant alone (FIG. 54).

Vaccination with Ac-CP-2 Protease Stunts the Growth of Hookworms

At necropsy, all worms recovered from the vaccinated dogs were fixed in formalin. The lengths of 100 undamaged worms from each group were measured, and the mean lengths compared statistically. The mean lengths of female worms recovered from dogs vaccinated with Ac-CP-2/ASO2 (P=0.003) and Ac-CP-2/ASO3 (P=0.033) were shorter than that of worms recovered from dogs immunized with adjuvant alone (Table XI). Statistically significant differences in male worm lengths were obtained when male worms from dogs that received Ac-CP-2/ASO3 were compared with worms recovered from dogs immunized with alum alone (P=0.035).

TABLE XI

Adult hookworms recovered from dogs that were vaccinated with Ac-CP-2 were shorter than those recovered from dogs immunized with adjuvant alone. P values compare the difference between each group that received the vaccine and the adjuvant alone group. N = number of worms measured.

| Group | N | mean length (cm) | SD | P value* |
|---|---|---|---|---|
| Ac-CP-2/ASO3 | | | | |
| Female | 100 | 0.534 | 0.22 | 0.033 |
| Male | 100 | 0.384 | 0.11 | 0.035 |
| Ac-CP-2/ASO2 | | | | |
| Female | 100 | 0.507 | 0.22 | 0.003 |
| Male | 100 | 0.432 | 0.12 | 0.844 |
| Ac-CP-2/ISA70 | | | | |
| Female | 100 | 0.572 | 0.21 | 0.567 |
| Male | 100 | 0.465 | 0.14 | 0.999 |
| Ac-CP-2/Alum | | | | |
| Female | 100 | 0.558 | 0.24 | 0.567 |
| Male | 100 | 0.471 | 0.14 | 1.000 |
| Alum only | | | | |
| Female | 100 | 0.612 | 0.28 | — |
| Male | 100 | 0.430 | 0.13 | — |

SD, standard deviation from mean.
*indicates P-value for Dunnett t-tests in which one group is treated as a control and the test groups are compared against it.

Anti-Ac-CP-2 Antibodies are Ingested by and Bind to the Intestine of Feeding Hookworms The site of anatomical expression of Ac-CP-2 within adult hookworms had not been previously reported. We therefore used sera from dogs immunized with Ac-CP-2/ASO3 to localize expression to the brush border membrane of the intestine of adult worms (not shown). Ac-CP-1 on the other hand was shown by Harrop et al. [6] and confirmed by us here (not shown) to be expressed in the cephalic and excretory glands of the parasite, accounting for its presence in excretory/secretory products of adult *A. caninum* [6].

To determine whether vaccination of dogs induced circulating antibodies that bound to the intestinal lumen during infection, parasites were removed from vaccinated dogs, fixed, sectioned and probed with secondary antibody (anti-dog IgG conjugated to Cy3) only. Worms recovered from dogs immunized with Ac-CP-2 (not shown) but not from dogs immunized with adjuvant alone (not shown) contained antibodies that were ingested with the blood-meal of the worm, and subsequently bound specifically to the intestine and intestinal contents.

IgG from Dogs Vaccinated with Ac-CP-2 Neutralizes Proteolytic Activity In Vitro

Purified IgG from dogs that were immunized with Ac-CP-2 was effective at neutralizing the catalytic activity of Ac-CP-2. Incubation of 50 ng of pooled IgG from dogs immunized with Ac-CP-2/ASO3 resulted in a 73% reduction in the cleavage of Z-Phe-Arg-AMC by 1.0 μg of Ac-CP-2 (Table XII). Fifty nanograms of IgG from dogs immunized with adjuvant alone resulted in a 3% reduction in proteolytic activity, implying that vaccination with Ac-CP-2 resulted in the production of antibodies that neutralized the function of the enzyme in vivo.

TABLE XII

Effect of pooled IgGs from vaccinated (Ac-CP-2/ASO3) and control (adjuvant alone) dogs on the proteolytic activity of recombinant Ac-CP-2 against the substrate Z-Phe-Arg-AMC. Values are expressed as mean percent reductions in proteolytic activity from triplicate experiments.

| Treatment | Ac-CP-2 only | Ac-CP-2 + αCP-2 IgG | Ac-CP-2 + norm IgG | Ac-CP-2 + E64 |
|---|---|---|---|---|
| % reduction in proteolytic activity | 0 ± 0 | 73 ± 3 | 3 ± 2 | 100 ± 0 |

Discussion for Example 13.

Here we describe vaccination of dogs with a recombinant cysteine protease that resulted in partial protection as measured by reduced fecal egg counts, stunting of adult worms, decreased proportion of female to male worms and the generation of protease-neutralizing antibodies that bind to the hookworm intestine in vivo. In the 1930's, the late Asa Chandler hypothesized that antibodies directed against critical parasite enzymes mediated a successful anti-helminthic immune response by preventing worms from digesting host proteins [11]. This is the first report of protective efficacy with a recombinant protease from a parasitic nematode, and provides support for Chandler's anti-enzyme theory.

Although secreted by *P. pastoris*, complete processing of recombinant Ac-CP-2 to yield a mature enzyme did not occur; nonetheless, proteolytic activity was detected in the purified protein. *P. pastoris* transformed with a cDNA encoding *F. hepatica* cathepsin L secrete a partially activated protease that also exhibits catalytic activity, however unlike Ac-CP-2, this enzyme completely auto-activated after 2 hours at pH 5.5 [12]. Ac-CP-2 displayed a broad pH range with optimal activity at pH 5-7, supporting earlier work that described an optimal pH range of 5-9 for ES products and somatic extracts of adult *A. caninum* using Z-Phe-Arg-AMC [3].

Hematophagous helminths require blood as a source of nutrients to mature and reproduce. Female schistosomes ingest 13 times as many erythrocytes and ingest them about nine times faster than male worms [13]. Moreover, mRNAs encoding hemoglobin-degrading proteases of schistosomes are over-expressed in female worms [14]. While similar studies have yet to be performed for hookworms, female hookworms are bigger than males and lay up to 10,000 eggs per day, implying that they have a greater metabolism and therefore demand for erythrocytes. Ac-CP-2 is expressed in the gut, and preliminary data described elsewhere [15] have shown that the enzyme is involved in hemoglobinolysis in the hookworm intestine. It is therefore not surprising that interruption of the function of Ac-CP-2 via the action of neutralizing antibodies had a deleterious effect on the growth of female worms and subsequent egg production.

Vaccination of livestock and laboratory animals with cysteine proteases of other nematodes as well as trematodes has resulted in anti-fecundity/anti-embryonation effects. Immunization of sheep with the intestinal brush border complex, H-gal-GP, confers high levels of protection (both anti-parasite and anti-fecundity) against *H. contortus* and at least three different protease activities, including cathepsin B cysteine proteases, have been detected in this extract. Immunisation of sheep with a cysteine protease-enriched fraction of *H. contortus* membranes resulted in 47% protection against adult worms and 77% reduction in faecal egg output [15]. To date, the success obtained in vaccinated laboratory animals with cysteine proteases purified from parasite extracts has not been reproduced with the corresponding recombinant proteins expressed in *Escherichia coli* presumably because the recombinant molecules are incorrectly folded (and catalytically inactive) and thereby fail to induce responses capable of inactivating native proteases [16].

Cysteine Proteases are also Efficacious as Anti-Trematode Vaccines.

Vaccination of cattle with cathepsin L cysteine proteases of *F. hepatica* results in decreased embryonation and hatch rates of eggs in addition to decreased worm burdens [12]. While these studies were performed with native proteins, trials with yeast-expressed recombinant proteases are in progress [12]. Vaccine trials using a DNA construct for *S. mansoni* Sm32, an asparaginyl endopeptidase that is cysteine protease-like in function but unrelated in sequence to cathepsins L and B, induced an anti-fecundity effect in a murine model of schistosomiasis when administered as a DNA construct [17].

We recently described partial protection of hamsters against another hookworm, *Ancylostoma* ceylanicum, by immunization with a larval antigen, Ay-ASP-2, as a model of human hookworm disease [1]. The orthologous protein from *A. caninum*, Ac-ASP-2, is expressed by the L3 stage of the parasite when it is stimulated to feed in vitro [18]. Vaccination with ASP-2 resulted in a 32% reduction in the number of worms that reached adulthood [1], and we envisage that a human hookworm vaccine would ultimately consist of multiple antigens targeting both the L3 and the blood-feeding adult-stage. The data presented here suggest that cysteine proteases lining the intestinal lumen of hookworms are a valid target in the design of vaccines against hookworm disease. We have identified other proteases of different mechanistic classes that line the intestinal brush border of adult hookworms where they digest host hemoglobin [7, 8, 15], and some of these molecules might also prove efficacious as recombinant vaccines against hookworm infection.

References for Example 13

1. Goud G N, Zhan B, Ghosh K, et al. Cloning, Yeast Expression, Isolation and Vaccine Testing of Recombinant *Ancylostoma* secreted protein 1 (ASP-1) and ASP-2 from *Ancylostoma ceylanicum*. J Infect Dis 2003; in press
2. Loukas A, Selzer P M and Maizels R M. Characterisation of Tc-cpl-1, a cathepsin L-like cysteine protease from *Toxocara canis* infective larvae. Mol Biochem Parasitol 1998; 92:275-89
3. Dowd A J, Dalton J P, Loukas A C, Prociv P and Brindley P J. Secretion of cysteine proteinase activity by the zoonotic hookworm *Ancylostoma caninum*. Am J Trop Med Hyg 1994; 51:341-7
4. Hotez P J, Ashcom J, Bin Z, et al. Effect of vaccinations with recombinant fusion proteins on *Ancylostoma caninum* habitat selection in the canine intestine. J Parasitol 2002;88:684-90
5. Ghosh K, Hotez P J. Antibody-dependent reductions in mouse hookworm burden after vaccination with *Ancylostoma caninum* secreted protein 1. J Infect Dis 1999; 180:1674-81
6. Harrop S A, Sawangjaroen N, Prociv P and Brindley P J. Characterization and localization of cathepsin B proteinases expressed by adult *Ancylostoma caninum* hookworms. Mol Biochem Parasitol 1995; 71:163-71
7. Williamson A L, Brindley P J, Abbenante G, et al. Hookworm aspartic protease, Na-APR-2, cleaves human hemoglobin and serum proteins in a host-specific fashion. J Infect Dis 2003; 187:484-94
8. Williamson A L, Brindley P J, Abbenante G, et al. Cleavage of hemoglobin by hookworm cathepsin D aspartic proteases and its potential contribution to host specificity. FASEB J 2002; 16:1458-60
9. Tort J, Brindley P J, Knox D, Wolfe K H and Dalton J P. Proteinases and associated genes of parasitic helminths. Adv Parasitol 1999; 43:161-266
10. Miller T A. Influence of age and sex on susceptibility of dogs to primary infection with *Ancylostoma caninum*. J. Parasitol. 1965; 51:701-4
11. Chandler A C. Susceptibility and resistance to helminthic infections. J Parasitol 1932; 3:135-52
12. Dalton J P, Neill S O, Stack C, et al. *Fasciola hepatica* cathepsin L-like proteases: biology, function, and potential in the development of first generation liver fluke vaccines. Int J Parasitol 2003; 33:1173-81
13. Hota-Mitchell S, Siddiqui A A, Dekaban G A, Smith J, Tognon C and Podesta R B. Protection against *Schistosoma mansoni* infection with a recombinant baculovirus-expressed subunit of calpain. Vaccine 1997; 15:1631-40
14. Hu W, Yan Q, Shen D K, et al. Evolutionary and biomedical implications of a *Schistosoma japonicum* complementary DNA resource. Nature Genet 2003; 35:139-147
15. Knox D P, Smith S K and Smith W D. Immunization with an affinity purified protein extract from the adult parasite protects lambs against infection with *Haemonchus contortus*. Parasite Immunol 1999; 21:201-10
16. Dalton J P, Brindley P J, Knox D P, et al. Helminth vaccines: from mining genomic information for vaccine targets to systems used for protein expression. Int J Parasitol 2003; 33:621-40
17. Chlichlia K, Bahgat M, Ruppel A and Schirrmacher V. DNA vaccination with asparaginyl endopeptidase (Sm32) from the parasite *Schistosoma mansoni*: anti-fecundity effect induced in mice. Vaccine 2001; 20:439-47
18. Hawdon J M, Narasimhan S and Hotez P J. *Ancylostoma* secreted protein 2: cloning and characterization of a second member of a family of nematode secreted proteins from *Ancylostoma caninum*. Mol Biochem Parasitol 1999;99: 149-65

Example 14

Canine Vaccine Trial with Antigens Ac-ASP-2, Ac-MEP-1, Ac-APR-1, and Ac-API

A canine vaccine trial was carried out to examine the protective efficacy of four antigens formulated with the adjuvant, ASO3. These antigens are Ac-ASP-2, Ac-MEP-1, Ac-APR-1, and Ac-API. The trial confirmed our earlier findings that ASP-2 is a promising vaccine antigen (based on both human serology and hamster animal trials). This was evidenced by reduction in worm number, worm size, and fecal egg counts. The trial also provided preliminary data that APR-1 and MEP-1 also offer promise as protective antigens.

Experimental Design and Methods

Vaccine Study Design and Antigen-Adjuvant Formulation

The vaccine trial was designed to test Ac-API, Ac-ASP-2, Ac-MEP-1, Ac-APR-1 formulated with Adjuvant System 03 (AS03) obtained from GlaxoSmithKline (GSK). The rationale for selecting AS03 as an adjuvants is discussed elsewhere (Stoute et al, 1997). The ten purpose bred beagles were randomized into five arms: immunized with the adjuvant-formulated recombinant proteins or adjuvant only (control). To make six doses of antigen formulated with AS03, 600 g of recombinant protein (0.3 ml of antigen at a concentration of 2 $mg.ml^{-1}$) was mixed with 1.2 ml of 20 mM Tris-HCl, 0.5 M NaCl, pH 7.9 and 1.5 ml of AS03; the contents of the tube were vortex mixed for 30 seconds then shaken at low speed for 10 minutes. Dogs were immunized with 100 g of formulated antigen in a final volume of 0.5 ml. ASO3 only control was prepared as described above, with PBS included instead of antigen. Formulation of GSK adjuvants were conducted according to the protocol provided by GSK. All injections were performed intramuscularly (IM). Test and control articles were prepared on the day of injection. All animals received 4 immunizations approximately 3 weeks apart.

Hookworm Infections and Parasite Recovery

*A. caninum* larvae were cultured from eggs collected in the feces of infected dogs. All hookworms in the infective challenge were approximately equal age (17±7 days post hatching). The species identity of the infective larvae were validated using PCR. All dogs were infected by the footpad method with the same dose of 500 L3 of *A. caninum* (Zhan et al, 2001). Larval challenge occurred on one of three consecutive days (at age 120+/−9 days). Fourteen-sixteen days after the final immunization, dogs were anesthetized using a combination of ketamine and xylazine (20 $mg.kg^{-1}$ and 10 $mg.kg^{-1}$ respectively), and 500 *A. caninum* L3 in a final volume of 50 l were applied to the footpad.

Canine Immunizations and Antibody Measurements

Beagles were immunized with formulated Ac-ASP-2 as previously described (Loukas et al, 2004). The vaccines were administered IM three times beginning at age 62+/−4 days. Boosts were administered to the dogs at intervals of 21 days. Blood was drawn at least once every 21 days and serum was separated from cells by centrifugation. Each animal's specific antibody response was evaluated by indirect ELISA using serum taken prior to the infective challenge (Loukas et al, 2004). Recombinant Ac-ASP-2 was coated onto microtiter plates at a concentration of 5 $g.ml^{-1}$. Dog sera were titrated between 1:100 and 1:2×$10^6$ to determine endpoint titers. Anti-canine IgG1, IgG2 and IgE antibodies conjugated to horse-radish peroxidase (Bethyl Laboratories) were used at a dilution of 1:1,000.

L3 Skin Penetration Assays

Live *A. caninum* L3 were incubated with sera (neat) from immunized dogs then L3 were placed on canine skin to observe whether serum antibodies interfered with the penetration of skin in vitro (Williamson et al, 2003). Briefly, fresh skin from the ear of a dog was shaved, and approx. 4 $cm^2$ section of skin was stretched and sandwiched between 2×20 mL syringe barrels that were clamped together with bulldog clips. The lower syringe was filled to the top with PBS so that the buffer was in contact with the underside of the skin. One milliliter of PBS was placed on the skin for 15 min to check integrity of the skin. L3 (300 L3/group) were then incubated in 0.05 ml of PBS, pH 7.2, or undiluted serum from different vaccinated or control dogs for 30 min at 37 C. Each group of L3 were then placed on the upper side of the skin (added to the 1.0 ml of PBS already present) and allowed to migrate for 30 min at RT. L3 that remained on the surface of the skin were collected and counted, by removing the remaining liquid with a pipette and washing the skin with 2 volumes of PBS. Each assay was performed in triplicate.

Expression and Purification of the Recombinant Proteins

Ac-ASP-2. The cloning of Ac-ASP-2 is reported elsewhere (Hawdon et al, 1999).

Other antigens. Details of the cloning and/or expression of Ac-MEP-1 and Ac-APR-1 are reported elsewhere (Harrop et al, 1996; Brinkworth et al, 2001; Jones and Hotez, 2002; Hotez et al, 2002). Briefly, both of these proteins are hemoglobin-degrading proteasese from the alimentary canal of adult hookworms.

Antibody Responses Following Immunization

The individual and geometric means of the IgG1, IgG2, and IgE antibody titers are shown in Table XIII.

TABLE XIII

| | Pre-challenge antibody titer to recombinant proteins following immunization | | |
|---|---|---|---|
| | IgG1 | IgG2 | IgE |
| Ac-ASP2 | | | |
| A1 | 13,500 | 40,500 | 100 |
| A2 | 13,500 | 13,500 | 100 |
| A3 | 13,500 | 13,500 | 100 |
| A4 | 13,500 | 40,500 | 100 |
| A5 | 4,500 | 13,500 | 100 |
| GEOMEAN | 10,837 | 20,950 | 100 |
| Ac-API | | | |
| B1 | 4,500 | 40,500 | N/A |
| B2 | 4,500 | 40,500 | N/A |
| B3 | 1,500 | 40,500 | N/A |
| B4 | 4,500 | 40,500 | N/A |
| B5 | 4,500 | 13,500 | 100 |
| GEOMEAN | 3,612 | 32,511 | 100 |
| Ac-MEP | | | |
| C1 | 100 | 1,500 | N/A |
| C2 | 100 | 500 | N/A |
| C3 | 100 | 1,500 | N/A |
| C4 | N/A | 1,500 | N/A |
| C5 | 100 | 1,500 | N/A |
| GEOMEAN | 100 | 1,204 | N/A |
| Ac-APR1 | | | |
| D1 | N/A | 500 | N/A |
| D2 | 100 | 4,500 | N/A |
| D3 | N/A | 100 | N/A |

TABLE XIII-continued

Pre-challenge antibody titer to recombinant proteins following immunization

| | IgG1 | IgG2 | IgE |
|---|---|---|---|
| D4 | N/A | 500 | N/A |
| D5 | N/A | 500 | N/A |
| GEOMEAN | 100 | 562 | N/A |

The antibody responses to both ASP-2 and API were robust. However, only a single dog developed a substantial antibody titer to APR-1 and the overall antibody response to Ac-MEP-1 was weak. Closer analysis reveals that canines immunized with recombinant Ac-ASP-2/AS03 produced strong IgG1 and IgG2 antibody titers to recombinant Ac-ASP-2. The IgE titers to Ac-ASP-2 in the test canines were one log lower than the IgG1 and IgG2 titers. Dogs immunized with AS03 adjuvant alone did not generate detectable antibody responses to Ac-ASP-2 prior to larval challenge. Sera from dogs vaccinated with recombinant ASP-2 immunoprecipitated native ASP-2 from biotinylated *A. caninum* extracts (L3E), while sera from animals immunized with adjuvant alone did not precipitate any L3E proteins.

Reductions in Adult Worm Burden Following Vaccination

The overall worm burden data in vaccinated vs. control (AS03) dogs is presented in Tables XIV and XV. Briefly, there was good consistency in the number of worms from each group, with the exception of the two hemoglobinase groups. Of all of the groups, the greatest mean worm burden reduction was among the ASP-2-vaccinated dogs, while the greatest median worm burden was in the MEP-1 vaccinated dogs.

TABLE XIV

Summary results of the worm burdens in vaccinated and control dogs

| | Intestine | | Colon | | |
|---|---|---|---|---|---|
| | Male | Female | Male | Female | Total |
| A1 | 107 | 115 | 1 | 3 | 226 |
| A2 | 85 | 72 | 9 | 8 | 174 |
| A3 | 54 | 28 | 1 | 6 | 89 |
| A4* | 62 | 87 | 5 | 5 | 160 |
| A5 | 72 | 101 | 4 | 4 | 181 |
| Average | 76 | 81 | 4 | 5 | 166 |
| B1 | 54 | 86 | 3 | 3 | 146 |
| B2 | 83 | 83 | 0 | 1 | 167 |
| B3 | 80 | 66 | 2 | 12 | 160 |
| B4 | 105 | 91 | 9 | 24 | 229 |
| B5 | 115 | 91 | 10 | 21 | 237 |
| Average | 87 | 83 | 5 | 12 | 188 |
| C1 | 65 | 64 | 0 | 0 | 129 |
| C2 | 47 | 58 | 1 | 2 | 108 |
| C3 | 131 | 153 | 2 | 7 | 293 |
| C4 | 124 | 130 | 5 | 9 | 268 |
| C5 | 49 | 50 | 8 | 12 | 119 |
| Average | 87 | 91 | 3 | 6 | 183 |
| D1 | 65 | 76 | 0 | 1 | 168 |
| D2 | 47 | 41 | 11 | 18 | 119 |
| D3 | 131 | 69 | 3 | 3 | 146 |
| D4 | 124 | 87 | 5 | 8 | 202 |
| D5* | 49 | 122 | 0 | 0 | 250 |
| Average | 83 | 79 | 4 | 6 | 177 |
| El | 76 | 59 | 7 | 23 | 165 |
| E2 | 103 | 119 | 1 | 3 | 227 |
| E3 | 87 | 113 | 7 | 8 | 215 |

TABLE XIV-continued

Summary results of the worm burdens in vaccinated and control dogs

| | Intestine | | Colon | | |
|---|---|---|---|---|---|
| | Male | Female | Male | Female | Total |
| E4 | 99 | 82 | 7 | 8 | 196 |
| E5 | 114 | 100 | 1 | 2 | 217 |
| Average | 96 | 95 | 5 | 9 | 204 |

*1 intestinal worm of unknown gender
**1 colon worm of unknown gender

TABLE XV

Mean and Medians of the worm burdens in vaccinated dogs relative to control (ASO3) dogs

| | | |
|---|---|---|
| Ac-ASP-2 | Valid | 5 |
| | Mean | 166.0000 |
| | Median | 174.0000 |
| | Minimum | 89.00 |
| | Maximum | 226.00 |
| Ac-API | | 5 |
| | Mean | 187.800 |
| | Median | 167.0000 |
| | Minimum | 146.00 |
| | Maximum | 237.00 |
| Ac-MEP | | 5 |
| | Mean | 183.4000 |
| | Median | 129.0000 |
| | Minimum | 109.00 |
| | Maximum | 293.00 |
| Ac-APR-1 | | 5 |
| | Mean | 177.0000 |
| | Median | 168.0000 |
| | Minimum | 119.00 |
| | Maximum | 250.00 |
| ASO3 (adjuvant) | | 5 |
| | Mean | 203.8000 |
| | Median | 215.0000 |
| | Minimum | 165.00 |
| | Maximum | 226.00 |

The number of adult hookworms recovered from each of the ASP-2 vaccinated dogs was lower than the mean of the control dogs, with the exception of dog A1. This accounted for the overall mean worm burden reduction. Dog A3 in the ASP-2 group exhibited the greatest worm burden reduction for the entire study (58%). The worm burden reduction is statistically significant if dog A1 is removed (P=0.03).

Among the MEP-1 vaccinated dogs, three out of the five exhibited significant protection as evidenced by worm burden reductions that exceeded 36%. However in two of the vaccinated dogs, the number of hookworms recovered exceeded the mean of the control dogs. These findings accounted for the large reduction in median worm burden, but not the mean.

Among the APR-1 vaccinated dogs, only dog D2 exhibited a significant reduction in worm burden (42%). Of interest, this was the only dog that acquired significant anti-APR-1 antibody titers following vaccination.

Figure 55:
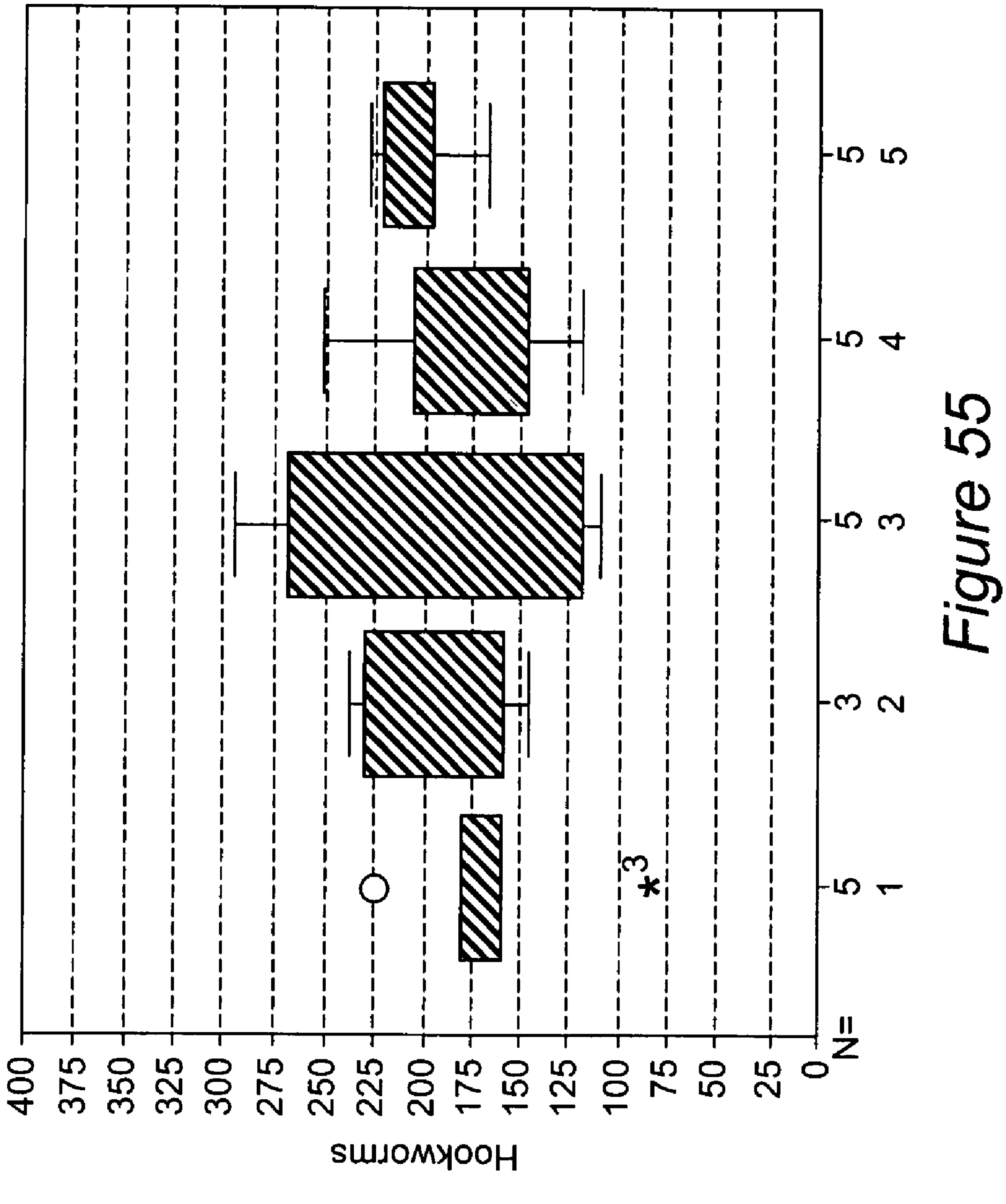
FIG. 55. Mean and medians of the worm burdens in vaccinated dogs relative to control (AS03) dogs. 1=Ac-ASP-2; 2=Ac-API; 3=Ac-MEP; 4=Ac-APR-1; 5=AS03 (adjuvant).

There was no remarkable reduction in worm burden following API vaccination. These data are also pictorially represented in FIG. 55.

Reduction in Quantitative Egg Counts (QECs)

Figure 56:
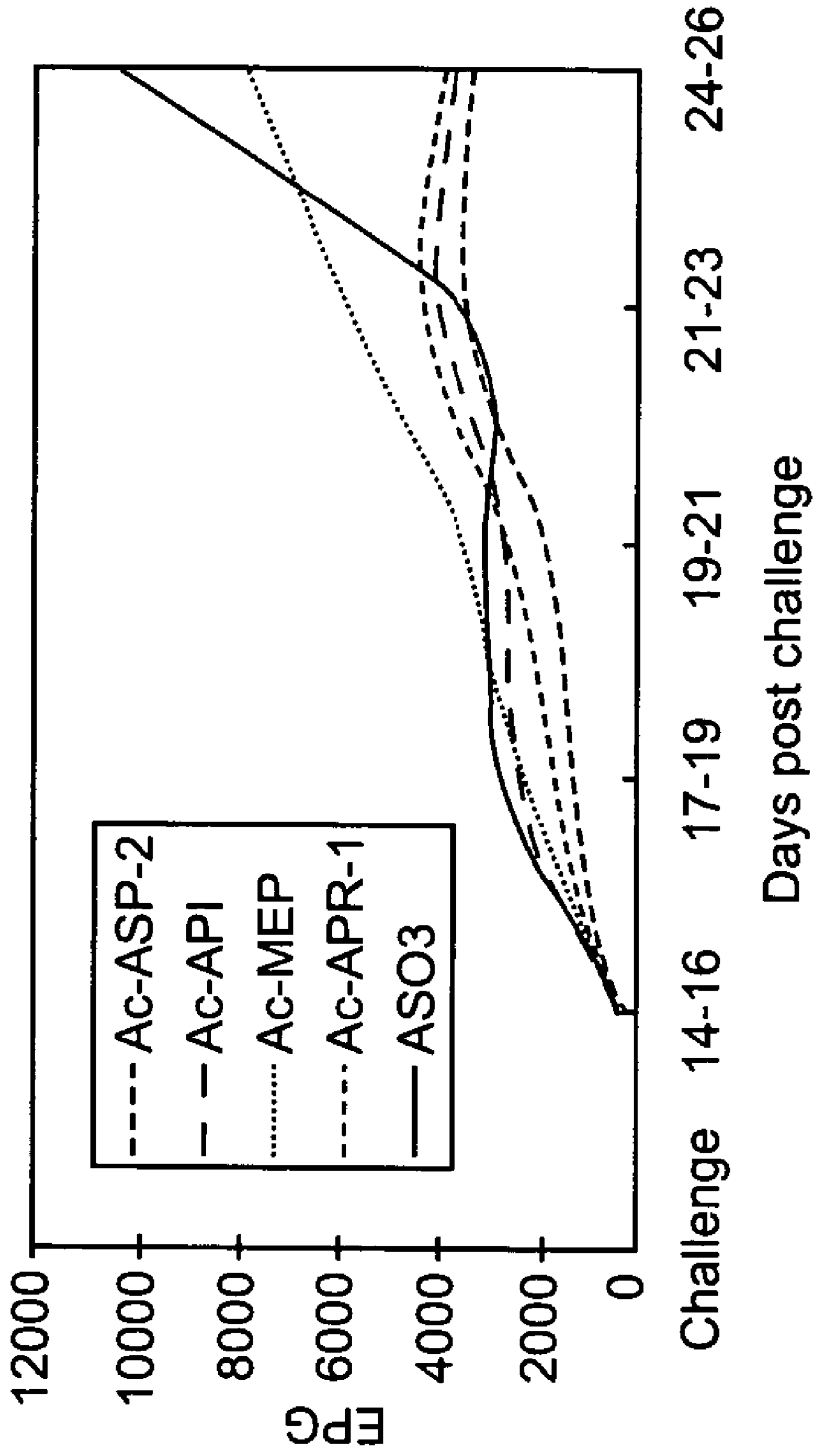
FIG. 56. Reduction in QECs (Quantitative Egg Counts) following vaccination and challenge.
Figure 58A:
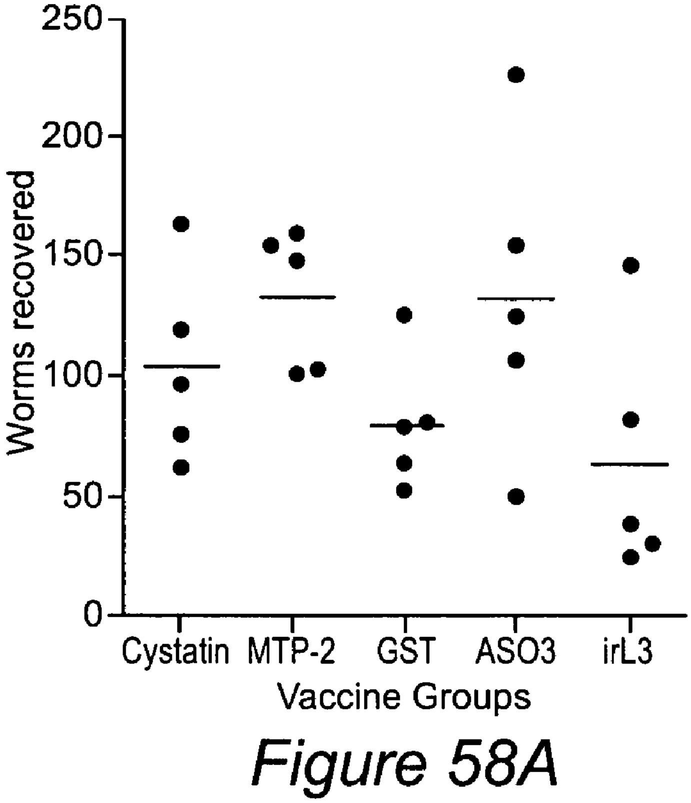
FIGS. 58A and B. Graphic representation of adult worms recovered from the vaccinated and control dogs.
Figure 58B:
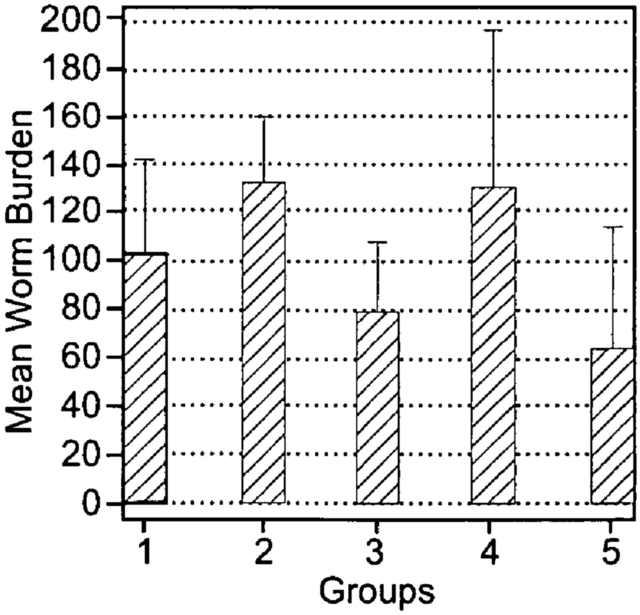

As shown in FIG. 56, there was a significant reduction in fecal eggs (fecundity) for the ASP-2, API, and APR-1 group relative to the control group. Fecal eggs were lowest in the ASP-2 vaccinated dogs. These data indicate that ASP-2 is an immunogenic molecule and a promising protective antigen. In addition, both MEP-1 and APR-1, each a adult hookworm hemoglobinase, show some promise at protection. MEP-1 vaccinations resulted in reduced median hookworm burdens, while in a single dog that developed anti-APR-1 antibody titers there was also a reduction in the number of adult hookworms. However, the overall low antibody titers in response to these molecules suggests that the results of this trial could be improved if the immunogenicity of each hemoglobinase was increased. Studies are underway to re-express the proteases in yeast in an effort to improve immunogenicity. Previously a third hemoglobinase, CP-2, was successfully expressed in yeast, and shown to be immunogenic and protective (Loukas et al, 2004).

References Cited for Example 14

Brinkworth, R I, et al. Hemoglobin-degrading aspartic proteases of blood-feeding parasites: substrate specificity revealed by homology models. *JBC* 276: 38844-51 (2001).

Harrop, SA, et al. Acasp, a gene encoding cathepsin D-like aspartic protease from the hookworm *Ancylostoma caninum. Biochemical and Biophysical Research Communications* 227: 294-302 (1996).

Hawdon, J. M., Narasimhan, S. & Hotez, P. J. *Ancylostoma* secreted protein 2: cloning and characterization of a second member of a family of nematode secreted proteins from *Ancylostoma caninum. Mol Biochem Parasitol* 99, 149-65 (1999).

Hotez, P J, et al. Effect of vaccinations with recombinant fusion proteins on *Ancylostoma caninum* habitat selection in the canine intestine. *J Parasitol.* 88: 684-90 (2002)

Jones B F, Hotez P J. Molecular cloning and characterization of Ac-mep-1, a developmentally regulated gut luminal metalloendopeptidase from adult *Ancylostoma caninum* hookworms. *Mol Biochem Parasitol* 119: 107-16 (2002).

Loukas, A. et al. Vaccination of dogs with a recombinant cysteine protease from the intestine of canine hookworms diminishes fecundity and growth of worms. *Journal of Infectious Diseases* in press (2004).

Stoute, J. A. et al. A preliminary evaluation of a recombinant circumsporozoite protein vaccine against *Plasmodium falciparum* malaria. RTS,S Malaria Vaccine Evaluation Group. *N Engl J Med* 336, 86-91 (1997).

Williamson, A. L. et al. Hookworm aspartic protease, Na-APR-2, cleaves human hemoglobin and serum proteins in a host-specific fashion. *J Infect Dis* 187, 484-94 (2003).

Zhan, B., Li, T., Xiao, S., Zheng, F. & Hawdon, J. M. Species-specific identification of human hookworms by PCR of the mitochondrial cytochrome oxidase I gene. *J Parasitol* 87, 1227-9 (2001).

Example 15

Cloning, Transformation and Expression in *Pichia Pastoris* of Na-asp-2

The purpose of this study was to identify the major orthologue of Ac-asp-2 (Hawdon et al, 1999) from *Necator americanus*. To identify the orthologue, a cDNA library was prepared as described in a research report published in the *Chinese Journal of parasitology and Parasitic Diseases* (Zhan et al, 2000). Briefly, these L3 were obtained from hamsters infected with *Necator americanus* as described (Xue et al, 2003). The L3 have now gone through approximately 100 passages through hamsters, but were originally derived by coproculture from an *N. americanus* infected individual from Hunan Province (Xue et al, 2003). From 500,000 plaques screened using Ac-asp-2 cDNA, only 2 positive clones were obtained. These two positive clones were subjected to DNA sequencing. Neither of these clones contained the full-length signal peptide.

Based on the sequence obtained, forward and reverse primers were selected (both with and without histag, and all with EAEAEF (SEQ ID NO: 116) vector sequence) and synthesized (Integrated DNA Technologies, Inc., Coralville, Iowa). These primers were used to amplify Na-asp-2 cDNA from the $1^{st}$ strand Na-L3 cDNA. Na-L3 cDNA from mRNA extracted from L3 as described previously (Zhan et al, 2000). The L3 were obtained from golden hamsters infected with *N. americanus* as described previously (Xue et al, 2003). The PCR products were ligated into pPICZ A using EcoR1 and Xba1 sites. The ligation product was transformed into *E. coli* DH5 competent-rendered cells and the recombinants were selected by growing on LB-Zeocin plates. Eight colonies were picked from each transformation (with and without histag) and analyzed by PCR with vector primers. Each of the positive clones contained an insert of the predicted size. From two clones (one with histag and the other without) the plasmid was extracted and sent for DNA sequencing (Nevada Genomics Center).

The clones obtained did not contain the 5' end of the Na-asp-2 cDNA, which encoded the N-terminus of the full signal peptide. Therefore, concurrent with the amplification of Na-asp-2 cDNA from L3 it was of additional interest to unambiguously determine the 5' end of the full length clone. 5' RACE was conducted to obtained a full-length cDNA. This was done using the Gene Racer Kit from Invitrogen. Reverse primers for 5'RACE were selected from a portion of the cDNA encoding the C-terminus of Na-ASP-2. The primers were synthesized by IDT (Integrated DNA Technologies, inc., Coralville, Iowa). The 5' RACE clones were sequenced.

Rescreening: The purpose of rescreening was to make certain that there were no other major orthologues cDNAs to Ac-asp-2 (SEQ ID NO: 19). We wished to make certain that our clone represented the only *Necator* ASP-2 found in L3. To conduct this work, two fragments of Ac-asp-2 (SEQ ID NO: 19) cDNA were selected as probes based on the most conserved areas compared with asp-2 from other species of hookworm. On this basis, 4 separate primers (two forward and two reverse) were synthesized. Two PCR products were amplified from Ac-asp-2/pPICZ A plasmid, labeled with $^{32}P$-CTP, and hybridized under stringent conditions (65° C.). Approximately 500,000 plaques were screened. Of the remaining colonies not worked up under the above section, the remaining colonies were pooled and re-screened with Ac-asp-2 cDNA fragment.

Preparation of *Necator Americanus* cDNA Library and Original Screening of the Library with Ac-asp-2 Clone.

The 2 positive clones obtained from heterologous library screening were subjected to DNA sequencing. The 2 positive clones were identical, each encoding an ORF with homology to Ac-asp-2 (SEQ ID NO: 19)(designated as Na-asp-2). The Na-asp-2 cDNA consisted of 731 bp with a 3' poly (A) tail. However, no 5-initiation codon was identified. The Na-asp-2 cDNA encodies a predicted ORF of 206 amino acids, lacking initial Met at the N-terminus.

Amplification of Na-asp-2 cDNA and Ligation into pPICZ A

Copy DNA was amplified and successfully ligated into pPICZ A. Except for the histag at the C-terminus both of the two clones described above were identical. However, compared with the original sequence, there was a single mutation at position 119 from T to A. This resulted in a conservative substitution of a Leu to Met at amino acid 36 (the position is based on the original full length sequence).

5'-RACE to Obtain the 5'-end of Na-asp-2 cDNA

Two clones were obtained by 5'RACE. Each contained the full length 5' end. These were designated 4a1 and 4a2. Sequence alignment of the full length clone revealed that 4a1 exhibited three bp changes. However, 4a2 showed no bp changes from the original cDNA clone. The predicted ORF of 4a2 revealed that Na-ASP-2 (SEQ ID NO: 69) exhibits approximately 60-70% amino acid identity with Ac-ASP-2 (SEQ ID NO: 12).

Re-screening of Na L3 cDNA Library with Ac-asp-2 cDNA Fragment 16 positive clones were identified, each exhibiting different intensities. By secondary screening 6 single colonies were obtained, PCR amplified and sequenced. Four of the 6 clones were identical. One of the other clones was identical except at position 119 which exhibited a T to A mutation. A sixth clone was an entirely new gene product that represented a double-domain pathogenesis related protein superfamily gene product (tentatively designated as Na-asp-7).

Repeat Re-screening of Na L3 Library 11 additional plaques were obtained, and their cDNA inserts were sequenced. At NGC. From this re-screening a total of 11 cDNAs were obtained. Each of these contained clearly defined Na-asp-2 sequences, which were identical except for variation at positions 55, 61, 66, 119, 193, 451, 496, and 650. However only two of these mutations resulted in amino acid alterations. These included, mutation at position 119, which resulted in either the appearance of a methionine or leucine and a mutation at position 66, which resulted in either the appearance of an alanine or glycine.

Transformation of Na-asp-2 cDNA into *Pichia Pastoris* pPICZ A DNA containing the Na-asp-2 coding sequence was prepared as described in RR-3001 and transformed into *Pichia pastoris* by electroporation. Four X33 strain colonies containing the presumptive Na-asp-2 sequence were selected, and the presence of an insert was confirmed by PCR in three of the four colonies. To generate Research Seed Stock #1, colony number 2 was selected and grown in YPD, prior to storage at −70 C in YPD containing 25% glycerol. Subsequently, Research Seed Stock #1 was expanded twice, first in BMG, and subsequently in YPD. The DNA sequence and copy number was confirmed.

Transformation of Na-asp-2 DNA into *Pichia Pastoris* pPICZ A DNA containing the Na-asp-2 coding sequence (without histag and without N-terminal signal peptide) was prepared. Plasmid DNA containing the Na-asp-2 coding sequence was transformed into *Pichia pastoris* as described in the Invitrogen *Pichia* expression manual (EasySelect™ *Pichia* Expression Kit, Version F 000526; 25-0172).Zeocin (all transformants integrate at 5' AOX1 locus by single crossover). Briefly, the plasmid DNA was linearized with Sac1 and transformed into *Pichia pastoris* strain X33 and GS115 (Mut+) using electroporation. The transformants were plated on medium containing Zeocin (all transformants integrate at 5' AOX1 locus by single crossover; Mut phenotype is determined by the strain used).

Four colonies containing the presumptive Na-asp-2 DNA were selected. Each of these was from the X33 strain. The presence of Na-asp-2 DNA was confirmed by PCR using the following vector primers:

```
3' AOX1
5'-GCAAATGGCATTCTGACATCC-3'   (SEQ ID NO: 74)

α-factor
5'-TACTATTGCCAGCATTGCTGC-3'   (SEQ ID NO: 75)
```

The presence of an insert was confirmed by PCR in three of the four colonies.

Sequencing

Expanded research seed stocks were subjected to PCR using the vector primers described above, and subjected to DNA sequencing. DNA sequencing was conducted at the Nevada Genomics Center. Na-asp-2 cDNA without signal peptides at the 5' end and with stop codon at the 3' end was cloned with the correct reading frame. There were no nucleotide mutations observed following Na-Asp-2/pPICZA transformation into *Pichia pastoris* X-33 and subsequent expansions. Only a single copy of Na-asp-2 DNA was observed in both the research seed stock as well as colonies from the original Zeocin plate.

Determination of Copy Number

Genomic DNA was extracted both from colonies of the original Zeocin plate and expanded. This was done using the YeaStar Genomic DNA Kit (Zymo Research, Cat. # D2002). Na-asp-2 probe was amplified from Na-asp-2-pPICZαA plasmid and labeled with digoxin as described in PCR DIG Probe Synthesis Kit (Roche, Cat #1636090) and used to probe a Southern blot containing research seed clone DNA. Only a single copy of Na-asp-2 DNA was observed in both the research seed stock as well as colonies from the original Zeocin plate.

References for Example 15

Hawdon J M, Narasimhan S, Hotez P J. *Ancylostoma* secreted protein 2: cloning and characterization of a second member of a family of nematode secreted proteins from *Ancylostoma caninum*. Molec. Biochem. Parasitol. 1999; 99: 149-65.

Zhan B, Hawdon J, Shan Q, Ren H N, Qiang H Q, Xiao S H, Li T H, Feng Z, Hotez P. Construction and analysis of cDNA library of *Necator americanus* third stage larvae. Chin. J. Parastiol. Parasitic Dis. 2000; 18: 26-9.

Xue J, Liu S, Qiang H Q, Ren H N, Li T H, Xue H C, Hotez P J, Xiao S H. *Necator americanus*: maintenance through one hundred generations in golden hamsters (*Mesocricetus auratus*). I. Host sex-Associated Differences in Hookworm Burden and Fecundity. Exp. Parasitol. 2003; 104: 62-6.

Example 16

Cloning and Canine Vaccine Trial of Ac-GST

Cloning

Cloning of the protein GST from *Ancylostoma caninum* was carried out by identifying homologous EST fragments of Ac-GST from *A. caninum* an L3 cDNA library by searching with WU-Blast2 using the Sj28 (*S. japanicum*) GST sequence. Primers were designed based on sequence information and the 5' and 3' ends of Ac-GST were isolated from *A. caninum* L3 cDNA by using GeneRacer kit (Invitrogen). A full length AcGST was obtained (FIG. 57A, SEQ ID NO: 76). The deduced amino acid sequence is shown in FIG. 57B (SEQ ID NO: 77), and the alignment of the cDNA and the amino acid sequence is shown in FIG. 57C. The coding sequence was claimed into pPICZaA in the correct reading frame and the entire sequence was confirmed by re-sequencing from both strands.

Vaccine Trial

A canine vaccine trial was completed with the following vaccine antigens tested as shown in

TABLE XVI

Canine vaccine trial description

| Antigen | Expression Vector | Amount | Immunization | Aduvant | Route |
|---------|-------------------|--------|--------------|---------|-------|
| Ac-CYS | Pichia pastoris | 100 ug | Four | AS03 | i.m. |
| Ac-MTP-2 | Pichia pastoris | 100 ug | Four | AS03 | i.m. |
| Ac-GST | Pichia pastoris | 100 ug | Four | AS03 | i.m. |
| Adjuvant alone | — | — | Four | AS03 | i.m. |
| Irradiated L3 | — | 1000 L3 | Four | — | sc |

Experimental Design and Methods

Purpose of the Study: The purpose of the study is to test the protective effects in laboratory dogs of vaccines containing various recombinant protein antigens derived from the canine hookworm Ancylostoma caninum. These include recombinant glutathione S transferase (GST), cystatin, and MTP-2. All antigens are given in combination with the GSK adjuvant AS03 and are compared with an AS03 negative control. In addition, a fifth arm of the study employs radiation-attenuated (irradiated) infective larvae, a positive control.

Brief Outline of Study Sections: Purpose bred beagles were randomized into five groups. Four groups were given one of three candidate vaccines: Ac-Cystatin, Ac-MTP-2 and Ac-GST in combination with the adjuvant ASO3. One group will serve as the negative control receiving the adjuvant only. Another group will be a positive control immunized with irradiated infective larvae. Each animal's specific antibody response was evaluated by direct ELISA using serum taken prior to the infective challenge. Cellular immune responses were assessed by peripheral (blood cells) lymphoproliferative responses to specific recombinant antigens and/or crude extract of infective larvae (L3) or adult worms. Local cellular immune responses were performed post mortem with lymphocytes extracted from mesenteric lymph nodes and, if considered, spleen. After immunization, animals were challenged with a known number dose of infective third stage larvae of A. caninum. Quantitative ova counts, used to evaluate worm burden, were determined from fecal samples collected three times per week. These data were augmented by periodic blood values to monitor any anemia induced by the parasites and finally necropsy examination to confirm parasite load by counting, weighing, sexing and measuring adult worms. Tissues from different organs were examined macro and microscopically to assess any consequence of the vaccine, parasite or immune related lesions.

Test and Control Identification: Test and control articles were prepared for injection by mixing with the adjuvant. The experimental vaccines were comprised of the antigens Ac-Cystatin and Ac-MTP-2 and Ac-GST (expressed all in Pichia pastoris) in combination with the adjuvant ASO3.

Animals: The test and control animals were purpose bred, parasite naïve male beagles 56±7 days of age. The trial was terminated twenty seven (27) days after parasite infection.

Administration of Test and Control Articles: The vaccines and adjuvant were administered intramuscularly (IM) three (3) times beginning when the dogs are 62+/−4 days old. The vaccines are boosted at 21+/−3-day intervals. Four doses of the vaccines were given 21 days apart (days 0, 21, 42, and 52). The dogs were challenged percutaneously with 500 A. caninum L3, 14 days after the final vaccination.

Serum Samples for Quantitative ELISA Antibody Titers: Animals treated with vaccines containing foreign proteins develop an immune response resulting in an increased level of high affinity serum antibodies that are directed against the antigen. Quantitative ELISA using the antigenic proteins demonstrated the relative avidity of the immune response and provide a data set that can be applied to the identification and analysis of hookworm resistant animals. White blood cells were collected for immunological measurements nine (9) days after the last boost and at the time of euthanasia to address the cellular immune response status and cytokine production upon in vitro restimulation of lymphocytes.

Cellular Immunology Studies: Blood samples were taken from each animal at scheduled intervals by the veterinary technologist in heparinized tubes. Lymphoproliferation assays were performed in vivo on blood, and post mortem on blood and mesenteric lymph nodes.

Challenge Infection: Ancylostoma caninum larvae were cultured from the eggs collected in the feces of infected dogs. All hookworms in the infective challenge were approximately equal age (17±7 days). The species identity of the infective larva dose were validated using PCR DNA amplification and specific oligonucleotide primers. Overnight-collected feces of A. caninum-infected dogs were cultured, extracted and counted. All dogs were infected by the footpad method with the same dose (500+/−5%, of 3rd stage larvae of A. caninum. Larval challenge occurs on one of three consecutive days (at age 120+/−9 days) in 5 series. To minimize the difference in the infective L3 doses, each series included one dog from each (A-E group).

Larval Irradiation: The irradiated larvae vaccinations were performed in 2 subcutaneous doses of 1,000 L3 at each vaccination with intervals of 3 weeks between the doses. The challenge was performed 4 weeks after the second dose of vaccination. The irradiated larvae were obtained by irradiation with 40 krad from Cesium (137) as described in SOP 38.1 and a single batch of irradiated larvae was used for both doses of vaccinations.

Observations, Hematology, Serum Chemistries: The dogs were observed daily and were weighed at least every 18 days. Dogs that develop signs of moderate to severe anemia, diarrhea or develop a loss of body weight greater than 15% were observed more frequently. Anemia is considered mild (HCT 27-33%), moderate (HCT 21-26%) or severe (HCT<20). Prior to larval infection and at least one time every 21 days, blood samples are collected from all dogs. Blood withdrawal should be approximately equal in amount from all dogs. At this time, the mucous membranes are examined for pallor. A pre-vaccination blood sample was utilized for CBC (hematology), serum chemistries, and a sample of serum will be frozen. The CBC includes: HCT (hematocrit), Hb (hemoglobin), MCHC (mean corpuscular hemoglobin content) and count of WBC (white blood cells), neutrophils, eosinophils, platelets, and monocytes/lymphocytes. Serum chemistries include: ALB (albumin), ALKP (alkaline phosphatase), ALT (alanine aminotranspherase), TBIL (total bilirubin), TP (total protein), Phos (phosphorous), Ca (calcium), BUN (urea nitrogen), CREA (creatinine), AMYL (amylase), Chol (cholesterol), & Glu (glucose). The first CBC was performed approximately five (5)± two (2) after parasite infection.

Quantitative Egg Counts (QEC): Twelve days (12±3) following parasite dosing, fecal examination for ova began and continued three times a week (generally M, W, F) until termination. The ova count method was performed according to the current version of SOP 7, which is a modification of the McMaster technique (Veterinary Clinical Pathology, 6th ed., 1994, page 9-10). The test was performed in the same way each time in order to quantitate the ova count. The ova were counted in a McMaster chamber under a binocular microscope and recorded. At this time fecal specimens were examined for the presence of gross blood and notation made on the animal observation form if blood is observed.

Adult Worm Count. Adult worms retained in the small and large intestines were collected. The small and large bowel will be collected and the small intestine will be suspended (the large bowel will not be suspended) in a container and incubated for at least two hours at 35° C. saline to collect the adult parasites. The adult worms were separated from the intestinal contents, counted, and preserved in formalin for subsequent count and analysis of sex, length and weight.

Results and Analysis

The different groups in this vaccine trial are labeled as follows: A or 1: Cystatin+AS03; B or 2: MTP-2+AS03; C or 3: GST+AS03; D or 4: AS03; E or 5: Irradiated 3. As shown in Table XVII high antibody titers were achieved with each group following four immunizations.

TABLE XVII

Antibody titers in HV-12

| Antigen/Dog | IgG1 | IgG2 |
|---|---|---|
| Cystatin | | |
| A1 | 40,500 | 121,500 |
| A2 | 121,500 | 364,500 |
| A3 | 364,500 | 1,093,500 |
| A4 | 121,500 | 364,500 |
| A5 | 121,500 | 364,500 |
| GEOMEAN | 121,500 | 364,500 |
| Ac-MTP2 | | |
| B1 | 121,500 | 364,500 |
| B2 | 40,500 | 121,500 |
| B3 | 121,500 | 121,500 |
| B4 | 40,500 | 121,500 |
| B5 | 40,500 | 40,500 |
| GEOMEAN | 62,850 | 121,500 |

TABLE XVII-continued

Antibody titers in HV-12

| Antigen/Dog | IgG1 | IgG2 |
|---|---|---|
| GST | | |
| C1 | 13,500 | 40,500 |
| C2 | 13,500 | 121,500 |
| C3 | 13,500 | 40,500 |
| C4 | 13,500 | 40,500 |
| C5 | 13,500 | 40,500 |
| GEOMEAN | 13,500 | 50,452 |
| L3 Extract | | |
| E1 | 13,500 | 4,500 |
| E2 | 13,500 | 1,500 |
| E3 | 13,500 | 4,500 |
| E4 | 13,500 | 500 |
| E5 | 13,500 | 4,500 |
| GEOMEAN | 13,500 | 2,328 |

The adult hookworms recovered from each of the vaccinated dogs is shown in Table XVIII.

TABLE XVIII

Adult Hookworm Worm Counts in HV-12

| | Intestine | | | Colon | | | |
|---|---|---|---|---|---|---|---|
| | Male | Female | Unk. Sex | Male | Female | Unk. Sex | Total |
| A1 | 81 | 85 | | 1 | 0 | | 167 |
| A2 | 38 | 29 | | 0 | 0 | | 67 |
| A3 | 48 | 67 | 1 | 3 | 5 | | 124 |
| A4 | 36 | 41 | | 0 | 2 | | 79 |
| A5 | 44 | 56 | | 0 | 0 | | 100 |
| Average | 49 | 56 | | | | | 107 |
| B1 | 64 | 71 | | 11 | 10 | | 156 |
| B2 | 49 | 51 | | 2 | 3 | | 105 |
| B3 | 41 | 41 | | 1 | 2 | | 85 |
| B4 | 64 | 65 | | 9 | 15 | | 153 |
| B5 | 87 | 73 | | 1 | 0 | | 161 |
| Average | 61 | 60 | | | | | 132 |
| C1 | 50 | 81 | | 0 | 0 | | 131 |
| C2 | 34 | 26 | | 4 | 3 | | 67 |
| C3 | 19 | 36 | | 0 | 0 | | 55 |
| C4 | 33 | 36 | | 7 | 4 | | 80 |
| C5 | 33 | 41 | | 2 | 5 | | 81 |
| Average | 34 | 44 | | | | | 83 |
| D1 | 49 | | | 0 | 1 | | 113 |
| D2 | 27 | 29 | | 0 | 0 | | 56 |
| D3 | 62 | 61 | | 0 | 2 | | 125 |
| D4 | 75 | 82 | | 0 | 2 | | 159 |
| D5 | 108 | 119 | | 3 | 2 | | 232 |
| Average | 64 | 71 | | | | | 137 |
| E1 | 7 | 10 | | 4 | 9 | | 30 |
| E2 | 43 | 40 | | 0 | 1 | | 84 |
| E3 | 28 | 118 | | 4 | 5 | | 155 |
| E4 | 20 | 24 | | 0 | 0 | | 44 |
| E5 | 12 | 15 | | 3 | 5 | | 35 |
| Average | 22 | 41 | | 2 | 4 | | 70 |

Figure 59:
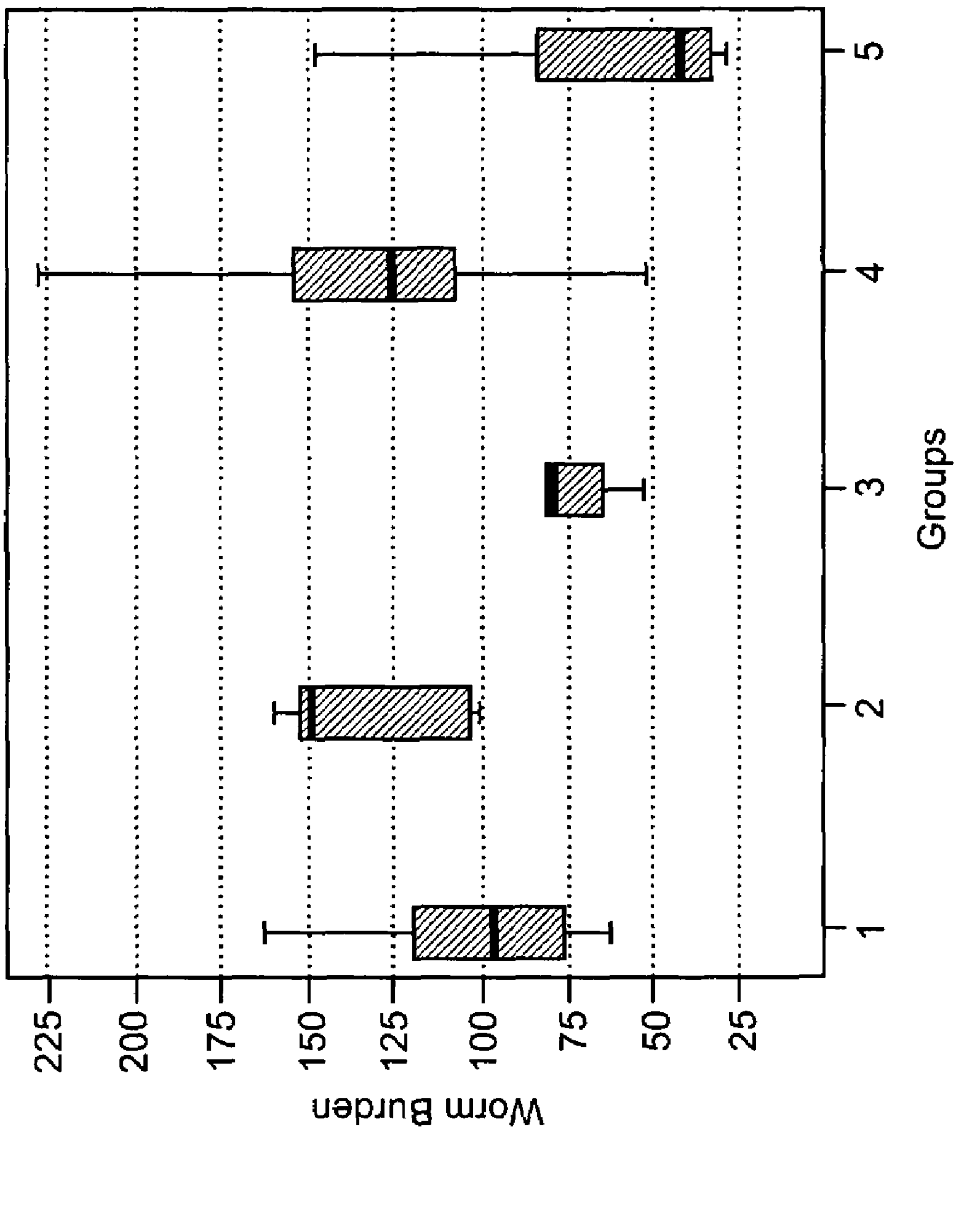
FIG. 59. Median adult hookworm counts after use of trimmed mean calculation.

Although a promising trend was noted in the GST and cystatin vaccinated group (40 and 51 percent reduction relative to AS03 controls, respectively), for this trial the variance was too great for the small sample size and that only the IrL3 is statistically significant and, then only when the Dunnett 2-sided post hoc test (the standard for clinical trials) was used. However as shown in the Appendix, if an outlier is removed from the control group, statistical significance is obtained. An outlier is defined as an observation far from the rest of the data; it may represent valid data or a mistake in experimentation, data collection, or data entry. An outlier can have an extremely large effect on when testing for differences of means. While it is common to remove outliers, it must be done with some rules and with consistency. There is statistical significance for both GST and IrL3, by using the 5% Trimmed Mean. This is the arithmetic mean calculated when the largest 5% and the smallest 5% of the cases have been eliminated. Eliminating extreme cases from the computation of the mean results in a better estimate of central tendency, especially when the data are non-normal. This is common, well-accepted, and a method preferential to removing outliers because it is done by the statistical program itself. The results from an SPSS output for GST, IrL3, and Control groups are shown below in yellow for the 5% trimmed mean The results for the t-tests were: GST vs. Control (t=1.6874; p=0.0458); IrL3 vs. Control (t=1.8851; p=0.0297). A comparison of the resulting hookworm counts is given in FIG. 59.

Figure 60A:
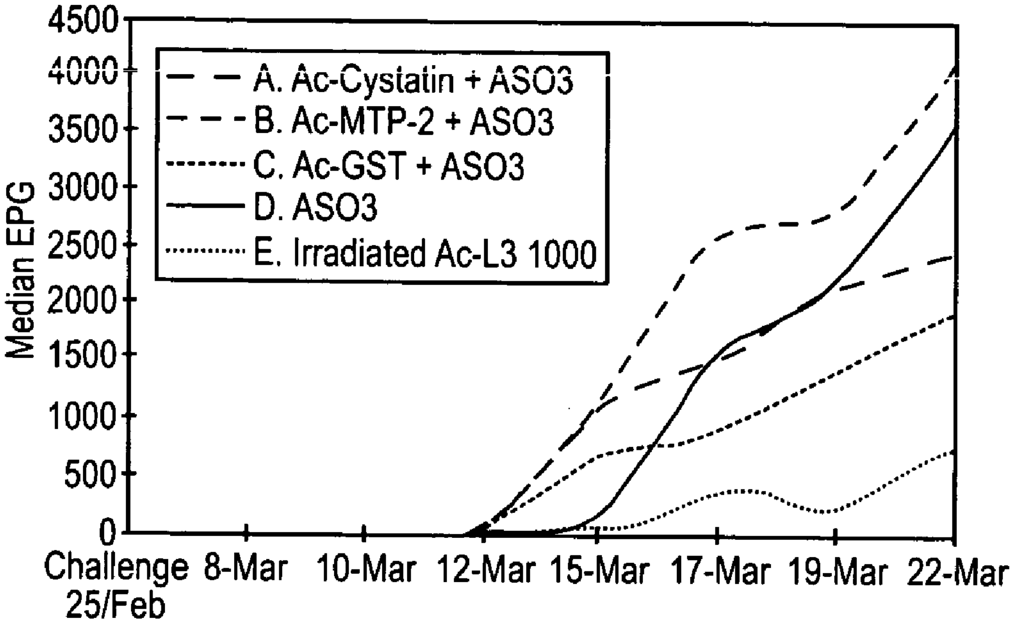
FIG. 60. A, Median and B, mean reduction in quantitative egg counts.
Figure 60B:
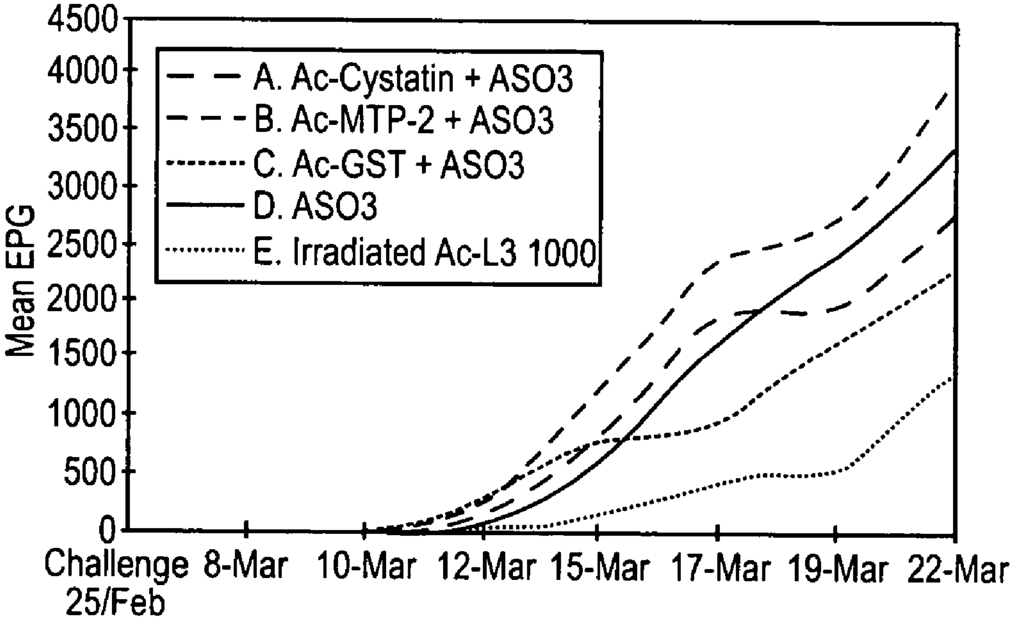

As shown in FIG. 60, there was also a reduction in the mean and median hookworm quantitative egg counts in dogs receiving L3 irradiated and Ac-GST.

This example shows that high antibody titers were produced to each of the recombinant antigens. After larval challenge, both GST and irradiated L3 vaccinated groups exhibited high levels of worm burden reduction (41 and 50%, respectively). However, because of high variation within the control group, the worm burden reduction was statistically significant with either removal of outliers or using trimmed means. In addition there was significant reduction in quantitative egg counts. These studies confirmed the protection afforded by irradiated L3 and indicate that GST is a promising vaccine antigen.

Example 17

Hamster Vaccine Trial

These studies were undertaken to confirm the protective effects of Ay-ASP-2 observed in Ham V-3 (Goud et al, 2004). The results confirm that ASP-2 is a protective antigen, both in terms of worm burden reduction and in worm fecundity. In addition there was less blood loss among the ASP-2 vaccinated group. The study also found that ASP-1 had greater protective efficacy than observed in Ham V-3. The results also found that the addition of MTP to the vaccine cocktail increases the protective effect.

Experimental Design and Methods

Purpose of the Study: The purpose of the study is to test the protective effects in laboratory hamsters of vaccines containing various recombinant protein antigens derived from hookworms and other parasites, against hookworm infection.

Brief Outline of Study Sections: Purpose bred Syrian hamsters are randomized into eight groups. Seven groups will receive candidate vaccines: ASP-1, ASP-2, MTP, and Irradiated larvae. One group receives only the adjuvant (Quil A) as experimental control. Each animal's specific antibody response is evaluated by direct ELISA using serum taken prior to the infective challenge. After the immunized animals demonstrate a positive immune response to the vaccines, they are challenged with a known number dose of infective third stage larvae of *A. ceylanicum*. Quantitative ova counts, used to evaluate worm burden, are made from fecal samples collected twice after larval challenge. Also, hemoglobin levels will be tested to detect anemia caused by the blood loss during adult hookworm infection. The final report will evaluate the data and provide conclusions regarding each vaccine's effectiveness both in terms of worm burden and blood loss.

Positive Result Indicators: A successful positive result in this study will be a demonstrated increase in specific antibody titers in immunized animals and protection against hookworm burden and hookworm-associated blood loss. The hemoglobin test detects anemia caused by the blood loss during adult hookworm infection. The experimental control data obtained from un-immunized animals will serve as a basis for evaluating the success of the study and also to check any parasitic infection.

Test and Control Identification: The antigens are ASP-1, ASP-2, and MTP. The antigen-adjuvant combinations will be ASP-1+Quil A, ASP-2+Quil A, MTP+Quil A, ASP-1+ASP-2+Quil A, ASP-2+MTP+Quil A and ASP-1+MTP+Quil A. One group, which receives irradiated L3 serve as the positive control. The negative control group will receive only Quil A. Details about the antigen and the adjuvants will be included in the study records when they become available.

The test articles are diluted to provide a dose of 0.025 mg of antigen in 200 ul of antigen-adjuvant mixture per animal per injection. All injections will be performed intramuscularly (i.m). The prescribed volume dose information is recorded by Dr. Ghosh. Fresh preparation of antigens will be made the day of injection.

Selection and Justification of Test System: Hamsters are selected as the test system because they are susceptible to infection by a hookworm species that causes a serious but often non-fatal disease. Hamsters make an excellent model because hookworm-induced anemia caused by *A. ceylanicum* is better reflected in hamsters. Previous studies have documented there are many parameters associated with hookworm induced anemia that contribute to the quantitative evaluation of the vaccine study success.

Animals: The test and control animals will be purpose bred, parasite naïve, 23±2 days old and 50±5 gm body weights on arrival. Following 5-9 days quarantine, the hamsters are started on the vaccination schedule. The hamsters will be identified by a small metallic ear tag plate, each of which contain a number for the identification of the hamster. Hamsters are randomized into five (6) vaccine test groups containing ten (10) hamsters each and two (2) control group of ten (10) hamsters. The hamsters are then assigned permanent hamster-study numbers (e.g. Ham V-IV) as follows: Ham V-IV (*A. ceylanicum* Vaccine Trial IV), vaccine or control groups A, B, C, D E, F, G and H. Each hamster will have unique Ear Tag number viz., 301. Attempts will be made to treat each hamster in the same manner. Each hamster on a trial will receive the same treatment, housing, dose of larvae and diet.

Administration of Test and Control Articles: The vaccines and adjuvant are administered intramuscularly (IM) three (3) times beginning when the hamsters are 28±2 days old. The vaccines are boosted at 21 days (3 weeks) intervals.

Serum Samples for Quantitative ELISA Antibody Titers: Animals treated with vaccines containing foreign proteins are expected to develop an immune response resulting in an increased level of high affinity serum antibodies that are directed against the antigen. Since the hookworms feed on blood, antibodies in the host circulatory system are likely to come in contact with the parasite. If these antibodies recognize an antigen that is essential for initiation or maintenance of the parasitic state, immune reactions may exert a protective effect that causes a significant change in the critical infection parameters (i.e. egg counts, blood values, worm number, or worm size). Quantitative ELISA using the antigenic proteins will demonstrate the relative avidity of the immune response and will provide a data set that can be applied to the identification and analysis of hookworm resistant animals.

Challenge Infection: *Ancylostoma ceylanicum* larvae are cultured from the eggs collected in the feces of infected hamsters by qualified technicians in the Dr. Hotez lab. All hookworms in the infective challenge are approximately equal age (10±5 days). The species identity of the infective larva dose is validated, using PCR DNA amplification and specific oligonucleotide primers. All hamsters are infected by orally with the same dose of 100+/−10 3rd stage larvae of *A. celyanicumfs*. Larval challenge occurs on the same day for all hamsters (at age 82±2 days). Clinical Observations: The hamsters are observed daily and are weighed at least every 7 days post-challenge. Hamsters that develop signs of moderate to severe anemia, or develop a loss of body weight greater than 15% are observed more frequently. Prior to larvae infection and at least one time every 7-10 days, blood samples are collected from all hamsters. Blood withdrawal should be approximately equal in amount from all hamsters and at this time, the stool will be checked for blood.

A pre-vaccination blood sample will be examined for Hemoglobin; a sample of serum will be frozen. A hemoglobin test is performed 6-10 days and 12-18 days post-challenge. Samples of serum will be collected from each hamster; pre-immune, after 2 boosts, and after larval challenge. These samples will be labeled with unique identifiers (nature of the specimen, study-hamster number and collection date) and frozen for possible future analysis.

Quantitative Egg Counts (QEC): One week following parasite dosing, fecal examination for ova begins and will be repeated once a week until the study is terminated. The ova count method will be performed according to the SOP, which is a modification of the McMaster technique (Veterinary Clinical Pathology, $6^{th}$ ed., 1994, page 9-10). The test will be performed the same way each time in order to quantitate the ova count. Fecal specimens from the hamsters will be identified by the hamster study number and the unique hamster identification number. The ova are counted in a McMaster chamber under a binocular microscope and recorded.

Termination: Hamsters that appear to be suffering (and the pain cannot be relieved) or become moribund are euthanized. All hamsters that are euthanized or die spontaneously are necropsied. The study is terminated 4 to 5 weeks (+/−3 days) after parasite infection. Three groups of hamsters will be euthanized on each day of necropsy with one of the groups being a group of control hamsters. Halothane will be used for euthanasia.

Necropsy: A complete necropsy is performed. Lesions are described, the entire small and large intestine is collected, and tissues are fixed in formalin. The ear tags will be retained with the tissues in formalin.

Adult Worm Count: The small and large intestines are collected and incubated in a petri dish for a few minutes at 37° C.±7° in saline to facilitate the collection of adult parasites. The adult worms are separated from the intestinal contents, counted, and preserved in formalin for subsequent count and analysis of sex.

Statistical Methods: Both parametric and non-parametric tests will be used to analyze the data. Statistical comparisons for each outcome variable will be performed at the two-sided=0.05 level of significance. Variables that will be analyzed are: Number of worms in the intestine and the colon; Egg counts per gram; Antibody titers; Hemoglobin and Body Weight of hamsters.

Results and Discussion.

Figure 77A:
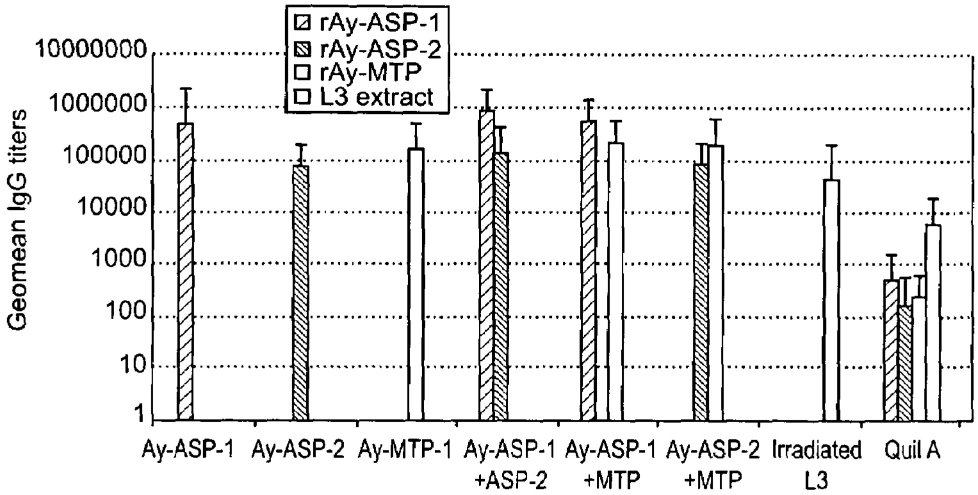
FIGS. 77A and B. A, Geometric mean of antibody titers; B, reduction in worm burdens.
Figure 77B:
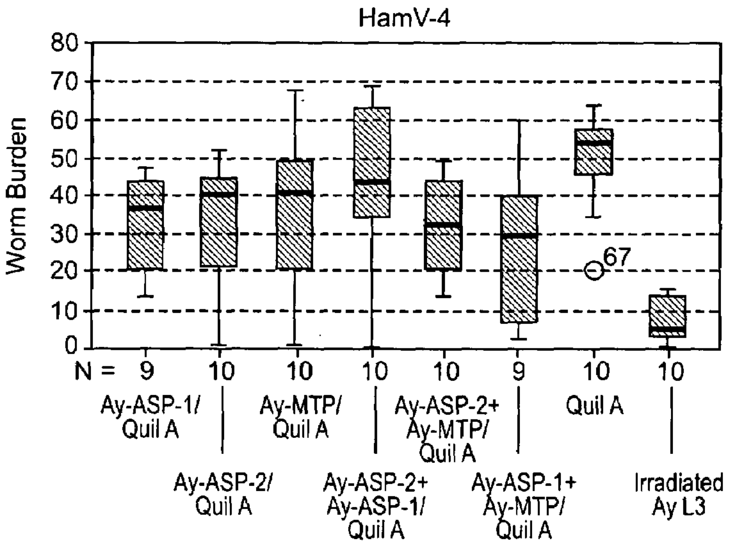

The Geometric mean of antibody titers for each group under study are given in FIG. 77A, and the reduction in worm burden is depicted in Table XIX and graphically in FIG. 77B. As can be seen, the results confirm that ASP-2 is a protective antigen, both in terms of worm burden reduction and in worm fecundity. In addition, there was less blood loss among the ASP-2 vaccinated group. The study also found that ASP-1 had greater protective efficacy than observed in Ham V-3. The results also found that the addition of MTP to the vaccine cocktail increases the protective effect.

TABLE XIX

Hookworm burden reductions following vaccination with recombinant antigens or irradiated *A. ceylanicum* L3 followed by *A. ceylanicum* L3 challenge.

| Experimental Groups | Adult Hookworms Mean (Median) ± 1 SD | Percentage Reduction Relative to Quil A | P (one sided) |
|---|---|---|---|
| Ay-ASP-1 | 30.9 (36.0) ± 13.8 | 36.8 | 0.003* |
| Ay-ASP-2 | 33.2 (39.5) ± 15.2 | 32.1 | 0.005* |
| Ay-MTP | 35.3 (40.0) ± 19.6 | 27.8 | 0.026 |
| Ay-ASP-2 + Ay-ASP-1 | 43.7 (43.5) ± 20.4 | 10.6 | 0.29 |
| Ay-ASP-2 + Ay-MTP | 31.4 (31.5) ± 13.4 | 35.8 | 0.002* |
| Ay-ASP-1 + Ay-MTP | 27.0 (29.0) ± 20.0 | 44.8 | 0.011 |
| Quil A (Adjuvant control) | 48.9 (53.0) ± 12.9 | — | — |
| Irradiated L3 | 6.8 (4.5) ± 5.5 | 86.1 | 0.001* |

* P ≦ 0.007 is considered significant after Bonferroni correction

Table XX shows data regarding hookworm egg reduction.

TABLE XX

Hookworm eggs (EPG) reductions following vaccination with recombinant antigens or irradiated *A. ceylanicum* L# followed by *A. ceylanicum* L3 challenge.

| Experimental Groups | EPG Mean ± SD | Percent reduction relative to Quil A |
|---|---|---|
| Ay-ASP-1 | 912.5 ± 17.7 | 59.0 |
| Ay-ASP-2 | 1175.0 ± 176.7 | 47.2 |
| Ay-MTP | 1275.0 ± 777.8 | 42.7 |
| Ay-ASP-2 + Ay-ASP-1 | 1312.5 ± 1007.6 | 41.0 |
| Ay-ASP-2 + Ay-MTP | 1012.5 ± 512.7 | 54.9 |
| Ay-ASP-1 + Ay-MTP | 1025.0 ± 707.11 | 53.9 |
| Quil A (Adjuvant control) | 225.0 ± 1343.5 | — |
| Irradiated L3 | 25.0 ± 0.000 | 98.9 |

Additional date concerning blood loss is given in Table XXI.

TABLE XXI

Hemoglobin reduction at necropsy relative to hemoglobin at the time of experimental infection of hamsters with *A ceylanicum* L3, and its comparison with control group.

| Experimental Groups | Hb % change Mean (Median) ± 1 SD | Percentage Hb Increase Relative to control (QuilA) | P (one sided) |
|---|---|---|---|
| Ay-ASP-1 | −13.3 (−20.0) ± 20.0 | 32.7 | 0.022 |
| Ay-ASP-2 | −9.2 (−13.3) ± 16.0 | 55.2 | 0.003* |
| Ay-MTP | −3.5 (−11.9) ± 30.0 | 59.9 | 0.018 |
| Ay-ASP-2 + Ay-ASP-1 | −17.9 (−23.2) ± 24.3 | 21.9 | 0.11 |
| Ay-ASP-2 + Ay-MTP | −15.2 (−17.2) ± 10.3 | 42.1 | 0.008 |
| Ay-ASP-1 + Ay-MTP | 0.8 (5.4) ± 18.0 | 118.2 | 0.002* |
| Quil A (Adjuvant control) | −29.7 (−32.5) ± 14.8 | — | — |
| Irradiated L3 | 13.7 (21.4) ± 17.6 | 172.1 | <0.0001* |

Figure 78A:
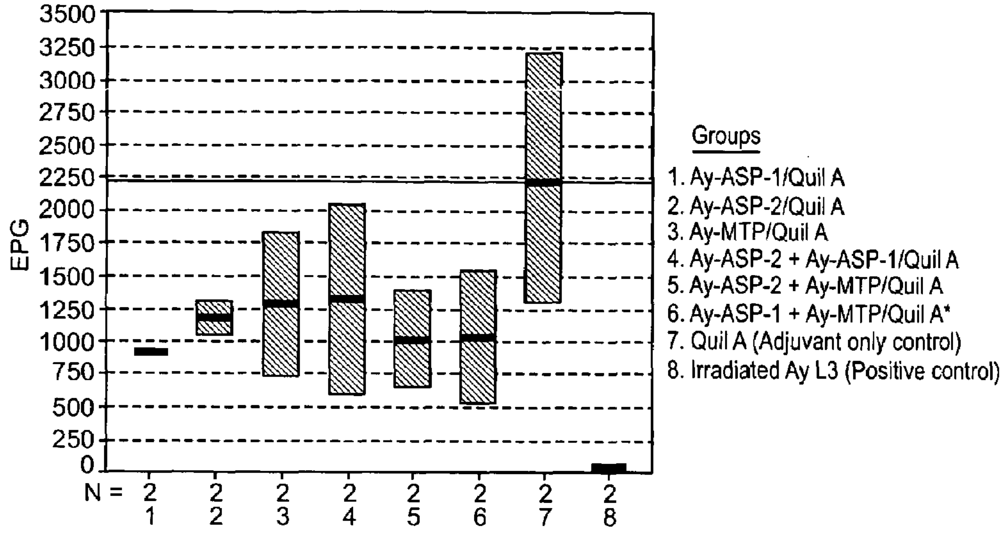
FIGS. 78A and B. A, EPG per group, the average of two cages per group of 10 hamsters. B, Percentage of change of Hb at necropsy relative to pre-challenge values.
Figure 78B:
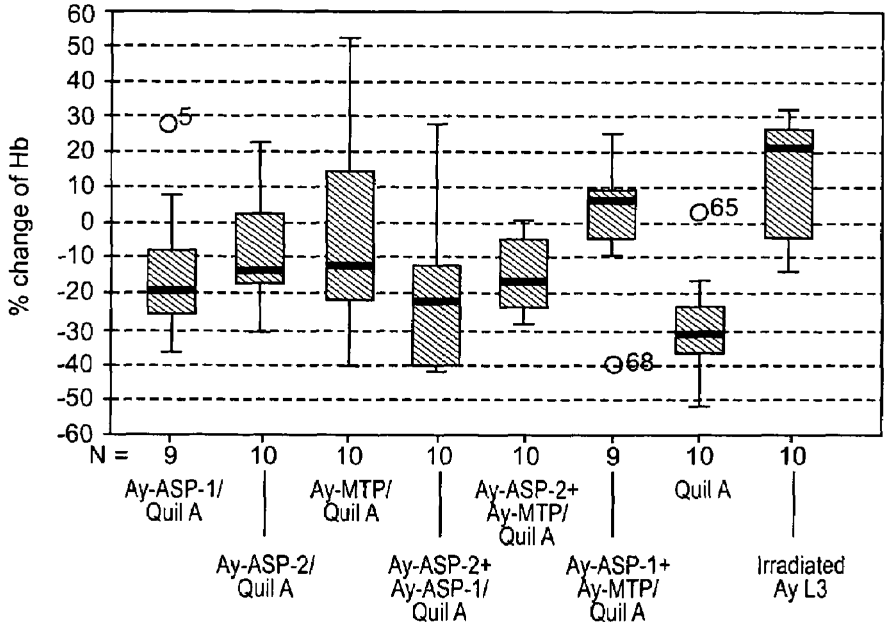
Figure 79A:
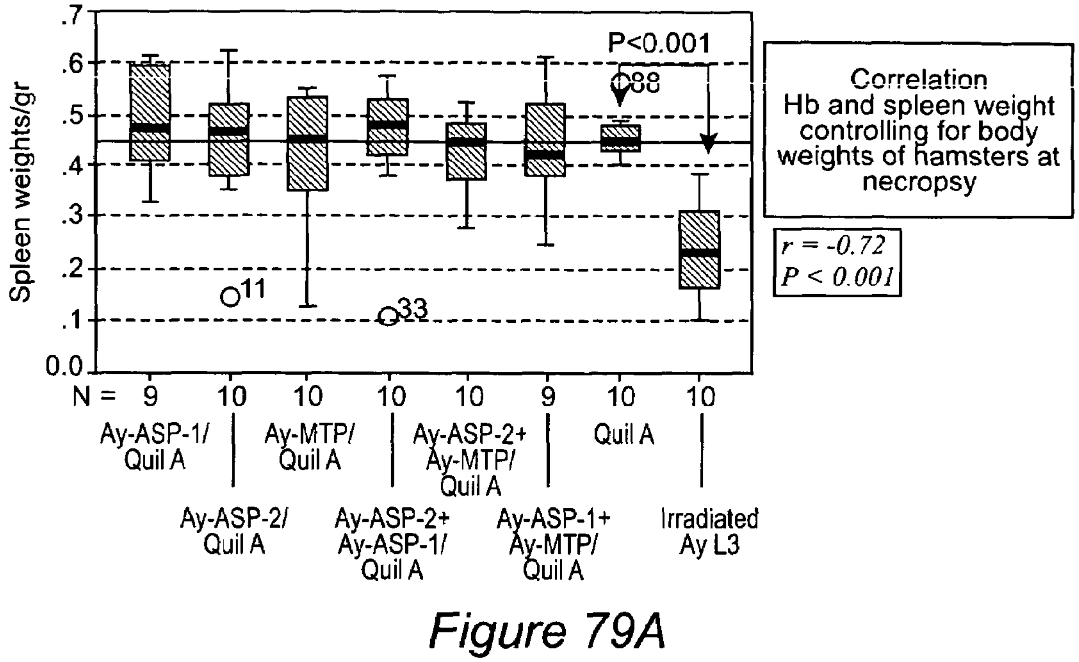
FIGS. 79A and B. A, spleen weights of hamsters by group; B, percentage body weight change at necropsy relative to pre-challenge.
Figure 79B:
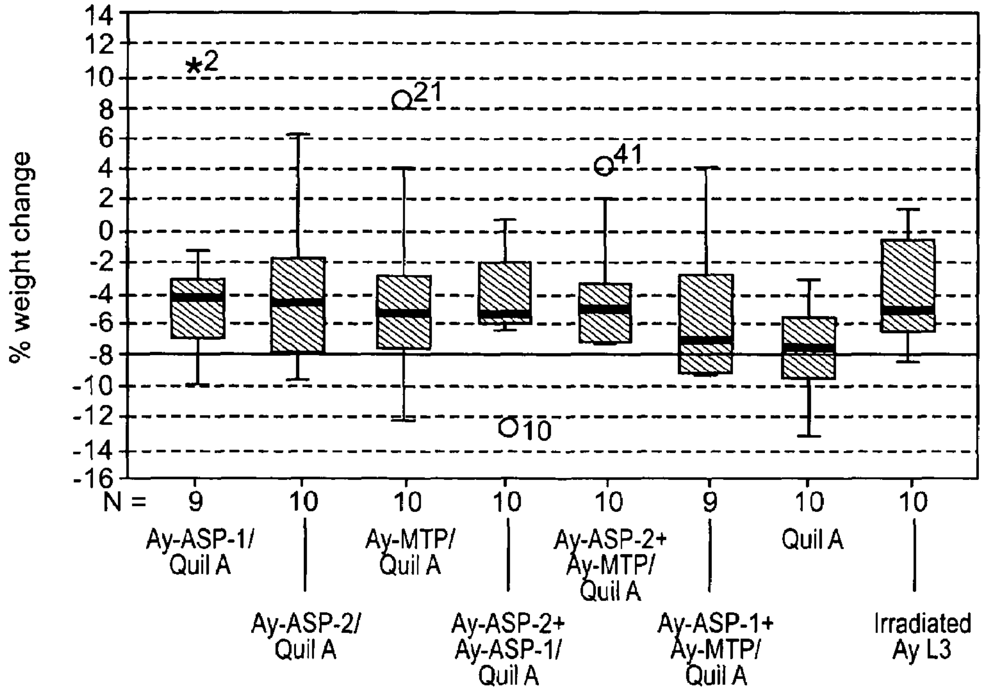

Minus sign means percentage decrease
*P ≦ 0.007 is considered significant after Bonferroni correction FIG. 78B display this data graphically.

Table XXII gives spleen weights of hamsters per experimental group.

TABLE XXII

Spleen weights of hamsters per group.

| Experimental groups | Spleen weights (gr) Mean (Median) ± 1 SD |
|---|---|
| Ay-ASP-1 | 0.48 (0.48) ± 0.10 |
| Ay-ASP-2 | 0.44 (0.47) ± 0.13 |
| Ay-MTP | 0.42 (0.45) ± 0.13 |
| Ay-ASP-2 + Ay-ASP-1 | 0.45 (0.48) ± 0.13 |
| Ay-ASP-2 + Ay-MTP | 0.42 (0.44) ± 0.08 |
| Ay-ASP-1 + Ay-MTP | 0.44 (0.42) ± 0.12 |
| Quil A (Adjuvant control) | 0.47 (0.45) ± 0.06 |
| Irradiated L3 | 0.23 (0.23) ± 0.09 |

Table XXIII shows data concerning body weight reduction of hamsters at necropsy.

TABLE XXIII

Body weight reduction of hamsters at necropsy relative to their weight at the time of experimental infection with *A. ceylanicum* L3, and its comparison with control group.

| Group | Body Weight % Reduction Mean (Median) ± 1 SD | P |
|---|---|---|
| Ay-ASP-1 | 3.4 (4.4) ± 5.9 | 0.02 |
| Ay-ASP-2 | 4.2 (4.9) ± 4.8 | 0.03 |
| Ay-MTP | 4.0 (5.4) ± 6.0 | 0.04 |
| Ay-ASP-2 + Ay-ASP-1 | 4.7 (5.4) ± 3.9 | 0.04 |
| Ay-ASP-2 + Ay-MTP | 4.0 (5.2) ± 4.1 | 0.04 |
| Ay-ASP-1 + Ay-MTP | 5.5 (7.2) ± 4.4 | 0.20 |
| Quil A (Adjuvant control) | 7.9 (7.8) ± 3.0 | — |
| Irradiated L3 | 4.2 (5.2) ± 3.3 | 0.02 |

Figure 80A:
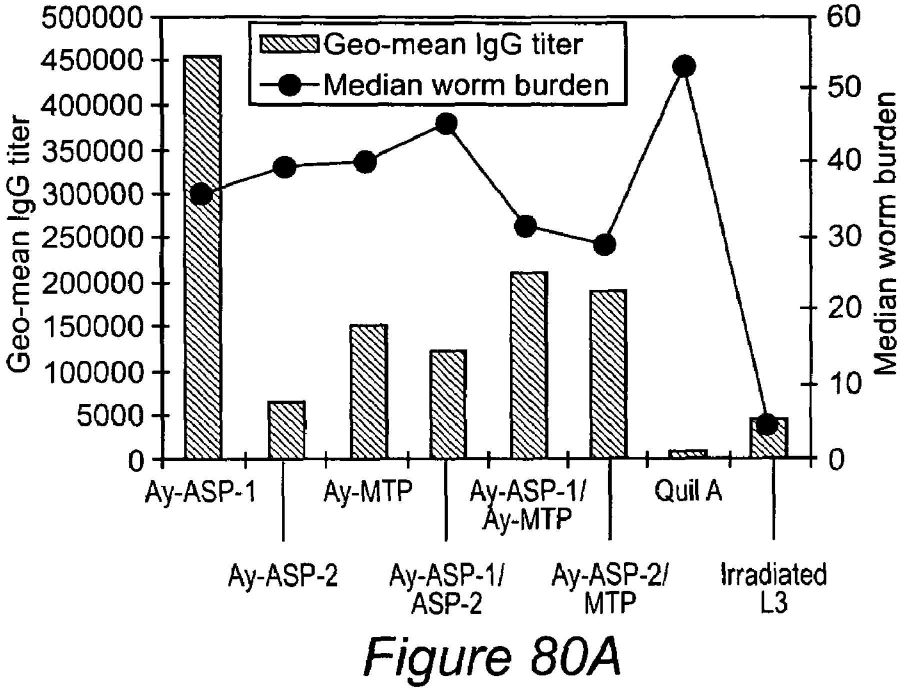
FIGS. 80A and B. geometric mean of IgG titers. Relationship between antibody titers and A, worm burden and B, QECs.
Figure 80B:
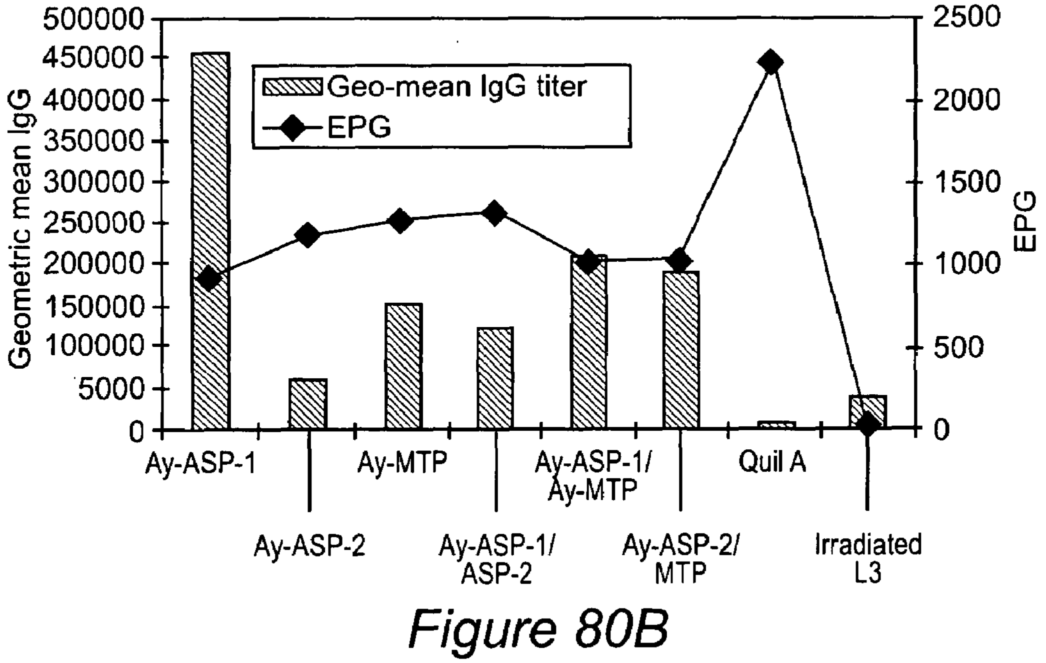

In addition, FIGS. 80A and B illustrate IgG titers vs median worm burden (A) and EPG (B).

This example demonstrates that a significant reduction in worm burden was observed for animals vaccinated with ASP-1, ASP-2, ASP-2+MTP, and irradiated L3. In these animals, an overall reduction in egg count from 41% to 98.9% was observed. Significantly higher hemoglobin was observed in animals vaccinated with ASP-2, ASP-1+MTP and irradiated L3 (P≦0.007, and for ASP-2+MTP, P=0.008). Further, a statistically significant negative correlation was observed between spleen weight and hemoglobin (P<0.001).

Reference Cited in Example 17

Goud G N et al. 2004. Cloning, yeast expression, isolation, and vaccine testing of recombinant *Ancylostoma*-secreted protein (ASP)-1 and ASP-2 from *Ancylostoma ceylanicum*. Journal of Infectious Diseases 189: 919-29

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of reducing the worm burden of human hookworm *Necator americanus* in a mammal or eliciting an immune response in said mammal comprising the step of:

administering to said mammal an effective amount of a composition comprising Na-ASP-2 having the amino acid sequence of SEQ ID NO:69; an adult stage hookworm antigen selected from the group consisting of Na-APR-1 having the amino acid sequence of SEQ ID NO:8 and Na-CP-2 having the amino acid sequence of SEQ ID NO:84; and at least one adjuvant, wherein the immune response is directed against the *Necator americanus* antigens of the administered composition.

2. The method of claim 1, wherein said adult stage hookworm antigen is Na-APR-1 having the amino acid of SEQ ID NO:8.

3. The method of claim 1, wherein said at least one adjuvant comprises two different adjuvants.

4. The method of claim 3, wherein one of said two different adjuvants is an aluminum hydroxide gel.

* * * * *